(12) United States Patent
Sirhan et al.

(10) Patent No.: US 10,383,750 B1
(45) Date of Patent: *Aug. 20, 2019

(54) UNCAGING STENT

(71) Applicant: Elixir Medical Corporation, Milpitas, CA (US)

(72) Inventors: Motasim Sirhan, Los Altos, CA (US); John Yan, Los Gatos, CA (US); Vinayak Bhat, Cupertino, CA (US); Joseph Paraschac, Campbell, CA (US); Brett Cryer, Lafayette, CA (US); Benjamyn Serna, Gilroy, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/356,933

(22) Filed: Mar. 18, 2019

Related U.S. Application Data

(63) Continuation of application No. 16/039,194, filed on Jul. 18, 2018, now Pat. No. 10,271,976, which is a
(Continued)

(51) Int. Cl.
*A61F 2/89* (2013.01)
*A61F 2/915* (2013.01)
(Continued)

(52) U.S. Cl.
CPC .................. *A61F 2/89* (2013.01); *A61F 2/90* (2013.01); *A61F 2/915* (2013.01); *A61F 2/2442* (2013.01);
(Continued)

(58) Field of Classification Search
CPC .... A61F 2/89; A61F 2/90; A61F 2/915; A61F 2/2442; A61F 2/07; A61F 2/24;
(Continued)

(56) References Cited

U.S. PATENT DOCUMENTS

| 3,867,190 A | 2/1975 | Schmitt et al. |
| 5,298,276 A | 3/1994 | Jayaraman et al. |

(Continued)

FOREIGN PATENT DOCUMENTS

| CN | 1328853 A | 1/2002 |
| CN | 1569270 A | 1/2005 |

(Continued)

OTHER PUBLICATIONS

Abstracts—Oral and Poster Presentations. 21 Annual Meeting. The Society for Cardiac Angiography and Interventions. May 13-16, 1998; Le Sheraton Centre, Montreal, Quebec, Canada. pp. 106-127.
(Continued)

*Primary Examiner* — Alvin J Stewart
(74) *Attorney, Agent, or Firm* — Wilson Sonsini Goodrich & Rosati

(57) ABSTRACT

A stent (scaffold) or other luminal prosthesis comprising circumferential structural elements which provides high strength after deployment and allows for scaffold to uncage, and/or allow for scaffold or luminal expansion thereafter. The circumferential scaffold may be formed from degradable material, or may be formed from non-degradable material and will be modified to expand and/or uncage after deployment.

30 Claims, 134 Drawing Sheets

Related U.S. Application Data continuation of application No. 15/921,508, filed on Mar. 14, 2018, now Pat. No. 10,076,431, which is a continuation of application No. 15/605,601, filed on May 25, 2017, now Pat. No. 9,943,426, which is a continuation of application No. PCT/US2017/032748, filed on May 15, 2017.

(60) Provisional application No. 62/480,121, filed on Mar. 31, 2017, provisional application No. 62/430,843, filed on Dec. 6, 2016, provisional application No. 62/424,994, filed on Nov. 21, 2016, provisional application No. 62/414,593, filed on Oct. 28, 2016, provisional application No. 62/374,689, filed on Aug. 12, 2016, provisional application No. 62/337,255, filed on May 16, 2016.

(51) Int. Cl.
*A61F 2/90* (2013.01)
*A61F 2/07* (2013.01)
*A61F 2/24* (2006.01)
*A61F 2/82* (2013.01)

(52) U.S. Cl.
CPC ... *A61F 2002/075* (2013.01); *A61F 2002/825* (2013.01); *A61F 2002/91558* (2013.01); *A61F 2002/91566* (2013.01); *A61F 2002/91575* (2013.01); *A61F 2002/91591* (2013.01); *A61F 2210/0004* (2013.01); *A61F 2210/0014* (2013.01); *A61F 2210/0076* (2013.01); *A61F 2220/0033* (2013.01); *A61F 2220/0091* (2013.01); *A61F 2230/001* (2013.01); *A61F 2230/0006* (2013.01); *A61F 2230/0008* (2013.01); *A61F 2230/0069* (2013.01); *A61F 2250/0031* (2013.01); *A61F 2250/0036* (2013.01); *A61F 2250/0048* (2013.01); *A61F 2250/0067* (2013.01); *A61F 2250/0071* (2013.01)

(58) Field of Classification Search
CPC ...... A61F 2/82; A61F 2/88; A61F 2/86; A61F 2002/91583
See application file for complete search history.

(56) References Cited

U.S. PATENT DOCUMENTS

| | | |
|---|---|---|
| 5,306,286 A | 4/1994 | Stack et al. |
| 5,383,926 A | 1/1995 | Lock et al. |
| 5,441,483 A | 8/1995 | Avitall et al. |
| 5,441,515 A | 8/1995 | Khosravi et al. |
| 5,447,724 A | 9/1995 | Helmus et al. |
| 5,449,384 A | 9/1995 | Johnson et al. |
| 5,500,013 A | 3/1996 | Buscemi et al. |
| 5,556,413 A | 9/1996 | Lam |
| 5,607,466 A | 3/1997 | Imbert et al. |
| 5,670,161 A | 9/1997 | Healy et al. |
| 5,674,286 A | 10/1997 | D'Alessio et al. |
| 5,695,516 A | 12/1997 | Fischell et al. |
| 5,741,293 A | 4/1998 | Wijay |
| 5,741,329 A | 4/1998 | Agrawal et al. |
| 5,766,237 A | 6/1998 | Cragg |
| 5,797,951 A * | 8/1998 | Mueller ............... A61F 2/93 606/191 |
| 5,824,053 A | 10/1998 | Khosravi et al. |
| 5,824,059 A | 10/1998 | Wijay |
| 5,843,172 A | 12/1998 | Yan |
| 5,902,333 A | 5/1999 | Roberts et al. |
| 5,922,020 A | 7/1999 | Klein et al. |
| 5,935,119 A | 8/1999 | Guy et al. |
| 5,957,975 A | 9/1999 | Lafont et al. |
| 5,961,545 A | 10/1999 | Lentz et al. |
| 5,964,798 A | 10/1999 | Imran et al. |
| 5,980,564 A | 11/1999 | Stinson et al. |
| 6,022,371 A | 2/2000 | Killion |
| 6,027,526 A | 2/2000 | Limon et al. |
| 6,039,755 A | 3/2000 | Edwin et al. |
| 6,120,847 A | 9/2000 | Yang et al. |
| 6,190,405 B1 | 2/2001 | Culombo et al. |
| 6,224,803 B1 | 5/2001 | Tiernan et al. |
| 6,245,103 B1 | 6/2001 | Stinson et al. |
| 6,251,134 B1 | 6/2001 | Alt et al. |
| 6,258,117 B1 | 7/2001 | Camrud et al. |
| 6,322,847 B1 | 11/2001 | Zhong et al. |
| 6,323,256 B1 | 11/2001 | Delmain et al. |
| 6,325,825 B1 | 12/2001 | Kula et al. |
| 6,395,326 B1 | 5/2002 | Castro et al. |
| 6,409,754 B1 | 6/2002 | Smith et al. |
| 6,485,510 B1 | 11/2002 | Camrud et al. |
| 6,537,312 B2 | 3/2003 | Datta et al. |
| 6,540,777 B2 | 4/2003 | Stenzel |
| 6,547,814 B2 | 4/2003 | Edwin et al. |
| 6,565,599 B1 | 5/2003 | Hong et al. |
| 6,585,755 B2 | 7/2003 | Jackson et al. |
| 6,599,314 B2 | 7/2003 | Mathis |
| 6,602,282 B1 | 8/2003 | Yan |
| 6,626,939 B1 | 9/2003 | Burnside et al. |
| 6,652,582 B1 | 11/2003 | Stinson |
| 6,719,934 B2 | 4/2004 | Stinson |
| 6,726,701 B2 | 4/2004 | Gilson et al. |
| 6,761,784 B1 | 7/2004 | Hage et al. |
| 6,773,455 B2 | 8/2004 | Allen et al. |
| 6,774,278 B1 | 8/2004 | Ragheb et al. |
| 6,776,796 B2 | 8/2004 | Falotico et al. |
| 6,805,898 B1 | 10/2004 | Wu et al. |
| 6,863,757 B1 | 3/2005 | Gonzalez et al. |
| 6,896,695 B2 | 5/2005 | Mueller et al. |
| 6,920,677 B2 | 7/2005 | Dolan et al. |
| 6,945,995 B2 | 9/2005 | Nicholas |
| 6,964,677 B2 | 11/2005 | Osypka |
| 6,997,948 B2 | 2/2006 | Stinson |
| 7,001,421 B2 | 2/2006 | Cheng et al. |
| 7,011,678 B2 | 3/2006 | Tenerz et al. |
| 7,108,716 B2 | 9/2006 | Burnside et al. |
| 7,128,023 B2 | 10/2006 | Otsuji et al. |
| 7,141,063 B2 | 11/2006 | White et al. |
| 7,144,420 B2 | 12/2006 | Lenz |
| 7,153,322 B2 | 12/2006 | Alt et al. |
| 7,169,173 B2 | 1/2007 | Hossainy et al. |
| 7,235,093 B2 * | 6/2007 | Gregorich ............. A61F 2/91 623/1.11 |
| 7,258,697 B1 | 8/2007 | Cox et al. |
| 7,279,005 B2 | 10/2007 | Stinson |
| 7,285,304 B1 | 10/2007 | Hossainy et al. |
| 7,291,166 B2 | 11/2007 | Cheng et al. |
| 7,329,366 B1 | 2/2008 | Gale et al. |
| 7,354,450 B2 | 4/2008 | Bicek et al. |
| 7,377,939 B2 | 5/2008 | Williams et al. |
| 7,390,333 B2 | 6/2008 | Dutta et al. |
| 7,402,168 B2 | 7/2008 | Acosta et al. |
| 7,455,687 B2 | 11/2008 | Saunders et al. |
| 7,550,005 B2 | 6/2009 | Bates et al. |
| 7,563,277 B2 | 7/2009 | Case et al. |
| 7,572,287 B2 | 8/2009 | Stinson |
| 7,594,928 B2 | 9/2009 | Headley et al. |
| 7,618,448 B2 | 11/2009 | Schmitz et al. |
| 7,622,070 B2 | 11/2009 | Atladottir et al. |
| 7,645,409 B2 | 1/2010 | Saunders et al. |
| 7,666,342 B2 | 2/2010 | Limon et al. |
| 7,722,662 B2 | 5/2010 | Steinke et al. |
| 7,731,890 B2 | 6/2010 | Gale et al. |
| 7,758,636 B2 | 7/2010 | Shanley et al. |
| 7,763,065 B2 | 7/2010 | Schmid et al. |
| 7,789,906 B2 * | 9/2010 | Blank ............. A61F 2/91 623/1.16 |
| 7,824,601 B1 | 11/2010 | Stankus et al. |
| 7,829,008 B2 | 11/2010 | Gueriguian et al. |
| 7,829,273 B2 | 11/2010 | Roof et al. |
| 7,875,233 B2 | 1/2011 | Huang et al. |
| 7,892,273 B2 | 2/2011 | George et al. |

(56) References Cited

U.S. PATENT DOCUMENTS

| | | | |
|---|---|---|---|
| 7,947,071 B2 | 5/2011 | Schmid et al. |
| 7,964,136 B2 | 6/2011 | Sabaria |
| 7,967,998 B2 | 6/2011 | Gale et al. |
| 7,971,333 B2 | 7/2011 | Gale et al. |
| 8,002,818 B2 | 8/2011 | Bregulla |
| 8,025,694 B2 | 9/2011 | Strauss et al. |
| 8,043,553 B1 | 10/2011 | Durcan et al. |
| 8,052,743 B2 | 11/2011 | Weber et al. |
| 8,057,534 B2 | 11/2011 | Boismier et al. |
| 8,062,465 B1 | 11/2011 | Huang et al. |
| 8,070,794 B2 | 12/2011 | Issenmann |
| 8,128,679 B2 | 3/2012 | Casey |
| 8,157,855 B2 | 4/2012 | Eidenschink et al. |
| 8,172,897 B2 | 5/2012 | Gale et al. |
| 8,173,062 B1 | 5/2012 | Durcan et al. |
| 8,182,890 B2 | 5/2012 | Zheng et al. |
| 8,202,313 B2 | 6/2012 | Shanley et al. |
| 8,241,554 B1 | 8/2012 | Abbate et al. |
| 8,268,228 B2 | 9/2012 | Huang et al. |
| 8,292,944 B2 * | 10/2012 | Schmid | A61F 2/92 623/1.15 |
| 8,323,760 B2 | 12/2012 | Zheng et al. |
| 8,414,638 B2 | 4/2013 | Pacetti et al. |
| 8,425,587 B2 | 4/2013 | Trollsas et al. |
| 8,435,281 B2 | 5/2013 | Weber |
| 8,501,079 B2 | 8/2013 | Glauser et al. |
| 8,545,546 B2 | 10/2013 | Wang et al. |
| 8,562,670 B2 | 10/2013 | Pacetti et al. |
| 8,568,469 B1 * | 10/2013 | Gale | A61F 2/82 623/1.12 |
| 8,636,792 B2 | 1/2014 | Zheng et al. |
| 8,636,793 B2 | 1/2014 | Hoerstrup et al. |
| 8,652,192 B2 * | 2/2014 | St. Germain | A61F 2/91 623/1.1 |
| 8,652,198 B2 | 2/2014 | Andreas et al. |
| 8,663,311 B2 | 3/2014 | Besselink et al. |
| 8,709,071 B1 | 4/2014 | Huang et al. |
| 8,740,839 B2 | 6/2014 | Eaton et al. |
| 8,778,256 B1 | 7/2014 | Huang et al. |
| 8,795,030 B2 | 8/2014 | Huang et al. |
| 8,814,930 B2 | 8/2014 | Zheng et al. |
| 8,834,556 B2 | 9/2014 | Papp et al. |
| 8,840,660 B2 | 9/2014 | Weber et al. |
| 8,852,263 B2 | 10/2014 | Wang et al. |
| 8,870,940 B2 | 10/2014 | Venturelli et al. |
| 8,872,062 B2 | 10/2014 | Chen et al. |
| 8,900,292 B2 | 12/2014 | Gregorich et al. |
| 8,956,403 B2 | 2/2015 | Gregorich et al. |
| 8,961,585 B2 | 2/2015 | Ma et al. |
| 9,004,182 B2 | 4/2015 | O'Connor et al. |
| 9,005,276 B2 | 4/2015 | Fox et al. |
| 9,056,157 B2 | 6/2015 | Cho et al. |
| 9,119,905 B2 | 9/2015 | Zheng et al. |
| 9,149,378 B2 * | 10/2015 | Morris | A61F 2/915 |
| 9,180,005 B1 * | 11/2015 | Lashinski | A61F 2/2463 |
| 9,192,471 B2 | 11/2015 | Bolling |
| 9,192,494 B2 * | 11/2015 | Limon | A61F 2/91 |
| 9,259,339 B1 | 2/2016 | Yan et al. |
| 9,265,866 B2 | 2/2016 | Kramer-Brown et al. |
| 9,295,570 B2 | 3/2016 | Schwager et al. |
| 9,314,354 B2 | 4/2016 | Morris et al. |
| 9,433,519 B2 | 9/2016 | Osypka et al. |
| 9,439,788 B2 | 9/2016 | Gale et al. |
| 9,445,924 B2 | 9/2016 | Wolf et al. |
| 9,480,588 B2 | 11/2016 | Yan et al. |
| 9,566,371 B2 | 2/2017 | Zheng et al. |
| 9,730,819 B2 | 8/2017 | Yan et al. |
| 9,943,426 B2 * | 4/2018 | Sirhan | A61F 2/89 |
| 1,007,643 A1 | 9/2018 | Sirhan et al. |
| 10,076,431 B2 * | 9/2018 | Sirhan | A61F 2/89 |
| 10,271,976 B2 * | 4/2019 | Sirhan | A61F 2/89 |
| 2001/0016729 A1 | 8/2001 | Divino et al. |
| 2001/0016769 A1 | 8/2001 | Hojeibane et al. |
| 2001/0016770 A1 | 8/2001 | Allen et al. |
| 2001/0021871 A1 | 9/2001 | Stinson |
| 2001/0047199 A1 | 11/2001 | Wijay |
| 2001/0053929 A1 | 12/2001 | Vonesh et al. |
| 2002/0007209 A1 | 1/2002 | Scheerder et al. |
| 2002/0026230 A1 | 2/2002 | Moll et al. |
| 2002/0038146 A1 | 3/2002 | Harry et al. |
| 2002/0107563 A1 * | 8/2002 | Shanley | A61F 2/91 623/1.15 |
| 2002/0111671 A1 * | 8/2002 | Stenzel | A61F 2/91 623/1.16 |
| 2002/0120323 A1 | 8/2002 | Thompson et al. |
| 2002/0161430 A1 | 10/2002 | Jang et al. |
| 2002/0165597 A1 | 11/2002 | Clerc et al. |
| 2002/0183581 A1 | 12/2002 | Yoe et al. |
| 2002/0188347 A1 | 12/2002 | Mathis |
| 2002/0193336 A1 | 12/2002 | Elkins et al. |
| 2003/0004563 A1 | 1/2003 | Jackson et al. |
| 2003/0033007 A1 | 2/2003 | Sirhan et al. |
| 2003/0050687 A1 | 3/2003 | Schwade et al. |
| 2003/0050692 A1 | 3/2003 | Sirhan et al. |
| 2003/0064097 A1 | 4/2003 | Patel et al. |
| 2003/0083732 A1 | 5/2003 | Stinson et al. |
| 2003/0088307 A1 | 5/2003 | Shulze et al. |
| 2003/0093143 A1 | 5/2003 | Zhao et al. |
| 2003/0105513 A1 | 6/2003 | Moriuchi et al. |
| 2003/0135266 A1 | 7/2003 | Chew et al. |
| 2003/0139798 A1 | 7/2003 | Brown et al. |
| 2003/0144726 A1 | 7/2003 | Majercak et al. |
| 2003/0144729 A1 | 7/2003 | Bicek et al. |
| 2003/0153971 A1 | 8/2003 | Chandrasekaran |
| 2003/0195609 A1 | 10/2003 | Berenstein et al. |
| 2003/0199993 A1 | 10/2003 | Gellman et al. |
| 2003/0236320 A1 | 12/2003 | Martin et al. |
| 2004/0006382 A1 | 1/2004 | Sohier et al. |
| 2004/0073290 A1 | 4/2004 | Chouinard et al. |
| 2004/0093077 A1 | 5/2004 | White et al. |
| 2004/0127970 A1 | 7/2004 | Saunders et al. |
| 2004/0147999 A1 | 7/2004 | Udipi et al. |
| 2004/0167610 A1 | 8/2004 | Fleming |
| 2004/0199242 A1 | 10/2004 | Hong et al. |
| 2004/0236406 A1 * | 11/2004 | Gregorich | A61F 2/91 623/1.16 |
| 2004/0260389 A1 | 12/2004 | Case et al. |
| 2005/0031704 A1 | 2/2005 | Ahn et al. |
| 2005/0060020 A1 | 3/2005 | Jenson et al. |
| 2005/0070991 A1 | 3/2005 | Pienknagura et al. |
| 2005/0070996 A1 | 3/2005 | Dinh et al. |
| 2005/0075625 A1 | 4/2005 | Dao et al. |
| 2005/0075716 A1 | 4/2005 | Yan et al. |
| 2005/0123588 A1 | 6/2005 | Zhu et al. |
| 2005/0125051 A1 | 6/2005 | Eidenschink et al. |
| 2005/0171595 A1 | 8/2005 | Feldman et al. |
| 2005/0182479 A1 * | 8/2005 | Bonsignore | A61F 2/91 623/1.15 |
| 2005/0187615 A1 | 8/2005 | Williams et al. |
| 2005/0203607 A1 | 9/2005 | Scherrible |
| 2005/0209680 A1 | 9/2005 | Gale et al. |
| 2005/0216074 A1 | 9/2005 | Sahatjian et al. |
| 2005/0222671 A1 | 10/2005 | Schaeffer et al. |
| 2005/0232964 A1 | 10/2005 | Fennimore, Jr. et al. |
| 2005/0283229 A1 | 12/2005 | Dugan et al. |
| 2006/0020324 A1 | 1/2006 | Schmid et al. |
| 2006/0025852 A1 | 2/2006 | Armstrong et al. |
| 2006/0030932 A1 * | 2/2006 | Kantor | A61F 2/91 623/1.16 |
| 2006/0069424 A1 * | 3/2006 | Acosta | A61F 2/91 623/1.12 |
| 2006/0076708 A1 | 4/2006 | Huang et al. |
| 2006/0100695 A1 | 5/2006 | Peacock, III et al. |
| 2006/0111485 A1 | 5/2006 | Laghi et al. |
| 2006/0122694 A1 | 6/2006 | Stinson et al. |
| 2006/0122697 A1 | 6/2006 | Shanley et al. |
| 2006/0129222 A1 | 6/2006 | Stinson |
| 2006/0136048 A1 | 6/2006 | Pacetti et al. |
| 2006/0147538 A1 | 7/2006 | Craig et al. |
| 2006/0173527 A1 | 8/2006 | Scherrible |
| 2006/0193892 A1 | 8/2006 | Furst et al. |
| 2006/0195175 A1 * | 8/2006 | Bregulla | A61F 2/91 623/1.15 |
| 2006/0229711 A1 | 10/2006 | Yan et al. |

(56) References Cited

U.S. PATENT DOCUMENTS

| | | |
|---|---|---|
| 2006/0251618 A1 | 11/2006 | Dennis et al. |
| 2006/0265048 A1 | 11/2006 | Cheng et al. |
| 2006/0271170 A1 | 11/2006 | Gale et al. |
| 2006/0287710 A1 | 12/2006 | Lendlein et al. |
| 2007/0023974 A1 | 2/2007 | Wu et al. |
| 2007/0073373 A1 | 3/2007 | Bonsignore et al. |
| 2007/0100431 A1 | 5/2007 | Bonsignore et al. |
| 2007/0129789 A1 | 6/2007 | Cottone, Jr. et al. |
| 2007/0135904 A1 | 6/2007 | Eidenschink et al. |
| 2007/0213810 A1* | 9/2007 | Newhauser ............... A61F 2/91 623/1.16 |
| 2007/0219612 A1 | 9/2007 | Andreas et al. |
| 2007/0219613 A1* | 9/2007 | Kao ............... A61B 17/12022 623/1.11 |
| 2007/0231365 A1 | 10/2007 | Wang et al. |
| 2007/0233232 A1* | 10/2007 | St. Germain ............ A61F 2/91 623/1.15 |
| 2007/0253999 A1 | 11/2007 | Huang et al. |
| 2007/0259099 A1 | 11/2007 | Van Sciver et al. |
| 2007/0270941 A1 | 11/2007 | Headley et al. |
| 2007/0271763 A1 | 11/2007 | Huang et al. |
| 2007/0278720 A1 | 12/2007 | Wang et al. |
| 2007/0281117 A1 | 12/2007 | Kaplan et al. |
| 2007/0282426 A1 | 12/2007 | Wang et al. |
| 2007/0282434 A1 | 12/2007 | Wang et al. |
| 2007/0283552 A1 | 12/2007 | Gale et al. |
| 2007/0290412 A1 | 12/2007 | Capek et al. |
| 2007/0299505 A1 | 12/2007 | Gregorich et al. |
| 2008/0051866 A1 | 2/2008 | Chen et al. |
| 2008/0051873 A1 | 2/2008 | Cottone et al. |
| 2008/0081063 A1 | 4/2008 | Wang et al. |
| 2008/0082162 A1 | 4/2008 | Boismier et al. |
| 2008/0097571 A1 | 4/2008 | Denison et al. |
| 2008/0097580 A1 | 4/2008 | Dave et al. |
| 2008/0103584 A1 | 5/2008 | Su et al. |
| 2008/0147165 A1 | 6/2008 | Hossainy et al. |
| 2008/0177373 A1 | 7/2008 | Huang et al. |
| 2008/0177374 A1 | 7/2008 | Zheng et al. |
| 2008/0183275 A1 | 7/2008 | Schmid et al. |
| 2008/0243243 A1 | 10/2008 | Williams et al. |
| 2008/0249608 A1 | 10/2008 | Dave et al. |
| 2008/0306579 A1 | 12/2008 | Dolan et al. |
| 2009/0030507 A1 | 1/2009 | Klocke et al. |
| 2009/0076584 A1 | 3/2009 | Mao et al. |
| 2009/0095715 A1 | 4/2009 | Sabaria et al. |
| 2009/0096137 A1 | 4/2009 | Williams et al. |
| 2009/0099639 A1 | 4/2009 | Sabaria et al. |
| 2009/0105800 A1 | 4/2009 | Sabaria et al. |
| 2009/0146348 A1 | 6/2009 | Huang et al. |
| 2009/0205840 A1 | 8/2009 | O'Connor et al. |
| 2009/0208555 A1 | 8/2009 | Kuttler et al. |
| 2009/0216309 A1 | 8/2009 | Granada et al. |
| 2009/0228094 A1 | 9/2009 | Yan et al. |
| 2009/0234429 A1* | 9/2009 | Lau ............... A61F 2/91 623/1.12 |
| 2009/0264979 A1 | 10/2009 | Kao et al. |
| 2010/0036478 A1 | 2/2010 | Wang et al. |
| 2010/0038822 A1 | 2/2010 | Wang et al. |
| 2010/0049300 A1 | 2/2010 | Harder et al. |
| 2010/0198331 A1 | 8/2010 | Rapoza et al. |
| 2010/0217370 A1 | 8/2010 | Scheuermann et al. |
| 2010/0244329 A1 | 9/2010 | Hossainy et al. |
| 2010/0252965 A1 | 10/2010 | Wang et al. |
| 2010/0262224 A1 | 10/2010 | Kleiner et al. |
| 2010/0292773 A1 | 11/2010 | Schmid et al. |
| 2010/0324657 A1 | 12/2010 | Bogert et al. |
| 2011/0022163 A1 | 1/2011 | Wang et al. |
| 2011/0054591 A1 | 3/2011 | Sahatjian et al. |
| 2011/0062638 A1 | 3/2011 | Glauser et al. |
| 2011/0130822 A1 | 6/2011 | Cottone |
| 2011/0152997 A1* | 6/2011 | Kelly ............... A61F 2/958 623/1.12 |
| 2011/0160757 A1 | 6/2011 | Ferrera et al. |
| 2011/0190861 A1* | 8/2011 | Pericevic ............... A61F 2/91 623/1.11 |
| 2011/0215505 A1 | 9/2011 | Kleiner et al. |
| 2011/0238158 A1 | 9/2011 | Heringes et al. |
| 2011/0238162 A1 | 9/2011 | Busold et al. |
| 2011/0260352 A1 | 10/2011 | Tang et al. |
| 2011/0260358 A1 | 10/2011 | Wang et al. |
| 2012/0071962 A1 | 3/2012 | Huang et al. |
| 2012/0187606 A1 | 7/2012 | Zheng et al. |
| 2012/0191177 A1* | 7/2012 | Costa ............... A61F 2/88 623/1.16 |
| 2012/0226345 A1 | 9/2012 | Zheng et al. |
| 2012/0271396 A1 | 10/2012 | Zheng et al. |
| 2012/0290070 A1 | 11/2012 | Wang et al. |
| 2012/0290071 A1 | 11/2012 | Wang et al. |
| 2013/0046373 A1 | 2/2013 | Cartledge et al. |
| 2013/0084322 A1 | 4/2013 | Wu et al. |
| 2013/0085564 A1 | 4/2013 | Papp et al. |
| 2013/0150943 A1 | 6/2013 | Zheng et al. |
| 2013/0178926 A1* | 7/2013 | Denison ............... A61F 2/88 623/1.16 |
| 2013/0190676 A1 | 7/2013 | Dickinson et al. |
| 2013/0211499 A1* | 8/2013 | Bonsignore ............. A61F 2/915 623/1.16 |
| 2013/0331927 A1 | 12/2013 | Zheng et al. |
| 2014/0004312 A1 | 1/2014 | Foreman et al. |
| 2014/0012362 A1 | 1/2014 | Gale et al. |
| 2014/0018903 A1 | 1/2014 | Eli et al. |
| 2014/0025161 A1 | 1/2014 | Stankus et al. |
| 2014/0081381 A1 | 3/2014 | Kim et al. |
| 2014/0114398 A1 | 4/2014 | Hossainy et al. |
| 2014/0121294 A1 | 5/2014 | Huang et al. |
| 2014/0188243 A1 | 7/2014 | Zheng et al. |
| 2014/0252683 A1 | 9/2014 | Huang et al. |
| 2014/0277373 A1 | 9/2014 | Huang et al. |
| 2014/0296961 A1* | 10/2014 | Blaser ............... A61F 2/915 623/1.12 |
| 2014/0350659 A1 | 11/2014 | Zheng et al. |
| 2014/0364935 A1* | 12/2014 | Eli ............... A61F 2/91 623/1.12 |
| 2015/0025619 A1 | 1/2015 | Zheng et al. |
| 2015/0073536 A1 | 3/2015 | Rapoza et al. |
| 2015/0320577 A1 | 11/2015 | Zheng et al. |
| 2015/0374521 A1 | 12/2015 | Zheng et al. |
| 2016/0045343 A1 | 2/2016 | Yan et al. |
| 2016/0045344 A1 | 2/2016 | Yan et al. |
| 2016/0166414 A1 | 6/2016 | Yan et al. |
| 2016/0206450 A1* | 7/2016 | Mitsudo ............... A61L 31/022 |
| 2016/0213499 A1 | 7/2016 | Zheng et al. |
| 2016/0278952 A1 | 9/2016 | Ngo et al. |
| 2016/0278953 A1 | 9/2016 | Zheng et al. |
| 2017/0128245 A1* | 5/2017 | Minami ............... A61F 2/93 |
| 2017/0156899 A1 | 6/2017 | Zheng et al. |
| 2017/0216067 A1 | 8/2017 | Leblanc et al. |
| 2017/0290686 A1 | 10/2017 | Sirhan et al. |
| 2018/0200091 A1 | 7/2018 | Sirhan et al. |
| 2018/0318113 A1 | 11/2018 | Sirhan et al. |

FOREIGN PATENT DOCUMENTS

| | | |
|---|---|---|
| DE | 10103000 B4 | 8/2007 |
| DE | 102004027108 B4 | 1/2009 |
| EP | 1563806 A1 | 8/2005 |
| EP | 2229919 A2 | 9/2010 |
| JP | H11512626 A | 11/1999 |
| JP | 2000202032 A | 7/2000 |
| JP | 2003500101 A | 1/2003 |
| JP | 2004149692 A | 5/2004 |
| JP | 2005298617 A | 10/2005 |
| JP | 2006192111 A | 7/2006 |
| JP | 2006223860 A | 8/2006 |
| JP | 2011502195 A | 1/2011 |
| WO | WO-9204393 A1 | 3/1992 |
| WO | WO-0195834 A1 | 12/2001 |
| WO | WO-02091956 A1 | 11/2002 |
| WO | WO-03034940 A2 | 5/2003 |
| WO | WO-2004052420 A2 | 6/2004 |
| WO | WO-2004080332 A2 | 9/2004 |

(56) References Cited

FOREIGN PATENT DOCUMENTS

| WO | WO-2004110315 A1 | 12/2004 |
|---|---|---|
| WO | WO-2004110515 A1 | 12/2004 |
| WO | WO-2004080332 A3 | 4/2005 |
| WO | WO-2005096992 A1 | 10/2005 |
| WO | WO-2005115277 A2 | 12/2005 |
| WO | WO-2005115277 A3 | 5/2007 |
| WO | WO-2007126599 A2 | 11/2007 |
| WO | WO-2007146354 A2 | 12/2007 |
| WO | WO-2008002479 A2 | 1/2008 |
| WO | WO-2008002636 A2 | 1/2008 |
| WO | WO-2008005390 A1 | 1/2008 |
| WO | WO-2008008416 A1 | 1/2008 |
| WO | WO-2008011048 A2 | 1/2008 |
| WO | WO-2007146354 A3 | 2/2008 |
| WO | WO-2008016667 A2 | 2/2008 |
| WO | WO-2008016696 A2 | 2/2008 |
| WO | WO-2008016696 A3 | 3/2008 |
| WO | WO-2008033263 A2 | 3/2008 |
| WO | WO-2008002636 A3 | 4/2008 |
| WO | WO-2008051867 A2 | 5/2008 |
| WO | WO-2007126599 A3 | 7/2008 |
| WO | WO-2008089434 A2 | 7/2008 |
| WO | WO-2008051867 A3 | 8/2008 |
| WO | WO-2008098434 A1 | 8/2008 |
| WO | WO-2008002479 A3 | 9/2008 |
| WO | WO-2008016667 A3 | 11/2008 |
| WO | WO-2008137821 A1 | 11/2008 |
| WO | WO-2008011048 A3 | 3/2009 |
| WO | WO-2008033263 A3 | 4/2009 |
| WO | WO-2011025945 A1 | 3/2011 |
| WO | WO-2014045068 A1 | 3/2014 |
| WO | WO-2014091438 A2 | 6/2014 |
| WO | WO-2017200956 A1 | 11/2017 |
| WO | WO-2019033121 | 2/2019 |

OTHER PUBLICATIONS

Bae, et al. Drug delivery. Fundamentals and methods of tissue engineering. From 'Frontiers in Tissue Engineering' edited by Patrick et al. Feb. 20, 1998; Ch II.14:263-272.
Breiby, et al. Quantification of preferential orientation in conjugated polymers using X-ray diffraction. J. Polymer Science Part B: Polymer Physics. 2003; 41(20):2375-2393.
Cruz, et al. Quantitative mapping of the orientation of fibroin beta-sheets in B. mori cocoon fibers by scanning transmission X-ray microscopy. Biomacromolecules. Mar. 2006;7(3):836-43.
Donald, et al. Electron Microscopy of Banded Structures in Oriented Thermotropic Polymers. J. Materials Science. 1983; 18:1143-1150.
European search report and search opinion dated Feb. 18, 2015 for EP Application No. 12804895.6.
European search report and search opinion dated Dec. 20, 2012 for Application No. 8727927.9.
Ewert, et al. Early and mid-term results with the Growth Stent—a possible concept for transcatheter treatment of aortic coarctation from infancy to adulthood by stent implantation? Catheter Cardiovasc Interv. Jan. 1, 2008;71(1):120-6.
Ewert, et al. Novel growth stent for the permanent treatment of vessel stenosis in growing children: an experimental study. Catheter Cardiovasc Interv. Aug. 2004;62(4):506-10.
Fuhrman, et al. Central nervous system. From 'Tissue Engineering: From Lab to Clinic' edited by Pallua et al. 2010; Ch12:221-244.
Hacker, et al. Synthetic polymers. From 'Principles of Regenerative Medicine 2nd ed.' Edited by Atala et al. 2011; Ch 33:587-622.
Hara. Ion-containing polymers and their biological interactions. Polyelectrolytes Science and Technology. 1993; Ch 6:321-325.
Hombreiro-Perez, et al. Non-degradable microparticles containing a hydrophilic and/or a lipophilic drug: preparation, characterization and drug release modeling. J Control Release. Mar. 26, 2003;88(3):413-28.

International search report and written opinion dated Apr. 13, 2015 for PCT/US2015/012780.
International search report and written opinion dated Aug. 1, 2008 for PCT/US2008/051479.
International search report and written opinion dated Aug. 1, 2008 for PCT/US2008/051497.
International search report and written opinion dated Aug. 7, 2017 for PCT Application No. PCT/US2017/032748.
International search report and written opinion dated Aug. 25, 2016 for PCT Application No. PCT/US2016/026821.
International search report and written opinion dated Sep. 25, 2012 for PCT/US2012/44736.
International search report and written opinion dated Oct. 7, 2014 for PCT Application No. PCT/US2014/038508.
Lamberti , et al. Real-time orientation and crystallinity measurements during the isotactic polypropylene film-casting process. J. Polymer Science Part B: Polymer Physics. 2003; 41(9):998-1008.
Lee, et al. Retardation of enzymatic degradation of microbial polyesters using surface chemistry: effect of addition of non-degradable polymers. Surface Science. 2003; 542(3):235-243.
Ma, et al. Scaffolding in Tissue Engineering. 2005; pp. 78-80.
Majoros, et al. Poly(amidoamine) dendrimer synthesis and characterization. Dendrimer-based Nanomedicine. 2008; Ch 3:35-57.
Mullins, et al. Cardiac Catheterization in Congenital Heart Disease: Pediatric and Adult. John Wiley & Sons, Apr. 15, 2008. Chapter 22 Intravascular stents—general information; pp. 582.583.
Notice of allowance dated Apr. 18, 2017 for U.S. Appl. No. 14/800,536.
Notice of allowance dated May 12, 2014 for U.S. Appl. No. 13/897,302.
"Notice of Allowance dated Jun. 4, 2018 for U.S. Appl. No. 15/921,508".
Notice of allowance dated Jul. 15, 2015 for U.S. Appl. No. 14/461,159.
Notice of allowance dated Sep. 8, 2016 for U.S. Appl. No. 14/697,537.
Notice of allowance dated Oct. 27, 2017 for U.S. Appl. No. 15/605,601.
Notice of allowance dated Dec. 13, 2013 for U.S. Appl. No. 13/539,770.
Notice of allowance dated Dec. 13, 2016 for U.S. Appl. No. 14/804,415.
Notice of allowance dated Dec. 23, 2015 for U.S. Appl. No. 14/682,014.
Office action dated Feb. 16, 2017 for U.S. Appl. No. 14/800,536.
Office action dated Feb. 16, 2017 for U.S. Appl. No. 15/043,331.
Office action dated Mar. 2, 2010 for U.S. Appl. No. 12/016,077.
Office action dated Mar. 10, 2016 for U.S. Appl. No. 14/611,043.
Office action dated Mar. 10, 2017 for U.S. Appl. No. 14/604,621.
Office action dated Mar. 28, 2016 for U.S. Appl. No. 14/697,537.
Office action dated Mar. 30, 2011 for U.S. Appl. No. 12/016,085.
Office action dated Apr. 1, 2011 for U.S. Appl. No. 12/016,077.
Office action dated Apr. 24, 2015 for U.S. Appl. No. 14/461,159.
Office action dated Jul. 1, 2016 for U.S. Appl. No. 14/604,621.
Office action dated Jul. 2, 2013 for U.S. Appl. No. 12/016,077.
Office action dated Jul. 12, 2012 for U.S. Appl. No. 13/473,354.
Office action dated Jul. 15, 2015 for U.S. Appl. No. 14/682,014.
Office action dated Jul. 17, 2013 for U.S. Appl. No. 13/539,770.
Office action dated Aug. 1, 2014 for U.S. Appl. No. 14/097,087.
Office action dated Aug. 10, 2016 for U.S Appl. No. 14/804,415.
Office action dated Aug. 10, 2017 for U.S. Appl. No. 15/605,601.
Office action dated Aug. 21, 2017 for U.S. Appl. No. 15/420,615.
Office action dated Oct. 4, 2012 for U.S. Appl. No. 13/539,770.
Office action dated Oct. 27, 2011 for U.S. Appl. No. 12/016,077.
Office action dated Nov. 4, 2016 for U.S. Appl. No. 15/178,506.
Office action dated Nov. 10, 2010 for U.S. Appl. No. 12/016,077.
Office action dated Nov. 14, 2014 for U.S. Appl. No. 14/461,159.
Office action dated Nov. 21, 2016 for U.S. Appl. No. 14/800,536.
Office action dated Dec. 5, 2012 for U.S. Appl. No. 12/016,077.
Office action dated Dec. 15, 2011 for U.S. Appl. No. 12/016,085.
Office action dated Dec. 18, 2013 for U.S. Appl. No. 13/897,302.
PCT/US18/46561 International Search Report and Written Opinion dated Oct. 25, 2018.

(56) References Cited

OTHER PUBLICATIONS

Kucharavy, et al. Application of S-Shaped Curves. TRIZ-Future Conference 2007: Current Scientific and Industrial Reality, Nov. 2007, Frankfurt, Germany. pp. 81-88, 2007.<hal-00282758.

Qin, et al. Synthesis and Characterization of Unsaturated Thermotropic Polyesters Prepared via Acyclic Diene Metathesis Polymerization. Macromolecules. 2004; 37:5239-5249.

Rao, S. Future Directions in the Management of Aortic Coarctation in Young Patients. Pediat Therapeut. 2014; 4:e125. doi:10.4172/2161-0665.1000e125.

Sanders. Controlled delivery systems for peptides. From 'Peptide and protein drug delivery' Edited by Vincent Lee, Advances in Parenteral science vol. 4. 1990; Ch 19:785-806.

Seal, et al. Polymeric biomaterials for tissue and organ regeneration. Materials Science and Engineering. R34. 2001; 147-230.

Shastri. Non-degradable biocompatible polymers in medicine: past, present, and future. Current Pharmaceutical Biotechnology. 2003; 4:331-337.

Sigler, et al. Breakable stent for interventions in infants and neonates: an animal study and histopathological findings. Heart. Feb. 2006; 92(2): 245-248.

Tanimoto, et al. Comparison of in vivo acute stent recoil between the bioabsorbable everolimus-eluting coronary stent and the everolimus-eluting cobalt chromium coronary stent: insights from the ABSORB and SPIRIT trials. Catheter Cardiovasc Interv. Oct. 1, 2007;70(4):515-23.

U.S. Appl. No. 15/605,601 Notice of Allowance dated Feb. 21, 2018.

Valimaa, et al. Viscoelastic memory and self-expansion of self-reinforced bioabsorbable stents. Biomaterials. Sep. 2002;23(17):3575-82.

Weir, et al. Processing, Annealing and Sterilisation of Poly-L-Lactide. Biomaterials. 2004; 25:3939-3949.

U.S. Appl. No. 16/039,194 Office Action dated Sep. 11, 2018.

U.S. Appl. No. 16/039,194 Notice of Allowance dated Dec. 6, 2018.

\* cited by examiner

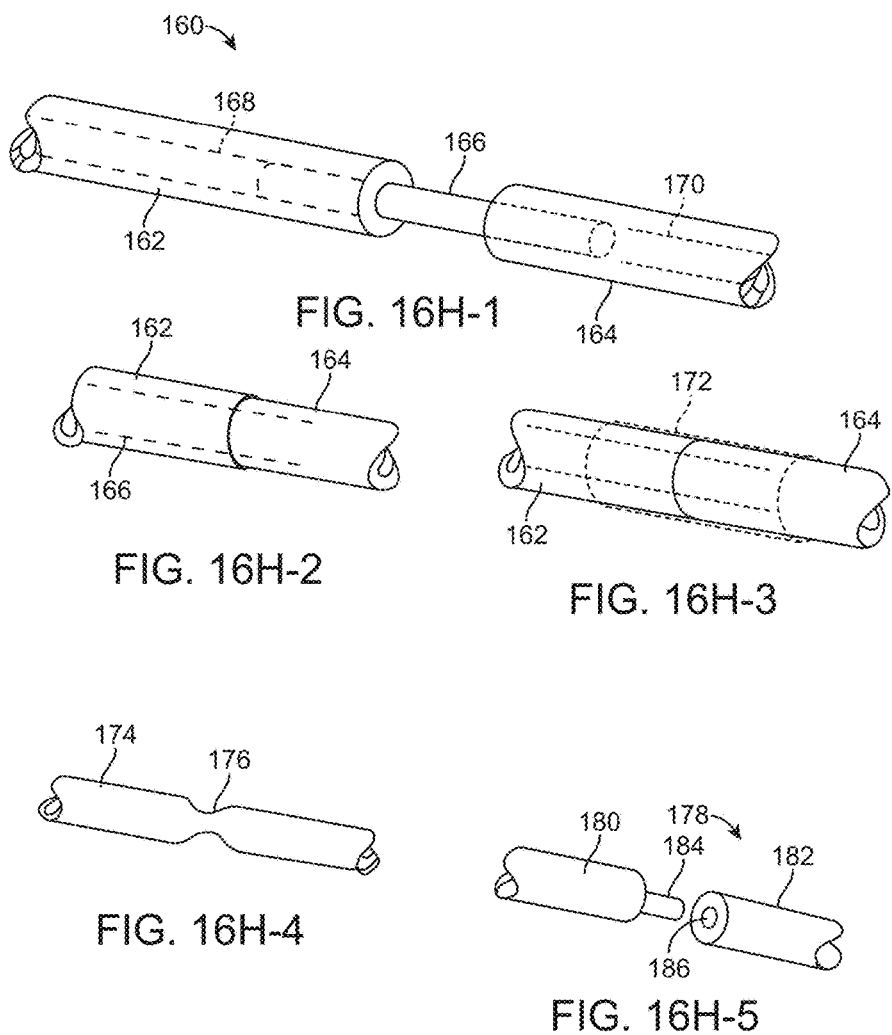

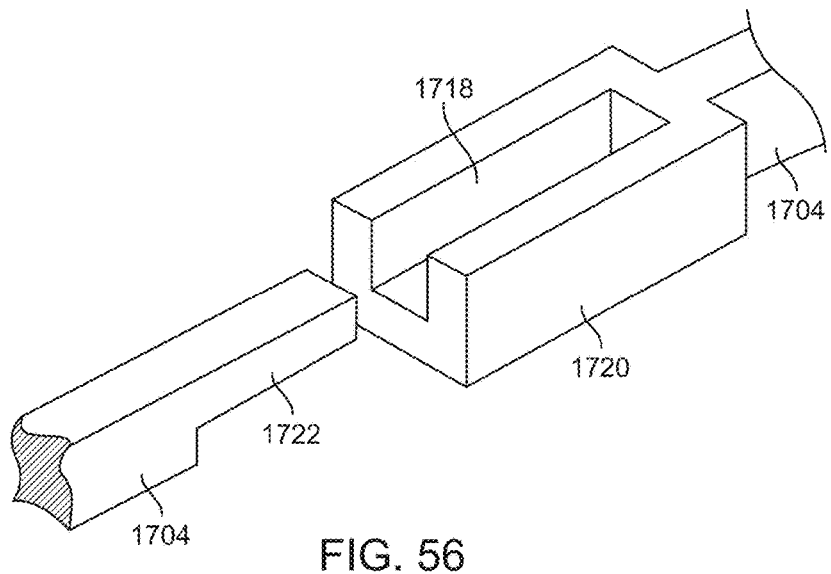
FIG. 56
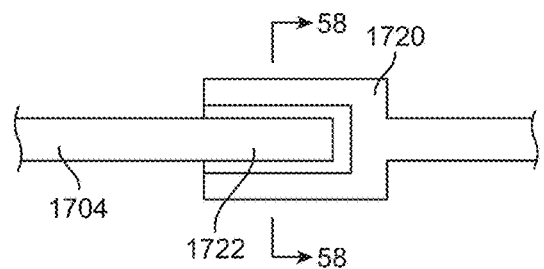
FIG. 57
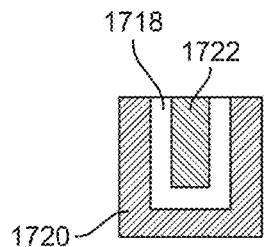 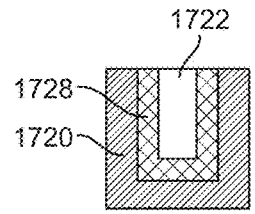
FIG. 58A    FIG. 58B

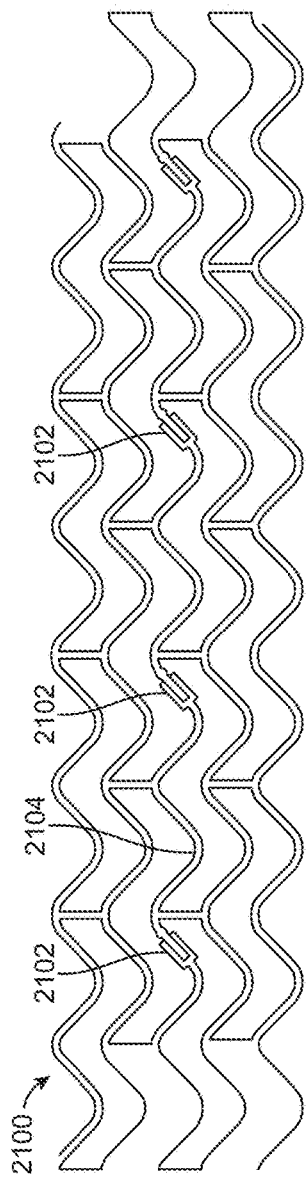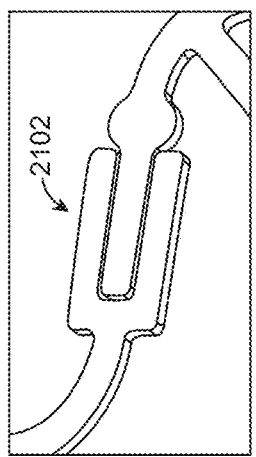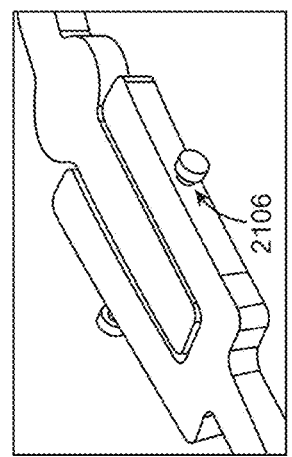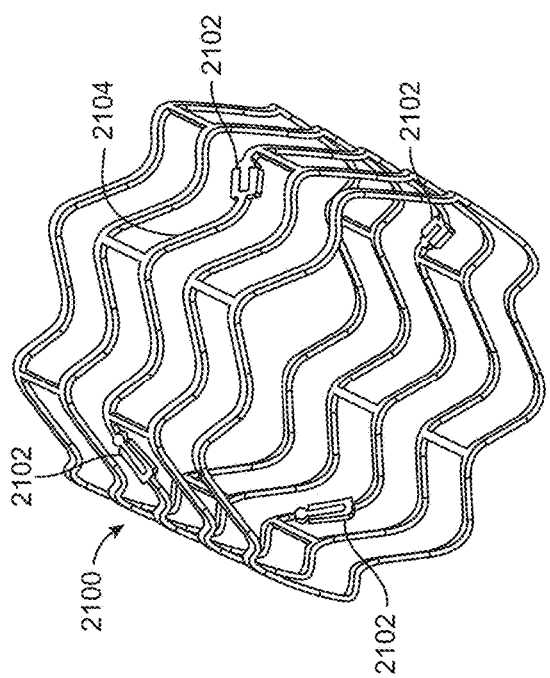

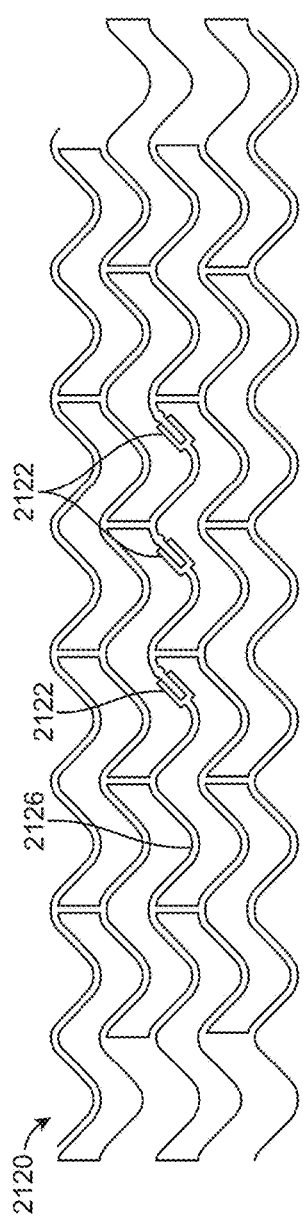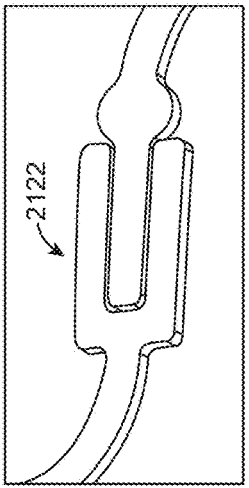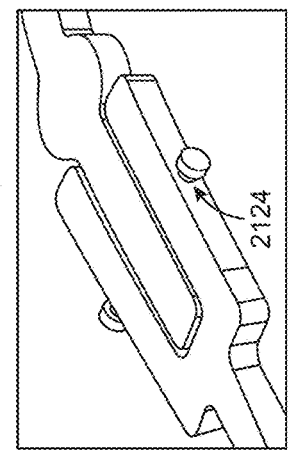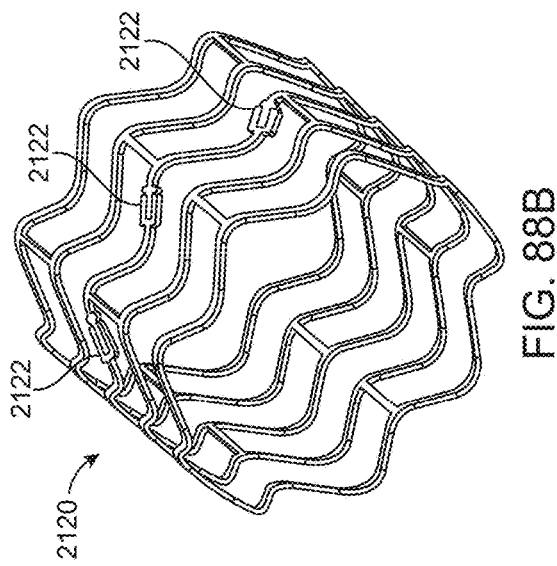

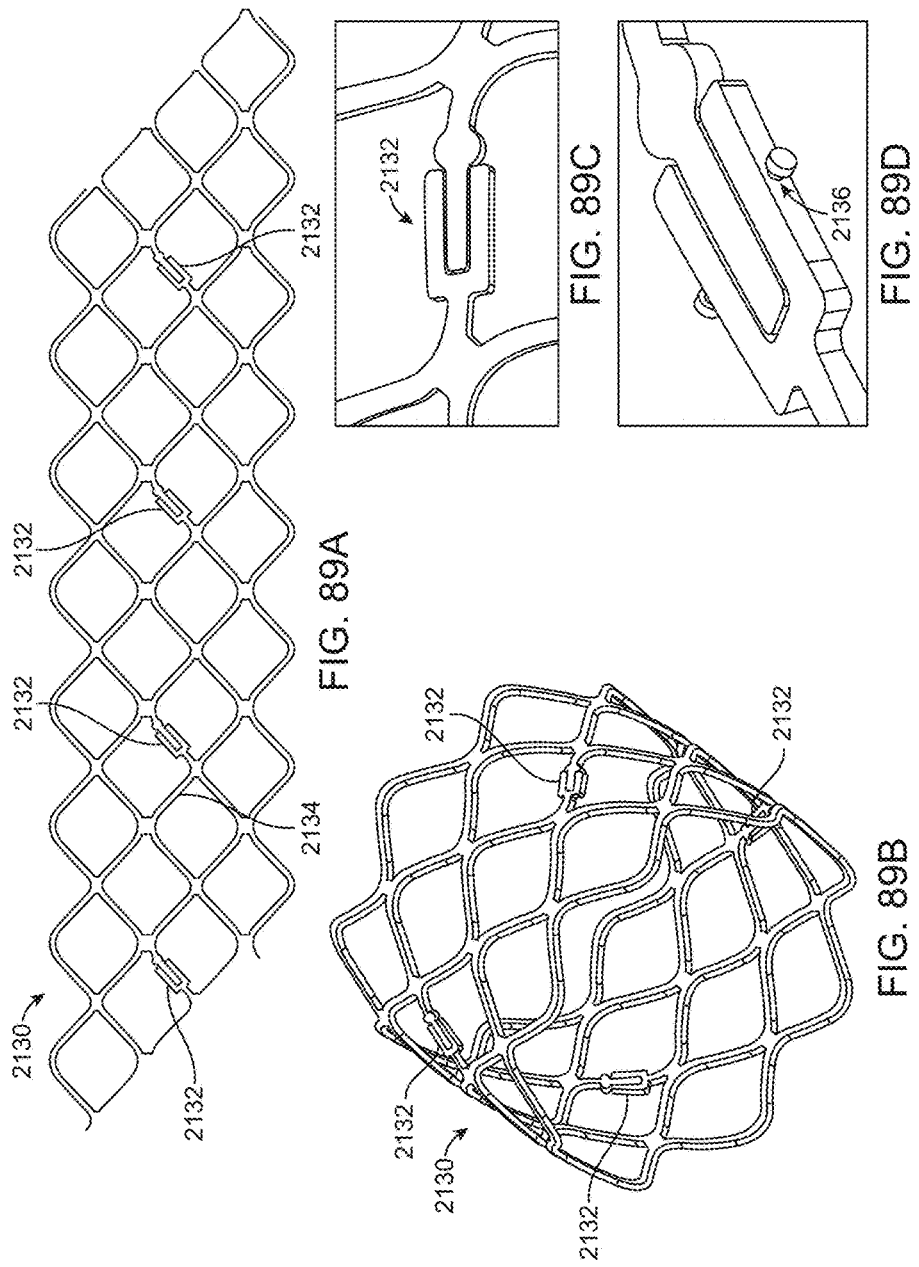

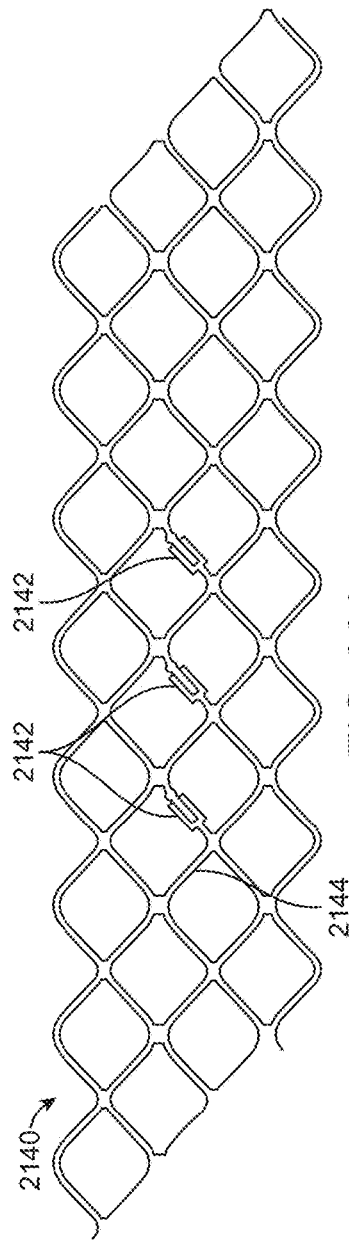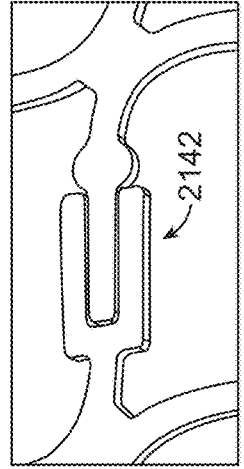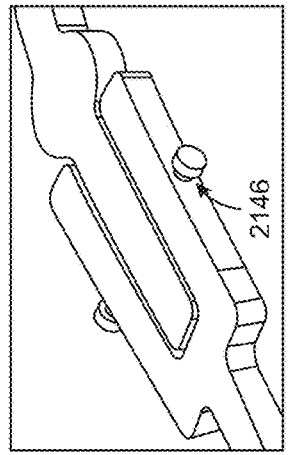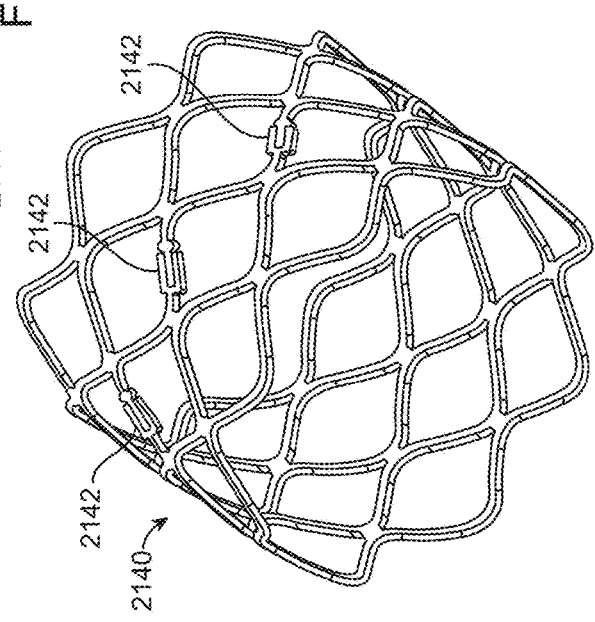

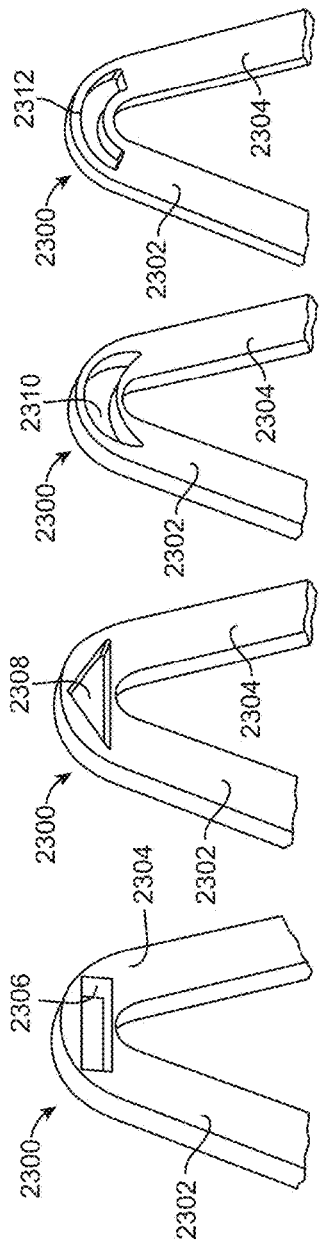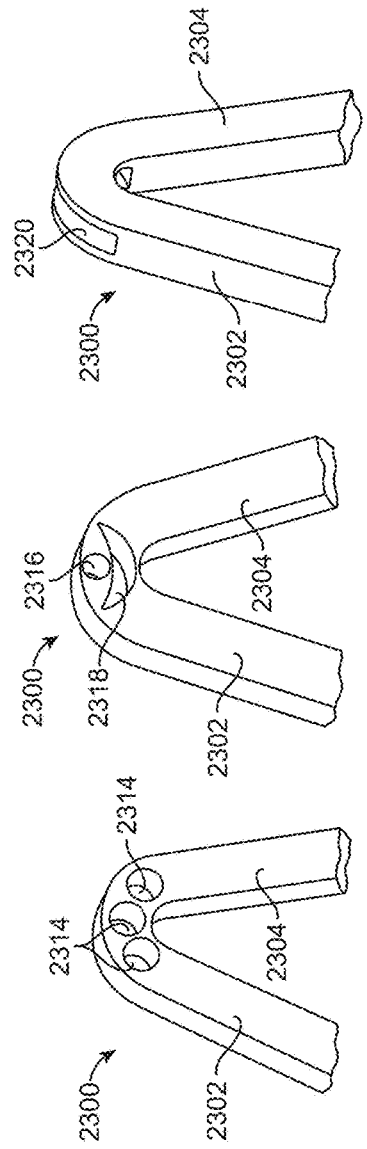

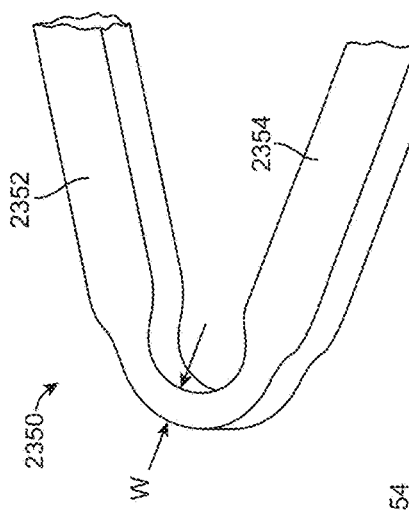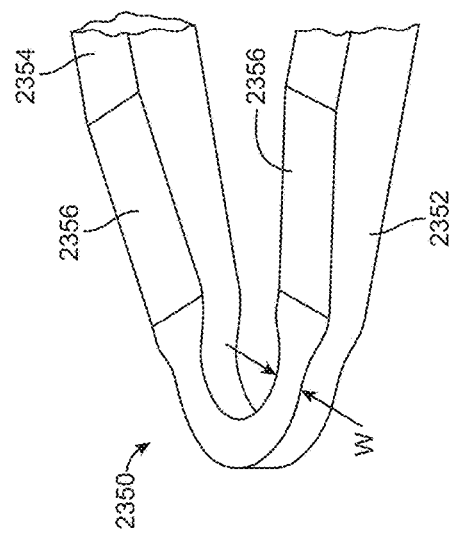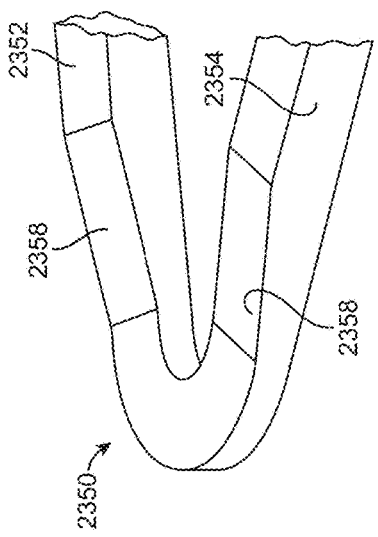

Post Implant 2 month 3 month 5 month

UNCAGING STENT

CROSS REFERENCE TO RELATED APPLICATIONS

This application is a continuation of U.S. patent application Ser. No. 16/039,194, filed Jul. 18, 2018, now U.S. Pat. No. 10,271,976, which is a continuation of U.S. patent application Ser. No. 15/921,508, filed Mar. 14, 2018, now U.S. Pat. No. 10,076,431, which is a continuation of U.S. patent application Ser. No. 15/605,601, filed May 25, 2017, now U.S. Pat. No. 9,943,426, which is a continuation of PCT Application No. PCT/US2017/032748, filed May 15, 2017, which claims the benefit of provisional patent application nos. 62/480,121, filed Mar. 31, 2017; 62/430,843, filed Dec. 6, 2016; 62/424,994, filed Nov. 21, 2016; 62/414,593, filed on Oct. 28, 2016; 62/374,689, filed on Aug. 12, 2016; and 62/337,255, filed on May 16, 2016, the full disclosures of which are incorporated herein by reference.

BACKGROUND OF THE INVENTION

1. Field of the Invention

Balloon angioplasty was introduced to open vessels, particularly blood vessels which have narrowed as a result of plaque progression or a heart attack. In successful cases, the blood vessel remained open and/or exhibited positive remodeling over time and/or exhibited vasodilation ability mimicking to a degree the natural vessel ability. In other cases, however, the blood vessel would re-occlude within few days or within months due to various causes such as recoil of the vessel, thrombus formation, or other type of plaque morphology progression.

Metallic stents were developed to provide a structure, often referred to as a scaffold, with sufficient radial strength (crush resistance) to address recoil and hold the vessel open over time. Stents were formed from wire(s), coils, braids, a sheet, and/or tubular bodies. Balloon expandable stents formed from patterned non-degradable metallic tubes, wires, or sheet, are now most commonly used as they display desirable structural characteristics such as limited inward recoil, high strength (crush resistance or crush force), and limited axial shortening upon expansion, when compared to some earlier coiled or braided stents.

Despite their success and widespread adoption, metallic stents such as stainless steel alloys, Platinum iridium alloys, and cobalt chrome alloy stents, suffer from certain shortcomings, such as they jail the lumen or vessel, they do not further expand (after inward recoil) after implantation under physiologic conditions, preventing the lumen or vessel from further expanding which in turn inhibits positive remodeling, and/or such stent inhibits vasodilation or vasomotion of the treated vessel stent segment which is important to healing of the vessel or the normal functioning of the vessel. This phenomenon is commonly referred to as "jailing" or "caging" the vessel. High radial strength is important to support a body lumen upon implantation and/or to maintaining it open upon implantation of the stent and/or high strength is important in preventing the lumen from getting smaller after implantation. In some cases where shape memory self expandable alloys stents are used such stents typically do not exhibit high radial strength (high crush force resistance) like the metallic stents due to the material properties (and as a result the lumen in some cases become smaller after implantation of such stents due to excessive inward recoil due to lumen inward force on the stent and/or due to the lower radial strength of these stents, making such stent less likely to further expand after implantation in a lumen or diseased lumen segment, and/or such stents are less likely to exhibit vaso-dilatation or vaso-motion of the stented segment. In some cases shape memory stents penetrate the lumen wall moving towards the adventitia causing irritation, inflammation of the vessel or lumen, sometimes resulting in unwanted negative clinical events and/or re-occlusion of the body lumen or vessel. Also, the stent is typically maintained in the crimped configuration using a constraint upon delivery into the vessel or lumen which makes the profile of the stent system large and less deliverable. Stents of this type are usually pre-programmed to expand to a certain diameter/configuration which makes sizing limited to such pre-programmed diameter/configuration and less likely to expand or maintain an expanded diameter beyond such pre-programmed diameter, which makes stent sizing more difficult, and/or such stents do not expand further beyond such pre-program diameter/configuration after deployment, to name a few.

To address some of these shortcomings, biodegradable stents or scaffolds made from metallic or polymeric materials were developed. By allowing the stent to degrade or resorb, the jailing or caging effect would diminish or decrease over time and the scaffold would finally disappear over time. Present biodegradable stents, however, and in particular polymeric biodegradable stents and corrodible metallic stents, have their own shortcomings, including stent fractures, and/or limited ability to over-expand the stent above a nominal expanded diameter, and/or have excessive or high initial inward recoil, and/or have additional inward recoil after implantation and after the initial inward recoil. In some cases they may have insufficient strength to accommodate various lesion types after deployment, and/or limited ability to maintain a lumen or vessel open after deployment. Biodegradable stents typically have lower radial strength (crush resistance/strength) than balloon expandable metallic non-degradable stents, typically are bulky thick strut stents in order to address some of the mechanical shortcomings such as suboptimal crush strength, or having thick struts, which can cause negative clinical events, may cause excessive inflammation (due at least in part to the degradation of the material and the quantity of the degradation material), and/or cause excessive hyperplasia such as neo-intimal hyperplasia (due to at least in part to the degradation of the material and the quantity of the degradation material), to name a few problems.

Attempts have also been made to make scaffolds from a combination of polymeric and metallic materials. However, such designs have displayed their own shortcomings. Such combination designs can lack sufficient initial crush resistance to effectively open a lumen, or maintain it open, after implantation of the stent, or such designs do not uncage the stent, or do not uncage the stent along the entire stent segment, or do not uncage the vessel, or do not further expand the stent under physiologic conditions, or do not further expand the stent and/or allow it to contract using or after use of vaso-dilators and/or vaso-constrictors after implantation. Alternatively, some other such designs will not be able to further expand to a larger configuration (after inward recoil if any) after implantation. Still other designs have so many separate metallic or other non-degradable pieces that they risk releasing the small pieces into the blood stream potentially causing a clinical event. One or more needs as described above in the the following exemplary issues remain unmet by present non-degradable stents: having a stent with low inward recoil, and/or having a stent with low initial inward recoil after expansion while the diameter of the stent is substantially maintained after implantation and after the initial inward recoil, and/or having a non-degradable stent configured to be able to further expand (after inward recoil if any) after deployment under physiologic condition, and/or having a stent able to expand or further expand (after inward recoil if any) after deployment without a pre-programmed temperature trigger setting or without a pre-programmed expanded diameter/configuration setting, and/or having a stent able to expand or further expand (after inward recoil if any) without a programmed temperature, and/or having a stent able to further expand (after inward recoil if any) after deployment under physiologic condition without penetrating or without substantially penetrating the vessel or lumen wall into the adventitia, and/or having a stent that does not cause excessive inflammation, and/or having a stent that does not penetrate the lumen or vessel wall after implantation into the adventitia, and/or having a stents that expands further following any inward recoil, after deployment (implantation) further expanding the lumen or vessel diameter, and/or having a stent maintained or substantially maintained in the crimped configuration upon delivery into the vessel or lumen without a constraint and which further expands after any inward recoil to a larger configuration after deployment, and/or having a stent that can be deployed to a wide range of diameters and still uncages the vessel or lumen after deployment, and/or having a stent that can be deployed to a wide range of diameters and still further expand after any inward recoil to a larger configuration after implantation, and/or having a stent able to further expand after any inward recoil beyond the pre-programmed expanded diameter/configuration after implantation, and/or having a stent that exhibit vaso-motion, vaso-dilation, or vaso-constriction, after implantation, and/or having a stent that has sufficient strength after deployment to support a body lumen, has low inward recoil, and where the stent exhibits radial strain of 1% or larger than 1% after deployment, and/or having a non-degradable stent having an initial compliance upon expansion from a crimped configuration to an expanded configuration, wherein the initial compliance increases after implantation, and/or having a non-degradable stent having an initial radial strength (crush resistance) upon expansion from a crimped configuration to an expanded configuration, wherein the initial radial strength decreases after implantation, and/or having a balloon expandable non-degradable stent capable of expanding from a crimped configuration to an expanded configuration, where the expanded configuration comprises diameters ranging from 2.0 mm to 4.0 mm, and wherein the stent exhibits initial inward recoil after an initial expansion, and said stent after initial recoil has an initial diameter, said stent maintains said initial diameter (or configuration) after said initial inward recoil, and wherein the stent responds to a vaso-dilator after implantation sufficient to expand the stented segment to a second diameter wherein the second diameter (or configuration) is larger than the initial diameter.

A particular concern in vascular and other body lumens after implementation of the stent or other prosthesis is the loss of vessel or lumen remodeling or enlargement, or the loss of vessel or compliance or contractility, referred to above as "caging" or "jailing" of the blood vessel or body lumen. Vessel compliance is necessary for the vessel or body lumen under physiologic conditions such as responding to changes in the internal pressure, external pressure, muscle contraction, muscle relaxation, chemical change, and the like. Such changes can result from many sources, such as the presence of natural, or artificial substances, which can relax or contract the body lumen and/or muscles such as smooth muscle cells, for example within the walls of the body lumen. The implantation of a stent in a blood vessel or body lumen will necessarily contribute to a reduction in the overall or "composite" compliance of the body lumen and the stent. Each of the body lumen's natural compliance and the stent's additional compliance will contribute to a total or overall "composite" compliance which will necessarily be less than that of the body lumen had the stent not been implanted. Thus, it is desirable for a stent implanted in body lumen, particularly implanted in a blood vessel, to minimize the reduction of body lumen compliance which naturally occurs as a result of the implantation of the stent. While a reduction of the compliance may be acceptable for a period of time immediately following implantation, particularly during that period (such as upon implantation or the initial period after implantation) when high radial strength is desired to maintain patency of the vessel (or body lumen) and prevent further inward recoil after implantation. Such strength is less necessary or not necessary after the initial period when healing of the vessel has occurred and eventually the strength of the stent becomes unnecessary or less important. During such healing phase or after such healing phase, it is highly desirable that the compliance of the vessel returned to levels at, or approaching, or closer to the natural compliance of the lumen in the absence of the implanted stent. Thus, it is an object of the present invention to provide stents, stent scaffolds, and other luminal prostheses which, after implantation, display a compliance which increases over time, in response to the vascular or other luminal environment, so that the total or composite compliance of the stents scaffold and the body lumen increase to levels which are closer or approach that of the body lumen in the absence of the stent scaffold.

Loss of compliance is also a problem for valves, rings, and other appliances implanted in heart valve annuluses. While valve scaffolds may not always need a high radial strength, particularly after an initial period of implantation, it is beneficial that they be sufficiently compliant to be able to conform to the annulus as the annulus deforms during the normal systoloic-asystolic cycle, or it deforms to conform to the deformed annulus due to disease progression thus maintaining the integrity of the valve function, or it dilates to conform to the annulus dilation due to physiologic conditions or progression of disease, while maintaining the integrity of valve function.

What is needed are implants, stents, stent scaffolds, vascular prostheses, ecto-prosthesis, and/or other luminal prostheses that addresses at least some of these shortcomings as well as others described herein.

2. Listing of Background Art

Relevant background patents and applications include: U.S. Pat. Nos. 7,011,678; 5,922,020; US2003/0153971; U.S. Pat. No. 9,056,157; US2005/0222671; U.S. Pat. Nos. 9,265,866; 7,169,173; 8,435,281; US2003/0195609; U.S. Pat. Nos. 7,402,168; 7,829,273; 5,695,516; 6,540,777; 8,652,192; 8,128,679; 8,070,794; 6,599,314; 8,961,585; 7,455,687; 7,645,409; 8,202,313; EP2229919; U.S. Pat. Nos. 6,251,134; 6,409,754; 5,766,237; 5,957,975; 5,306,286; 5,961,545; 8,052,743; 9,180,005; 9,192,471; US2008/177373; and US2005/283229.

SUMMARY OF THE INVENTION

The present invention provides numerous examples and embodiments of stents, in particular vascular and luminal stents and prostheses which display strength, modified (or controlled) strength, and/or modified (or controlled) compliance characteristics after expansion and/or implantation. In one particular example, metal, metal alloy, and other non-degradable stents may be modified in numerous ways to control their radial strengths and compliances initially at the time of expansion in the body lumen as well as subsequently during the days, months, and years following the initial expansion and/or implantation. In particular, many of the stent and scaffold designs described and claimed in the present application will provide for a variable (or controlled) compliance which has at an initial compliance, which is relatively low, and increases over time after implantation, and a radial strength which has an initial strength, which is relatively high (e.g. having substantial hoop strength or crush resistance) at the time of implantation or initial expansion, and decreases (or may be reduced) over time after implantation. The increase in compliance and decrease in radial strength may occur over a time period of days, weeks, or months after implantation and may be caused by any one or more of a number of structural transformations in a scaffold which forms all or a portion of the prostheses.

Methods for measuring and quantitatively expressing the strength (radial strength) and the compliance and of vascular and other luminal stents and scaffolds are well known and described in the patent and medical literature.

Compliance, as the term is used in many of the examples or embodiments, is a non-dimensional measurement which expresses a percentage change in diameter (or configuration) of a luminal structure, or a segment of a luminal structure, in response to physiologic conditions such as a change in internal pressure within or adjacent to the luminal structure, usually such change in pressure is 100 mmHg. In some other instances, compliance measurement can be expressed as mm/atmosphere, mm/psi, %/atm, %/psi, or the like. The term compliance and radial compliance are used interchangeably.

Body lumens, stents, scaffolds, prostheses, and other tubular structures will each have their own compliance. Body lumens having implanted stents, scaffolds, prosthesis, and other tubular structures will also have a compliance which is a composite of the individual compliances of the lumen and the implant, where the composite is typically lower than the lumen and many cases lower than the implant alone. In many cases or examples, it is the "composite" compliance that will be measured to define the compliance characteristics of the stent, however, it can also be in some cases the stent alone measured compliance, scaffolds, prosthesis, and other tubular structures in many of the examples being claimed herein. In many instances or examples throughout this application, the term "radial strain" is used to mean compliance and is used interchangeably with the term "compliance" (or the composite compliance) as the term compliance or composite compliance is described in this or other paragraphs. Usually, when radial strain is measured at 100 mmHg change in pressure, it refers to the compliance of the implant (or composite compliance), but compliance can also refer to % change in diameter of the implant or composite at a given change in pressure different than 100 mmHg.

In particular, the radial compliance of a stent, scaffold, or other luminal prosthesis will be measured as a composite compliance in vitro in a mock vessel in accordance with well-known principles and techniques, such as those described in ASTM F2477-07R13 which measures compliance at a pressure change of 100 mmHg, but the test can also provide the method required for testing compliance at a given change in pressure other than 100 mmHg, such as at about 176 mm Hg, or other pressure. Also, stent compliance can be tested by having a stent implanted in a vessel, such as a coronary artery vessel, of a porcine animal and the compliance is measured in the stented segment of the vessel.

In a first aspect or example of the present invention, a prosthesis, in particular an endoluminal prosthesis comprises a scaffold having a plurality of circumferential rings formed or patterned from a non-degradable material, typically a metal or metal alloy, where the scaffold is configured to expand from a crimped configuration to an expanded configuration. At least some of the circumferential rings will have at least one separation region, where the separation region(s) are configured to form at least one discontinuity in the circumferential ring after the scaffold has been expanded in a physiologic environment. In a preferred example, after such expansion and exposure to the physiologic environment, typically a vascular or other body lumen environment, at least two of the circumferential rings remain axially joined after all discontinuities are formed, typically being axially adjacent rings. Frequently, all circumferential rings of such endoluminal prostheses will remain axially joined after the discontinuities are formed. For example, the circumferential rings may be joined by axial links, which are typically short structural elements joining a region on one circumferential ring to a region on an adjacent another circumferential ring. In other examples, however, regions on successive adjacent circumferential rings may be directly joined, for example being welded or otherwise joined crown-to-crown, strut-to-strut, or the like, as will be described in more detail hereinafter in this application. In specific examples, adjacent crowns on adjacent rings may be joined by welding, wrapping, binding with wires or other filaments, adhesives, or the like.

Such endoluminal prostheses according to the present invention, for example, will have circumferential rings with a circumferential structure having an initial radial compliance, typically a composite compliance as discussed above, prior to formation of any discontinuities. After formation of the discontinuities, however, at least some of the circumferential rings will have a radial compliance which is increased relative to the initial radial compliance of the at least some rings prior to formation of the discontinuities. For example, the initial radial compliance of at least some of the circumferential rings of a scaffold (or the composite compliance of the scaffold segment) in accordance with the principles of the present invention may be 0.1% to 1%, typically from 0.1% to 0.5%, while the radial compliance after formation of the discontinuities will typically be from 1.2% to 10%, often being from 1.2% to 5%, or 1.5%-3%.

The composite compliance of a scaffold may be measured using a mock vessel system as follows. The scaffold being tested, the mock vessel, the water used to pressurize the mock vessel, and all other test equipment are held at room temperature. All diameter measurements are made with a calibrated non-contact system capable of measuring a diameter to within ±0.01 mm without contacting the scaffold. Suitable measurement instruments include microscopic video measuring system, laser microscopes, and optical comparator. Pressure measurements of water used to pressurize the mock vessel are made with a gauge that can accurately measure fluid gauge pressure to within ±0.05 PSI. Pressure measurements are made at the time the diameter measurements are taken. The length of all connecting tubes used in the setup are under 10 inches and to eliminate any restrictions in the tubes and connectors are eliminated to assure that any dynamic changes in pressure throughout the mock vessel are accurately reflected by the pressure gauge. Diameter measurements should be performed with 30 minutes from initial pressurization of the mock vessel.

The mock vessel is an elastomeric silicone tube with a uniform cross sections and uniform material properties throughout its length. For stents smaller than 2.5 mm diameter, the mock vessel wall thickness is 0.25±0.03 mm. For stents of 2.5 mm diameter and larger, the mock vessel wall thickness is 0.5 mm±0.03 mm. The test pressure within the mock vessel will be 3.4±1 PSI (or approximately 176 mmHg), and the system will be sufficiently leak proof to maintain this pressure for the duration of the test. The stent-mock vessel system is fixtured to prevent changes in length and of the mock vessel resulting from longitudinal forces) that could affect the resting length of the mock vessel and the diameter of the mock vessel. The stent-mock vessel system is further fixtured to prevent changes in diameter from forces other than internal pressurization.

Balloon expandable, non-degradable scaffolds are deployed in air to an ID after inward recoil from the expanded configuration which equal to or 0.1 mm less than the outer diameter of the mock vessel without pressurization. The scaffold is expanded using a balloon or other delivery system suitable for use with the scaffold being tested. The inner diameter (ID) is verified using the non-contact measuring system. Self-expanding scaffolds are deployed in air to their free diameter, and the ID verified using the non-contact measuring system. A mock artery is selected to have an outer diameter equal to or 0.1 mm larger than the inner diameter of the deployed stent.

The expanded test scaffold is slid over the outside of the mock vessel, stretching the mock vessel tubing as necessary to temporarily reduce the tube diameter to allow the stent to be passed over it. After releasing tension on the mock vessel, actual contact between the ID of the scaffold and the outer diameter (OD) of the mock vessel along the entire contact length is verified.

The interior of the mock vessel tube is connected to an Indeflator (an inflation/deflation device used to inflate and deflate angioplasty balloon during angioplasty) capable of providing at least 3.4 psi and having a gauge capable of measuring the pressure in the tube to within 0.05 psi at such pressures.

The OD of the stent and the OD of a reference section of mock vessel away from the stented segment are both measured using the non-contact system at a distance from the stent equal to twice the diameter of the mock vessel, and a similar distance from any fixtures holding the mock vessel. Three OD measurements are made and averaged to obtain a baseline mock vessel OD value. Three OD measurements are made about the mid-length of the scaffold and averaged to obtain a baseline scaffold OD value. The interior of the mock vessel is pressurized with water to 3.4 PSI (176 mmHg), and the OD's of the scaffold and mock vessel measured at the same locations used to establish baseline using the non-contact system while the pressure reading is maintained at 3.4 PSI. The composite compliance is determined dividing the OD value measured when the mock vessel is pressurized by the baseline OD value, subtracting one, and multiplying by 100 to determine the composite compliance as a percentage.

For example, if the applied pressure in the mock vessel causes the OD of the test scaffold to increase in diameter from 3.50 mm OD to 3.73 mm OD, the composite compliance is $((3.73/3.50)-1) \times 100 = 6.6\%$. As a second example, if the applied pressure in the mock vessel causes the OD of the test scaffold to increase in diameter from 3.50 mm OD to 3.52 OD, the composite compliance is $((3.52/3.50-1)-1) \times 100 = 0.6\%$.

The composite compliance of the scaffold can be measured before and after opening of the separation regions to form discontinuities. To obtain the composite compliance before formation of discontinuities, the scaffold is measure as described above while all separation regions remain intact. To obtain the composite compliance after formation of discontinuities, the scaffold is treated to open all discontinuities while the scaffold remains on the mock vessel. The separation regions may be opened by techniques specific to the nature of the particular separation region. For separation regions immobilized by polymeric sleeves, glues, or solvents, the scaffold is exposed to solvents, enzymes, or other chemicals to form discontinuities, without damaging the mock vessel. Alternatively, and for non-polymeric separation regions, the separations regions may be physically separated using mechanical means, laser cutter, ultrasound, or other energy-based cutters form discontinuities. For locking designs or separation regions that open in response to fatigue, the mock artery can be cyclically pressurized at a 5-8 Hz rate until discontinuities form. See Example 5 and FIG. 35. If the scaffold falls apart while the separation regions are being opened, the composite compliance will be considered to be equal to mock vessel compliance without the scaffold.

Radial strength (crush resistance) is measured with parallel flat plates (reference ISO25539-2) which are fixated onto an Instron tensile test machine with a 5N load cell to allow force and displacement measurement. The bottom plate is flat and remains stationary during testing. The upper plate is mounted onto the load cell to record force measurement as a function of displacement. The plates are visually verified to be parallel to each other at the mating surfaces. Both the bottom and upper plates are rectangular in shape with the surfaces completely covering the test stent in length and diameter. Both plates are configured to stay submerged in a bath of body temperature water, maintained by a circulation heater at body temperature of 37±2° C. The circulation pump is turned off during the force measurement to prevent currents from altering the results. The top plate is formed from delrin and the bottom plate is formed from brass.

A test scaffold is deployed at its nominal inner diameter using a standard indeflator or other delivery system. The deployed test stent is removed from the delivery system and the diameter of the test stent is verified by a non-contact measuring system. The test stent is then slid onto a 0.035" diameter mandrel approximately 50 mm in length before placing between the parallel plates submerged in water at 37° C. mimicking physiological conditions. The mandrel will prevent the test stent from rolling at the initial contact with the parallel plates. The upper plate is then slowly jogged down using the displacement controller from the Instron tensile test machine until it is approximately 1 mm above the stent, and the force gauge is zeroed. It is then lowered until it barely touches the test stent, and a force of 0.01 N is detected. The stent is then allowed to stabilize in the bath for 60 seconds. The test cycle is started and the crush resistance force is then measured by decreasing distance between the parallel plates up to 50% of the test stent diameter. A force-distance curve is generated during the test. The rate of decreasing distance (crosshead speed) is 1.5 mm/min. The load force at 10% of stent deformation (compression) is determined in Newtons. For example, for a 3.0 mm labeled stent expanded to nominal diameter (3.0 mm), report the force required to compress it by 0.3 mm (10% compression). The load force in Newtons (N) is then divided by the expanded stent length in mm to normalize the strength in N to the stent length and thus the radial strength of the stent is expressed as N/mm of stent length.

The expanded stent baseline radial strength is measured (in N/mm of stent length), and again after formation of discontinuities (if any), as described in the crush resistance method. For a stent of the present invention, the radial strength decreases after formation of discontinuities compared to baseline radial strength before formation of discontinuities, preferably decreases compared to the baseline radial strength, by a range from 10% to 100% of the baseline radial strength.

The above protocols for measuring composite compliance and radial strength are particularly effective for measuring those values in scaffolds having a nominal diameter from 2 mm to 4 mm and having dedicated or conventional deployment systems. For stents, valves, prostheses, and any other scaffold having other size and deployment systems, including non-standard sizes and non-standard deployment systems, the scaffold should be deployed according to the manufacturer's published instructions for use, and the test apparatus adjusted or modified to have the same fit with the deployed scaffold, as described above. In the case of a mock vessel for the measurement of composite compliance, the outer diameter of the mock vessel should be equal to or up to 0.1 mm larger than the inner diameter of the deployed scaffold. In the case of flat plate separation distance for measurement of crush resistance, the scaffold OD should be measured with an accuracy of ±0.01 mm via non-contact methods, and 10% deflection calculated from this measurement. All other parts of the test methods should be followed as much as possible.

In preferred examples, the scaffolds of such endoluminal prostheses may separate into segments after the discontinuities have formed in the circumferential rings. The separation may be along axial, circumferential, helical, irregular, or other lines. For example, two, three or more segments may separate along axial, helical, or irregular lines, allowing the segments to radially expand and contract which increases the composite compliance of the scaffolds when implanted in a body lumen. Often, all or substantially all of the segments will remain axially joined along their entire lengths (or along the entire stent length) so that, while the discontinuities provide for an enhanced (or increased) radial compliance, the structural elements of the scaffolds remain axially joined to continue provide support (or scaffolding) to the lumen (or vessel) wall, and/or so that the elements are at a reduced risk of being dislodged or otherwise released after implantation in the vasculature or body lumen. Other examples of segments include closed cell segments, and the like. In such a preferred example, the scaffold (endoluminal prosthesis) forms a tubular body in the crimped configuration and/or the expanded configuration, and wherein the scaffold maybe formed from a wire, a substantially continuous tube, a sheet, molding, or by printing.

In other embodiments or/and examples, the scaffold will not separate into segments. That is, while at least one and usually a plurality of discontinuities will form in the scaffold, all circumferential rings, struts, crowns, links, and other structural elements (or components) of the scaffold will remain physically connected so that no portion (or element) of the scaffold is fully disconnected from the remainder of any other portion of the stent. Such physical linkage of all portions of a scaffold even after discontinuities are formed can be an advantage as the risk of any portion of the scaffold being released into the vasculature or other body lumen is reduced.

In one particular example, discontinuities in adjacent circumferential rings may separate along axial lines so that the stent divides into two or more axially aligned segments, each of which extend from a first (usually terminal) end of the scaffold to a second (usually terminal) end of the scaffold. Such axially aligned segments of the individual circumferential rings separate circumferentially along axial (usually straight), helical, or irregular separation lines but remain axially joined or intact (by on or more axial links for example) after all discontinuities are formed. Such intact axial, helical or irregular segments will be elongated, typically having a length corresponding to the full length of the scaffold in its expanded configuration.

While such elongated axial, helical or irregular segments will usually be fully separated along their entire lengths, in other cases one or two circumferential connections may remain after all discontinuities have be formed in the scaffold. In particular, the elongated segments may remain joined at either or both terminal end of the scaffold in order to reduce "dog-boning" or for other purposes.

In some examples, the circumferential rings of the scaffolds of the present invention may have continuous perimeters or peripheries, usually circular perimeters, in which case the adjacent continuous rings are typically joined by axial links or by direct connection, e.g. by welding, fusing, tying, gluing, or otherwise adhering crowns on adjacent circumferential rings together for example. In other instances, at least some of the circumferential rings may have discontinuous perimeters where the end regions are joined to form a helical scaffold. In specific examples and embodiments, the axial links will be composed of a non-degradable metal, metal alloy, or other non-gradable material. Most commonly, such axial links will be patterned from the same tubular component (or material) used to form the scaffolds. Thus, many scaffolds will be formed as integral or monolithic structures from the same metal, metal alloy, or other material forming the stent.

Exemplary endoluminal prostheses of the present invention will often comprise scaffolds having repeating structural elements, such as circumferential rings, closed cells, or the like. Some or all of the circumferential rings, for example, may comprise similar or identical structures, e.g. a plurality of struts joined by crowns in similar or identical patterns (but can also have varying one or more of structure, pattern, and structural elements (thickness, width, shape), etc). The separation regions may be located in the struts, the crowns, or both. Often, at least one separation region will be located in a strut, and at least one to five struts within a ring will have separation regions. Alternatively or additionally, at least one separation region may be located in a crown and from one to five crowns within a ring may have separation regions. Often, however, most or all crowns will be free from separation regions as crowns or crown regions are subjected to high stresses as a scaffold is radially expanded by balloon inflation or otherwise from a crimped configuration to an expanded configuration. Such high stresses can result in premature formation of discontinuities in the scaffold, and loss of structural integrity of the scaffold. The struts are thus a preferred location for the formation of separation regions. Separation regions may also be formed in axial links or other regions of direct axial connection between adjacent circumferential rings. Separation regions in axial connectors between adjacent rings typically will not contribute to the radial compliance of the rings or the stented segment, or typically will not affect the radial strength of the rings or the scaffold, after the formation of discontinuities and are thus optional, and in many cases the axial links and other axial connector regions will be free from discontinuities, and remain intact. Thus, in many examples of the present invention, the scaffold will comprise or consist of a plurality of axially linked circumferential rings wherein the rings comprising or consisting of struts connected by crowns where the separation regions are formed in only the struts and not in the crowns (or crown region) or the axial links or other axial connector regions. Placing the separation regions in the circumferential rings, for example in struts and/or crowns, have the advantage of providing the ability to alter the circumferential properties of the stent at various time points after implantation. The circumferential arrangement of the rings makes the ring structures critical for various stent properties such as radial strength (flat plate), composite compliance of the stented segment, further expansion to a larger diameter after implantation, responding to vaso-dilatation, to name a few. For example, placing the separation regions in the circumferential ring structure provides the stent with altered, improved properties after the discontinuities form following implantation. The needs for luminal stent are inherently time dependent and different at different points in time. Over short period of time after implantation, the stent is required to have high radial strength to support the vessel open, then over the next period, after the tissue remodels and healing starts to occur or is completed, the requirement for high stent strength to maintain the vessel open is no longer necessary, on the contrary, having high strength may impair the physiological function of the vessel. While current non-degradable (non-corrodible) stents such as stainless steel alloy stents, cobalt chrome alloy stents, and Platinum iridium alloy stents, address the immediate initial high radial strength need of a vessel, they typically do not respond to the changing vessel requirements over time after implantation, wherein the vessel no longer requires high radial strength to maintain the vessel open, and by having such high radial strength maintained over time may irritate the vessel and cause further progression of disease or poor healing. A stent, preferably formed from non-degradable material (the stent can also be formed from degradable material), having separation regions within the stent rings which form discontinuities in the circumferential rings after implantation provide the stent with altered, improved properties after the discontinuities form following implantation. Such stents of the present invention are configured to provide high initial radial strength after expansion, where such high initial radial strength then decreases over time after implantation, helping to address the physiological needs of the vessel while maintaining the vessel open. Similarly, current non-degradable stents have low composite compliance of the stented segment "caging the vessel" typically for the life of the stent inhibiting the vessel natural vaso-motion ability, inhibiting the vessel's ability to respond to a vaso-dilator, or inhibiting the stented segment from expanding further to a larger diameter after implantation. The stent of the present invention having discontinuities formed within the circumferential rings following implantation may be configured to have higher (or increased) composite compliance after expansion allowing the stented segment of the vessel to respond to the natural variations in blood pressure (vasomotion), allowing the stent (or the stented segment) to further expand after the initial expansion (and after inward recoil if any), and maintaining the vessel's ability to respond to a vaso-dilator. The stent of the present invention may be configured to have increased composite compliance in the stented segment shortly after expansion or after a longer period of time after implantation.

There are advantages of placing the separation regions in the struts include they usually are lower stress regions of the ring and thus subject to less plastic deformation than the crowns. The location and size of the struts may also offer additional options for more types of separation regions because they are typically larger and have less torque than some other area of a stent, such as the crowns or other curved region of the ring. The struts typically can accommodate more changes within it (such as having separation regions) without impairing the function integrity of the stent, such as being able to expand the stent from a crimped configuration to an expanded configuration. The orientation of the strut changes (opening) as the stent is expanded, allowing for separation regions designs configured to take advantage of the strut angle prior to deployment that is configured to keep the separation region held together upon expansion of the stent, and opening the struts to an angle in the expanded stent configuration that allows for the desired movement direction of the separated strut element such as radial, circumferential, and/or axial movement.

There may be advantages to the placement of the separation regions in the crowns. As a ring expands or contracts, the crowns are typically subject to high bending moments (torques), causing high stress and plastic deformation. Joining elements that are resistant to high moments (torques) can be advantageously used in the crown regions. The motion of deployment in the crown region causes a rotation between adjacent struts. Joining elements that function to free this rotation, for example through a ball and socket like joint or other joints as depicted throughout the application, could lower the ring stiffness while maintaining cohesion between separable regions of the ring so that they maintain a "tubular" overall shape, matching the lumen even after separation. Having separation regions within the crown (in the crown) can have a achieve higher composite compliance as maybe desired in some application. In addition, having separation regions in crowns may allow for use of other material that were not suitable for stent applications due to their limited mechanical properties such as elongation or brittleness, where a separation region in the crown may allow for expansion of the ring without breakage.

In said exemplary endoluminal prostheses, the struts may be joined by crowns to define an angle between them, typically referred as an "included angle." The included angle while the scaffold is in the crimped configuration will typically be small or sometimes even negative. The included angle will increase as the scaffold expands from the crimped configuration to an expanded stent configuration. Typically, the included angle in the crimped configuration of at least some struts joined by crowns ranges from −25° to +25°, more usually ranges from −15° to +55°. The included angle in the expanded configuration typically ranges from 35° to 180°, more usually ranging from 45° to 150°. When present in struts, the separation region(s) can be located anywhere along a length of a strut, typically being located in or about a middle of the struts, typically bisecting the struts. Similarly, when present in crowns, the separation region(s) can be formed at a point on the crown, typically being located about a middle of the crown, e.g. a location which bisects the crown which is typically a semicircle. In a preferred example, the separation region in the at least one strut is a pre-formed break (or gap) bisecting the at least one strut into two separate elements. Examples of the separation regions in the at least one strut include butt joint design, key and lock design, comb design, and/or other, wherein the bisected strut element adjacent to the separation region may have various geometry, shape, dimensions, pattern, configured to have a uniform stent expansion, and/or maintain the structural integrity of the stent upon expansion. The at least one bisected strut (separation region) is usually held together by one or more material as described throughout this application.

In preferred examples, at least some of the separation regions are located on or in "low stress regions" of at least some circumferential rings, i.e. those regions which experience less stress as the scaffold is expanded, either by a balloon or by self-expansion, such as strut regions. As the scaffold expands from a crimped configuration to an expanded configuration, the low stress regions, such as the struts, will experience less stress than high stress regions, such as the crowns, which deform as the result of concentrated stress as the scaffold radially expands. In a particular example, at least some circumferential rings each having one or more separation regions have an initial strength upon expansion of the stent in a physiologic environment, where the initial strength of at least some circumferential rings decreases after formation of discontinuities. In a preferred example, the one or more separation regions are preferably located in struts, where the struts undergo reduced (or minimal) stress as the scaffold is expanded from a crimped configuration to an expanded configuration, thus enhancing the structural integrity of the scaffolds during expansion by inhibiting all, or substantially all, formation of discontinuities during expansion.

The separation regions in the scaffolds of the endoluminal prostheses may take a variety of forms. For example, the separation regions may comprise a pre-formed break or gap in the crown region and/or in the strut region), thereby bisecting the crown and/or strut structural element into two separate sections of said crown and/or said strut) which is joined by, covered by, or embedded in a material which will degrade in the physiologic environment, typically a degradable polymer but sometimes a degradable metal or metal alloy, with many specific examples described in detail below. The degradable material comprising on or more material, in turn, can be provided in a variety of forms and geometries, including sleeves, coatings, solders, adhesives, laminations, and the like, which can be applied to at least one surface of the separation region, applied to at least one surface of the stent, applied to all separation regions surfaces, and/or applied to all stent surfaces. In some examples, at least one surface, most, or all of a separation region surface or a scaffold surface can be coated or laminated with a degradable material. In a preferred example, the material fills all the space between opposed surfaces of a separation region, and the stent abluminal, and luminal surfaces, and acts as an adhesive, glue, or attachment element, holding the surfaces together to maintain the stent structural integrity upon expansion of the stent. In other instances, the degradable material can be located on or in only the separation region and optionally a short distance on either side thereof, e.g. 2 mm, 1 mm, 0.5 mm, or the like. In yet another example, a non-degradable material comprising one or more non-degradable material can additionally be applied to at least one separation region surface and/or additionally applied to at least one stent surface, and/or additionally applied to all separation region surfaces and/or additionally applied to all stent surfaces. The non-degradable material can be applied before the degradable material, or applied after the degradable material. In a preferred example, the degradable and/or the non-degradable material placed on the non-degradable stent are polymeric material. In another example, the polymeric material (degradable and/or non-degradable) contains at least one drug which may be coated on at least one surface of the stent, preferably to cover at least the abluminal surface of the stent.

In a particular example, the degradable material can be applied by spray coating, dip coating, sleeve encapsulating, printing, soldering, gluing with an adhesive, or the like. The degradable material can be polymeric, metallic, or any other degradable material, as described in greater detail elsewhere herein. Typically, the degradable material has sufficient strength to hold the separation region together to immobilize adjacent structural elements in a separation region while the scaffold of the stent or other prosthesis is expanding from a crimped configuration to an expanded configuration in a physiologic environment. The degradable material usually degrades after expansion of the stent from a crimped configuration to the expanded configuration. The degradable material may have a thickness that is substantially the same as that of adjacent regions of the non-degradable structural elements, i.e. the degradable material will fill the gap or other space between the adjacent structural elements but will not extend over these adjacent regions. In other examples, however, the degradable material may have a thickness adjacent to said separation region, ranging from 5 µm to 30 µm thicker than the non-degradable structural elements thickness adjacent to said separation region, and may extend over said adjacent regions, may extend over, or cover, at least one surface of the stent, or may covers all stent surfaces. The degradable material thickness can be substantially the same for all separation regions or can have different thicknesses, for example, to control timing of the formation of discontinuities.

In preferred examples, the degradable material covers the non-degradable structural elements of the stent substantially uniformly, i.e. having substantially the same thickness over substantially all abluminal surfaces of the structural elements and having the same thickness for substantially all luminal surfaces of the structural elements, but the degradable material can also have different thicknesses for different surfaces of the scaffold structural elements. Typically, a coating or other cover over abluminal and/or luminal surface regions of the scaffold structural elements ranges from 3 µm to 50 µm, more usually ranges from 5 µm to 30 µm. The degradable material may cover and/or fill the separation region(s) only, may cover and/or fill the separation region and surface(s) of adjacent structural element(s), may cover and/or fill the separation region as well as the surfaces of adjacent structural element(s) and adjacent ring(s), or may cover the entire stent and fill all separation regions.

Some or all separation regions can be configured to form discontinuities at about the same time, or at different time periods, as described elsewhere herein. In preferred examples, the degradable material degrades after a period ranging from 1 month to two years after implantation, preferably ranging from 2 months to one year after implantation, more preferably ranging from 3 months to 9 months after implantation.

In another preferred example, a non-degradable scaffold having separation regions held together by at least one degradable material will have an initial stent mean volume (or mean area) after expansion and after initial inward recoil after expansion if any, and wherein said mean area (or mean volume) is from 0.75% to 0.90% of the initial stent mean volume (or mean area), substantially the same (maintained) initial mean stent volume (or mean stent area), or increased mean stent area (or mean stent volume), after degradation of said degradable material after implantation of the stent, and/or within a period ranging from 1 month to 9 months after implantation, in a physiologic environment.

In another example, a non-degradable scaffold (or a stent), or other prosthesis comprises a plurality of circumferential rings having one or more separation regions along the path of each of said circumferential rings. The scaffold has an initial strength, sufficient to maintain a mean stent area (or mean stent volume) after expansion and after initial inward recoil (if any), and the scaffold after formation of discontinuities exhibits a decrease in said initial strength while substantially maintaining or increasing the stent mean area (or mean volume), in a physiologic environment. Such non-degradable scaffolds typically will have degradable material which can be stretchable (elastic), usually sufficiently stretchable (elastic) to hold structural elements adjacent to separation regions together upon expansion of the scaffold, and/or sufficiently stretchable (elastic) to allow the scaffold, or a scaffold segment, to accommodate, or respond to, vaso-motion or vaso-dilatation after deployment, or after deployment and before degradation of the degradable material, or after degradation of the degradable material. The stent or other prosthesis in such examples may accommodate (or exhibit) an increase in diameter (or a change in diameter) in one or more scaffold segments (or in the stented segment) when a vaso-dilator is used, or when a change in pressure of about 180 mmHg is applied. Such change in diameter ranges from 0.05 mm to 0.5 mm, more typically 0.7 mm to 0.4 mm, after expansion under physiologic conditions. In another example, the elastic material adjacent (including in, on, around) at least one or more separation regions is non-degradable material, such as a polymeric material, such as polyurethane material. In a preferred example, the non-degradable material(s) have sufficient strength to contain the separation region together upon initial deployment of the stent from a crimped configuration to an expanded configuration, said elastic non-degradable material allowing the one or more rings or stented segment to further expand and/or contract, after initial expansion of the stent, and/or after formation of discontinuities, under physiologic conditions.

In yet another example, the separation regions may comprise an elastic material disposed in, on, and/or adjacent to a gap, space, or other break formed in a structural element of the ring, usually a strut, and/or a crown. The elastic material typically remains intact after expansion of the scaffold in the physiologic environment, and the elastic material may act as an "expansion joint" allowing expansion and in some cases contraction of the ring in order to increase radial compliance under physiologic conditions. In some examples, such expansion joints will be immobilized by a bio absorbable material in the form of a coating, a sleeve, an adhesive, or any other form as described elsewhere herein connecting or bonding or holding together adjacent separated regions of the scaffold while the scaffold is being deployed. In other examples, the one or more expansion joints will not be immobilized and the elastic material will provide sufficient strength to remain intact during balloon or other expansion while still providing a desired radial compliance or strength after expansion. The elastic material in separation regions may be utilized alone, or in combination with other separation regions immobilized during balloon or other expansion by means such as degradable material.

In still other exemplary embodiments, the separation regions may comprise "key-and-lock" junctions which are immobilized during expansion but configured to separate after the initial expansion in the physiologic environment. In some instances, the key-and-lock junctions may have combed interface surfaces that allow separation in circumferential and/or radial directions but which inhibit separation in an axial direction. In other instances, the key-and-lock junction will have a smooth or straight interface surfaces that allows separation in circumferential, radial and/or axial directions. In other cases, the key-and-lock junction will have non straight interface surface regions such as "saw", "v", "u", inverted "v", inverted "u", or other surface region interface, where such non straight surface region interface can have or more surface region interfaces and where the one or more surface region interfaces can have the same or different shapes, sizes, thickness, lengths, widths. Such key-and-lock junctions are typically immobilized during expansion but configured to separate after the initial expansion in the physiologic environment, for example being covered by, embedded in, or joined by a degradable material such as a biodegradable polymer.

In still other examples, the separation regions of the present invention may comprise a butt joint joined by, covered by, or embedded in the material which degrades in the physiologic environment.

The scaffolds of the endoluminal prostheses of the present invention will comprise a non-degradable material, typically a metal or a metal alloy material. The discontinuities forming in the metal scaffolds allow the scaffolds to further expand after recoil from an initial expansion. The discontinuities will typically further allow the scaffold to further expand to an expansion diameter larger than an initial expansion diameter.

In some embodiments and examples, the circumferential rings may be substantially perpendicular to a longitudinal axis of the scaffold in the expanded and/or crimped configurations. In other embodiments and examples, the circumferential rings may be inclined at an angle relative to the longitudinal axis of the scaffold in one or both the expanded and crimped configurations. In still further examples and embodiments, successive circumferential rings will be joined end-to-end in a continuous helical pattern where each ring defines a single turn of the helix.

In another aspect or example, the present invention provides a variably compliant stent (or a controllable compliance stent, or an increasing compliance stent), scaffold, or other luminal or valve prosthesis comprising a non-degradable metal or metal alloy scaffold, such as cobalt chrome alloys, platinum iridium alloys, and stainless steel alloys, expandable from a crimped configuration to an expanded larger configuration. The scaffold has sufficient strength to support a vascular lumen after expansion, preferably for at least a time period after expansion (or implantation) sufficient for the vessel to heal, and/or for at least a time period after expansion when the risk of further, or additional, vascular lumen inward recoil (after any initial inward recoil of the stent following initial expansion) risk diminishes or is reduced, and/or for at least a time period ranging from 30 days to 6 months after implantation, and/or for at least a time period ranging from 60 days to 6 months after implantation. The stent in some examples has an initial strength after expansion (or immediately after expansion or within 24 hours after implantation (expansion) or within 6 months after implantation (expansion), or within 3 months after implantation or within two months after implantation), said initial strength being sufficient to support a body lumen and where the stent is expanded in air or under physiologic conditions (such as water at 37° C.), then under physiological conditions, the initial strength decreases to a second strength, lower than the initial strength, preferably decreasing within a period ranging from 3 days to 6 months, preferably said initial strength decreases to a second lower strength in a period ranging from 30 days to 6 months. The decrease in strength to said second strength occurs without mass loss, or without degradation of the non-degradable metal or non-degradable metal alloy. The second lower strength in some examples ranges from 10% to 100% of the initial strength, or ranges from 10% to 90% of the initial strength, or ranges from 20% to 80% of the initial strength, or ranges from 30% to 60% of the initial strength. The stent in some other examples has an initial strength after expansion (or immediately after expansion or within 1 hour after implantation (expansion) or within 2 hours after implantation, said initial strength being sufficient to support a body lumen and where the stent is expanded in air or under physiologic conditions, then the initial strength under physiological conditions increases to a first strength, larger than the initial strength typically by 5% to 50%, preferably larger than the initial strength by 10% to 30%, said first strength occurring after initial strength (or after initial strength measurement after implantation (expansion), or after one hour after implantation, or after two hours after implantation, or between one hour after implantation and one month after implantation), wherein said initial strength increases under physiological conditions to a first larger strength then said first strength decreases to a second strength, lower than the initial strength under the same or similar physiological conditions, said first strength preferably decreasing to below initial strength (second strength) within a period ranging from 15 days to 9 months, preferably said first strength decreases to the second lower strength (lower than initial strength) in a period ranging from 30 days to 6 months (or within a period ranging from 60 days to 6 months). The decrease in strength to said second strength being (or occurs) without degradation of the non-degradable metal or metal alloy (without mass loss). The second lower strength in some examples ranges from 10% to 100% of the initial strength, or ranges from 20% to 85% of the initial strength, or ranges from 30% to 65% of the initial strength. Immediately after deployment (or expansion), the scaffold has a composite compliance when measured in the mock vessel (or a thin tube) of no greater than 1%, typically no greater than 0.7%, and often no greater than about 0.5%, typically being in a range from 0.1% to 1%, usually from 0.2% to 0.5%. After expansion under physiologic conditions (including simulated physiologic conditions) or after exposure to vascular conditions, the composite compliance or the stent compliance when measured in a mock vessel will increase to at least 1.2%, often to at least 1.5%, and sometimes to at least 2% or greater. In other examples of the variably compliant stent prosthesis, the composite compliance of the stent when measured in a mock vessel may increase by a factor of at least two, often at least three, and sometimes at least four, five, ten, or more, when compared to an initial composite compliance when measured in the mock vessel.

Such variably compliant stent prostheses may have a variety of specific design features which provide the variable compliance. As described in greater detail below, for example, the stent prostheses comprising non-degradable metal or metal allow scaffolds having separation regions which separate or form discontinuities, after exposure to vascular conditions for a threshold time. For example, some of the separation regions may be initially prevented from separating by a bioabsorbable material which degrades over time when exposed to vascular conditions. More specifically, the bioabsorbable material may be in the form of a coating, a sleeve, an adhesive, or any other form suitable for initially connecting or bonding or holding together adjacent separated regions of the scaffold (or of the scaffold separated struts, or of the scaffold separated crowns, or of the scaffold separated structural elements) together. The bioabsorbable material may degrade over a time period ranging from 30 days to 3 years, often from 3 months to 2 years, and more often from 3 months to 1 year when exposed to the vascular conditions. For purposes of determining whether the stent meets these conditions, the stent may be exposed in vitro to vascular conditions (physiological conditions), as defined elsewhere herein' which are intended to mimic those conditions experienced when implanted in a human blood vessel or lumen. It can also be tested after in vivo vascular conditions. It can also be tested using in vitro test under physiologic conditions as described in the application. In some other examples, one or more rings containing one or more separation regions contain non-degradable material, preferably elastic material, preferably non-degradable polymeric material. The non-degradable material can have sufficient strength to hold such separation region together upon expansion of the stent, or together with another material (such as a degradable material, or other non-degradable material). The elastic non-degradable material can provide for a desired radial compliance immediately after expansion, or within 24 hours after expansion) such as responding to use of nitroglycerin or another vaso-dilator by expanding one or more stent segments (or rings, or the stented segment) containing the elastic material. The elastic non-degradable material in this example controls desired compliance, control further expansion after initial inward recoil, controls desired radial strength, and/or other mechanical properties of the stent, immediately after the initial expansion, and/or within 30 minutes after the initial expansion (or implantation), and/or within 24 hours after initial expansion (implantation). The stent can additionally comprise one or more rings (the same or different rings containing the separation regions containing the non-degradable elastic material) containing one or more separation regions, wherein the one or more additional separation regions contain degradable material (such as degradable polymeric material). The one or more separation regions containing the non-degradable material typically inhibits forming discontinuities after expansion in physiologic environment but allow for the ring containing said separation region (or the stent segment) to have a desired compliance, or allows for further expansion after initial recoil after initial expansion, or allows for responding of the stented segment (or the one or more rings) to a vaso-dilator, due to the stretching or elasticity of the non-degradable material. In yet another example, all or substantially all separation regions on one or more rings (or all separation region contained on the stent) contain non-degradable material, wherein the non-degradable material inhibits formation of discontinuities, but allows the stent (or the one or more rings) to have a desired compliance and/or radial strength, and or responding to a vaso-dilator, due to the stretching of the material, elasticity, and/or other material property.

In other specific examples and embodiments, the non-degradable metal or metal alloy scaffold may comprise regions reinforced with a reinforcement material which degrades after exposure to vascular conditions for the threshold time period described above or elsewhere. The reinforcement material may comprise a bioabsorbable material which degrades over said time period. For example, the reinforcement material may fill voids in a crown and/or a strut of the non-degradable metal or metal allow scaffold. Still further alternatively, the reinforcement material may cover or coat at least a region of a surface of the non-degradable metal or metal alloy scaffold.

In addition to displaying the variable compliance, as described above and/or elsewhere, the variably compliant stents of the present invention will display sufficient radial strength after expansion and implantation to hold the vascular lumen open and to inhibit or prevent vascular recoil after initial recoil after initial expansion, for some minimum threshold of time, usually at least 30 days, more usually at least 60 days, and often at least 90 days or longer. Typically, for example for a coronary artery stent, the stent strength, measured using the flat plate compression of 10% test for example, (or the initial stent strength of the expanded stent) will be in the range from 0.030 Newton per millimeter of stent length to 0.14 Newton per millimeter of stent length, particularly being from 0.04 Newton per millimeter of stent length to 0.1 Newton per millimeter of stent length, and often being from 0.05 Newton per mm of stent length to 0.1 Newton per millimeter of stent length, preferably when such stent strength is measured, using the flat plate 10% compression, after the stent is expanded to nominal stent expanded diameter. Usually, although not necessarily, the radial strength of the stent (scaffold) will decrease (in some other example, the initial radial strength of the expanded stent increases to a first strength larger than initial strength before decreasing to a second strength smaller than the initial expanded stent strength) after expansion and exposure to vascular conditions as the composite compliance increases from an initial composite compliance (in some other example, the initial composite compliance decreases before increasing). The decrease in radial strength occurs concurrently (or correspondingly, or at a similar time, or at the same time, or approximately about the same time) with the increase in radial compliance. In most cases, the radial compliance and the radial strength of the expanded stent will vary inversely to each other. Often, the radial strength of the stent scaffolds will decrease in a range from 20% to 100% of the initial radial strength which typically is measured immediately after expansion or shortly after expansion (such as within an hour, after expansion) and exposure to vascular conditions, sometimes decreasing in the range from 20% to 80%, or in some cases, the initial radial strength of the expanded stent increases before decreasing to substantially the initial strength or to a lower strength than the initial strength while the compliance increases from an initial compliance after implantation in physiological conditions, or in some other cases the initial radial strength of the expanded stent is substantially maintained while the compliance increases after expansion in physiological conditions from an initial compliance.

In a particular example or embodiment of the variably compliant stent, the non-degradable metal or metal alloy scaffold has a nominal expanded diameter (the diameter to which the stent or other scaffold is intended to be expanded by a balloon), and the strength and composite compliance are both measured after the stent has been expanded to a diameter which is from 80% to 120% of the nominal expanded diameter. More commonly, the strength and composite compliance will be measured when the stent has been expanded to 100% of the nominal extended diameter.

In other examples, the stent has sufficient strength after deployment to an expanded configuration to support a body lumen, has inward recoil from 1% and 10% after deployment, and where the stent exhibits compliance of 1% or larger than 1% after deployment, and/or having a stent that has sufficient strength after deployment to support a body lumen, and has an inward recoil from 1% to 10% after deployment to the expanded configuration, and then where the stent exhibits outward recoil ranging from 3% to 20% after deployment and after said inward recoil, under physiologic conditions, or under the use of vaso-dilators.

In some other examples, the composite compliance magnitude under physiologic conditions (including vaso-dilator use) ranges from 0.05 mm to 0.5 mm, preferably ranges from 0.07 mm to 0.4 mm, more preferably ranges from 0.1 mm to 0.4 mm. The magnitude of such diameter changes are measured in one or more of the stented segment, or the mean of the stented segment), or preferably in a region about the middle of the stented segment.

In other examples, the stent outward recoil magnitude under physiologic conditions ranges from 0.05 mm to 0.5 mm, preferably ranges from 0.07 mm to 0.4 mm, more preferably ranges from 0.1 mm to 0.4 mm.

In another aspect or example, the present invention provides polymeric prostheses with reinforcement elements and methods for their use and fabrication. An endoluminal prosthesis comprises a circumferential scaffold patterned from a biodegradable polymer and having expansion regions which deform as the circumferential scaffold expands from a small diameter configuration to a larger diameter configuration. In one example, the endoluminal prostheses of the present invention may comprise coronary stent prosthesis. In another example, the endoluminal prostheses of the present invention may comprise a vascular stent prosthesis. In yet another example the stent prosthesis is a non-vascular stent prosthesis. Reinforcement elements are coupled to at least some regions of the circumferential scaffold to stiffen the circumferential scaffold after the scaffold has been expanded to the larger diameter configuration. The reinforcement elements will preferably be deformable and can be degradable (which also includes corrodible and erodible) or non-degradable (which also included non-corrodible and non-erodible). In particular, the reinforcement elements may be malleable or elastic, may comprise metals and metal alloys, may comprise polymers, or may be formed in whole or in part from other materials having mechanical properties that can reinforce the expansion regions and/or other structures of the stent prosthesis as described below or in this application.

The circumferential scaffolds in one example will typically comprise stent scaffolds of the type patterned from a tube or cylinder formed in whole or in part from a biodegradable polymer. The tube or cylinder can be formed by extrusion, dipping, spraying, molding, or printing. The tube or cylinder of the biodegradable polymer will be patterned using any one of many techniques well known in the art of forming stents from polymers, such as laser cutting, photo-lithography, three-dimensional printing, stereolithography (SLA), and the like. The expansion regions will typically comprise joints, hinges, crowns, curves, bends, and/or deformable feature or structures or structural elements which may be joined to adjacent struts, beams, or other less-deformable or non-deformable features or structures or structural elements so that expansion region may open to increase an angle between the adjacent less deformable or non-deformable regions or structural elements, the struts for example, as the diameter of the circumferential scaffold is expanded (or is increased). Stents can also be formed from a wire (solid or hollow) or a fiber, and patterned or braided.

The reinforcement elements, for example, may be provided in order to improve the stiffness, crush strength, crush resistance strength, radial strength, hoop strength, or the like, of the circumferential scaffold upon or after the scaffold has been expanded to the larger diameter configuration from a crimped configuration. In particular, the one or more reinforcement elements may be coupled to one or more expansion regions and/or other region such as struts and/or links on the circumferential scaffold in order to enhance such strength, particularly as measured by a "plate" or "flat plate" test for example as commonly known in the art where the circumferential scaffold is placed between parallel, space-apart plates and a force needed to reduce the expanded scaffold diameter by a pre-determined amount (or % such as 10% compression force (N) or N/mm to normalize to stent length) is measured. Other type of tests to measure radial strength can also be utilized (and measured in psi for example) as commonly known in the art.

Most commonly in another example, the reinforcement elements will be coupled to at least some of the joints, hinges, crowns, bends, or other expansion regions so that such expansion regions, after expansion or opening, are better able to resist closing forces (or crushing resistance force) than they would be without the addition of the reinforcement elements. It will be appreciated that the expansion regions undergo deformation as the circumferential scaffold is expanded and that the presence of the reinforcement elements will open with the expansion regions so that, once opened, the reinforcement elements will assist the scaffold to resist closure forces exerted by the blood vessel or other body lumen or body lumen lesions into which the scaffold has been implanted. In addition to the deformable expansion regions the circumferential scaffold will typically also include non-deformable or less deformable regions which usually retain or substantially retain their shape as the circumferential scaffold is expanded. The reinforcement elements may also be coupled to at least some of these non-deformable or less-deformable regions. In many examples or most embodiments, the expansion regions will be curved joints, crowns, hinges, bends, or the like, as described above, while the non-deformable regions will typically be struts, straight struts, or other usually linear elements of the scaffold, but sometimes may have non-linear or other shapes such as wave, S-, M-, V-, wavy liner, or wavy nonlinear, and U-shapes. Typically, expansion of the circumferential scaffolds of the endoluminal prostheses will be effected by inflatable balloons or other conventional apparatus, but in other cases the circumferential scaffold could be fabricated from an elastic polymer or other material and can be self-expanding where expansion is achieved by release of the circumferential scaffold from constraint.

In one example, the reinforcement elements increase the stiffness or strength of the reinforced region, the reinforced rings or expansion regions, and/or the stent.

In another example the reinforcement elements increase the strength of at least one region of the stent by a range from 15% to 100%, preferably increase the strength by a range from 25% to 150%, more preferably increases the strength by a range from 25% to 200%.

In another example the reinforcement elements increase the strength of the stent by a range from 0.015 N/mm of stent length to 0.035 N/mm of stent length, preferably increases the strength of the stent by a range from 0.015 N/mm to 0.05 N/mm of stent length, more preferably increase the strength of the stent by a range from 0.015 N/mm to 0.09 N/mm of stent length, when measure using flat plate test 10% compression. For example, the strength (using flat plate test method for example) of 0.015 N/mm for a 3.0 mm stent by 28 mm stent length equates to 0.015 N/mm times 28 mm (stent length) which equals to 0.42N strength.

In another example the stent having reinforcement elements has a strength ranging from 0.03 N/mm to 0.06 N/mm of stent length, preferably has strength ranging from 0.025 N/mm to 0.07 N/mm of stent length, more preferably has a strength ranging from 0.025 N/mm to 0.09 N/mm of stent length, when measuring strength using flat plate test 10% compression. For example, a 0.03 N/mm stent length strength (using flat plate test for example) for a 3.5 mm diameter stent by 18 mm stent length equates to 0.03 N/mm times 18 mm of stent length which equals 0.54N.

In another example, the reinforcement elements decrease initial inward recoil (or recoil after expansion or recoil after deployment) or decrease subsequent inward recoil (recoil after implantation, or recoil after procedure completion, or recoil within 30 days from implantation, or recoil within 6 months from implantation, or recoil after implantation initial recoil and 6 months' time period, or recoil after implantation initial recoil and 1 day, or recoil after implantation recoil and 30 days).

In another example, the reinforcement elements decrease the inward recoil of the stent to a range from 1% to 10%, preferable to a range from 1% to 7%, more preferably to a range from 1% to 5%, after implantation. In another example, the reinforcement elements decrease the subsequent inward recoil of the stent to a range from zero to 5%, preferably to a range from zero to 3%, more preferably to a range from zero to 2%, at the various time points discussed.

In another example, the stent having reinforcement elements has an inward recoil ranging from 1% to 10%, preferable ranging from 1% to 7%, more preferably ranging from 1% to 5%, after expansion or deployment. In another example, the stent having reinforcement elements has subsequent inward recoil ranging from zero to 5%, preferably ranging from zero to 3%, more preferably to a range from zero to 2%, most preferably said stents have substantially zero inward subsequent recoil (or said stent substantially maintain the initial recoil after implantation), at the various time points discussed.

In another example, at least some reinforcement elements are coupled to at least some expansion regions on at least some rings of the stent, wherein the stent expands from a crimped configuration to an expanded larger configuration, and wherein the reinforcement elements provide sufficient strength in the expanded stent configuration to support a body lumen.

The reinforcement elements in one example may be coupled to the circumferential scaffold in a large variety of patterns. The reinforcement elements may be attached to some or all of the expansion regions while not necessarily being attached to any of the non-deformable or less deformable regions. In particular, the reinforcement elements may be attached to one, two, three, or more of the expansion regions of the scaffold or scaffold ring. In some examples or embodiments, the reinforcement elements are attached to all of the expansion regions of the scaffold or scaffold ring, and in other preferred examples or embodiments, the reinforcement elements are attached to all but one of the expansion regions of the scaffold or scaffold ring. In other examples or embodiments, the reinforcement elements may be attached to both expansion regions as well as to some or all of the non-deformable or less-deformable regions. In other examples or embodiments, the reinforcement elements may be attached to at least some expansion regions extending at least partially into the non-deformable or less-deformable regions. In other examples or embodiments, the reinforcement elements may be attached to at least some expansion regions extending to at least a mid-point of the non-deformable or less-deformable regions length. In other examples or embodiments, the reinforcement elements may be attached to at least some expansion regions extending substantially the entire length of the non-deformable or less-deformable regions. The reinforcement elements may be embedded (fully or partially) into the material of the circumferential scaffold, for example being embedded into at least some of the expansion regions (or embedded into any of the surface regions of the expansion regions such as abluminal surface region, luminal surface region, and/or side surface regions). Alternatively, the reinforcement elements in another example may be attached or otherwise disposed on the scaffold so that they lie at least partly on an exterior of least some of the expansion or non-deformable regions.

The reinforcement elements can be coupled to the stent prosthesis (including or comprising embedded, attached, or disposed on) after patterning the stent, where the coupling of the reinforcement elements to the patterned stent regions is performed by a variety of ways such as press fitting the reinforcement element onto the stent or stent region, creating or pre-forming a groove or a space or a slot by a variety of means such as laser or mechanical or chemical means and then press fitting the reinforcement elements onto the stent or stent region, dissolving the polymer material partially or softening the material to press fit or insert, to contain the reinforcement element, and/or adhesively attaching the reinforcement elements to the patterned structure surface or region (such as polymeric structure) to name few methods. Alternatively, the reinforcement elements can be coupled to the stent before patterning such as coupled to the tube (such a polymeric tube) from which the stent is patterned, and wherein the tube and reinforcement elements are patterned together (or separately) to form a patterned stent using the methods discussed above and/or throughout the application and the patterning means discussed in the application such as laser patterning. The reinforcement elements can also be formed with the tube (such as polymeric tube) that forms the stent using dipping, spraying, or molding for example, or the reinforcement element is one or more wires (solid or hollow) that is patterned or woven into a stent, or the reinforcement elements can be a wire (solid or hollow) encapsulated by a material (such as the main polymer material) and is woven or patterned into a stent. The reinforcement elements are coupled as pieces, solid wire, tube, or patterned structure. The reinforcement elements are coupled to the stent structure (such as the polymeric stent material) while having discontinuities or separation regions before coupling to the stent prosthesis as described in this application to uncage the lumen and/or allow scaffold or lumen enlargement, or the discontinuities or separation regions are formed onto the reinforcement elements (through a variety of means such as laser cutting, dissolving, cutting, etc.,) after coupling to the stent, wire, or tube, and then the discontinuities or separation regions are reconnected or held together by means such as adhesives, main polymer, different polymer, sleeve, or other means that holds the stent structural element together upon expansion from a crimped configuration to an expanded larger configuration.

Typically, stents including the circumferential scaffolds will comprise a plurality of adjacent rings where the expansion regions comprise curved, bent, hinged, jointed, crowns, or other regions of the rings which straighten or open as the scaffold is radially expanded. Most typically, such rings will be sinusoidal, serpentine rings, zig-zag rings, diamond (Palmaz-type) rings, or any other type of radially expandable stent ring known in the vascular stent art, including open cell design, closed cell design, or combination, or other known to one skilled in the art. Usually, individual rings will be oriented in planes which are oriented perpendicularly to a central axis, or perpendicular to a longitudinal axis, of the circumferential scaffold in the crimped or expanded configuration. In other embodiments or examples, however, the planes of the rings or expansion regions or circumferential structural elements can be inclined at an angle relative to the scaffold longitudinal axis (e.g. from 1° to 85°, or from 1° to 45°, or from 10° to 75°, or from 25° to 75°, or usually from 5° to 15°), and in some cases, the "rings" or expansion regions or circumferential structural elements may be formed in a helical structure, or joined in a continuous helical arrangement. The individual rings, or adjacent turns of a helical stent structure, may be axially joined together by axial links between hinges, crowns, beams, struts and/or other components of the rings or turns. In other example, the scaffold can be formed from a wire (solid or hollow in at least some regions) and patterned into a stent, where adjacent rings are connected in one or more locations (or regions). In one example stents comprising rings having an orientation ranging from being perpendicular to the longitudinal axis of the stent, to having an angle to such longitudinal axis of the stent ranging from 1° to 85°, to having a helical configuration ring pattern, wherein at least some rings have at least one separation region. In some other example, a stent, such as a valve containing stent, can comprise one or more circumferential rings (or one or more circumferential structural elements). In such example, the stent comprises one or more separation regions, hinges, or other structures as described in this application. In a particular preferred example, the stent comprises one or more circumferential rings, wherein the one or more rings comprise a plurality of struts joined by crowns. Usually, every two struts are joined by a crown, or every crown joins two struts, on a ring. At least some, preferably all rings are joined to adjacent rings by at least one axial link, or by joining one or more crown regions (using solder, adhesive, or fusing of the material) of adjacent rings.

The reinforcement elements in one example may be disposed in segments about the rings, or alternatively may be disposed to extend around substantially an entire circumferential length of at least some of the rings. The reinforcement element(s), however, will be configured to have or form at least one break, discontinuity, or separation region, in their circumferential direction or length so that the reinforcement elements can circumferentially separate or/and uncage, or incrementally expand after deployment as the blood vessel or other body lumen remodels during the healing process. In this way, the reinforcement elements will be able to provide a desired initial strength and resistance to collapse during deployment and/or an initial period after deployment, but will not constrain or inhibit the scaffold from uncaging and/or expanding, and/or the blood vessel/lumen from expanding after the biodegradable polymer (such as the main polymer) of the circumferential scaffold has softened, and/or the polymer's molecular weight has decreased, and/or the polymer has degraded, and/or the polymer has at least partly eroded (including degraded or corroded) leaving the reinforcement elements (which have not eroded or not fully eroded) free to further expand in response to vessel remodeling or other physiologic conditions.

The circumferential scaffolds of the present invention may include some or all conventional features found in the patterns of conventional stents. For example, the stent patterns may include axial links which hold adjacent rings together to form closed-cells of a type well known in the stent arts. In such cases, the reinforcement elements for example may be coupled to at least some of the axial links, in which cases a plurality of individual reinforcement elements may together form box structures which are coupled to substantially parallel rings as well as substantially parallel axial links. In one example the reinforcement element is coupled to at least one axial link has at least one break.

The reinforcement elements in one example can be individual pieces having the shape or geometry, or substantially having the shape or geometry, or having smaller shape or geometry, or having larger shape or geometry, or having different shapes or geometry, from the structural element to be coupled to such as crowns, struts, and/or links. Examples of shapes include square, round, rectangle, triangle, semicircle, and other shapes. In these examples the pieces are discontinuous or discrete pieces (either in contact or not with other adjacent reinforcement elements). The pieces can have deburred end regions, rounded end regions, ball end region, or other types or geometries to prevent inflammation after the polymeric material has degraded and or resorbed. In a preferred example, substantially all of the expansion regions of at least some rings have reinforcement elements pieces coupled to said expansion regions wherein the reinforcement elements pieces span substantially the entire expansion regions segment or at least part of the expansion regions segment. In another example, substantially all of the expansion regions of at least some rings have reinforcement elements pieces coupled to said expansion regions wherein the reinforcement elements pieces span the entire expansion regions segment and extend at least partially into the non-deformable or substantially non deformable (such as struts) segments. In a preferred example, the reinforcement elements, the reinforcement elements pieces' shape and/or geometry generally substantially mimic or contour to the shape and/or geometry of the structural elements to be coupled to. The reinforcement elements pieces in one example can be larger size in at least one dimension, smaller size in at least one dimension, or the same size in at least one dimension to the structural element the pieces are coupled to. Reinforcement elements pieces coupled to at least some structural elements of a biodegradable material allow the stent to further expand, and/or allows the stent to uncage, and/or allows the vessel to exhibit vaso-motion or vaso-dilation, after implantation (or after expansion or after deployment) under physiologic conditions (and/or through the introduction of therapeutic agents such as nitro) while stiffening or strengthening the stent upon expansion of the stent to support a body lumen.

In another example, the reinforcement elements can be one or more reinforcement elements segments coupled to at least some rings and/or other structural elements such as a link. For example, a reinforcement element segment is coupled to (or spans) one crown and one strut on a ring, and/or coupled to (or spans) one crown and one strut on a ring, and one link, and/or coupled to (or spans) multiple crowns and struts on a ring, and multiple links. In another example, the reinforcement elements segments form a pattern on the stent, said pattern is usually symmetrical pattern (but can also be non-symmetrical pattern), said pattern can be a variety of shapes including closed patterns and open pattern. When the reinforcement element segment span the entire structural elements of a ring crowns and/or struts, said reinforcement element segment would have at least one break or discontinuity in said crowns and/or struts (said break or discontinuity is formed before or after coupling to said structural element) to allow the stent to further expand after degradation of the polymeric material, or to allow the stent to uncage, or to allow the vessel to have vaso-motion, or to allow the vessel to have vaso-dilation, after expansion (or after deployment), under physiologic conditions (and/or through the introduction of therapeutic agents such as nitro), said reinforcement elements segment stiffens or strengthens the stent, by having sufficient strength to support a body lumen after deployment.

In another example, the reinforcement elements can be one or more reinforcement elements segments coupled to at least some rings (or circumferential structural elements), or coupled to substantially all rings (or circumferential elements). When the reinforcement elements, or reinforcement element segment spans the entire ring length (or circumferential structural element) without breaks, discontinuities, or separation region, or spans more than one ring entire lengths without breaks, discontinuities, or separation regions, or when the reinforcement elements span substantially the entire stent without breaks, discontinuities, or separation regions, said reinforcement element(s), or reinforcement element segment(s) would have at least one or more regions along the circumferential path for each ring (crowns or struts for example), and/or one or more crown regions along the circumferential path of each ring, and/or one or more strut regions along the circumferential path of each ring, wherein the one or more said region contain a reinforcement element (or one or more reinforcement elements) having a cross sectional area ranging from 200 micron squared to 4000 micron squared, preferably a cross sectional area ranging from 400 micron squared to 3000 microns squared, more preferably a cross sectional area ranging from 700 micron squared to 2500 micron squared, wherein the one or more said regions allow the said one or more rings, and/or the stent, to further expand after degradation of the polymeric material (or metallic degradable material), and/or allow the stent to uncage, and/or allow the vessel to have vaso-motion, and/or allow the vessel to have vaso-dilation, and/or allow the stent to have radial strain ranging between 1% and 5% at 3.0 mm expanded diameter, after stent expansion (or after deployment), under physiologic conditions (and/or through the introduction of therapeutic agents such as nitro), said reinforcement elements segment stiffens or strengthens the stent, by having sufficient strength to support a body lumen after deployment. In another example, the said region having said cross sectional area above spans substantially the entire length of at least some rings, or substantially spans the entire stent. In another example, the said region having said cross sectional area spans at least some rings, or spans substantially all rings, but does not span at least some axial links. In another example, the said regions having said cross sectional area, wherein the reinforcement element width ranges from 10% to 50% of the width of the structural element at said region, preferable ranges from 20% to 40%, more preferably ranges from 25% to 35%. In another example, the said regions having said cross sectional area, wherein the reinforcement element thickness ranges from 10% to 70% of the thickness of the structural element at said region, preferable ranges from 20% to 50%, more preferably ranges from 30% to 40%. In another example, the one or more regions having said cross section area wherein the ratio of thickness to width of the structural elements 1.5:1 to 3:1, and wherein the ratio of the structural element at said one or more regions thickness to width ranges from 0.7:1.4, preferably ranges from 0.8:1. In a preferred example of this example, the reinforcement element is non-degradable metal or metal alloy, and the stent frame material (which the reinforcement element is coupled to) is a polymeric degradable material. In another preferred example of this example, the reinforcement element is a non-degradable metal or metal alloy and the stent frame material is a degradable metal or metal alloy. The stent in this example containing reinforcement elements and having a degradable frame material has sufficient strength to support a body lumen when expanded from a crimped configuration to an expanded configuration, and wherein the stent radial compliance increases after expansion while the strength of said stent decreases after expansion. In another example, the stent radial strain increases after degradation of the degradable polymeric material and wherein the initial strength after expansion decreases after degradation of the polymeric material. In another example of this example, the reinforcement elements combined with the degradable frame stent material, have sufficient strength to support a body lumen, wherein the reinforcement elements alone does not have sufficient strength to support a body lumen. In another example of this example, the reinforcement elements combined with the degradable frame stent material, have sufficient strength to support a body lumen, wherein the reinforcement elements alone, or the stent frame material alone, do not have sufficient strength to support a body lumen.

In another example, the stent having reinforcement elements, bridging elements, separation regions, breaks, and other features described in this application exhibit increase in radial strain (or compliance) after expansion and decrease in radial strength after said expansion. In another example, said increase of radial strain (or compliance) and decrease in strength, begins (or occurs) from a period ranging from one week after expansion of the stent to 9 months after expansion of the stent, preferable begins one month after expansion to 6 months after expansion, more preferably begins 2 months after expansion to 6 months after expansion.

Most commonly, the reinforcement elements will comprise a non-degradable, usually being a metal (including metal alloy), more usually being a malleable metal which can be opened and deformed together with the circumferential scaffold but which has a higher strength to resist closure after the scaffold has been partially or fully expanded. In other examples, however, the reinforcement elements may be a polymer which has a higher stiffness than the main polymer (or the degradable patterned polymer or the polymer the reinforcement elements are coupled to at least in part) of the circumferential scaffold. Polymeric reinforcement elements may be formed from the same or different polymers than those which form the circumferential scaffold. When the reinforcement elements are formed from the same polymer, the reinforcement element polymer will typically have a higher molecular weight and/or higher crystallinity, or will otherwise be a stiffer polymer than that of the main body polymer (or the degradable patterned polymer or the polymer the reinforcement elements are coupled to at least in part) of the circumferential scaffold, the reinforcement polymer in this example can be degradable or non-degradable. In yet another example, the reinforcement elements can also comprise a degradable metal (which includes metal alloys) such as magnesium and/or magnesium alloys.

In yet another example, a stent prosthesis comprising a biodegradable polymeric material where the polymeric degradable material degrades in 1 months to 5 years, preferably degrades in 2 months to 3 years, more preferably degrades in 3 months to 2 years, wherein reinforcement elements are coupled to at least some expansion regions of at least some rings of said stent. The reinforcement elements can be non-degradable or degradable material, metal or metal alloys, polymers (degradable or non-degradable), or other material, that stiffens (or strengthens) said expansion regions (or stent) in the stent expanded configuration. Typically, the polymeric material degrades faster than the reinforcement elements, but can also (the polymeric material) be configured to degrade at the same time (or rate) as the reinforcement elements, or slower than the reinforcement elements. In another example the reinforcement elements do not degrade or corrode.

In yet another example, a stent prosthesis comprising a biodegradable metallic material such as magnesium alloy where the metallic degradable material degrades in 1 months to 5 years, preferably degrades in 2 months to 3 years, more preferably degrades in 3 months to 2 years, wherein reinforcement elements are coupled to at least some expansion regions of at least some rings of said stent in accordance of any of the examples of this application. The reinforcement elements can be non-degradable or degradable material, metal or metal alloys, polymers (degradable or non-degradable), or other material, that stiffens (or strengthens) said expansion regions (or stent) in the stent expanded configuration. Typically, the metallic material degrades faster than the reinforcement elements, but can also (the metallic material) be configured to degrade at the same time (or rate) as the reinforcement elements, or slower than the reinforcement elements. In another example the reinforcement elements do not degrade or corrode.

In still other examples, the reinforcement elements may be formed from an elastic metal or polymer (including spring and/or shape memory like NiTi). For example, for reinforcement elements which are curved or bent to conform (or contour) to a joint or hinge or an expansion region on the polymeric or metallic circumferential scaffold, the reinforcement element will typically be in a closed or constrained configuration when coupled to the corresponding hinge or joint on the circumferential scaffold in the crimped configuration. In this way, the typically metal reinforcement element will act to help open and/or keep open the circumferential scaffold as it is balloon expanded or self-expanded to its larger diameter configuration. Moreover, even after implantation in the blood vessel or other body lumen, the elastic, shape memory, and/or spring-like reinforcement elements will typically still be at least partially constrained by a polymer (such as the main polymer) or metal so that they will continue to bias the circumferential scaffold to open at least in the region where they are coupled to while simultaneously enhancing the strength and crush-resistance of the deployed prosthesis such as endoluminal prostheses themselves and/or through other reinforcement elements with high stiffness disposed on the same, adjacent, or other expansion regions or structural elements of said circumferential scaffold. Optionally, the scaffold may have additional metal, polymer, or other non-elastic (malleable) reinforcement elements coupled to same or other expansion regions, e.g. hinges or joints, on the circumferential scaffolds. For example, as one or more polymers comprising the scaffold or rings (such as main polymer) thereof start to soften, and/or degrade, and/or start to decrease in a molecular weight, and/or as the blood vessel or other body lumen heals and remodels over time, the elastic reinforcement elements will be able to continue to provide an opening bias to enhance enlargement of the scaffold. The magnitude of the opening bias is controlled by the elastic (including spring, shape memory) material properties and/or processing, and/or controlled by the degradation of the polymeric material (such as main polymer) containing the reinforcement elements. The terms stent and scaffold are used interchangeably in this application. In another example, the typically metallic shape memory or spring reinforcement element having two ends can be coupled to adjacent struts (non-deformable or substantially non-deformable structural elements) wherein the reinforcement element is configured as an expansion region connecting the two adjacent struts (along the length of the struts), where the reinforcement element expansion region is in the crimped configuration when the stent is in the crimped configuration, and wherein the reinforcement element expansion region expands as the stent expands to the deployed configuration. The reinforcement elements continue to push open (increasing the angle between said adjacent struts) after deployment of the stent (after the stent inward recoils from the deployed configuration). The reinforcement elements further expand the stent after deployment. The reinforcement elements are attached or coupled to the structural elements as described throughout this application. In one example, the reinforcement elements further expand the stent prosthesis by a mean range from 0.05 mm to 1 mm, from 0.1 mm to 0.5 mm, preferably from 0.1 mm to 0.3 mm, or corresponding mean cross sectional areas, after stent deployment and after stent recoil. In another example, the reinforcement elements increase the stent mean diameter or mean cross sectional area by a range from 2% to 15%, preferably 3% to 10%, of the stent mean expanded diameter or mean cross sectional area, after stent deployment and stent inward recoil). In another example, stent prosthesis comprises a non-degradable shape memory alloy comprising NiTi or other type material, the stent has one or more separation region (and/or one or more hinges), and wherein the stent expands from a crimped configuration to an initial expanded configuration and wherein the one or more separation region (or hinges) form discontinuities (or allow the stent to have radial displacement), allowing the stent to respond to a vaso-dilator, or contours to a changing lumen (or annulus) configuration.

In a preferred example the degradable polymeric stent comprising degradable main polymer (the polymer forming substantially the polymeric scaffold structure, or the polymer forming substantially a continuous scaffold structure, or the polymer forming substantially a scaffold structure without separation regions, or the polymer forming the scaffold structure except for at least some separation regions or discontinuities). The degradable polymeric stent can comprise more than one polymer in addition to the main polymer (adjacent, blended, mixed, etc.). Reinforcement elements are preferably non-degradable metal and metal alloys, having higher crush resistance (strength) compared to the main polymer or other additional polymers, such reinforcement elements are coupled to at least some regions of the scaffold structural elements such as crowns and/or struts, wherein the reinforcement elements have separation regions or discontinuities allowing the stent to uncage and/or expand in a physiological environment. The reinforcement elements can also be polymers (degradable or non-degradable) or corrodible metal and metal alloy.

In a preferred example, the reinforcement elements can have a variety of shapes and geometries including rod (or solid) or hollow wire, circular, semi-circle, triangle, rectangle, square, oval or other shapes and geometries. In a preferred example, the cross sectional area of at least some structural elements (such as crowns and/or struts) containing or coupled to the reinforcement elements, have the reinforcement elements representing 5% to 90% of the cross section area of said structural element, preferably represent 10% to 75% of the cross section area, more preferably represent 15% to 75% of the cross section area of said structural element. The structural element can be fully embedded in the structural element, partially embedded, or attached to one or more surface regions of the structural element, as described in this application.

In another example or aspect of this invention, a stent comprises a biodegradable polymeric material (or biodegradable metallic material) patterned into a structure comprising structural elements where at least one crown region (preferably at least some crown regions, more preferably at least half of the crown on the at least some rings), and/or at least one strut region (preferably at least some strut regions, more preferably at least ¼ of the struts regions on the at least some rings), are not formed (or are partially formed), on at least some rings, and said regions are formed or replaced with reinforcement elements, preferably non-degradable reinforcement elements preferably metallic such as CoCr alloys, Stainless steel alloys, or other metal or metal alloys, or can also be non-degradable polymeric reinforcement elements. The polymeric stent is formed (or formed with the region which is then removed) in one example without the at least one crown region and/or without the at least one strut region, on at least some rings, and where the metallic reinforcement elements having substantially the same size (or preferably smaller size) compared to adjacent polymeric crown regions and/or strut regions, and the reinforcement elements are shaped (or bent or curved) into a crown region shape and/or a strut region shape, and the reinforcement elements crown region two ends are attached to the strut end regions of the not-formed crown. The two ends of the reinforcement elements can be attached to the two strut ends of the polymeric stent as a butt joint and adhesively bonding the two materials together at the junction, and/or containing both reinforcement element and polymeric material junction region with a sleeve, and/or forming a slot in each of the polymeric stent two strut end regions (during laser patterning or after) and inserting or press fitting the reinforcement element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the reinforcement element end regions where the polymeric ends press fit into, to hold the reinforcement elements and the polymeric material junction together, or to hold the butt joint together, during expansion from a crimped configuration to expanded larger configuration. Similarly, reinforcement elements can connect to not-formed polymeric strut ends (or partially formed struts) as discussed above. The reinforcement elements stiffen the expansion region and/or the non-deformable or substantially non deformable regions in the expanded stent configuration. The stent is expandable from a crimped configuration to an expanded larger configuration and have sufficient strength to support a body lumen. In one example, the stent polymeric biodegradable material degrades from 3 months to 3 years, while the non-degradable reinforcement elements remain in the vessel wall. The stent after deployment, uncages the vessel, exhibits vaso-motion, exhibits vaso-dilation, exhibits vaso-constriction, and/or further expands to a larger configuration, and/or has radial strain ranging from 1% to 10%, preferably ranging between 1% to 7%, more preferably ranging from 1.5% to 7%, under physiologic conditions. The stent in one example comprises degradable polymeric material comprising structural elements comprising crowns and struts where at least some of the crowns and/or struts have been not formed, detached, or removed after forming (such as mechanically such as cutting them or chemically such as using solvents or other material to removing them), and replaced with non-degradable metallic reinforcement elements. The stent is formed from polymeric tube or formed from filaments that are patterned into a stent, or other methods known to one skilled in the art. The reinforcement elements can be formed from a tube or a wire and shaped or patterned into the shape of the structural element it would be replacing such as crown. In one example the reinforcement elements are formed from a patterned tube and then components of said patterned tube are removed (mechanically for example) and inserted (or attached) into the location of the not formed polymeric structural element (to replace it in one example). In another example a wire reinforcement element is shaped into the structural element to be replaced and attached. Other methods of forming the structural elements can include a variety of ways such as forming a pattern flat sheet, injection molding, or other. The shapes and sizes of the reinforcement elements can vary and is discussed throughout the application in more detail.

In another example, a biodegradable metallic stent such as magnesium alloy stent is patterned into a structure comprising structural elements where at least one crown region (preferably at least some crown regions, more preferably at least half of the crown on the at least some rings), and/or at least one strut region (preferably at least some strut regions, more preferably at least ¼ of the struts regions on the at least some rings), are not formed (or are partially formed), on at least some rings, and said regions are formed or replaced with reinforcement elements, preferably non-degradable reinforcement elements preferably metallic such as CoCr alloys, Stainless steel alloys, or other metal or metal alloys, or can also be non-degradable polymeric reinforcement elements. The metallic stent is formed (or formed with and then removed) in one example without the at least one crown region and/or without the at least one strut region, on at least some rings, and where the metallic reinforcement elements having substantially the same size (or preferably smaller size) compared to adjacent metallic stent crown regions and/or strut regions, and the reinforcement elements are shaped (or bent or curved) into a crown region shape and/or a strut region shape, and the reinforcement elements crown region two ends are attached to the strut end regions of the not-formed crown. The two ends of the reinforcement elements can be attached to the two strut ends of the metallic stent as a butt joint and adhesively bonding the two materials together at the junction, and/or containing both reinforcement element and metallic stent junction region with a sleeve, and/or forming a slot in each of the metallic stent two strut end regions (during laser patterning or after) and inserting or press fitting the reinforcement element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the reinforcement element end regions where the metallic stent structural element ends press fit into, and/or laser welding (or fusing) the two material, to hold the reinforcement elements and the metallic stent junction together, or to hold the butt joint together, during expansion from a crimped configuration to expanded larger configuration. Similarly, reinforcement elements can connect to not-formed metallic stent strut ends (or partially formed struts) as discussed above. The reinforcement elements stiffen the expansion region and/or the non-deformable or substantially non deformable regions in the expanded stent configuration. The stent is expandable from a crimped configuration to an expanded larger configuration and have sufficient strength to support a body lumen. In one example, the stent metallic biodegradable material degrades or substantially degrades in a period of time ranging from 3 months to 3 years, while the non-degradable reinforcement elements remain in the vessel wall. The stent after deployment, uncages the vessel, exhibits vaso-motion, exhibits vaso-dilation, exhibits vaso-constriction, and/or further expands to a larger configuration, and/or has radial strain ranging from 1% to 10%, preferably ranging between 1% to 7%, more preferably ranging from 1.5% to 7%, under physiologic conditions. The stent in one example comprises degradable metallic material comprising structural elements comprising crowns and struts where at least some of the crowns and/or struts have been not formed, detached, or removed after forming (such as mechanically such as cutting them or chemically such as using solvents or other material to removing them), and replaced with non-degradable metallic reinforcement elements. The stent is formed from a metallic tube or formed from filaments (or wires) that are patterned into a stent, or other methods known to one skilled in the art. The reinforcement elements can be formed from a tube or a wire and shaped or patterned into the shape of the structural element it would be replacing such as crown. In one example the reinforcement elements are formed from a patterned tube and then components of said patterned tube are removed (mechanically for example) and inserted (or attached) into the location of the not formed metallic stent structural element (to replace it in one example). In another example a wire reinforcement element is shaped into the structural element to be replaced and attached. Other methods of forming the structural elements can include a variety of ways such as forming a pattern flat sheet, injection molding, or other. The shapes and sizes of the reinforcement elements can vary and is discussed throughout the application in more detail.

In another aspect or preferred example, it is desirable to a have as stent comprised from a non-degradable high strength material, such as metallic material, in order to have sufficient strength upon deployment of the stent in a body lumen (in some cases a degradable material such as degradable metallic material having high crush resistance can also be used for this example, such materials tend to degrade slowly caging the vessel for a long time). However, such stents cage the vessel or segment adjacent to the stent and prevent one or more of the following from occurring potentially reducing the utility, safety, and/or effectiveness of the stent: uncaging the vessel or stented segment, exhibiting vaso-dilation within or spanning the stented segment, exhibiting vaso-constriction within or spanning the stented segment, exhibiting further enlargement of the stent, exhibiting radial strain over the stented segment in the range from 1.5% to 5%, after deployment. In order to solve or address on or more of the previous needs, the non-degradable metallic stent, such as L605 CoCr alloy stent, is configured by patterning into a structure comprising structural elements where at least one crown region (preferably at least some crown regions, more preferably less than half of the crowns on the at least some rings), and/or at least one strut region (preferably at least some strut regions, more preferably at least ¼ of the struts regions on the at least some rings), are not formed (or are partially formed, or are formed and then removed), on at least some rings, and said regions are formed or replaced with degradable bridging elements, such as degradable polymeric material (for example PLLA based polymers) or such as degradable metallic material (for example magnesium alloy). The non-degradable metallic stent is formed (or formed with and then removed) in one example without the at least one crown region and/or without the at least one strut region, on at least some rings, and where the degradable bridging elements having substantially the same size (or preferably smaller size, but can also be larger size) compared to adjacent metallic stent crown regions and/or strut regions, and the degradable bridging elements are shaped (or bent or curved) into a crown region shape and/or a strut region shape and/or the shape of the stent structural elements they are replacing, and the degradable bridging elements crown region two ends are attached to the strut end regions of the not-formed crown. The two ends of the degradable bridging elements can be attached to the two strut ends of the metallic stent as a butt joint and adhesively bonding the two materials together at the junction, and/or containing both degradable bridging element and metallic stent junction region with a sleeve, and/or forming a slot in each of the metallic stent two strut end regions (during laser patterning or after) and inserting or press fitting or fusing or melting the degradable bridging element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the larger size degradable bridging element end regions where the metallic stent structural element ends press fit into, and/or laser welding (or fusing) the two material, to hold the degradable bridging elements and the metallic stent junction together, or to hold the butt joint together, upon expansion of the stent, or during expansion of the stent from a crimped configuration to expanded larger configuration. Similarly, degradable bridging elements can connect to not-formed metallic stent strut ends (or partially formed struts) as discussed above. The degradable bridging elements are less stiff, or substantially less stiff and therefore weakens the expansion region, and/or the non-deformable or substantially non deformable regions in the expanded stent configuration. However, the degradable bridging elements provide for one or more of the following benefits: provide continuity of the circumferential structural element (such as rings) at least upon expansion (or for a period of time after expansion) which helps the stent to uniformly expands (or improve expansion uniformity), provide for drug release in said region to inhibit neo-intimal hyperplasia, provide for partial or full expansion of the stent circumferential ring in the said expansion region, provide for lesion coverage and minimize plaque pro-lapse, provide for temporary scaffolding and then uncaging of the stent and/or vessel as the degradable bridging elements degrade or corrode in a period ranging from 1 months to 4 years, preferably ranging from 3 months to 4 years, provide support to the vessel wall. The stent is expandable from a crimped configuration to an expanded larger configuration and have sufficient strength to support a body lumen, The non-degradable stent structural elements remain in the vessel wall substantially intact in one example (or substantially held together, or substantially in place, in one example). The stent after deployment, uncages the vessel, exhibits vasomotion, exhibits vaso-dilation, exhibits vaso-constriction, and/or further expands to a larger configuration, and/or has radial strain ranging from 1% to 10%, preferably ranging between 1% to 7%, more preferably ranging from 1.5% to 7%, under physiologic conditions (and/or through introduction of therapeutic agents such as nitro). The stent in one example comprises non-degradable metallic material comprising structural elements comprising crowns and struts where at least some of the crowns and/or struts have not been formed, or have been detached, or have been removed after forming (such as mechanically removed such as cutting them or chemically removing them such as using solvents or other material to removing them or to melt them), and are replaced (or formed) with degradable bridging elements in said regions. The stent is formed from metallic tube, metallic sheet, or formed from filaments (or wires) that are patterned into a stent, or formed using other methods known to one skilled in the art. The degradable bridging elements can be formed from a tube or a filament/wire and shaped or patterned into the shape of the structural element it would be replacing such as crown for example. In one example the reinforcement elements are formed from a patterned tube and then components of said patterned tube are removed (mechanically for example) and inserted (or attached or press fitted) into the location (or region) of the not formed metallic stent structural element. In another example a filament degradable bridging element is shaped into the structural element shape replace and attached the ends as described. Other methods of forming the degradable bridging elements can include a variety of ways such as forming a pattern from a flat sheet and using components from the sheet to replace the not formed structural element, injection molding of said degradable bridging elements, or other. The shapes and sizes of the degradable bridging elements can vary (smaller, same, or larger, than the replaced structural element) as discussed throughout the application in more detail.

In one example, the bridging elements are degradable. In another example the bridging elements are non-degradable but provides for one or more of the objectives of this invention. The bridging elements can also be a suture (or wire) tying both ends of the structural element that is not formed, or that is modified or removed partially or completely. The suture can tie both ends of the structural element through a hole adjacent to each end of the structural element where the suture (or wire) is threaded through the holes and tied forming a continuity of the not formed structural element (said suture or wire bridging two crowns or two struts for example).

In another example, the bridging elements can be formed from shape memory material or spring material (which can also be reinforcement elements in other examples), where the bridging elements help bias open at least some crowns to expand further after implantation.

In another example, the non-degradable metallic stent (such as Cobalt Chrome alloy L605 or MP35 for example) comprises a wire (round or substantially round, or oblong, or other shapes), where the wire is patterned into a stent. The stent comprises structural elements comprising a plurality of rings, each ring comprises crowns and struts. At least one strut and/or at least one crown, on at least some rings, are removed. The ends of the stent where the strut and/or crowns were removed are treated to create a hollow space in the wire. A degradable bridging element is inserted in the hollow space at each of the ends of the wire stent to bridge the gap of the removed strut and/or crown. Optionally an adhesive, or degradable sleeve are applied to the junctions or overlap further reinforcing the junction segment so that the junction is held together as the stent expands from a crimped configuration to an expanded larger configuration. In another example, the degradable bridging elements are treated to create a hollow space, where the stent wire structural element is inserted or press fitted into. Optionally an adhesive or sleeve are applied to further hold the junction together.

In another example, the stent prosthesis is formed as a tube where the tube comprises a non-degradable material layer (such as cobalt chrome alloy layer) that is either sandwiched between, on top of, or on the bottom of a magnesium alloy layer. The tubing is patterned into a stent.

At least some regions on at least some rings (or at least some crown regions, and/or strut regions, on at least some rings) have the non-degradable material (such as the cobalt chrome alloy layer) substantially removed by laser, chemical means, or mechanical means, to provide the stent to uncage after expansion under physiological conditions. The stent prosthesis in another example can be formed as a sheet where the degradable layer is on top or bottom of the non-degradable material, the stent is patterned and processed as described above. The sheet is rolled and attached (or fused) forming a patterned stent.

In another example, the stent prosthesis is formed as a wire where the wire comprises a non-degradable material layer (such as cobalt chrome alloy layer) on top, or on the bottom of a degradable polymeric or metallic material layer (such as magnesium alloy layer or PLLA based polymer). The wire is patterned into a stent. At least some regions on at least some rings (or at least some crown regions, and/or strut regions, on at least some rings) have the non-degradable material (such as the cobalt chrome alloy layer) substantially removed (forming degradable bridging elements connecting the two ends of the non-degradable structural element, by laser, chemical means, or mechanical means, to provide the stent to uncage after expansion under physiological conditions, preferably uncaging as the degradable material degrades.

In another example, the stent prosthesis is formed as a tube where the tubing comprises a non-degradable material layer (such as cobalt chrome alloy layer) that is on top or inside of a degradable polymeric material layer (such as PLLA based polymer layer). The tubing is patterned into a stent. At least some regions on at least some rings (or at least some crown regions, and/or strut regions, on at least some rings) have the non-degradable material layer (such as the cobalt chrome alloy layer) substantially removed by laser, chemical means, or mechanical means, to provide the stent to uncage after expansion under physiological conditions. The stent prosthesis in another example can be formed as a sheet where the degradable layer is on top or bottom of the non-degradable material, the stent is patterned and processed as described above. The sheet is rolled and attached (or fused) forming a patterned stent.

In one example of any of the examples in this application, the stent is tested, or deployed (expanded) under one or more of the following conditions: in air, in water bath, in water bath at 37° C., under physiologic conditions, in a pulsating (or contracting) environment, under administration of one or more agents that causes vaso-dilation or vaso-constriction of the stented segment, in a tube, in a vessel, in a body lumen, under a pressure difference (gradient) ranging from 100 mmHg to 200 mmHg, under pressure difference (or magnitude) of 100 mmHg, under pressure difference (or magnitude) of about 176 mmHg, or under conditions to test compliance or strength as described in this application, or any other condition described in this application. In some cases, all of the conditions described in this paragraph are referred to as physiologic conditions.

In one example, physiologic conditions comprises one or more of: in ambient air, in water bath, in water bath at about 37° C., at about 37° C. environment, in a radial strain tester (compliance tester), in a fatigue tester, in a pulsating environment, in a pressure or pressure differential environment, in a pulsating environment approximately simulating body lumen or body organ environment, administration of therapeutic agents such as vaso-dilators, or vaso-constrictors, in a contracting and/or expanding environment, in a body lumen, in a body vessel, in a body annulus, or other.

In a preferred example, the stent prosthesis further comprises at least one coating on at least one surface of the stent prosthesis. The coating in one example contains at least one drug, preferably an m-tor inhibitor. In another example the stent prosthesis comprises at least one drug. In another example, the stent prosthesis comprises at least two drugs, an m-tor inhibitor, and a vaso-dilator. In yet another example, the at least one coating degrades at a rate slower than the degradable (polymeric or metallic) material rate of degradation. In another example, the at least one coating degrades at a rate faster than the degradable material rate. In yet another example, at least one coating covering at least one surface of the non-degradable stent. In yet another example, at least one degradable coating covers at least one surface of the non-degradable stent. In yet another example, at least one degradable coating covers at least one surface of the non-degradable stent, and at least one non-degradable coating covers at least one surface of the non-degradable stent.

In one example, the stent prosthesis exhibits, provide, or is configured to do one or more of the following: uncaging the stent, uncaging the stented segment of the lumen or vessel, uncaging at least some circumferential structural elements (rings) of the stent, uncaging at least some rings of the stent, uncaging the vessel or vessel wall, exhibiting vaso-motion, exhibiting vaso-dilation, exhibits vaso-constriction, further expansion of the stent to a larger configuration after implantation, and/or the stent has composite radial strain (or compliance) ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example. The stent prosthesis in this example exhibits or provides the one or more properties described above (uncaging, etc.) in (or over) one or more of the following: at least some circumferential structural elements, at least some rings, substantially all circumferential structural elements, substantially all rings, at least some regions, spanning substantially the entire stent or the entire stent segment, the stent region, and/or the stent segment.

In one example of any of the examples, the bridging elements can also bridge at least one link (or link region), in addition to bridging one or more structural elements (such as struts and/or crowns) on at least some rings.

In another aspect of this invention, or another example, a non-degradable (such as metal (including alloy) but can also be polymeric) stent prosthesis comprises structural elements, said structural elements in one example comprise a plurality of rings, each ring comprises struts and crowns, and each ring is connected to an adjacent ring in at least one location (or region). At least one strut (or part of a strut, or a strut region ranging) and/or at least one crown (or part of a crown, or a crown region), on at least some rings are not-formed (or removed after forming), forming a gap (or discontinuity) between said remaining crown ends (or remaining crown regions) and/or between remaining strut ends (or remaining strut regions), wherein the gap magnitude ranges from 1 microns to 3 mm, preferably ranges from 2 microns to 2 mm, more preferably ranges from 3 microns to 1 mm, when said gap is measured as a straight line between the remaining struts and/or remaining crowns in the expanded stent configuration (or in the crimped stent configuration). The ends of the remaining struts and/or crowns can be configured to have different, preferably larger dimensions, geometry, and/or surface area than an adjacent struts and/or crown, and can have various shapes such as round, square, semi-circle, rectangle, etc. In one example, at least some rings have at least one gap (or discontinuity) along said rings. In another example, at least some rings have at least three gaps (or discontinuities) along said rings. In yet another example, at least some rings have from 1 to 3 gaps (or discontinuities). The stent prosthesis is expandable from a crimped configuration to an expanded larger configuration and have sufficient strength to support a body lumen. The stent in a preferred example has a substantially uniform expansion. The stent in another preferred example has a maximum circular diameter of 0.7 mm to 1.5 mm in the gap region. The stent in a further preferred example has sufficient coverage to inhibit (or minimize) smooth muscle cell proliferation. The stent prosthesis exhibits, provide, or is configured to do one or more of the following: uncaging the stent, uncaging at least some circumferential structural elements of the stent, uncaging at least some rings of the stent, uncaging the vessel or vessel wall, exhibiting vaso-motion, exhibiting vaso-dilation, exhibits vaso-constriction, further expansion of the stent to a larger configuration after implantation, and/or the stent has radial strain ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example. In a preferred example, the not formed (or removed) strut and/or crown remaining end region is connected to the same or adjacent structural element provided that such connection does not complete the gap (or discontinuity) of said ring and the gap in said ring remains discontinued.

In another example, the stent prosthesis comprises a plurality of rings comprising struts and crowns, where at least one strut and/or crown regions on at least some rings are severed (or cut) during laser patterning for example but can also be done mechanically, or other methods. The severed region is deburred and/or shaped into a geometry to be atraumatic and/or to create a contact, and/or to maintain a contact, and/or to substantially hold the cut region substantially together, to allow expansion of the stent prosthesis from a crimped configuration to an expanded larger configuration and have sufficient strength to support a body lumen. The stent in a preferred example have a substantially uniform pattern in the expanded configuration. The cut end regions can be abutting, overlapping, or have a temporary holding means, in the crimped configuration, to allow deployment into an expanded configuration, or to allow the stent to have a substantially uniform pattern in the expanded stent configuration, and/or to allow for a substantially sufficient coverage to support a body lumen.

During laser cutting, patterning, or other formation of the separation regions and discontinuities in the scaffold, portions of the partially formed scaffold may be temporarily together so that the structure does not prematurely separate after the discontinuities are formed and before the discontinuities are immobilized by gluing, coating, sleeve formation, or the like. For example, after a tubular member is laser cut or otherwise patterned to form circumferential rings including struts and crowns, the ends of the tubular member may be temporarily held by holding fixtures positioned at each end of the scaffold. In particular, one, two, three, or more terminal crowns at each end of the scaffold may be formed to have holding features, such as enlarged ears or similar features that can be grasped by the holding fixtures. In this way, the holding fixtures will hold the partially formed scaffold together as the separation regions are formed, e.g. by first cutting or bisecting a strut and/or crown in one or more of the circumferential rings and then coating the entire scaffold in a biodegradable sleeve to hold the stent together so that it may be removed from the fixtures and subsequently deployed.

In another example, a non-degradable (such as metal (including alloy) but can also be polymeric) stent prosthesis comprises circumferential structural elements, said structural elements comprises in one example a plurality of rings, each ring comprises struts and crowns, and each ring is connected to an adjacent ring in at least one location. At least some rings are configured (patterned and/or treated for example) to have a gap (or discontinuity) in said rings. For example, the stent can be patterned to have wherein the gap magnitude ranges from 1 microns to 3 mm, preferably ranges from 2 microns to 2 mm, more preferably ranges from 3 microns to 1 mm, when said gap is measured as a straight line to complete (or connect or provide continuity) said rings. In a preferred example, the maximum circular inter-strut (or inter-ring or between rings) distance in the region where the gap is ranges from 0.9 mm to 2 mm, preferably ranges from 1 mm to 1.5 mm. In one example, at least some rings have at least one gap (or discontinuity) along said rings. In another example, at least some rings have at least three gaps (or discontinuities) along said rings. In yet another example, at least some rings have from 1 to 3 gaps (or discontinuities). The stent prosthesis is expandable from a crimped configuration to an expanded larger configuration and have sufficient strength to support a body lumen. The stent in a preferred example has a substantially uniform expansion, sufficient vessel coverage to inhibit SMC proliferation. The stent prosthesis exhibits, provide, or is configured to do one or more of the following: uncaging the stent, uncaging at least some circumferential structural elements of the stent, uncaging at least some rings of the stent, uncaging the vessel or vessel wall, exhibiting vaso-motion, exhibiting vaso-dilation, exhibits vaso-constriction, further expansion of the stent to a larger configuration after implantation, and/or the stent has radial strain ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example.

In one example, the stent prosthesis where at least some rings have at least one gap (or discontinuity) on each said ring. In one example, the region (or end region) of the structural elements (ring) where the gap is (or where the gap begins or ends) can be free (not connected to any structural element, or any adjacent structural element), or can be connected to other structural elements such as connected to a strut, and/or crown, (or can be connected to other adjacent structural elements such as connected to a strut, and/or crown) at the end region, or adjacent to the end region, or anywhere along the structural element leading to said end region. The connection to said region can be substantially straight connection, and/or a crown connection, and/or other connection having a variety of shapes, dimensions, and/or geometries from said region to other structural elements (or adjacent structural elements). Examples of connection (including connection shapes) include Z, S, M, U, W, Y, L, or other type connection. The dimension of said connection can be different or substantially the same as other adjacent structural elements. The connections can also be larger or smaller in width and/or thickness in other examples. The connections shapes and/or dimensions can be substantially the same or different on at least some rings.

In another example, the stent prosthesis comprises structural elements comprising a plurality of rings, each ring comprises struts and crowns, and each ring is connected to an adjacent ring in at least one region. At least some rings have at least one region between two crown and/or between two struts, configured (patterned or otherwise) to have two struts (or two strut regions) and/or two crown (or two crown regions) where the two strut regions and/or crown regions overlap over some length. The struts and/or crowns are connected at opposite ends, while the other end region forms a discontinuity in said ring. The struts and/or crowns free end region can have various shapes and geometry to restrain or hold together the stent prosthesis upon deployment of the stent. The strut and/or crown regions can also have grooves or other shapes to hold the restrain the sliding struts and/or crowns upon expansion of the stent prosthesis. The stent prosthesis is typically expandable from a crimped configuration to an expanded larger configuration and has sufficient strength to support a body lumen. The stent allows the body lumen to uncage upon deployment. The stent has sufficient structural elements surface region coverage (thickness, width, and/or geometry) in the discontinuity region to support a body lumen.

In one example of any of the examples in this application, a stent prosthesis comprising circumferential structural elements, wherein the structural elements comprise struts and crowns, and wherein the stent is configured (for example patterned and/or treated) to allow the stent to be expandable from a crimped configuration to an expanded larger configuration, and wherein the stent has sufficient strength in the expanded configuration to support a body lumen, said stent prosthesis uncages, and/or has radial strain (or compliance) ranging between 1% and 5%, and/or further expands, as formed, upon expansion, and/or after expansion, in a body lumen (or under physiologic condition and/or under therapeutic condition such as introduction of nitroglycerine). Examples of said stent prosthesis comprise one or more from the examples comprising reinforcement elements, bridging elements, separation regions, struts and/or crowns having gap regions, or other. Said stent prosthesis can be degradable, non-degradable, metallic (including alloys) or polymeric, over a period ranging from 3 months to 5 years under physiologic condition. The stent prosthesis in an example can be formed from a tube and patterned into a stent or formed from one or more wires (or filaments) and patterned into a stent. The stent can also be formed from a flat sheet and rolled to form a stent. The flat sheet can be patterned before rolling it to form a stent or the flat sheet can be rolled to form a tube and then patterned. In one example the circumferential structural elements comprise a plurality of rings each ring comprising crowns and struts having one or more of the configurations described in this application. In another example the structural elements comprise crowns and struts having one or more discontinuities allowing the stent to uncage as formed, and/or further expands, as formed, upon deployment, and/or after deployment.

In another example of any of the example in this application, at least some struts and/or crowns have at least one separation region, discontinuity, or break. In another example, at least some struts and/or crowns have at least two separation regions, discontinuities, or breaks, on said struts and/or crowns. In still further examples, at least some of the struts and/or crowns will be free from separation regions. In still further and often preferred examples, at least some struts will have separation regions while all crowns in a circumferential ring will be free from separation regions. It has been found that locating separation regions in struts which normally do not deform during expansion is preferable to locating separation regions in crowns which deform as the scaffold expands.

In another aspect or in another example, the present invention provides non-degradable or slowly degradable prostheses material having structural elements such as circumferential elements and/or rings with separation regions and/or environmentally responsive separation regions. By "environmentally responsive," it is meant that the separation regions will separate, become void from material such as a degradable polymer material, create a gap, open, break, allow for movement in one or more direction, and/or degrade, in response to physiologic conditions which includes vascular conditions, and/or other luminal conditions, and/or in response to being placed in water at ambient temperature or at 37° C., and/or in response to being placed in a buffered solution, and/or in saline, and/or in response to the physiologic conditions (e.g. the vascular or luminal conditions), and/or the physiologic pressure, to which the scaffold is exposed to such as after implantation in the blood vessel or other body lumen, and/or in response to the scaffold being exposed to pressure ranging from 30 mmHg to 200 mmHg, preferably ranging from 40 mmHg to 120 mmHg, more preferably ranging from 50 mmHg to 80 mmHg, and/or in response to the scaffold being exposed to pulsating pressure ranges from 30 mmHg to 150 mmHg, preferably pulsating pressure ranges from 30 mmHg to 120 mmHg, and more preferably pulsating pressure ranges from 30 mmHg to 90 mmHg, or in response to therapeutic agents such as vaso-dilators or vaso-constrictors introduction.

The stent in a preferred example in any of the examples in this application can uncage, can uncage in at least some circumferential cross sections or regions, uncages over the stent segment, and/or expand to a larger diameter (or configuration) in physiologic conditions (includes physiologic environment) in at least some circumferential cross sections or regions of the stent prosthesis. The larger stent diameter can be larger than the deployed diameter and/or larger than the diameter of the stent after recoil from the deployed expanded configuration. The stent diameter in response to said pressures and/or pulsating pressure (as described in this application) in one example changes and/or increases from expanded and/or deployed diameter (after recoil if any from said expanded and/or deployed diameter) to a larger diameter permanently or temporarily while exposed to the pressure and/or pulsating pressure, the stent diameter changes and/or increases ranges from 0.045 mm to 1 mm, preferably ranges from 0.05 mm to 0.6 mm, and more preferably ranges from 0.06 mm to 0.3 mm, or changes from 0.1 to 0.3 mm. The stent radial strength after deployment, in the same example or other example, ranges from 12 psi to 30 psi, preferably ranges from 13 psi to 25 psi, more preferably ranges from 15 psi to 25 psi. The stent flat plate strength (10% crush) after expanding the scaffold and/or after deployment, in the same example or a different example, ranges from 0.03 N/mm stent length to 0.95 N/mm stent length, preferably ranges from 0.035 N/mm stent length to 0.9 N/mm stent length, more preferably ranges from 0.0.04 N/mm stent length to 0.085 N/mm stent length. The scaffold inward recoil after expansion of the scaffold and/or after deployment in the same example or a different example ranges from 1% to 10%, preferably ranges from 2% to 7%, more preferably ranges from 2% to 5%. The stent inward recoil preferably remains substantially the same after deployment. The stent prosthesis preferably expands further to a larger configuration after introduction of a vaso-dilator in the body. The stent preferably has radial strain (or compliance) in the expanded configuration ranging between 1% and 5%. In the same example or a different example, the non-degradable stent radial strength after deployment decreases by at least 25%, decreases by at least 50%, decreases by at least 75%, decreases by 100% of the scaffold initial radial strength upon deployment. The period of time in the same example or a different example where the strength decreases ranges from 1 day to 2 years, preferably ranges from 1 month to 1 year, more preferably ranges from 2 months to 9 months, more preferably ranges from 3 months to 9 months. In the same example or a different example, the non-degradable stent radial strength after deployment (initial deployment) decreases by a range from 0% to 25% within 30 days from such initial deployment radial strength, and/or decreases by a range from 10% to 50% within 90 days from such initial deployment radial strength, and/or decreases by a range from 25% to 90% within 180 days from such initial deployment radial strength, and/or decreases by a range from 50% to 100% within 270 days from such initial deployment radial strength. The non-degradable stent in this example further comprises at least one degradable polymer, and further comprises at least one drug. In a preferred example the at least one drug is contained in a polymer. In another example or in addition to the previous example, the stent comprises at least one non-degradable polymer. In yet another example or in addition to the previous examples, the stent further comprises radiopaque markers (degradable or non-degradable).

In a preferred example throughout this application after deployment, there is uncaging of the stent, and further expansion of the stent after deployment, lumen enlargement, and other properties of the stent and/or lumen comprising one or more of the whole stent or lumen, at least one part or region of the stent or lumen, at least one circumferential cross section or region of the stent or lumen, or at least some circumferential cross sections or regions of the stent or lumen segments, or the stented segment.

In another example, the present invention provides non-degradable prosthesis material having circumferential elements and/or rings with separation regions. Separation regions are regions that have discontinuity as formed, and/or as patterned (including after patterning), and/or after processing or treatment, and/or before implantation, and/or after implantation, and/or after implantation in physiologic conditions. Discontinuity includes completely and/or substantially one or more of the following: being separate, becoming void from material, having a gap, forming a gap, open, having a break, forming a break, unlocking, un-touching, un-contacting, removal of material between separation regions or adjacent to separation regions, removal of material holding separation regions together, ability of separation region to move in one or more directions, and/or degrade. In this example, the stent has sufficient strength upon deployment to support a body lumen, and wherein the stent after deployment may recoil to a smaller configuration before further expanding to a larger configuration (larger than the recoil configuration and/or larger than the deployed expanded configuration). The stent can expand to the larger configuration in a body lumen and/or under physiologic condition. In another example the stent uncages, or uncages at least in some regions and/or rings, or the stented segment.

In another example, one or more circumferential rings containing one or more separation regions may contain at least one or more non-degradable material (such as a non-degradable polymeric material) wherein said material inhibits forming a gap or other discontinuity. The one or more circumferential rings containing separation regions comprising a non-degradable material are configured to expand to a larger diameter or cross-section after initial expansion (and recoil if any), due to the elasticity and stretching of the non-degradable material under physiological conditions in response to vascular pulsation and/or expansion in response to a vaso-dilator agent. In this way, one or more rings and typically the entire stented segment exhibits a desired compliance after implantation under physiological conditions. The non-degradable material in such embodiments and examples typically has sufficient elasticity to continuously expand and/or contract under physiologic conditions including systolic pulsation of the blood vessel.

In yet another example, one or more separation regions comprising non-degradable materials may still form a gap or other discontinuity after the initial expansion, preferably after a period ranging from 30 days to one year after the initial expansion. Although non-degradable, the material may deteriorate or fatigue over time and/or under physiologic conditions and thus allow the separation regions to separate, to form gaps or other discontinuities.

In yet another example, the one or more separation regions may be constrained by one or more non-degradable material, such as a polymeric sleeve or a polymeric coating, wherein the one or more of the separation regions after formation of gaps or other discontinuities remain constrained by the non-degradable material even after formation of gaps or other discontinuities. The non-degradable material, formed as a sleeve or coating for example, can also cover one or more rings of the stent, cover one or more stent surfaces, or can cover the entire stent surface. The sleeve or coating constraining the separation regions allow the one or more rings or the stented segment) to have a desired compliance, further expand after initial recoil, and/or respond to an introduction of a vaso-dilator.

In another example, an endoluminal prosthesis according to this and/or one aspect of the invention and/or a preferred example comprises a scaffold having structural elements such as circumferential elements and/or rings patterned from a non-degradable material, such as a non-degradable metal, metal alloy, or hard non-degradable plastic, where the scaffold is configured to expand from a crimped configuration to an expanded configuration and the scaffold has sufficient strength in the expanded configuration to support a body lumen. At least some of the circumferential elements and/or rings will have at least one separation region configured to form discontinuities in the circumferential element and/or ring soon or immediately after deployment (initial deployment), and/or over time, and/or after an initial expansion in a physiologic environment, and/or after exposure to one or more of the other conditions disclosed in this application. Such discontinuities allow the scaffold or at least some circumferential cross sections of the scaffold to further expand to a larger configuration in at least, preferably to further expand after an initial recoil which may occur after deployment, more preferably to further expand beyond the initial expansion, most preferably allowing the scaffold to uncage or uncage in at least some circumferential cross sections or regions of the stent, preferably uncage in the circumferential direction. That is, after the scaffold has been initially deployed by a balloon or in some instances by self-expanding from constraint, the discontinuities allow portions of the scaffold to move apart and the rings to expand, preferably together with luminal expansion, more preferably together with luminal expansion as a result of luminal remodeling. In one example, the ring separation regions may be present in crowns regions, hinge regions, and/or strut regions. The stent preferably responds to vasodilation stimuli by enlarging the lumen in the stented segment. The stent preferably has composite radial strain (or compliance) ranging from 1.5% to 7%.

In another example, the discontinuities which form in the circumferential elements and/or rings will typically comprise partial or total breaks, separations, gaps in the structure of the circumferential scaffold which reduce or eliminate the stress areas, stiffness, hoop, circumferential, and/or radial strength of the scaffold (or ring component of the scaffold as described more particularly below and/or in this application) and/or in the separation region. Most commonly, the discontinuities will be total breaks which allow two resulting free ends in the scaffold or ring or circumferential element to move apart from each other in response to remodeling or other expansion of the body lumen and/or the stent. In one example the discontinuities where the two free ends are contained by a material comprising a sleeve or a coating wherein the sleeve or coating material can be non-degradable or degradable such as a polymer, wherein the sleeve or coating stretches when the free ends move apart. In another example the discontinuities are contained by means of the discontinuity geometry (such as certain key and lock designs and other type of geometry) to hold the structural element containing discontinuities together upon deployment from a crimped configuration to an expanded configuration, wherein the discontinuity is formed before patterning, during patterning, or after patterning, and is held together by the design configuration of the separation region forming said discontinuities as described above and/or in the entire application. The discontinuity in this case allows for crimping and/or deployment of the stent while maintaining the free ends of the structural elements containing said discontinuities to be held together and providing for sufficient strength after deployment of the stent to support a body lumen. The discontinuities in this case can allow movement of the free ends of the structural element in one or more directions after deployment, preferably in the radial direction only after deployment, more preferably substantially only in the radial direction, most preferably said movement primarily in the radial direction, or said movement is in a radial and/or circumferential direction. In one example, At least some of the rings or other portions of the scaffold will have at least one such discontinuity, but more typically each ring will have at least one discontinuity and some or all of the rings may have two or more discontinuities. Individual scaffold rings may have the same number or different numbers of discontinuities, and not all scaffold rings need have discontinuities. For example, rings at or near an end of the scaffold may be free from discontinuities, e.g. to limit the wishbone effect. In a further example at least some rings will have a number of discontinuities ranging from 1 to the same number of crowns, preferably a number of discontinuities ranging from 1 to ¾ of the number of crowns on said ring, and/or will have a number of discontinuities ranging from 1 to same number of the struts on said rings, preferably a number of discontinuities ranging from 1 to ¾ of the number of struts on said ring, and/or will have a number of discontinuities ranging from 1 to ½ of the number of crowns on said ring, and/or will have a number of discontinuities ranging from 1 to ½ of the number of struts on said ring, and/or will have a number of discontinuities ranging from 1 to ¼ of the number of crowns on said ring, and/or will have a number of discontinuities ranging from 1 to ¼ of the number of struts on said ring, and/or will have a number of discontinuities ranging from 1 to 10 on said ring, preferably a number of discontinuities ranging from 1 to 5 on said ring, more preferably a number of discontinuities ranging from 1 to 4 on said ring, and/or a number ranging from 1 to 3 on said ring, and/or a number ranging from 1 to 2 on said ring.

In one example, the physiologic environment causes such discontinuities to form (in other examples the discontinuities are formed independent of the physiologic environment) may be characterized by any physical condition associated with the body lumen into which the prosthesis is to be implanted. For example, the physiological environment or condition may comprise any one or more of the following: a physiologic temperature, e.g. 37° C., as maintained in the body lumen, or in a water bath heated to about 37° C., and/or a physiologic pressure, and/or, pressure and/or pulsating pressure, and/or introduction of a drug agent such as vasodilator or vaso-constrictor, as described in this application. Additionally, the physiologic environment may comprise blood or other aqueous media into which the scaffold has been implanted, particularly oxygenated blood that may enhance corrosion of certain feature. Often, the physiologic environments will comprise pulsation of a blood vessel, particularly an artery, which can subject the implanted scaffold to mechanical stress which in turn can fatigue and break particular features formed in the scaffold structure. The discontinuities, whether resulting from degradation, corrosion, dissolution, or mechanical stress, will in one example typically form from thirty days to six months, but can also form from few days to 1 year after initial expansion of the circumferential scaffold and exposure of the expanded scaffold to the environment of the body lumen. In other embodiments, discontinuities form in a water bath at ambient temperature.

In one example, the separation regions may comprise any one of a variety of structures in or modifications of the scaffold, for example including notches, variations in the grain structure, pre-formed breaks which are rejoined by degradable polymers, adhesives, sleeves, rivets, or the like.

In one particular example of the separation regions comprises a key and key hole, and/or a key and lock, and/or ball and socket, and/or hook junction which is immobilized and/or held together as formed, and/or after forming, and/or before deployment, and/or before expansion, and/or during deployment, and/or during expansion, and configured to separate and/or form a discontinuity, after deployment, and/or after additional expansion in the physiologic environment. For example, the key and key hole, and/or key and lock, and/or ball and socket, and/or hook junctions may be initially held together by means, such as by a material such as a polymer, cement, adhesive, solder, and/or the like, which degrades in the physiologic environment, where the key and key hole, and/or key and lock, and/or ball and socket, and/or hook are configured to separate or form a gap once the means holding the junctions comes apart or degrades, or once the key and key hole, and/or key and lock, and/or hook junction is free from the material such as polymer, cement, adhesives, solder, e.g., in response to normal pulsations of the blood vessel or other body lumen, or other physiologic conditions described throughout this application. In one example, the key and key hole, and/or key and lock, and/or ball and socket, and/or hook junctions may be substantially held together by the geometry of the junction which restricts or substantially restrict movement of the junction in one or more directions sufficiently to allow for stent deployment and for the stent to have a strength sufficient to support a body lumen after deployment (initial deployment). In a preferred example such junction remains substantially held together upon deployment (expansion from crimped configuration to an expanded larger configuration) and wherein the stent has sufficient strength in the expanded configuration to support a body lumen. In this preferred example, the junction means to hold it together is the geometry of the junction such as the type of key and key hole, and/or key and lock, and/or ball and socket, and/or hook, and/or other type of junction. The separation region junction can also be a butt junction connecting and/or joining two ends of a stent structural element and/or a ring, said ends having various shapes and/or cross sectional shapes (including substantial shapes type) such as round, and/or ball, and or square, and/or rectangle, and/or a nerve synapse type junction, and/or other type shapes, and/or substantially such shape. In one example the deployment means such as balloon catheter provides for holding the discontinuities together upon deployment of the stent and wherein the stent is allowed to have controlled movement after deployment in one or more directions, preferably in the radial direction, after deployment, and wherein the stent has sufficient strength after deployment from a crimped configuration to an expanded larger configuration.

The separation regions in another example may also comprise a simple butt joint or overlapping sections of stent structural elements where the structural elements are solid wire (having various shapes such as substantially round, rectangle, and/or square, and/or nerve synapse, and/or other shapes), and/or hollow wire/tube structural elements (hollow at least in regions adjacent to the separation regions) having opposed free ends which are temporarily joined by means, such as an adhesive and/or connector and/or polymer and/or solder and/or sleeve which degrades and/or separate and/or discontinue in the physiologic environment. Such means can hold the free ends together by placing them between the free ends, adjacent to the free ends, covering the free ends, inside the hollow section of the free ends, and/or combination of all the above, of said structural elements.

In still other instances or examples, the separation regions may comprise notches or thinned sections formed in the circumferential rings and/or circumferential structural elements, where these notches or thinned sections will preferentially erode or fatigue in the physiologic environment, forming partial or complete separations which allow expansion of the circumferential rings thereafter. In still other embodiments or examples, the separation regions may comprise modifications to the material of the circumferential ring itself. For example, in metallic rings, the separation regions may have modified grain boundaries which are selected to preferentially break and/or erode (including corrode) in the physiologic environment when compared to the remaining regions of the circumferential ring. Other examples are joints may be formed beginning with an intact circumferential ring, forming one of more breaks in the ring, and thereafter rejoining the breaks with means such as sleeve, adhesives, solder, connectors, coating, and/or the like, which are configured to degrade or erode or fatigue or break or separate in the physiologic environment. For example, solder, adhesives and/or polymer may be applied to the butt and/or or overlapping and/or hollow ends of the resulting joint. Alternatively, connectors may comprise sleeves, rings, coils, or other circumscribing structure which holds the joint together until such structures degrade and/or separate in the physiologic environment. In a preferred example a sleeve or coating comprising a polymer such as parylene can be applied which allows the separate free ends of the joint and/or junction to be contained within such sleeve or coating.

In another example the stent comprising a non-degradable metal or metal alloy, said stent comprising a structure comprising a plurality of rings where the rings comprising struts joined by crowns where at least some of the rings have at least one crown and no more than ¾ of the number of crowns (preferably at least one and no more than ½ the number of crowns) are formed and/or patterned to have said crowns cross sectional area being smaller and/or smallest than the cross sectional area of an adjacent crown and/or the largest crown cross sectional area within said ring. Cross sectional area can be measured at approximately the peak of the crown and/or at any other point/section on the crown. The cross sectional area of the smaller (including smallest) crowns ranges from 25% to 90% smaller than an adjacent crown cross sectional area and/or the largest crown cross sectional area within said ring, (preferably 50% to 75% smaller). The cross sectional area of the smaller (including smallest) crowns ranges from 400 micron squared to 3000 micron squared, preferably ranges from 400 micron squared to 2500 micron squared, and more preferably ranges from 400 micron squared to 1500 micron squared, such smaller cross sectional area crowns allowing said crowns to open up further after expansion. The smaller (including smallest) crowns can optionally have a sleeve, and/or coating, and/or solder comprised from polymer and/or adhesive and/or other material to hold the crown (and/or struts joined by said crown) in a crimped or substantially crimped configuration upon deployment of the stent, and where the sleeve and/or coating and/or solder degrade and/or dissolve and/or loosen after deployment (expansion) allowing the stent to further expand as the smaller cross sectional crowns are allowed to open and/or expand under physiologic conditions. The stent has sufficient strength upon deployment to support a body lumen. In another example the stent has sufficient strength to support a body lumen upon deployment where the stent strength decreases after the sleeve, and/or coating, and/or adhesive, and/or solder, dissolves and/or degrades under physiologic conditions after deployment. The cross sectional area of at least ¼ to ¾ of the crowns, preferably at least ½ to ¾ of the crowns, more preferably at least ¾ of the crowns, ranges from 3500 micron squared to 25000 micron squared, preferably ranges from 4000 micron squared to 10,000 micron squared, and more preferably ranges from 4500 micron squares to 8000 microns squared. The cross sectional area measurements in the above example are of same type (or same) non-degradable material (metal or metal alloy material) of the stent or structural element such as the crown and does not include other materials such as polymers, metals, coatings, etc. that are on or within the crown, when comparing smaller cross sectional area crowns to larger cross sectional area crowns. Alternatively, smaller cross sectional area crowns can be accomplished by incorporating a different material from the non-degradable metal or metal alloy in the crown region, or having less dense or weaker material, and/or having one or more of a groove, a hole, a dent, a crescent shape, a crown shaped, and/or a channel, in, on, and/or through the crown region. The groove, the hole, the dent, the crescent shape, the crown shaped, and/or the channel in, on, and/or through the crown region can be filled and/or coated with at least one material comprising a polymer, metal or metal alloy (preferably different from metal or metal alloy forming the stent), adhesive, and/or solder, and/or other suitable material. In this example the smaller cross sectional area is accomplished by having a softer or weaker or less dense material or gap in the crown region which effectively reduces the cross sectional area of the non-degradable metal or metal alloy in the crown (even though the total cross sectional area of said crown maybe similar to other crown cross sectional areas) compared to cross sectional area of same type metal or metal alloy in adjacent crown (or larger cross sectional area of same type metal or metal alloy). The material preferably is different from the crown material. The material can remain in the crown region, dissolve, and/or degrade/erode after deployment to allow the stent to uncage and/or further expand under physiologic conditions. The stent upon deployment has sufficient strength to support a body lumen and where the stent strength does not decrease after deployment, or decreases after deployment, preferably decreases within 30 days after deployment, more preferably decreases within 3 months after deployment, and/or within one year after deployment. The material has lower stiffness than the crown material (preferably 2-10 times lower stiffness), softer, stretchable, and/or lighter than the crown material. The said crowns can have in one example a sleeve and/or a coating and/or adhesive containing said crown region and/or struts joined by said crowns. In another example, the stent exhibit increase in radial strain after expansion, and/or decrease in radial strength after said expansion. In another example, said increase of radial strain and/or decrease in strength, begins one week after expansion of the stent to 9 months after expansion of the stent, preferable begins one month after expansion to 6 months after expansion, more preferably begins 2 months after expansion to 6 months after expansion. In another example at least some struts have thinned cross sectional areas as described in this paragraph, In another example, the stent formed from non-degradable metal or metal alloy is patterned to have one or more regions on at least some rings or other structure "hollowed out" to create void regions or "voids" within the crown, strut, or other structural component of the stent scaffold where the metal has been removed, e.g. by patterning, cutting (such as laser cutting), abrading, or the like. Optionally, the voids may be entirely or partially filled with a degradable or non-degradable filling material which contributes to the strength of the scaffold for at least a time after implantation so that the scaffold has sufficient initial strength to support a body lumen. The filling material may be more or less stiff than the metal or metal alloy material of the stent, or in some cases may have an equivalent stiffness. The void may be completely filled, partially filled, or in some cases over-filled so that the filler material extends beyond the boundary of the stent scaffold prior to void formation.

Such filled-voids on crown regions for example will deform upon expansion of the stent and allow the compliance and strength of the stent to vary over time. In many examples, the filled-voids on the crowns will enhance strength of the scaffold at the time of expansion and implantation, but will also reduce compliance. By using a filler material that degrades, softens, or otherwise loses strength when exposed to a vascular or other physiologic environment, however, the compliance of the scaffold will increase which in turn increases the composite or composite compliance of the stent and blood vessel or other body lumen. While the strength may concurrently decrease, such reduction in strength is usually acceptable after the vessel or other body lumen has been opened and the luminal wall at least partially healed. In this way, at least some rings of the stent to uncage, to further expand, and/or to exhibit vaso-reactivity. The thickness of the metal or metal alloy surrounding the hollowed-out or void region in the crown regions (side surface region, luminal surface region, or abluminal surface region) ranges from 10 microns to 50 microns, preferable ranging from 20 microns to 40 microns. The hollowed out crown region can have a variety of ways to be hollowed out such as: two side surface regions of the crown region remain intact and the region between the two side surface regions is hollowed out, one side region and a luminal surface region remain intact while the other side region and abluminal surface region is hollowed out, two side surface regions and a luminal surface region remain intact while the abluminal surface region gets hollowed out, all surface region (abluminal, luminal, 2 sides) remain intact but the inner core of the crown region is hollowed out, and/or one side region, the abluminal surface region, and luminal surface region remain intact while the core gets hollowed out from the other side surface region, or other; such that the crown region allows uncaging of the stent after expansion. The combined total cross section area of the non-degradable metal or metal alloy for the said one or more crown regions at at least one section of the crown region ranges from 200 micron squared to 4000 micron squared, preferably ranges from 400 to 3000 micron squared, and more preferably ranges from 500 to 2500 micron squared. In another example, the hollowed-out region is filled with another material (degradable or non-degradable), wherein the material after expansion allows the crown region, the ring, and/or the stent to uncage, and/or to have increase in radial strain, and/or to have increase in radial strain and decrease in radial strength. In another example, at least some of the struts along at least some rings are hollowed out as described in this section.

Voids may also be formed in the struts, and other components of a scaffold ring or other scaffold structure. For example, channels, slots, and the like can be formed over some or all of a length of at least some rings, including struts, crowns, and any other structural components. As with other voids described previously, the channels, slots, and the like may be partially or fully filled with a second degradable polymeric or metallic material, referred to herein as a "reinforcement material," to provide sufficient combined material strength to enhance the radial strength of the stent immediately following expansion, wherein the reinforcement material typically degrades after expansion and implantation to enhance compliance while typically also reducing stent strength. The base non-degradable material of the struts, and other components of a scaffold ring or other scaffold structure will typically have a cross-sectional area in a range from $1000\ \mu m^2$ to $4000\ \mu m^2$, preferably from $1500\ \mu m^2$ to $3500\ \mu m^2$, where the degradable reinforcement material covering all or portions of the non-degradable material adds an additional $40\ \mu m$ to $120\ \mu m$ to a thickness and/or a width of the scaffold base material component, and wherein the combined base and covering reinforcement materials have sufficient strength to support a body lumen (and prevent recoil in vascular lumens) upon expansion, and wherein the compliance increases and strength in at least some rings decreases following expansion and implantation to uncage the stent. Channel depths are typically from 40% to 90% of the non-degradable material thickness, preferably from 50% to 85%, and more preferably from 60% to 80%, and the widths of the channels and slots are typically from 40% to 90% of the non-degradable material width, preferably 50% to 85%, more preferably 60%-80%. Channel and slot widths and thickness can vary along the length of the channels and slots on at least some rings. Channels may be disposed on abluminal surface regions, luminal surface regions, and/or both abluminal and luminal surface regions. Slots will typically penetrate from an abluminal surface to a luminal surface.

One or more thinned regions may alternatively or also be formed be along some or all of the rings or other circumferential elements of a non-degradable scaffold in order to increase scaffold compliance and promote uncaging of the scaffold after implantation. Such thinned out regions may be present in crown regions, strut regions, or on other components of a ring or other structure that affects circumferential compliance. By "thinned out," it is meant that a crown, strut, or other scaffold component has baseline cross-sectional dimensions over a majority of a length of that component, and that the baseline cross-sectional dimensions are reduced in a region is referred to as being "thinned out." Thinned-out regions can be located in adjacent crowns, in alternating crowns, in every third crown, or in other patterns or configurations to achieve sufficient strength to support a body lumen upon deployment and to increase compliance after expansion. Such thinned out regions can have a smaller thickness and/or width and/or cross section relative to the baseline dimensions sufficient to promote uncaging after implantation. Without any further modification, the thinned out regions will usually provide both lower scaffold strength and an increased compliance in at least the thinned out region of the component. Optionally, the thinned out regions can be reinforced with a coating, lamination, or other coupling of a reinforcement material to provide strength upon expansion while usually degrading after expansion to increase compliance. Such bio-degradable reinforcement materials can be similar to the filler materials described elsewhere herein, typically being degradable polymers but also being degradable metals. Suitable reinforcement materials will degrade over a time period after implantation in or expose to a vascular environment ranging from 30 days to 3 years, preferably from 3 months to 2 years, more preferably from 3 months to 1 year. The base non-degradable material (base stent), usually metal or metal alloy comprises one or more rings (or circumferential structural elements), usually a plurality of rings, each ring comprises struts and crowns along the length of said ring, and wherein the base stent in some examples does not have sufficient strength to support a body lumen (or to maintain a body lumen) in the absence of a reinforcement material coupled to the base stent, said reinforcement material having sufficient weight and thickness (such as a polymer coating) to increase the strength of the base strength to being sufficient to support a body lumen (or maintain a body lumen open).

For example, thinned-out cross-sectional regions along a length of a circumferential ring may be coated, laminated, or otherwise covered with sufficient reinforcement material to reinforce the stent scaffold upon expansion where the stent strength decreases and compliance increases as the material degrades after expansion and exposure to a vascular or other luminal environment. The scaffold may be formed from a non-degradable base material component having a cross-sectional area in a range from 1000 µm² to 4000 µm², preferably from 1500 µm² to 3500 µm², wherein the degradable reinforcement material covering the non-degradable material adds additional 40 µm to 120 µm to a thickness and/or a width of the scaffold base material forming an underlying component, and wherein the combined base and covering materials have sufficient strength to support a body lumen upon expansion, and wherein the compliance increases and strength in at least some rings decreases following expansion and implantation to uncage the stent.

In another example in any of the examples in this application, the stent prosthesis exhibits one or more of the following: uncages after expansion (which also includes one or more of the following): increase in radial strain (or compliance), increase in radial strain (or compliance) and decrease in radial strength, exhibit vaso-reactivity or vas-dilatation of the stented segment, further expand to a second larger configuration, being able to expand and/or contract after deployment, change in the shape configuration from the deployed shape configuration, change in the displacement of the stent in at least one dimension, have a displacement after expansion in at least one direction larger.

Suitable stent material including polymeric, metallic (matel and metal alloys), adhesives, coatings, solder, sleeves, sealants, fixation materials, cement, energy fixation, include but are not limited to the following: adhesives and fixation materials include but are not limited to adhesives, sealants, and potting compounds such as cyanoacrylate such as polyalkyl-2-cyanoacrylate, methyl-2-cyanoacrylate, ethyl-2-acrylate; n-butyl cyanoacrylate, 2-octyl cyanoacrylate, or others; epoxy; epoxamine; UV-curable from Loctite, Dymax, Master Bond, or other; acrylic; silicone; hot melt; polyurethane; gorilla glue; lysine based adhesive such as TissueGlu, Sylys Surgical Sealant, or others; fibrin glue; beeswax. Other fixation materials may also be used, such as solder or fusible alloy material such as tin or its alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.51n4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as B57Sn42Ag1, Bi58Sn52, or others; gold or its alloy such as Au80Sn20, Au98Si2, Au87.5Ge12.5, Au82In18, Other means for fixation includes laser bonding or welding or fusing, or other means of energy fixation (including bonding or joining), or solvent based, polymer dispersion or neat adhesives, sealants, and potting compounds such as cyanoacrylate such as polyalkyl-2-cyanoacrylate, methyl-2-cyanoacrylate, ethyl-2-acrylate; n-butyl cyanoacrylate, 2-octyl cyanoacrylate, or others; epoxy; epoxamine; UV-curable from Loctite, Dymax, Master Bond, Henkel, or other; acrylic; silicone; hot melt; polyurethane; gorilla glue; polyester; polylactide and their copolymers and blends; polytrimethylene carbonate and their copolymers or blends; polyvinyl alcohol; polyvinyl acetate; ethylene-vinyl acetate (a hot-melt glue); phenol formaldehyde resin; polyamide; polyester resins; polyethylene (a hot-melt glue); polypropylene; polystyrene; Polycarbonate; polychloroprene; natural rubber; silicone rubber; lysine based adhesive such as TissueGlu, Sylys Surgical Sealant, or others; fibrin glue; beeswax; bioadhesives such as casein, mussel adhesive proteins, and collagen, combination thereof, or the like, solder or fusible alloy material such as tin or its alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.51n4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as B57Sn42Ag1, Bi58Sn52, or others; gold or its alloy such as Au80Sn20, Au98Si2, Au87.5Ge12.5, Au82In18, combination thereof, or the like. Suitable stent materials non-degradable in the vascular or other physiologic environment include but are not limited to metals and metal alloys, such as stainless steel, such as 304V, 304L, and 316LV stainless steel; steel alloys such as mild steel; cobalt-based-alloys such as cobalt chrome; L605, Elgiloy®, Phynox®; platinum-based alloys such as platinum chromium, platinum iridium, and platinum rhodium; tin-based alloys; rhodium; rhodium based-alloys; palladium; palladium base-alloys; aluminum-based alloys; titanium or their alloy; rhenium based-alloys such 50:50 rhenium molybdenum; molybdenum based-alloys; tantalum; gold and gold alloys; silver and silver alloys; shape memory metal or alloys; chromium-based alloys; nickel-titanium alloys such as linear-elastic and/or super-elastic nitinol; nickel alloys such as nickel-chromium-molybdenum alloys (e.g., INCONEL 625, Hastelloy C-22, Hatelloy C276, Monel 400, Nickelvac 400, and the like); nickel-cobalt-chromium-molybdenum alloys such as MP35-N; nickel-molybdenum alloys; platinum enriched stainless steel; combinations thereof; or the like, and other malleable metals of a type commonly employed in stent and prosthesis manufacture. In other examples, the non-degradable material may comprise a non-degradable polymer, such as polyaryletherketone; polyetheretherketone; polyimide, polyethylenes such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; poly-vinylchloride; acrylobutadiene styrene; Delrin; polymethylmethacrylate; polystyrene; polyacrylamide, polyphenylsufide; PEBAX; or other materials. In still other examples, the non-degradable material may comprise an elastic metal, such as a shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based-alloys such as Fe—Mn—Si; copper-based-alloys such as Cu—Zn—Al and Cu—Al—Ni; poly(ε-caprolactone)dimethacrylate; PVDF/PMMA; PVDF/PVA; PLA/PVAc; or other, or the like. Examples of degradable material such as degradable polymeric material comprise one or more of: lactides, caprolactones, trimethylene carbonate, glycolides, poly(L-lactide), poly-DL-Lactide, polylactide-co-glycolide (e.g., poly(L-lactide-co-glycolide), copolymer of poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly-caprolactone, poly (glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids, polymers, blends, and/or co-polymers, or combination thereof.

In another example, suitable materials including suitable stent material including polymeric and metallic (degradable or non-degradable), adhesives, coatings, solder, sleeves, sealants, sealants, potting compounds, fixation materials, cement, energy fixation, elastomers and other type material, include but are not limited to: adhesives such as cyanoacrylate such as polyalkyl-2-cyanoacrylate, methyl-2-cyanoacrylate, ethyl-2-acrylate; n-butyl cyanoacrylate, 2-octyl cyanoacrylate, or others; gorilla glue; lysine based adhesive such as TissueGlu, Sylys Surgical Sealant, or others; fibrin glue; beeswax. Non-degradable adhesives, sealants, and potting compounds such as epoxy; epoxamine; UV-curable from Loctite, Dymax, Master Bond, or other; acrylic; silicone; hot melt; polyurethane; Degradable sleeve materials, stent material, and coatings such as polyester; polylactide and their copolymers and blends; copolymers of lactide, caprolactone, trimethylene carbonate, glycolide; poly(L-lactide), poly-DL-Lactide, polylactide-co-glycolide (e.g., poly (L-lactide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. Corrodible solder or fusible alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.5In4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as Bi57Sn42Ag1, Bi58Sn52, or others. Non-corrodible solder or fusible alloy such as gold or its alloy such as Au80Sn20, Au98Si2, Au87.5Ge12.5, Au82In18. Degradable and non-degradable polymers include: polyester; polylactide and their copolymers and blends; copolymers of lactide, caprolactone, trimethylene carbonate, glycolide; poly(L-lactide), poly-DL-Lactide, polylactide-co-glycolide (e.g., poly(L-lactide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. polyvinyl alcohol; polyvinyl acetate; ethylene-vinyl acetate (a hot-melt glue); phenol formaldehyde resin; polyamide such as nylon 12, nylon 6, nylon 6-6, or others; polyester resins; polyethylene (a hot-melt glue), UHMW, HDPE, LDPE, or others; polychloroprene; polyaryletherketone; polyetheretherketone; polypropylene; polystyrene; polyester; polyethylene terephthalate; polycarbonate; polysulfone; polyphenylsulfone, polyethersulpone, Ultem; polyetherimide; polyurethane; polyvinylchloride; PTFE; FEP; ETFE; PFA; PVDF; polyvinylchloride; acrylobutadiene styrene; polyacetal such as Delrin; polymethylmethacrylate; polystyrene; polyacrylamide, polyphenylsufide; PEBAX; and/or co-polymers, and/or combination thereof. Elastic non-absorbable polymeric or elastomers such as silicone rubber; C-flex; poly(n-butylmethacrylate); poly(n-butylmethacrylate) blended with poly(methamethacrylate), Poly(hexyl methacrylate), and polyvinylpyrrolidone; Kraton; poly(styrene-ethylene/butylene-styrene) (SEBS); poly (styrene-ethylene/propylene-styrene) (SEPS), poly(acrylic acid-b-styrene-b-isobutylene-b-styrene-b-acrylic acid; poly (styrene-b-isobutylene-b-styrene); polybutadiene; PVDF-HFP poly(vinylidene fluoride-hexafluorpropylene); polyvinylpyrrolidone; poly(ethylene-co-vinyl acetate); phosphorylcholine; PEBAX; polyurethane elastomers; Tecoflex; Biomer; Pellethane; corethane; silicone rubber; rubbers; elastomers; blends; copolymers; combination thereof; or the like. Non-corrodible elastic metal or metal alloys such as shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based alloy such as Fe—Mn—Si; copper-based alloy such as Cu—Zn—Al and Cu—Al—Ni; or the like. Metals or metal alloys that have high initial strength and weaken over time include Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230. Non-corrodible (non-degradable) metals or metal alloys such as conventional titanium alloys such as Ti6Al4V, Ti5Al2.5Sn, or Ti-10V-Fe-3Al; stainless steel such as SAF2507; platinum metal and its alloys; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy (degradable); shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hatelloy C276, Monel 400, Nickelvac 400, and the like); nickel-cobalt-chromium-molybdenum alloy such as MP35-N; Nickel Alloys such as Ni21Cr17Mo or Haynes 230; or other; nickel-molybdenum alloy; platinum enriched stainless steel; combination thereof; or the like. Corrodible metals or metal alloys (degradable) include nickel, cobalt, tungsten; tungsten alloys of rhenium, cobalt, iron, zirconium, zinc, titanium; magnesium, magnesium alloys, magnesium alloy AZ31, magnesium alloy with less than 20% zinc or aluminum by weight, without or with one or more impurities of less than 3% iron, silicone, manganese, cobalt, nickel, yttrium, scandium or other rare earth metal, AZ31B or MG11li5Al1Zn0.034Sc (LAZ1151); zinc or its alloy such as zinc alloys such as Zn5al, Zn10Al, Zn18Al, Zn30Al; bismuth or its alloy; indium or its alloy, tin or its alloy such as tin-lead, Sn3.9Ag0.6Cu, Sn-3.8Ag-0.7Cu, SnPb, or SnPbAt; silver or its alloy such as silver-tin alloy; cobalt-iron alloy; iron or its alloys such as 80-55-06 grade cast ductile iron, other cast ductile irons, AISI 1010 steel, AISI 1015 steel, AISI 1430 steel, AISI 8620 steel, AISI 5140 steel, Fe29.7Mn8.7Al1C, 30HGSA alloy steel, 4140, C45 steel, Fe36Ni, low carbon steel or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In another example or aspect, the present invention provides non-degradable prostheses having rings with energy-responsive separation regions. Such endoluminal prostheses comprise a scaffold having circumferential rings patterned from a non-degradable material, where the scaffold is configured to expand from a crimped configuration to an expanded configuration. At least some of the circumferential rings will have separation regions configured to form one or more discontinuities in said circumferential rings in response to energy applied to the separation regions after deployment, and/or after implantation of said prosthesis in a body lumen. Such discontinuities allow the scaffold to uncage and/or further expand, e.g. beyond an initial expansion diameter after recoil if any, typically achieved by balloon expansion, self-expansion, or the like.

The energy which promotes or causes the discontinuity may be energy associated with the site of implantation or may be energy from an external source directed at the site of implantation. For example, the separation regions may be configured to fatigue in response to, introduction of a drug agent, and/or pulsation of a blood vessel or other body lumen in which the endoluminal prosthesis has been implanted. Alternatively, the separation regions may be configured to respond to external energy which results in heat and/or mechanical motion, e.g., vibration, of the separation region. In particular, such motion-responsive separation regions may comprise notches, thinned regions, junction, butt joints, key and lock designs, or other localized regions or foci which in one example preferentially fatigue and breaking response to the applied energy and/or pre-formed separation regions which discontinue in response to the applied energy. For example, the separation regions may comprise "living hinges" which cycle open and close in response to the pulsation or application of external energy and separate or eventually fatigue and break. In still other examples, the separation regions may comprise modified grain boundaries in metal rings, where the grain bodies are particularly susceptible to vibration-induced fatigue.

In other embodiments or examples, the separation regions may comprise pre-formed breaks or pre-formed separations regions in the circumferential rings, where those breaks or discontinuities are reconnected with connectors configured to open in response to applied or endogenous energy (or in response to physiologic condition). Typical forms of externally applied energy include ultrasound, drug agents, heat, magnetism, radio frequency energy, high intensity focused ultrasound (HIFU), and the like.

In other examples and/or embodiments, the separation regions may comprise a key and lock junction formed in the circumferential rings and/or circumferential structural elements, where the key and lock junctions are initially immobilized before or during expansion or upon expansion but configured to open in response to applied energy, or physiologic condition, either external or endogenous. In still other examples or embodiments, the separation regions may comprise a rivet or other fastener joining breaks in the circumferential elements, where the fasteners are configured to open in response to applied energy, either external or endogenous, or in response to physiologic conditions.

In another example and/or fourth aspect, the present invention provides non-degradable or slowly degradable prostheses having rings with constrained hinges and methods for their use and fabrication. An endoluminal prosthesis comprises a scaffold as having a circumferential ring pattern from a non-degradable material. The scaffold is configured to deploy from a crimped configuration to an expanded configuration, and the circumferential rings have hinges which open as the scaffold is being deployed and/or after deployment. At least some of the hinges on at least some of the rings are constricted from expansion during deployment and are configured to open in response to a physiologic environment or application of external energy after deployment. Particular physiologic environments and external energies which can release the hinges from constriction have been well described above or throughout this application.

In one example, by initially constraining at least some of the hinges of the circumferential rings, the scaffold will be initially expanded to a diameter which is appropriate for the body lumen being treated and will possess sufficient strength to maintain patency of that body lumen while still in its configuration with the constrained hinge(s). After deployment and/or over time, however, the initially constrained hinges will be released from constraint, which lowers the effective circumferential rigidity of the scaffold. That is, with the addition of more hinges or other expansion regions, the force required to incrementally open the scaffold, preferably beyond its initially expanded configuration, will be lowered. In this way, the endoluminal prosthesis will have a reduced energy to cage or jail the treated body lumen, thereby allowing the scaffold to enlarge and/or lumen to enlarge.

In another example or aspect, the present invention provides a non-degradable prosthesis having rings with joint or active joints and methods for their fabrication and use. An endoluminal prosthesis comprises a scaffold having circumferential rings patterned from a non-degradable material. This scaffold is configured to deploy from a crimped configuration to an expanded configuration, and the circumferential rings include struts connected by joints which open as the scaffold is being deployed, typically by balloon expansion. At least some of the joints will be pivoted to allow the scaffold in its expanded configuration to uncage and/or further expand. The pivots or "active joints" may in some cases be asymmetric. That is, the joints will allow radial expansion of the circumferential rings, but will limit radial contraction of the rings.

In different embodiments or examples, the shapes of the reinforcing elements or bridging element can be substantially round (solid round wire or hollow round wire), rectangular, square, egg-shaped, or other shapes and geometries. The size of the reinforcing elements in some examples may be substantially the same size/geometry as the hinges, expansion regions, and/or struts to which the reinforcing elements are coupled, while in other examples the size/geometry of the reinforcing elements may be smaller or larger than the expansion regions. In one example, the ends of the reinforcing elements are atraumatic, and/or smooth, and/or have bulbous shapes or rounded shapes, and/or have larger cross sectional area to reduce trauma to the vessel. In one example a surface finish of the reinforcing elements is similar to that of a polished vascular metallic stents. In another example, the surface finish is textured.

In one example of degradable material, the polymeric body of the circumferential scaffold is configured to substantially degrade under physiologic conditions within a period from 1 month to 3 years, preferably from 3 months to 2 years, more preferably from 6 months to 1 year, after deployment of the endoluninal prosthesis. In another example, the reinforcement elements are encapsulated at least in part by a material, such as a thin polymer material. Examples include Parylene and C-Flex material.

In another example, the separation regions of a non-degradable scaffold are configured to separate in a period of up to 3 years after deployment, typically ranging from 1 day to 3 years, 1 month to 3 years, preferably from 3 months to 2 years, more preferably from 6 months to 1 year. In one example the separation region separate about the same time period, in another example the separation regions separate at different time periods.

In another example the endoluninal prosthesis further comprises at least one coating, preferably a degradable coating, on at least one surface of the stent prosthesis (scaffold prosthesis). In another example the stent prosthesis further comprises at least one drug on at least one surface of the stent prosthesis. In another example the stent prosthesis further comprises at least one coating containing at least one drug, on at least one surface of the stent prosthesis. In a preferred example, the polymeric material or adhesive joining or containing or holding together the separation regions are stretchable type polymers or adhesive materials (degradable or non-degradable) to allow no movement to some movement of the separation regions without prematurely forming the discontinuities (before deployment, or after deployment). This also allows for consistent performance of the scaffold and improved storage conditions and shelf life of the stent and separation regions to allow for extended shelf life under various typical environmental conditions of heat, humidity, and time. The material can withstand temperature ranging from 5° Celsius to 50° Celsius, preferably from 10° Celsius to 40° Celsius, and from 1 months to 3 years shelf life, preferably from 1 month to two years, or from one month to 18 months. At relative humidity from 10% to 95%, preferably from 20% to 70% relative humidity. Examples of material are described in this application.

In one example the endoluminal prosthesis further comprises radiopaque markers. In a more specific example the radiopaque markers comprise non-degradable radiopaque marker. In a preferred example the non-radiopaque radio markers comprises a metal or metal alloy.

In one example the reinforcing elements and/or the separation regions and/or the environmentally responsive separation regions are formed from non-degradable materials such as non-degradable metals and/or polymers or other material. The reinforcing elements and/or the separation regions and/or environmentally responsive separation regions may alternatively be formed in whole or in part from a degradable (corrodible) material, such as a degradable metal (such as magnesium and magnesium alloys), or a degradable polymer (such as a lactide polymer, co-polymer, and blends thereof); or a combination thereof. In one example the reinforcing elements and/or separation regions and/or environmentally responsive separation regions are formed from a corrodible material which corrode after implantation to uncage the stent or other endoluminal prosthesis, preferably uncaging the stent prosthesis without formation of unwanted by products such as hydroxyapatite materials adjacent to the separation region.

In one example, the endoluminal prosthesis is a stent prosthesis comprising a substantially tubular structure, the tubular structure is patterned, the stent prosthesis comprises separation regions, and the stent prosthesis is crimped to a smaller diameter, and being deployed from the crimped configuration to a larger expanded configuration, where the stent in the expanded larger configuration has sufficient strength to support a body lumen and/or does not fracture and/or has low recoil. The stent after deployment in this example is configured to do one or more of the following: the stent and/or circumferential structural elements and/or rings are configured to separate, expand, form discontinuities, and/or come apart at least in one section and/or region or more after deployment and/or after implantation, and/or the stent undergoes modification comprises unlocking, degradation, or containment by a sleeve or material that does not prevent the separation region from uncaging, of the separation region or material adjacent to the separation region after deployment or implantation causing at least one part of the stent structures and/or to separate, expand, and/or come apart, and/or the stent expands further after deployment, and/or the stent expands further after deployment and after modification, and/or the stent expands further after deployment radially, and/or the stent expands circumferentially after deployment, and/or the stent expands further after deployment and after assisted modification from a source (chemical, energy), and/or the stent is configured to push the lumen to expand for a period after deployment or implantation, and/or the stent is configured to allow the lumen or vessel to expand/enlarge, or a combination thereof. The stent comprises a non-degradable material, or comprising two non-degradable materials, or comprising a degradable material, or comprising two degradable materials, or comprising two degradable materials and one non-degradable material, or comprising non-degradable material and a corrodible material, or comprising a degradable material and a corrodible material, or comprising a degradable material, and a corrodible material, and a non-degradable material. The stent may further comprise at least one coating on at least one surface of the stent prosthesis, said coating is degradable and/or non-degradable coating. The materials above exclude marker material(s) that can be degradable or non-degradable. The stent may further comprise at least one drug on at least one surface of the stent. The stent can also comprise at least one coating on at least one surface of the stent prosthesis.

In one example, the stent prosthesis comprises a structure, preferably substantially tubular structure, more preferably substantially tubular patterned structure having separation regions. The stent prosthesis is typically expandable from a crimped configuration to a deployed expanded larger configuration. The stent structure comprises at least one main or principle material on at least one section of the stent, preferably the frame material is degradable material such as a polymer material, and the stent structure further comprises at least one piece of a second material, preferably a stronger material than the frame material, more preferably a metal material, more preferably a non-degradable metal material, interfacing with or coupled to at least said section of the frame material, preferably said section is a crown section of the stent structure. The stent is deployed to a larger expanded configuration. The stent in the expanded deployed configuration has sufficient strength to support a body lumen, and/or expand without fracture, and/or expand with low recoil. The stent undergoes modification after deployment where the modification comprises degradation of at least part of the frame material, and/or degradation of at least part of the second material, and/or corrosion of at least first material, and/or corrosion of at least part of the second material, or combination thereof. The stent after modification comprises one or more discontinuity in at least one ring, and/or at least one discontinuity in at least one crown, and/or at least one discontinuity in at least one strut, and/or a combination thereof. In another example the stent after modification has at least one discontinuity in at least part of the frame material, and/or at least one discontinuity in at least part of the second material, and/or at least one discontinuity in adjacent parts of the frame and second material. In another example, the stent after modification further expands to a larger configuration from the configuration before modification, and/or further expands to a larger configuration from the deployed configuration, and/or further expands to a larger configuration from a "recoil after deployment" configuration, and/or further expands to a larger configuration for any of the previous causes in at least one ring of the stent prosthesis, and/or further expands to a larger configuration in at least one ring other stent prosthesis wherein the ring is located about the mid portion of the stent length. In another example, the at least one discontinuity of at least one ring of said stent after modification allows the stent to further expand at said at least one ring under physiologic pressure. In another example, the stent prosthesis comes apart after deployment and/or modification in at least one ring, crown, and/or strut. In one example the stent prosthesis after deployment and/or after modification and/or after coming apart has a structure, and/or has a tubular structure, and/or has a tubular patterned structure, and/or has a substantially maintained tubular structure, and/or has at least part of a structure, and/or has a at least one window, and/or substantially has no structure, and/or comprises at least one crown structure, and/or comprises at least one strut, and/or comprises at least one link, and/or has a strength, and/or a combination thereof.

In a particular example, the stent comprises a substantially tubular patterned structure comprising a plurality of rings, (serpentine, diamond, zig-zag, and/or other open cell or closed cell structure), wherein the ring comprises crowns and struts, wherein at least some rings are connected to adjacent rings by at least one link, or in some cases some adjacent rings are connected together in at least one location.

In an example a scaffold or ring material comprises metal and/or metal alloy. The metal and/or metal alloy may be non-degradable or degradable/corrodible. The metal herein excludes markers and marker material which can be metal or metal alloy and can be degradable or non-degradable. The corrodible metal or metal alloy corrodes in a period ranging from 1 month to 10 years, preferably in a period ranging from 3 months to 5 years, and more preferably in a period ranging from 3 months to 3 years.

In an example the second material (or reinforcement elements) has at least two ends, wherein the ends are deburred, shaped into a ball, a shape like a "nerve synapse," and/or smoothed, to prevent injuring the lumen or vessel, and/or causing inflammation after the stent come apart, and/or after modification. In another example the stent is configured to not break apart other than in the separating region and/or the section configured to break apart by reducing stress areas and/or fatigue areas, on the stent after modification, and/or after separation of the separation region forming discontinuities and/or breaking apart of the stent.

In an example the main or frame material comprises a polymeric material. The polymeric material may be degradable or non-degradable. In one example the polymeric material degrades in a period ranging from 1 month to 10 years, preferably ranging from 3 months to 5 years, more preferably degrades in a period ranging from 3 months to 3 years.

In an example the main or frame material is non-degradable, and/or degradable at a faster rate than the second material (reinforcement elements), and/or degradable at a substantially the same rate as the second material, and/or degradable at a slower rate than the second material.

In an example, the stent in any of the examples and/or embodiments in this application is formed from one or more of the following: a tube, a continuous wire or filament, a wire, a hollow wire hollow either hollow entirely or in certain regions such as less stress regions and/or substantially straight regions, or a braid, or mold, or by printing, or by extrusion, or by spraying, or by dipping, or by stamping, or a combination thereof. The stent has separation regions formed before patterning, during patterning, or after patterning, or after treatment to form such separation regions and/or discontinuities. Means to hold said discontinuities are describes throughout this application.

In an example, a second reinforcing material coupled to or interfacing with a structural scaffold material is embedded entirely inside the frame, or at least one surface or surface region is embedded inside at least one surface or surface region of the frame, or at least two surfaces embedded inside at least one surface of the frame, or at least three surfaces embedded inside at least one surface of the frame, or at least one surface of the second material attached (and/or joined, and/or abut, and/or glued, and/or force fit) to at least one surface of the frame material. The at least one surface of the frame material may be an abluminal surface, may be the luminal surface, or may be a side surface of the frame material. The second material may be sandwiched within the frame material. In one example the second material has a discontinuity, where the second material discontinuity is held together or joined together by said frame material, and/or glue, and/or a coating.

In an example, the second reinforcing material may in the form of one or more pieces comprising one or more of a wire, ribbon, strut, crown, link, and/or filament. A cross-section of the piece(s) may have any one of a variety of shapes comprising round or substantially round, rectangle or substantially rectangle, square or substantially square, oblong or substantially oblong, egg shaped or triangle, or other shapes. The length, number, and location of the pieces vary and maybe at least one or more on at least one or more stent rings, ranging from the length of a stent strut or smaller, the length of a stent crown or smaller, the length of a stent link or smaller, and/or the length of a stent ring or smaller. Preferably, the pieces of the second material are on/in/around at least one stent crown in at least one stent ring, and/or on/in/around at least two stent crowns in at least one stent ring, and/or on/in/around substantially all stent crowns or part of a stent crown in at least one stent ring of the stent, and/or on/in/around all except one of a stent crown on at least one stent ring, and/or on at least one ring, on/or on at least one ring about the middle of the stent length, and/or on at least one window of the stent patterned structure, and/or on at least one strut or part of a strut, and/or on at least one link or part of a link, and/or other variety or combination thereof. In one example a patterned stent structure comprises plurality of windows each window comprises reinforcing material comprising at least two crown, and at least four struts. In another example the window comprises at least four crowns, and at least four struts, and at least one or at least two links. In another examples links maybe straight, and/or or have shapes such as S-shaped link, V-shaped link, M-shaped link, and/or other link shapes. In an example, at least one structural element (comprising crown, strut) in each window has a separation region configured to expand and/or have a discontinuity and/or separate. In another example, the structural element comprises a plurality of circumferential rings comprising one or more windows, wherein each window has at least one separation region configured to expand and/or have a discontinuity and/or separate.

In a preferred example it is desired to have a stent structure having separation regions, wherein the stent after deployment forms discontinuities in said separation regions (or such discontinuities are formed before deployment and held together by means of design geometry or deployment means such as balloon catheter), or other type of embodiments of this application, wherein the stent structure is substantially maintained after said separation regions come apart (or separate), and/or move in one or more direction. The benefit of having a stent structure, preferably along the length of the stent length or part of the stent length, helps prevent vulnerable material underneath the stent such as vulnerable plaque from rupturing into the blood vessel and causing harm. The stent structure is sufficient to prevent (or hold) a vulnerable material (such as vulnerable plaque) in a body lumen. In another example, the stent structure after deployment and/or after coming apart and/or after forming discontinuities is substantially sufficient to support a body lumen. In another example, the stent structure after deployment and/or after coming apart and/or after forming discontinuities is substantially sufficient to support a body tissue.

In one example the at least some structural elements of the stent uncage and/or come apart and/or have separation regions comprises one or more of un-fix, un-hold, un-done, un-latched, un-attach, detached, disconnected, break up, break apart, push, push apart, separate, pull apart, create a gap, create a space, disintegrate, corrode, degrade, fragment, fracture, shatter, splinter, decompose, unlock, break down, deteriorate, degenerate, decay, discontinue, become free, and/or combination thereof, of said stent or said stent structural element, as formed, after treatment (including modification), and/or after deployment, under physiologic conditions. Stent structural elements in one example comprises one or more of rings, crowns, struts, and/or links. Stent structural elements in another example comprises one or more of rings, said rings comprise crowns, and/or struts.

In an example, the stent prosthesis is deployed to the expanded larger configuration under physiologic conditions and/or simulating conditions comprising in air, and/or in air at ambient temperature, and/or in air at 37° C. temperature, and/or in water, and/or in water at ambient temperature, and/or in water at 37° C., and/or in a body lumen, and/or at body temperature, and/or in a tube, under pressure, under pulsating pressure, and/or combination thereof.

In an example, the stent prosthesis is deployed to the expanded larger configuration and undergoes modification in air, and/or in air at ambient temperature, and/or in air at 37° C. temperature, and/or in water, and/or in water at ambient temperature, and/or in water at 37° C., and/or in a body lumen, and/or at body temperature, and/or in at least one solvent, and/or in at least one solvent or corrosion inducing agent at ambient temperature, and/or in solvent or corrosion inducing agent at 37° C., and/or in a tube, and/or pressurizing the stent at 1.5 psi to 5 psi, under pressure, under pulsating pressure, and/or accelerated fatigue, and/or accelerated any of the conditions, and/or combination thereof.

In another example or aspect of this invention, a non-degradable stent prosthesis comprises a structure, wherein the structure comprising a wire, hollow wire (hollow at least in some regions where it is hollow as formed and/or after treatment (modification)) where the wire and/or hollow wire are patterned into a stent, preferably a substantially tubular stent structure, more preferably a substantially tubular patterned stent structure wherein the stent is patterned from a tube. The stent prosthesis is expandable from a crimped configuration to a deployed larger or expanded configuration. The stent structure comprises a strong material, such as a non-degradable polymeric or metal (including metal alloy) such as metal stainless steel or cobalt chrome. The material is configured to have a at least one section and/or region in at least one ring where the material will come apart (environmentally responsive separation region, or separation regions) after deployment, and/or after modification; and/or the material is configured to have at least one discontinuity in at least one ring, and/or at least one discontinuity in at least one strut, and/or at least one discontinuity in at least one crown, and/or combination thereof. The discontinuity in the material is held together and does not substantially affect the crimping and/or deployment of the stent to the larger expanded configuration, and/or the stent prosthesis has sufficient strength in the deployed configuration to support a body lumen; and/or the material is configured to have at least one discontinuity in at least one ring, and/or at least one discontinuity in at least one strut, and/or at least one discontinuity in at least one crown, and/or combination thereof. The discontinuity in the material is held together and does not substantially affect the crimping and/or deployment of the stent to the larger expanded configuration, and/or the stent prosthesis has sufficient strength in the deployed configuration to support a body lumen. The material being held together comprises holding, latching, attaching, connecting, pushing together, pulling together, removing a gap, removing a space, and/or locking, together the material discontinuity adjacent parts. The means to hold the material discontinuity parts together comprises a sleeve, an adhesive, a press fit, a lock, a coating such as polymer or metallic coating, a gel, solder, and/or designs such as key and lock design. The stent in the expanded deployed configuration has sufficient strength to support a body lumen, and/or expand without fracture, and/or expand with low recoil. The stent in one example undergoes modification after deployment where the modification comprises uncaging, un-fixing, un-holding, un-done, un-latching un-attaching, detaching, disconnecting, breaking up, breaking apart, pushing, pushing apart, separating, pulling apart, creating a gap, creating a space, disintegrating, corroding, degrading, fragmenting, fracturing, shattering, splintering, decomposing, unlock, break down, deteriorate, degenerate, decay, and/or discontinue, of at least part of the material and/or the means holding the material discontinuity parts together. The stent after modification comprises one or more come apart material sections and/or discontinuity in at least one ring, and/or at least one or more come apart material sections and/or discontinuity in at least one crown, and/or at least one or more come apart material sections and/or discontinuity in at least one strut, and/or a combination thereof. In another example, the stent after modification allows the lumen or vessel to further enlarge from after implantation, and/or allows the stent to further expands to a larger configuration from the configuration before modification, and/or further expands to a larger configuration from the deployed configuration, and/or further expands to a larger configuration from a "recoil after deployment" configuration, and/or uncage, and/or further expands to a larger configuration for any of the previous causes in at least one ring of the stent prosthesis, and/or further expands to a larger configuration in at least one ring of the stent prosthesis wherein the ring is located about the mid portion of the stent length. In another example, the at least one or more come apart material sections (separation regions) and/or discontinuity of at least one ring of said stent after modification allows the stent to uncage and/or further expand at said at least one ring under physiologic pressure. In another example, the stent prosthesis comes apart after deployment and/or modification in at least one ring, crown, and/or strut. In one example the stent prosthesis after deployment and/or after modification and/or after coming apart and/or after the material discontinue has a structure, and/or has a tubular structure, and/or has a tubular patterned structure, and/or has a substantially maintained tubular structure, and/or has at least part of a structure, and/or has a at least one window, and/or substantially has no structure, and/or comprises at least one crown structure, and/or comprises at least one strut, and/or comprises at least one link, and/or has a strength, and/or a combination thereof.

In one example the means to hold the material together and/or to hold the material separation regions and/or discontinuity together, and/or to prevent the stent from coming apart before deployment, comprise adhesive, metal, polymer, coating, solder, press fit, welding, weaving or braiding a material, and/or other. In one example said means decomposes, degrades, corrodes, come unlocked, and/or unfit in a period ranging from 1 months to 5 years, preferably from 3 months to 3 years, more preferably from 3 months to one year. In one example the stent material degrades after said means degrades and/or corrodes and/or unlocks, etc.

In another preferred example a stent prosthesis comprising a structure, where in the structure separation regions and/or discontinuity is located in areas not affecting radial expansion, and/or or circumferential expansion, preferably in lower stress areas such as struts, or strut regions.

In another example a stent prosthesis is configured to have a patterned structure where the structure has separation regions discontinuity such as a key and lock, an abut, two plates, press fit, ratchets, rivets, inserts, magnets, or other, on at least one strut, and/or on at least one crown, such that the stent after deployment, and/or after deployment and after modification, allows the lumen or vessel to further enlarge, and/or uncage, and/or separate.

In another example a stent prosthesis is configured to have a patterned structure where the structure comprises a plurality of rings wherein the rings in one example is serpentine rings, wherein the rings comprises crowns and struts, wherein at least one crown and two struts are held in the crimped configuration by a coating and/or a sleeve, wherein the stent after deployment and modification comprising degradation of said sleeve and/or coating allows the stent to uncage and/or further expand to a larger configuration, and/or allow the lumen or vessel to enlarge.

In another example a stent prosthesis is configured to have a patterned structure where the structure comprises a plurality of rings wherein the rings in one example is serpentine rings, wherein the rings comprises crowns and struts, wherein at least one crown and/or at least one strut, on at least one ring are configured to have separation regions and/or come apart at at least in one section or region after deployment and under physiologic condition such as after fatiguing of said section or region. Said stent structure after coming apart allows the stent to uncage, and/or further expand to a larger configuration, and/or allow the lumen or vessel to enlarge.

In another example a stent prosthesis is configured to have a patterned structure where the structure comprises a plurality of rings wherein the rings in one example is serpentine rings, wherein the rings comprises crowns and struts, wherein at least one crown and/or at least one strut, on at least one ring are configured to come apart at at least one section or region after deployment and under physiologic conditions such as after fatiguing of said section or region. Said stent structures after coming apart allows the stent to uncage, and/or further expand to a larger configuration, and/or allow the lumen or vessel to enlarge.

In another example, a stent as in any of the examples above is configured to further expand after implantation using an external energy source wherein the energy source comprises magnetic field, infrared heat, inducing heat, ultrasound, and the like.

In another example in any of the examples above wherein the stent material comprising the stent structure is a shape memory material wherein the stent can uncage, and/or further expand after deployment using a shape memory material such as nickel-titanium alloy (NiTi available under the tradename Nitinol®), and where in the shape memory material expands the stent further after deployment to a larger configuration, wherein the stent undergoes modification such as having separation regions wherein the stent comes apart or forms discontinuities in at least one section or region of the stent, and/or comes apart in at least one ring, wherein the stent structure(s) after coming apart slows the further stent expansion, and/or stops the stent further expansion, and/or stops causing injury or inflammation to the vessel wall.

In another example in any of the examples above wherein the stent material comprises a material that additionally softens after modification or after expansion under physiologic condition, such as Platinum alloys, wherein the softening of said material reduces the stresses after deployment on the vessel wall and potentially brings the compliance of the vessel and stent closer from before softening of the material.

In a preferred example, the pieces, and/or structure of stent, and/or structure or part of a structure after modification and after the stent comes apart is configured to have a shape and/or structure to avoid dislodging such pieces or structure elements into the blood stream. Examples include 2-D, and/or 3-D structures, stent windows, structures comprising part of stent windows, structures comprising at least one crown shape, structure comprising at least one crown and at least one link shapes, structure comprising at least one crown, at least two struts, and at least one link shapes, a structure comprising at least one crown and at least two struts shapes.

In another example, the stent prosthesis is capable of being deployed from the crimped configuration to the larger expanded configuration under one or more of the deployment condition in a previous example.

In another example the stent can be deployed at a rate of 1-2 atm per seconds, the stent is capable of being deployed beyond the labeled (nominal/intended deployed) diameter without fracture.

In preferred example of corrodible material such as magnesium, the stent is configured to have sections or regions wherein the material does not degrade (corrode), and wherein said section or region would not degrade, providing stent sections or regions that do not cage the lumen or vessel providing for a lumen or vessel capable of enlarging as a result of not having by product from the magnesium stent in said sections that would result in caging the stent due to the hydroxyapatite by product caging the vessel.

In one example the stent comprising the separation regions or sections coming apart, and/or degrading, and/or corroding, and/or the stent section discontinue, and/or unlock, after deployment in a period from 1 day to 3 years, 1 month after deployment to 3 years, preferably from a period ranging from 3 months to one year.

In another example, the number sections or regions per at least one ring or in at least some rings that come apart, and/or unlock, and/or degrade, and/or corrode for at least one ring ranges from 1 to 4, preferably ranges from 1 to 3, more preferably ranges from 1 to 2, wherein the stent has a structure after coming apart, and/or wherein the stent has no structure after coming apart, and/or wherein the stent in the absence of tissue has an unsupported structure, or collapses, and/or wherein stent in the absence of tissue recoils, and/or wherein the stent in the absence of tissue recoils, or shrinks.

In another example, the number of sections per at least one ring that come apart, and/or unlock, and/or degrade, and/or corrode for at least one ring ranges from 1 to 4, preferably ranges from 1 to 3, more preferably ranges from 1 to 2, wherein the stent has a structure after coming apart, said structure has sufficient strength to support a body lumen, or has no strength, and/or wherein the stent has no structure after coming apart, and/or wherein the stent in the absence of tissue has unsupported structure, or collapses, and/or wherein stent in the absence of tissue recoils, and/or wherein the stent in the absence of tissue shrinks.

In another example, the number of sections per at least one ring that come apart, and/or unlock, and/or degrade, and/or corrode for at least one ring ranges from 1 to 4, preferably ranges from 1 to 3, more preferably ranges from 1 to 2, wherein the stent has a structure after coming apart, said structure has sufficient strength to support a body lumen, or has no strength, and/or wherein the stent has no structure after coming apart, and/or wherein the stent in the absence of tissue has unsupported structure, collapses, and/or wherein stent in the absence of tissue recoils, and/or wherein the stent in the absence of tissue shrinks.

In any one of the previous examples, the lumen or vessel is uncaged, and/or allowed to further enlarge or expand when the stent prosthesis comprising reinforcing elements and/or comprising non-degradable material for stent strength, and/or when the remaining stent prosthesis non-degradable material weight is lighter than the weight of the stent prosthesis comprising non-degradable and degradable material. In a preferred example, the stent prosthesis weight after degradation (or removal) of degradable material (if any) ranging from 0.1 mg/mm to 1.5 mg/mm, preferably ranging from 0.1 mg/mm to 1.2 mg/mm, and more preferably ranging from 0.2 mg/mm to 0.9 mg/mm, and most preferably ranging from 0.2 mg/mm to 0.6 mg/mm. These weights exclude the weight of non-degradable radiopaque markers.

In another example, the conformability of the stent prosthesis (3-point bend test) after formation of discontinuities, or after degradation of degradable material (if any) forming discontinuities is desirable to be as conformable as possible to avoid potential irritation and inflammation to the vessel wall after implantation. For example, the conformability of the stent prosthesis after formation of discontinuities, or after removal (or degradation of degradable material) is preferably ranging from 0 N/mm to 0.05 N/mm, preferably ranging from 0 N/mm to 0.03 N/mm, more preferably ranging from 0 N/mm to 0.1 N/mm. In another example the conformability of the stent after formation of discontinuities in the deployed configuration is improved (compared to before formation or compared to upon deployment of the stent) by at least 10%, or improved by at least 25%, or improved by at least 50%, or improved by at least 75%. In another example the conformability after formation of discontinuities is improved (compared to before formation or compared to upon deployment of the stent) by a range from 10% to 100%, preferably from 20% to 75%. In another example the radial strain of the stent after formation of discontinuities or after deployment ranges from 2% to 5% in a simulated bench test (as describe but not limited to example 5). In another example, the radial strain (or compliance) for the stent after formation of discontinuities and/or after deployment is larger than stent not having discontinuities by a factor ranging from 2 times to 10 times, preferably ranging from 2 times to 5 times (as described but not limited to example 5).

In another example the stent or other endoluminal prosthesis is in an uncaged configuration prior to being deployed from a crimped configuration, wherein the stent or other endoluminal prosthesis has strength in the deployed configuration to support a body lumen. In another example, the stent or other endoluminal is in an uncaged configuration in a circumferential direction prior to implantation or deployment.

In another example, the stent or other endoluminal prosthesis is configured to uncage after deployment or after implantation, in a physiologic environment, preferably configured to uncage in a circumferential fashion or direction by having at least one or more gaps (discontinuities) along the path of at least some, preferably every ring in the circumferential direction. Optionally, the stent can also unzip along the longitudinal axes of the stent in one or more paths (or lines) through the formed discontinuities in a variety of patterns separating the stent into one or more segments. In one example, the stent does not unzip along the longitudinal axis, or unzips at least part of the longitudinal axis of the stent.

In another example, uncaging of the stent or other endoluminal prosthesis comprises one or more of separation of the stent in at least one region or section in at least one ring, at least one discontinuity, at least one break, at least one gap, ability of the stent to further expand after deployment, ability of the lumen or vessel to positively remodel in the presence of the stent or re-enforcement elements or in the presence of the stent, ability of the stent or other endoluminal prosthesis to further expand after deployment without having stent breaks, separation, or discontinuities, ability of the lumen or vessel to positively remodel in the presence of the stent or other endoluminal prosthesis without having discontinuities, breaks, or separations.

In one example, the endoluminal prostheses of the present invention will typically comprise scaffolds with circumferential structures such as rings which comprise a plurality of struts joined by crowns, commonly referred to as zig-zag stents, serpentine stents, closed cell designs, and the like. In accordance with a further aspect of the present invention, at least some of the struts in at least some of the zig-zag or serpentine rings will include at least one separation region configured to form a discontinuity and/or uncage in the circumferential ring after expansion of the stent and/or strut in a physiologic environment. In these examples, the crowns of the rings and connected links which joins adjacent rings are preferably free from separation regions. This allows for a controlled expansion of the individual rings as well as of the stent as a whole in response to luminal remodeling.

In another example, endoluminal prostheses having separation regions in individual struts of their circumferential rings will form discontinuities which allow the scaffold to uncage, and/or expand beyond an initial expansion after deployment in a target blood vessel or other body lumen. The physiologic environment in which the prostheses are expanded will typically be physiologic conditions such as that of a body lumen, such as a vascular environment which may be mimicked by a water bath at 37° C. In the vascular environment, the discontinuities which form in the rings will allow the scaffold to circumferentially uncage, and/or open as the blood vessel and/or lumen positively remodels after placement of the stent or other prosthesis. The discontinuities will typically form in a period from 30 days to 6 months after the initial expansion of the circumferential scaffold within the physiologic environment but can have such discontinuities form 1 day after deployment to 3 years after deployment. In one example the discontinuities are formed and/or occur before implantation wherein such discontinuities still allow for crimping, and/or allow for stent deployment from a crimped configuration to an expanded configuration and have sufficient strength to support a body lumen. In such case the stent or stent structures regions uncages, and/or allows for further expansion in at least said region of discontinuity of the stent structure.

In another example, the separation regions within the struts of the circumferential rings may comprise "key and lock" or similar type junctions in the struts and/or other structural elements, which junctions are held together and/or immobilized during expansion but configured to open or release after the initial expansion in the physiologic environment. In one specific type of key and lock junction, the key and lock will open to allow the joined segments of the strut to separate from each other in a radial direction only after the separation region is free to separate (i.e. is mobilized). In other specific example, the key and lock type junctions are configured to allow the joined segments of the strut to separate from each other in both radial direction and axial direction after they are mobilized. The key and lock junctions type may be held together and/or immobilized by a polymer, coating, a sleeve material, cement, and/or adhesive which is applied to abutting surfaces of the junctions where the coating, cement, sleeve, or adhesive is selected to degrade in the physiologic environment over time.

In another example of suitable adhesives, stent material, sleeve material, coatings, and cements, include but not limited to polylactide; poly(L-lactide); poly(D-lactide); poly-DL-Lactide, polyglycolide; polylactide-co-glycolide (e.g., poly(L-lactide-co-glycolide) with 85% L-lactide to 15% glycolide); copolymer of poly(L-lactide-co-epsilon-caprolactone (e.g., weight ratio of from 50 to around 95% L-lactide to about 50 to about 5% caprolactone; poly (L-lactide-co-trimethylene carbonate); polytrimethylene carbonate; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); or the like; and combinations thereof.

In other examples, the key and lock junctions type are held together and/or immobilized by an overlying sleeve or similar external structure which envelopes the junction and which prevents the junction from completely and/or partially releasing and/or opening while the sleeve remains intact and/or substantially intact and/or non-degraded but which degrades in the physiologic environment over time in order to open and release the junctions.

In still other examples, the separation regions located within the struts of the circumferential rings may comprise butt joints, notches or thinned regions within the struts, modified grain boundaries within the struts, and the like, which preferentially erode or fatigue within the struts, or any of the other specific separation regions described elsewhere herein.

In further specific examples of the endoluminal prostheses of the present invention, a scaffold comprises circumferential rings patterned from a metal or other non-degradable material, where the scaffold is configured to expand from a crimped configuration to an expanded configuration. In these embodiments, at least some of the circumferential rings comprise a plurality of struts joined by crowns and at least some of the struts have at least one separation region which is pre-formed as a break in the structure of the strut, e.g. formed by laser or otherwise cutting across the strut as or after it has been patterned, which is immobilized by a sleeve or an adhesive which will degrade in physiologic environment over time.

While the separation region examples may be any of those described previously herein, a preferred separation region examples comprises a key and lock junction where the struts are held together and/or substantially held together or immobilized during expansion and configured to open after an initial expansion within the physiologic environment. The key and lock junction types in this example may be configured to allow the joined segments of the strut to separate from each other in a radial direction only after the joints are free. Alternatively, the key and lock junctions may be configured to allow the joined segments of the strut to separate from each other in both a radial direction and an axial direction after the junctions are free, i.e. opened or released from constraint. In both cases, the key and lock junctions may be initially immobilized by a cement or adhesive or a sleeve or a coating which holds the budding surfaces of the strut segments together or close together and which degrades in physiologic environment. Alternatively, the strut segments joined by the key and lock junctions may be immobilized by an overlying sleeve which degrades in the physiologic environment. Such junctions are immobilized, substantially immobilized, held together, substantially and/or held together; to restrict or substantially restrict movement, in one or more directions (preferably substantially restrict movement in an axial direction) upon deployment from a crimped configuration to an expanded configuration. Immobilization of such junction are accomplished using a material such as polymer, sleeve, or adhesive, or by the configuration of junction design.

In a preferred example, the stent (scaffold) prosthesis in this invention is formed from a substantially tubular body (said tubular body in a preferred example is substantially free from holes and/or discontinuities). The stent comprises structural elements capable of radial expansion from a crimped configuration to an expanded deployed larger configuration. The structural elements in a preferred example comprises a plurality of circumferential rings, said rings comprising struts joined (connected) by crowns. At least some of said rings are connected to adjacent rings. The stent in preferred examples can be crimped onto a balloon delivery system or a delivery system (optionally constrained in the crimped configuration by a sleeve). The stent in a preferred example is balloon deployable and/or self-expanding stent. The stent prosthesis can also be formed from a wire or a fiber (round or substantially round, square or substantially square, rectangle or substantially rectangle, and/or other shapes, wherein the wire or fiber is patterned into a stent capable of radial expansion from a crimped configuration to a deployed larger configuration. The stent can also be formed from a hollow or partially hollow wire (having hollow regions within the wire or fiber) or fiber wherein the hollow or partially hollow wire or fiber is patterned into a stent capable of radial expansion from a crimped configuration to a deployed larger configuration. The stent pattern in preferred examples can be serpentine rings, zig zag rings, diamond, interwoven and/or mesh pattern, closed cell design, open cell design, and/or combination thereof. Preferably, the stent shape in the deployed configuration is substantially tubular (cylindrical), tapered stent, hour glass stent, and/or other shapes. The rings, crowns, struts, dimensions (length, thickness, angle of curvature, width) are configured in to allow the stent to deploy (expand) and have the various shapes above.

One skilled in the art would appreciate the applicability of the embodiments and/or examples throughout this application to prosthesis across various mammalian body applications where a stent prosthesis is implanted, such as endoluminal prosthesis, outer-luminal prosthesis, annulus prosthesis such as valves comprising circular or other shapes, and/or other type of lumen, duct, annulus, cavities, sinus, etc. within a mammalian body.

In one example the stent prosthesis comprises a valve such as an aortic and/or mitral valve and/or tricuspid valve, wherein the stent prosthesis comprising an expandable stent prosthesis (balloon expandable or self-expanding) wherein the stent circumferential structural elements such as for example struts joined by crowns (and/or including for example a plurality of rings), or other type stents formed from a tube, a wire, a sheet, or a braided stent formed from one or more wires, and the stent is configured into an open cell design pattern, a closed cell design pattern, or combination of open cell and closed cell pattern, or other, and wherein the stent prosthesis comprises shape memory alloy such as NiTi, and/or non-degradable metal or metal alloy such as stainless steel 316L or L605, or other materials described in this application, or other, and wherein at least some struts (but can also be crowns, circumferential links/connector, or combination) in at least one ring or at least one segment of the stent (a proximal segment, a mid-segment, and/or distal segment, and/or regions within a segment) have at least one or more of: junctions, bridging elements, joints, discontinuities, and/or separation regions as described throughout this application, which are configured to uncage, and/or configured to have a displacement (or movement) in one or more directions or movement pattern, and/or configured to have radial strain, and/or configured to have radial contraction and expansion, or configured to have inferior contraction and/or expansion, or configured to have superior contraction and/or expansion, after deployment of the stent prosthesis within, in, or around, or above, or adjacent to, an annulus of a body valve, wherein the displacement magnitude (or radial strain magnitude, or contraction magnitude, or further expansion magnitude, or movement magnitude) ranges from 0.05 mm to 10 mm, preferably ranges from 0.1 to 7 mm, preferably ranges from 0.2 mm to 5 mm, more preferably ranges from 0.3 mm to 3 mm, and wherein the displacement or radial strain movement is in at least one or more of the following: radial direction, circumferential direction, longitudinal direction, superior direction, inferior direction, valve leaflets closure direction, annulus (or lumen) contraction and/or expansion direction, or combination thereof, and wherein the stent prosthesis is substantially cylindrical, oblong, annulus shape, saddle shape, circular, or other shape to conform to the anatomy where the stent prosthesis is to be implanted in, wherein the separation regions, junctions, bridging elements, gaps, joints, form discontinuities, and/or allow at least one or more structural elements to have movement (displacement) in one or more direction such as circumferential, radial, and/or longitudinal, or combination thereof (as formed, before implantation, and/or after implantation) wherein the stent prosthesis have sufficient strength to support (including hold, or maintaining) the implantation site (including valve annulus, cavity)) open, and/or have sufficient strength to hold (including maintaining) a structure associated with the implanted stent prosthesis in place (including the valve and/or sheath associated with the stent prosthesis as deployed or after deployment), wherein the stent prosthesis upon deployment (expansion from a crimped configuration to an expanded larger configuration) has sufficient strength to support the valve annulus and/or associated stent valve open and/or in place, and wherein said discontinuities, and/or movement, allow uncaging, displacement, contraction, and/or further expansion, of at least one or at least some regions of at least one or at least some segments of the stent prosthesis or stent prosthesis structural elements, and/or said discontinuities, and/or movement (displacement), allow expansion and/or contraction of at least one or at least some regions of at least one or at least some segments of the stent prosthesis or stent prosthesis structural elements, and/or said discontinuities, and/or movement, allow the stent and/or at least one or at least some regions of the stent to be less rigid (including more compliant (radial strain) in at least one or more directions such as the circumferential direction, the radial direction, the longitudinal direction, or combination thereof).

In a preferred example, the separation regions, junctions, bridging elements, gaps, joints, are placed (including located) in a pattern that allows for the stent (or at least some regions or segments of the stent) to have sufficient strength after deployment, and allows at least some regions or segments of the stent prosthesis (including the circumferential regions of said stent regions) to uncage, to be more compliant (radial strain) under physiologic conditions, to expand and/or contract under physiologic condition, and/or prevent (including minimize, reduce) blood leakage after stent (including valve) implantation. The prevention of the blood leakage can be minimized by having the stent in at least some region be and/or become more compliant (including less rigid) making the stent in at least said regions more conformable to the anatomy the stent is implanted in as the anatomy moves or changes shape under physiological conditions (more dynamically compliant). The prevention of blood leakage can occur upon implantation or after implantation. The separation regions, junctions, bridging elements, gaps, joints, can be placed in at least one ring, or at least some regions of at least one segment of the stent prosthesis such as the proximal segment of the stent, a mid-segment of the stent such as the segment holding the valve, and/or a distal segment of the stent, and/or all three segments of the stent prosthesis. Optionally, a sheath surrounding at least a region or segment of the stent prosthesis can be configured to respond (including contour, expand, adapt) to the corresponding discontinuities, and/or movement of the stent prosthesis adjacent to the sheath region. The sheath can be configured and/or formed from stent like structure having separation regions, junctions, bridging elements, gaps, joints, and/or a sheath capable to adapt to the adjacent stent region in expansion and/or contraction or in other ways. In a preferred embodiment or example the stent prosthesis in at least one ring or in at least some regions (preferably the entire stent) maintain sufficient strength after implantation, in other examples the stent prosthesis strength decreases over time after implantation ranging from 30 days to 3 years, preferably ranging from 3 months to 2 years, more preferably ranging from 6 months to 2 years. In this other example the residual strength is either sufficient strength to perform one or more of the functions described and/or other functions, or the stent prosthesis in at least some regions (or all the stent) will have no residual strength over the said time period ranges.

In one example, a stent prosthesis for valve replacement or repair, wherein the stent is substantially cylindrical or have other shapes conforming to the annulus where the stent is to be implanted in, and wherein the stent is patterned from a tube, a wire, or braided, and wherein the stent is balloon deployable or self-expandable, and wherein the stent is configured to expand from a crimped configuration to an expanded larger configuration, and have sufficient strength in the expanded larger configuration to hold the annulus open (or to support an annulus). The stent prosthesis optionally comprises a valve (such as bicuspid or tricuspid) coupled to said stent prosthesis. The stent prosthesis optionally comprises at least one skirt on at least one surface region such as the abluminal and/or luminal surface region of the stent prosthesis coupled to the stent prosthesis and/or the prosthetic valve. The at least one skirt in one example can also be weaved into the abluminal and/or luminal surface regions. The at least one skirt in another example can be coupled to at least one segment of the stent prosthesis, such as a proximal segment of the stent prosthesis, a distal segment of the stent prosthesis, a mid-segment of the stent prosthesis, and/or the entire stent segments, on the abluminal and/or luminal surface regions. The at least one skirt in one example can have a pouch configured to swell or fill up with blood after the stent prosthesis implantation. In one example, the stent is configured to have at least one segment (or region) of the stent to have at least one or more of separation regions, discontinuities, bridging elements, junctions, joints, gaps, to allow uncaging and/or higher displacement in one or more of the following after expansion of the stent prosthesis: higher strain, higher displacement, higher contractility and/or expandability, better valve closure, less valve leakage, better accommodation of valve closure when the heart is dilated, said displacement in at least one segment and/or stent taking place in one or more of: stent radial direction of the stent, stent circumferential direction, stent longitudinal direction, towards a superior direction of the stent, towards an inferior direction of the stents, and/or other type directions or movements such as a saddle shape direction to accommodate a mitral valve annulus. The at least one or more separation regions, discontinuities, joints, junctions, bridging elements, gaps, etc., are configured (or positioned, or located, or placed) along the desired stent, stent segment, or stent region, to provide for the required movement (or displacement). Examples for placement locations of such uncaging and/or displacement features include: the stent segment (or region) adjacent to the synthetic valve, attached at least in part to the synthetic valve in at least one region, placement in a mid-segment of the stent prosthesis, placement in a distal segment of the stent prosthesis, placement, placement in a proximal segment of the stent prosthesis, placement on at least one side of at least one segment of the stent prosthesis, placement on one half side of at least one segment of the stent prosthesis (while the other half of said segment is free from such uncaging features) in a cylindrical shape stent for example, or combination thereof. The at least one segment having displacement magnitude in at least one direction in one example ranging from 0.1 mm to 10 mm, preferably ranging from 0.2 mm to 7 mm, more preferably ranging from 0.35 mm to 7 mm. The stent prosthesis optionally have supporting features (such as additional struts joined by crowns within the stent prosthesis rings) to further provide strength, support, or other mechanical properties, to the main stent prosthesis structural elements. The supporting features can have uncaging features or be free from uncaging features. The stent prosthesis in this example has sufficient strength in the expanded configuration to support a body annulus (or to maintain a body annulus open, or to hold the stent in a body annulus in place) while providing after expansion one or more of: higher (or larger or increased) radial strain (or compliance), larger (or higher or increased) displacement, higher (or increased) compliance, larger contraction and/or expansion, in at least one stent segment (or region) of the stent prosthesis compared to an adjacent stent segment (or region), or the stented segment, under physiological conditions.

In one example, an implant having length, width, and thickness, is attached (or held in place) adjacent to a body lumen or a body annulus (or within a body lumen or within a body annulus) and wherein the implant is configured to be coupled with (or attached) to an expandable prosthesis, and wherein at least one of the implant and the stent prosthesis are configured to have one or more of separation regions, junctions, joints, hinges, bridging elements, gaps, on at least one segment or region of the implant and/or stent allowing the at least one segment or region of implant and/or stent to have displacement, in one or more directions, that is larger than an adjacent segment (or region) of the said implant or stent prosthesis, under physiological conditions.

In one example, an implant having length, width, and thickness, is attached (or held in place) adjacent to a body lumen or a body annulus (or within a body lumen or within a body annulus) and wherein the implant is configured to be coupled with (or attached) a prosthetic (or natural) valve, and wherein at least one segment or region of the implant is configured to have one or more of separation regions, junctions, joints, hinges, bridging elements, gaps, allowing the at least one segment or region of implant to have displacement, in one or more directions, that is larger than an adjacent segment (or region) of the said implant, and wherein said displacement is configured to allow the valve to operate (or to function or to open and close) under physiological conditions, or allows (or enhance) the valve to conform (or contour) to the annulus or deformed annulus preserving the function of the valve.

In another example, a stent prosthesis formed from a shape memory material, or formed from a spring (or coil) material, and is patterned from one or more wires into a braided pattern, or is patterned from a tube into a closed cell type design or an open cell type design, or is patterned from a wire into a closed cell type design or an open cell type design, or combination thereof, and wherein the stent is self-expandable from a crimped configuration to an expanded larger configuration and have sufficient strength to support a body annulus, and wherein the stent prosthesis is coupled to a valve, said stent having one or more of separation regions, junctions, hinges, discontinuities, in at least one segment: distal, proximal, or adjacent, to the coupled valve, and wherein said segment after expansion and formation of discontinuities (or after uncaging) has lower outward radial force while the stent is in the expanded configuration but smaller than the nominal or maximum expansion diameter force, preferably between 5-15% smaller than the maximum expansion diameter outward force, more preferably between 15% and 75% smaller than the nominal or maximum expansion diameter outward force.

In preferred example, the composite radial strain/compliance (or vessel dilation under pressure or therapeutic drug such as nitroglycerine) in one example of the stent prosthesis having at least one or more separation regions forming discontinuities after expansion ranges from 1% to 10%, or from 1% to 5%, preferably ranges from 1.5% to 4%, and/or has a diameter change ranging from 0.03 mm to 3 mm, preferably ranging from 0.05 mm to 0.15 mm, or more preferably ranging from 0.07 mm to 0.15 mm, or most preferably ranging from 0.1 mm to 0.3 mm, under physiologic conditions or simulated physiologic conditions. The pattern of separation regions can be configured for example to adapt to the anatomy the stent prosthesis is implanted in to accommodate the forces of such anatomy and/or dynamic movement and thereby comprising one or more planes to uncage or allow movement (and/or expand, etc) ranging from circumferential to axial planes and/or in between, and/or radial. One skilled in the art would appreciate the application of these embodiments to balloon expandable stents and/or self-expanding stents, including open cell designs, closed cell design, coil design, or weaving stent patterns, etc. In another example the stent prosthesis uncages, and/or allows movement, and/or further expands, and/or have higher radial strain (compliance), and/or etc., upon deployment or after deployment by incorporating other means described in this application.

In a preferred embodiment or example where in many instances an implant such as s stent prosthesis is implanted to open, hold open, to hold in place, to support, to repair and/or replace a malfunctioning structure such as a valve, or other; the stent in such instances are implanted in a variety of anatomy such as an artery, a vein, a duct, a valve annulus, sinus, cavity, and/or other mammalian body lumen, where such artery, a vein, a duct, a valve annulus, sinus, cavity, and/or other mammalian body lumen, are usually undergoing various physiologic conditions such as pressure, pulsating pressure (systole and diastole), movements (or displacement) in one or more planes/directions, shaping and/or reshaping of said lumen or annulus, expansion and/or contraction, forces from one or more planes/directions, where the implant is desired to have sufficient strength at least upon implantation to open, hold open, support, repair and/or replace a malfunctioning structure; and at the same time, and/or over time after implantation the implant/stent is desired to have the ability to comply with (accommodate, and/or to conform) at least partially to the physiological conditions of movements (displacement), forces, expansion and/or contraction, shaping or re-shaping of the lumen, etc thereby preserving the function of the implant and the integrity of the stent support (or valve contained within the stent). The implant prosthesis described throughout this application allows the artery, vein, duct, cavity, annulus, and/or other body lumen, to at least partially restore (or accommodate or comply with at least partially) some of said movement (displacement), expansion and/or contraction, forces, and/or shaping or re-shaping of lumen; thereby reducing and/or preventing the unwanted effects of an implant and thereby reducing and/or preventing unwanted adverse events such as narrowing and/or re-narrowing of a lumen, restenosis, blood leakage, occlusion, thrombus formation, angina, ischemia, aneurysm, etc., the stent as described throughout this application allows at least one or more regions, and/or at least one segment (and/or the entire stent) to uncage, to allow to move, to expand, to further expand, to further expand from the deployed/expanded configuration, to shape and/or re-shape into a new configuration from the deployed configuration, to expand and/or contract, to have a radial strain (compliance) closer to the natural radial strain (compliance) of the lumen (and/or anatomy where the stent is implanted in), to have a higher radial strain (compliance) than immediately after deployment radial strain/compliance (or before forming discontinuities in some cases), to accommodate at least some of the lumen (annulus, cavity etc.,) physiological conditions (including dynamic movement/displacement, and/or dynamic forces, and/or dynamic expansion and/or contraction, and/or dynamic shaping and/or re-shaping), and/or to lessen the resistance of the implant (stent) to the physiologic conditions of the implant site, and/or to provide sufficient stent structure after deployment (or after formation of the discontinuities) to protect body lumen, protect vessel lumen, support body lumen, and/or support vessel lumen, from potential harmful plaque such as vulnerable plaque. The stent after formation of discontinuities maintains sufficient stent structure which can have radial strength, or no radial strength after formation of discontinuities and/or after deployment.

In a preferred example, the stent prosthesis is formed from and/or comprises a non-degradable material that has high radial strength (for example sufficient to support a body lumen upon deployment of the stent), wherein the material is preferably a metal or metal alloy but can also be a polymer, or other material of high radial strength upon deployment. In a preferred example non-degradable material does not degrade within at least five years from implantation in a body lumen (or under physiologic conditions), preferably does not degrade within at least ten years from implantation in a body lumen (or under physiologic conditions, more preferably does not degrade within at least 20 years from implantation, and/or within at least 50 years from implantation. Examples of non-degradable metal or metal alloys include but not limited to the following: stainless steel alloys such as 304 stainless steel (including 304V and 304L), 316 stainless steel (including 316 L and 316 LV), stainless steel alloys having % Fe by weight ranging from 30% to 80%, Cobalt alloys such as Cobalt Chrome including L605, MP 35, cobalt alloys having % Co by weight ranging from 25% to 60%, Platinum alloys including platinum alloys having % Pt by weight ranging from 25% to 40%, metal alloys having Chrome in the alloy including alloys having % chrome by weight ranging from 15% to 25%, Mo—Re based alloys (including Icon-Nuloy alloy), Tantalum and Tantalum alloys, gold and gold alloys. Tungsten and Tungsten alloy and/or silver and silver alloys, are corrodible (degradable) metals.

The words corrodible and degradable are used interchangeably in this application.

In another example, the expandable stent having separation regions, and/or other configurations as described throughout this application, wherein at least some regions of the stent form discontinuities after deployment, uncage upon or after deployment, expand further, have higher (or increased) radial strain, allow less resistance to the implant site or lumen, and/or have the strength decreases ater implantation, wherein at least said regions of the separation regions (and/or other configurations) maintain substantially their position within the stent prosthesis structural elements after expansion, protrude (or move) outwardly from the stent prosthesis structure, protrude (or move) inwardly from the stent prosthesis structure, move in an adjacent way (or direction) to the stent prosthesis, and/or combination of the above, after deployment of the stent and/or after forming discontinuities.

In another example the stent prosthesis in any of the examples described throughout this application, wherein the stent prosthesis upon deployment has sufficient strength to support a body lumen (and/or hold in place a valve while maintaining a body lumen (such as valve open) and wherein the strength is substantially maintained after deployment (and/or after forming discontinuities). In another example, the strength after deployment decreases in a step function (or the strength decreases as step function after deployment, and/or the strength decreases after forming discontinuities) within 30 days, preferably within 3 months, more preferably within one year). In yet another example, the strength after deployment decreases in a gradual manner, and/or decreases in a linear decay manner, within 30 days, preferably within 3 months, more preferably within one year, after deployment (and/or after forming discontinuities). In yet another example the stent prosthesis strength after deployment (and/or after forming discontinuities) decreases, said decreased strength sufficient to support a body lumen (and/or hold a structure in place, and/or hold a lumen or annulus open). In yet another example the stent prosthesis strength after deployment (and/or after forming discontinuities) decreases and reaches a plateau, said plateau strength sufficient to support a body lumen (and/or hold a structure in place, and/or hold a lumen or annulus open). In yet another example the stent prosthesis strength after deployment (and/or after forming discontinuities) decreases but does not reach zero. In yet another example the stent prosthesis strength after deployment (and/or after forming discontinuities decreases to zero within one months, within 3 months, and/or within one year. In a preferred example, the stent having decreased strength compared to initial strength but larger that zero strength, or having zero strength, maintains (or has) a sufficient circumferential structure to support a body lumen.

In another example of any of the examples of this application, preferably wherein the stent prosthesis comprises and/or formed from a non-degradable material such as non-degradable metal or metal alloy, the stent prosthesis upon deployment from crimped configuration to an expanded larger configuration has, low inward recoil, preferably zero inward recoil to low inward recoil, preferably zero inward recoil to 6% inward recoil, more preferably zero inward recoil to 10% inward recoil, when deployed/expanded from the crimped configuration to the expanded configuration/diameter. In another example the stent prosthesis after deployment (after initial recoil (if any)) has substantially zero inward recoil to 3% inward recoil from the expanded configuration (preferably has substantially zero inward recoil), within 30 days after deployment, preferably within 60 days after deployment, more preferably within 3 months after deployment. In another example, the stent prosthesis after deployment from a crimped configuration to an expanded larger configuration (after initial recoil (if any)) and/or after forming discontinuities, further expands (on its own or unaided) to a larger configuration, further expands to a larger configuration larger than the expanded configuration after recoil, and/or further expands to a larger configuration larger than the deployed configuration (before initial recoil). The stent prosthesis in the example further expands within 360 days, preferably within 270 days, more preferably within 6 months, more preferably within 3 months, most preferably within one month, from deployment and/or implantation. In another example the stent prosthesis after deployment and/or after forming discontinuities, will expand and/or contract by a total magnitude of 2%-15% of the deployed diameter/configuration (after initial recoil (if any)), preferably by a total magnitude of 3% to 10% of the deployed diameter/configuration (after initial recoil (if any)), or more preferably by a total magnitude 4% to 15%) of the deployed diameter/configuration, within one month after deployment, preferably within 3 months after deployment, more preferably within 6 months after deployment, most preferably within one year after deployment.

In another example the stent prosthesis having separation regions (and/or other configurations describes throughout this application) as described throughout this application, preferably wherein the stent prosthesis comprises and/or formed from non-degradable material such as non-degradable metal or metal alloy, wherein the stent after deployment forms at least some discontinuities in at least some circumferential structural elements separation regions, and wherein the stent prosthesis after deployment (and/or after forming said discontinuities) substantially maintains the stent prosthesis structure and/or shape. In another example, the stent prosthesis substantially maintains the stent prosthesis circumferential structure and/or shape. In yet another example the stent prosthesis after deployment (and/or after forming said discontinuities) substantially maintains the stent prosthesis deployed configuration. In yet another example the stent prosthesis after deployment (and/or after forming said discontinuity/discontinuities) has no more than one discontinuity per any ring (or per at least some rings), preferably no more than two discontinuities per any ring (or per at least some rings), more preferably no more than three discontinuities per any ring (or per at least some rings), more preferably no more than four discontinuities per any ring (or per at least some rings). The stent prosthesis having separation regions forming discontinuities in one example along the length of the stent prosthesis in a substantially straight, or helical, or other shape, along the stent length, slicing the stent in this example along the longitudinal stent length (while maintaining intact one, some, or all or axial links connecting (joining) adjacent rings) in straight, helical, or other configurations. In another example, the stent prosthesis forming discontinuities slicing the substantially cylindrical stent structure along (or extending) the length of the stent prosthesis (while maintaining intact one, some, or more axial links connecting (joining) adjacent rings) into two structures or segments (such as two circumferential semi circles structures along (or extending) the stent length), In another example the stent prosthesis forming discontinuities slicing the substantially cylindrical stent structure along the length of the stent prosthesis (while maintaining intact one, some, or all axial links joining adjacent rings) into three structure (such as three partial circumferential structures extending along the stent length). In another preferred example, the separation regions and/or discontinuities are located onto strut structural elements, such that no more than one separation region and/or discontinuity per strut (or per some struts), and no separation regions and/or discontinuities on crowns, and/or no separation region and/or discontinuities in regions joining struts to crowns. In another preferred example, the separation regions and/or discontinuities are located at least within a strut region of a ring(s), or substantially in the middles of struts, or along the length of the strut (away from the crown and/or away from the junction joining the strut to the crown), and/or located in regions that are substantially non deformable or less deformable of the ring, and/or located in regions that have less or has reduced stress forces of a ring as the stent expands from a crimped configuration to an expanded deployed configuration, and/or located in regions that are substantially non deformable or less deformable on a ring when the stent expands from the crimped configuration to an expanded configuration, and/or located in regions where the separation regions are substantially maintained together (or substantially held together) upon deployment of the stent, on a ring, from a crimped configuration to an expanded configuration.

In another example, the separation regions have (or defines, or comprises) a gap between the two opposite ends of the structural elements adjacent to the separation, and/or between the two adjacent ends of the structural element adjacent to the separation region (for examples the two ends of the non-degradable metal alloy containing or defining or comprising a separation region). The gap width ranges from zero to 50 microns, preferably ranges from zero to 30 microns, more preferably ranges from zero to 15 microns, more preferably ranges between zero and 10 microns, most preferably ranges from 5 micros to 30 microns. The gap can be filled with a coating such as a degradable polymer coating. The coating can extend beyond the separation region to further hold in place the separation regions upon deployment of the stent from a crimped configuration to an expanded larger configuration.

In a preferred example, the stent prosthesis comprises structural elements, preferably circumferential structural elements comprising plurality of rings, each ring comprises struts joined by crowns, and each ring is connected to an adjacent ring (or non-adjacent ring) through (or by) a link or joined directly without a link. The stent prosthesis is expandable from a crimped configuration to an expanded configuration to support a body lumen and/or to hold a lumen open and/or to hold a structure (connected or attached to the stent) in place. The stent prosthesis can have a sheath surrounding and/or attached to the stent or at least a segment of the stent (preferable in a circumferential direction). The stent can hold in place (and/or attached before deployment or after deployment) a structure such as a valve (synthetic or biologic). The stent can also have means to anchor the stent or regions within the stent to body lumen, tissue, etc. The stent can also have tendons or wires attached to some regions of the stent to anchor the stent or pull it inwardly from at least one region or segment. In another example, the stent comprises one circumferential structural element comprising. In another example the stent prosthesis comprises one ring, said ring comprises struts joined by crowns. In another example, the stent and/or implant comprises a structure capable of expansion from a crimped configuration to an expanded larger configuration.

In another example, the coating thickness, and/or sleeve thickness, covering at least part of the separation regions, and/or crowns, ranges from 3 microns to 100 microns, preferably ranges from 5 microns to 50 microns, more preferably ranges from 10 microns to 50 microns. The coating, sleeve, material can be degradable or non-degradable such as degradable polymer or non-degradable polymer. In case of non-degradable polymer example, such as parylene or C-flex or polyurethane, in one example the polymer contains (holds together) the separation region together within the epolymer, wherein the separation region and/or discontinuity after deployment is allowed to uncage and/or separate (form discontinuities) within the non-degradable polymer (i.e. the non-degradable polymer continues to encapsulate the separation region and/or discontinuity), but allows the stent and/or stent region to uncage, and/or further expand, and/or become more compliant, or have increased compliance after formation of discontinuities.

In a preferred example in any of the examples in this application, the stent prosthesis is capable to expand from a crimped configuration to an expanded larger configuration without coming apart, and/or is capable to expand from a crimped configuration to an expanded larger configuration while maintaining structural integrity, and/or is capable to expand from a crimped configuration to an expanded larger configuration while maintaining the separation regions being held together, and/or is capable to expand from a crimped configuration to an expanded larger configuration while maintaining the discontinuities being held together. The expansion from crimped configuration to an expanded configuration ranges from deployment to nominal stent diameter to 3 mm above nominal stent diameter, preferably ranges from nominal stent diameter to 2 mm diameter above nominal stent diameter, more preferably ranges from nominal stent diameter to 1 mm above nominal stent diameter. Nominal stent diameter includes nominal delivery system balloon diameter, labeled delivery system balloon diameter, nominal delivery system labeled diameter, and/or labeled delivery system diameter.

In one example the measurements of any parameter such as strength compliance, diameter, configuration, recoil, displacement, dimensions, etc., such measurements are specific measurements of one sample, mean of multiple samples, mean of multiple samples from one lot, mean from multiple samples from multiple lots, and/or measurements from different samples (for examples testing strength) where the samples are built to the same or similar specifications. In another example the measurement is the mean of multiple measurements, examples include the mean lumen area representing measurement for lumen area, mean stent diameter representing stent diameter measurement, etc. In another example, standard testing methods or commonly used test methods known to those skilled in the art can be utilized for the various tests such as dimensions, size, radial strength, recoil, expansion, contraction, diameters, radial strain (or compliance), resistance, etc., it is also applicable for example to utilize IVUS, OCT, MSCT, QCA, or other measurements apparatus to measure bench, in-vitro, and/or in-vivo measurements. Measurements can also be on bench, in-vitro, ex-vivo, or in-vivo. Measurements can also be on the stented segment, the segments of the stent ring having separation region(s), a proximal stent segment, a mid stent segment, and/or a distal stent segment.

In one example, a stent prosthesis comprising a non-degradable material (such as polymeric material) which has been patterned into a stent comprising structural elements comprising rings, said rings comprise expansion regions (such as crowns), and struts, wherein at least some reinforcement elements (such as metallic non-degradable) are coupled to at least some expansion regions of the non-degradable stent, and at least some rings have at least one separation region, and wherein the stent prosthesis expands from a crimped configuration to an expanded larger configuration and have sufficient strength to support a body lumen, and wherein the separation region forms discontinuity on said rings after implantation allowing the stent to further expand in a physiologic environment.

In an example, metallic stent prosthesis are formed from a tube, or a wire (solid, or hollow at least in certain region of the wire (preferably hollow in the non-deformable regions of the wire) and patterned into a structure expandable from a crimped configuration to an expanded larger configuration. The stent structure in one example comprises plurality of rings (and at least some rings having one or more separation regions) composed of structural elements of struts and crowns, non-deformable elements (or substantially non deformable elements) such as struts, and deformable elements such as crowns. At least some of the rings are connected to adjacent rings in at least one region by for example a link. The metallic stents can also be formed from a patterned sheet that is then rolled into a tube and joined forming a stent. In yet another example, the stent prosthesis can be formed by 3-D printing.

In another example, a polymeric stent prosthesis is formed from a tube by spraying, extrusion, dipping, molding, or 3-D printing, and patterned into a stent. Alternatively, the stent prosthesis can be formed from one or more fibers or filaments and patterned or woven into a stent.

In a preferred example, the stent prosthesis is configured to uncage upon or after deployment, to exhibit vaso-dilation in a body lumen after deployment, to further expand to a larger configuration after deployment, and/or to have a radial strain ranging between 1% and 10%, preferably to have radial strain ranging between 1% and 7%, over (or on or across or along) substantially the entire stent segment, the stent segment, the stent length, the stent circumferential diameter, and/or the stent. In another example, the stent prosthesis is configured uncage upon or after deployment, to exhibit vaso-dilation in a body lumen after deployment, to further expand to a larger configuration after deployment, and/or to have a radial strain ranging between 1% and 10%, preferably to have radial strain ranging between 1% and 7%, over (or on or across or along) at least one segment of the stent, at least one region of the stent, at least some stent length, at least some stent circumferential diameter, and/or the stent.

In a preferred example, the stent prosthesis for coronary arteries application is configured to have one or more of the following in at least some rings, preferably in substantially all rings: reinforcement elements reinforcing a degradable ring structural elements (frame) of the stent (strut and/or crown), bridging elements bridging non-degradable ring structural elements (frame) of the stent (strut and/or crown), separation regions in a non-degradable ring structural elements (frame) of the stent, gaps in non-degradable ring structural elements (frame) of the stent, and/or discontinuities on overlapping or non-overlapping non-degradable ring structural elements (frame) of the stent (struts and/or crowns). The stents are configured to have 10% flat plate compression initial strength ranging from 0.025 N/mm of stent length (0.45N for a 3.0 mm by 18 mm stent length for example) to 0.07 N/mm stent length or higher (up to 0.3 N/mm stent length) after initial expansion, and the stents is configured to have dimensions range from 60 microns thick to 130 microns thick, while the width dimension ranges from 60 microns wide to 150 microns wide. The inward recoil is configured to range from 1% to 10%, and is substantially maintained after expansion (deployment). The stents are deployed in water at about 37° (or in a body lumen) and tested either in water or in air after expansion (deployment). The stents are configured to uncage upon deployment or after deployment, expand to a larger configuration after the inward recoil, and/or exhibit vaso-dilatation (or allow the stented body lumen to exhibit enlargement (or expansion or further expansion) after introduction of a vasodilator in the body lumen, when the stent is deployed (or expanded) in a body lumen. The stents are expandable from a crimped configuration to an expanded larger configuration without fracture. The stent has sufficient strength to support a body lumen. In a preferred example, the stent has sufficient strength to support a body lumen without additional recoil after initial inward recoil after expansion (deployment), when the stent is expanded in water at about 37 C or in a body lumen.

In a preferred example of any aspect, example, or embodiment of this invention, the stent prosthesis has sufficient strength to support a body lumen ranging from 0.025 N/mm stent length to 0.07 N/mm of stent length, preferably ranging from 0.04 N/mm stent length to 0.3 N/mm of stent length.

In another example, at least some struts and/or crowns, on at least some rings are configured to have one or more of discontinuities, separation regions, bridging elements, and/or reinforcement elements. At least one discontinuity, separation region, bridging element, and/or reinforcement element, are configured or formed on the said each strut, and/or each crown, of the at least some rings, or combination thereof.

In another example, the stent comprising structural elements, said stent patterned in a closed cell type design, a diamond shape rings, mesh type stent design, coil type design, and/or weaved (or braided) type stent design. The stent circumferential structural elements (such as rings) are configured to have one or more of discontinuities, separation regions, bridging elements, and/or reinforcement elements, and/or combination thereof, sufficient to uncage the stent circumferentially after expansion in a body lumen, to exhibit vaso-dilation in a body lumen after deployment, to further expand to a larger configuration after deployment, and/or to have a radial strain ranging between 1% and 10%. The stent upon deployment to the expanded larger configuration has sufficient strength to support a body lumen.

In a preferred example of any aspect, example, or embodiment of this invention, the stent prosthesis has an initial inward recoil after the stent is deployed (expanded) from a crimped configuration to an expanded larger configuration, where the initial inward recoil is substantially maintained, after the stent is expanded in water at 37 C (or after the stent is expanded under physiologic conditions, or after the stent is expanded in a body lumen). The stent initial recoil is measured within 1 minute after deployment (expansion) of the stent, or the stent initial recoil is measured within 5 minutes after deployment (expansion) of the stent. The inward recoiled is substantially maintained after deployment, maintained after deployment for at least 30 minutes, for at least 1 hour, or for at least 1 day. In all cases in this example, the stent inward recoil is measured after deployment and deflation of the deploying balloon or deploying means. The stent prosthesis in a most preferred example further expands after said initial recoil over a period ranging from 1 minute to 1 year or more, preferably over a period ranging from 30 minutes to 1 year or more, wherein the stent further expansion configuration is less than the initial recoil magnitude, preferably larger than the initial recoil magnitude (or diameter or mean diameter), or more preferably wherein the stent further expansion configuration is larger than the deployed (expanded) stent configuration magnitude (or diameter or mean diameter). In a preferred example the stent prosthesis comprises non-degradable metal or metal alloy comprising a plurality of rings.

In another example of any of the examples, the stent prosthesis has at least one, or some links that connect (or join) at least some adjacent rings, wherein the one or some links remain substantially intact (or remain intact) upon, or after expansion (deployment), or after formation of all discontinuities. In another example, all the stent prosthesis links remain intact upon or after expansion (deployment). In another example, at least some rings (or substantially all rings) are connected to adjacent rings in at least one region (or at least by one connection or by at least one link) and where the at least one connection remains substantially intact upon or after deployment or after formation of discontinuities. In another example, at least some rings are connected to adjacent rings in at least two regions (or by at least two connections, or by at least two links) and where the at least two connection remains substantially intact upon or after deployment or after formation of all discontinuities. In yet another example, at least one link, preferably at least some links (or connections), joining at least some rings are configured to have one or more of reinforcement elements. The stent prosthesis in this examples is also configured to have at least some struts and/or crowns on at least some rings having one or more of reinforcement elements. In yet another example, substantially all links (or connections), joining at least some rings are configured to have one or more of reinforcement elements. The stent prosthesis in this example is also configured to have at least some struts and/or crowns on at least some rings having one or more reinforcement elements.

In an example of any of the examples in this application, the stent prosthesis (or at least one segment of the stent prosthesis) is configured to have high crush resistance after deployment (or expansion) from a crimped configuration to an expanded larger configuration, where the stent circumferentially uncages, the stent circumferentially uncages the stented segment, further expands to a larger configuration, responds to a vaso-dilator introduction, and/or has a radial composite strain (or compliance) in the range of 1.5% to 7%, after expansion. The stent prosthesis in a preferred example substantially maintains the initial high crush resistance after expansion. The stent prosthesis in another example exhibits a reduction (decrease) in crush resistance over a period of time ranging from after deployment and 1 year, where the crush resistance decreases ranges from 20% to 80%, over a period of time ranging from one month to one year, said remaining crush resistance is sufficient to support a body lumen. In yet another example the stent prosthesis exhibits a decrease in crush resistance after deployment from a period of time ranging from after deployment and one year, said stent prosthesis after said period of time substantially has no crush resistance.

In a preferred example of any of the examples in this application, the stent prosthesis has a patterned structure after deployment (expansion), where the structure is substantially maintained (or intact, or substantially intact). In another example, the stent prosthesis has an initial patterned structure after deployment (expansion), where the initial patterned structure changes (or becomes different or is modified) after expansion. In another example, the stent prosthesis has a patterned structure comprising structural elements (comprising in a preferred example struts, crown, and links (or connections), wherein the stent after deployment (expansion), maintains (or has) at least one longitudinal structural elements segment along substantially the length of the stent. The longitudinal structural element segment has (or comprise) one or more breaks, separation regions, and/or discontinuities along the longitudinal segment (excluding the link or connection regions which are axial connectors and which remains intact). The longitudinal segment circumference in one example ranges from ¼ the circumference of the stent to ½ the circumference of the stent. The longitudinal segments pattern can be substantially straight along substantially the length of the stent, or can be helical along the stent length, or other longitudinal pattern along the length of the stent. The at least one longitudinal structural elements segment remains substantially intact (preferably remains substantially intact through the one or more links (or connections) along the length of the stent). In another example, the stent prosthesis has a patterned structure comprising structural elements (comprising in a preferred example struts, crown, and links (or connections), wherein the stent after deployment (expansion), maintains (or has) at least one circumferential structural elements segment along substantially the circumference of the stent. The circumferential structural element segment has (or comprise) one or more breaks, separation regions, and/or discontinuities along the circumferential segment (excluding the link or connection which are axial connectors and which remains intact). The number of circumferential segments in one example ranges from 1 to 4. In another example, the stent prosthesis has a patterned structure comprising structural elements (comprising in a preferred example struts, crown, and links (or connections), wherein the stent after deployment (expansion) maintains at least one circumferential segment along the stent circumference and/or at least one longitudinal segment along the stent length, wherein the segment comprises at least one crown and at least two struts, preferably comprises at least one crown and at least two struts and at least one link (or connection) remain intact or connected, more preferably, comprises two or more rings, partial rings (or ring regions). The segment has at least one separation region, break, and/or discontinuity on at least some rings (or partial rings or ring regions).

In another example, a stent comprising a degradable (including corrodible) material, wherein the material degrades in a period ranging from 1 year to 20 years, preferably from 2 years to 15 years, more preferably from 3 years to 10 years, wherein the material is patterned into a stent comprising structural elements, said structural elements comprising a plurality of rings, each ring comprises struts and crowns. At least struts and/or crowns, on at least some rings have one or more of separation regions, discontinuities, breaks, gaps, and/or bridging element, and wherein the stent prosthesis uncages after expansion from a deployed configuration to an expanded larger configuration. The stent in one example uncages upon deployment. The stent in another example uncages from a period ranging from 1 month to one year. The degradable material comprises one or more of a metal or metal alloy, a polymeric material, or other material that degrades from 1 year to 20 years. The stent prosthesis upon expansion has 10% flat plate crush resistance ranging from 0.025 N/mm stent length to 0.085 N/mm of stent length, but can also range from 0.05 N/mm to 0.2 N/mm of stent length.

In another example, a stent prosthesis comprising structural elements, said structural elements comprise a plurality of rings, each ring comprises struts, crowns, and each ring is connected to an adjacent ring by at least one link (or connection), at least some struts and/or crowns on at least some rings have one or more of separation regions, bridging regions, discontinuities, gaps, and/or breaks, or combination thereof. In another example, a stent prosthesis comprising structural elements, said structural elements comprise a plurality of interconnected rings, substantially all rings have one or more of separation regions, bridging regions, reinforcement element, discontinuities, gaps, and/or breaks, or combination thereof. In yet another example, a stent prosthesis comprising structural elements, said structural elements comprise a plurality of interconnected rings, at least half of all rings have one or more of separation regions, bridging regions, reinforcement element, discontinuities, gaps, and/or breaks, or combination thereof.

In another example, a stent prosthesis comprises structural elements, said structural elements comprises a plurality of rings each ring comprises struts and crowns, said stent prosthesis is plastically deformable from a crimped configuration to an expanded larger configuration, where the stent in the expanded larger configuration has composite radial strain (or compliance) ranging between 1% and 5%. The stent in the expanded configuration is crush resistant and have sufficient strength to support a body lumen. The stent in preferred example further expands to a larger configuration after deployment and after an inward recoil (if any). The stent in another preferable example is plastically deformable over a range of diameters ranging from 1 mm to 2 mm diameter range, preferably ranging from 2 mm to 4 mm diameter range, more preferably ranging from 3 mm to 4.5 mm diameters.

In another example, a stent prosthesis as in any of the examples, wherein the stent prosthesis is delivered to a body lumen without a restrain (or sleeve), said stent expands from a crimped configuration to an expanded larger initial configuration, then said stent exhibits inward recoil, before expanding to a second configuration (smaller or larger than initial configuration).

In another example or aspect of this invention, a stent prosthesis comprised of metal and metal alloys material wherein the stent prosthesis is expandable from a crimped configuration to an expanded larger configuration and has sufficient strength to support a body lumen upon (or after) expansion. The stent material is pre-formed, or treated, and/or configured to exhibit one or more of the following after expansion: softening of the material, weakening of the material, becoming less stiff, has reduced crush resistance, has reduced strength, and/or has no strength, has an initial strength sufficient to support a body lumen wherein the strength decreases over time, has an initial strength sufficient to support a body lumen wherein the strength remains substantially the same over time, and/or has an initial compliance upon expansion and wherein the compliance increases after expansion, and/or has an initial compliance immediately after expansion (or within 24 hours after expansion) and wherein the compliance increases after expansion (or within 6 months after expansion), under one or more of the following conditions: physiologic conditions (which also includes one or more of the following): in water at 37 C, cyclic physiologic fatiguing (pulsation), and/or physiologic temperature, in a period ranging from 1 month to 5 years, preferably ranging from 3 months to 3 years, more preferably ranging from 3 months to 2 years, after expansion, pressure differential ranging from 50 mmHg to 200 mmHg. The stent material treatment comprises, heat, quenching, cyclic fatiguing, or other, said treatment taking place at one or more of the following: before forming, during forming, after forming, before stent patterning, or after stent patterning. The stent after expansion exhibits one or more of the following: being further expandable to a larger configuration, expands further in response to vaso-dilator introduction, and/or has a composite radial strain (or compliance) ranging from 1.5% to 5%, in water at 37 C, or under physiologic condition, and/or in a body lumen.

In another example, the stent material comprises, or composed of, one or more of the following metals or alloys such as conventional titanium alloys such as Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230; Tungsten or Tungsten alloys, or other. In a preferred example, the material strength after expansion decreases by at least 25%, preferably by at least 50%, more preferably by at least 75%, compared to the strength just after deployment (initial strength), over a period ranging from 1 month to 3 years. The material in a preferred example softens (decreased strength) comprising one or more of the following reasons: body temperature, time, cycling (or fatigue), creep, recrystallization, grain growth, dislocation, precipitation interaction, dislocate interactions or other. The stent material is degradable (including corrodible) or non-degradable. The stent material can be formed as a tube and patterned into a stent, formed as a wire (or formed from a wire) and patterned into a stent, or formed as a patterned sheet (or formed from a patterned sheet) into a stent.

In another example or aspect of this invention, a degradable stent prosthesis comprising degradable polymeric material or degradable metallic or metallic alloy material, wherein the stent is configured to have one or more separation regions, uncage after expansion (or deployment), exhibit radial strain (or compliance) ranging from 1.5% to 5%, further expands to a larger configuration after deployment (including after initial recoil), and/or expand in response to a vaso-dilator. The stent is configured to have one or more of the following: at least some rings (preferably substantially all rings) have one or more of the following: gaps, bridging elements, separation regions, discontinuities. In a preferred example, the separation regions are configured to form discontinuities before (or substantially before) the degradable stent degrades. In another example, the separation regions are configured to form discontinuities before the degradable stent degrades by a period ranging from 1 month to 5 years, preferably by a period ranging from 2 months to 3 years, more preferably by a period ranging from 3 months to 1 year. In yet another example, the separation regions are configured to form discontinuities within a period ranging from after initial expansion to 1 year after initial expansion, preferably within a period ranging from one month after initial expansion to 9 months after initial expansion, more preferably, within a period ranging from one month after initial expansion to six months after initial expansion.

In another example, the degradable stent material comprises metal or metal alloy of Nickel, Cobalt, Tungsten, Iron, Zinc, Magnesium, Magnesium alloy AZ31, Tin, 1010 Steel, Steel, 5140 Steel, 8620 Steel, Iron Nickel Alloy, Cellulose, or other. In one example, the degradable material substantially degrades in a period ranging from 1 year to 20 years, preferably degrades from 1 year to 10 years, more preferably in a period ranging from 1 year and 5 years, or most preferably in a period ranging from 6 months to 3 years. In one example, the degradable stent material comprises (or composed of) polymeric stent material comprises PLLA polymeric material. In yet another example, the degradable stent comprises polymeric material comprising poly-lactide polymeric material. In yet another example, corrodible metal or metal alloy (degradable) that corrodes (degrade) from 1 to 10 years such as tungsten, tungsten alloys, Tungsten alloys of rhenium, cobalt, iron, zirconium, zinc, titanium; alloy of cobalt; magnesium alloy AZ31, tin, 1010 steel, steel, 5140 steel, 8620 steel, iron nickel alloy; or the like. In yet another example of Degradable polymer and copolymers that degrade from 3 to 10 years examples include cellulose; chitin; chitosan; PLLA or its copolymer; or the like.

In still further examples, the stents and other endoluminal prostheses of the present invention may be formed from non-degradable metals or metal alloys and/or other non-degradable materials and will be configured to have breaks, or openings formed (usually pre-formed) in the scaffold circumferential structure (such as one or more rings) to allow uncaging of the stent after implantation in a vascular or other body lumen. The scaffold will typically be defined by a plurality of circumferential rings which are configured to expand from a crimped condition to an expanded configuration, where at least some of the circumferential rings follow a circumferential path about the circumference of the scaffold. There will be at least one break or opening in the circumference of at least some of the rings, and adjacent circumference rings will be axially linked so that substantial portions or segments of the scaffold remain connected and intact (by the axial links) after the scaffold has been expanded to its expanded configuration and the breaks (gaps) or discontinuities have formed in the one or more rings. In some examples, the entire scaffold will remain both axially and circumferentially connected so that no portion of the scaffold may inadvertently disconnect from the remainder of the scaffold after expansion and after the breaks (or discontinuities) have formed. In other examples, the expanded scaffold may separate into two, three, or more axially intact segments. In still other examples, the scaffold may separate into random segments after expansion, where such random segments will have sufficient size and persistence so they will not dislodge or substantially migrate from the implantation location in blood vessel or other body lumen after expansion. An example of that is a plurality of crowns and/or struts remaining connected within one or more rings, and/or along the length of the scaffold.

In a first set of examples, the openings or breaks in the scaffold will (or may) comprise gaps in the circumferential rings. For example, the gaps may be formed in either or both of the struts and the crowns of the circumferential rings. In some examples, the gaps will be closed when the scaffold is in its crimped (unexpanded) configuration and will open when the scaffold is expanded to its expanded configuration. Such examples include breaks in the struts or crowns where the adjacent edges formed by the breaks remain in contact with each. Such "breaks" may be formed as part of the initials fabrication of the scaffold, e.g. patterning of a tube or bending of a wire, or may be formed after the initial fabrication but cutting of severing a previously formed strut or crown. In other examples, the gaps in the circumferential rings may be present even when the scaffold is in its unexpanded (crimped) condition or the separation distance between the opposed ends of the gap and the strut or crown will increase upon expansion of the scaffold. Such initially open gaps may also be formed during or after initial fabrication of the scaffold.

The gaps formed in the circumferential rings may be rotationally staggered or rotationally aligned along a longitudinal or central axis of the scaffold. When the gaps in the circumferential rings are rotationally staggered, the adjacent rings may be joined by axially links which are also formed in a staggered pattern which may be the same or different than that of the rotationally staggered gaps. Similarly, when the gaps are rotationally aligned, the axially links may also be rotationally aligned or rotationally staggered.

In a second set of examples, the openings or breaks in the circumferential rings will (or may) comprise biodegradable segments which form "bridges" between opposed surfaces or portions of the struts or crowns which contain the break or opening. The biodegradable segments may be configured to remain intact while the scaffold is expanded in a vascular environment, forming gaps in the rings only after the bridging segments have degraded in the vascular or other luminal environment. Biodegradable segments may be configured to degrade in the vascular or other luminal environment over a time period in the range from 1 month to 3 years, preferably degrade over a period ranging from 3 months to one year.

As with the gap embodiments described previously, the biodegradable "bridge" segments may be rotationally aligned or rotationally staggered within the scaffold structure. Similarly, the axial links which hold adjacent circumferential rings together may also be rotationally aligned or staggered, and when staggered may be staggering in a pattern which is similar to that of the staggered biodegradable segments.

For both the gap and the bridge examples, the scaffolds may display a composite compliance (radial strain) in the range from 1% to 10%, usually from 1.5% to 5%, when expanded within a vascular environment (or under physiologic conditions) and subjected to systolic/diastolic pressure cycling.

In yet another aspect of the present invention, in the vascular prostheses having a biodegradable bridging segment (element) in their struts and/or crowns may be made (or fabricated) as follows. A scaffold is fabricated having a plurality of rings which define a circumference of the scaffold. The plurality of rings is (or maybe formed) formed from a non-degradable material, typically a metal. A second scaffold having a plurality of rings which define a circumference of the scaffold is also fabricated but from a biodegradable material. Typically, the first and second scaffolds will (or may have) have identical geometries, at least over the regions where the bridging structures are to be located. After the first and second scaffolds are formed, gaps may be cut into at least into the struts and/or crowns of at least some of the rings of the first non-degradable scaffold. Corresponding segments are then cut from the second scaffold, where the segments are selected to fill in the gaps formed in the first scaffold. The segments cut from the second scaffold are (or maybe) secured into the gaps formed in the first scaffold to form a complete scaffold having a non-degradable base structure with a plurality of degradable bridges in selected struts and/or crowns thereof.

In still further examples of the present invention, the scaffold separation regions of the present invention can (or maybe used) be used in helical stents of the type having a helical backbone including a plurality of struts joined by a plurality of crowns. The helical backbone is formed to include a multiplicity of adjacent turns where at least some of the adjacent turns are attached or otherwise coupled to each other by a separation region. For example, the separation regions may be formed between immediately adjacent turns of the helical backbone, with specific examples including between adjacent pairs of crowns, between a crown on one turn and a strut on an adjacent turn, and between a pair of struts on adjacent turns. The helical backbone typically has a serpentine arrangement, a zig-zag arrangement, or follows another "meandering path" of the type commonly utilized in stent fabrication. The stents may be formed from a bent wire or alternatively may be formed by patterning a tube in a conventional manner. The separation regions may comprise any one or more of the separation regions described elsewhere herein, such as degradable regions, mechanically separable regions, fatigue-responsive regions, bridging elements, and the like.

In yet additional examples of the present invention, luminal prostheses may compromise scaffolds having a plurality of circumferential rings formed from a non-degradable material, such as a metal, metal alloy, or a non-degradable polymer, where the scaffold is configured to expand from a crimped configuration to an expanded configuration. At least some of the circumferential rings will be formed from structural elements (such as crowns and/or struts) having divided regions which overlap and lie adjacent to each other when the scaffold is in its crimped configuration. For example, the adjacent regions which overlap and lie adjacent to each other may be straight, typically together forming a "divided" portion of a strut of the scaffold, or may be curved, typically together forming a "dived" portion of a crown of the scaffold. Such straight adjacent regions will typically separate from each other when the scaffold is expanded to its expanded configuration. In contrast, such curved overlapping adjacent regions will typically deform when the scaffold is expanded to its expanded configuration, for example, straightening in response to the bending forces applied by expansion of the stent.

The overlapping adjacent regions may be initially unattached when the scaffold in its crimped configuration. Alternatively, the overlapping regions of the scaffold may be temporarily joined to each other, for example, being held together by an adhesive, by an overlying sleeve, by a coating, and/or by any of the other permanent or temporary immobilization material, methods, and/or structures described herein previously. Such temporary immobilization material (or structures), comprises degradable materials such as degradable polymeric material, will be configured to degrade in a physiologic environment, to fatigue, or to otherwise separate after implantation to enhance the compliance of the scaffold after the prosthesis has been implanted in a body lumen for a desired period of time. Permanent immobilization material comprises non-degradable material such as non-degradable polymeric material, wherein the material is typically elastic, allowing the stent prosthesis to have enhanced compliance after the prosthesis has been implanted in a body lumen for a desired period of time.

In still other examples, the scaffold separation technology (separation regions and other methods to uncage the circumferential structural elements (or to allow for uncaging the stented segment of the lumen) as described in various examples and/or aspects of this application) of the present invention may be applied to a variety of otherwise conventional closed-cell stent patterns. For example, the scaffold may have a plurality of circumferential rings formed from a non-degradable material to expand from a crimped configuration to an expanded configuration. At least some of the circumferential rings will be formed as expandable closed cell structures which are joined circumferentially, and such circumferential rings will have one or more separation regions configured to form discontinuities in the rings after deployment in the luminal environment, uncaging the stented segment of the lumen. In some cases, at least two or more separation regions, in a circumferential ring, configured to form discontinuities, are necessary to uncage a circumferential ring, in other cases, at least three or more separation regions in a circumferential ring are required to uncage a circumferential ring. The one, two, three, or more separation regions may be located in the expandable closed cell structures and/or in circumferential connectors between the closed cell structures.

In specific examples, the closed cells may comprise quadrangles having opposed axial sides and opposed circumferential sides. The scaffolds may further comprise circumferential connectors which join the axial sides of circumferentially adjacent closed cells, where the separation regions may be located in the circumferential connectors and/or in the closed cell structures themselves.

Typically, at least some of the closed cells in axially adjacent circumferential rings will be joined by axial links, where the axial links are typically non-degradable and free from separation regions in order to enhance the integrity of the stent after deployment, and/or in order to enhance the stent uniformity of expansion, and/or in order to maintain the structural integrity of the stent upon expansion, or after expansion.

The discontinuities which form in the scaffold after implantation will typically allow the stent to display a compliance (or radial strain) and range from 1% to 10%, preferably ranging from 1.5% to 5% once subjected to systolic/diastolic pressure cycling (or vaso-dilator) after implantation, usually in a blood vessel of a mammalian.

In alternative closed cell configurations, the scaffolds may comprise closely packed quadrangles formed from a plurality of common crossing members where the separation regions are present in the common crossing members and/or at junctions where the crossing members cross one another. The separation regions may comprise any of the separation regions described herein, often being biodegradable regions in the closed cell scaffolds just described.

In still further examples of the present invention, a stent prosthesis may comprise a patterned circumferential scaffold including non-degradable structural elements. The structural elements may have expansion regions configured to plastically deform as the scaffold is radially expanded from a crimped configuration to a first expanded configuration. The structural elements (such as rings) may be further configured to allow the scaffold to passively (unaided by a mechanical means and/or human intervention) expand to a second, larger configuration after experiencing (or exhibiting) inward recoil from the first expanded configuration after implantation. The scaffold will retain sufficient strength to support a body lumen for at least an initial time period following implantation. The initial time period will typically be at least about 1 day, often being at least 3 months, and typically being in a range from 30 days to 9 months. The expansion regions may be any of the separation regions described previously herein. The second larger configuration may be larger than the first expanded configuration, or can be smaller than the first expanded configuration. In one example, the non-degradable structural elements comprise a plurality of rings wherein each ring is composed of struts and crowns, said non-degradable structural elements are composed of metal or metal alloy that plastically deforms when expanded from a crimped configuration to an expanded configuration. In one example, at least some rings are configured to have one or more separation regions (in one or more struts and/or crowns of the at least some rings), wherein the separation regions are configured to form discontinuities after expansion in physiologic environment.

In still further examples, the stent prosthesis of the present invention may comprise a non-degradable patterned, circumferential scaffold including structural elements. The structural elements (such as rings) may have expansion regions configured to plastically deform as the scaffold is radially expanded from a crimped configuration to a first expanded configuration, and the scaffold may be further configured to have a radial strain (or composite compliance) in a range from 1.1% to 15%, preferably in a range from 1.2% to 10%, more preferably in a range from 1.5% to 7% after the stent is expanded in a body and to retain sufficient strength to support the body lumen. These scaffolds are often further configured to have an inward recoil after deployment in a range from 1.5% to 7%, and may further be configured to have an initial radial strain (or compliance) after deployment of 1% or less before increasing to the radial strain in said range above. In additional examples, the radial strain of the stent prostheses just described may reach a value in the desired range within two months to one year after deployment, and a diameter magnitude of the radial strain (or compliance) may be in a range of 0.07 mm to 0.5 mm, or of 0.1 mm to 0.5 mm. In a preferred example, at least some rings are configured to have one or more separation regions, wherein the separation regions are configured to form discontiutities after expansion of the stent under physiologic conditions. In another preferred example, all rings are configured to have one or more separation regions, wherein the separation regions are configured to form discontiutities after expansion of the stent under physiologic conditions. In yet another example, at least some rings have two or more separation regions, have three or more separation region, have one to four separation regions, or have 2 to 4 separation regions.

In other examples, stent prostheses according to the present invention may comprise a non-degradable, patterned circumferential scaffold including structural elements, where the structural elements have expansion regions configured to plastically deform as the scaffold is radially expanded from a crimped configuration to a first expanded configuration. In some of these examples, the scaffold in the deployed configuration has a sufficient strength to support a body lumen, and the scaffold may be further configured by incorporating one or more aspects (or examples) of the present invention as described throughout this application, such as separation regions on at least some rings for example) to allow a stented segment of the body lumen to vaso-dilate in the presence of a vaso-dilator in the body lumen. The stented segment of the body lumen may vaso-dilate in the range of 0.05 mm to 0.5 mm and frequently in a range from 0.1 mm to 0.3 mm, or in a range from 0.07 mm to 0.5 mm.

In yet additional examples of the stent prostheses of the present invention, a non-degradable, patterned circumferential scaffold may include structural elements, where the structural elements have expansion regions configured to plastically deform as the scaffold is radially expanded from a crimped configuration to a first expanded configuration. The scaffold in the deployed configuration will have sufficient strength to support a body lumen, and the scaffold will typically also be configured (by incorporating one or more of the various aspects (or examples) described in this application) to contract and/or expand after deployment in the body lumen under physiologic conditions. The expansion and/or contraction may occur passively or alternatively may occur in response to vaso-dilation and/or vaso-constriction of the body lumen. The expansion and/or contraction may also occur under physiologic pulsation. Such expansion and/or contraction often has a magnitude in a range from 0.05 mm to 1 mm, more typically range from 0.1 mm to 0.5 mm relative to a deployed diameter or mean diameter of the body lumen.

In some examples, one or more of the following: at least one ring of the stent prosthesis, at least some rings of the stent prosthesis, all rings of the stent prosthesis, at least some circumferential elements of the stent prosthesis, all circumferential elements of the stent prosthesis, and/or the stent prosthesis, of this invention is configured (by incorporating one or more of the present invention aspects (or examples) as described within this application) to do one or more of the following: Un-caging of the lumen or vessel while having high crush resistance upon or after implantation of the stent, and/or uncaging the stented segment of the lumen or vessel, and/or a stent having sufficient strength to support or hold the vessel or lumen open after implantation and further expands (after inward recoil if any) after implantation, and/or not having pieces of stents such as small components dislodging into the blood stream potentially causing a clinical event, and/or having a stent with low inward recoil after initial expansion, and/or having a stent with low inward recoil after initial expansion that is substantially maintained after implantation, and/or having a stent with low inward recoil after initial expansion that increases by no more than 1%-5% after said initial inward recoil, after implantation, and/or having a stent configured to be able to further expand (after inward recoil if any) after deployment under physiologic condition, and/or having a stent able to expand or further expand (after inward recoil if any) after deployment without a pre-programmed temperature trigger setting or without a pre-programmed expanded diameter/configuration setting, and/or having a stent able to expand or further expand (after inward recoil if any) without a programmed temperature, and/or having a stent able to further expand (after inward recoil if any) after deployment under physiologic condition without penetrating or without substantially penetrating the vessel or lumen wall, and/or having a stent that does not cause excessive inflammation, and/or having a stent that does not penetrate the lumen or vessel wall after implantation, and/or having a stents that expands further (after inward recoil if any) after deployment (implantation) further expanding the lumen or vessel, and/or having a stent maintained or substantially maintained in the crimped configuration upon delivery into the vessel or lumen without a constraint and further expand (after inward recoil if any) to a larger configuration after deployment, and/or having a stent that can be deployed to a wide range of diameters and still uncages the vessel or lumen after deployment, and/or having a stent that can be deployed to a wide range of diameters and still further expand (after inward recoil if any) to a larger configuration after implantation, and/or having a stent able to further expand (after inward recoil if any) beyond the pre-programmed expanded diameter/configuration after implantation, and/or having a stent that exhibit vaso-motion, vaso-dilation, or vaso-constriction, after implantation, and/or having a stent that has sufficient strength after deployment to support a body lumen, has low inward recoil (or said stent undergoes inward recoil) after the initial expansion, and where the stent exhibits radial strain (or compliance) below 1% immediately after expansion (deployment), and a radial strain (or compliance) of 1% or larger than 1% after deployment, and/or having a stent that has sufficient strength after deployment to support a body lumen, said stent undergoes inward recoil after the initial expansion of the stent, and where the stent has an initial radial strain (or compliance) after initial expansion, and wherein the radial strain (or compliance) increases after deployment (or increases over time after deployment), and/or having a stent that has sufficient strength after deployment to support a body lumen, said stent undergoes inward recoil after the initial expansion of the stent, and where the stent has an initial radial strain (or compliance) after expansion (deployment), and wherein the radial strain (or compliance) increases, wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and/or having a stent that has sufficient initial strength after deployment (initial expansion) to support a body lumen, said stent undergoes inward recoil after the initial expansion of the stent, and where the stent has an initial radial strain (or compliance) after expansion (deployment), and wherein the radial strain (or compliance) increases after initial expansion, preferably wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and wherein the initial strength decreases after deployment (or decreases after deployment over time, or preferably decreases after deployment from 30 days to 1 year after deployment), and/or any of the above examples, wherein the stent does not undergoe an inward recoil after initial expansion, and/or a stent as in any of the above examples, wherein one or more of the stented segment further expand by a magnitude ranging from 0.07 mm to 0.5 mm under physiologic conditions (including the infusion of vaso-dilator) into the vessel or lumen, and/or any of the examples under physiologic conditions, and/or having a stent that has sufficient initial strength after deployment (initial expansion) to support a body lumen (or annulus), and where the stent has an initial radial strain (or compliance) after expansion (deployment), and wherein the radial strain (or compliance) increases, after expansion, preferably wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and wherein the stent prosthesis has an initial configuration after an initial expansion of the stent preosthesis, and wherein the stent configuration changes after implantation (or after completion of the procedure), and/or any of the examples under physiologic conditions, and/or having a stent that has sufficient initial strength after deployment (or after an initial expansion) to support a body lumen (or annulus), and wherein the stent prosthesis has an initial diameter (or configuration (after an inward recoil if any), or wherein one or more segments of the stent has an initial configuration) after an initial expansion (and after an inward recoil, if any) of the stent preosthesis, and wherein the stent diameter (or configuration, or one or more segments of the stent circumferential elements (such as rings) changes after implantation (or after completion of the procedure, or changes over time, or changes over a period ranging from 30 days to one year, in one or more of the x-axis, y-axis, or z-axis of the stent, or one or more segments of the stent, and/or having a stent that has sufficient initial strength after deployment (or after an initial expansion) to support a body lumen (or annulus), and wherein the stent prosthesis has an initial diameter after an inward recoil, if any, (or configuration, or wherein one or more segments of the stent has an initial configuration) after an initial expansion of the stent preosthesis and after an inward recoil, if any, and wherein the stent diameter (or configuration, or one or more segments of the stent circumferential elements (such as rings) becomes smaller or larger after implantation (or after completion of the procedure, or changes over time, or changes over a period ranging from 30 days to one year, in one or more of the x-axis, y-axis, or z-axis of the stent, or one or more segments of the stent, to contour to the luminal (or annulus) configuration (or diameter) change.

In a preferred example, the stent prosthesis having (or may have) one or more separation regions on at least some rings, preferably on substantially all rings, wherein the stent is expandable from a crimped configuration to an expanded larger configuration and have sufficient strength in the expanded configuration to support a body lumen, and wherein at least one separation region per at least some rings forms a discontinuity in the circumferential path of said ring uncaging said ring, and wherein the stent after formation of discontinuities maintains a structure pattern with the substantially the same number of discontinuities as the number of separation region, wherein the number of separation regions per ring ranges from 1 to 4.

In a preferred example, the stent prosthesis having (or may have) one or more separation regions on at least some rings, preferably on substantially all rings, wherein the stent is expandable from a crimped configuration to an expanded larger configuration and have sufficient strength in the expanded configuration to support a body lumen, and wherein at least one or more separation regions per at least some rings sufficient to form at least one discontinuity in the circumferential path of said ring uncaging said ring, and wherein the stent after formation of discontinuities maintains a structure pattern with the substantially the same number of discontinuities as the number of separation region, wherein the number of separation regions per ring ranges from 1 to 4.

In one example, the stent in accordance of this invention is configured to uncage upon expansion or after expansion from a crimped configuration to an expanded larger configuration and have sufficient strength to support a body lumen or annulus in the expanded configuration. At least some rings, or at least some stent segments, or at least some stent regions, or substantially all rings, ring segments, or ring regions, or the stent, uncage after expansion. Uncaging comprises one or more of the following: having one or more breaks, discontinuities, separations, in a circumferential path of each of the at least some rings, or of each of the at least some circumferential structural elements, or of the stent circumferential elements, sufficiently to separating the rings, circumferential structural elements, and/or the stent in at least one or more circumferential direction; having the stent or a stent segment being able to expand to a larger configuration after expansion and after formation of discontinuities, having a stent or a stent segment in the expanded configuration exhibiting radial strain (or compliance) ranging from 1% to 10%, preferably ranging from 1.5% to 7%, more preferably from 2% to 5%; having a stent or a stent segment in the expanded configuration (after expansion) exhibiting contraction or expansion, expansion and contraction, expansion and/or contraction ranging from 0.1 mm to 1 mm, preferably ranging from 0.15 mm to 0.7 mm, more preferably ranging from 0.2 mm to 0.5 mm, and/or having a stent in the expanded configuration being responsive to vasodilators and/or vaso-constrictors, and/or other therapeutic agents; or other.

In some examples, a non-degradable stent material is preferred for its high strength (or high crush resistance) properties or other mechanical properties. A degradable material such as metallic or metallic alloy can be configured to have high crush resistance and properties substantially similar to non-degradable material or to non-degradable alloy and therefore can also be suitable for these examples or embodiments. In some examples, the biodegradable material can be configured to have sufficient strength in the stent expanded configuration to support a body lumen and degrade in a period ranging from 3 months to 10 years, preferably degrade in a period ranging from 1 year to 5 years. A degradable material can also be polymeric material having sufficient strength in the expanded configuration and degrades over a time period ranging from 3 months to 10 years, preferably degrading in a period ranging from 1 year to 5 years.

In one example, a coronary stent comprising 2.0 mm to 4.0 mm diameter expansion range by one or in some cases multiple stents to accommodate such range, 15 mm to 40 mm stent length range, formed from a wire, a tube, or a sheet rolled up into a tube (patterned before or after rolling into a tube), having strut thickness ranging from 50 microns to 150 microns, preferably thickness ranging from 50 microns to 120 microns.

In a preferred example, a stent configured to uncage after expansion in accordance with one or more aspects of this invention, is desired to have the ability to withstand fatigue for at least 400M cycles, or to have stresses and/or strains on structural elements such as rings, expansion regions (such as crowns), non-deformable regions (such as struts), or axial links connecting adjacent rings, to be sufficiently in a range to withstand 400M cycles of stent fatigue without uncontrolled fracture. In one example, the expansion region of the stent is configured to uncage, can have a wider neck, a key hole type design, or other design, shape, geometry to maintain stresses or to distribute stresses along a longer or larger area, when one or more separation regions on the same ring or adjacent ring form discontinuities. Other examples include larger width or thickness of structural elements, longer structural elements, and/or varying the number, location, shapes, and geometry of separation regions. Another example is manipulating the axial links locations, shape, and number. In another example, having one or more rings with one or more separation regions followed by one or more adjacent rings that do not have separation regions or a different number of separation region on said rings to manage overall stresses on the stent structure and on the rings with separation regions. In a preferred example, the stent of this invention is configured after expansion to have support to the body lumen or annulus without substantial incremental stresses to the body lumen or annulus, while the stent remain axially connected.

In another example of any of the examples in this application, at least one ring having one or more separation regions and/or joints, and/or the stent prosthesis is desired to withstand an approximately 400 million cycles simulating approximately 10 years of heart beats. The stent is configured to have a safety factor of one, preferably greater than one, more preferably greater than 1.2 safety factor on the Goodman line. The Goodman line in one example is generated as follows: In a graph of Alternating stress measured in MPa of the stent material, versus mean stress measured in MPa also of the stent material, the mean and alternating stress for every point in the stent subject to physiological conditions (for example using FEA or physical testing to generate such points simulating physiological conditions) is desired to fall on or below a line connecting the fatigue limit measured in MPa (measured from the stent material sample) on the alternating stress axis, and the ultimate stress on the mean stress axis (that is the Goodman line), giving a factor of safety of one, greater than one, or preferable 1.2 or greater factor of safety. This allows simulating approximately ten year fatigue cycle of the stent prosthesis under physiologic condition without breakage. In another example, the stent prosthesis is configured to have controlled breakage or discontinuities at certain location on one or more circumferential structural element (such as rings), and at approximate time duration within ten years, or beyond.

In one example, a non-degradable stent prosthesis comprising a non-degradable metal alloy such as L605 that is patterned from a tube or a wire, wherein the stent is configured in accordance with one or more aspects or examples of this invention to uncage after expansion in a body lumen or under physiological conditions, said stent has sufficient strength in the expanded configuration to support a body lumen, and wherein the stent strength after expansion decreases. The stent further comprises a degradable coating and a drug agent (incorporated in the coating or separate from the coating) to suppress neointimal proliferation. In one example the stent strength decreases from the deployed strength (after deployment immediately or within 1 hour) by a range from 25% to 75% over a period ranging from 1 month to 1 year after deployment. In another example, the stent strength decreases from the deployed configuration strength by a range from 50% to 90% over a period ranging from 1 month to 1 year after deployment. In yet another example, the stent strength decreases to zero after deployment in a period ranging from 1 month to 2 years.

In one example, a stent prosthesis comprising a non-degradable metal alloy such as L605 that is patterned from a tube or a wire, wherein the stent is configured to uncage after expansion in a body lumen (or under physiological conditions), said stent has sufficient strength in the expanded configuration to support a body lumen, and wherein the stent strength after expansion is substantially maintained. The stent optionally further comprises a degradable coating and/or a drug agent to suppress neointimal proliferation. In one example the stent strength decreases from the deployed strength (after deployment immediately or within 1 hour) by a range from 25% to 75% over a period ranging from 1 month to 1 year after deployment. In another example, the stent strength decreases to a level still sufficient to support a body lumen. In another example, the stent strength decreases to a level insufficient to support a body lumen in the absence of neointimal proliferation maintaining the uncaged stent substantially in place.

In another example, a stent prosthesis comprising a degradable metallic material, such as Tungsten or Tungsten alloy, wherein the stent prosthesis is configured to uncage (by incorporating one or more example or aspects of this invention such as one or more separation regions) after expansion in a body lumen and wherein the stent prosthesis in the expanded configuration has sufficient strength to support a body lumen, and wherein the metallic material degrades in a period ranging from 1 year to 5 years. The stent optionally further comprises a degradable coating and/or a drug agent to suppress neointimal proliferation. In an example where separation region provide discontinuities providing for uncaging of the stent, the discontinuities are usually configured to form before the degradation of the degradable metal or metal alloy.

In another example, the stent prosthesis as in any of the examples or aspects of this application, comprises circumferential structural elements patterned to expand from a crimped configuration to an expanded larger configuration, and wherein the stent in the expanded configuration has sufficient strength to support a body lumen and wherein the stent is configured to circumferentially uncage (forming discontinuities in at least some rings or all rings) after expansion under physiologic conditions. The stent in one example comprises a plurality of rings connected by one or more axial links, wherein at least one or more links are configured to separate at about the same time as the stent uncages circumferentially, or separate after the stent uncages circumferentially, or separate before the stent uncages, or a combination thereof, while at least one link remains intact between two adjacent rings, or while at least one link remains intact between all adjacent rings, or while at least some adjacent rings remain joined in one region.

In another example of any of the examples in this application, the stent prosthesis is configured to have one or more of separation regions, gaps, bridging elements, and/or discontinuities, etc., wherein the structural elements adjacent to said separation regions, gaps, bridging elements, and/or discontinuities, are configured (or allowed) to move in a circumferential direction, and/or configured (or allowed) to move in a longitudinal direction, and/or configured (or allowed) to move in a radial direction, and/or allow movement in a combination of the above.

In another example of any of the examples in this application, the stent prosthesis is configured to have one or more of separation regions, gaps, and/or discontinuities, etc., wherein the structural element opposite ends adjacent to said separation regions, gaps, and/or discontinuities, are configured to do one or more of the following: move freely in relationship to one another, move in a confined direction (or manner), move in an unconfined direction (or manner), move in a constrained fashion (or manner), move in an unconstrained fashion (or manner), wherein such movement is longitudinal, radial, circumferential, or combination thereof.

In another example of any of the examples in this application, the stent prosthesis in the expanded configuration comprising structural elements wherein at least some of the structural elements are configure to allow movement of the at least some circumferential elements in one or more directions (such as circumferential, longitudinal, radial, or combination thereof) wherein said movement uncages at least said structural elements, further expands said at least some structural elements, allow vaso-dilation of the at least some structural elements, allows the at least some structural elements to contract and/or expand, under physiologic conditions. In another example the stent prosthesis comprising structural elements (crowns and/or struts) wherein at least some of the structural elements are configured to have one or more of separation regions, joints, gaps, bridging elements, junctions, wherein the separation regions, gaps, bridging elements, joints, junctions, form discontinuities after expansion of the stent prosthesis, wherein said discontinuities uncages the at least said structural elements, further expands said at least some structural elements, allow vaso-dilation of the at least some structural elements, allows the at least some structural elements to contract and/or expand, under physiologic conditions. In another example the stent prosthesis comprising structural elements (crowns and/or struts) wherein at least some of the structural elements are configured to have one or more of separation regions, joints, junctions, gaps, bridging elements, wherein the one or more of separation regions, gaps, bridging elements, joints, junctions, allow the said structural elements to move, after expansion of the stent prosthesis, in one or more directions (such as radial, circumferential, and/or radial), and wherein said movement uncages the at least said structural elements, further expands said the at least some structural elements, allow vaso-dilation of the at least some structural elements, allows the at least some structural elements to contract and/or expand, under physiologic conditions.

In another example of any of the examples in this application, the stent prosthesis comprising structural elements (crowns and/or struts) wherein at least some of the structural elements are configured to uncage after expansion of the stent prosthesis from a crimped configuration to an expanded larger configuration, and wherein the uncaging of the stent comprises allowing the at least some structural elements to move in one or more directions (comprising one or more directions of circumferential, radial, or combination thereof), and wherein said movement allows the at least some structural elements (or the stent) to further expands, to exhibit vaso-dilation, to contract and/or expand, to have higher radial strain (be more compliant), under physiologic conditions.

In one example the stent prosthesis comprising structural elements formed from a metallic or polymeric material, and wherein the structural elements forms the stent pattern, and wherein the stent pattern comprises open cell type design, closed cell type design, helical stent type design, coil stent type design, braided stent type design, and/or combination thereof, and wherein at least one segment of the stent and/or the stent prosthesis is configured to uncage in accordance with this invention (comprising one or more of separation regions, gaps, reinforcement elements, junctions, joints, discontinuities, etc.,) in at least one segment (preferably the entire stent segment) in the expanded stent configuration, allowing the at least one segment and/or the stent to move in one or more directions comprising a circumferential direction, a radial direction, a longitudinal direction, and/or combination thereof, where such movement allows the at least one segment and/or the stent to have one or more of the following: increased radial compliance (radial strain), contraction and/or expansion from the expanded configuration, further expansion after recoil (if any), exhibiting or responding to a vaso-dilator, under physiologic conditions, wherein the movement is substantially higher after uncaging of the at least one stent segment and/or the stent.

In one example the stent prosthesis comprising structural elements wherein the structural elements comprises a plurality of rings wherein at least some rings comprises struts joined by crowns, and wherein at least some rings are connected to adjacent rings at one or more surface regions, and wherein the at least some rings have one or more separation regions, discontinuities, junctions, gaps, joints, bridging elements, reinforcement elements, and wherein the stent prosthesis being expandable from a crimped configuration to an expanded larger configuration, and wherein the at least some rings and/or the stent uncages after deployment to the expanded configuration, and wherein the at least some rings and/or the stent exhibit one or more of the following after uncaging compared to before uncaging in the expanded stent configuration: increased radial strain (radial compliance), increased vaso-dilatation or vaso-constriction, further expand to a second expanded configuration (after inward recoil if any from the deployed configuration), increased contraction and/or expansion after deployment, under physiological conditions.

In another example, the stent prosthesis as in any of the examples in this application, wherein the stent being expandable from a crimped configuration to an expanded larger configuration (first expanded configuration or initial expansion) and have sufficient strength in the expanded configuration sufficient to support a body lumen, and wherein the stent is configured in accordance with one or more aspects of this invention to uncage after expansion allowing for one or more of the following: increased radial strain, further expand to a second expanded configuration after inward recoil from first expanded configuration, increased radial contraction and/or expansion, increased radial or circumferential displacement, than before uncaging, under physiologic conditions.

In another example, the stent prosthesis as in any of the examples in this application, wherein the stent being expandable from a crimped configuration to an expanded larger configuration (first expanded configuration) and have sufficient strength in the expanded configuration sufficient to support a body lumen, and wherein the stent is configured to have (or to allow) movement of at least some of the stent structural elements and/or the stent in one or more directions (such as circumferential, radial, longitudinal, and/or combination thereof) after expansion allowing for (or resulting in) one or more of the following: higher radial strain, further expansion to a second expanded configuration after inward recoil from first expanded configuration, higher radial contraction and/or expansion, higher radial, or circumferential displacement, than before allowing said movement of the at least some structural elements and/or the stent, under physiologic conditions.

In another example, the stent prosthesis comprising structural elements, wherein said structural elements comprise a stent pattern, and wherein the stent being expandable from a crimped configuration to an expanded larger configuration and have sufficient strength to support a body lumen, and wherein the stent is configured to uncage and to have movement (in one or more directions) in the expanded configuration, larger than the movement in the caged configuration, under physiological conditions. In another example of this example, the stent strength after expansion is substantially maintained until at least some of the stent structural elements are covered with biological tissue (or material, or cells). In another example of this example, the stent strength after expansion is substantially maintained until at least substantially all of the stent structural elements are covered with biological material (or tissue, or cells). In another example of this example, the stent strength after expansion is substantially maintained until at least some of the stent structural elements are covered with biological material (or tissue, or cells), and wherein the stent is configured to uncage in some regions along the stent as described in various aspects or examples in this application, and wherein the biological material substantially holds the uncaged patterned stent in place.

In another example, the stent prosthesis as in any of the examples of this application, wherein the stent is configured to have a movement in one or more directions in at least one segment of the stent prosthesis, wherein the movement comprises displacement in said one or more directions, under physiologic conditions. In another example of this example, the one or more direction comprises circumferential, radial, and/or longitudinal, combination thereof, and/or other directions, or other directions patterns. In another example of this example, the stent prosthesis comprises uncaging of the at least one segment allowing said movement (or displacement), and wherein the movement (or displacement) in one or more direction is larger than said movement (or displacement) before uncaging, under physiologic conditions.

In another example, the stent prosthesis can have a variety of shapes, forms, and structures. For example, structural elements can comprise struts or screw like elements, crowns or knots or bolts type joining struts and/or screw type elements together. The examples of this application apply to the various types of stents, prosthesis, and other implants such as vascular or non vascular stents, stents containing valves, and/or other prosthesis or implants, where one or more of the following is desired: uncaging of the stented segment lumen or part of the stented segment lumen, increased radial compliance from an initial compliance, high initial strength that decreases after implantation (or over time), provide for one or more stent segments (or the stented segment) to further enlarge after implantation, provide for having one or more stent segments (or the stent) having an initial configuration (shape, and/or diameter) substantially contouring to a vessel, lumen, or annulus, upon expansion, to continue to contour (or to continue to substantially contour) to the vessel, lumen, or annulus, after implantation, in response to a change in the vessel, lumen, or annulus configuration, under physiologic conditions, and/or a desired displacement after implantation is required in one or more diameter dimensions of one or more stent segment (or the stent).

In another example, the various examples and aspects of this invention applies to not only expandable prosthesis, but applies to a variety of implants such as non-expandable implants where they are attached or placed in a body lumen (or placed adjacent to a body lumen or annulus, or placed in tissue) and wherein such implants are configured to provide uncaging, and/or provide desired displacement (in diameter for example) after implantation in at least one segment or region of the implant.

In one example, an implant having length, width, and thickness, is attached (or held in place) adjacent to a body lumen or a body annulus and wherein the implant is configured to be coupled with (or attached) to an expandable prosthesis, and wherein at least one of the implant and the stent prosthesis are configured to have one or more of separation regions, junctions, joints, hinges, bridging elements, gaps, on at least one segment or region of the implant and/or stent allowing the at least one segment or region of implant and/or stent to have displacement (change in diameter), in one or more direction or one or more axis (x, y, or z), that is larger than an adjacent segment (or region) of the said implant or stent prosthesis.

In yet another example or aspect of the present invention, a stent prosthesis comprises a scaffold having circumferential rings patterned from a polymeric or metallic material. The scaffold is configured to expand from a crimped configuration to an expanded configuration, and at least some of the circumferential rings have at least one circumferential displacement region which allows the circumferential ring to circumferentially expand and contract in a physiologic luminal environment, such as a blood vessel, and more particularly an arterial blood vessel. For example, the displacement regions may allow the one or more circumferential rings to circumferentially expand and contract in response to a patient's systolic/diastolic rhythm in an arterial lumen.

The displacement regions in one example will allow such circumferential expansion and contraction after implantation of the stent prosthesis in the blood vessel or other body lumen. While the displacement region could be any of the separation regions, open gap, or key-and-lock structures, or others, described previously, they will frequently be regions which are joined or filled by a material (including polymeric material) such as an elastomeric cushion material, such as an elastomeric polymer. In such cases, the elastomeric cushion material will frequently join or connect adjacent regions on the circumferential rings, thus acting as an elastic restraint which permits relative movement of adjacent segments and/or regions to accommodate pulsing of the blood vessel or other body lumen, or other physiologic condition. The amount or degree of relative movement between immediately adjacent stent regions may vary widely, often being in the range from 0.01 mm to 1 mm, often from 0.03 mm to 0.5 mm, and frequently from 0.05 mm to 0.5 mm. The amount or degree of stent circumferential elasticity may also vary widely, often being in the range from 0.05 mm to 0.2 mm, often from 0.07 mm to 0.15 mm, and frequently from 0.07 mm to 0.012 mm.

The scaffolds having circumferential displacement regions in accordance with the principles of the present invention in one example will typically include a plurality of circumferential rings coupled together along an axis. In such instances, at least some of the circumferential rings will often comprise struts joined by crowns, where at least some of the struts or crowns will have circumferential displacement regions that allow the circumferential ring(s) to circumferentially expand and contract in response to the systolic/diastolic rhythm in an arterial lumen, and/or other physiologic conditions. Such regions may comprise discontinuities such as gaps, channels, breaks, junctions, bridging elements, and the like, between adjacent or opposed segments of a strut or crown. In specific examples, the gaps may be defined by opposed segments of a strut and comprise a female coupling element, typically having a pair of opposed constraining walls attached at one end of the strut segment, and a male coupling element disposed on an opposed strut segment. By locating the male strut segment between the pair of opposed constraining walls on the adjacent strut segment, the male element and female element will be free to at least circumferentially move relative to each other to provide the desired circumferential expansion and contraction.

As described previously in other examples, the gaps may be left open or in other instances may be filled with an elastomeric cushion material which dampens the circumferential movement of the male element between the opposed walls of the circumferential rings. Depending on the size of the gap, the male element will be able to move axially, laterally, and/or in elevation relative to the adjacent strut segment. Such ability to move with multiple ° of freedom enhances the elasticity of the stent in response to body lumen pulsation. In other examples, the gap between two opposed segments of a strut may comprise a coupling element having a channel that includes a pair of opposed constraining walls and a bottom surface. A male coupling element opposed on an adjacent strut segment will be located within the channel defined by the opposed constraining walls and bottom surface, allowing the male element to move at least circumferentially between the opposed walls and axially within the channel. As with previous examples or embodiments, the channel may be left open or may be filled with an elastic material or other material (including polymeric).

In yet another example of a circumferential displacement region in accordance with the principles of the present invention, gaps may be defined between opposed segments of the strut and further comprise a coupling element there between. For example, a pin may be positioned to span a gap between a pair of opposed walls of a female coupling element and to further pass through a pivot hole and a male coupling element there between, allowing for movement, and/or for expansion and substantially maintaining said expansion, and/or for expansion and contraction. In still another example or aspect of the present invention, a method for fabricating a stent prosthesis comprises patterning two or more panels or sheets of stent material to include a plurality of partial ring structures. Each partial ring structure will be formed to terminate in two or more attachment ends so that the two or more panel structures, which are typically initially flat, may be formed into a cylindrical assembly with each attachment and on one panel being joined to an adjacent attachment structure on another panel. After properly positioning the adjacent panel structures, the attachment ends will be joined to complete the circumferential stent structure.

The partial ring structures in one example will typically comprise struts joined by crowns and the attachment ends will often be patterned as male and female elements configured to mate with a gap there between, where the gap allows the circumferential scaffold to circumferentially expand and/or contract in the physiologic luminal environment. Optionally, the gaps may be left open but more often will be filled with a material, preferably a polymeric material, more preferably with an elastomeric material to provide an elastic attachment between the attachment ends. The material can be degradable or non-degradable.

Forming the two or more panel structures into a cylindrical assembly in one example typically comprises bending the panels over a mandrel, usually a cylindrical mandrel. After the two or more panels are formed into their desired shapes, the adjacent end structures on each panel may be joined, typically by applying an elastomeric material between or over the adjacent end structures.

In still another example or aspect of the present invention, a stent prosthesis comprises a scaffold having circumferential rings patterned from a polymeric or metallic material (including non-degradable and degradable). The scaffold is configured to expand from a crimped configuration to an expanded configuration, and at least some of the circumferential rings are joined by axial links where at least some of the axial links are joined to an adjacent circumferential ring by a circumferential displacement region. The circumferential displacement region(s) allow the circumferential ring to circumferentially expand and/or contract in a physiologic environment, while maintaining the axial link(s) intact (connecting two adjacent rings) in a preferred example.

In certain examples, at least one displacement region wherein the displacement is in at least one direction, such as circumferential displacement region allows the circumferential ring to circumferentially expand and/or contract in response to a systolic/diastolic rhythm in an arterial lumen, or other physiologic conditions. Usually, the scaffold includes a plurality of circumferential rings coupled together along an axis by axial links. In such instances, at least some of the circumferential rings typically comprise struts joined by crowns, and a strut on the adjacent circumferential ring terminates in the circumferential displacement region which is joined to the axial link.

As with previous examples, the displacement regions wherein the displacement is in at least one direction, such as circumferential displacement regions may comprise discontinuities which allow the circumferential ring(s) to at least circumferentially expand and/or contract in response to a systolic/diastolic rhythm in an arterial lumen, typically comprising gaps between opposed segments of a strut or a crown. More typically, the circumferential displacement regions comprise a male segment and a female coupling element. Where the male segment will typically be at a terminal end of a strut and the female coupling element is on the axial link. Conversely, the female segment may be at a terminal end of a strut and the male coupling element be located on an axial link.

In one example of any of the examples of this application, the implant comprises a stent, a substantially tubular stent in the crimped configuration, a substantially tubular stent in the expanded (deployed) configuration, a tubular stent in the expanded and/or crimped configuration, a cylindrical or substantially cylindrical stent in the crimped and/or expanded configuration, a non-cylindrical stent in the crimped and/or expanded configuration; wherein the stent is expandable from a crimped configuration to an expanded larger configuration and has sufficient strength to support a body lumen (including annulus).

In another example of any of the examples of this application, the implant is a fixation device to anchor to a body lumen, adjacent to a body lumen (including annulus), or anchor to an anatomy; where the fixation device connects to another implant (such as stent, a valve (native or synthetic).

In another example of any of the examples of this application, the implant (prosthesis) is an arterial stent, a stent for valve repair or replacement, a fixation device for valve repair or replacement, and/or a luminal stent.

In another example of any of the examples of this application, the implant comprises a stent wherein the stent is expandable from a crimped configuration to an expanded larger configuration and has sufficient initial strength in the expanded configuration to support a body lumen (or annulus), and has one or more of the following: an initial shape, an initial displacement, an initial radial strain, an initial vaso-motion reactivity; and wherein the stent prosthesis after expansion will have one or more of the following: increased radial strain, increased radial strain and decreased strength from the initial strength, decreased strength below the initial strength, increased displacement in at least one direction wherein the initial displacement in said direction is substantially small, having displacement in at least one direction where the initial displacement is substantially zero in said at least one direction, and/or changes the shape of the stent from the initial shape after expansion. The stent in the above example is configured to have one or more of the following: Uncaging, having variable compliance (radial strain) after expansion, having controlled compliance (radial strain) after expansion that is different from the radial compliance upon expansion, having adaptive to lumen or vessel compliance (radial strain) after expansion, having variable displacement, having controlled displacement different from initial expanded configuration, having adaptive to lumen or vessel displacement after expansion or deployment, having variable movement, having controlled movement, having adaptive to lumen or vessel movement after expansion, and/or allowing vaso-reactivity after expansion. The stent in this example includes stents that are degradable and stents that are non-degradable stents, metal stents, polymer stents, or combination. The implants include but are not limited to stents, tubular structures, non-tubular structures, and other implants having a structure in the expanded and/or crimped configuration. In another example the stent prosthesis has a substantially cylindrical shape upon deployment (expansion) from a crimped configuration to an expanded configuration, wherein the stent shape changes after expansion to one of: non cylindrical, substantially non cylindrical, oblong, oval, or other shape; to accommodate changes in a body lumen (including annulus).

In another example of any of the examples of this application, the stent prosthesis after expansion has an initial shape (or shape configuration) that substantially fits or suited to a body lumen (including annulus shape), and wherein the said shape (or shape configuration) of the stent after expansion changes to accommodate a change in the body lumen (including annulus shape changes) shape (or shape configuration); preventing or minimizing said fit mismatch, or having improved fit compared to an initial fit before said change of lumen shape or configuration after initial expansion of the stent. In another example, the change in shape (or shape configuration) after expansion is dynamically changing shape (or shape configuration) corresponding to the forces exerted by the lumen, while substantially maintaining the expanded configuration of the stent.

In one example of any of the examples of this application, the implant is a fixation device having initial shape, displacement, and fixation strength, and wherein the implant after fixation adjacent to a body lumen or within a body lumen has one or more of the following: larger displacement in at least one direction, changes the shape in at least one dimension, decreases strength in at least part of the implant, or other.

In another example, the stent prosthesis configured to have separation region or joints further expand to a second larger configuration under physiologic environment, wherein the stent would not further expand if not exposed to physiologic conditions. In another example, the stent prosthesis as in any of the examples of this application further expands to a second larger configuration (after initial inward recoil if any) only under physiologic conditions.

In another example, the stent prosthesis exhibit vaso-reactivity after deployment, and prior to formation of discontinuities, and/or exhibit vaso-reactivity over substantially the entire stented segment.

In one example of any of the examples of this application, the stent comprises one or more separation regions (or discontinuities), wherein the separation regions (or discontinuities) comprises one or more joints, wherein the joints allows movement or displacement in at least one direction or dimension after expansion, and wherein the joints do not come apart in physiological conditions.

In one example of any of the examples of this application, the stent comprises one or more separation regions (or discontinuities), wherein the separation regions (or discontinuities) comprises one or more joints, wherein the joints allow movement or displacement in at least one direction or dimension after expansion, and wherein the joints come apart after expansion in physiological conditions.

In one example of any of the examples of this application, wherein the stent comprises a plurality of rings and wherein at least some rings have one or more separation regions (or joints), configured to form discontinuities (or displacement) at substantially the same, or different time periods.

In one example of any of the examples of this application, the implant (including stents) has one or more separation regions wherein the separation regions comprise joints, wherein the joints allow displacement in at least one direction after expansion. Example of joints include but are not limited to: pivot type joint, hinge type joint, ratchet type joints, saddle type joint, ball-and-socket type joint, condyloid type joint, and/or plant type joint. In one example the joint do not come apart. In another example the joints come apart, after expansion. In another example, the implant has an initial displacement upon expansion that is less than the displacement magnitude after expansion.

In one example, the separation region comprises a joint. In another example, the separation region is a joint.

In one example of any of the examples of this application, the implant (including stent) has an initial shape upon expansion, and one or more separation regions wherein the separation regions comprise joints, wherein the joints allow change in said shape after expansion. Example of joints include but are not limited to: pivot type joint, hinge type joint, ratchet type joint, saddle type joint, ball-and-socket type joint, condyloid type joint, and plant type joint. In one example the joint do not come apart. In another example the joints come apart, after expansion.

In one example of any of the examples of this application, the stent prosthesis comprises a plurality of circumferential rings, wherein at least one ring has one or more separation regions (or joints) forming discontinuities (or displacement(s)) after expansion in physiologic conditions.

In another example of any of the examples of this application, the physiologic conditions comprise one or more of: body lumen (including annulus), physiologic pressure, heart beat, muscle contraction, temperature of about 37 C, temperature of about 37 C where the implant is in a water bath at said temperature, a sleeve mimicking a body lumen (or annulus), and/or a test fixture mimicking physiologic conditions.

In one example of any of the examples in this application, the stent prosthesis comprises at least one ring, wherein the ring comprises struts joined by crown, and wherein the rings comprise one or more separation regions, or one or more joints along the circumferential path of said ring, configured to form discontinuities, and/or displacement, and/or change in shape configuration. In one example, the one or more separation regions or joints are located on struts and/or crown regions, allowing at least the ring to uncage, to have displacement, to further expand and/or contract, and/or change shape configuration, after expansion of the stent prosthesis in physiologic environment.

In one example of any of the examples of this application, wherein the stent prosthesis comprise one or more separation regions (or discontinuities) and wherein said separation region or discontinuities after expansion has one or more of the following: displacement in one or more directions, increased displacement in one or more directions, change in shape configuration from initial expanded shape configuration, change in radial strain from initial expanded radial strain, increased radial strain from initial expanded radial strain, decreased strength, decreased strength from initial expanded strength, increased radial strain while decreased strength from initial radial strain and initial strength.

In one example, the stent prosthesis or implant comprises one or more separation regions wherein the separation regions comprise linkages. Linkages allow for displacement (movement) in the same direction (Push Pull Linkages) or in opposite directions (Reverse Motion Linkages). Linkages may be connected in a variety of ways including pins, screws, split pins, polymer fasteners, pop rivets, clevis pins, and/or nut and bolts, etc. The linkages may change the magnitude or direction of the displacement, increase displacement magnitude, reverse displacement direction or magnitude, or combination thereof.

In one example, the stent prosthesis or implant comprises one or more joints wherein the joints are connected in a variety of ways including pins, screws, split pins, polymer fasteners, pop rivets, clevis pins, and/or nut and bolts, etc.

In one example of any of the examples of this application, the prosthesis is an implant comprising one of: stent, implant having a structure, implant having a structure, implant having a structure and a fixation means, or other.

In one example of any of the examples of this application, the stent prosthesis comprising a plurality of adjacent rings, wherein substantially all rings comprise one or more separation regions, discontinuities, or joints, and wherein substantially all rings are capable of one or more of the following: similar radial strain (or compliance) magnitude or change, vaso-motion reactivity of substantially all rings that is substantially similar, uncaging of substantially all rings, further expansion to a larger configuration of substantially all rings, expansion and/or contraction of substantially all rings, displacement in at least one direction (or dimension), change in shape configuration, after expansion from a crimped configuration to an expanded larger configuration under physiological conditions. In another example, the substantially all rings have similar one or more of: radial strain initially and subsequently, further expansion, radial contraction and/or expansion, similar uncaging, similar displacement, similar change in shape configuration, in the expanded configuration under physiological conditions. In another example, some rings have different one or more of: radial strain after expansion, displacement magnitude, shape configuration, contraction and/or expansion, vaso-reactivity, in the expanded configuration under physiologic conditions.

In another example, the stent prosthesis is configured to uncage, wherein uncaging comprises one or more of: having variable compliance (radial strain) after expansion, having controlled compliance (radial strain) after expansion that is different from the radial compliance upon expansion, having adaptive to lumen or vessel compliance (radial strain) after expansion, having variable displacement, having controlled displacement different from initial expanded configuration, having adaptive to lumen or vessel displacement after expansion or deployment, having variable movement, having controlled movement, having adaptive to lumen or vessel movement after expansion, and/or allowing vaso-reactivity after expansion, after said stent expands from a crimped configuration to an expanded configuration under physiologic conditions.

In another example of any of the examples in this application, at least some circumferential structural elements (such as rings) or the implant or stent prosthesis after expansion has a composite radial strain (or compliance) ranging from 1% to 20%, preferably ranging between 1% and 15%, more preferably ranging from 1.5% to 10%, most preferably ranging from 2% to 7%. In another example the radial strain magnitude ranges from 0.07 mm to 3 mm, preferably ranging from 0.1 mm to 2 mm, more preferably ranging from 0.1 mm to 1 mm, and most preferably ranging from 0.1 mm to 0.5 mm. In another example the vaso-reactivity magnitude ranges from 0.07 mm to 3 mm, preferably ranging from 0.1 mm to 2 mm, more preferably ranging from 0.1 mm to 1 mm, and most preferably ranging from 0.1 mm to 0.5 mm.

One skilled in the art would appreciate the various examples and aspects described in this application can be employed to facilitate movement in radial, and/or circumferential, or other direction, or combination thereof.

As with prior examples or embodiments, the male element will typically be free to move circumferentially between opposed walls of the female coupling member to allow circumferential expansion (and/or radial) and/or contraction of the stent prosthesis. The male segment and the female coupling element may be separated by a gap, and the gaps may be left open or conversely may be filled with a material such as an elastomeric cushion material which dampens the circumferential movement of the male element between opposed walls of the circumferential ring.

As one of skill in the art would appreciate, the various examples and embodiments and aspects described and claimed herein can be combined in part or in whole throughout this application.

The following numbered clauses describe other examples, aspects, and embodiments of the inventions described herein:

1. An endoluminal prosthesis comprising: a circumferential scaffold patterned from a biodegradable polymer and having expansion regions which deform as the circumferential scaffold expands from a small diameter configuration to a large diameter configuration; and at least one reinforcement elements coupled to the circumferential scaffold to stiffen the circumferential scaffold after the scaffold has expanded to the large diameter configuration.

2. An endoluminal prosthesis as in clause 1, wherein at least some of the reinforcement elements are coupled to at least some of the expansion regions.

3. An endoluminal prosthesis as in clause 1 or 2, wherein the circumferential scaffold has non-deformable regions which substantially retain their shape as the circumferential scaffold expands.

4. An endoluminal prosthesis as in clause 3, wherein at least some of the reinforcement elements are coupled to at least some of the non-deformable regions.

5. An endoluminal prosthesis as in clause 3, wherein the expansion regions are curved and the non-deformable regions are straight.

6. An endoluminal prosthesis as in clause 5, wherein the curved expansion regions are substantially C-shaped, V-shaped, or U-shaped hinges and the non-deformable regions are struts.

7. An endoluminal prosthesis as in clause 3, wherein at least some of the reinforcement elements are coupled to both an expansion region and a non-deformable region.

8. An endoluminal prosthesis as in clause 1, wherein at least some of the reinforcement are embedded in at least some of the expansion regions.

9. An endoluminal prosthesis as in clause 1 or 2, wherein at least some of the reinforcement elements are disposed at least partly on an exterior of at least some of the expansion regions.

10. An endoluminal prosthesis as in clause 3, wherein at least some of the reinforcement span and are embedded in at least some of the expansion regions and an adjacent non-deformable region.

11. An endoluminal prosthesis as in clause 1, wherein individual reinforcement elements span and are disposed at least partly or an exterior of at least some of the expansion regions and an adjacent non-deformable region.

12. An endoluminal prosthesis as in clause 1, wherein the circumferential scaffold comprises a plurality of adjacent rings, wherein the expansion regions comprise curved regions in the rings which straighten as the scaffold is radially expanded.

13. An endoluminal prosthesis as in clause 12, wherein the scaffold rings are serpentine rings.

14. An endoluminal prosthesis as in clause 13, wherein the scaffold rings are zig-zag rings.

15. An endoluminal prosthesis as in clause 13, wherein individual reinforcement elements are coupled to curves and do not span straight non-deformable regions.

16. An endoluminal prosthesis as in clause 13, wherein individual reinforcement elements span both curves and straight non-deformable regions.

17. An endoluminal prosthesis as in clause 12, wherein the at least one reinforcement element circumscribes substantially an entire circumferential length of at least some of the rings but have at least one break.

18. An endoluminal prosthesis as in clause 12, wherein the at least one reinforcement element circumscribes substantially an entire circumferential length of at least some of the rings but has at least one break after the polymeric material of the circumferential scaffold has degraded in at least one location.

19. An endoluminal prosthesis as in clause 12, wherein there are a plurality of reinforcement elements circumscribing substantially an entire circumferential length of at least some of the rings but each reinforcement element has a at least one break.

20. An endoluminal prosthesis as in clause 12, wherein there are a plurality of reinforcement elements circumscribing substantially an entire circumferential length of at least some of the rings but each reinforcement element has a at least one break after the circumferential scaffold has degraded.

21. An endoluminal prosthesis as in any one of clauses 17-20, wherein the at least one break decreases the resistance of the reinforcement element to radial expansion.

22. An endoluminal prosthesis as in clause 12, wherein the circumferential scaffold further comprises axial links which hold the adjacent rings together and form closed cells.

23. An endoluminal prosthesis as in clause 18, wherein at least some of the reinforcement elements are coupled to at least some axial links.

24. An endoluminal prosthesis as in clause 23, wherein the individual reinforcement elements comprise box structures which are coupled to two substantially parallel rings and two substantially parallel axial links.

25. An endoluminal prosthesis as in clause 1, wherein the biodegradable polymer is selected from a group as set forth in the specification.

26. An endoluminal prosthesis as in clause 1, wherein the reinforcement elements comprise a non-degradable material.

27. An endoluminal prosthesis as in clause 26, wherein the reinforcement elements comprise a non-degradable polymer.

28. An endoluminal prosthesis as in clause 26, wherein the reinforcement element comprises a metal or metal alloy.

29. An endoluminal prosthesis as in clause 28, wherein the metal is selected from a group consisting of stainless steel, shape memory alloys, cobalt chromium alloy, platinum chromium alloy, and others as set forth in the specification.

30. An endoluminal prosthesis as in clause 28, wherein the reinforcement element comprises an elastic material coupled to an expansion region and biased to open the expansion region after the circumferential scaffold has been deployed.

31. An endoluminal prosthesis as in clause 26, wherein the reinforcement elements comprise V-shaped springs coupled to V-shaped expansion regions, C-shaped springs attached to C-shaped expansion regions, or U-shaped springs attached to U-shaped expansion regions.

32. An endoluminal prosthesis comprising: a scaffold having circumferential rings patterned from a non-degradable material, said scaffold being configured to expand from a crimped configuration to an expanded configuration;

wherein at least some of the circumferential rings have separation regions configured to form discontinuities in said circumferential rings in response to energy applied to the separation regions after deployment.

33. An endoluminal prosthesis as in clause 32, wherein the discontinuities form after implantation of said prosthesis in a body lumen, whereby the discontinuities allow the scaffold further expand beyond the initial expansion.

34. An endoluminal prosthesis as in clause 32, wherein the separation regions are configured to fatigue and separate in response.

35. An endoluminal prosthesis as in clause 32, wherein the separation regions are configured to fatigue in response to an externally applied energy source.

36. An endoluminal prosthesis as in clause 34 or 35, wherein the separation regions comprise notches or thinned regions in the circumferential rings which preferentially fatigue and break in response to applied energy.

37. An endoluminal prosthesis as in clause 34 or 35, wherein the separation regions comprise living hinges which cycle open and closed in response to the energy to fatigue and break.

38. An endoluminal prosthesis as in clause 34 or 35, wherein the separation regions comprise modified grain boundaries in metal circumferential rings which preferentially fatigue and break in response to applied energy.

39. An endoluminal prosthesis as in clause 34 or 35, wherein the separation regions are formed by breaking circumferential rings at one or more sites over their circumference and rejoining the breaks with connectors which are configured to open in response to applied energy.

40. An endoluminal prosthesis as in clause 39, wherein the connectors will break in response to externally applied energy selected from the group consisting of ultrasound, heat, and magnetism.

41. An endoluminal prosthesis as in clause 34 or 35, wherein the separation regions comprise a key and lock junction formed in the circumferential rings, wherein said key and lock junctions are immobilized during expansion but configured to open in response to applied energy.

42. An endoluminal prosthesis as in clause 34 or 35, wherein the separation regions comprise a rivet or other fastener joining breaks in the circumferential element and configured to open in response to applied energy.

43. An endoluminal prosthesis a sin clause 32, wherein the circumferential rings comprise serpentine rings.

44. An endoluminal prosthesis as in clause 32, wherein the circumferential rings comprise zig-zag rings.

45. An endoluminal prosthesis as in clause 32, wherein the non-degradable material comprises a metal or a metal alloy.

46. An endoluminal prosthesis as in clause 45, wherein the metal selected from a group consisting of stainless steel, and other metals set forth in the specification.

47. An endoluminal prosthesis comprising: a scaffold having circumferential rings patterned from a non-degradable material, said scaffold being configured to expand from a crimped configuration to an expanded configuration; wherein at least some of the circumferential rings have at least one separation region configured to form discontinuities in said circumferential rings after expansion in a physiologic environment.

48. An endoluminal prosthesis as in clause 47, wherein discontinuities allow the scaffold further expand beyond the initial expansion.

49. An endoluminal prosthesis as in clause 48, wherein the physiologic environment is a water bath, water at 37° C., or a body lumen.

50. An endoluminal prosthesis as in clause 47, wherein the physiologic environment is a body lumen.

51. An endoluminal prosthesis as in clause 47, wherein the body lumen is a blood vessel.

52. An endoluminal prosthesis as in clause 47, wherein the discontinuities in the rings allow the scaffold to circumferentially open as the blood vessel positively remodels.

53. An endoluminal prosthesis as in clause 47, wherein the separation regions comprise key and lock junctions which are immobilized during expansion but configured to separate after the initial expansion in the physiologic environment.

54. An endoluminal prosthesis as in clause 53, wherein the key and lock junction is cemented by a material which degrades in the physiologic environment.

55. An endoluminal prosthesis as in clause 47, wherein the separation regions comprise a butt joint joined by an adhesive or connector which degrades in the physiologic environment.

56. An endoluminal prosthesis as in clause 47, wherein the separation regions comprise notches or thinned sections in the circumferential rings which preferentially erode in the physiologic environment.

57. An endoluminal prosthesis as in clause 47, wherein the separation regions comprise modified grain boundaries in metal circumferential rings which preferentially erode in the physiologic environment.

58. An endoluminal prosthesis as in clause 47, wherein the separation regions are formed by breaking circumferential rings at one or more sites over their circumference and rejoining the breaks with adhesives or connectors which are configured to erode in the physiologic environment.

59. An endoluminal prosthesis as in clause 58, wherein the connectors comprise sleeves or rings spanning the breaks.

60. An endoluminal prosthesis as in clause 47, wherein the separation regions comprise a rivet or other fastener joining breaks in the circumferential ring, wherein the fastener erodes in the physiologic embodiment.

61. An endoluminal prosthesis as in clause 47, wherein the circumferential rings comprise serpentine rings.

62. An endoluminal prosthesis as in clause 45, wherein the circumferential rings comprise zig-zag rings.

63. An endoluminal prosthesis as in clause 45, wherein the non-degradable material comprises a metal.

64. An endoluminal prosthesis as in clause 47, wherein the metal is selected from a group consisting of stainless steel, and the metals set forth in the specification.

65. An endoluminal prosthesis as in clause 47, wherein there is one or more separation regions on at least some rings wherein the separation regions are located on crowns, and/or struts.

66. An endoluminal prosthesis as in clause 47, wherein the separation regions locations and number are configured to allow positive lumen remodeling.

67. An endoluminal prosthesis as in clause 65, wherein additionally the weight of the stent prosthesis after deployment in physiologic environment allows for positive lumen remodeling.

68. An endoluminal prosthesis as in clause 47, wherein the separation region provides uncaging of the stent prosthesis after deployment in a physiologic environment.

69. An endoluminal prosthesis as in clause 68, wherein the stent prosthesis uncages in a circumferential direction.

70. An endoluminal prosthesis comprising: a scaffold having circumferential rings patterned from a non-degradable material, said scaffold being configured to deploy from a crimped configuration to an expanded configuration and said circumferential rings having hinges which open as the scaffold is being deployed; wherein at least some of the hinges on at least some of the rings are constricted from expansion during deployment and are configured to open in a physiologic environment after deployment or in response to the application of internal or external energy after deployment.

71. An endoluminal prosthesis as in clause 70, wherein the scaffold is released to further expand circumferentially after said hinges are opened.

72. An endoluminal prosthesis as in clause 70, wherein the wherein the physiologic environment is a water bath, water at 37° C., or a body lumen.

73. An endoluminal prosthesis as in clause 70, wherein the physiologic environment is a body lumen.

74. An endoluminal prosthesis as in clause 73, wherein the body lumen is a blood vessel.

75. An endoluminal prosthesis as in clause 74, wherein the scaffold is circumferentially released to open as the blood vessel positively remodels.

76. An endoluminal prosthesis as in clause 70, wherein the hinges open 30 days to 6 months after the initial expansion of the circumferential scaffold.

77. An endoluminal prosthesis as in clause 70, wherein the hinges are constricted by one or more of adhesives, polymer filaments and polymer sleeves.

78. An endoluminal prosthesis as in clause 70, wherein the non-degradable material comprises a metal or a metal alloy as set forth in the specification.

79. An endoluminal prosthesis comprising: a scaffold having circumferential rings patterned from a non-degradable material, said scaffold being configured to deploy from a crimped configuration to an expanded configuration and said circumferential rings including struts connected by joints which open as the scaffold is being deployed; wherein at least some of the joints are pivoted to allow the scaffold in its expanded configuration to further expand.

80. An endoluminal prosthesis as in any of the independent clauses, wherein the stent prosthesis further comprises non-degradable radiopaque markers.

81. An endoluminal prosthesis as in any of the independent clauses, wherein the stent comprises at least one coating on at least one surface of the stent 82. An endoluminal prosthesis as in any of the independent clauses, wherein the stent prosthesis comprises at least one drug.

83. An endoluminal prosthesis as in 82, wherein the drug tissue concentration adjacent to the stent lasts beyond the time period of un-caging the stent, forming the discontinuity, and/or breaking of the stent.

84. An endoluminal prosthesis comprising: a scaffold having one or more circumferential rings patterned from a non-degradable material, said scaffold being configured to expand from a crimped configuration to an expanded configuration; wherein one or more of the circumferential rings comprises a plurality of struts joined by crowns and at least one of the struts has at least one separation region configured to form a discontinuity in said circumferential ring(s) after expansion in a physiologic environment.

85. An endoluminal prosthesis as in clause 84, wherein discontinuities allow the scaffold further expand after an initial expansion.

86. An endoluminal prosthesis as in clause 84, wherein the physiologic environment is a water bath at about 37° C., or a body lumen.

87. An endoluminal prosthesis as in clause 84, wherein the physiologic environment is a body lumen.

88. An endoluminal prosthesis as in clause 84, wherein the body lumen comprises a blood vessel or valve annulus.

89. An endoluminal prosthesis as in clause 88, wherein the discontinuity in the ring allows at least a portion of the scaffold to circumferentially open within the body lumen after deployment.

90. An endoluminal prosthesis as in clause 84, wherein the discontinuities form 30 days to 6 months after the initial expansion of the circumferential scaffold in the physiologic environment.

91. An endoluminal prosthesis as in clause 84, wherein the separation regions comprise key and lock junctions in the struts which are immobilized during expansion but configured to open after the initial expansion in the physiologic environment.

92. An endoluminal prosthesis as in clause 91, wherein the key and lock junctions are configured to allowed the joined segments of the strut to separate from each other in a radial direction only after they are mobilized.

93. An endoluminal prosthesis as in clause 91, wherein the key and lock junctions are configured to allowed the joined segments of the strut to separate from each other in both a radial direction and an axial direction after they are mobilized.

94. An endoluminal prosthesis as in clause 91, wherein the key and lock junctions are immobilized by a cement, adhesive, or polymer which degrades in the physiologic environment.

95. An endoluminal prosthesis as in clause 91, wherein the key and lock junctions are immobilized by an overlying a sleeve which degrades in the physiologic environment.

96. An endoluminal prosthesis as in clause 84, wherein the separation regions comprise a butt joint joined by an adhesive, cement, polymer, sleeve, or connector which degrades in the physiologic environment.

97. An endoluminal prosthesis as in clause 84, wherein the separation regions comprise notches or thinned sections in the circumferential rings which preferentially erode in the physiologic environment.

98. An endoluminal prosthesis as in clause 84, wherein the separation regions comprise modified grain boundaries in metal circumferential rings which preferentially erode in the physiologic environment.

99. An endoluminal prosthesis as in clause 84, wherein the separation regions are formed by breaking circumferential rings at one or more sites over their circumference and rejoining the breaks with cement, adhesive, or polymer which are configured to erode in the physiologic environment.

100. An endoluminal prosthesis as in clause 99, wherein the connectors comprise sleeves or rings spanning the breaks.

101. An endoluminal prosthesis as in clause 84, wherein the separation regions comprise a rivet or other fastener joining breaks in the circumferential ring, wherein the fastener erodes in the physiologic embodiment.

102. An endoluminal prosthesis as in clause 84, wherein the circumferential rings comprise serpentine rings.

103. An endoluminal prosthesis as in clause 84, wherein the circumferential rings comprise zig-zag rings.

104. An endoluminal prosthesis as in clause 84, wherein the non-degradable material comprises a metal.

105. An endoluminal prosthesis as in clause 84, wherein the scaffold further comprises a coating on at least one surface of the scaffold.

106. An endoluminal prosthesis as in clause 84, wherein the scaffold further comprises a coating on at least one surface of the scaffold, and wherein the coating comprises a drug.

107. An endoluminal prosthesis as in clause 84, wherein the scaffold in the expanded configuration has sufficient strength to support a body lumen.

108. An endoluminal prosthesis comprising: a scaffold having circumferential rings patterned from a non-degradable material, said scaffold being configured to expand from a crimped configuration to an expanded configuration; wherein at least some of the circumferential rings comprise a plurality of struts joined by crowns and at least some of struts have at least one separation region wherein the strut has a pre-formed break which is immobilized by a sleeve or an adhesive which will degrade in a physiologic environment.

109. An endoluminal prosthesis as in clause 108, wherein the separation regions comprise key and lock junctions in the struts which are immobilized during expansion but configured to open after the initial expansion in the physiologic environment.

110. An endoluminal prosthesis as in clause 109, wherein the key and lock junctions are configured to allowed the joined segments of the strut to separate from each other in a radial direction only after they are mobilized.

111. An endoluminal prosthesis as in clause 109, wherein the key and lock junctions are configured to allowed the joined segments of the strut to separate from each other in both a radial direction and an axial direction after they are mobilized.

112. An endoluminal prosthesis as in clause 109, wherein the key and lock junctions are immobilized by a cement which degrades in the physiologic environment.

113. An endoluminal prosthesis as in clause 109, wherein the key and lock junctions are immobilized by an overlying a sleeve which degrades in the physiologic environment.

114. An endoluminal prosthesis a sin clause 108, wherein the circumferential rings comprise serpentine rings.

115. An endoluminal prosthesis as in clause 108, wherein the circumferential rings comprise zig-zag rings.

116. An endoluminal prosthesis as in clause 108, wherein the non-degradable material comprises a metal or a metal alloy.

117. An endoluminal prosthesis as in clause 116, wherein the metal selected from a group consisting of stainless steel, and other metals set forth in the specification.

118. An endoluminal prosthesis as in clause 108, wherein at least one strut on each ring has a separation region.

119. An endoluminal prosthesis as in clause 118, wherein all crowns and links are free from separation regions.

120. An endoluminal prosthesis as in clause 118, wherein the separation regions locations and number are configured to allow positive lumen remodeling.

121. An endoluminal prosthesis as in clause 119, wherein additionally the weight of the stent prosthesis after deployment in physiologic environment allows for positive lumen remodeling.

122. An endoluminal prosthesis as in clause 108, wherein the separation region provides uncaging of the stent prosthesis after deployment in a physiologic environment.

123. An endoluminal prosthesis as in clause 122, wherein the stent prosthesis uncages in a circumferential direction.

124. An endoluminal prosthesis comprising: a scaffold having circumferential rings patterned from a non-degradable material, said scaffold being configured to expand from a crimped configuration to an expanded configuration; wherein at least some of the circumferential rings comprise a plurality of struts joined by crowns and at least some of crowns have at least one separation region which is immobilized by a sleeve or an adhesive which will degrade in a physiologic environment.

125. An endoluminal prosthesis as in clause 124, wherein the separation region comprises a thinned region in the crown(s) allowing the scaffold to uncage after degradation of the sleeve or the adhesive material.

126. An endoluminal prosthesis as in clause 122, wherein the separation region is a break in the crowns allowing the scaffold to uncage after degradation of the sleeve or the adhesive material.

Gap Clauses

127. An endovascular prosthesis comprising: a scaffold having a plurality of rings which define a circumference of the scaffold, said scaffold being configured to expand from a crimped configuration to an expanded configuration and the plurality of rings are formed from a non-degradable material; wherein at least some of the circumferential rings follow a circumferential path about the circumference of the scaffold and have at least one gap in said path when the scaffold is in its expanded configuration and wherein adjacent rings are axially linked so that all portions of the scaffold remain connected when the scaffold is in its expanded configuration.

128. An endovascular prosthesis as in clause 127, wherein the gaps are open in the rings when the scaffold is in its crimped configuration.

129. An endovascular prosthesis as in clause 128, wherein the gaps in the rings open further when the scaffold is in its expanded configuration 130. An endovascular prosthesis as in clause 127, wherein the gaps are open in the rings only after the scaffold is in its expanded configuration.

131. An endovascular prosthesis as in clause 127, wherein the gaps in the circumferential rings are rotationally staggered.

132. An endovascular prosthesis as in clause 131, wherein the circumferential rings are axially linked in a staggered pattern which is rotationally offset from the staggered gap pattern.

133. An endovascular prosthesis as in clause 127, wherein the circumferential rings comprise serpentine rings.

134. An endovascular prosthesis as in clause 127, wherein the circumferential rings comprise zig-zag rings.

135. An endovascular prosthesis as in clause 127, wherein the non-degradable material comprises a metal.

136. An endovascular prosthesis as in clause 128, wherein the circumferential rings comprise a plurality of struts joined by crowns.

137. An endovascular prosthesis as in clause 136, wherein the gaps are present in the crowns.

138. An endovascular prosthesis as in clause 127, wherein the gaps are present in the struts.

139. An endovascular prosthesis as in clause 127, wherein the gaps span a crown and a strut.

140. An endovascular prosthesis as in clause 127, wherein the scaffold displays a compliance from 1% to 5%, often from 1% to 3%, when subjected to systolic/diastolic pressure cycling.

Bridge Clauses

141. An endovascular prosthesis comprising: a scaffold having a plurality of rings which define a circumference of the scaffold, said scaffold being configured to expand from a crimped configuration to an expanded configuration and the plurality of rings are formed from a non-degradable material; wherein at least some of the circumferential rings follow a circumferential path about the circumference of the scaffold and have at least one biodegradable segment in said path and wherein adjacent rings are axially linked so that all portions of the scaffold remain connected after the biodegradable segments in the scaffold have degraded.

142. An endovascular prosthesis as in clause 141, wherein the biodegradable segments are configured to remain intact while the scaffold is expanded in a vascular environment and to form gaps in the rings after the segments have degraded in the vascular environment.

143. An endovascular prosthesis as in clause 141, wherein the biodegradable segments are configured to degrade in a vascular environment over a time period in the range from 3 months to 3 years.

144. An endovascular prosthesis as in clause 141, wherein the biodegradable segments in the circumferential rings are rotationally staggered.

145. An endovascular prosthesis as in clause 144, wherein the circumferential rings are axially linked in a staggered pattern which is rotationally offset from the staggered gap pattern.

146. An endovascular prosthesis as in clause 141, wherein the circumferential rings comprise serpentine rings.

147. An endovascular prosthesis as in clause 141, wherein the circumferential rings comprise zig-zag rings.

148. An endovascular prosthesis as in clause 141, wherein the non-degradable material comprises a metal.

149. An endovascular prosthesis as in clause 148, wherein the biodegradable segments comprises a biodegradable polymer.

150. An endovascular prosthesis as in clause 141, wherein the circumferential rings comprise a plurality of struts joined by crowns.

151. An endovascular prosthesis as in clause 150, wherein the biodegradable segments are present in the crowns.

152. An endovascular prosthesis as in clause 141, wherein the biodegradable segments are present in the struts.

153. An endovascular prosthesis as in clause 141, wherein the biodegradable segments span a crown and a strut.

154. An endovascular prosthesis as in clause 141, wherein the scaffold displays a radial compliance often from 1.2% to 3%, or more often from 1.2% to 3% in its expanded configuration without the biodegradable segments when subjected to systolic/diastolic pressure cycling.

155. An endovascular prosthesis as in clause 154, wherein the scaffold displays a compliance from 1% to 5%, often between 1% to 3%, in its expanded configuration with the biodegradable segments in place when subjected to systolic/diastolic pressure cycling.

Method of Making Clauses

156. A method of making an endovascular prosthesis, said method comprising: fabricating a first scaffold having a plurality of rings which define a circumference of the scaffold, wherein the plurality of rings are formed from a non-degradable material; fabricating a second scaffold having a plurality of rings which define a circumference of the scaffold, wherein the plurality of rings are formed from a biodegradable material and wherein the first and second scaffolds have identical geometries; forming gaps in portions of at least some of the rings of the first scaffold; cutting segments from the second scaffold, wherein the segments are selected to fill in the gaps in the first scaffold; and securing the segments cut from the second scaffold into the gaps formed in the first scaffold.

157. A method of making an endovascular prosthesis as in clause 156, wherein the biodegradable material is selected to remain intact while the scaffold is expanded in a vascular environment and to form gaps in the rings after the segments have degraded in the vascular environment.

158. A method of making an endovascular prosthesis as in clause 156, wherein the biodegradable material is selected to degrade in a vascular environment over a time period in the range from 3 months to 3 years.

159. A method of making an endovascular prosthesis as in clause 156, wherein the gaps in the circumferential rings of the first scaffold are rotationally staggered.

160. A method of making an endovascular prosthesis as in clause 159, wherein the circumferential rings in the first scaffold are axially linked in a staggered pattern which is rotationally offset from the staggered gap pattern.

161. A method of making an endovascular prosthesis as in clause 156, wherein the circumferential rings in the first scaffold comprise serpentine rings.

162. A method of making an endovascular prosthesis as in clause 156, wherein the circumferential rings in the first scaffold comprise zig-zag rings.

163. A method of making an endovascular prosthesis as in clause 156, wherein the non-degradable material comprises a metal.

164. An endovascular prosthesis as in clause 163, wherein the biodegradable material comprises a biodegradable polymer.

165. A method of making an endovascular prosthesis as in clause 156, wherein the circumferential rings comprise a plurality of struts joined by crowns.

166. A method of making an endovascular prosthesis as in clause 165, wherein the gaps are present in the crowns.

167. A method of making an endovascular prosthesis as in clause 156, wherein the gaps are present in the struts.

Alternative Clauses

168. A degradable stent prosthesis comprising: a circumferential scaffold patterned from a biodegradable material and having expansion regions which deform as the circumferential scaffold expands from a small diameter configuration to a larger diameter configuration; and at least one reinforcement element is coupled to the circumferential scaffold to stiffen the circumferential scaffold after the scaffold has expanded to the large diameter configuration.

169. A stent prosthesis as in clause 168, wherein the stent prosthesis comprises an endoluminal prosthesis.

170. A stent prosthesis as in clause 168, wherein the small diameter is the crimped configuration, and wherein the larger expanded diameter is the deployed configuration.

171. A stent prosthesis as in clause 168, wherein the degradable material comprises polymeric material.

172. A stent prosthesis as in clause 168, wherein the degradable material comprises metal or metal alloy.

173. A stent prosthesis as in clause 168, wherein the degradable material is a polymeric material comprises one or more of: lactides, caprolactones, trimethylene carbonate, glycolides, poly(L-lactide), poly-DL-Lactide, polylactide-co-glycolide (e.g., poly(L-lactide-co-glycolide), poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly-caprolactone, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids, polymers, blends, and/or co-polymers, or combination thereof.

174. A stent prosthesis as in clause 168, wherein the degradable material is metal or metal alloy comprising magnesium.

175. A stent prosthesis as in clause 168, wherein at least some of the reinforcement elements are coupled to at least some of the expansion regions.

176. A stent prosthesis as in clause 168, wherein substantially all expansion regions are coupled to reinforcement elements.

177. A stent prosthesis as in clause 168, wherein substantially most expansion regions are coupled to reinforcement elements.

178. A stent prosthesis as in clause 168, wherein at least half of the expansion regions are coupled to reinforcement elements.

179. A stent prosthesis as in clause 168 or 175, wherein the circumferential scaffold has non-deformable regions which substantially retain their shape as the circumferential scaffold expands.

180. A stent prosthesis as in clause 179, wherein at least some of the reinforcement elements are coupled to at least some of the non-deformable regions.

181. A stent prosthesis as in clause 179, wherein the expansion regions are curved and the non-deformable regions are straight.

182. A stent prosthesis as in clause 181, wherein the curved expansion regions are substantially C-shaped, V-shaped, or U-shaped hinges and the non-deformable regions are struts.

183. A stent prosthesis as in clause 179, wherein at least some of the reinforcement elements are coupled to both an expansion region and a non-deformable region.

184. A stent prosthesis as in clause 168, wherein at least some of the reinforcement are embedded in at least some of the expansion regions.

185. A stent prosthesis as in clause 168 or 175, wherein at least some of the reinforcement elements are disposed at least partly on an exterior of at least some of the expansion regions.

186. A stent prosthesis as in clause 179, wherein at least some of the reinforcement span and are embedded in at least some of the expansion regions and an adjacent non-deformable region.

187. A stent prosthesis as in clause 168, wherein individual reinforcement elements span and are disposed at least partly on an exterior of at least some of the expansion regions and an adjacent non-deformable region.

188. A stent prosthesis as in clause 168, wherein the circumferential scaffold comprises a plurality of adjacent rings, wherein the expansion regions comprise curved regions in the rings which straighten as the scaffold is radially expanded, and wherein the curved regions join substantially straight non deformable regions in the rings.

189. A stent prosthesis as in clause 188, wherein the scaffold rings are serpentine rings.

190. A stent prosthesis as in clause 188, wherein the scaffold rings are zig-zag rings.

191. A stent prosthesis as in clause 188, wherein individual reinforcement elements are coupled to curved regions and do not span straight non-deformable regions.

192. A stent prosthesis as in clause 188, wherein the scaffold pattern is closed cell pattern.

193. A stent prosthesis as in clause 188, wherein individual reinforcement elements span both curves and straight non-deformable regions.

194. A stent prosthesis as in clause 188, wherein individual reinforcement elements span the curved regions and at least some of the non-deformable regions.

195. A stent prosthesis as in clause 188, wherein the at least one reinforcement element circumscribes substantially an entire circumferential length of at least some of the rings but have at least one break in each ring.

196. A stent prosthesis as in clause 188, wherein the at least one reinforcement element per ring circumscribes substantially an entire circumferential length of at least some of the rings but have at least one break in each ring.

197. A stent prosthesis as in clause 188, wherein the adjacent rings are connected in at least one region by a link, and wherein at least one of the links are coupled to the at least one reinforcement element.

198. A stent prosthesis as in clause 188, wherein the at least one reinforcement element circumscribes substantially an entire circumferential length of at least some of the rings but has at least one break after the degradable material of the circumferential scaffold has degraded in at least one location.

199. A stent prosthesis as in clause 188, wherein the at least one reinforcement element circumscribes substantially an entire circumferential length of at least some of the rings but has at least one break after the degradable material of the circumferential scaffold has degraded in the at least one break region.

200. A stent prosthesis as in clause 188, wherein there are a plurality of reinforcement elements circumscribing substantially an entire circumferential length of at least some of the rings but each reinforcement element has a at least one break.

201. A stent prosthesis as in clause 188, wherein there are a plurality of reinforcement elements circumscribing substantially an entire circumferential length of at least some of the rings but each reinforcement element has a at least one break after the circumferential scaffold has degraded.

202. A stent prosthesis as in any one of clauses 195-201, wherein the at least one break decreases the resistance of the reinforcement element to radial expansion.

203. A stent prosthesis as in any one of clauses 195-201, wherein the at least one break diminishes the resistance of the reinforcement element to radial expansion.

204. A stent prosthesis as in clause 188, wherein the circumferential scaffold further comprises axial links which hold the adjacent rings together and form closed cells.

205. A stent prosthesis as in clause 198, wherein at least some of the reinforcement elements are coupled to at least some axial links.

206. A stent prosthesis as in clause 205, wherein the individual reinforcement elements comprise box structures which are coupled to two substantially parallel rings and two substantially parallel axial links.

207. A stent prosthesis as in clause 168, wherein the biodegradable material is a polymeric material selected from a group as set forth in the specification.

208. A stent prosthesis as in clause 168, wherein the biodegradable material is a metal or metal alloy material selected from a group as set forth in the specification.

209. A stent prosthesis as in clause 168, wherein the reinforcement elements comprise a non-degradable material.

210. A stent prosthesis as in clause 168, wherein the reinforcement elements comprise degradable material, wherein said degradable material is stiffer than the scaffold patterned biodegradable material.

211. A stent prosthesis as in clause 168, wherein the reinforcement elements comprise a non-degradable polymer.

212. A stent prosthesis as in clause 168, wherein the reinforcement element comprises a metal or metal alloy.

213. A stent prosthesis as in clause 212, wherein the metal or metal alloy is selected from a group consisting of stainless steel, shape memory alloys, cobalt chromium alloy, platinum chromium alloy, and others as set forth in the specification.

214. A stent prosthesis as in clause 212, wherein the reinforcement element comprises an elastic material coupled to an expansion region and biased to open the expansion region after the circumferential scaffold has been deployed.

215. A stent prosthesis as in clause 212, wherein the reinforcement element comprises an elastic material coupled to two adjacent substantially non-deformable regions and biased to open the expansion region joining the two adjacent non-deformable regions after the circumferential scaffold has been deployed, and wherein the reinforcement element has an expansion region shape.

216. A stent prosthesis as in clause 168, wherein the reinforcement element has a substantially similar shape to the expansion region.

217. A stent prosthesis as in clause 168, wherein the stent further comprises radiopaque markers.

218. A stent prosthesis as in clause 168, wherein the stent further comprises a drug and polymer matrix coating.

219. A stent prosthesis as in clause 168, wherein the stent further comprises a coating on at least one surface of the stent.

220. A stent prosthesis as in clause 219, wherein the stent further comprises a degradable coating on at least one surface of the stent.

221. A stent prosthesis as in clause 168 or any of the clauses, wherein the patterned biodegradable scaffold material degrades in a period ranging from 1 month to 3 years.

222. A stent prosthesis as in clause 168 or any of the clauses, wherein the reinforcement element remains substantially intact after degradation of the stent material.

223. A stent prosthesis as in clause 168, wherein the stent after expansion exhibit one or more of: vaso-dilation, vaso-constriction, radial strain of 1.5% to 5%, further expand to a larger configuration after recoil from said expansion, 224. A stent prosthesis as in clause 168 or any clause, wherein the reinforcement element is degradable material stiffer than the stent biodegradable patterned material, and wherein the said reinforcement elements degradable material degrades at a rate slower than the stent degradable material.

225. A stent prosthesis as in clause 168 or any clause, wherein the stent after degradation of the patterned degradable material comprises a plurality of adjacent reinforcement elements in a circumferential and/or longitudinal direction.

226. A stent as in clause 168, wherein the stent at body temperature is expanded to the deployed diameter and has sufficient strength to support a body lumen.

227. A stent as in clause 168, wherein the stent after degradation of the patterned material comprises reinforcement elements, said stent does not have sufficient strength to support a body lumen.

228. A stent as in clause 168, wherein the stent after degradation of the patterned material does not have sufficient strength to support a body lumen, but comprises reinforcement elements in a pattern sufficient to support a body lumen.

229. A stent prosthesis as in clause 168, wherein the reinforcement elements comprise V-shaped springs coupled to V-shaped expansion regions, C-shaped springs attached to C-shaped expansion regions, or U-shaped springs attached to U-shaped expansion regions.

230. An stent prosthesis comprising: a scaffold having circumferential rings patterned from a non-degradable material, said scaffold being configured to expand from a crimped configuration to an expanded configuration; wherein at least some of the circumferential rings have separation regions configured to form discontinuities in said circumferential rings in response to energy applied to the separation regions after deployment.

231. A stent prosthesis as in clause 230, wherein the stent is expanded under physiologic conditions.

232. A stent prosthesis as in clause 230, wherein the discontinuities form after implantation of said prosthesis in a body lumen, whereby the discontinuities allow the scaffold further expand after recoil from said initial expansion.

233. A stent prosthesis as in clause 230, wherein the separation regions are configured to fatigue and separate in response to pulsation of a blood vessel in which the stent prosthesis has been implanted.

234. A stent prosthesis as in clause 233, wherein the separation regions are contained by a sleeve that continues to substantially contain the separation regions after the separation.

235. A stent prosthesis as in clause 230, wherein the separation regions are configured to fatigue and separate in response to physiological pressure of a blood vessel in which the stent prosthesis has been implanted.

236. A stent prosthesis as in clause 230, wherein the discontinuities form after expansion of said scaffold under physiologic conditions, whereby the discontinuities allow the scaffold to have radial compliance ranging between 1% and 5%.

237. A stent prosthesis as in clause 230, wherein the discontinuities form after expansion of said scaffold under physiologic conditions, whereby the discontinuities allow the scaffold to expand or restrict in response to a vaso-dilator or vaso-constrictor.

238. A stent prosthesis as in clause 230, wherein the separation regions are configured to fatigue in response to an externally applied energy source.

239. A stent as in clause 230 or 233, wherein the energy applied is physiological conditions.

240. A stent prosthesis as in clause 233 or 238, wherein the separation regions comprise notches, hollowed out expansion regions, or thinned regions in the circumferential rings which preferentially fatigue and break in response to applied energy.

241. A stent prosthesis as in clause 233 or 238, wherein the separation regions comprise living hinges which cycle open and closed in response to the energy to fatigue and break.

242. A stent prosthesis as in clause 233 or 238, wherein the separation regions comprise modified grain boundaries in metal circumferential rings which preferentially fatigue and break in response to applied energy.

243. A stent prosthesis as in clause 233 or 238, wherein the separation regions are formed by breaking circumferential rings at one or more sites over their circumference and rejoining the breaks with connectors which are configured to open in response to applied energy.

244. A stent prosthesis as in clause 243, wherein the connectors will break in response to externally applied energy selected from the group consisting of ultrasound, heat, and magnetism.

245. A stent prosthesis as in clause 233 or 238, wherein the separation regions comprise a key and lock junction formed in the circumferential rings, wherein said key and lock junctions are immobilized during expansion but configured to open or separate in response to applied energy.

246. A stent prosthesis as in clause 233 or 238, wherein the separation regions comprise a rivet or other fastener joining breaks in the circumferential element and configured to open in response to applied energy.

247. A stent prosthesis as in clause 230, wherein the circumferential rings comprise serpentine rings.

248. A stent prosthesis as in clause 230, wherein the circumferential rings comprise zig-zag rings.

249. A stent prosthesis as in clause 230, wherein the rings comprise closed cell pattern.

250. A stent prosthesis as in clause 230, wherein the non-degradable material comprises a metal or a metal alloy.

251. A stent prosthesis as in clause 250, wherein the metal selected from a group consisting of stainless steel, cobalt chromium alloy, platinum chromium alloy, and other metals set forth in the specification.

252. A stent prosthesis comprising; a scaffold having circumferential rings patterned from a degradable material, said scaffold being configured to expand from a crimped configuration to an expanded configuration; wherein at least some of the circumferential rings have separation regions configured to form discontinuities in said circumferential rings after deployment of the stent under physiological condition.

253. A stent prosthesis as in clause 252 wherein the degradable material comprises a polymeric material or metallic material.

254. A stent prosthesis as in clause 252 or 253 wherein the degradable material is one or more of the following: lactides, caprolactones, trimethylene carbonate, glycolides, poly(L-lactide), poly-DL-Lactide, polylactide-co-glycolide (e.g., poly(L-lactide-co-glycolide), poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly-caprolactone, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids, polymers, blends, and/or co-polymers, or combination thereof, Nickel; Cobalt; Tungsten; Tungsten alloys of rhenium, cobalt, iron, zirconium, zinc, titanium; Magnesium, Magnesium alloy AZ31, magnesium alloy with less than 20% zinc or aluminum by weight, without or with one or more impurities of less than 3% iron, silicone, manganese, cobalt, nickel, yttrium, scandium or other rare earth metal; zinc or its alloy; bismuth or its alloy; indium or its alloy, tin or its alloy such as tin-lead; silver or its alloy such as silver-tin alloy; cobalt-iron alloy; iron; iron containing alloys such as 80-55-06 grade cast ductile iron, other cast ductile irons, AISI 1010 steel, AISI 1015 steel, AISI 1430 steel, AISI 8620 steel, AISI 5140 steel, or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or combination thereof.

255. A stent prosthesis comprising: a scaffold having circumferential rings patterned from a non-degradable material, said scaffold being configured to expand from a crimped configuration to an expanded configuration; wherein at least some of the circumferential rings have at least one separation region configured to form discontinuities in said circumferential rings after expansion in a physiologic environment.

256. A stent prosthesis as in clause 255, wherein discontinuities allow the scaffold further expand beyond the initial expansion, have radial strain ranging from 1.5% to 5%, or further expand in response to a vaso-dilator.

257. A stent prosthesis as in clause 256, wherein the physiologic environment is a water bath, water at 37° C., pressure pulsation, or a body lumen.

258. A stent prosthesis as in clause 255, wherein the physiologic environment is a body lumen.

259. A stent prosthesis as in clause 255, wherein the body lumen is a blood vessel.

260. A stent prosthesis as in clause 255, wherein the discontinuities in the rings allow the scaffold to circumferentially open as the blood vessel positively remodels.

261. A stent prosthesis as in clause 255, wherein the discontinuities form 30 days to 6 months after the initial expansion of the circumferential scaffold in the physiologic environment.

262. A stent prosthesis as in clause 255, wherein the separation regions comprise key and lock junctions which are immobilized during expansion but configured to separate after the initial expansion in the physiologic environment.

263. A stent prosthesis as in clause 262, wherein the key and lock junction is cemented by a material which degrades in the physiologic environment.

264. A stent prosthesis as in clause 255, wherein the separation regions comprise a butt joint joined by an adhesive or connector which degrades in the physiologic environment.

265. A stent prosthesis as in clause 255, wherein the separation regions comprise notches or thinned sections in the circumferential rings which preferentially erode in the physiologic environment.

266. A stent prosthesis as in clause 255, wherein the separation regions comprise modified grain boundaries in metal circumferential rings which preferentially erode in the physiologic environment.

267. A stent prosthesis as in clause 255, wherein the separation regions are formed by breaking circumferential rings at one or more sites over their circumference and rejoining the breaks with adhesives or connectors which are configured to erode in the physiologic environment.

268. A stent prosthesis as in clause 267, wherein the connectors comprise sleeves or rings spanning the breaks.

269. A stent prosthesis as in clause 255, wherein the separation regions comprise a rivet or other fastener joining breaks in the circumferential ring, wherein the fastener erodes in the physiologic embodiment.

270. A stent prosthesis as in clause 255, wherein the circumferential rings comprise serpentine rings.

271. A stent prosthesis as in clause 250, wherein the circumferential rings comprise zig-zag rings.

272. A stent prosthesis as in clause 255, wherein the non-degradable material comprises a metal or metal alloy.

273. A stent prosthesis as in clause 255, wherein the metal is selected from a group consisting of stainless steel, and the metals set forth in the specification.

274. A stent prosthesis as in clause 255, wherein there is one or more separation regions on at least some rings wherein the separation regions are located on crowns, and/or struts.

275. An endoluminal prosthesis as in clause 255, wherein the separation regions locations and number are configured to allow positive lumen remodeling.

276. An endoluminal prosthesis as in clause 274, wherein additionally the weight of the stent prosthesis after deployment in physiologic environment allows for positive lumen remodeling.

277. An endoluminal prosthesis as in clause 255, wherein the separation region provides uncaging of the stent prosthesis after deployment in a physiologic environment.

278. An endoluminal prosthesis as in clause 277, wherein the stent prosthesis uncages in a circumferential direction.

279. A stent prosthesis comprising: a scaffold having circumferential rings patterned from a degradable material, said scaffold being configured to expand from a crimped configuration to an expanded configuration; wherein at least some of the circumferential rings have at least one separation region configured to form discontinuities in said circumferential rings after expansion in a physiologic environment.

280. A stent prosthesis as in clause 279, wherein the stent degrades in a period ranging from 3 months to 10 years.

281. A stent prosthesis comprising: a scaffold having circumferential rings patterned from a polymeric or metallic material, said scaffold being configured to expand from a crimped configuration to an expanded configuration; wherein at least some of the circumferential rings have at least one separation region forming discontinuities in said circumferential rings prior to expansion in a physiologic environment.

282. A stent prosthesis comprising; a scaffold having circumferential rings patterned from a non-degradable material, said scaffold being configured to deploy from a crimped configuration to an expanded configuration and said circumferential rings having hinges which open as the scaffold is being deployed; wherein at least some of the hinges on at least some of the rings are constricted from expansion during deployment and are configured to open in a physiologic environment after deployment or in response to the application of internal or external energy after deployment.

283. A stent prosthesis as in clause 282, wherein the scaffold is released to further expand circumferentially after said hinges are opened.

284. A stent prosthesis as in clause 282, wherein the physiologic environment is a water bath, water at 37° C., or a body lumen.

285. A stent prosthesis as in clause 282, wherein the physiologic environment is a body lumen.

286. A stent prosthesis as in clause 285, wherein the body lumen is a blood vessel.

287. A stent prosthesis as in clause 286, wherein the scaffold is circumferentially released to open as the blood vessel positively remodels.

288. A stent prosthesis as in clause 282, wherein the hinges open 30 days to 6 months after the initial expansion of the circumferential scaffold.

289. A stent prosthesis as in clause 282, wherein the hinges are constricted by one or more of adhesives, polymer filaments, and polymer sleeves.

290. An endoluminal prosthesis as in clause 282, wherein the non-degradable material comprises a metal or a metal alloy as set forth in the specification.

291. A stent prosthesis comprising: a scaffold having circumferential rings patterned from a non-degradable material, said scaffold being configured to deploy from a crimped configuration to an expanded configuration and said circumferential rings including struts connected by joints which open as the scaffold is being deployed; wherein at least some of the joints are pivoted to allow the scaffold in its expanded configuration to further expand.

292. A stent prosthesis as in any of the independent clauses, wherein the stent prosthesis further comprises non-degradable radiopaque markers.

293. A stent prosthesis as in any of the independent clauses, wherein the stent comprises at least one coating on at least one surface of the stent 294. A stent prosthesis as in any of the independent clauses, wherein the stent prosthesis comprises at least one drug.

295. A stent prosthesis as in 294, wherein the drug tissue concentration adjacent to the stent lasts beyond the time period of un-caging the stent, forming the discontinuity, and/or breaking of the stent.

296. A stent prosthesis comprising: a scaffold having one or more circumferential rings patterned from a non-degradable material, said scaffold being configured to expand from a crimped configuration to an expanded larger configuration; wherein one or more of the circumferential rings comprises a plurality of struts joined by crowns and at least one of the struts and/or crowns regions have at least one separation region configured to form a discontinuity in said circumferential ring(s) after expansion in a physiologic environment.

297. A stent prosthesis as in clause 296, wherein discontinuities allow the scaffold further expand after inward recoil from an initial expansion.

298. A stent prosthesis as in clause 296, wherein the physiologic environment is a water bath at about 37° C., or a body lumen.

299. A stent prosthesis as in clause 296, wherein the physiologic environment is a body lumen.

300. A stent prosthesis as in clause 296, wherein the body lumen comprises a blood vessel or valve annulus.

301. A stent prosthesis as in clause 300, wherein the discontinuity in the ring allows at least a portion of the scaffold to circumferentially open within the body lumen after deployment.

302. A stent prosthesis as in clause 296, wherein the discontinuities form 30 days to 6 months after the initial expansion of the circumferential scaffold in the physiologic environment.

303. A stent prosthesis as in clause 296, wherein the separation regions comprise key and lock junctions in the struts which are immobilized during expansion but configured to open after the initial expansion in the physiologic environment.

304. A stent prosthesis as in clause 303, wherein the key and lock junctions are configured to allowed the joined segments of the strut to separate from each other in a radial direction only after they are mobilized.

305. A stent prosthesis as in clause 303, wherein the key and lock junctions are configured to allowed the joined segments of the strut to separate from each other in both a radial direction and an axial direction after they are mobilized.

306. A stent prosthesis as in clause 303, wherein the key and lock junctions are configured to allowed the joined segments of the strut to separate from each other in an axial direction after they are mobilized.

307. A stent prosthesis as in clause 303, wherein the key and lock junctions are immobilized by solder, adhesive, or polymer which degrades in the physiologic environment.

308. A stent prosthesis as in clause 303, wherein the key and lock junctions are immobilized by fusing the material together which degrades or fatigues in the physiologic environment.

309. A stent prosthesis as in clause 303, wherein the key and lock junctions are immobilized by an overlying a sleeve which degrades in the physiologic environment.

310. A stent prosthesis as in clause 296, wherein the separation regions comprise
a butt joint joined by an adhesive, solder, polymer, sleeve, fusing the material, or connector which degrades or fatigues in the physiologic environment.

311. A stent prosthesis as in clause 296, wherein the separation regions comprise notches or thinned sections in the circumferential rings which preferentially erode or fatigue in the physiologic environment.

312. A stent prosthesis as in clause 296, wherein the separation regions comprise modified grain boundaries in metal circumferential rings which preferentially erode or fatigue in the physiologic environment.

313. A stent prosthesis as in clause 296, wherein the separation regions are formed by breaking circumferential rings at one or more sites over their circumference and rejoining the breaks with adhesive, or polymer which are configured to erode in the physiologic environment.

314. A stent prosthesis as in clause 313, wherein the connectors comprise sleeves or rings spanning the breaks.

315. A stent prosthesis as in clause 296, wherein the separation regions comprise a rivet or other fastener joining breaks in the circumferential ring, wherein the fastener erodes in the physiologic embodiment.

316. A stent prosthesis as in clause 296, wherein the circumferential rings comprise serpentine rings.

317. A stent prosthesis as in clause 296, wherein the circumferential rings comprise zig-zag rings.

318. A stent prosthesis as in clause 296, wherein the circumferential rings comprise closed ring type design.

319. A stent prosthesis as in clause 296, wherein the non-degradable material comprises a metal or metal alloy.

320. A stent prosthesis as in clause 296, wherein the scaffold further comprises a coating on at least one surface of the scaffold.

321. A stent prosthesis as in clause 296, wherein the scaffold further comprises a coating on at least one surface of the scaffold, and wherein the coating comprises a drug.

322. A stent prosthesis as in clause 296, wherein the scaffold in the expanded configuration has sufficient strength to support a body lumen.

323. A stent prosthesis comprising: a scaffold having circumferential rings patterned from a non-degradable material, said scaffold being configured to expand from a crimped configuration to an expanded configuration; wherein at least some of the circumferential rings comprise a plurality of struts joined by crowns and at least some of struts and/or crowns have at least one separation region wherein the strut has a pre-formed break which is immobilized by a solder, a polymer, a sleeve, or an adhesive which will degrade in a physiologic environment.

324. A stent prosthesis as in clause 323, wherein the separation regions comprise key and lock junctions in the struts and/or crowns which are immobilized during expansion but configured to open after the initial expansion in the physiologic environment.

325. A stent prosthesis as in clause 324, wherein the key and lock junctions are configured to allowed the joined segments of the strut and/or crowns to separate from each other in a radial direction only after they are mobilized.

326. A stent prosthesis as in clause 324, wherein the key and lock junctions are configured to allowed the joined segments of the strut and/or crowns to separate from each other in a radial direction and/or an axial direction after they are mobilized.

327. A stent prosthesis as in clause 324, wherein the key and lock junctions are immobilized by a cement which degrades in the physiologic environment.

328. A stent prosthesis as in clause 324, wherein the key and lock junctions are immobilized by an overlying a sleeve which degrades in the physiologic environment.

329. A stent prosthesis as in clause 323, wherein the circumferential rings comprise serpentine rings.

330. A stent prosthesis as in clause 323, wherein the circumferential rings comprise zig-zag rings.

331. A stent prosthesis as in clause 323, wherein the circumferential rings comprise closed cell (ring) type design.

332. An endoluminal prosthesis as in clause 323, wherein the non-degradable material comprises a metal or a metal alloy.

333. A stent prosthesis as in clause 332, wherein the metal or metal alloy selected from a group consisting of stainless steel, Cobalt Chrome, Platinum alloys, and other metals and metal alloys set forth in the specification.

334. A stent prosthesis as in clause 323, wherein at least one strut and/or crown on each ring has a separation region.

335. A stent prosthesis as in clause 323, wherein at least two struts and/or crowns on each ring have a separation region.

336. A stent prosthesis as in clause 323, wherein at least three struts and/or crowns on each ring have a separation region.

337. A stent prosthesis as in clause 323, wherein at least four struts and/or crowns on each ring have a separation region.

338. A stent prosthesis as in clause 323, wherein substantially all struts and/or crowns on each ring have a separation region.

339. A stent prosthesis as in clause 334, wherein all crowns and links are free from separation regions.

340. A stent prosthesis as in clause 334, wherein all links are free from separation regions.

341. A stent prosthesis as in clause 334, wherein at least one link connecting each two adjacent rings is free from separation regions.

342. A stent prosthesis as in clause 334, wherein at least two links connecting each two adjacent rings are free from separation regions.

343. A stent prosthesis as in clause 334, wherein at least three links connecting each two adjacent rings are free from separation regions.

344. A stent prosthesis as in clause 334, wherein at least four links connecting each two adjacent rings are free from separation regions.

345. A stent prosthesis as in clause 334, wherein each ring is connected to an adjacent ring by links ranging from 2 to 4 links, and wherein said links are free from separation regions.

346. A stent prosthesis as in clause 334, wherein at least one crown region of each ring is joined to an adjacent crown region on another ring, by solder, fusing, or melting, and wherein said crown region has a separation region uncaging at least one ring.

347. A stent prosthesis as in clause 334, wherein at least two crown regions of each ring is joined to an adjacent two crown regions on another ring, by solder, fusing, or melting, and wherein said crown regions have a separation region uncaging the two adjacent rings in a circumferential direction.

348. A stent prosthesis as in clause 334, wherein adjacent rings are joined or linked in one or more locations, and wherein the links are intact at the time of the separation regions separate.

349. A stent prosthesis as in clause 334, wherein adjacent rings are joined or linked in one or more locations but not all such that the links do not form a closed cell design, and wherein the links are intact at the time of the separation regions separate.

350. A stent prosthesis as in clause 323, wherein at least one strut and/or crown on each ring has a separation region, and wherein the stent uncages in a circumferential direction and uncages in the stent longitudinal direction while the links are substantially intact.

351. A stent prosthesis as in clause 323, wherein at least one strut and/or crown on each ring has a separation region, and wherein each ring of the stent uncages in a circumferential direction and the stent uncages in the longitudinal direction, and wherein the stent prosthesis separates from 1 to 4 longitudinal sections.

352. A stent prosthesis as in clause 323, wherein at least one strut and/or crown on each ring has a separation region, and wherein the stent uncages in the circumferential direction and uncages in the stent longitudinal direction while keeping the axial links substantially intact, and wherein the stent prosthesis separates from 1 to 4 longitudinal sections.

353. A stent prosthesis as in clause 323, wherein at least one strut and/or crown on each ring has a separation region, and wherein the stent uncages in the circumferential direction and separates the stent in the longitudinal direction spanning from 1 to 5 adjacent rings, while keeping the axial links substantially intact, wherein the stent separates from 2 to 4 sections of said adjacent rings.

354. A stent prosthesis as in clause 323, wherein at least one strut and/or crown on each ring has a separation region, and wherein the stent uncages in the circumferential direction and wherein the stent in the longitudinal direction remains substantially intact.

355. A stent prosthesis as in clause 323, wherein at least one strut and/or crown on each ring has a separation region, and wherein the stent uncages in the circumferential direction and wherein the stent in the longitudinal direction remains substantially intact and the axial links are maintained.

356. A stent prosthesis as in clause 323, wherein at least one strut and/or crown on each ring has a separation region, and wherein the at least one separation region on each ring forms a discontinuity in each ring, and wherein the stent in the longitudinal direction remains substantially intact and the axial links are maintained.

357. A stent prosthesis as in clause 323, wherein at least two struts and/or crown on each ring have separation regions, and wherein the at least two separation regions on each ring forms at least two discontinuities in each ring, and wherein the stent in the longitudinal direction remains substantially intact.

358. A stent prosthesis as in clause 323, wherein at least three struts and/or crown on each ring have separation regions, and wherein the at least three separation regions on each ring forms at least three discontinuities in each ring, and wherein the stent in the longitudinal direction remains substantially intact.

359. A stent prosthesis as in clause 323, wherein at least one strut and/or crown on each ring has a separation region, and wherein the at least one separation region on each ring forms a discontinuity in said ring, and said stent have one or more separate longitudinal sections, and wherein the links are substantially intact connecting the stent in the longitudinal direction.

360. A stent prosthesis as in clause 334, wherein the separation regions locations and number are configured to allow one or more of: stent radial strain between 1% and 5%, stent further expansion after inward recoil from first expanded configuration, uncaging the stent in a circumferential direction, allowing the stent to respond (expand or contract) to a vaso-dilator or vaso-constrictor, or positive lumen remodeling.

361. A stent prosthesis as in clause 339, wherein additionally the weight of the stent prosthesis after deployment in physiologic environment allows for positive lumen remodeling 362. A stent prosthesis as in clause 323, wherein the separation region provides uncaging of the stent prosthesis after deployment in a physiologic environment.

363. A stent prosthesis as in clause 362, wherein the stent prosthesis uncages in a circumferential direction.

364. A stent prosthesis comprising: a scaffold having circumferential rings patterned from a non-degradable material, said scaffold being configured to expand from a crimped configuration to an expanded configuration; wherein at least some of the circumferential rings comprise a plurality of struts joined by crowns and at least some of crowns have at least one separation region which is immobilized by a sleeve or an adhesive which will degrade in a physiologic environment.

365. A stent prosthesis as in clause 364, wherein the separation region comprises a thinned region in the crown(s) allowing the scaffold to uncage after degradation of the sleeve or the adhesive material.

366. A stent prosthesis as in clause 362, wherein the separation region is a break in the crowns allowing the scaffold to uncage after degradation of the sleeve or the adhesive material.

367. A stent prosthesis comprising: a scaffold having circumferential rings patterned from a degradable material, said scaffold being configured to expand from a crimped configuration to an expanded configuration; wherein at least some of the circumferential rings comprise a plurality of struts joined by crowns and at least some of struts and/or crowns have at least one separation region which is immobilized by a solder, polymer, sleeve, or an adhesive which will degrade in a physiologic environment.

368. A stent prosthesis as in clause 367, wherein the degradable material is polymeric or metallic.

369. A stent prosthesis as in clause 367, wherein the degradable material is metal or metal alloy.

370. A stent prosthesis comprising: a scaffold comprising non-degradable material having a plurality of rings which define a circumference of the scaffold, said scaffold being configured to expand from a crimped configuration to an expanded larger configuration; wherein at least one of the circumferential rings follow a circumferential path about the circumference of the scaffold and have at least one gap in said path when the scaffold is in its expanded configuration and wherein adjacent rings are axially linked so that all portions of the scaffold remain connected when the scaffold is in its expanded configuration.

371. A stent prosthesis as in clause 370, wherein each ring defines a circumference of the scaffold 372. A stent prosthesis as in clause 370, wherein at least some of the circumferential rings follow a circumferential path about the circumference of the scaffold and have at least one gap in said path of each ring.

373. A stent prosthesis as in clause 370, wherein the gaps are open in the rings when the scaffold is in its crimped configuration.

374. A stent prosthesis as in clause 373, wherein the gaps in the rings open further when the scaffold is in its expanded configuration 375. A stent prosthesis as in clause 370, wherein the gaps are open in the rings only after the scaffold is in its expanded configuration.

376. A stent prosthesis as in clause 370, wherein the gaps in the circumferential rings are rotationally staggered.

377. A stent prosthesis as in clause 370, wherein there is more than one gap in each of the circumferential rings which are spaced symmetrically in each ring.

378. A stent prosthesis as in clause 370, wherein there is more than one gap in each of the circumferential rings which are rotationally offset from an adjacent ring.

379. A stent prosthesis as in clause 370, wherein there is more than one gap in each of the circumferential rings which are rotationally offset from an adjacent ring by 45 degrees to 90 degrees.

380. An endovascular prosthesis as in clause 375, wherein the circumferential rings are axially linked in a staggered pattern which is rotationally offset from the staggered gap pattern.

381. An endovascular prosthesis as in clause 370, wherein the circumferential rings comprise serpentine rings.

382. An endovascular prosthesis as in clause 370, wherein the circumferential rings comprise zig-zag rings.

383. An endovascular prosthesis as in clause 370, wherein the circumferential rings comprise closed cell rings.

384. An endovascular prosthesis as in clause 370, wherein the non-degradable material comprises a metal or metal alloy.

385. An endovascular prosthesis as in clause 370, wherein the circumferential rings comprise a plurality of struts joined by crowns.

386. An endovascular prosthesis as in clause 385, wherein the gaps are present in the crowns region.

387. An endovascular prosthesis as in clause 370, wherein the gaps are present in the struts regions.

388. An endovascular prosthesis as in clause 370, wherein the gaps span a crown and a strut regions.

389. A stent prosthesis as in clause 370, wherein the gaps are present in the struts region, and wherein the strut end regions adjacent to the gaps are rounded.

390. A stent prosthesis as in clause 370, wherein the gaps are present in the struts region, and wherein at least one strut region adjacent to the gap is connected to same or adjacent ring.

391. A stent prosthesis as in clause 370, wherein the gaps are present in the struts region, and wherein the struts adjacent to the gap overlap along at least some struts length.

392. A stent prosthesis as in clause 385, wherein the gaps are present in the crowns and/or struts regions.

393. A stent prosthesis as in clause 385, wherein the gaps are present in the crowns region, and wherein the crowns adjacent to the gap overlap along the at least some crown length.

394. A stent prosthesis as in clause 385, wherein the gaps are present in the crowns regions, and wherein at least one crown region adjacent to the gap is connected to same or adjacent ring.

395. A stent prosthesis as in clause 370, wherein the stent in the expanded configuration has sufficient strength to support a body lumen.

396. A stent as in clause 370, wherein the stent strength after deployment to the expanded configuration remains substantially the same.

397. A stent prosthesis as in clause 370, wherein the stent pattern after deployment remains substantially the same.

398. A stent prosthesis as in clause 370, wherein the stent further comprises radiopaque markers.

399. A stent prosthesis as in clause 370, wherein the stent uncages the body lumen after deployment 400. A stent prosthesis as in clause 370, wherein the stent is capable of vaso-dilation or vasoconstriction after deployment 401. A stent prosthesis as in clause 370, wherein the scaffold displays a compliance (radial strain) between 1% to 5% when subjected to systolic/diastolic pressure cycling.

402. A stent prosthesis comprising: a scaffold comprising a degradable material having a plurality of rings which define a circumference of the scaffold, said scaffold being configured to expand from a crimped configuration to an expanded larger configuration; wherein at least one of the circumferential rings follow a circumferential path about the circumference of the scaffold and have at least one gap in said path when the scaffold is in its expanded configuration and wherein adjacent rings are axially linked so that all portions of the scaffold remain connected when the scaffold is in its expanded configuration.

403. A stent prosthesis as in clause 402, wherein the degradable material is polymeric or metallic material.

404. A stent prosthesis as in clause 370 or 402, wherein at least some of the axial links connect the struts and/or crown regions adjacent to the gap to same or different ring.

405. A stent prosthesis as in clause 370, wherein the scaffold displays a radial contraction and/or expansion displacement ranging from 0.1 mm to 0.5 mm when subjected to systolic/diastolic pressure cycling.

406. A stent prosthesis as in clause 370 or 402, wherein the axial links connect strut region to strut region, strut region to crown region, crown region to crown region, on adjacent rings.

407. A stent prosthesis comprising: a scaffold comprising a non-degradable material having a plurality of rings which define a circumference of the scaffold, said scaffold being configured to expand from a crimped configuration to an expanded larger configuration; wherein at least one of the circumferential rings follow a circumferential path about the circumference of the scaffold and have at least one biodegradable segment in said path and wherein adjacent rings are axially linked so that all portions of the scaffold remain connected after the biodegradable segments in the scaffold have degraded.

408. A stent prosthesis as in clause 407, wherein the biodegradable segment is a bridging element.

409. A stent prosthesis as in clause 407, wherein each ring defines a circumference of the scaffold 410. A stent prosthesis as in clause 407, wherein at least some of the circumferential rings follow a circumferential path about the circumference of the scaffold and have at least one gap in said path of each ring.

411. A stent prosthesis as in clause 407, wherein the at least one ring without said biodegradable segment would have a gap or discontinuity in said ring path.

412. A stent prosthesis as in clause 407, wherein the biodegradable segments are configured to remain intact while the scaffold is expanded and to form gaps or discontinuities in the rings after the segments have degraded.

413. A stent prosthesis as in clause 407, wherein the scaffold is expanded in a vascular environment and to form gaps in the rings after the segments have degraded in the vascular environment.

414. A stent prosthesis as in clause 407, wherein the biodegradable segments are configured to substantially degrade in a vascular environment over a time period in the range from 30 days to 2 years.

415. A stent prosthesis as in clause 407, wherein the biodegradable segments are configured to substantially degrade in a vascular environment over a time period in the range from 30 days to 1 year.

416. A stent prosthesis as in clause 407, wherein the biodegradable segments are configured to substantially degrade in a vascular environment over a time period in the range from 30 days to 9 months.

417. A stent prosthesis as in clause 407, wherein the biodegradable segments in the circumferential rings are rotationally staggered.

418. A stent prosthesis as in clause 417, wherein the circumferential rings are axially linked in a staggered pattern which is rotationally offset from the staggered gap pattern.

419. A stent prosthesis as in clause 407, wherein the circumferential rings comprise serpentine rings.

420. A stent prosthesis as in clause 407, wherein the circumferential rings comprise zig-zag rings.

421. A stent prosthesis as in clause 407, wherein the circumferential rings comprise a closed cell design.

422. A stent prosthesis as in clause 407, wherein the non-degradable material comprises a metal or metal alloy.

423. A stent prosthesis as in clause 422, wherein the biodegradable segments comprise a biodegradable polymer.

424. A stent prosthesis as in clause 407, wherein the circumferential rings comprise a plurality of struts joined by crowns.

425. A stent prosthesis as in clause 423, wherein the biodegradable segments are present in the crown regions.

426. A stent prosthesis as in clause 407, wherein the biodegradable segments are present in the strut regions.

427. A stent prosthesis as in clause 407, wherein the biodegradable segments span a crown and strut regions.

428. A stent prosthesis as in clause 407, wherein the biodegradable segment bridges a gap or discontinuity in a strut region 429. A stent prosthesis as in clause 407, wherein the biodegradable segment bridges a gap or discontinuity in a crown region.

430. A stent prosthesis as in clause 407, wherein the biodegradable segment bridges a gap or discontinuity spanning at least one strut region and a crown region.

431. A stent prosthesis as in clause 407, wherein the biodegradable segment bridging a gap or discontinuity in a strut and/or crown region overlaps at least a portion of the non-degradable strut and/or crown regions.

432. A stent prosthesis as in clause 407, wherein the biodegradable segment bridging a gap or discontinuity in a strut and/or crown region contains at least a portion of the non-degradable strut and/or crown regions.

433. A stent prosthesis as in clause 407, wherein the non-degradable strut and/or crown region contains at least a portion of the biodegradable segment.

434. A stent prosthesis as in clause 407, wherein the biodegradable segment bridging a gap or discontinuity in a strut and/or crown region forms a but joint with the non-degradable strut and/or crown regions.

435. A stent prosthesis as in clause 407, wherein the biodegradable segment bridging a gap or discontinuity in a strut and/or crown region forms a separation region with the non-degradable strut and/or crown regions.

436. A stent prosthesis as in clause 407, wherein the biodegradable segment bridging a gap or discontinuity in a strut and/or crown region forms a separation region with the non-degradable strut and/or crown regions, wherein the separation region comprises key and lock separation region or key type separation region.

437. A stent prosthesis as in clause 407, wherein the scaffold displays compliance between 1% to 5% in its expanded configuration without the biodegradable segments when subjected to systolic/diastolic pressure cycling.

438. A stent prosthesis as in clause 407, wherein the scaffold displays a compliance between 1% to 5% in its expanded configuration after the biodegradable segments have degraded when subjected to systolic/diastolic pressure cycling.

439. A stent prosthesis as in clause 407, wherein the scaffold displays a compliance from 1.2% to 5%, often from 1.5% to 3%, in its expanded configuration with the biodegradable segments in place when subjected to systolic/diastolic pressure cycling.

440. A stent prosthesis as in clause 407, wherein at least some of the axial links connect the struts and/or crown regions adjacent to the biodegradable segment on adjacent rings.

441. A stent prosthesis as in clause 407, wherein the scaffold displays a radial contraction and/or expansion displacement ranging from 0.1 mm to 0.5 mm when subjected to systolic/diastolic pressure cycling.

442. A stent prosthesis as in clause 407, wherein the axial links connect strut region to strut region, strut region to crown region, crown region to crown region, on two adjacent rings.

443. A stent prosthesis as in clause 407, wherein the axial links connecting two adjacent crowns is formed by connecting the apex regions of both crowns.

444. A stent prosthesis as in clause 407, wherein the axial links is formed by joining the two adjacent crown regions.

445. A stent prosthesis comprising: a scaffold comprising a degradable material having a plurality of rings which define a circumference of the scaffold, said scaffold being configured to expand from a crimped configuration to an expanded larger configuration; wherein at least one of the circumferential rings follow a circumferential path about the circumference of the scaffold and have at least one biodegradable segment in said path and wherein adjacent rings are axially linked so that all portions of the scaffold remain connected upon deployment of the stent.

446. A stent prosthesis as in clause 445, wherein the degradable material comprises a polymer, metal, or metal alloy.

447. A stent prosthesis as in clause 445, wherein the degradable material degrades at a slower rate than the biodegradable segment 448. A stent prosthesis as in clause 445, wherein the degradable material degrades in a period ranging from 2 years to 10 years while the biodegradable segment degrades in a period ranging from 30 days to 1 year.

449. A stent prosthesis as in clause 407, wherein the stent in the expanded configuration has sufficient strength to support a body lumen.

450. A stent as in clause 407, wherein the stent strength after degradation of the biodegradable segment decreases.

451. A stent prosthesis as in clause 407, wherein the stent pattern after degradation of the biodegradable segment remains substantially the similar.

452. A stent prosthesis as in clause 407, wherein the stent further comprises radiopaque markers.

453. A stent prosthesis as in clause 407, wherein the stent uncages the body lumen after degradation of the biodegradable segment.

454. A stent prosthesis as in clause 407, wherein the stent is capable of vaso-dilation or vasoconstriction after deployment or after degradation of the biodegradable segment.

455. A stent prosthesis as in clause 407, wherein at least some rings have at least two biodegradable segments each.

456. A stent prosthesis as in clause 407, wherein at least some rings have at least three biodegradable segments each.

457. A stent prosthesis as in clause 407, wherein substantially all rings have at least one biodegradable segment 458. A stent prosthesis as in clause 407, wherein the biodegradable segment length is substantially the same, longer, or shorter, than an adjacent strut and/or crown region.

459. A stent prosthesis as in clause 407, wherein the biodegradable segment has a crown shape, a strut shape, a crown region shape, or a strut region shape.

460. A stent prosthesis as in clause 407, wherein the biodegradable segment bridges a discontinuity or a gap, wherein the discontinuity or gap magnitude ranges from 0 to 2 mm 461. A stent prosthesis as in clause 407, wherein a coating covers at least a portion of the biodegradable segment.

462. A stent prosthesis as in clause 407, wherein the stent comprises at least one drug 463. A stent prosthesis as in clause 407, wherein a sleeve covers the biodegradable segment and at least one portion of the non-degradable material.

464. A method of making an endovascular prosthesis, said method comprising: fabricating a first scaffold having a plurality of rings which define a circumference of the scaffold, wherein the plurality of rings are formed from a non-degradable material; fabricating a second scaffold having a plurality of rings which define a circumference of the scaffold, wherein the plurality of rings are formed from a biodegradable material and wherein the first and second scaffolds have identical geometries; forming gaps in portions of at least some of the rings of the first scaffold; cutting segments from the second scaffold, wherein the segments are selected to fill in the gaps in the first scaffold; and securing the segments cut from the second scaffold into the gaps formed in the first scaffold.

465. A method of making an endovascular prosthesis as in clause 464, wherein the biodegradable material is selected to remain intact while the scaffold is expanded in a vascular environment and to form gaps in the rings after the segments have degraded in the vascular environment.

466. A method of making an endovascular prosthesis as in clause 464, wherein the biodegradable material is selected to degrade in a vascular environment over a time period in the range from 30 days to 2 years.

467. A method of making an endovascular prosthesis as in clause 464, wherein the gaps in the circumferential rings of the first scaffold are rotationally staggered.

468. A method of making an endovascular prosthesis as in clause 467, wherein the circumferential rings in the first scaffold are axially linked in a staggered pattern which is rotationally offset from the staggered gap pattern.

469. A method of making an endovascular prosthesis as in clause 464, wherein the circumferential rings in the first scaffold comprise serpentine rings.

470. A method of making an endovascular prosthesis as in clause 464, wherein the circumferential rings in the first scaffold comprise zig-zag rings.

471. A method of making an endovascular prosthesis as in clause 464, wherein the non-degradable material comprises a metal.

472. An endovascular prosthesis as in clause 472, wherein the biodegradable material comprises a biodegradable polymer.

473. A method of making an endovascular prosthesis as in clause 464, wherein the circumferential rings comprise a plurality of struts joined by crowns.

474. A method of making an endovascular prosthesis as in clause 473, wherein the gaps are present in the crowns.

475. A method of making an endovascular prosthesis as in clause 464, wherein the gaps are present in the struts.

476. A method of making an endovascular prosthesis as in clause 464, wherein the g span a crown and a strut.

477. A method of making an endovascular prosthesis as in clause 464, wherein the scaffold displays a compliance from 1% to 5%, often from 1.5% to 3%, in its expanded configuration without the biodegradable segments when subjected to systolic/diastolic pressure cycling.

478. An endovascular prosthesis as in clause 477, wherein the scaffold displays a compliance from 1.2% to 5% in its expanded configuration with the biodegradable segments in place when subjected to systolic/diastolic pressure cycling.

Helical Stent

479. An endoluminal prosthesis comprising: a helical backbone having a plurality of struts joined by a plurality of crowns, wherein the helical backbone includes a multiplicity of adjacent turns and wherein at least some of the adjacent turns are attached to each other by a separation region.

480. An endoluminal prosthesis as in clause 479, wherein the separation regions are disposed between immediately adjacent turns of the helical backbone.

481. An endoluminal prosthesis as in clause 480, wherein the separation region are disposed between adjacent pairs of crowns.

482. An endoluminal prosthesis as in clause 480, wherein the separation region are disposed on struts between a crown on one turn and strut on an adjacent turn.

483. An endoluminal prosthesis as in clause 480, wherein the separation region are disposed on struts between adjacent pairs of struts.

484. An endoluminal prostheses as in clause 479, wherein the helical backbone has a serpentine arrangement.

485. An endoluminal prosthesis as in clause 479, wherein the helical backbone has a zig-zag arrangement.

486. An endoluminal prosthesis as in clause 479, wherein the helical backbone is formed from a bent wire.

487. An endoluminal prosthesis as in clause 479, wherein the helical backbone is formed from a patterned tube 488. An endoluminal prosthesis as in clause 479, wherein the separation region comprises any of the separation regions described herein.

Overlapping Parallel Elements

489. An endoluminal prosthesis comprising: a scaffold having circumferential rings formed from a non-degradable material, said scaffold being configured to expand from a crimped configuration to an expanded configuration; wherein at least some of the circumferential rings are formed from structural elements having divided regions which overlap and lie adjacent to each other when the scaffold is in its crimped configuration.

490. An endoluminal prosthesis as in clause 489, wherein the adjacent regions which overlap and lie adjacent to each other are straight.

491. An endoluminal prosthesis as in clause 490, wherein the straight adjacent regions separate from each other when the scaffold is expanded to its expanded configuration.

492. An endoluminal prosthesis as in clause 490, wherein the straight adjacent regions are immobilized by a sleeve or an adhesive which will degrade in a physiologic environment when the scaffold is in its crimped configuration prior to deployment in the physiologic environment.

493. An endoluminal prosthesis as in clause 490, wherein the straight adjacent regions comprise a plurality of struts joined by crowns.

494. An endoluminal prosthesis as in clause 489, wherein the adjacent regions which overlap and lie adjacent to each other are curved.

495. An endoluminal prosthesis as in clause 489, wherein the curved adjacent regions which overlap and lie adjacent to each other deform when the scaffold is expanded to its expanded configuration.

496. An endoluminal prosthesis as in clause 494, wherein the curved adjacent regions are immobilized by a sleeve or an adhesive which will degrade in a physiologic environment when the scaffold is in its crimped configuration prior to deployment in the physiologic environment.

497. An endoluminal prosthesis as in clause 490, wherein the curved adjacent regions comprise a plurality of crowns joined by struts.

Circumferentially Linked Closed Cells

498. An endoluminal prosthesis comprising: a scaffold having circumferential rings formed from a non-degradable material, said scaffold being configured to expand from a crimped configuration to an expanded configuration; wherein at least some of the circumferential rings are formed as expandable closed cell structures and wherein said expandable closed cell structures are joined circumferentially; and wherein at least some of the circumferential rings have separation regions configured to form discontinuities in said circumferential rings after deployment in a luminal environment.

499. An endoluminal prosthesis as in clause 498, wherein the closed cells comprise quadrangles having opposed axial sides and opposed circumferential sides, further comprising circumferential connectors which join axial sides of circumferentially adjacent closed cells, wherein the separation regions are in the circumferential connectors.

500. An endoluminal prosthesis as in clause 498, wherein at least some of the closed cells in axially adjacent circumferential rings are joined by axial links.

501. An endoluminal prosthesis as in clause 498, wherein at least one axial link between each pair of axially adjacent circumferential rings in the scaffold is configured to remain intact after implantation so that all circumferential rings of the scaffold will remain joined after discontinuities have formed in the separation regions in the circumferential connectors after deployment in the luminal environment.

502. An endoluminal prosthesis as in clause 498, wherein the discontinuities which form after implantation of said prosthesis in a body lumen allow the scaffold to display compliance from 1% to 5%, often from 1.2% to 3%, when subjected to systolic/diastolic pressure cycling after implantation in a blood vessel.

503. An endoluminal prosthesis as in clause 498, wherein the closed cells comprise closely packed quadrangles formed from common crossing members, wherein the separation regions are in the common crossing members.

504. An endoluminal prosthesis as in clause 498, wherein the separation regions are configured to degrade in response to implantation in the luminal environment.

505. An endoluminal prosthesis as in clause 504, wherein the separation regions are configured to fatigue and separate in response to systolic/diastolic pressure cycling after implantation in a blood vessel.

506. An endoluminal prosthesis as in clause 505, wherein the separation regions comprise notches or thinned regions in the circumferential rings which preferentially fatigue and break in response to applied energy.

507. An endoluminal prosthesis as in clause 498, wherein the separation regions are configured to fatigue in response to an externally applied energy source.

508. An endoluminal prosthesis as in clause 498, wherein the separation regions comprise a key and lock junction formed in the circumferential connectors, wherein said key and lock junctions are immobilized during expansion but configured to open in response to applied energy.

509. An endoluminal prosthesis as in clause 498, wherein the separation regions comprise a rivet or other fastener joining breaks in the circumferential element and configured to open in response to applied energy.

510. An endoluminal prosthesis as in clause 498, wherein the non-degradable material comprises a metal or a metal alloy.

511. A stent prosthesis comprising: a non-degradable patterned circumferential scaffold including structural elements, said structural elements having expansion regions configured to plastically deform as the scaffold is radially expanded from a crimped configuration to a first expanded configuration, wherein the structural elements are configured to allow the scaffold to passively expand to a second larger configuration after inward recoil from the first expanded configuration wherein the scaffold retains sufficient strength to support a body lumen for at least an initial time period.

512. A stent prosthesis as in clause 511, wherein the time period ranges from 30 days to 9 months 513. A stent prosthesis as in clause 511, wherein the time period is at least 30 days 514. A stent prosthesis as in clause 511, wherein the time period is in a range from after deployment day to 9 months.

515. A stent prosthesis as in clause 511, wherein the expansion regions comprise separation regions.

516. A stent prosthesis as in clause 515, wherein the separation regions are selected from a group consisting one or more of gaps, bridge elements, controlled breaks, adjacent struts joined by sleeves, adjacent crowns joined by sleeves, and/or key- and lock regions.

517. A stent prosthesis as in clause 511, wherein the expansion regions are configured to weaken under physiologic cycling.

518. A stent prosthesis as in clause 517, wherein the expansion regions configured to weaken under physiologic cycling are selected from a group consisting of hollowed out crown regions, hollowed out strut regions, and metals having predictable fatigue characteristics.

519. A stent prosthesis as in clause 518, wherein the expansion regions configured to weaken under physiologic cycling comprise hollowed out crown regions filled with a degradable material or, hollowed out strut regions filled with a degradable material.

520. A stent prosthesis as in clause 511, wherein the structural elements are configured to allow the scaffold to passively expand to a second larger configuration after systolic/diastolic cycling.

521 A stent prosthesis as in clause 520, wherein the systole/diastole cycling comprises a pressure difference of at least 40 mmHG at a rate from 2-30 Hz.

522. A stent prosthesis as in clause 511, wherein the patterned circumferential scaffold comprises a plurality of axially joined circumferential rings.

523. A stent prosthesis as in clause 522, wherein the circumferential rings comprise struts joined by crowns in a serpentine or zig-zag pattern.

524. A stent prosthesis as in clause 511, wherein the patterned circumferential scaffold comprises a plurality of circumferentially joined closed cells.

525. A stent prosthesis as in clause 511, wherein the second larger configuration is larger the first expanded configuration.

526. A stent prosthesis as in clause 511, wherein the scaffold is balloon deployable.

527. A stent prosthesis as in clause 511, wherein scaffold is deployable at body temperature.

528. A stent prosthesis as in clause 511, wherein the stent comprises a proximal segment, a mid-segment, and a distal segment, and wherein the stent expands to a second larger configuration in at least one segment of the stent.

529. A stent prosthesis as in clause 511, wherein at least some of the expansion regions comprise a non-degradable metal or metal alloy.

530. A stent prosthesis as in clause 511, wherein the stent further comprises radiopaque markers.

531. A stent prosthesis as in clause 511, wherein the stent comprises at least one drug.

532. A stent prosthesis as in clause 511, wherein the stent comprises at least one coating on at least one surface of the stent.

533. A stent prosthesis as in clause 511, wherein the scaffold has been patterned from a tubular body.

534. A stent prosthesis as in clause 511, wherein the scaffold comprises a material which degrades in a luminal environment over a period in the range from 3 months to 3 years.

535. A stent prosthesis as in clause 534, wherein the degradable material comprises a polymeric material.

536. A stent prosthesis as in clause 534, wherein the degradable material comprises a metal or metal alloy.

537. A stent prosthesis as in clause 511, wherein the scaffold has at least one segment configured to expand to a second larger configuration in response to introduction of a vaso-dilator to a patient after the stent has been expanded in a body lumen.

538. A stent prosthesis as in clause 537, wherein the scaffold is configured so that larger second configuration is substantially maintained after introduction of the vaso-dilator to the patient.

539. A stent prosthesis as in clause 511, wherein the second expanded configuration is larger than the first expanded configuration by a distance in a range from 0.05 mm to 1 mm.

540. A stent prosthesis comprising: a non-degradable patterned circumferential scaffold including structural elements, said structural elements having expansion regions configured to plastically deform as the scaffold is radially expanded from a crimped configuration to a first expanded configuration, wherein the scaffold is configured to have a radial strain in a range from 1.2% to 7% after the stent is expanded in a body and to retain sufficient strength to support the body lumen.

541. A stent prosthesis as in clause 540, wherein the scaffold is configured to have an inward recoil after deployment in a range from 1.5% to 7%.

542. A stent prosthesis as in clause 540, wherein the scaffold is configured to have an initial radial strain after deployment of 1% or less before increasing to the radial strain in said range.

543. A stent prosthesis as in clause 540, wherein the radial strain reaches a value in said range within 2 months to 1 year after deployment.

544. A stent prosthesis as in clause 540, wherein a magnitude of the radial strain is in a range from 0.1 mm to 0.5 mm.

545. A stent prosthesis as in clause 540, wherein the patterned circumferential scaffold comprises a plurality of axially joined circumferential rings.

546. A stent prosthesis as in clause 545, wherein the circumferential rings comprise struts joined by crowns in a serpentine or zig-zag pattern.

547. A stent prosthesis as in clause 540, wherein the patterned circumferential scaffold comprises a plurality of circumferentially joined closed cells.

548. A stent prosthesis as in clause 540, wherein the second larger configuration is larger the first expanded configuration.

549. A stent prosthesis as in clause 540, wherein the scaffold is balloon deployable.

550. A stent prosthesis as in clause 540, wherein scaffold is deployable at body temperature.

551. A stent prosthesis as in clause 540, wherein the stent comprises a proximal segment, a mid-segment, and a distal segment, and wherein the stent expands to a second larger configuration in at least one segment of the stent.

552. A stent prosthesis as in clause 540, wherein at least some of the expansion regions comprise a non-degradable metal or metal alloy.

553. A stent prosthesis as in clause 540, wherein the stent further comprises radiopaque markers.

554. A stent prosthesis as in clause 540, wherein the stent comprises at least one drug.

555. A stent prosthesis as in clause 540, wherein the stent comprises at least one coating on at least one surface of the stent.

556. A stent prosthesis as in clause 540, wherein the scaffold has been patterned from a tubular body.

557. A stent prosthesis as in clause 540, wherein the scaffold comprises a material which degrades in a luminal environment over a period in the range from 3 months to 3 years.

558. A stent prosthesis as in clause 557, wherein the degradable material comprises a polymeric material.

559. A stent prosthesis as in clause 557, wherein the degradable material comprises a metal or metal alloy.

560. A stent prosthesis as in clause 540, wherein the scaffold has at least one segment configured to expand to a second larger configuration in response to introduction of a vaso-dilator to a patient after the stent has been expanded in a body lumen.

561. A stent prosthesis as in clause 560, wherein the scaffold is configured so that larger second configuration is substantially maintained after introduction of the vaso-dilator to the patient.

562. A stent prosthesis as in clause 540, wherein the second expanded configuration is larger than the first expanded configuration by a distance in a range from 0.05 mm to 1 mm.

563. A stent prosthesis comprising: a non-degradable patterned circumferential scaffold including structural elements, said structural elements having expansion regions configured to plastically deform as the scaffold is radially expanded from a crimped configuration to a first expanded configuration, wherein the scaffold in the deployed configuration has sufficient strength to support a body lumen and wherein the scaffold is configured to allow a stented segment in the body lumen to vaso-dilate and/or vaso-constrict in the presence of a vaso-dilator and/or vaso-constrictor agent in the body lumen.

564. A stent prosthesis as in clause 563, wherein the stented segment of the body lumen vaso-dilates in a range from 0.05 mm to 0.5 mm.

565. A stent prosthesis as in clause 563, wherein the stented segment of the body lumen vaso-dilates in a range from 0.1 mm to 0.3 mm.

566. A stent prosthesis as in clause 563, wherein the patterned circumferential scaffold comprises a plurality of axially joined circumferential rings.

567. A stent prosthesis as in clause 565, wherein the circumferential rings comprise struts joined by crowns in a serpentine or zig-zag pattern.

568. A stent prosthesis as in clause 563, wherein the patterned circumferential scaffold comprises a plurality of circumferentially joined closed cells.

569. A stent prosthesis as in clause 563, wherein the second larger configuration is larger the first expanded configuration.

570. A stent prosthesis as in clause 563, wherein the scaffold is balloon deployable.

571. A stent prosthesis as in clause 563, wherein scaffold is deployable at body temperature.

572. A stent prosthesis as in clause 563, wherein the stent comprises a proximal segment, a mid-segment, and a distal segment, and wherein the stent expands to a second larger configuration in at least one segment of the stent.

573. A stent prosthesis as in clause 563, wherein at least some of the expansion regions comprise a non-degradable metal or metal alloy.

574. A stent prosthesis as in clause 563, wherein the stent further comprises radiopaque markers.

575. A stent prosthesis as in clause 563, wherein the stent comprises at least one drug.

576. A stent prosthesis as in clause 563, wherein the stent comprises at least one coating on at least one surface of the stent.

577. A stent prosthesis as in clause 563, wherein the scaffold has been patterned from a tubular body.

578. A stent prosthesis as in clause 563, wherein the scaffold comprises a material which degrades in a luminal environment over a period in the range from 3 months to 3 years.

579. A stent prosthesis as in clause 578, wherein the degradable material comprises a polymeric material.

580. A stent prosthesis as in clause 578, wherein the degradable material comprises a metal or metal alloy.

581. A stent prosthesis as in clause 563, wherein the scaffold has at least one segment configured to expand to a second larger configuration in response to introduction of a vaso-dilator to a patient after the stent has been expanded in a body lumen.

582. A stent prosthesis as in clause 581, wherein the scaffold is configured so that larger second configuration is substantially maintained after introduction of the vaso-dilator to the patient.

583. A stent prosthesis as in clause 563, wherein the second expanded configuration is larger than the first expanded configuration by a distance in a range from 0.05 mm to 1 mm.

584. A stent prosthesis comprising: a non-degradable patterned circumferential scaffold including structural elements, said structural elements having expansion regions configured to plastically deform as the scaffold is radially expanded from a crimped configuration to a first expanded configuration, wherein the scaffold in the deployed configuration has sufficient strength to support a body lumen and wherein the scaffold is configured to contract and/or expand after deployment in a body lumen under physiologic conditions.

585. A stent prosthesis as in clause 584, wherein expansion and/or contraction occurs passively.

586. A stent prosthesis as in clause 584, wherein expansion and/or contraction occurs in response to vaso-dilation and/or vaso-constriction.

587. A stent prosthesis as in clause 584, wherein expansion and/or contraction occurs under physiologic pulsation.

588. A stent prosthesis as in clause 584, wherein expansion and/or contraction has magnitude in a range from 0.05 mm to 0.5 mm from a deployed diameter or mean diameter of the body lumen.

589. A stent prosthesis as in clause 584, wherein expansion and/or contraction has magnitude in the range from 0.1 mm to 0.4 mm from a deployed diameter or mean diameter of the body lumen.

590. A stent prosthesis as in clause 584, wherein the scaffold has a radial compliance in a range from 1.2% and 5%.

591. A stent prosthesis as in clause 584, wherein the scaffold has a radial compliance in a range from 1.5% to 5%.

592. A stent prosthesis comprising: a non-degradable patterned circumferential scaffold including structural elements, said structural elements having expansion regions configured to plastically deform as the scaffold is radially expanded from a crimped configuration to a first expanded configuration, wherein the scaffold has sufficient strength to support a body lumen, and wherein the number, location, and pattern of the separation regions are configured to control stresses on the stent structural elements, wherein the stent structural elements do not fracture after deployment under physiologic conditions.

593. A stent prosthesis comprising: a non-degradable patterned circumferential scaffold including a plurality of axially joined circumferential rings, where at least some of the circumferential rings comprise struts joined by crowns and have at least one separation region which forms a discontinuity in said ring after deployment, wherein the scaffold is configured to withstand 10 million fatigue cycles under physiologic conditions without fracture.

594. A stent prosthesis comprising: a non-degradable patterned circumferential scaffold including a plurality of axially joined circumferential rings, where at least some of the circumferential rings comprise struts joined by crowns and have at least one separation region which forms a discontinuity in said ring after deployment, wherein after discontinuities are formed, substantially all resulting segments of the ring remain axially joined.

595. A stent prosthesis comprising: a non-degradable patterned circumferential scaffold including a plurality of axially joined circumferential rings, where at least some of the circumferential rings comprise struts joined by crowns and have at least some separation regions which form discontinuities in said rings after deployment, wherein the scaffold in the deployed configuration has sufficient strength to support a body lumen, and wherein the stent strength decreases after the at least some separation regions form discontinuities.

596. A stent prosthesis as in clause 595, wherein the stent strength decrease ranges from 15% to 75% in a period ranging from 30 days to 9 months.

597. A stent prosthesis as in clause 595, wherein the stent has inward recoil after deployment ranging from 1% to 10%.

598. A stent prosthesis as in clause 595, wherein the stent after inward recoil further expands after formation of discontinuities.

599. A stent prosthesis as in clause 595, wherein the stent after deployment has radial strain ranging from 1.2% to 5%.

600. A stent prosthesis as in clause 595, wherein the stent after deployment has radial strain ranging from 0.1% to 1%, and wherein the radial strain increases after formation of discontinuities to a range from 1.2% to 5%.

601. A stent prosthesis as in clause 595, wherein the stent strength after the at least some separation regions form discontinuities is insufficient to support a body lumen.

602. A stent prosthesis as in clause 595, wherein the stent after the at least some separation regions form discontinuities is held in place by the lumen tissue.

603. A stent scaffold comprising: a backbone; a plurality of circumferential rings distributed along the length of the backbone; wherein at least some of the circumferential rings have gaps and wherein at least some of the axially successive gaps are rotationally staggered to enhance uniformity of the circumferential strength of the stent scaffold.

604. A stent prosthesis as in clause 1600, wherein the backbone has an axially continuous structure which extend over the entire length of the stent scaffold.

605. A stent prosthesis as in clause 1600, wherein the backbone comprises a plurality of segments which are rotationally staggered over the length of the stent scaffold.

Stent Scaffolds with Circumferential Displacement Regions

606. A stent prosthesis comprising: a scaffold having circumferential rings patterned from a polymeric or metallic material, said scaffold being configured to expand from a crimped configuration to an expanded configuration; wherein at least some of the circumferential rings have at least one circumferential displacement region which allows the circumferential ring to circumferentially expand and contract in a physiologic luminal environment.

607. A stent prosthesis as in clause 606, wherein the at least one circumferential displacement region allows the circumferential ring to circumferentially expand and contract in response to a systolic/diastolic rhythm in an arterial lumen.

608. A stent prosthesis as in clause 607, wherein the scaffold includes a plurality of the circumferential rings coupled together along an axis, where at least some of the circumferential rings comprise struts joined by crowns and at least some of the struts or crowns have discontinuities that allow the circumferential ring(s) to circumferentially expand and contract in response to a systolic/diastolic rhythm in the arterial lumen.

609. A stent prosthesis as in clause 608, wherein the discontinuities that allow the circumferential ring(s) to circumferentially expand and contract in response to a systolic/diastolic rhythm in the arterial lumen comprise gaps between opposed segments of a strut or a crown.

610. A stent prosthesis as in clause 609, wherein the gaps are defined by between two opposed segments of a strut and comprise a female coupling element that comprises a pair of opposed constraining walls on one strut segment and a male coupling element disposed on an opposed strut segment and located between the pair of opposed constraining walls on the one strut segment, wherein the male element is free to move circumferentially between the opposed walls of the circumferential ring to circumferentially expand and contract.

611. A stent prosthesis as in clause 610, wherein the gaps defined by between two opposed segments are open.

612. A stent prosthesis as in clause 610, wherein the gaps defined by between two opposed segments are filled with an elastomeric cushion material which dampens the circumferential movement of the male element between the opposed walls of the circumferential ring.

613. A stent prosthesis as in clause 609, wherein the gaps are defined between spaced-apart ends of two opposed segments of a strut.

614. A stent prosthesis as in clause 613, wherein the gaps between the spaced-apart ends of two opposed segments of a strut are filled with an elastomeric cushion material which dampens the relative circumferential movement of the opposed segments.

615. A stent prosthesis as in clause 613, wherein the gaps defined by between two opposed segments are open.

616. A stent prosthesis as in clause 609, wherein the gaps are defined by between two opposed segments of a strut and comprise a coupling element having a channel that comprises a pair of opposed constraining walls and a bottom surface on one strut segment and a male coupling element disposed on an opposed strut segment and located between the pair of opposed constraining walls and over the bottom surface on the one strut segment, wherein the male element is free to move circumferentially between the opposed walls of the circumferential ring to circumferentially expand and contract.

617. A stent prosthesis as in clause 616, wherein the gaps between the spaced-apart ends of two opposed segments of a strut are filled with an elastomeric cushion material which dampens the relative circumferential movement of the opposed segments.

618. A stent prosthesis as in clause 615, wherein the gaps defined by between two opposed segments are open.

619. A stent prosthesis as in clause 609, wherein the gaps are defined by between two opposed segments of a strut and comprise a coupling element having a pin pivotally joining the two opposed segments.

Fabrication of Stents from Flat Panels

620. A method of fabricating a stent prosthesis, said method comprising: patterning two or more panels, each panel including a plurality of partial ring structures and each partial ring structure terminating in two or more attachment ends; forming the two or more panel structures into a cylindrical assembly with each attachment end on one panel being adjacent to an attachment structure on another panel; and joining the end structures together to form a cylindrical scaffold having a plurality of continuous ring structures about a circumference thereof.

621. A method as in clause 620, wherein at least some of the partial ring structures comprise struts joined by crowns.

622. A method as in clause 620 wherein the attachment ends are patterned as male and female elements configured to mate with a gap therebetween to allow the circumferential scaffold to circumferentially expand and contract in a physiologic luminal environment.

623. A method as in clause 622 further comprising filling the gaps with an elastomeric material to provide an elastic attachment between the attachment ends.

624. A method as in clause 620, wherein forming comprises bending the panels over a cylindrical mandrel.

625. A method as in clause 620, wherein joining the end structures together comprises applying an elastomeric material between adjacent end structures.

626. A method as in clause 620, wherein joining the end structures together comprises applying an elastomeric material over the adjacent end structures.

627. A method as in clause 620, wherein joining the end structures together comprises applying an elastomeric sleeve over the adjacent end structures.

Radially Oriented Tab Designs

628. A stent prosthesis comprising: a scaffold having circumferential rings patterned from a polymeric or metallic material, said scaffold being configured to expand from a crimped configuration to an expanded configuration; wherein at least some of the circumferential rings are joined by axial links and wherein at least some of the axial links are joined to an adjacent circumferential ring by a circumferential displacement region which allows the circumferential ring to circumferentially expand and contract in a physiologic luminal environment.

629. A stent prosthesis as in clause 628, wherein the at least one circumferential displacement regions allow the circumferential ring to circumferentially expand and contract in response to a systolic/diastolic rhythm in an arterial lumen.

630. A stent prosthesis as in clause 629, wherein the scaffold includes a plurality of circumferential rings coupled together along an axis by the axial links and wherein at least some of the circumferential rings comprise struts joined by crowns and a strut on the adjacent circumferential ring terminates in the circumferential displacement region which is joined to the axial link.

631. A stent prosthesis as in clause 630, wherein the discontinuities that allow the circumferential ring(s) to circumferentially expand and contract in response to a systolic/diastolic rhythm in the arterial lumen comprise gaps between opposed segments of a strut or a crown.

632. A stent prosthesis as in clause 630, wherein the circumferential displacement regions comprise a male segment and a female coupling element.

633. A stent prosthesis as in clause 632, wherein the male segment is at a terminal end of a strut and the female coupling element is on the axial link.

634. A stent prosthesis as in clause 632, wherein the female segment is at a terminal end of a strut and the male coupling element is on the axial link.

635. A stent prosthesis as in clause 632, wherein the male element is free to move circumferentially between opposed walls of the female coupling member to circumferentially expand and contract the stent prosthesis.

636. A stent prosthesis as in clause 632, wherein the male segment and a female coupling element are separated by gap.

637. A stent prosthesis as in clause 611, wherein the gaps are filled with an elastomeric cushion material which dampens the circumferential movement of the male element between the opposed walls of the circumferential ring.

Valve Clauses

638. A stent prosthesis for valve repair or replacement comprising: a stent prosthesis comprising patterned structural elements, said stent being expandable from a crimped configuration to an expanded larger configuration and having sufficient strength to support a body annulus in the expanded configurations; wherein at least one valve is coupled to the stent prosthesis allowing for blood to flow though the valve substantially in one direction during the cardiac cycle; and wherein at least one segment of the stent comprises one or more uncaging elements to allow said segment to have larger displacement than an adjacent stent segment in the expanded stent configuration under physiological condition.

639. A stent prosthesis as in clause 638, wherein the displacement comprises one or more of radial direction, circumferential direction, longitudinal direction, direction to bias the valve to close, direction to accommodate the annulus compliance, or combination thereof.

640. A stent as in clause 638, wherein the uncaging elements comprises one or more of separation regions, bridging element, reinforcement elements, junctions, joints, hinges, gaps, discontinuities.

641. A stent prosthesis as in clause 638, wherein the strength in the uncaging elements is lower than the adjacent segment 642. A stent prosthesis as in clause 638, wherein the stent is balloon expandable or self-expandable prosthesis 643. A stent prosthesis as in clause 638, wherein the stent further comprises at least one skirt on at least one surface of the stent prosthesis, and wherein the skirt accommodates the displacement 644. A stent prosthesis as in clause 638, wherein the stent is formed from a tube, a braided one or more wires, or from a wire, or combination thereof.

645. A stent prosthesis as in clause 638, wherein the stent prosthesis pattern is a closed cell pattern, and open cell pattern, or a combination thereof.

646. A stent prosthesis as in clause 638, wherein the stent is formed from a non-degradable metallic or polymeric material.

647. A stent prosthesis as in clause 638, wherein the stent is formed from a degradable metallic or polymeric material.

648. A stent prosthesis as in clause 638, wherein at least some of the structural elements contain uncaging elements.

649. A stent prosthesis as in clause 638, wherein the uncaging elements are adjacent to at least one coupled region of the valve to the stent.

650. A stent prosthesis as in clause 638, wherein the radial strain of the at least one segment is larger than the adjacent segment by a magnitude ranging from 0.1% to 20%, preferably ranging from 0.2% to 10%, more preferably ranging from 0.5% to 10%.

651. A stent prosthesis as in clause 638, wherein the at least one segment has radial strain ranging from 0.3% to 20%, preferably ranging from 0.5% to 10%, more preferably ranging 1% to 10%.

652. A stent prosthesis as in clause 638, wherein the pattern of the uncaging elements conforms to the pattern of the annulus.

653. A stent prosthesis as in clause 638, wherein the at least one segment has radial contraction and/or expansion in the expanded stent configuration larger than the adjacent segment.

654. A stent prosthesis as in clause 638, wherein the at least one segment has radial contraction and/or expansion in the expanded stent configuration larger than the adjacent segment by at least 10%, preferably larger by at least 20%.

655. A stent prosthesis as in clause 638, wherein the patterned structural elements comprises one or more of: one or more wires, braided one or more wires, struts, crowns, circumferential links, axial links.

656. A stent prosthesis as in clause 638, wherein the uncaging elements allow for larger displacement after expansion of the stent prosthesis.

657. A stent prosthesis as in clause 638, wherein the uncaging elements allow for the larger displacements in a period ranging from 3 months to 3 years after deployment (or expansion) in a body annulus.

658. A stent prosthesis for vale repair or replacement comprising: a stent prosthesis comprising patterned structural elements, said stent being self-expandable from a crimped configuration to an expanded larger configuration, and having sufficient strength to support a body annulus in the expanded configurations, and wherein at least one valve is coupled to the stent prosthesis allowing for blood to flow though the valve substantially in one direction during the cardiac cycle, and wherein at least one segment of the stent comprises one or more uncaging elements to reduce the strength of said segment compared to an adjacent stent segment in the expanded stent configuration under physiological condition.

659. A stent prosthesis as in clause 658, wherein the at least one segment is the segment nearest to the ventricle.

660. A stent prosthesis as in clause 658, wherein the at least one segment uncaging minimizes damage to the pacing node or coronary sinus.

661. A stent prosthesis as in clause 658, wherein the at least one segment has lower strength by at least 10%.

662. A stent prosthesis as in clause 658, wherein the at least one segment has lower strength than the adjacent segment in the expanded configuration and less than the maximum expanded configuration of the stent.

663. An implant for valve repair or replacement comprising: structural elements comprising one or more elements each having one or more of length, width, and thickness, said structural element is positioned adjacent to a valve annulus and affixed in place, and wherein the structural element is coupled to a stent containing a valve deployed in the annulus of the valve; wherein at least one segment of the structural element is configured to have uncaging elements to allow said segment to have a displacement larger than an adjacent segment of the structural element.

664. An implant as in clause 663, wherein at least one stent segment contracts and/or expands during the displacement of the at least one segment 665. An implant as in clause 663, wherein the valve closes or opens during the displacement of the at least one segment.

666. An implant as in clause 663, wherein the structural element contours at least part of the perimeter of the valve annulus 667. An implant as in clause 663, wherein the structural element is positioned adjacent to the annulus, superior to the annulus, or inferior to the annulus.

668. An implant as in clause 663, wherein the structural element substantially circles the annulus.

669. An implant as in clause 663, wherein the structural element comprises one or more structural elements.

670. An implant for valve repair or replacement comprising: structural element comprising one or more elements each having one or more of length, width, and thickness, said structural element is positioned adjacent to a valve annulus and affixed in place, and wherein the structural element is coupled to an implanted valve; wherein at least one segment of the structural element is configured to have uncaging elements to allow said segment to have a displacement larger than an adjacent segment of the structural element.

671. An implant as in clause 670, wherein at least one valve segment radially contracts and/or expands during the displacement of the at least one segment 672. A stent prosthesis as in clause 670, wherein the valve closes and/or opens during the displacement of the at least one segment.

673. A stent prosthesis as in clause 670, wherein the structural element contours at least part of the perimeter of the valve annulus 674. A stent prosthesis as in clause 670, wherein the structural element is positioned adjacent to the annulus, superior to the annulus, or inferior to the annulus.

Stent Prosthesis Clauses

675. A stent prosthesis comprising: a non-degradable metal or metal alloy material, said material patterned into a substantially cylindrical structure capable of being expandable from a crimped configuration to an expanded larger configuration and having sufficient strength in the expanded configuration to support a body lumen; wherein said structure comprises structural elements comprising a plurality of circumferential rings, wherein each ring is connected to an adjacent ring via one or more axial links, and/or via connecting at least one structural element region on said each ring to a structural element region on said adjacent ring; wherein each ring comprises struts joined by crowns; wherein at least some circumferential rings have one or more separation regions along the circumferential path of said rings, and wherein said separation regions form discontinuities after expansion; and wherein said stent and/or said at least some rings after formation of said discontinuities exhibit one or more of the following: a radial strain ranging between 1% and 5%, a radial displacement ranging from 0.05 mm to 1.5 mm, further expand to a larger expanded configuration after inward recoil from said expanded configuration, vaso-dilatation and/or vaso-constriction in the magnitude ranging from 0.05 mm to 0.5 mm, reduction in strength after stent expansion, uncaging circumferentially, or reduction in hoop stresses, under physiologic conditions, and wherein the at least some rings having one or more separation regions remain substantially connected to adjacent rings after expansion.

676. A stent prosthesis as in clause 675, wherein the at least some rings are connected to adjacent rings via two or more axial links, and/or via connecting two or more structural element regions on the at least some rings to two or more structural element regions on said adjacent rings, and wherein the at least some rings remain substantially connected to said adjacent rings after expansion.

677. A stent prosthesis as in clause 675, wherein the at least some rings are connected to adjacent rings via three or more axial links, and/or via connecting three or more structural element regions on the at least some rings to three or more structural element regions on said adjacent rings, and wherein the at least some rings remain substantially connected to said adjacent rings after expansion.

678. A stent prosthesis as in clause 675, wherein each ring remains substantially connected to an adjacent ring after expansion.

679. A stent prosthesis as in clause 675, wherein at least some separation regions form discontinuities after expansion ranging from 30 days to 9 months.

680. A stent prosthesis as in clause 675, wherein at least some separation regions form discontinuities after expansion ranging from 1 day to 30 days.

681. A stent prosthesis as in clause 675, wherein the radial strain ranges from 1.5%-5% under physiologic conditions where the unconstrained lumen or tube have a radial strain of approximately 5%.

682. A stent prosthesis as in clause 675, wherein the radial displacement ranges from 0.1 mm to 0.3 mm 683. A stent prosthesis as in clause 675, wherein the vaso-dilatation and/or vaso-constriction magnitude ranges from 0.07 mm to 0.3 mm 684. A stent prosthesis as in clause 675, wherein the reduction in strength ranges from 10% to 90% of the initial expanded configuration strength.

685. A stent prosthesis as in clause 675, wherein the reduction in hoop stresses after expanses ranges from 10% to 90% of the initial expanded configuration hoop stresses.

686. A stent prosthesis as in clause 675, wherein substantially all rings have one or more separation regions.

687. A stent prosthesis as in clause 675, wherein at least some separation regions form discontinuities during expansion.

688. A stent prosthesis as in clause 675, wherein at least some separation regions form discontinuities before expansion.

689. A stent prosthesis as in clause 675, wherein at least some separation regions are held together during deployment (expansion) from the crimped configuration to the expanded larger configuration.

690. A stent prosthesis as in clause 675, wherein at least some separation regions are held together during deployment (expansion) from the crimped configuration to the expanded larger. configuration and wherein the separation regions are held together by a joint configuration, key and lock type configuration, polymer material, adhesive material, solder, fusing structural elements, or combination thereof.

691. A stent prosthesis as in clause 675, wherein substantially all the rings remain connected to adjacent rings after expansion.

692. A stent prosthesis as in clause 675, wherein the stent is substantially cylindrical.

693. A stent prosthesis as in clause 675, wherein each ring extends around a circumference of the stent forming an angle with the longitudinal axis of the stent.

694. A stent prosthesis as in clause 675, wherein the stent prosthesis is plastically deformed when expanded from a crimped configuration to an expanded larger configuration.

695. A stent prosthesis as in clause 675, wherein the stent comprises at least one polymer coating on at least one surface of the stent.

696. A stent prosthesis as in clause 675, wherein the stent comprises at least one drug on at least one surface of the stent.

697. A stent prosthesis as in clause 675, wherein the stent is balloon deployable.

698. A stent prosthesis as in clause 675, wherein the stent is formed from a tube then patterned, patterned from one or more wires, or formed from a rolled up patterned sheet.

699. A stent prosthesis as in clause 675, wherein the stent is substantially cylindrical.

700. A stent prosthesis as in clause 675, wherein the non-degradable metal or metal alloy comprises one of: stainless steel, cobalt chrome, platinum iridium 701. A stent prosthesis as in clause 675, wherein the at least some rings after formation of said discontinuities separates into at least two strips along the length of the stent prosthesis, while the at least some rings remain substantially connected to adjacent rings.

702. A stent prosthesis as in clause 675, wherein each ring has one or more separation regions, and wherein the stent after formation of said discontinuities separates into at least two strips along the length of the stent prosthesis, while the rings remain connected to adjacent rings.

703. A stent prosthesis as in clause 675, wherein the initial radial strain of the stent after expansion to 4 mm ranges from 0.1% to 1% and increases to a range from 1.1% to 3.5% within a period ranging from 1 day to 9 months after expansion, under physiologic condition, said expansion within a lumen having unconstrained radial strain ranging from 4% to 5%.

704. A stent prosthesis as in clause 675, wherein the initial radial strain of the stent after expansion to 4 mm ranges from 0.1% to 1% and increases to a range from 1.1% to 3.5% within a period ranging from 1 day to 9 months after expansion, under physiologic condition, said expansion within a lumen having unconstrained radial strain ranging from 4% to 5%, and wherein the stent maintains a structure in the increased radial strain configuration preventing it from matching the unconstrained radial strain of the lumen.

705. A stent prosthesis as in clause 675, wherein the stent prosthesis has an initial radial strain after expansion and wherein the radial strain changes under physiologic conditions 706. A stent prosthesis as in clause 675, wherein the stent prosthesis has an initial radial strain after expansion and wherein the stent radial strain increases under physiologic conditions 707. A stent prosthesis as in clause 675, wherein the stent prosthesis has an initial radial strain after expansion and wherein the radial strain of the stent substantially increases under physiologic conditions in a period ranging from 1 day to 1 year.

708. A stent prosthesis as in clause 675, wherein the stent has an initial radial strain after expansion and wherein the radial expansion increases by a factor ranging from 1.2 to 15 times the initial radial strain after formation of discontinuities.

709. A stent prosthesis as in clause 675, wherein the stent has an initial radial strain after expansion and wherein the radial expansion increases by a factor ranging from 1.5 to 15 times the initial radial strain after formation of discontinuities.

710. A stent prosthesis as in clause 675, wherein the stent has an initial radial strain after expansion and wherein the radial expansion increases by a factor ranging from 1.7 to 15 times the initial radial strain after formation of discontinuities.

711. A stent prosthesis as in clause 675, wherein the radial strain of the stent after expansion ranges from 0.15% to 0.75% of the unstented lumen radial strain adjacent to the stented segment.

712. A stent prosthesis as in clause 675, wherein the radial strain of the stent after expansion ranges from 0.25% to 0.75% of the unstented lumen radial strain adjacent to the stented segment.

713. A stent prosthesis as in clause 675, wherein the radial strain of the stent after expansion ranges from 0.30% to 0.75% of the unstented lumen radial strain adjacent to the stented segment, and wherein the stent retains a patterned structure after formation of discontinuities.

714. A stent prosthesis as in clause 675, wherein the stent has an initial strength after expansion and wherein the strength decreases by at least 25% of said initial strength after formation of said discontinuities.

715. A stent prosthesis as in clause 675, wherein the stent has an initial strength after expansion and wherein the strength decreases by 25% to 75% of said initial strength after formation of at least some discontinuities.

716. A stent prosthesis as in clause 675, wherein the stent has an initial strength after expansion and wherein the strength decreases by 50% to 85% of said initial strength after formation of at least some discontinuities.

717. A stent prosthesis as in clause 675, wherein the stent has an initial strength after expansion and wherein the strength diminishes after formation of at least some discontinuities or substantially all discontinuities, and wherein the stent prosthesis retains a substantially interconnected 1 to 5 patterned strips along the length to support a body lumen.

718. A stent prosthesis as in clause 675, wherein the separation regions are positioned along the circumferential path of a circumferential structural element, and wherein the number of separation regions are sufficient to forma discontinuity in said circumferential structural element.

719. A stent prosthesis as in clause 675, wherein at least some rings have no more than one separation region for every one crowns connecting two struts.

720. A stent prosthesis as in clause 675, wherein at least some rings have no more than one separation region for every two crowns connecting a total of three struts.

721. A stent prosthesis as in clause 675, wherein at least some rings have no more than one separation region per ring segment wherein the ring segment comprises one strut connected to two crowns.

722. A stent prosthesis as in clause 675, wherein at least some rings have no more than one separation region per a ring segment wherein the ring segment comprises one strut connected two crowns, and wherein the separation region is located in the substantially non-deformable strut region.

723. A stent prosthesis as in clause 675, wherein at least some rings have no more than one separation region per a ring segment wherein the ring segment comprises three crowns connecting three struts, and wherein the separation region is located on the substantially non-deformable region of any of the struts.

724. A stent prosthesis as in clause 675, wherein at least some rings have no more than one separation region per a ring segment wherein the ring segment comprises three crowns connecting four struts, and wherein the separation region is located on the substantially non-deformable region of any of the struts.

725. A stent as in clause 675, wherein the radial strain of the body lumen is about 5%.

726. A stent as in clause 675, wherein the radial strain of the body lumen ranges from 3.5%-10%.

727. A stent prosthesis as in clause 675, wherein the at least some rings have no more than 4 separation regions per at least some rings.

728. A stent prosthesis as in clause 675, wherein the at least some rings have no more than 5 separation regions per at least some rings.

729. A stent prosthesis as in clause 675, wherein the at least some rings have no more than 6 separation regions per ring 730. A stent prosthesis as in clause 675, wherein the at least some rings have no more than three separation regions per ring.

731. A stent prosthesis as in clause 675, wherein the axial links range from 1 to 4 links, for a stent pattern having circumferential rings comprising crowns wherein the number of crowns ranges from 3 crowns to 9 crowns.

732. A stent prosthesis as in clause 675, wherein the links connecting at least some rings are spaced every crown, every other crown, every two crown, or every three crowns.

733. A stent prosthesis as in clause 675, wherein the location of at least some separation regions on at least some circumferential rings are located on struts or crowns adjacent to a link.

734. A stent prosthesis as in clause 675, wherein the location of at least some separation regions on at least some circumferential rings are located on struts or crowns not adjacent to a link.

735. A stent prosthesis as in clause 675, wherein the structural element regions comprises crown and/or strut regions.

736. A stent prosthesis as in clause 675, wherein the separation regions break the circumferential structural integrity of the at least some rings or stent.

737. A stent prosthesis as in clause 675, wherein the stent has an initial stiffness in the expanded configuration and wherein the stiffness decreases by a magnitude ranging from 10% to 100% within a period ranging from 1 day to 9 months after expansion.

738. A stent prosthesis as in clause 675, wherein the stent has an initial strength in the expanded configuration and wherein the strength decreases by a magnitude ranging from 10% to 100% within a period ranging from 1 day to 9 months after expansion.

739. A stent prosthesis as in clause 675, wherein the stent has initial strength after expansion and wherein the strength decreases after formation of at least some discontinuities, and wherein the decreased stent strength is sufficient to substantially maintain open the body lumen.

740. A stent prosthesis as in clause 675, wherein the stent has initial strength after expansion and wherein the strength decreases after formation of at least some discontinuities, and wherein the decreased stent strength is sufficient to support the body lumen.

741. A stent prosthesis as in clause 675, wherein the stent has initial strength after expansion and wherein the strength decreases after formation of at least some discontinuities, and wherein the stent retains a patterned structure sufficient to support the body lumen.

742. A stent prosthesis as in clause 675, wherein the stent has initial strength after expansion and wherein the strength diminishes after formation of said discontinuities, and wherein the stent retains a sufficient stent structure to support the body lumen.

743. A stent prosthesis as in clause 675, wherein the stent has initial strength after expansion and wherein the strength diminishes after formation of said discontinuities, and wherein the stent retains a sufficient stent structure to support a vulnerable body lumen.

744. A stent prosthesis as in clause 675, wherein at least some of the separation regions allow the structural elements adjacent to said separation regions to move in one or more direction 745. A stent prosthesis as in clause 675, wherein at least some of the separation regions allow the structural elements adjacent to said separation regions to move in one or more directions comprising radial, or circumferential.

746. A stent prosthesis as in clause 675, wherein at least some separation regions are held together in the stent crimped configuration by a key and lock junction to facilitate expansion of the stent 747. A stent prosthesis as in clause 675, wherein at least some separation regions are held together by adhesive, polymer, or combination thereof.

748. A stent prosthesis as in clause 675, wherein at least some separation regions have a gap, said gap magnitude ranges from 0.05 mm to 0.2 mm, and wherein the gap allows the structural elements adjacent to said separation regions to move in a circumferential direction after formation of discontinuities, and wherein the movement ranges from 0.05 mm to 2 mm.

749. A stent prosthesis as in clause 675, wherein at least some separation regions are located on non-deformable or substantially non-deformable regions of the circumferential rings 750. A stent prosthesis as in clause 675, wherein substantially all separation regions are located on non-deformable or substantially non-deformable regions of the circumferential rings 751. A stent prosthesis as in clause 675, wherein substantially all separation regions are located on strut regions of the circumferential rings 752. A stent prosthesis as in clause 675, wherein at least some separation regions are located on crown regions of the circumferential rings, and wherein the separation regions allow the crown region to deform open upon expansion of the stent without breaking of the crown region.

753. A stent prosthesis as in clause 675, wherein the stent longitudinal structure is substantially maintained after formation of said discontinuities.

754. A stent prosthesis as in clause 675, wherein the longitudinal structure of the stent remains substantially connected after formation of said discontinuities 755. A stent prosthesis as in clause 675, wherein the stent in the longitudinal direction forms one to four semi-circular strips connected in the longitudinal direction by one or more links after formation of said discontinuities, and wherein the stent substantially maintains a patterned structure.

756. A stent prosthesis as in clause 675, wherein at least some of the crowns and struts regions on every ring do not have separation regions.

757. A stent prosthesis as in clause 675, wherein substantially all crown regions on at least some rings do not have separation regions.

758. A stent prosthesis as in clause 675, wherein substantially all deformable regions on at least some rings do not have separation regions.

759. A stent prosthesis as in clause 675, wherein the separation regions are smaller than the strut and/or crown regions.

760. A stent prosthesis as in clause 675, wherein the separation regions form a gap in the crimped stent configuration.

761. A stent prosthesis as in clause 675, wherein the number of separation regions on at least some rings are equal to or less than ½ the number of crowns on said rings, or the number of separation regions on at least said rings are equal to or less than ¼ the number of struts on said rings, wherein the stent prosthesis after formation of discontinuities substantially maintains a patterned structure sufficient to support a body lumen.

762. A stent prosthesis as in clause 675, wherein the number of separation regions on each ring are equal to or less than ½ the number of crowns on said ring, and/or the number of separation regions on each ring are equal to or less than ¼ the number of struts on said ring, wherein the stent prosthesis after formation of discontinuities substantially maintains a patterned structure sufficient to support a body lumen.

763. A stent prosthesis as in clause 675, wherein the number of separation regions on each ring are equal to or less than ⅘ the number of crowns on said ring, and/or the number of separation regions on each ring are equal to or less than ½ the number of struts on said ring, wherein the stent prosthesis after formation of discontinuities substantially maintains a patterned structure sufficient to support a body lumen.

764. A stent prosthesis as in clause 675, wherein the number of separation regions on each ring are equal to or less than ⅘ the number of crowns on said ring, and/or the number of separation regions on each ring are equal to or less than ½ the number of struts on said ring, wherein the stent prosthesis after formation of discontinuities substantially maintains a patterned structure sufficient to support a body lumen, wherein the radial strain of said stent prosthesis is less than the radial strain of the unstented lumen adjacent to the stent prosthesis.

765. A stent prosthesis as in clause 675, wherein the stent is formed from a metal or metal alloy and patterned into a stent by laser.

766. A stent prosthesis as in clause 675, wherein at least some rings contain at least some separation regions, and wherein the separation regions comprise a gap region along the circumferential path of said at least some rings, and wherein the gap comprises a biodegradable material connecting the two ends of the separation regions and hold them together in the crimped configuration, and wherein the polymeric material degrades after expansion of the stent forming discontinuities in said circumferential rings.

767. A stent prosthesis as in clause 675, wherein the stent comprises open cell type design, closed cell type design, helical type design, coil type design, or combination thereof.

768. A stent prosthesis as in clause 675, wherein the distance between at least some adjacent rings ranges from 0.05 mm to 3 mm, preferably ranges from 0.1 mm to 2 mm, more preferably ranges from 0.2 mm to 1 mm.

769. A stent prosthesis as in clause 675, wherein the distance between any adjacent rings ranges from 0.05 mm to 3 mm, preferably ranges from 0.1 mm to 2 mm, more preferably ranges from 0.2 mm to 1 mm.

770. A stent prosthesis as in clause 675, wherein the shortest distance between any adjacent rings ranges from 0.01 mm to 1 mm, preferably ranges from 0.05 mm to 1 mm, more preferably ranges from 0.1 mm to 1 mm.

771. A stent prosthesis as in clause 675, wherein the longest distance between any adjacent rings ranges from 0.1 mm to 3 mm, preferably ranges from 0.15 mm to 2.5 mm, more preferably ranges from 0.15 mm to 2.3 mm.

772. A stent prosthesis as in clause 675, wherein the at least some rings in the absence of separation regions form circumferentially continuous rings in the expanded stent configuration.

773. A stent prosthesis as in clause 675, wherein the at least some separation regions are held together in the crimped configuration and remain held together upon expansion of the stent prosthesis from said crimped configuration.

774. A stent prosthesis as in clause 675, wherein the expansion of the stent prosthesis from said crimped configuration to said expanded larger configuration does not form discontinuities in said separation regions.

775. A stent prosthesis as in clause 675, wherein the discontinuities form passively under physiologic conditions 776. A stent prosthesis as in clause 675, wherein the discontinuities form after expansion of the stent to the expanded configuration and unaided by any device to form said discontinuities 777. A stent prosthesis as in clause 675, wherein the stent structural elements in the crimped configuration do not overlap.

778. A stent prosthesis as in clause 675, wherein substantially all the stent structural elements, with the exception of at least some separation regions, in the crimped configuration do not overlap.

779. A stent prosthesis as in clause 675, wherein the stent structural elements in the expanded configuration do not overlap 780. A stent prosthesis as in clause 675, wherein substantially all the stent structural elements in the expanded configuration with the exception of at least some separation regions do not overlap 781. A stent prosthesis as in clause 675, wherein the stent structural elements do not roll in the crimped configuration.

782. A stent prosthesis as in clause 675, wherein the stent structural elements are crimped as one layer over the delivery system.

783. A stent prosthesis as in clause 675, wherein the stent structural elements are crimped as one layer within the delivery system.

784. A stent as in clause 675, wherein the stent is a substantially cylindrical structure in the expanded configuration and wherein the stent have continuous circumferential elements with the exception of the at least some separation regions, and wherein the stent expands from a crimped configuration to an expanded configuration radially.

785. A stent as in clause 675, wherein the stent is a substantially cylindrical structure in the expanded configuration and wherein the stent have continuous circumferential elements with the exception of the separation regions, and wherein the expands from a crimped configuration to an expanded configuration not circumferentially 786. A stent as in clause 675, wherein the stent is a substantially cylindrical structure in the expanded configuration and wherein the stent expands from a crimped configuration to an expanded configuration not by a sliding means 787. A stent prosthesis as in clause 675, wherein the separation regions do not form discontinuities upon expansion of the stent prosthesis, and wherein the discontinuities form after expansion of the stent.

788. A stent prosthesis as in clause 675, wherein the separation regions do not form a substantially straight line of discontinuities along the length of the stent 789. A stent prosthesis as in clause 675, wherein the separation regions do not form a straight line of discontinuities along substantially the length of the stent 790. A stent prosthesis as in clause 675, wherein the stent prosthesis after formation of discontinuities have improved longitudinal flexibility in the expanded configuration while substantially all the axial links connecting at least some adjacent rings are substantially intact.

791. A stent prosthesis comprising: a non-degradable metal or metal alloy material, said material patterned into a substantially cylindrical structure capable of being expandable from a crimped configuration to an expanded larger configuration, and have sufficient strength in the expanded configuration to support a body lumen, said structure comprises structural elements comprises a plurality of circumferential rings, wherein at least some circumferential rings are connected to adjacent rings via one or more axial links, and/or via connecting at least some structural element regions on said at least some rings to structural element regions on said adjacent rings; wherein each ring comprises struts joined by crowns, and wherein the at least some circumferential rings have one or more separation regions along the circumferential path of said rings, and wherein said separation regions form discontinuities after expansion; wherein said stent and/or said at least some rings after formation of said discontinuities exhibit one or more of the following: a radial strain ranging between 1% and 5%, a radial displacement ranging from 0.05 mm to 1.5 mm, further expand to a larger expanded configuration after inward recoil from said expanded configuration, vaso-dilatation and/or vaso-constriction in the magnitude ranging from 0.05 mm to 0.3 mm, reduction in strength, uncaging circumferentially, or reduction in hoop stresses, under physiologic conditions; and wherein the at least some rings having one or more separation regions remain substantially connected to adjacent rings after expansion.

792. A stent prosthesis comprising: a degradable metal or metal alloy material, said material patterned into a cylindrical structure capable of being expandable from a crimped configuration to an expanded larger configuration, and have sufficient strength in the expanded configuration to support a body lumen, said structure comprises structural elements comprises a plurality of circumferential rings, wherein at least some circumferential rings are connected to adjacent rings via one or more axial links, and/or via connecting at least some structural element regions on said at least some rings to structural element regions on said adjacent rings; wherein each ring comprises struts joined by crowns, and wherein the at least some circumferential rings have one or more separation regions along the circumferential path of said rings, and wherein said separation regions form discontinuities after expansion; and wherein said stent and/or said at least some rings after formation of said discontinuities exhibit one or more of the following: a radial strain ranging between 1% and 5%, a radial displacement ranging from 0.05 mm to 1.5 mm, further expand to a larger expanded configuration after inward recoil from said expanded configuration, vaso-dilatation and/or vaso-constriction in the magnitude ranging from 0.05 mm to 0.3 mm, reduction in strength, uncaging circumferentially, or reduction in hoop stresses, under physiologic conditions, and wherein the at least some rings having one or more separation regions remain substantially connected to adjacent rings after expansion, and wherein the degradable material comprises on or more of magnesium, tungsten, or other degradable metal or metal alloys as described in the specifications.

793. A stent prosthesis comprising: a non-degradable metal or metal alloy formed from a tube or one or more wires and patterned into a substantially cylindrical stent capable of expansion from a crimped configuration to an expanded larger configuration and have sufficient strength in the expanded configuration to support a body lumen, said stent comprises structural elements comprising a plurality of circumferential rings wherein at least some rings have from 1 to 5 separation regions along the circumferential path of said rings, and wherein the separation regions form discontinuities after expansion reducing said stent strength but substantially maintaining open said body lumen, said stent has an initial radial strain and wherein said radial strain increases after formation of discontinuities.

794. A stent prosthesis comprising: formed from a non-degradable metal or metal alloy and patterned into a substantially cylindrical structure capable of expansion from a crimped configuration to an expanded larger configuration and have sufficient strength in the expanded configuration to support a body lumen, said stent structure comprises structural elements comprising a plurality of circumferential rings wherein at least some rings have from 1 to 5 separation regions along the circumferential path of said rings, and wherein the separation regions form discontinuities after expansion of the stent reducing the said at least some rings strength while increasing the said at least some rings radial strain, under physiologic conditions.

795. A stent prosthesis comprising: formed from a non-degradable metal or metal alloy and patterned into a substantially cylindrical structure capable of expansion from a crimped configuration to an expanded larger configuration and have sufficient strength in the expanded configuration to support a body lumen, said stent structure comprises structural elements comprising a plurality of circumferential rings wherein at least some rings have from 1 to 5 separation regions along the circumferential path of said rings, and wherein the separation regions form discontinuities after expansion of the stent increasing the displacement in at least one axis of the said at least some rings, under physiologic conditions.

796. A stent prosthesis comprising: formed from a non-degradable metal or metal alloy and patterned into a substantially cylindrical structure capable of expansion from a crimped configuration to an expanded larger configuration and have sufficient strength in the expanded configuration to support a body lumen, said stent structure comprises structural elements comprising a plurality of circumferential rings wherein at least some rings have from 1 to 5 separation regions along the circumferential path of said rings, and wherein the separation regions form discontinuities after expansion of the stent increasing the displacement in at least one direction of the said at least some rings, under physiologic conditions.

797. A stent prosthesis comprising: formed from a non-degradable metal or metal alloy and patterned into a substantially cylindrical structure capable of expansion from a crimped configuration to an expanded larger configuration and have sufficient strength in the expanded configuration to support a body lumen, said stent structure comprises structural elements comprising a plurality of circumferential rings wherein at least some rings have from 1 to 5 separation regions along the circumferential path of said rings, and wherein the separation regions form discontinuities after expansion of the stent increasing the displacement in at least one or more of axial, circumferential, radial, or longitudinal direction, of the said at least some rings, under physiologic conditions.

Variable Compliance Clauses

798. A variably compliant stent prosthesis comprising: a non-degradable metal or metal alloy scaffold expandable from a crimped configuration to an expanded larger configuration; wherein after expansion the scaffold has sufficient strength to support a vascular lumen; and wherein immediately but no later than 1 hour after expansion the scaffold has a composite compliance when measured in a mock vessel no greater than 1%; and wherein after expansion and exposure to vascular conditions, the composite compliance when measured in a mock vessel increases to at least 1.5%.

799. A variably compliant stent prosthesis comprising: a non-degradable metal or metal alloy scaffold expandable from a crimped configuration to an expanded larger configuration; wherein after expansion the scaffold has sufficient strength to support a vascular lumen; and wherein immediately but no later than 1 hour after expansion the scaffold has an initial composite compliance when measured in a mock vessel; and wherein after expansion and exposure to exposure to vascular conditions, the composite compliance when measured in a mock vessel increases by a factor of at least two.

800. A variably compliant stent prosthesis as in clause 798 or 799, wherein the non-degradable metal or metal alloy scaffold comprises separation regions which separate after exposure to vascular conditions for a threshold time period.

801. A variably compliant stent prosthesis as in clause 800, wherein at least some of the separation regions are initially prevented from separating by a bioabsorbable material which degrades over time when exposed to the vascular conditions.

802. A variably compliant stent prosthesis as in clause 801 wherein the bioabsorbable material is in the form of a coating, sleeve, or adhesive.

803. A variably compliant stent prosthesis as in clause 801 wherein the bioabsorbable material degrades over a time period in a range from 30 days to 12 months when exposed to the vascular conditions.

804. A variably compliant stent prosthesis as in clause 798 or 799, wherein the non-degradable metal or metal alloy scaffold comprises regions reinforced with a reinforcement material wherein the reinforcement material degrades after exposure to vascular conditions for a threshold time period.

805. A variably compliant stent prosthesis as in clause 804, wherein the reinforcement material comprises a bioabsorbable material which degrades over time when exposed to the vascular conditions.

806. A variably compliant stent prosthesis as in clause 804, wherein the reinforcement material fills voids in a crown and/or a strut of the non-degradable metal or metal alloy scaffold.

807. A variably compliant stent prosthesis as in clause 805, wherein the reinforcement material covers or coats at least a region of a surface of the non-degradable metal or metal alloy scaffold.

808. A variably compliant stent prosthesis as in clause 798 or 799, wherein immediately but no later than 1 hour after expansion the scaffold has a strength (initial strength) in the range from 0.035 Newton per millimeter of stent length to 0.1 Newton per millimeter of stent length.

809. A variably compliant stent prosthesis as in clause 808, wherein the radial strength of the stent scaffold decreases after expansion and exposure to vascular conditions.

810. A variably compliant stent prosthesis as in clause 808, wherein the radial strength of the stent scaffold increases from the initial strength before decreasing after expansion and exposure to vascular conditions.

811. A variably compliant stent prosthesis as in clause 809, wherein the radial strength of the stent scaffold decreases by from 20% to 100% after expansion and exposure to vascular conditions, optionally by from 20% to 80%.

812. A variably compliant stent prosthesis as in clause 798 or 799, wherein the non-degradable metal or metal alloy scaffold has a nominal expanded diameter, wherein the strength and composite compliance are measured after the stent has been expanded to a diameter of from 80% to 120% of the nominal expanded diameter, optionally at 100% of the nominal expanded diameter.

In a preferred example, the scaffold is a stent, wherein the stent comprises one or more circumferential rings joined axially, and wherein the one or more rings comprise struts and crowns. Stents include stent grafts, endoprostheses, ecto-prostheses (prostheses surrounding the exterior of a blood vessel or other body lumen), and other luminal prostheses intended to be implanted in a blood vessel, annulus, or other body lumen. The scaffold usually is a patterned cylindrical, substantially cylindrical, tubular, or substantially tubular circumferential structure and is constructed so that it can be introduced to the blood vessel, annulus, or other body lumen in a "crimped" configuration, i.e. in a low or reduced profile that allows the scaffold to be advanced to a target location within the body lumen where it is expanded to an "expanded configuration" where an outer surface of the scaffold contacts and/or supports the inner wall of the body lumen to maintain patency. In some cases, such as with "bare" stents, the scaffold may comprise a metal, metal alloy, plastic, or other conventional stent material which typically has been patterned from a tube, from a sheet, or from one or more wires, and is configured to be inserted into the lumen of an anatomic vessel or duct or other lumen in the crimped configuration. After insertion, the scaffold may be radially enlarged to the expanded configuration to keep a luminal passageway open or to open a closed, typically diseased passageway. In other cases, the scaffold may comprise one or more additional material (such as polymeric material) and/or one or more drugs, e.g. the scaffold may additionally have one or more coatings on at least one surface of the stent, the scaffold may be coated on at least one surface with a drug or other active substance to be a drug-coated stent, or the like. In still other instances, scaffold may form a portion of a prosthetic heart valve, vein valve, or other implantable valve.

In another preferred example, the separation region is a location in the scaffold which, prior to exposure to physiologic conditions and formation of discontinuities, will have sufficient structural integrity and strength to remain intact while the scaffold is expanded in a blood vessel or other similar or equivalent physiologic environment or conditions. Such expansion will typically be effected by inflation of a deployment balloon within a central lumen of the scaffold which can apply significant hoop stresses on the scaffold. The separation regions will be formed to withstand such stresses, e.g. by joining, covering, embedded, gluing, or otherwise immobilizing the separation region with a material which remains intact during scaffold expansion but which will subsequently degrade or otherwise detach from the scaffold in the physiologic environment to allow formation of a discontinuity. Alternatively, the scaffolds can be self-expanding, but the separation regions will still be formed to withstand stresses resulting from the self-expansion.

In another preferred example, a discontinuity comprises an opening, gap, joint, elastic junction, or the like, which forms in the scaffold at the locations of the separation regions after expansion of the scaffold and exposure of the scaffold to a blood vessel or other similar or equivalent physiologic environment or conditions. The discontinuities will increase the radial compliance of the scaffold or at least portions thereof. The discontinuities will be at locations in the expanded scaffold which decrease the hoop strength of the expanded scaffolds after the discontinuities form. For example, discontinuities may be in circumferential rings of a scaffold and will decrease the resistance to circumferential expansion of the ring, thus increasing radial compliance of the ring and of the scaffold as discussed in detail elsewhere in this application. In contrast, a discontinuity or break in an axial link or other axial connection which holds adjacent circumferential rings together typically will not decrease the hoop or radial strength of the expanded rings or scaffolds after the discontinuities form and typically will not increase radial compliance of the rings or scaffold as is an object of the present invention.

In another preferred example, the phrase "after all discontinuities are formed," refers to the scaffold when all separation regions in a scaffold have separated and all discontinuities have formed. While discontinuities may not always form in all separation regions in a scaffold after implantation in a blood vessel or other physiology environment, even though the separation regions maybe configured to form discontinuities at each separation region within the scaffold, all of the separation regions can be caused to form during in vitro tests run to determine if a scaffold meets the physical characteristics claimed herein. Thus, for the purposes of determining whether a scaffold meets the requirements of a claim which requires a determination that "all discontinuities are formed," the scaffold may be examined and tested after exposure to in vitro conditions selected to form all discontinuities by mimic in vivo physiologic condition, such as salinity, temperature, pressure, addition of agents or material to cause formation of dicontiuities, and the like, which would be expected to result in formation of discontinuities at each separation region within the scaffold. Examples of such in vitro physiologic conditions are provided in the Examples Section hereinbelow.

In another preferred example, the word "pattern" refers to the geometric arrangement of the structural elements of a scaffold. The most common pattern comprises a plurality of "circumferential rings" which are axially joined, either by axial links or by direct attachment of axially adjacent regions on the circumferential rings. The scaffolds of the present invention may also have helical patterns, diamond and other closed or open cell patterns, and other patterns known in the vascular and other stent fabrication arts. The circumferential rings will usually be formed as serpentine or zig-zag structures comprising struts joined by crowns, where the struts will usually be straight (but can be not straight) and the crowns will act as joints or hinges to allow the struts to open and the circumferential ring to expand both circumferentially and radially. That is, the distance around the circumference or perimeter of the circumferential ring will increase as will the radial distance of the ring perimeter from the axial center of the scaffold.

In another preferred example, the individual circumferential rings of a scaffold will usually be "intact" and will usually be "axially joined" when the scaffold is in its crimped configuration prior to expansion or formation of discontinuities. By "intact," it is meant that the circumferential ring will have a continuous serpentine, zig-zag, sinusoidal, or other circumferential structure free from discontinuities. By "axially joined," it is meant that axially adjacent circumferential rings will be joined by axial links, or by direct crown-to-crown attachment by fusing or soldering, for example. After expansion of the scaffold and exposure to a physiologic environment, discontinuities will form in at least some of the rings, typically being gaps, breaks, or bisections in a strut or crown region or other structural component which forms the peripheral path or perimeter of the ring so that the ring structure is no longer continuous. Even though the individual circumferential rings may thus divide into two or more separated portions (partial circumferential rings) after formation of discontinuities, they may also be referred to as "circumferential rings" as that phrase is used herein and in the claims and, in particular, adjacent circumferential rings will be considered to remain "axially joined" (intact) so long as at least one portion of one ring remains connected to at least one portion of an adjacent ring even if the joined portions of a circumferential ring are separated by discontinuities from other portions of the same ring.

In another preferred example, "radial compliance" is the composite compliance of the scaffold, stent, prosthesis or other structure measured as a composite compliance in vitro in a mock vessel (or tube) in accordance with ASTM F2477-07R13 which measures compliance at a pressure change of 100 mmHg, or radial strain (compliance measure at other pressure changes such as at about 176 mmHg), but the test can also provide the method for testing compliance at a given change in pressure other than 100 mmHg.

In another preferred example, "segment" and the phrase "segment of a scaffold" refer to a structural component of the scaffold which will remain joined or intact after all discontinuities have formed in the scaffold. For example, a circumferential ring is a segment as well as a closed cell structure. In many instances, two or more segments of the scaffold will remain joined after all discontinuities have formed in the scaffold. Thus, while segments will always remain joined or intact (where intact connotes that the structure is joined without any discontinuities, segments which are initially joined may or may not remain joined after all discontinuities have formed in the scaffold.

In another preferred example, "circumferential ring" refers both to rings with a continuous perimeter or periphery which extends over a full 360° as well as to discontinuous rings which have an offset in their perimeter or periphery. Such discontinuous circumferential rings will often be successively joined end-to-end so that they together form a helical pattern along all or a portion of the length of the scaffold. The individual circumferential rings will thus form successive turns of the helical scaffold. In one example, the circumferential ring pattern may be perpendicular to the longitudinal axis of the stent in the crimped and/or expanded configuration. In another example, the circumferential rings pattern may be at an angle between perpendicular to the stent longitudinal axis in the crimped configuration and/or expanded configuration and the stent longitudinal axis in the crimped and/or expanded configuration.

In another preferred example, "physiologic environment" refers both to natural or endogenous environments, typically a patient vasculature or other luminal environment, as well as to artificial or in vitro environments intended to mimic an endogenous vascular or other natural luminal environment. In particular, the artificial or in vitro environments will have at least some of the same temperature such as 37° C., aqueous solution (water bath), pressure change of about 100 mm Hg or of about 200 mmHg, mock tube having an inner diameter of 3.0 mm and a compliance of about 5%, agents to accelerate formation of discontinuities, and other characteristics of the endogenous environment that can be used to test the scaffolds to see if the separation regions will form discontinuities, stretch, or have enhanced compliance, in accordance with the principles of the present invention. In particular, to determine if a scaffold has separations regions, the scaffold can be examined for such separation regions, and/or be exposed to the physiologic conditions in vitro as described herein and observed to see if discontinuities form, or to test the scaffold for enhanced composite compliance, or to test the scaffold for initial compliance and increased composite compliance, or to test for the scaffold radial initial radial strength, or to test for radial strength after formation of discontinuities, the scaffold can be expanded in a tube "mock vessel" having ID of 3.0 mm, tube compliance of about 5%, in water bath at 37 C, and a pressure change of 100 mmHg, expand the inner scaffold diameter to about 110% of the tube inner diameter to ensure a good fit into the tube, measure initial composite compliance, dissolve the material holding the separation regions together forming discontinuities, and remeasure the composite compliance, the compliance of the stented segment at a mid segment of the stented segment, the compliance in accordance with the present invention increases from initial composite compliance after formation of discontinuities, typically increases by 200%-500% of the initial composite compliance, or usually increases by 200%-300%, or increases by at least 200% of the initial composite compliance, or increases by at least 300%.

In one preferred example, the stent after formation of discontinuities separates into 2, or 3, or 4 separate stent sections along the length of the stent, each section comprising a plurality of partial circumferential rings, where each partial ring remain axially connected (intact) to an adjacent partial ring, where the 2, 3, or 4 separate sections are formed after all the separation regions in each circumferential ring form discontinuities.

In a preferred example, the phrases "stent compliance," "stented segment compliance," and "stent vessel system compliance," all refer to the composite compliance of the stented/scaffolded segment as described in the composite compliance test method.

In a preferred example, the radial strength is measured using the flat plate (10% compression) test as described in the radial test method described in the application.

In a preferred example, at least some rings of the scaffold or stent of the present invention, are preferably which are formed from non-degradable metal or metal alloys, after expansion from a crimped configuration to an expanded configuration in a body lumen (or mock vessel), exhibit one or more of the following after formation of discontinuities compared to before formation of discontinuities: (1) uncage at least some, preferably all circumferential rings (the stent), or the stented segment, (2) display a change in configuration or diameter of at least some rings, preferably all rings of the stented segment, (3) display further expansion of at least some rings of the stented segment, (4) at least some rings of the stented segment, usually all, are able to expand and/or contract in a range from 0.1 mm to 0.5 mm, under physiologic conditions including contractility of the heart and/or change in pressure. Physiologic conditions may also include simulated physiologic conditions. Examples of the above are shown in example 22, showing OCT images of separation regions forming discontinuities in at least some rings uncaging said rings circumferentially, showing the opposite ends of at least some struts (containing the separation region) separate after formation of discontinuities and move radially and/or circumferentially (out of plane compared to each other), and/or showing a change in configuration or diameter of the at least some rings, or the stent further expand to a larger diameter or configuration after expansion and initial inward recoil from expansion of any, as shown in FIG. 100B-D or 101A-B. The above may also be shown in other tests bench, in-vitro, or in-vivo.

BRIEF DESCRIPTION OF THE DRAWINGS

FIGS. 16E-1 through FIG. 16E-3 illustrate an alternative separation region pattern examples which may be joined by a biodegradable sleeve or by a biodegradable adhesive or a biodegradable polymer and which separates by strut displacement or movement in a preferably radial direction only but can also move in circumferential, and/or in an axial direction in some cases.

FIGS. 16F-1 through FIG. 16F-5 illustrate another alternative separation region pattern which may be joined by a biodegradable sleeve or by a biodegradable adhesive or by a biodegradable polymer and which separates by strut displacement or movement in a radial direction, circumferential direction, and/or an axial direction.

FIGS. 16G-1 through FIG. 16G-3 illustrate still another alternative separation region pattern example which has an extended axial interface between the abutting strut segments which is particularly suitable for joining with a biodegradable adhesive but may be also joined by a biodegradable sleeve or biodegradable polymer and which separates by strut displacement or movement in a radial direction, circumferential direction, and/or an axial direction.

FIGS. 16G-4 through FIG. 16G-10 illustrate exemplary separation patterns for tubular prostheses as an example constructed in accordance with the principles of the present invention.

FIG. 16G-11 illustrates a stent having separation regions in combination with resilient reinforcement elements configured to control and/or assist opening of the stent.

FIGS. 16H-1 through FIG. 16H-5 illustrate still further examples of separation region patterns which rely on a core member received in hollow regions or receptacles in adjacent strut segments which preferentially separate by strut displacement in an axial direction and/or radial (or circumferential) direction.

FIGS. 16I-1 through FIG. 16I-4 illustrate additional examples of separation region having differently shaped interface surfaces on adjacent strut segments.

FIG. 16I-5 and FIG. 16I-6 illustrate still further examples of separation region having surface features for enhancing degradable immobilization with adhesives, cements, polymers, sleeves, or other immobilizing components.

FIGS. 16I-7 through FIG. 16I-16C illustrate separation regions characterized by gaps in struts and/or crowns, and/or optionally having degradable bridges in the gaps, and/or having separation regions with bridging elements.

FIGS. 23E-1 through 23E-3 illustrate the use of separation regions to form a stent which preferentially opens an aperture at a bifurcation region.

FIG. 35 is an example of a test apparatus for fatigue testing, radial strain (compliance) testing, displacement magnitude testing, contraction and/or expansion of the stent in the deployed configuration testing, and other, of the stent segment.

FIGS. 56, 57, 58A, and 58B illustrate a fourth alternative construction of a displacement region such as a circumferential displacement region of a type which could be utilized in the circumferential ring of FIG. 49.

FIGS. 87A-87D illustrate an example of a stent prosthesis for valve replacement having a sinusoidal pattern showing at least one ring having four separation regions, or joints, along the at least one ring circumferential path. The coupled valve elements are not shown.

FIGS. 88A-88D illustrate an example of a stent prosthesis for valve replacement (or repair) having a sinusoidal pattern showing at least one ring having three separation regions, or joints, clustered along one segment (or region) of the at least one ring. The coupled valve is not shown.

FIGS. 89A-89D illustrate an example of a stent prosthesis for valve replacement (or repair) having a closed cell stent pattern with symmetrically placed separation regions or joints.

FIGS. 90A-90D illustrate an example of a closed cell pattern of stent for valve replacement (or repair) having a closed cell stent pattern with clustered separation regions or joints.

FIGS. 97A-97G illustrate stent crowns having voids with different geometries.

FIGS. 99A-99C illustrate stent crowns with thinned and/or tapered regions.

DETAILED DESCRIPTION OF THE INVENTION

Figure 1:
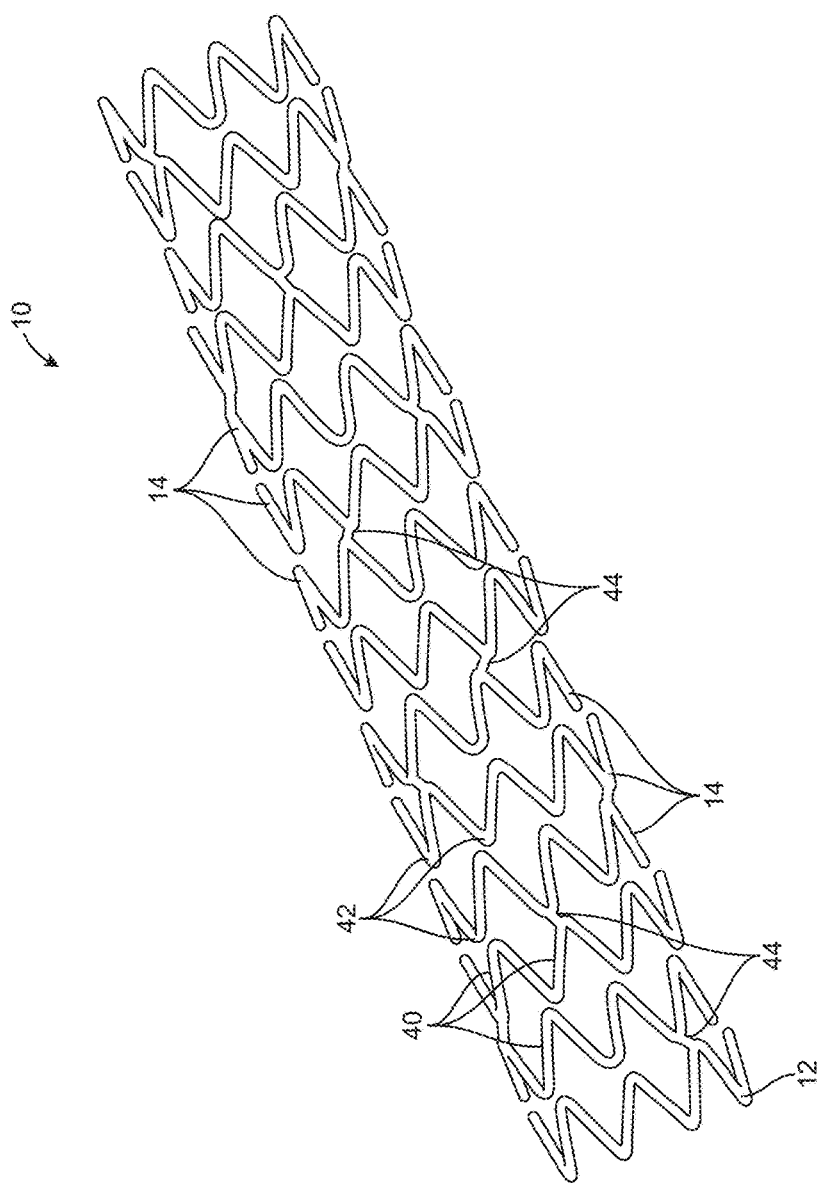
FIG. 1 illustrates a prior art endoluminal prostheses comprising a circumferential scaffold having a plurality of expansible rings.
Figure 2A:
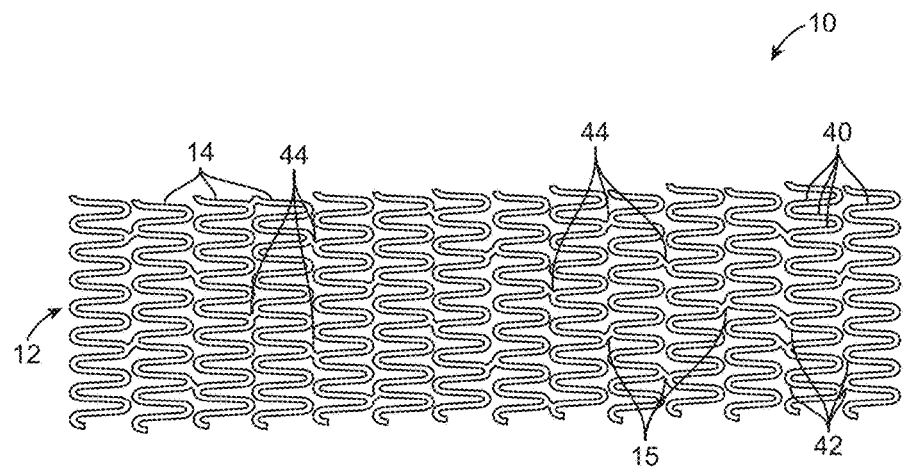
FIGS. 2A and 2B are "rolled-out" illustrations of the endoluminal prosthesis of FIG. 1.
Figure 2B:
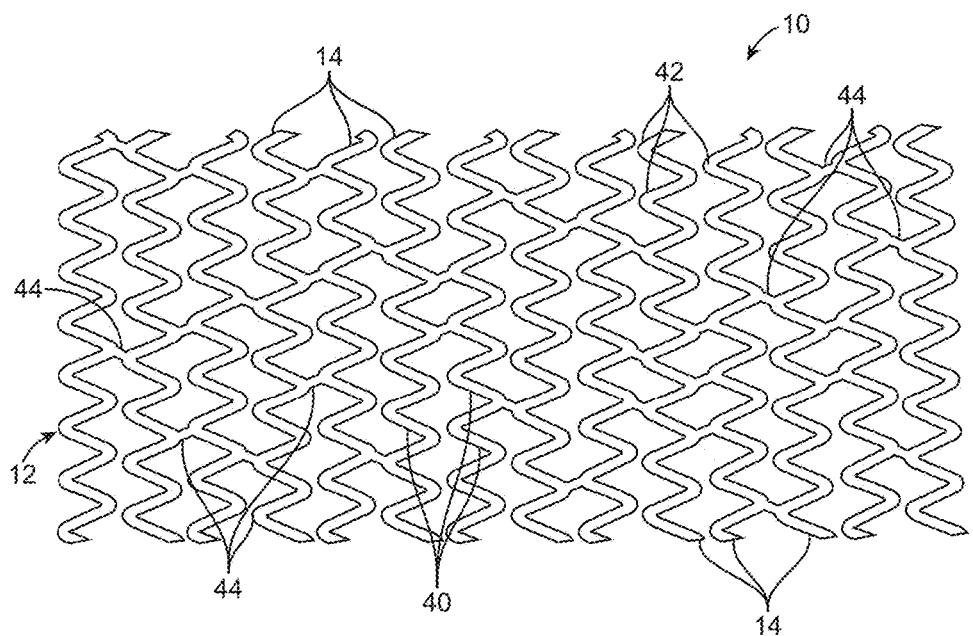
Figure 16A:
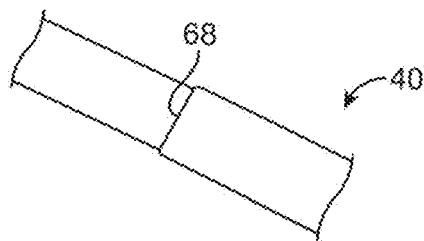
FIGS. 16A-16D illustrate different examples of separation regions suitable for strut separation in the circumferential rings of the present invention.
Figure 16B:
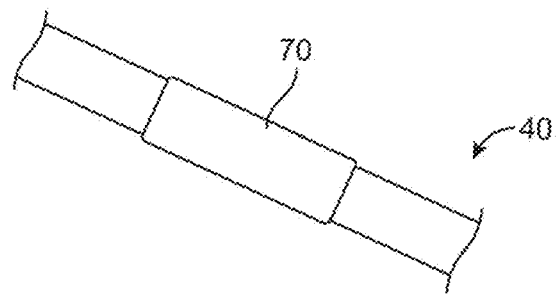
Figure 16C:
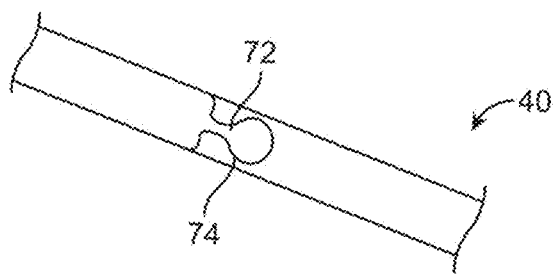
Figure 16D:
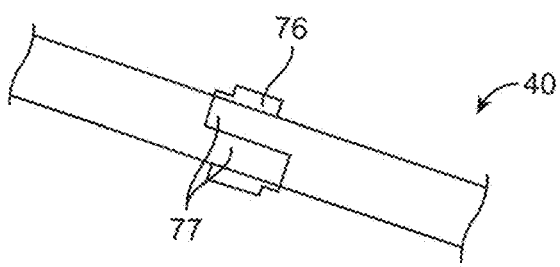
Figures 1, 16E:
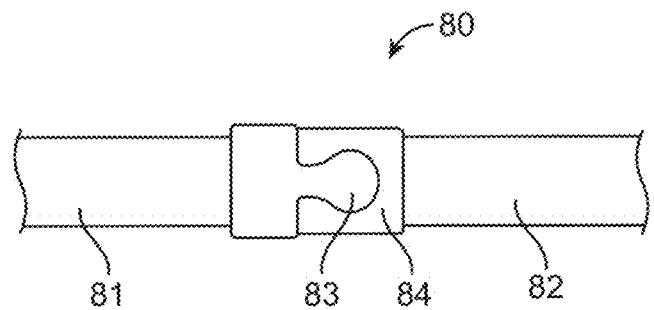
Figures 2, 16E:
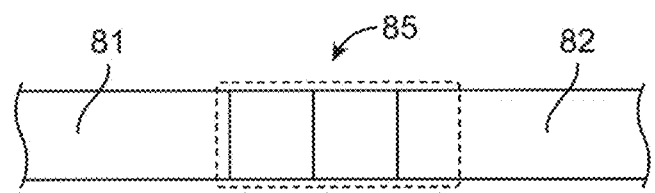
Figures 3, 16E:
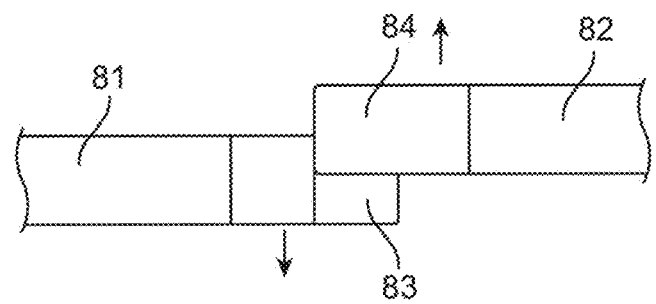

Referring to FIGS. 1-3, a conventional endoluminal prosthesis 10 comprises a generally tubular scaffold 12 including zig-zag rings 14. Each zig-zag ring 14 includes a plurality of generally straight struts 40 joined by curved hinges (expansion regions) 42. As shown in FIG. 2A, where the prosthesis 10 is in a "rolled-out" configuration, the hinges 42 are relatively close together and the diameter of the prosthesis is at a small diameter or at a minimum, typically referred to as non-expanded or "crimped." As shown in FIG. 2B, in contrast, the stent has been radially expanded so that the hinges 42 have opened and the struts 40 have moved circumferentially apart. Such zig-zag stent constructions are well known in the art in both metallic and polymeric materials.

Figure 3A:
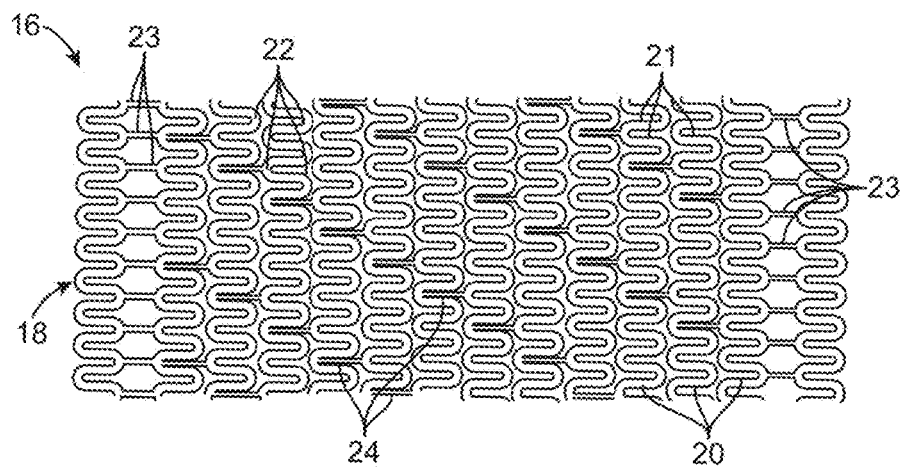
FIGS. 3A and 3B are "rolled-out" illustrations of a prior art endoluminal prosthesis similar to that of FIGS. 1, 2A and 2B, except that the rings are serpentine rings rather than zig-zag rings.
Figure 3B:
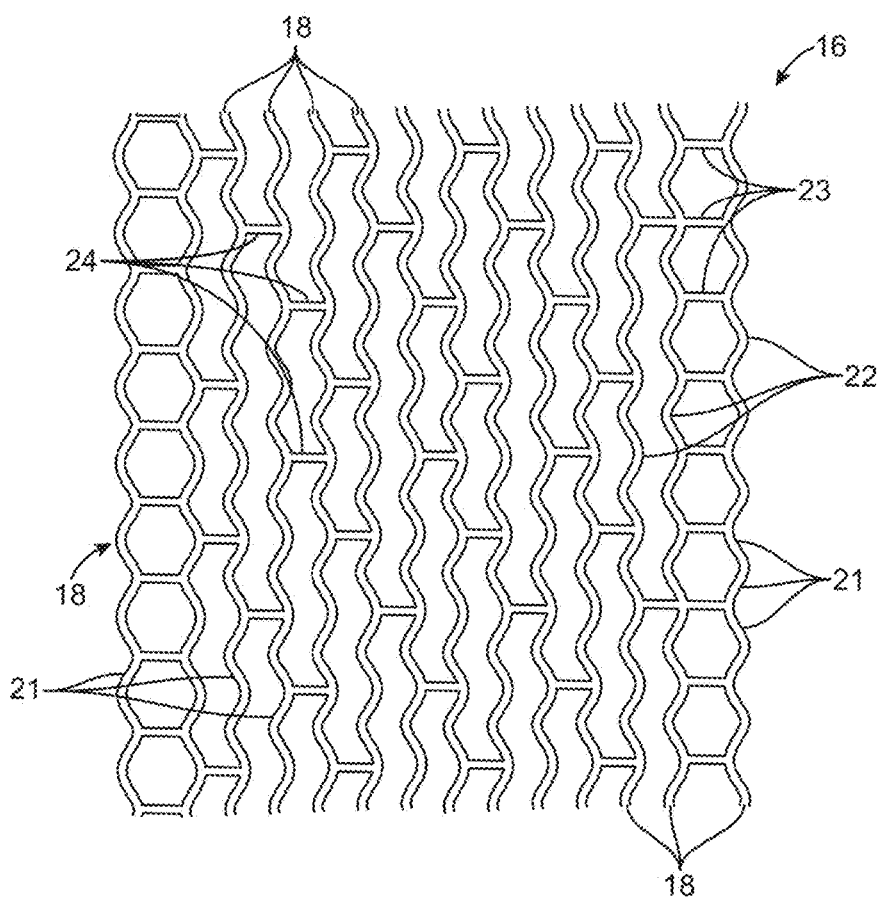

FIGS. 3A and 3B illustrate a second type of conventional endoluminal prosthesis commonly referred to as a "serpentine" stent. The serpentine stent or endoluminal prosthesis 16 comprises a circumferential scaffold 18 with a plurality of serpentine rings 20. Each ring 20 includes a plurality of generally linear struts 21 joined by curved or bent hinges 22. The hinges 22 generally have a larger diameter than those of the hinges 42 in the zig-zag stents, and the struts 21 will generally lie parallel to each other in the non-expanded or crimped configuration of FIG. 3A, as opposed to slightly offset or the non-parallel orientation of the struts 40 of the zig-zag stent. The serpentine stent 16 further includes a first type of axial link 23 which joins the outermost serpentine rings to the adjacent main body of the circumferential scaffold. The axial links 23 join the outer diameters of adjacent hinges 22 so that the hinges are spaced apart by the full length of the link. Within the main body of the circumferential scaffold 18, however, the links 24 are joined from the outer diameter of a first serpentine ring 20 to the inner diameter of an adjacent serpentine ring 20. In this way, the hinges 22 are spaced close together but out of phase when the stent is in its crimped or small diameter configuration, as shown in FIG. 3A. When the serpentine stent 16 is balloon or otherwise expanded, as shown in FIG. 3B, the hinges 22 open up and the struts 21 diverge much more greatly than shown with the struts 40 in the zig-zag endoluminal prosthesis 10. In one example, the angle between two adjacent struts joined by an expansion region can range from substantially zero in the crimped configuration to about 160° or more in the fully expanded configuration.

The present invention is directed at methods and structural modifications for many types of balloon-expandable and self-expanding endoluminal prosthesis including but not limited to prostheses with zig-zag structures and serpentine structures as just described. The methods and structural modification are also directed to the various types of stents such as closed ring type, closed cell type, open cell type, helical coil or wire type, wire mesh type, balloon expandable type, self-expanding type, to name a few, whether formed from wire(s), sheet, or a tube, or other. It is an object of the present invention to provide prostheses which will, upon implantation or after implantation and/or over time, uncage the body lumen, have a radial strain (compliance) ranging between 1% and 5%, expands and/or contracts in the deployed configuration ranging from 0.05 mm to 1 mm while having sufficient strength in the deployed configuration to support a body lumen, further expand to a larger diameter after inward recoil from initial expansion, exhibit vaso-constriction and/or vaso-dilation in response to a therapeutic agent, decrease resistance to circumferential expansion of the stent in order to accommodate luminal remodeling in blood vessels and other body lumens. In some specific embodiments or examples, the prostheses of the present invention will comprise or be composed primarily of biodegradable (degradable) polymers, or degradable metal, which will substantially degrade over time so that they no longer inhibit vessel expansion and remodeling. In such biodegradable stents, the present invention will provide modifications which increase the strength, or initial strength of the stents so that they can provide adequate structural support for the body lumen during the deployment, or after deployment, or healing process but limit interference with subsequent remodeling of the lumen during later stages of the healing process. In other examples or embodiments of the present invention, the endoluminal prosthesis will comprise a circumferential scaffold which is formed or fabricated from a high-strength material, such as a metal or hard plastic, which is non-degradable or slowly degradable in the luminal environment. With prostheses having inherently high strength, the present invention will provide for modifications which enable the stent to, break into pieces, or break into segments, or break into patterned structures, or have separation regions forming discontinuities upon deployment, or after deployment, such as during the later stages of the healing process so that there is minimum interference with vessel remodeling. In still other embodiments or examples, the endoluminal prostheses of the present invention may be provided with joints such as active joints which remain intact and provide resistance to vessel compression while allowing vessel expansion after deployment. In yet other examples or embodiments, the prosthesis of the present invention may comprise non-degradable material that provides high radial strength (crush resistance) upon expansion of the stent and the material weakens after implantation lowering the resistance of the stent to further expand in response to vessel or lumen remodeling.

I. Polymeric or Metallic Prostheses with Reinforcement Elements

Figure 4A:
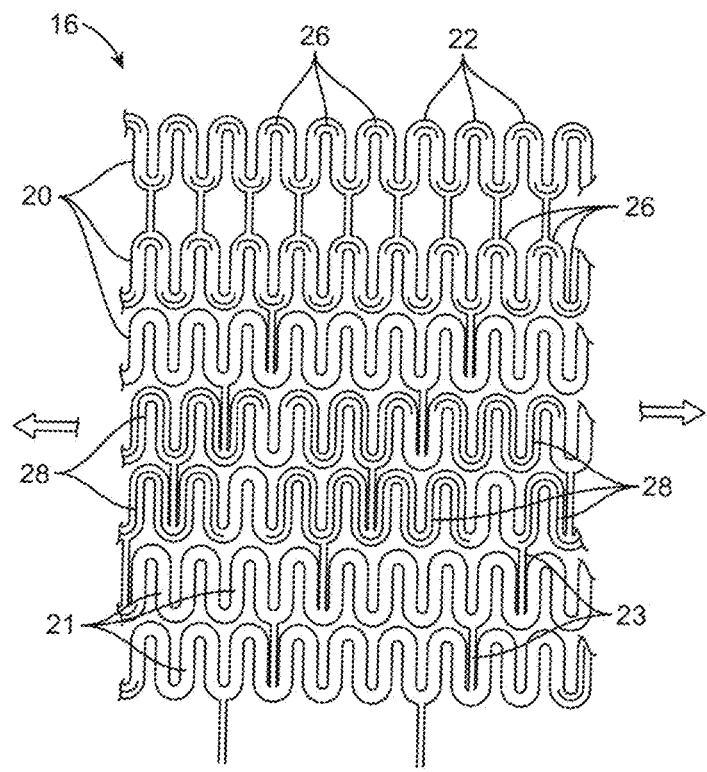
FIGS. 4A and 4B illustrate the serpentine circumferential scaffold of FIGS. 3A and 3B modified or configured with the reinforcement elements of the present invention in a first reinforcement pattern example.

Referring now to FIGS. 4-9, endoluminal prostheses of the present invention may be patterned from biodegradable polymeric materials (or biodegradable metallic material) in any conventional stent pattern. For example, a serpentine endoluminal prosthesis 16 having a pattern of struts 21, hinges 22, and links 23 and 24 may be provided with reinforcement elements 26, as shown in particular in FIGS. 4A and 4B. In FIG. 4A the prosthesis is in its crimped or small diameter configuration, and a first type of reinforcement element 26, typically formed as a curve or crescent, but can have various shapes, sizes, and geometries, is provided in selected ones of the hinges 22. It is particularly desirable to provide the reinforcement within the hinges as the hinges will be stressed during opening of the stent, as shown in FIG. 4B, and reinforcement will help the expanded hinges resist yielding to compressive forces which may be present after the initial expansion in the blood vessel or other body lumen.

Figure 4B:
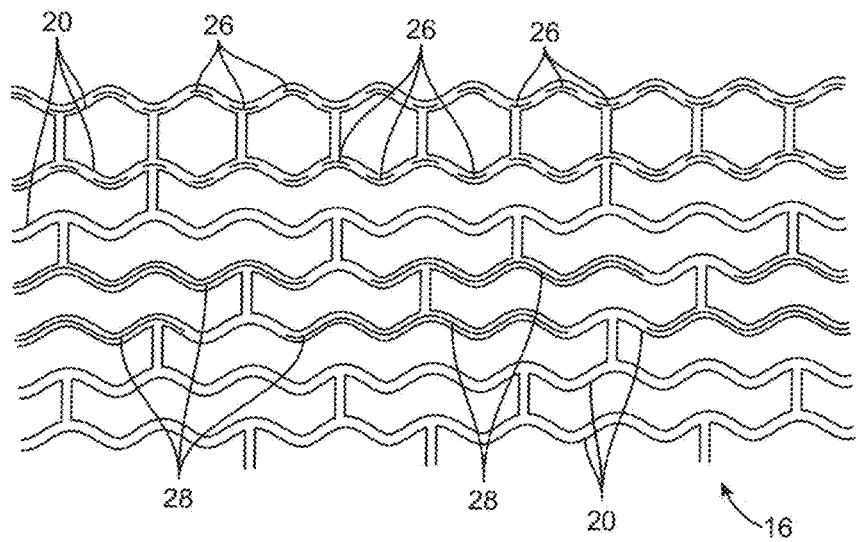

The reinforcement elements do not, however, need to be limited to the hinge regions 22 and may extend generally along two, three, four, or more contiguous hinges 22 and struts 24, as shown with reinforcement elements 28 in FIGS. 4A and 4B.

The reinforcement elements 26 and 28 will often be malleable, typically being formed from a malleable metal or metal alloy, and may be embedded or otherwise coupled or attached within the body of the hinge, strut, or in some cases links. In other cases, the reinforcement elements 26 and 28 could be formed from a resilient metal, such as a shape memory alloy or a spring stainless steel. In such cases, the reinforcement element 26 or 28 will typically be in a constrained configuration when the stent is in its closed pattern, as shown in FIG. 4A, such that the reinforcement element 22 or 28 will be biased to promote opening of the hinges 22 and the circumferential scaffold 18, as shown in FIG. 4B. Often, the reinforcement elements 26 and 28 will remain biased (partially closed) even when the scaffold is in a fully or partially expanded pattern, as shown in FIG. 4B, so that the biased hinges can continue promoting opening of the stent to accommodate luminal remodeling during the later stages of the healing process. The shape memory or spring reinforcement elements can be coupled to expansion regions, and/or coupled to two adjacent struts (as an expansion region/hinge), where such reinforcement elements can further expand the stent after implantation of the stent (after deployment) and before substantial degradation of the stent, or further expand the stent after implantation and before complete degradation of the stent, or further expansion of the stent after implantation. The amount of further expansion of the stent is controlled by the number of reinforcement elements, and opening angle such reinforcement elements are programmed to open to, the vessel or lumen resistance to the reinforcement elements opening, the resistance the degradable material coupled to the reinforcement elements provides at the time. Typically, such shape memory or spring material can further increase the stent diameter after implantation by 0.05 mm to 0.5 mm.

Figure 5A:
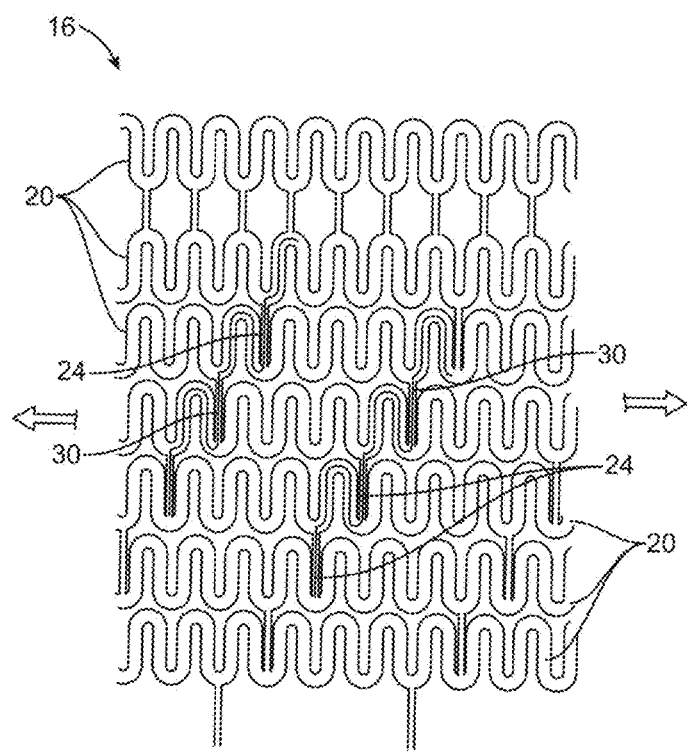
FIGS. 5A and 5B illustrate the serpentine circumferential scaffold of FIGS. 3A and 3B with reinforcement elements and a second reinforcement pattern example.
Figure 5B:
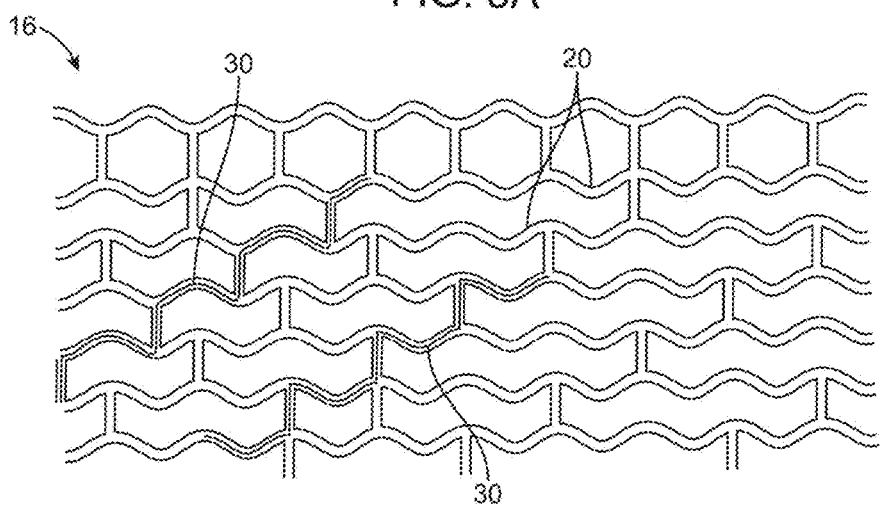

As shown in FIGS. 5A and 5B, reinforcement elements 30 may be placed in a serpentine endoprosthesis 16 so that they extend across axial links 24 in addition to struts 21 and hinges 22. In this way, the reinforcement element 30 will span both the circumference and the axial length of the scaffold 18.

Figure 6A:
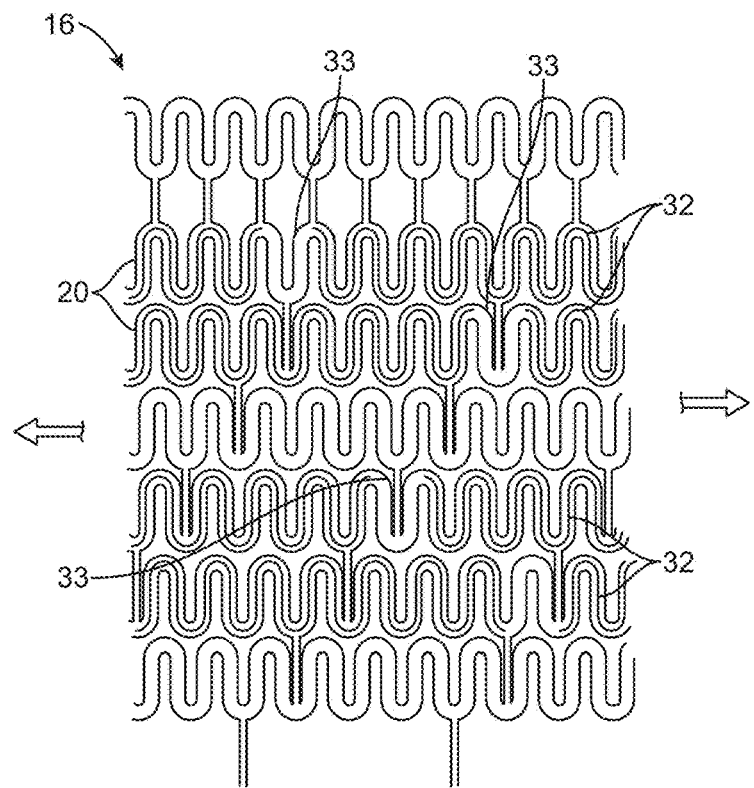
FIGS. 6A and 6B illustrate the circumferential scaffold of FIGS. 3A and 3B with reinforcement elements in a third reinforcement pattern example.
Figure 6B:
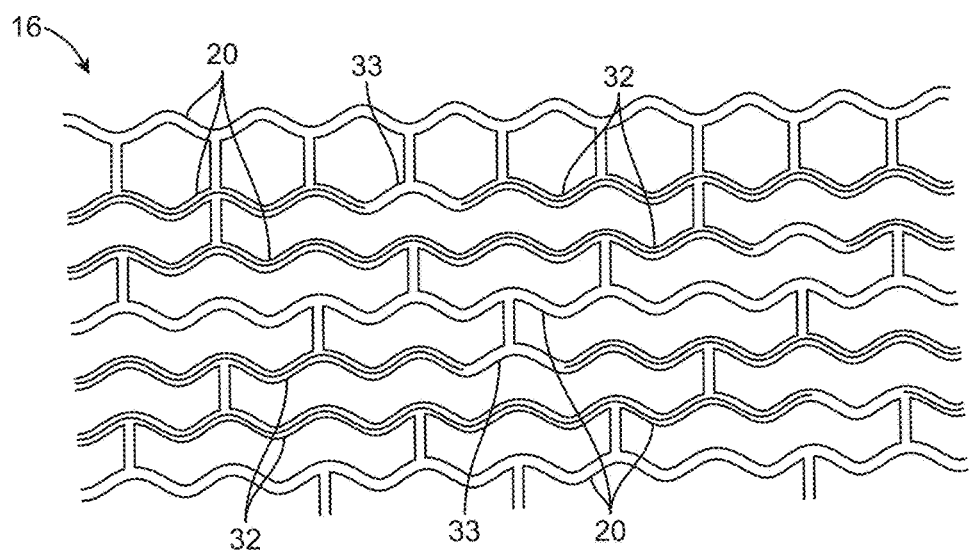

As shown in FIGS. 6A and 6B, reinforcement elements 32 extend substantially around an entire serpentine ring 20 with only or at least a single break or other discontinuity 33 in the circumference of the reinforcement element. In this way, a maximum of reinforcement is provided to the serpentine ring 20 while the remaining opening or gap 33 allows the reinforcement (which generally will not degrade or not degrade as quickly as the biodegradable material) to open and avoid caging or jailing the body lumen as the body lumen is in the later stages of the healing process. The opposite ends of the reinforcement element in the break region are either in contact or are apart (as shown in FIGS. 6A and 6B). The distance of the break region between the ends of the reinforcement elements often can range from 5 microns to 1 mm, typically ranges from 10 microns to 0.5 mm, more typically ranges from 15 microns to 0.2 mm. The ends of the reinforcement elements can be deburred, rounded, made into a ball, or configured into other shape, geometry, or size, in order to minimize trauma to the vessel wall.

Figure 7A:
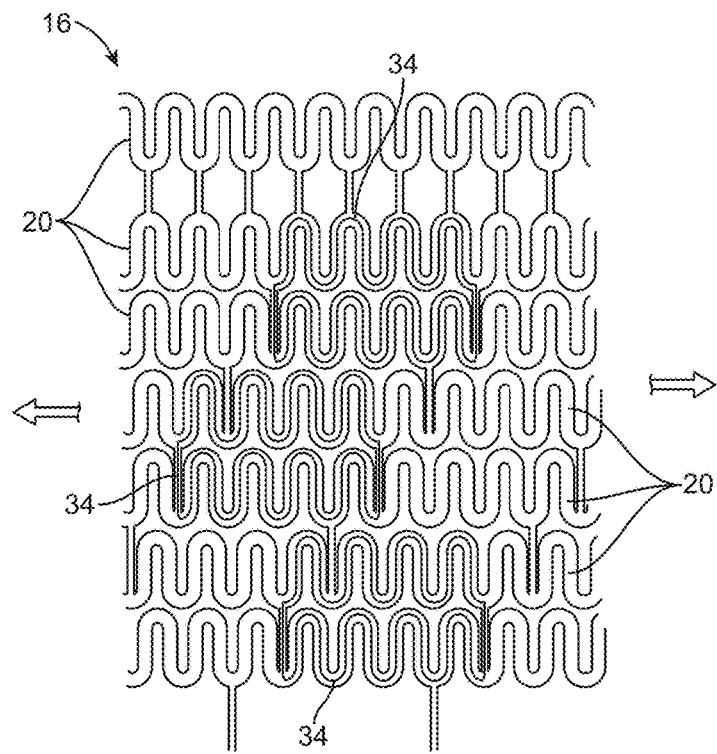
FIGS. 7A and 7B illustrate the serpentine circumferential scaffold of FIGS. 3A and 3B with reinforcement elements in a fourth reinforcement pattern example.
Figure 7B:
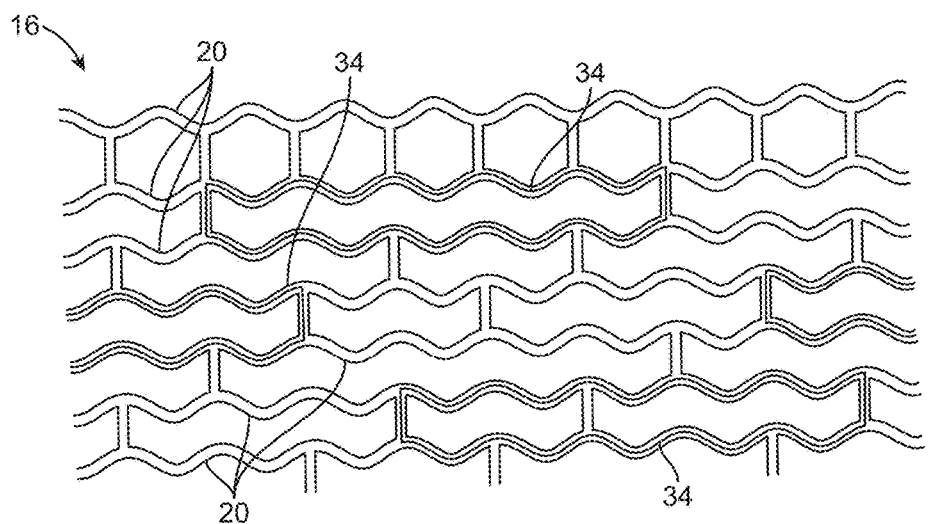

Referring now to FIGS. 7A and 7B, box-shaped reinforcement elements 34 may be provided to cover struts 21, hinges 22, and links 24 to provide both strong support and to leave structures, patterned structures, or relatively large structures behind after the biodegradable stent material has degraded. An advantage of such relatively large box structures is that they will not be inadvertently lost in the blood circulation after the biodegradable circumferential scaffold 18 has degraded or disappeared, and/or can provide luminal support after the stent has degraded.

Figure 8A:
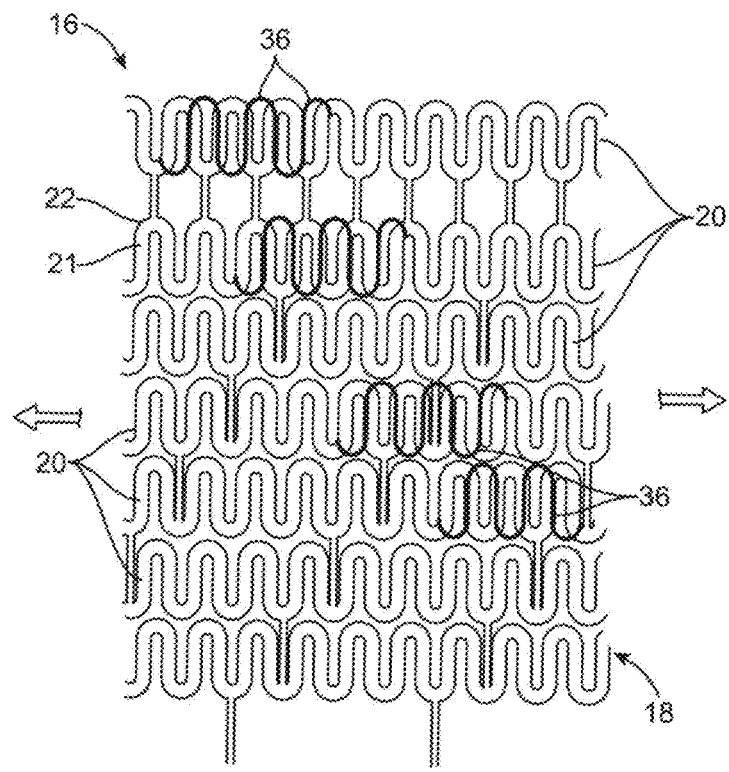
FIGS. 8A and 8B illustrate the serpentine circumferential scaffold of FIGS. 3A and 3B with reinforcement elements in a fifth reinforcement pattern example.
Figure 8B:
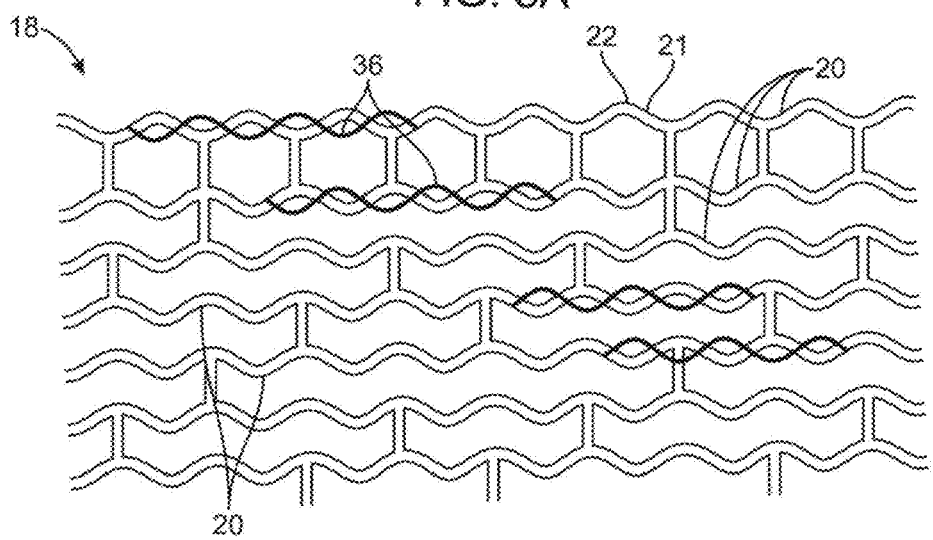

As shown in FIGS. 8A and 8B, reinforcement elements 36 need not be embedded within the structure of the circumferential scaffold 18 and need not even follow the pattern of the struts 21 and hinges 22. The reinforcement elements 36 are external to the circumferential scaffold 18 and coupled or attach to the struts and hinges only at selected locations, as shown in more detail in the example of FIG. 9D hereinafter.

Figure 9A:
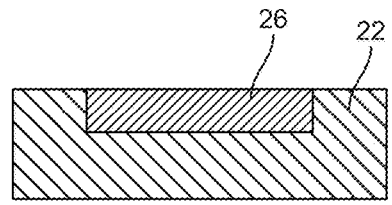
FIGS. 9A-9C illustrate various examples of coupled (attaching and/or embedding) reinforcement elements into a serpentine ring for example or other component or structural elements of a circumferential scaffold in accordance with the principles of the present invention.

Referring now to FIG. 9A, a metal or other reinforcement element 26 may be coupled to a hinge 22 by embedding or otherwise attaching the element into the hinge body, as described with greater particularity below. While illustrated with the short reinforcement elements 26 embedded in hinges 22 as shown in FIGS. 4A and 4B, it will be appreciated that such techniques for embedding reinforcement elements into a hinge will also apply to embedding such reinforcement elements into struts, axial links, or any other components of a biodegradable circumferential scaffold.

Figure 9B:
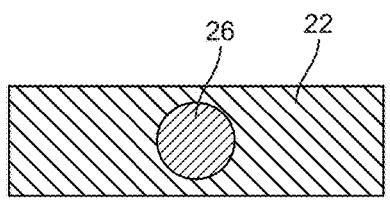

Referring now to FIG. 9B, in other instances which are sometimes preferred, the reinforcement element 26 may be formed as a rod and may be fully embedded into a hinge 22 so that no portion of the reinforcement element is visible on the surface of the hinge.

Figure 9C:
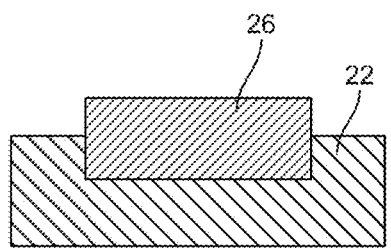

As illustrated in FIG. 9C, a reinforcement element 26 may be surface mounted on a hinge 22 or any other portion of a biodegradable polymeric or biodegradable metallic circumferential scaffold. Reinforcement elements may be surface mounted onto hinges, struts, links, and other components of a polymeric biodegradable circumferential scaffold, or metallic biodegradable stent.

Figure 9D:
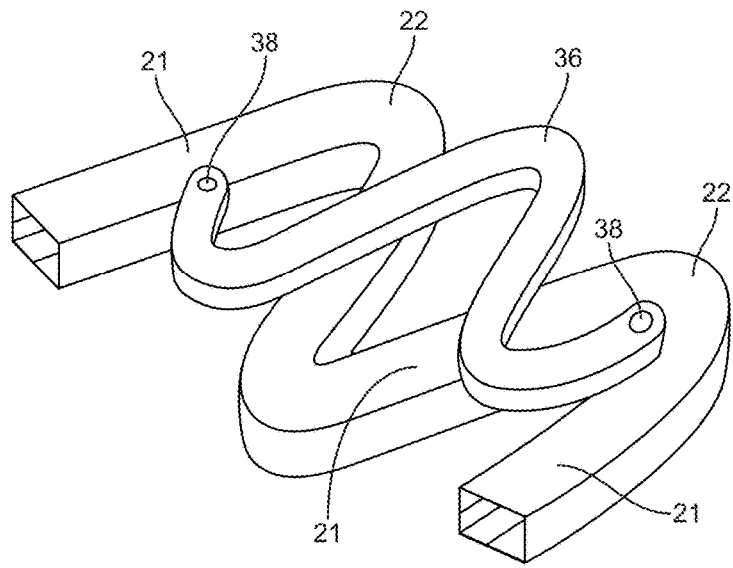
FIG. 9D illustrates coupling (attachment) of an external reinforcement element to a serpentine ring segment.

Referring now to FIG. 9D, the external reinforcement elements 36 illustrated in FIGS. 8A and 8B may be attached to struts 21, hinges 22, or other components of the biodegradable circumferential scaffold 18 by attaching with pins 38 for example. As illustrated, one pin 38 is attached at each end of the external reinforcement element 36, but additional pins could be added at intermediate locations where the reinforcement element crosses over a strut 21 or hinge 22.

In one example, grooves, fissures, slots, are formed in the polymeric or metallic material, where the reinforcement material is then press fitted, fitted, and/or inserted into said grooves, slots, fissures. In another example separately or in addition from the previous example, a coating, an adhesive, or other bonding, holding, filling, or removing gaps means are added to the polymeric material (or metallic material) and/or reinforcement material to hold, fill, or affix the metallic or polymeric frame (main polymer material) and the reinforcement material together. In another example, the reinforcement material is heated to a temperature above the melting temperature of the polymeric material to be coupled with and then press fitted onto or into the polymeric material. In yet another example, the polymeric material is treated with a solvent to soften (or partially melted or partially dissolved) the polymeric material and then inserting or fitting the reinforcement material onto or into the softened (or partially melted) polymeric material. In another example the reinforcement material is sandwiched between polymeric material layers (formed by dipping, spraying, molding, and/or extruding the reinforcement material with the degradable polymeric material), wherein the reinforcement material either has gaps, and/or discontinuities, before patterning the tubular structure comprising the polymeric material and the reinforcement material, or such gaps and/or discontinuities are formed after or during patterning the tubular structure. Once the tubular structure is patterned, additional polymer, adhesive, or other means can be applied to hold together the patterned structure.

II. Non-Degradable or Degradable (Having High Initial Strength Upon Expansion) Prosthesis Having Rings with Separation Regions, Environmentally-Responsive and/or Energy-Responsive Separation Regions Referring now to FIG. 10, an expandable zig-zag showing partial ring 14 is illustrated in detail with a plurality of struts 40 joined by hinges 42 and adjacent rings attached to each other by axial links 44. For the purposes of the following discussions and examples, the zig-zag ring 14 is formed from a metal or other non-degradable material (but it can also be formed from a degradable material such as metallic or polymeric material having high stiffness upon expansion of the stent), where the material will be modified at particular locations or regions to weaken the material (or to form a junction) so that it will form discontinuities or separations at those locations (separation regions) or in those regions over time and/or after expansion. In some cases, the discontinuities or dislocations will occur as a result of the luminal environment in which the prosthesis has been implanted. For example, when implanted in vasculature, the blood vessels will naturally pulsate providing a continuous mechanical stress to the endoluminal prosthesis, or a valve annulus contracting and expanding (or dilating) during beating of the heart. By modifying the physical properties of the circumferential scaffold at particular locations or separation regions, those locations will preferentially break (coming apart, and/or separation) over time, allowing the circumferential scaffold to uncage and/or further expand after deployment and/or after it has become incorporated into the vessel wall. In this way, undesirable caging or jailing of the blood vessel, or other body lumen, or the stented segment can be prevented. In other instances, the preferential breaking of certain locations or separation regions on the circumferential scaffold can be induced or enhanced by the application of external energy from any one of a variety of sources, including magnetism, ultrasound energy, heat, radio frequency energy, subsequent therapeutic drug such as a vasodilator or vaso constrictor, balloon expansion within the body lumen, or the like. In the following discussion, it should be appreciated that most or all of the particular structural or physical modifications to the circumferential scaffold could be configured or adapted to be responsive to either a physiologic environment within the body lumen and/or to the application of external energy.

Figure 11A:
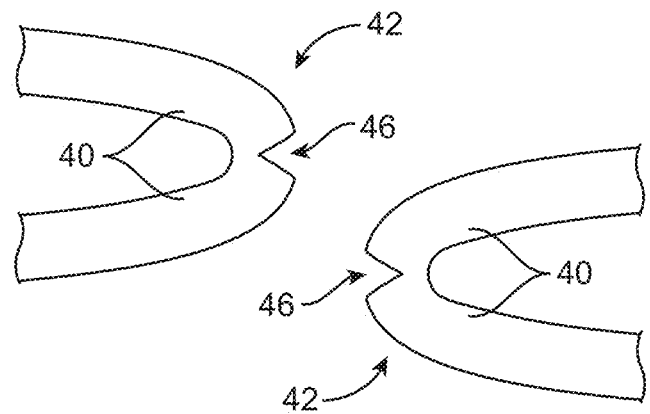
FIGS. 11A and 11B illustrate modification of a hinge of for example the serpentine ring of FIG. 10 which is suitable to promote formation of a break, discontinuity, and/or detachment in accordance with the principles of the present invention.
Figure 11B:
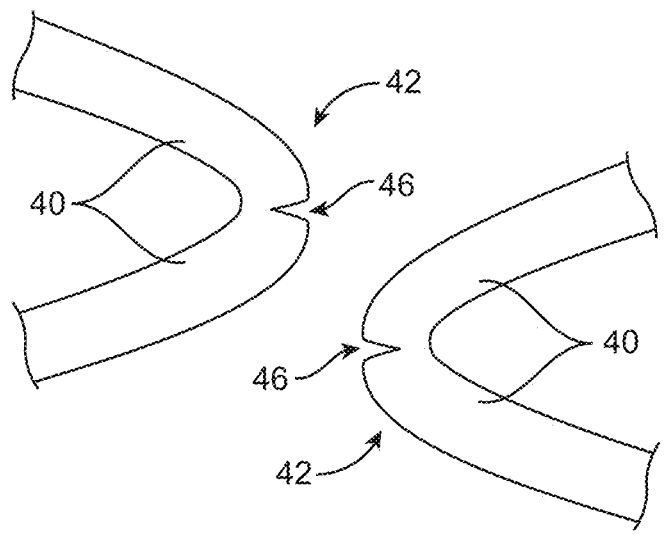

Referring now to FIGS. 11A and 11B, a first structural modification comprises notches 46 formed within a hinge 42 joining a pair of adjacent struts 40. In the crimped diameter configuration, as shown in FIG. 11A, the V-shaped notches 46 are open at a relatively large angle. After the circumferential scaffold is expanded, such as by balloon expansion, the notch 46 will partially close as shown in FIG. 11B. By leaving a remaining albeit smaller opening in the notch 46, as the circumferential scaffold repeatedly expands and contracts due to the luminal pulsation, the remaining attached portion of the hinge will act as a "living hinge" which is subjected to concentrated stress that will cause it to break over time. By properly selecting the amount of material which is left in the hinge 42, an expected lifetime for the hinge can be selected or programmed. Thus, a particular endoluminal prosthesis may be fabricated with a predictable life expectancy for remaining intact within the blood vessel or other body lumen but opening after expansion, typically after the body lumen has healed a sufficient amount and it is no longer necessary to have support from the intact scaffold. While primarily intended for being responsive to the mechanical pulsations of the blood vessel or other body lumen, or simulated pulsation ex-vivo, it will be appreciated that the weakening of the hinge 42 by a notch 46, as shown in FIGS. 11A and 11B, would also render the hinge more susceptible to fatigue or erosion from other conditions of the physiologic environment in the body lumen and/or the application of external energy, and/or breakage.

Figure 12A:
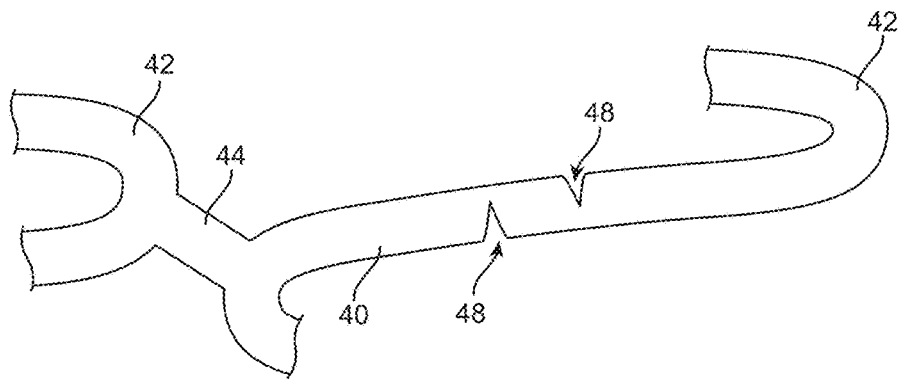
FIGS. 12A and 12B illustrate the modification of a strut of for example the zig-zag ring of FIG. 10 in order to promote formation of a break, discontinuity, and/or detachment.
Figure 12B:
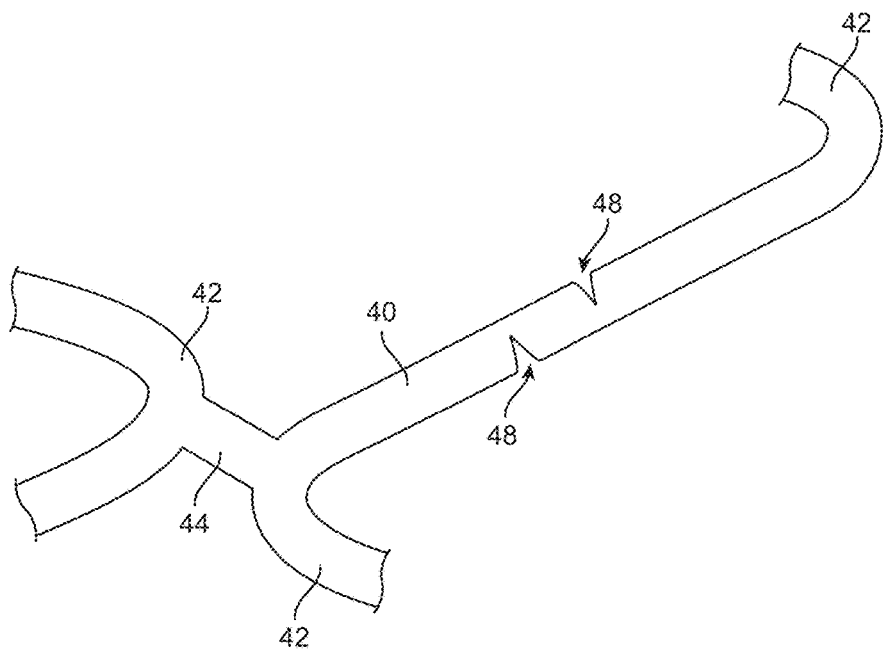

As an alternative or in addition to placing notches 46 in the hinge regions of a circumferential scaffold, notches 48 may be placed in the struts, beams or other generally non-deformable regions of the circumferential scaffold, as illustrated in FIGS. 12A and 12B. The struts 40 will also be subjected to stresses from the endoluminal environment, and can be programmed to break in response luminal pulsations over time.

Figure 13A:
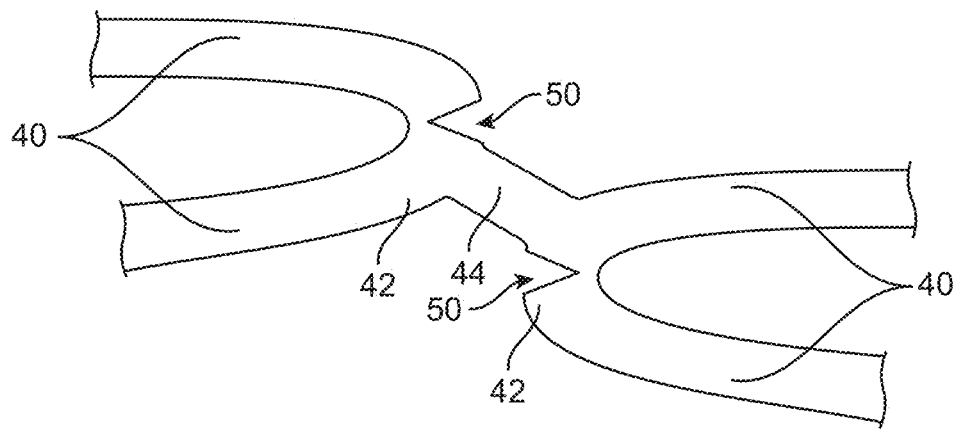
FIGS. 13A and 13B illustrate a modification to hinge regions in the vicinity of an axial link of the zig-zag ring of FIG. 10 in order to promote formation of a discontinuity and detachment in the hinge region in accordance with the principles of the present invention.
Figure 13B:
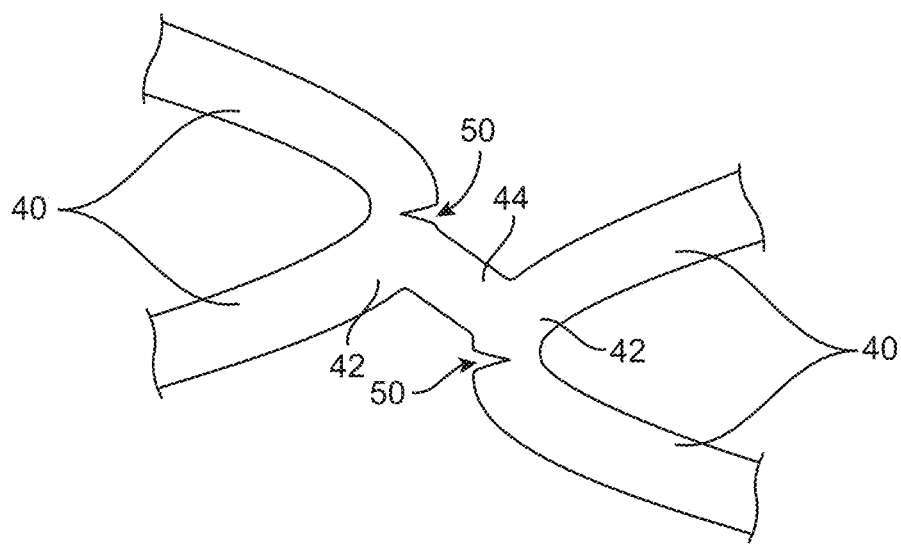

Referring now to FIGS. 13A and 13B. Notches 50 may also be placed adjacent to (as shown) the axial links 44 adjoining hinge regions 42 of the circumferential scaffold. The hinges 42 adjacent to axial links 44 would fatigue or erode at a pre-programmed approximate duration in physiological environment or be subjected to even greater stresses than notches in the other hinge regions, so these locations may provide alternative capabilities for programming the stent breaking. Also, in addition to releasing the rings 14 to expand radially and/or uncage, opening the scaffolds on the crowns, struts, and adjacent to the links 44 (on the crowns) would enhance the circumferential opening of the scaffolds. It can be appreciated that such notches, grooves, or other features, in these figures and examples can be coated with a material or contained with a sleeve, such as a polymeric material, where the coating or the sleeve would help protect the vessel wall from any atraumatic components of such notches when they break. The sleeve or coating can be non-degradable or degradable, where in the preferred example the degradable coating or sleeve would degrade after the ring breaks. In the case of the non-degradable material such as paralene, it would contain the notches after the notches break. In either case, the coating and/or the sleeve would allow the ring or circumferential structural element to uncaged, or be able to move at least in a radial, circumferential, and/or longitudinal direction.

Figure 14A:
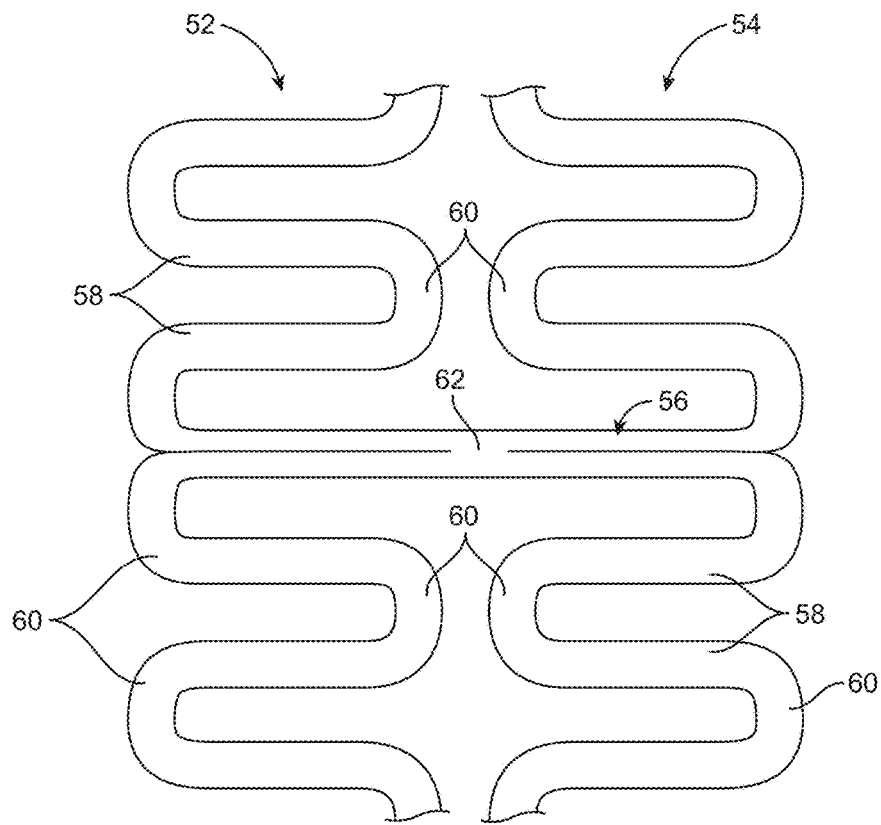
FIGS. 14A and 14B illustrate an alternative hinge or joint structure which may be used for example in a serpentine ring structure in order to promote formation of a break, separation, discontinuity, and/or detachment in accordance with the principles of the present invention.
Figure 14B:
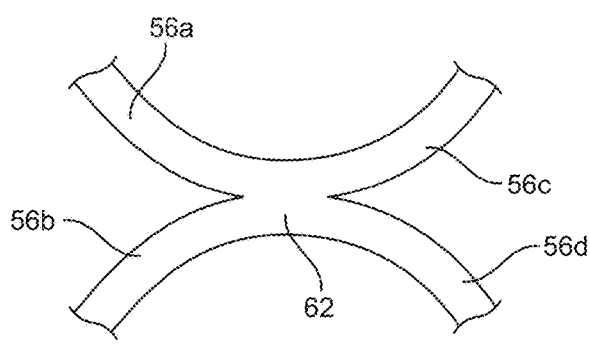

Referring now to FIGS. 14A and 14B, shows two serpentine rings 52 and 54, each ring contains two partial rings forming a separation region 56 between their adjacent struts. The separation region 56 extends between the two adjacent rings 52 and 54 which completely separates each of the two partial rings on ring 52 and ring 54 except for a region such as a center region 62 which remains attached or held together. As the rings 52 and 54 are radially expanded, the separation region opens so that four segments 56a, 56b, 56c, and 56d open to form a pattern such as X-pattern, as shown in FIG. 14B. The partial rings of 52 and partial rings of 54 remain held together by only the center section 62 in this example which can be configured to break, completely separating the two adjacent partial rings of 52 and completely separating the two adjacent partial rings of ring 54, after a desirable time period or after deployment. In particular, the width and thickness of the center portion can be chosen to break or separate in response to pulsation stresses, other intraluminal conditions, and/or the application of external energy and combinations thereof. Typically, the breakage of the center section 62 will not form a discontinuity in rings 52 and 54 without the presence of separation regions between the two partial rings of 52 and between the two partial rings 54.

Figure 15A:
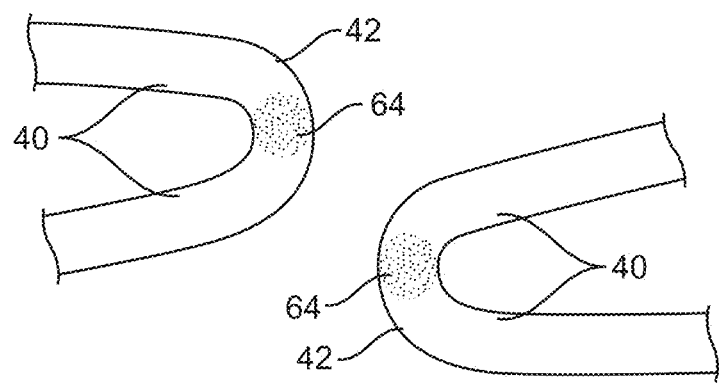
FIGS. 15A and 15B illustrate modification example of the grain structure of a hinge region of the zig-zag ring of FIG. 10 to promote formation of a break, discontinuity, and/or detachment in accordance with the principles of the present invention.
Figure 15B:
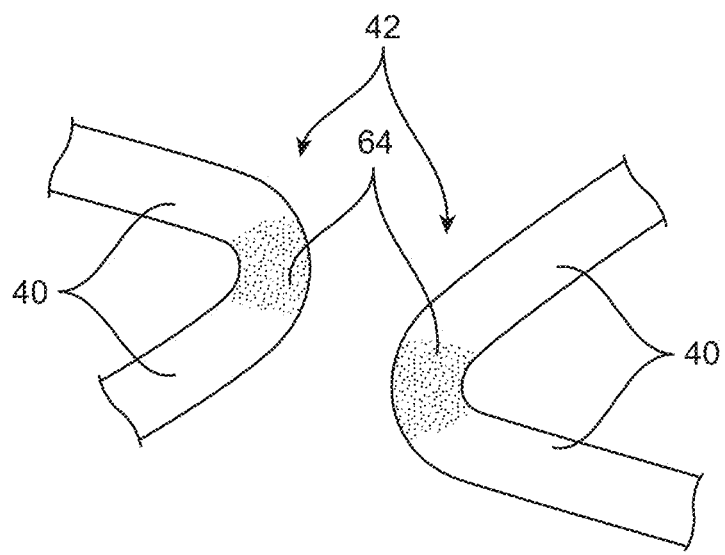

Referring now to FIGS. 15A and 15B, the properties of the material such as the metal in the hinge regions 42 (but can also be in other regions such as struts) may be modified to weaken these separation regions so that they break or separate or form a discontinuity after a predetermined time in the endoluminal environment and/or after exposure to external energy. For example, the grain boundaries within the hinge regions can be modified to provide such programmed breaking or separation. The grain boundaries can be modified, for example, by annealing the material at a high temperature to modifying the grain size and rendering the annealed area weaker and prone to break within a desire time period. As discussed, a sleeve, or a coating can be placed over at least a portion of the region to contain the at least part of the hinge region until breakage of said region, or until a longer time after breakage.

Referring now to FIGS. 16A through 16D, non-degradable circumferential scaffolds structural elements (but can also be degradable material such as metal or metal alloy having high initial strength upon expansion) such as crowns, struts, or other, can be pre-cut, or patterned as shown, or separated and then rejoined, and/or held together so that they remain intact during deployment of the endoluminal prosthesis and for a desired period of time thereafter. By properly choosing how the cut/severed (separation region discontinuities) ends of the scaffold component are rejoined, breaking (separation, gap formation, unlocking, and/or breaking apart, discontinuities) of these regions can be achieved within selected time periods as described throughout the application. For example, as shown in FIG. 16A, a butt joint 68 may be formed by cutting a strut 40 at a location and then rejoining the ends of the joint, for example, using an adhesive or a polymer. The adhesive can be chosen to remain intact for a desirable initial period but to break after that time has elapsed.

As an alternative or in addition to an adhesive, a biodegradable sleeve 70 may be placed around the severed location in the strut 40. The biodegradable sleeve may be formed from a polymeric or other material which degrades over time in response to the luminal environment and/or degrades in response to the application of external energy, forming a discontinuity, and uncaging the adjacent ring of the structural element. The sleeve may also be non-degradable but allows for movement of the structural elements (including the ends) in one or more directions such as the radial, circumferential, and longitudinal direction, after expansion. The sleeve in this case can be stretchable, deteriorates at least partially, or loosens, to allow for movement of the structural elements ends.

As shown in FIG. 16C, a key and lock junction 72 may be formed in two adjoining segments of a strut 50. The key and lock may then be held in place by an adhesive, sleeve, cement or polymer 74, either an adhesive, polymeric material, or other substance which will degrade within the endoluminal environment over a predetermined time, and/or erode by the application of an external energy. In another example, the key and lock are tightly fit (or substantially tightly fit) not requiring an adhesive or a polymer for the adjoining segments to function or to be held together for expansion of the stent and having sufficient strength to support a body lumen. The tight fit end will eventually separate, particularly in response to vessel pulsation, preferably in the radial direction, but can also move circumferentially and/or eventually move in a longitudinal direction.

As yet another alternative shown in FIG. 16D, a rivet 76 may be formed to join adjacent segments of a strut 40. For example, the ends of the struts may be formed to have overlapping elements 77 and the rivet placed there through. The rivet can be formed from any of the biodegradable materials discussed herein which erode (includes degrade or corrode) over time.

Referring now to FIGS. 16E-1 through FIG. 16E-3, a further exemplary "key and lock" separation region 80 includes a first strut segment 81 and a second strut segment 82. The key and lock separation region 80 is formed by an enlarged head 83 formed at one end of the first strut segment 81 and a slot or receptacle region 84 formed at one end of the second strut segment 82. The enlarged head 83 and slot receptacle region 84 are detachably joined in a manner similar to pieces of a "jigsaw" puzzle where the enlarged head 81 may be formed or patterned in this configuration or pressed into the slot or receptacle region 84, and once so joined, the strut segments 81 and 82 may not be axially pulled apart. They may be separated preferably only be a relative "vertical" or radial movement as shown by the arrows in FIG. 16E-3.

Conveniently, the enlarged head 83 and the slot or receptacle region 84 may be formed in the strut segments 81 and 82 by laser cutting of a tube while the rest of the scaffold structure of the stent or other luminal prostheses is being fabricated. A physical break or discontinuity between the enlarged head 83 and the slot or receptacle 84 will usually be formed as a single cut line so that a minimum of material is removed from the resulting prosthesis structure. Alternatively, additional material could be removed (by multiple curt lines) so long as preferably an interference fit remains between the enlarged head 83 and the slot or receptacle region 84 so that axial separation is inhibited under axial tension.

After the individual struts 81 and 82 are cut from the starting tube, and the cut line or space which separates the enlarged head 83 from the slot or receptacle region 84 is formed, the resulting free ends of the strut segments 81 and 82 will usually be temporarily immobilized so that they cannot be vertically displaced relative to each other to inhibit opening of the joint during deployment and enlargement (expansion) of the prosthesis. For example, the enlarged head 83 and slot or receptacle region 84 may be joined with an adhesive or polymer which is introduced into and typically fills the gap or region between the head and slot. In particular, the adhesive or glue or polymer will typically act to join the adjacent, abutting surfaces of the head 83 and the slot 84 together to inhibit any shear motion there between. The adhesive or polymer will usually be biodegradable so that it will degrade over time as set forth elsewhere in the present application in order to free the ends of the stent segments to permit the vertical motion/movement illustrated in FIG. 16E-3 but it can also be non-degradable yet allowing the uncaging of the scaffold or permitting vertical or radial or circumferential movement. Alternatively or additionally, the enlarged head 83 and slot or receptacle region 84 may be immobilized by circumscribing or encapsulating the head and slot region with a biodegradable sleeve 85, shown in broken line in FIG. 16E-2. The slot receptacle in these figures can also be configured to open up after expansion of the stent allowing the enlarged head to move in a longitudinal direction and/or radial direction. The slot receptacles can open as a result of physiologic conditions such as the pulsation of the heart or material fatigue. The slot receptacles can be configured in one example to have substantially small width around the enlarged head facilitating the opening of the slot receptacle in a pulsating environment or movement.

The biodegradable sleeve 85 can be formed over the cut line, space or other break in the strut by extrusion, spraying, dipcoating, brushing, molding, or the like, or combinations thereof. Suitable materials for sleeve, cement, polymers, adhesives, are described throughout this application, and/or include but are not limited to: lactides, caprolactones, trimethylene carbonate, and/or glycolides such as polylactide, poly(L-lactide), poly-DL-Lactide, polylactide-co-glycolide (e.g., poly(L-lactide-co-glycolide) with 85% L-lactide to 15% glycolide), copolymer of poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly(glycolide-trimethylene carbonate), poly (lactide-glycolide-trimethylene carbonate) or the like; polyhydroxybutyrate such as poly(3-hydroxybutyrate) and poly (4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer);

polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); or combinations thereof.

Figures 1, 16F:
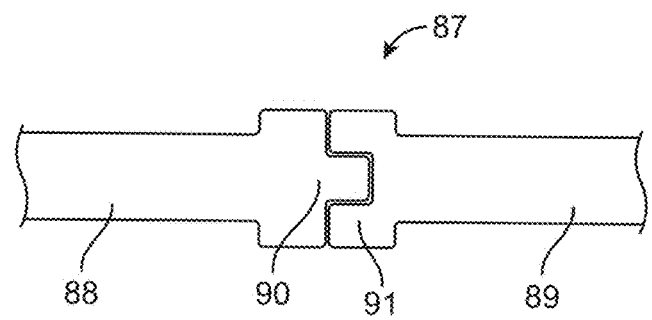
Figures 2, 16F:
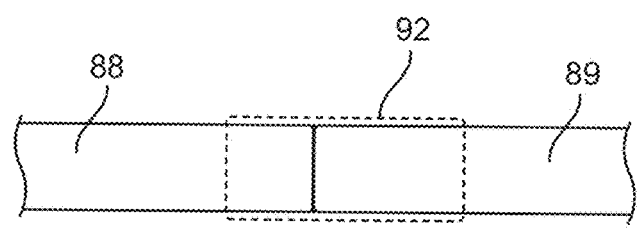
Figures 3, 16F:
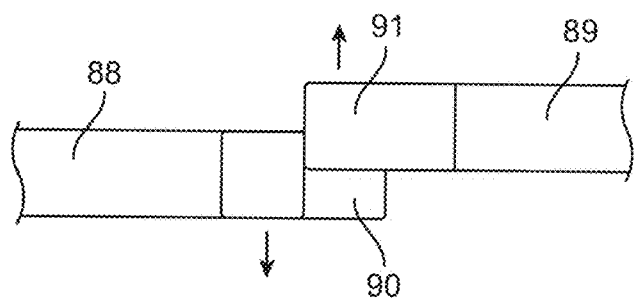
Figures 4, 16F:
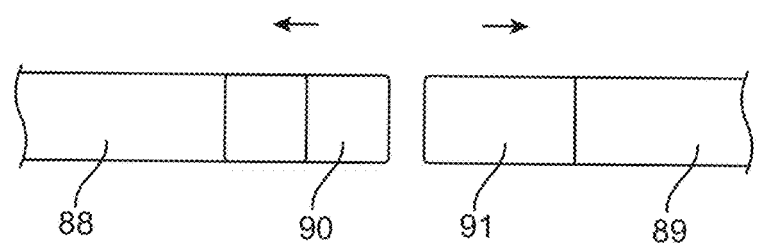

A further exemplary "key and lock" separation region 87 is illustrated in FIGS. 16F-1 through 16F-4. The key and lock region 87 joins a first strut segment 88 and a second strut segment 89. In contrast to the key and lock separation region 80 preferred separation direction, the key and lock separation region 87 allows separation of the strut segments 88 and 89 in both a relative vertical direction, as shown by the arrows in FIG. 16F-3, and in a relative axial direction as shown by the arrows in FIG. 16F-4. Such different performance in one example results from the tongue 90 not having an enlarged profile relative to the slot 91. In that way, the tongue 90 and slot 91 are able to freely move either axially or vertically relative to each other.

As with the key and lock separation region 80, however, the key and lock region 87 will also be immobilized so that it is stabilized during implantation and/or expansion of the prosthesis of which it forms a part. The immobilization may be using an adhesive, polymer, or using a sleeve 92, both of which are described in more detail elsewhere herein. Also, other means to hold the region can include grooves, hooks, or other features on the surfaces of the strut segments to create friction and/or fixation, as the stent expands from a crimped configuration to an expanded larger configuration.

Mobility in both the vertical and axial directions as provided by separation regions 87 and 95 (after sleeve or adhesive degradation) is beneficial as it maximizes the ability of the stent to radially enlarge after implantation. Mobility in the axial direction, however, increases the chance that the separation region will separate as the stent is radially expanded by the delivery catheter or other means, e.g. the sleeve 92 or 99 will be less able to hold the adjacent strut segments together under tension than under shear in this example. In contrast, separation regions with preferably radial or circumferential mobility, such as separation region 80, will be better able to resist separation forces while the stent is being radially expanded but will be somewhat less free to allow stent expansion after the sleeve degrades. Usually, however, both designs will allow separation in response to tissue and vessel contractions after the sleeve degrades or has been degraded.

Figures 5, 16F:
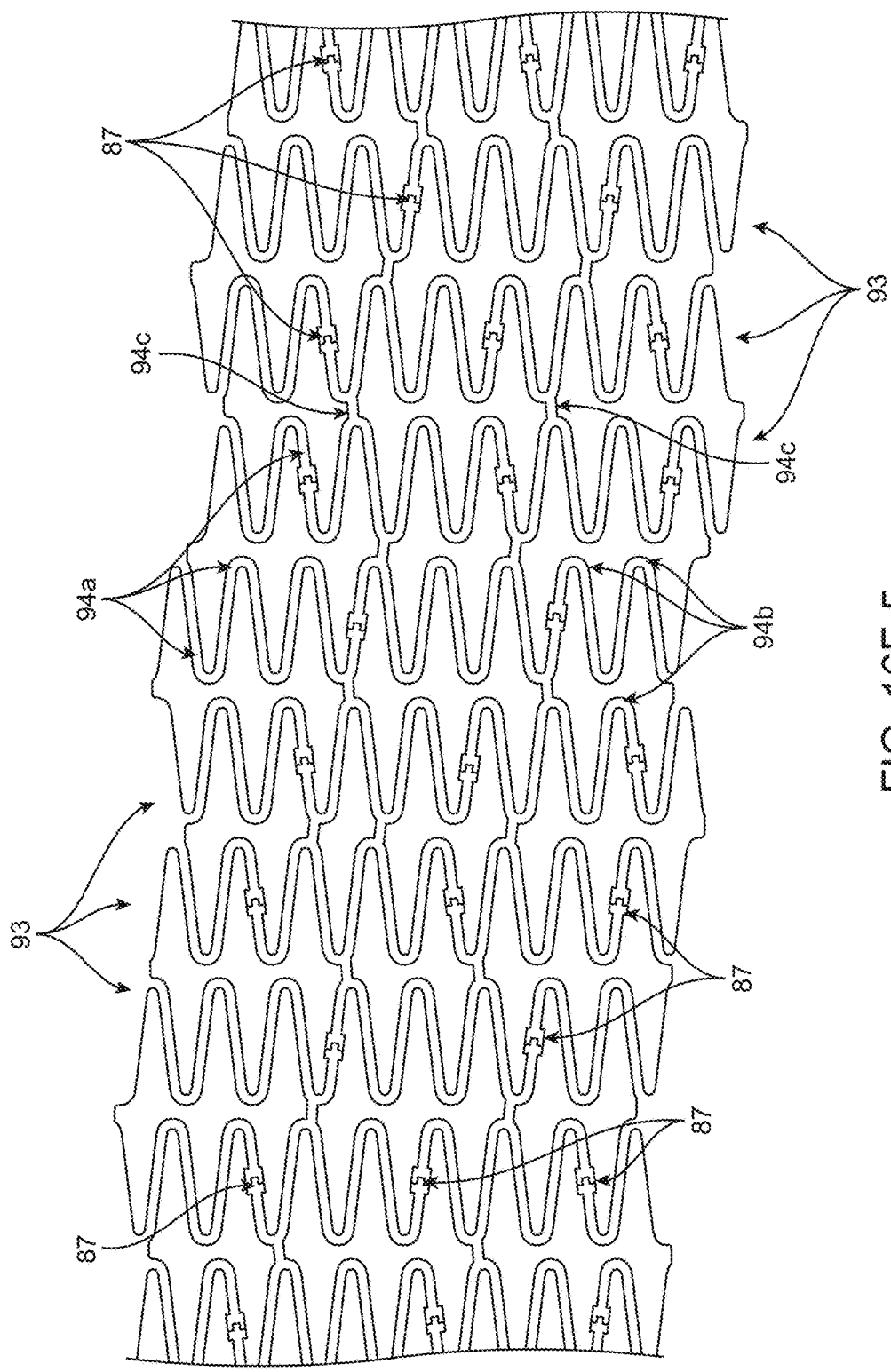

Both key and lock regions 80 and 87 will be preferably incorporated into a linear or about the middle region of strut (but can be positioned on any location of the strut) of a type for example which are joined by crowns in serpentine or zig-zag stent patterns or other stent design types, as shown for example in FIG. 16F-5 showing a serpentine pattern. The stent pattern shown in FIG. 16F-5 includes a plurality of circumferential rings 93 comprising strut elements 94a (which may or may not include a key and lock separation region), joined by crowns 94b. Axially adjacent serpentine rings 93 are joined by axial links 94c which are disposed between adjacent crown regions 94b. On the specific example illustrated in FIG. 16F-5, the circumferential rings 93 each include two or three key and lock separation regions 87. The same pattern of key and lock separation regions, however, could also utilize the key and lock regions 80 described above, or the key and lock regions 95 described herein below, or other types or patterns of separation regions. The stent pattern illustrated in FIG. 16F-5 is shown in a "rolled-out" configuration so that it appears flat and is easier to observe. The actual stent cutting pattern, however, will typically be drawn on a tubular structure which is then laser cut into the desired pattern, or the pattern can also be formed starting with a wire or coil and patterned into a stent. The rings of FIG. 16F-5 example show all the rings having separation regions (2 or 3 separation regions per ring) in a specific pattern. The separation regions are held together upon expansion of the stent from a crimped configuration to an expanded larger configuration, and allow the stent in the expanded configuration to have sufficient strength to support a body lumen. The separation regions form discontinuities after expansion, usually from 30 days to 1 year, preferably from 3 months to 9 months, but can also sometimes form discontinuities immediately after expansion of the stent provided that such separation regions in one example allow the stent to have sufficient strength to support a body lumen, the separation regions can be configured to form discontinuities about the same time, or form discontinuities at different times utilizing various methods comprising for example the amount (or thickness) of the material holding such separation regions together, the degradation time of the material holding the separation region together, the type and properties of the material holding the separation region together, and the location and number of the separation regions on the ring, controlling the separation force on the separation regions, the magnitude and frequency of stresses on the separation regions, the dimensions, angles, and thickness, of the structural element where the separation region is on, and/or the adjacent crown and/or adjacent struts, and the location of separation region on said crown region or strut region, or other. Each ring in this example FIG. 16F-5 uncages when at least one separation region in each ring forms a discontinuity. It is desirable sometimes to have multiple separation regions on each ring or on at least some rings in order to distribute more uniformly the stresses on the ring after formation of the separation regions, and/or provide for a larger uncaging magnitude. Stent types include closed ring type, closed cell type, open cell type, helical coil or wire type, wire mesh type, balloon expandable type, self-expanding type, to name a few, whether formed from wire(s), sheet, or a tube, or other. In some of the stent types such as some closed cell type designs for example diamond shaped closed cell design, it is necessary to have at least two separation regions per cell or ring to uncage such ring (in order to create a discontinuity in the circumferential path of said ring), or in other examples it might be necessary to have at least three separation regions per cell or ring to uncage such ring ((by creating at least one discontinuity in the circumferential path of said ring provided that such at least one discontinuity uncages said ring, otherwise at least one more discontinuity is required to uncage the ring, and so forth, until sufficient number and locations of discontinuities are sufficient to uncage said ring). Some closed cell type designs for example some diamond shape type have a circumferential connector (such as strut, crown, or adjacent to strut or crown regions) linking adjacent closed cells on the same ring. Having a separation region on said circumferential connector forms a discontinuity in such circumferential connector would uncage the ring, or having two separation regions on the diamond closed cell would uncage the ring by providing at least one break in the ring circumferential closed path. This can also apply to open cell design having a plurality of adjacent rings, where adjacent rings are joined (or linked) by a circumferential connector (a connector extending circumferentially in the crimped and/or expanded configuration of the stent), typically such connector is in the crown region or adjacent to the crown region. Having one or more separation regions on said circumferential connector forms a discontinuity in such circumferential strut, and would uncage the ring. FIG. 16F-5 also shows two links connecting two adjacent rings. It is desirable to have the number of axial links be less than the number of crowns per ring, it is more desirable to have the number of the axial links be ⅓ or less the number of crowns for improving axial flexibility of the stent. It is also desirable to have at least one link joining two adjacent rings (or at least one crown region on one ring is joined to an adjacent crown region on an adjacent rings) to remain intact after the separation regions form discontinuities so that the stent structure (or part of the stent structure) is held together (or remain intact) in at least longitudinal direction. It is more desirable to have at least two links joining two adjacent rings (or at least two crown regions on one ring be joined to two adjacent crown regions on an adjacent rings) to remain intact after the separation regions form discontinuities so that the stent structure (or part of the stent structure) is held together in a longitudinal. Having at least two axial links is desired to minimize fish-scaling and/or crown collisions. It is desirable to have the stent structure be held together (or remain intact) in the axial direction for at least some adjacent rings after formation of discontinuities (after uncaging circumferentially of the stent) while (or by) having at least one link connecting every two adjacent rings of said at least some adjacent rings, or while (or by) having at least two links connecting every two adjacent rings of said at least some adjacent rings, remain intact, or while (or by) having substantially all axial links connecting every adjacent rings of said at least some adjacent rings, remain intact. This (having at least part of the stent be axially connected, preferably the entire length of the stent be axially connected) would help provide support to the body lumen (or vessel), and prevent potential dislodgement of the structural elements into the blood stream. In some examples, at least some but not all separation regions on at least some rings remain held together (in place) and not separate, without affecting the uncaging of said rings as a result of having other separating regions on said rings separate creating at least one discontinuity along the circumferential path of each of said rings.

Figures 1, 16G:
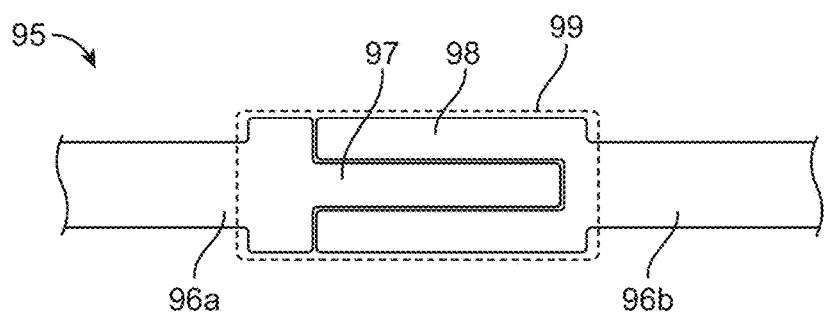
Figures 2, 16G:
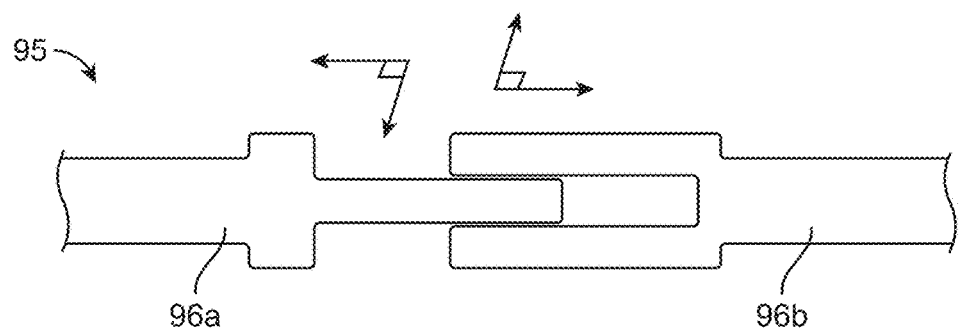
Figures 3, 16G:
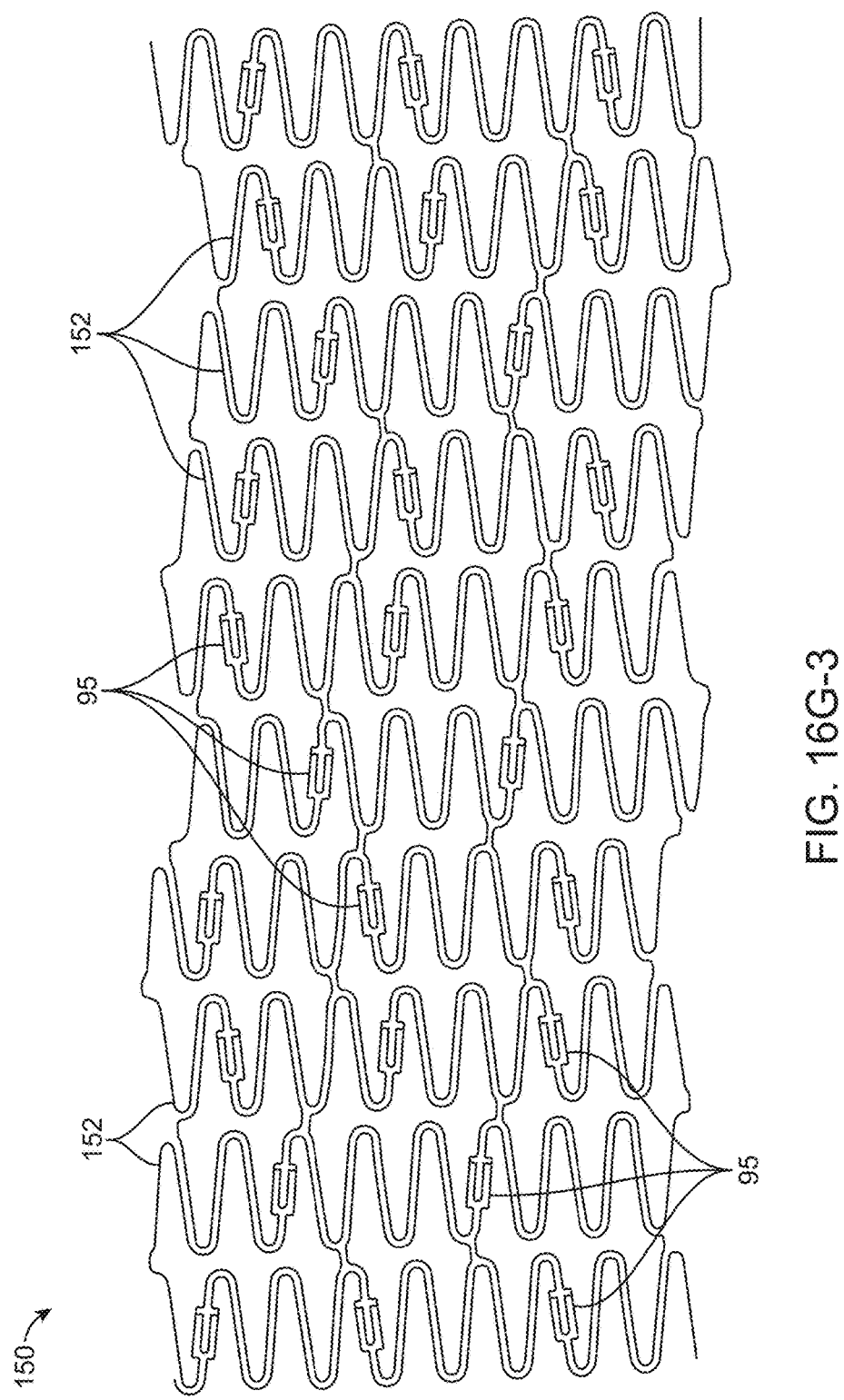
Figures 4, 16G:
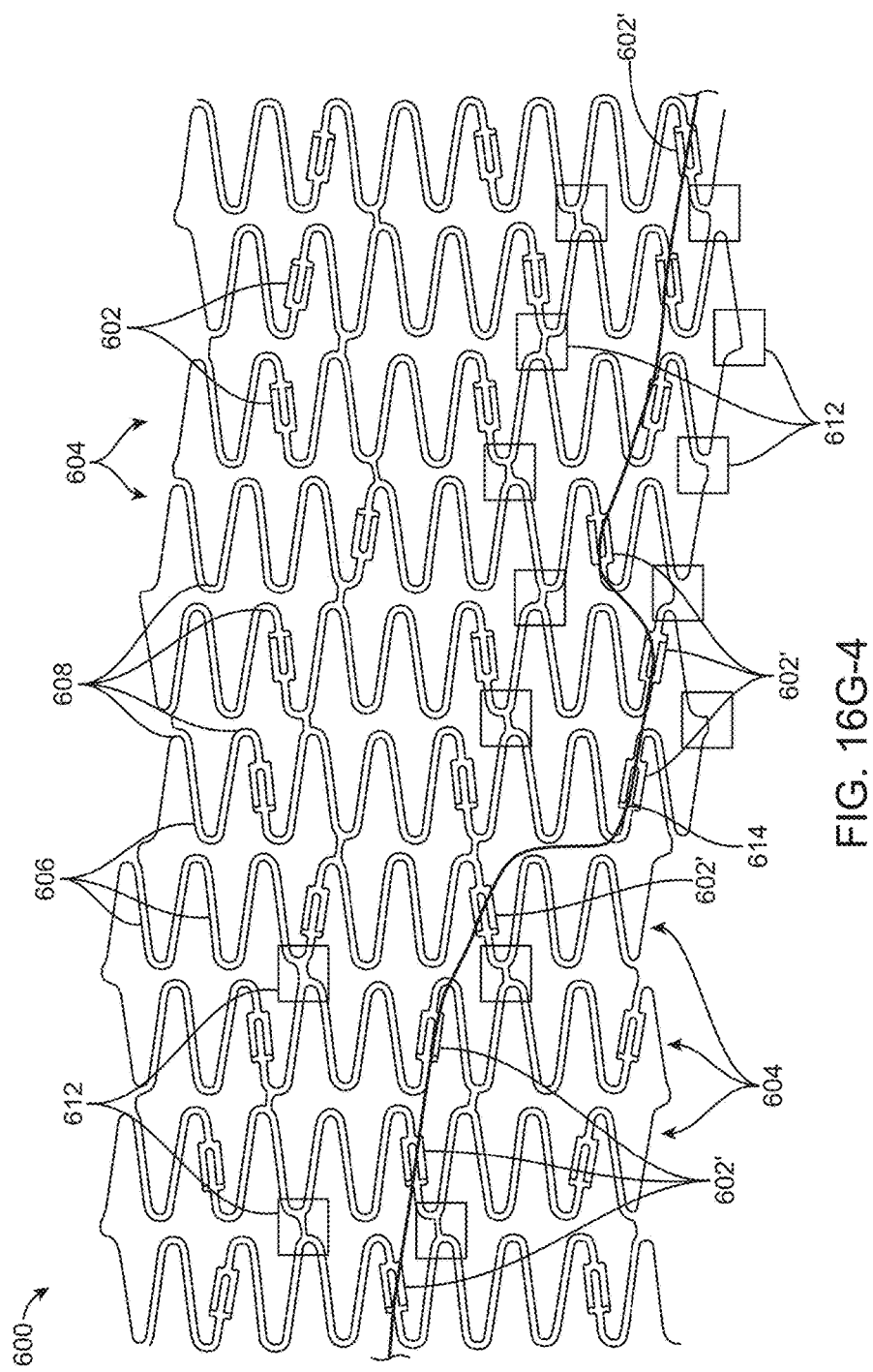
Figures 5, 16G:
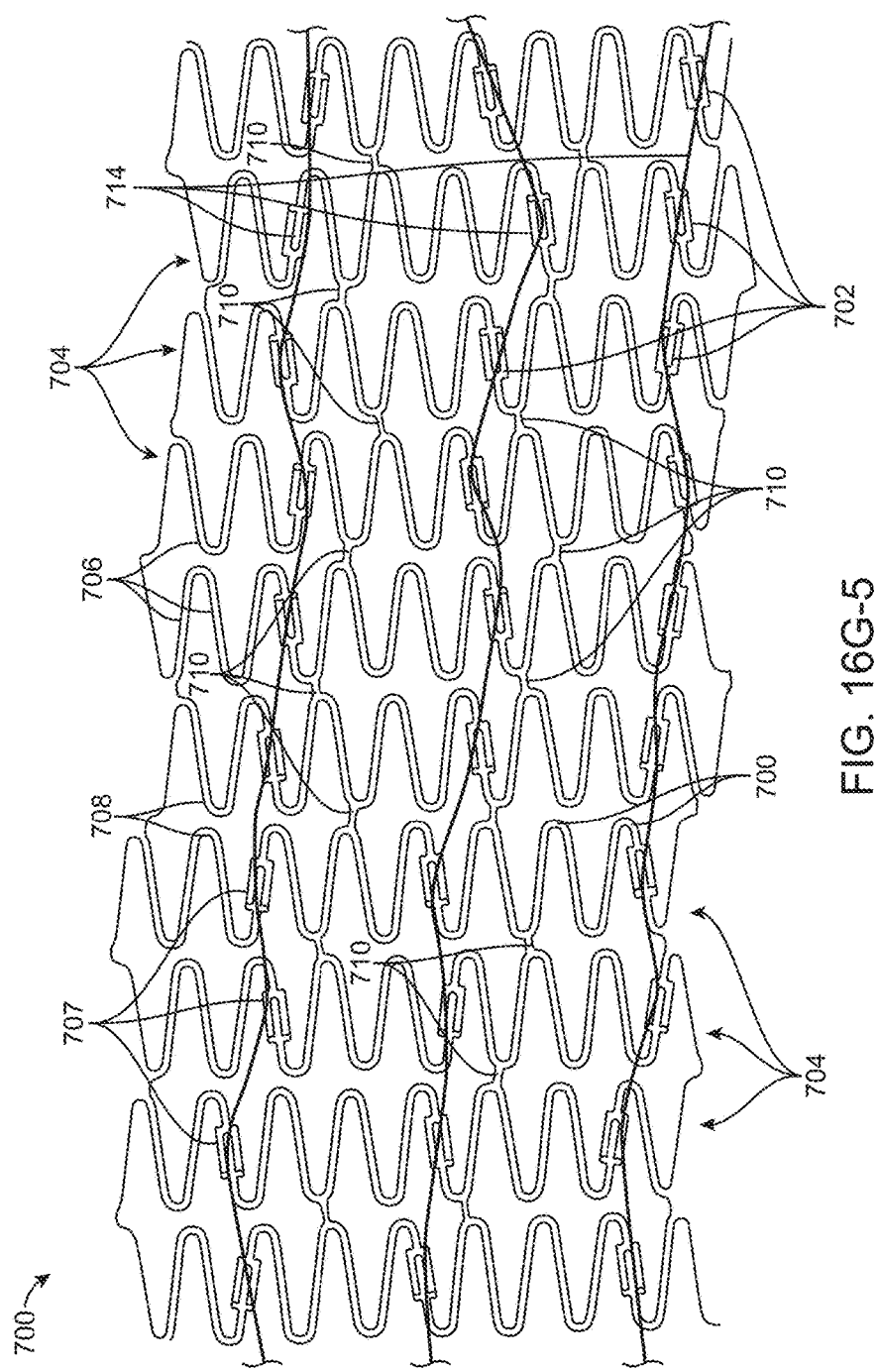

Referring now to FIGS. 16G-1 through 16G-3, a further example of a key and lock separation region 95 is illustrated. The key and lock separation region 95 is similar to the key and lock separation region 87 except that the tongue 97 on first strut segment 96a is significantly longer than the tongue 90 on strut segment 88. For example, the tongue 90 will typically have a length in the range from 0.15 mm to 0.90 mm, usually from 0.3 mm to 0.70 mm, while the tongue 97 will have a length in the range from 0.3 mm to 2 mm, usually from 0.4 mm to 0.9 mm. The corresponding slot 98 at an end of a second strut 96b will usually have a length which matches that of the tongue 97, but in some examples could be longer to allow a gap or open region within the slot when the stent or other prosthesis is fully assembled. As with the key and lock separation region 87, the key and lock region 95 allows separation in both an axial direction and a vertical or radial or circumferential direction, as indicated by the arrows in FIG. 16G-2. The tongue 97 and slot 98 may be immobilized or held together using either adhesives, polymer, or an external sleeve 99, as generally described with the key and lock separation regions 80 and 87, above. A stent 150 having the key and lock separation regions 95 is illustrated in FIG. 16G-3. The pattern of the key and lock separation regions 95 within individual struts 152 is generally similar as that shown for the stent in FIG. 16F-5, above.

The longer key and lock (or tongue and slot) elements of FIGS. 16G-1 to 16G-3 are advantageous as it provides for a larger surface area for adhesion or friction to prevent premature separation than does a shorter segment. Such elongated elements also protect the key/tongue from damaging the adjacent tissue during separation. In contrast, a shorter key and lock separation region can sometimes prematurely separate, and during fabrication a gap may form between the key (tongue) and lock (slot) before application of adhesive or sleeve, making it more difficult to adhere, requiring a greater fabrication. The shorter tongue and slot segment has less material than the longer segment so it is lighter and more mobile or flexible. The shorter tongue can have a thicker coating or sleeve to hold the separation region together, for example the sleeve thickness on top of the separation region can range from 10 microns to 50 microns, while the thickness of the sleeve on top of the separation region having longer tongue can be thinner ranging from 5 microns to 20 microns.

Figures 6, 16G:
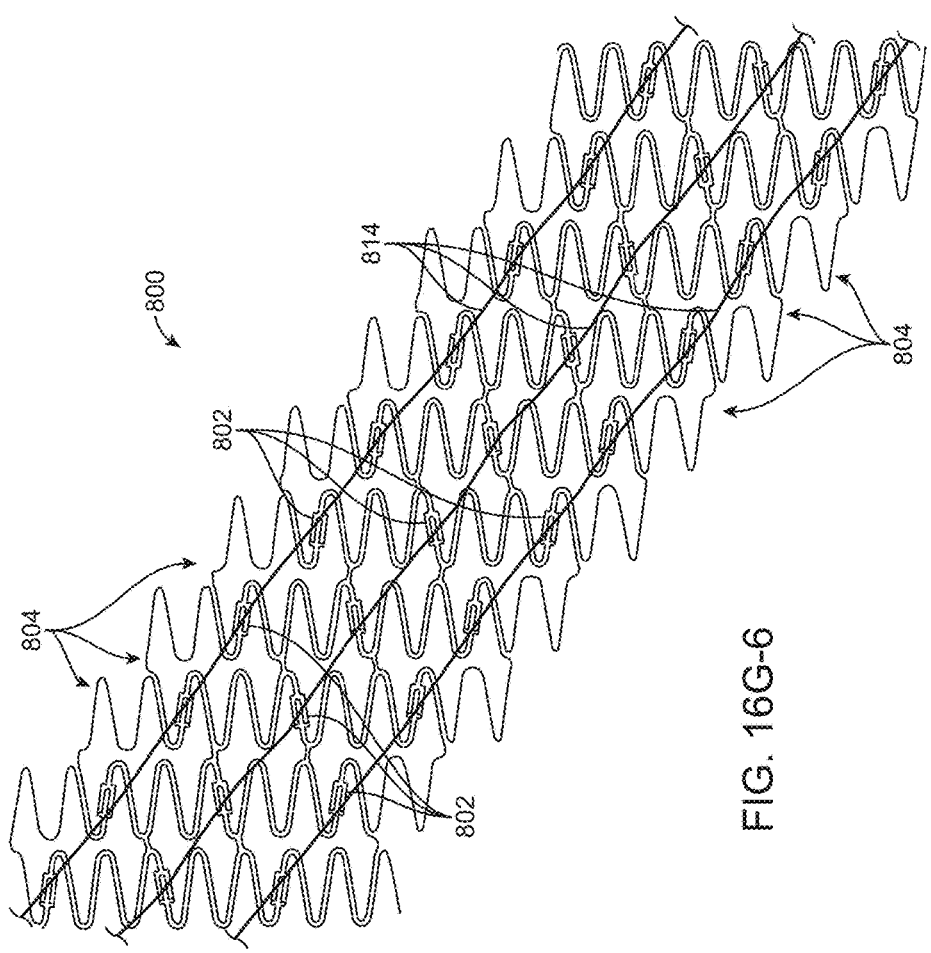
Figures 7A, 16G:
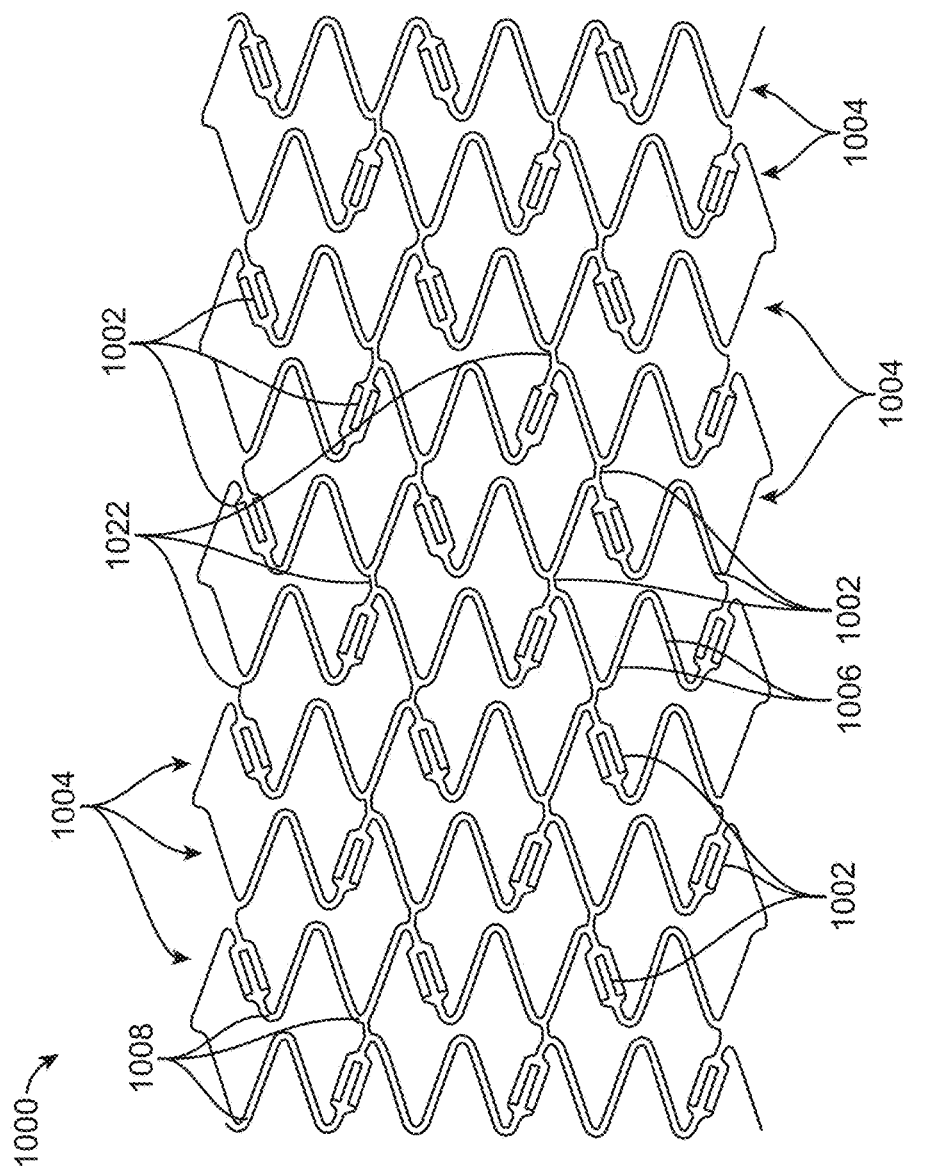
Figures 7B, 16G:
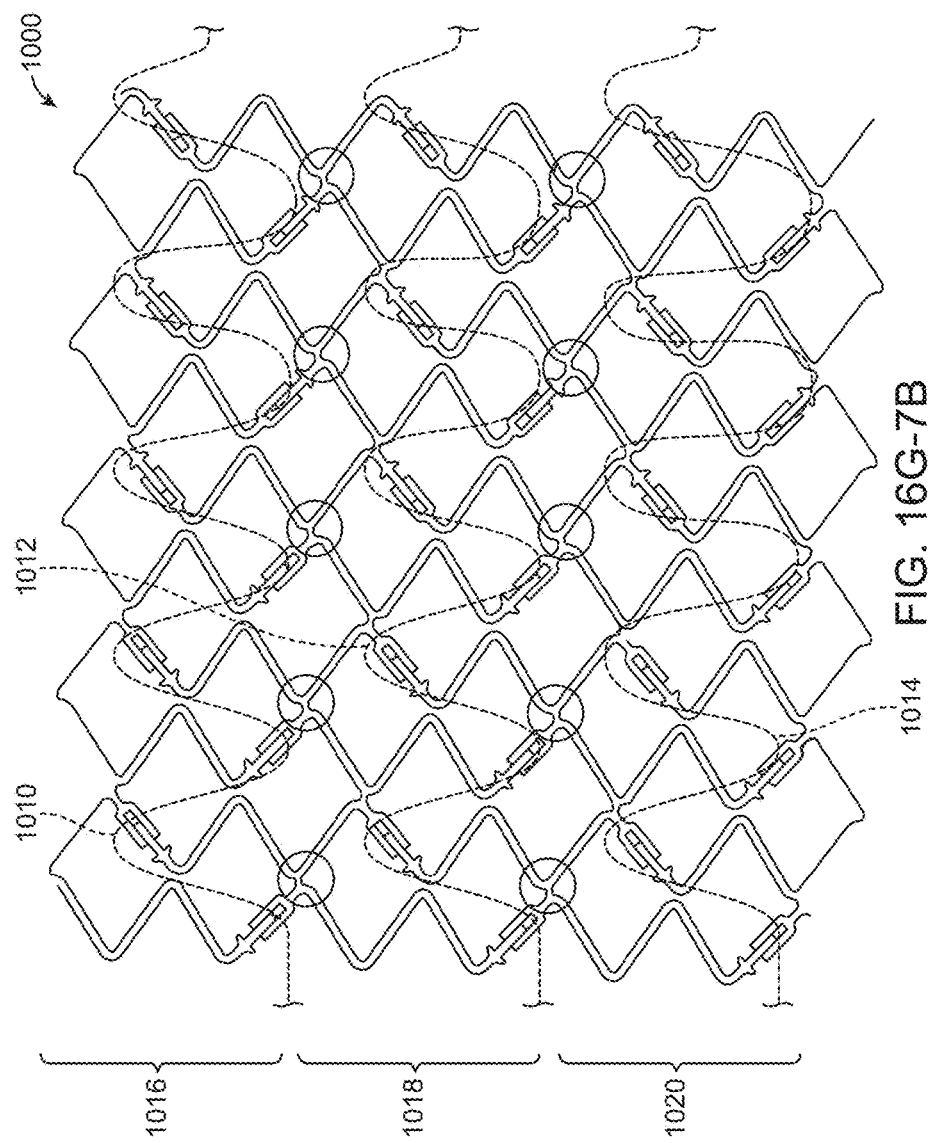
Figures 8A, 16G:
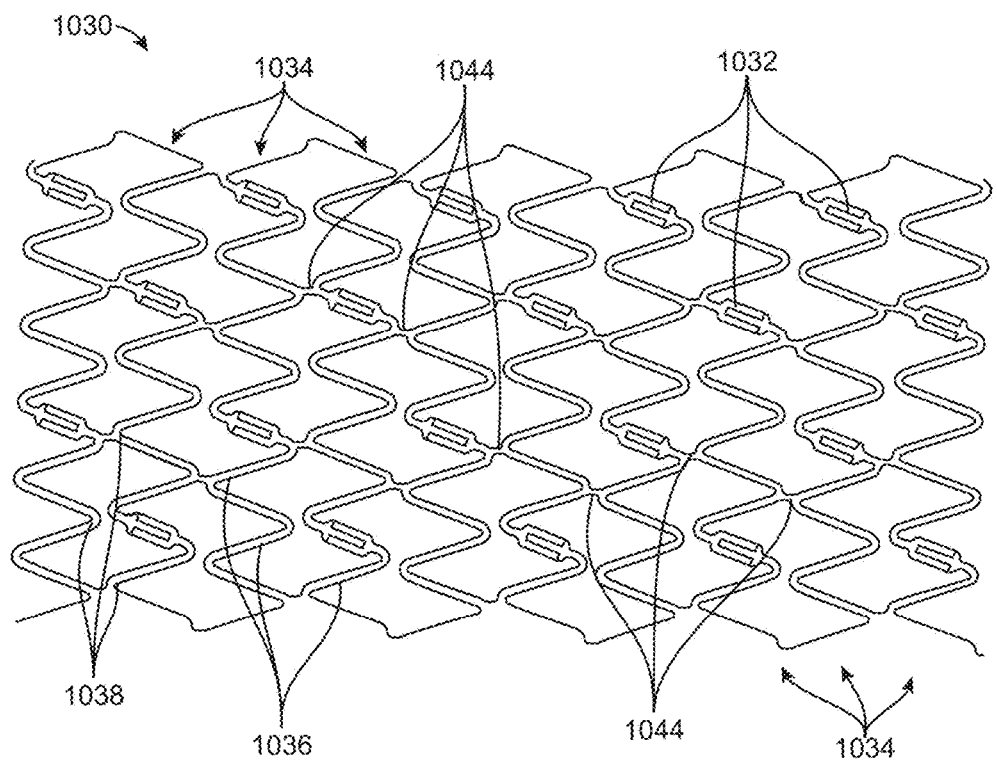
Figures 8B, 16G:
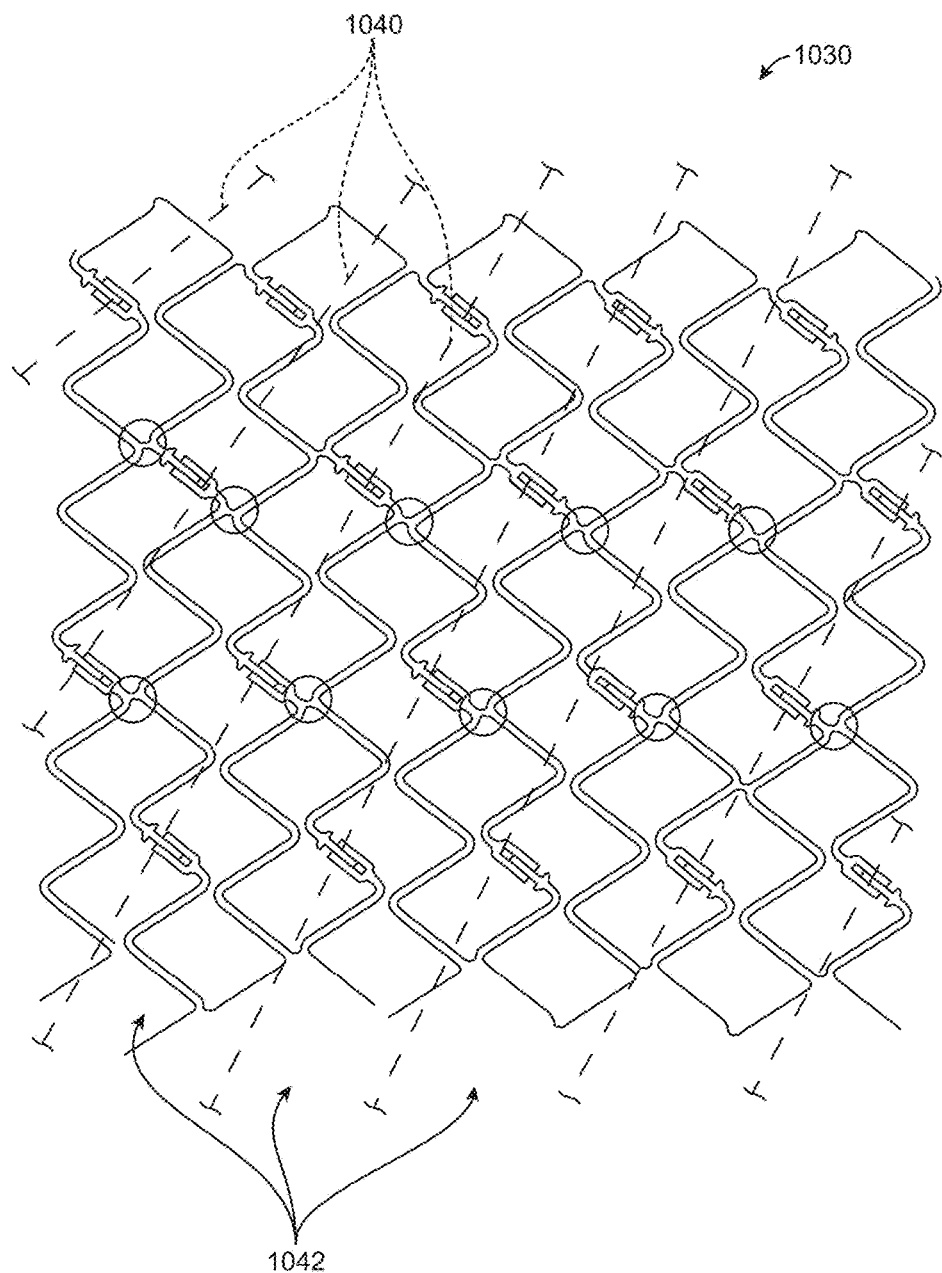
Figures 9A, 16G:
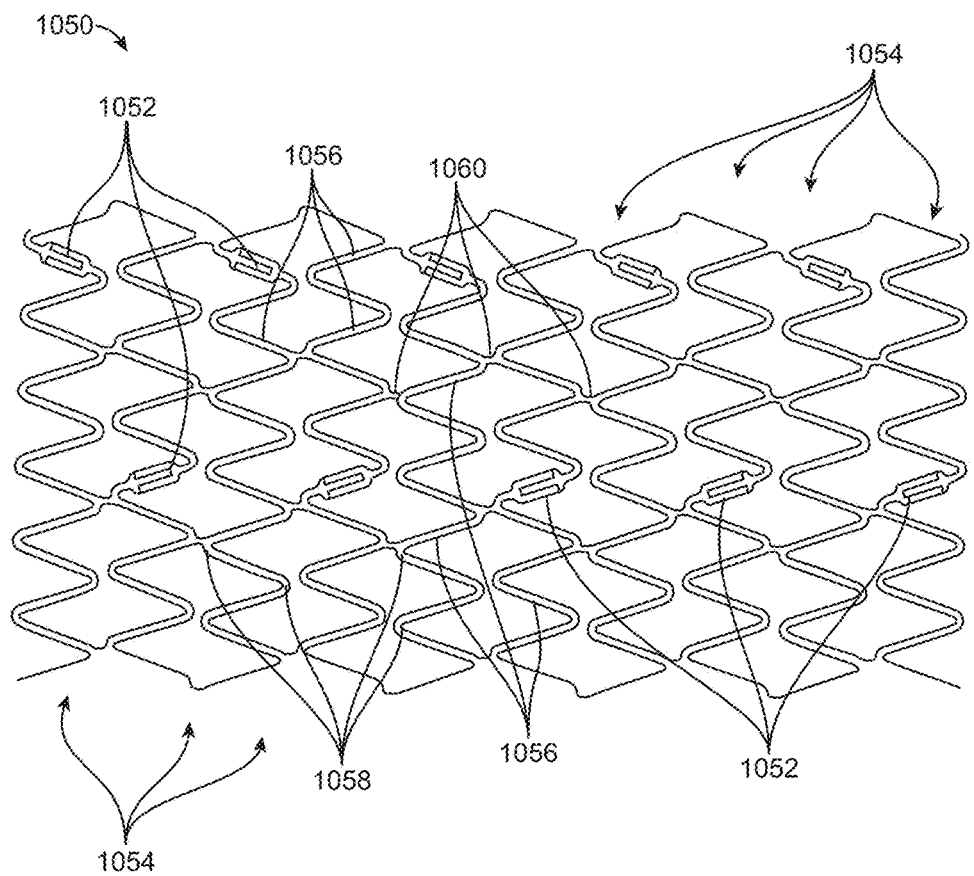
Figures 9B, 16G:
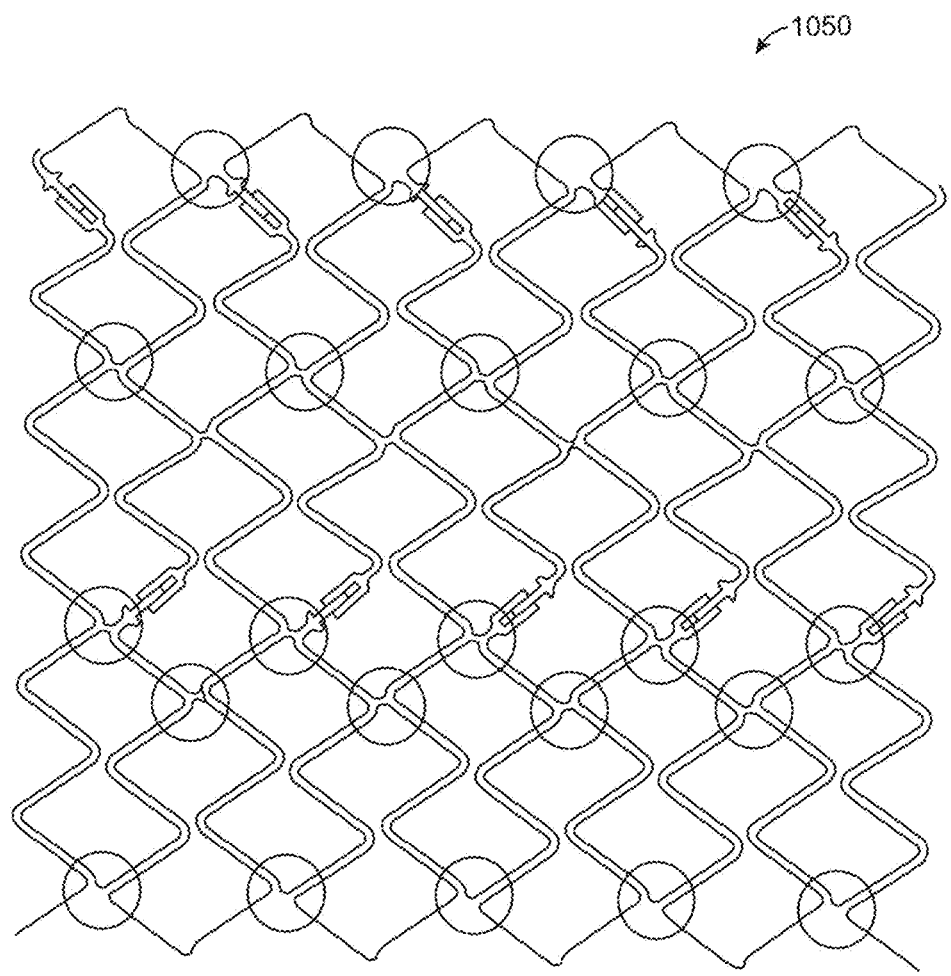
Figures 10, 16G:
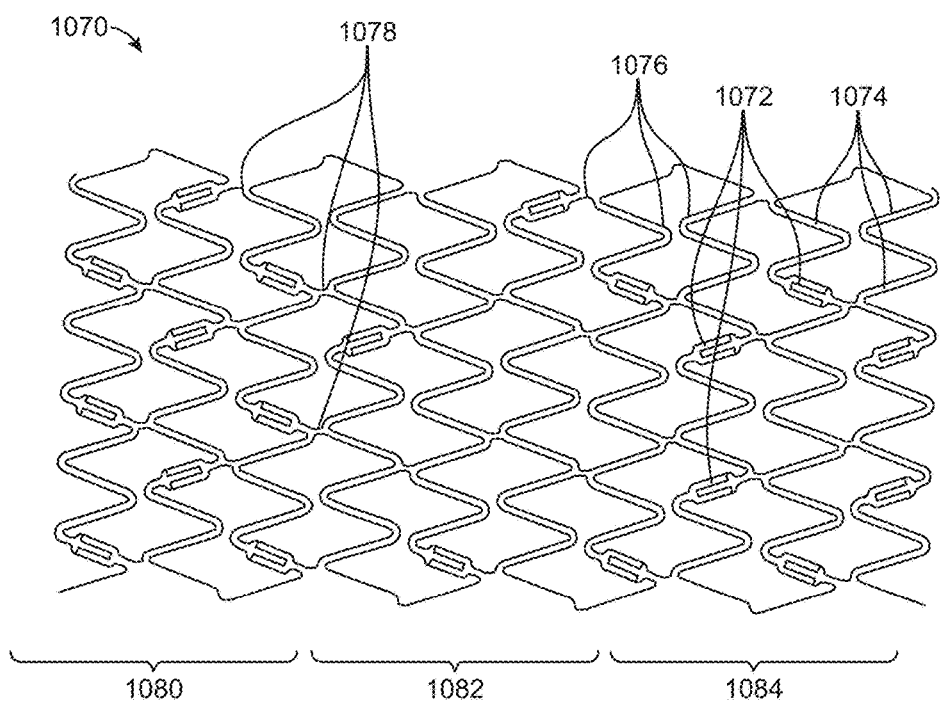

FIG. 16G-4 through FIGS. 16G-6 illustrate scaffold designs examples which allow full opening or unrolling along at least one axially continuous separation regions line (or path) of the stent length as shown in the black line(s). The figures also illustrate examples which allow opening (or unzipping) along axially continuous separation regions line (or path) of partial stent length comprising at least three rings. In other example the separation regions can be configured (by selecting a certain arrangement of separation regions, controlling the number of separation regions, and choosing the appropriate location of separation regions in relationship to the location of axial links connecting the same ring and/or adjacent rings) to allow opening (or unzipping) along axially continuous separation regions line (or path) of at least part of the stent length comprising at least two rings or more, or yet in another example comprising at least one ring or more. The axial links in many of the example maintain the structural intactness of the stent (at least two or more rings of the stent, preferably substantially all rings of the stent) in a longitudinal direction. Similarly, closed cell type designs for example can be configured to achieve a similar result.

As shown in FIGS. 16G-4, a scaffold 600 has separation regions 602 formed in circumferential rings 604 having struts 606 joined by crowns 608. Adjacent circumferential rings 604 are joined by axial links shown in boxes 612. One separation region 602' in each ring 604 in this example is positioned between adjacent axial links (shown in boxes 612) so that the separation regions lie along a continuous, irregular separation line 614 that does not go outside of the path between the circumferentially adjacent "boxed" separation regions. The figure also shows an example of the locations of separation regions on the struts (but can also apply to crowns) in relationship to crowns connected to axial links. In one example the separation region on a strut between (or connecting) two crowns on the same ring where one or both crowns are connected to adjacent rings by axial links, or in another example as shown in the figure where the separation region on a strut between (or connecting) two crowns on the same ring where neither one of the crowns is connected to an axial link. To be clear, the illustrated boxes are not part of the scaffold structure and are shown only to indicate at least one path for which of the adjacent separation regions define the axial separation path along the stent length.

As shown in FIGS. 16G-5, a scaffold 700 has separation regions 702 formed in circumferential rings 704 having struts 706 joined by crowns 708. Adjacent circumferential rings 704 are joined by axial links 710. In contrast to the scaffold 600 which opens along a single axial line (path) along the entire stent length 614 to form a "C-shaped" cross section after formation of discontinuities in the separation regions, the scaffold 700 will open along three axial separation lines 714 (or paths) along the entire stent length because each ring 704 has three separation regions 702 and all of the separation rings arranged along the lines 714 which line between axially adjacent axial links 710. Thus, after the separation regions 702 have all separated post-implantation, the scaffold will consist of three separate connected axial strips (sections or segments) of partial rings which are not structurally connected to each other after formation of discontinuities. The stent shown in FIG. 16G-5 can also have additional multiple shorter connected axial sections (or strips) on some rings by having separation regions on all axial links joining the at least some rings but maintaining axial links on at least two adjacent rings.

The scaffolds 600 and 700 will separate along generally axial lines, although as is the case with scaffold 600, the lines may meander in some cases. In other cases, as shown in FIG. 16G-6, a scaffold 800 may have separation regions 802 arranged in circumferential rings 804 to allow the scaffold to open along three helical or spiral separation lines (or paths) 814. Scaffold 800 includes struts 806 joined by crowns 808, and adjacent circumferential rings 804 are joined by axial links 810. While the separation lines appear to be linear in FIG. 16G-6, which is because the view has been rolled out along a spiral cut line. Thus, when the scaffold pattern is rolled back into its tubular form, the separation lines 814 will be three parallel spirals or helices formed over the tube or stent structure. Other scaffold having only a single (or two or four or more) straight, spiral or helical, or other regular or irregular patterns or geometries of separation line (path) along the stent axial length or part of the stent axial length, can also be fabricated by configuring the appropriate stent ring pattern, the appropriate number of links joining rings, the appropriate number of separation regions and locations within rings, and/or realigning the position of axial links to the separation regions locations on rings, to achieve the desired pattern and number of section (or strips) that the stent unzips into after uncaging.

Referring now to FIGS. 16G-7A and 7B, a scaffold 1000 has a plurality of separation regions 1002 formed in circumferential rings 1004 of the scaffold. As with previous examples, at least some of the rings 1004 of the scaffold may be formed from struts 1006 connected by crowns 1008. The separation regions are shown to be key-and-lock junctions, as described previously, but the patterns disclosed in the following FIGS. 16G-7A through 16G-10 may apply to any type of separation region described herein. The separation regions 1002 are shown in their closed or partially closed configuration in FIG. 16G-7A and in their partially opened or axially separated configurations in FIG. 16G-7B which illustrates the scaffold 1000 in its circumferentially expanded configuration.

As shown in FIG. 16G-7B, upon expansion of the scaffold 1000, the separation regions 1002 follow the meandering paths illustrated by broken lines 1010, 1012, and 1014. segments 1016, 1018, and 1020 thus form in the scaffold upon circumferential expansion, typically by balloon as described elsewhere herein. The segments are held together by links 1008 which are circled in FIG. 16G-7B. It should be appreciated, however, that different separation and segmentation patterns can be programmed into the scaffold depending on the separation pattern desired. Different available separation patterns examples are discussed below with regard to different figures.

As shown in FIGS. 16G-8A and 8B, a scaffold 1030 comprises separation regions 1032, circumferential rings 1034, struts 136, crowns 138, and axially links 144 connecting adjacent rings. While these basic components are the same as for scaffold 1000, the arrangement of separation regions 1032, and axially links 1044 connecting adjacent rings, are selected so that, upon circumferential expansion or after circumferential expansion as shown in FIG. 16G-8B, a helical separation boundary 1040 will form about the scaffold to form a single helical structural segment 1042 which remain intact (held together by the circled axial links in FIG. 16G-8B) after expansion and after uncaging in a circumferential direction. In the scaffold 1030, both the separation regions 1032, and the axially links 1044 connecting adjacent rings, are arranged in complementary helical patterns to insure both the helical separation and the remaining helical connection of the stent elements after radial expansion.

Referring now to FIGS. 16G-9A and 9B, a scaffold 1050 comprises rings 1054 each having a single separation region 1052 formed therein. The rings 1054 are formed from struts 1056 and crowns 1058, and three axial links 1060 are formed between each adjacent pair of circumferential rings 1054, as best seen in the circled regions of FIG. 16G-9B. This particular pattern of separation regions 1052, and axially links 1060 connecting adjacent rings, allow the scaffold 1050 to circumferentially expand while all elements of the scaffold remain interconnected so that there are no discrete separated segments (no unzipping along the axial length of the stent) formed after expansion. However, each ring uncages by forming at least one discontinuity in the circumferential path of each ring, thus uncaging the stent.

Figure 10:
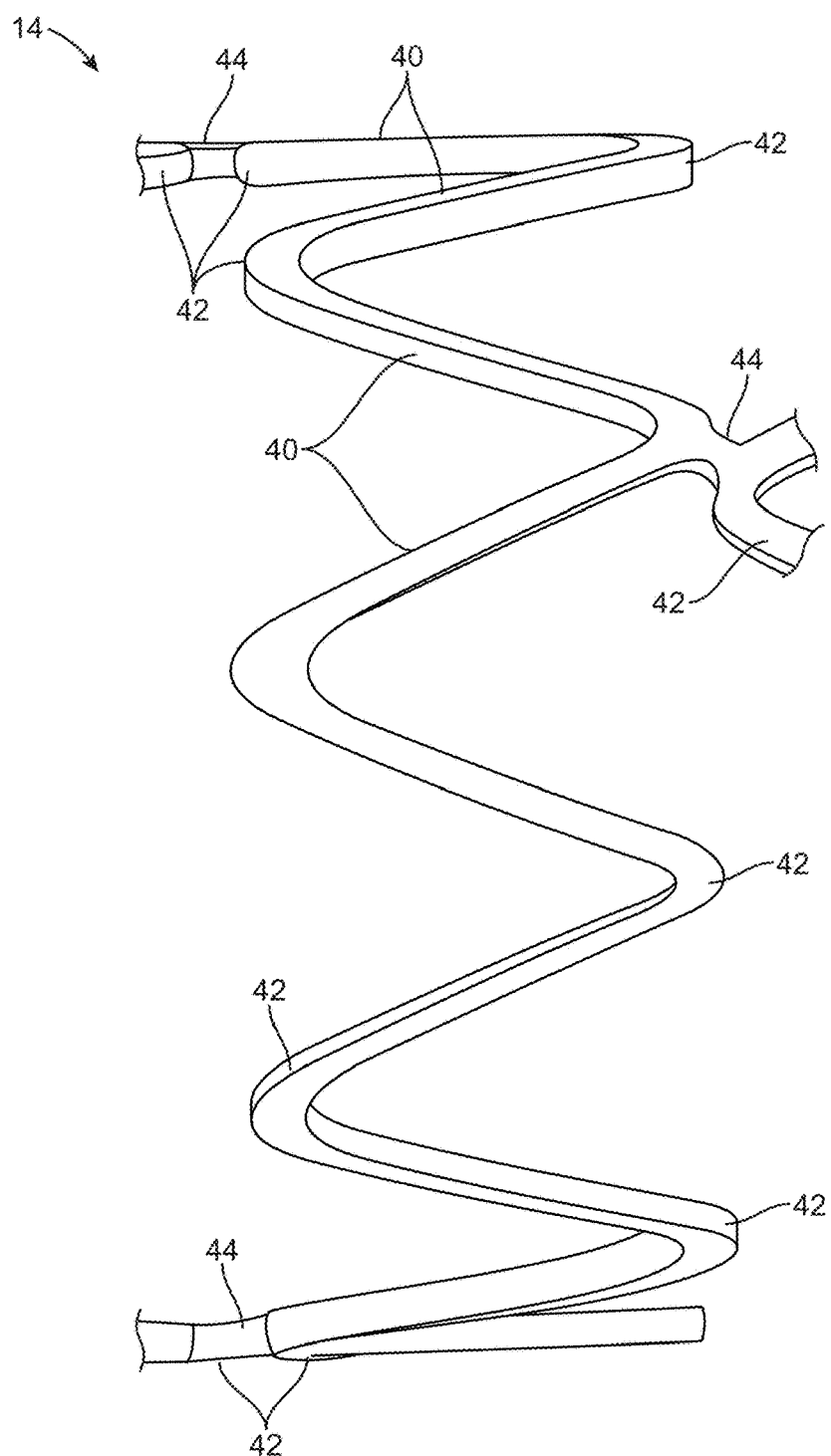
FIG. 10 is an enlarged view of a single zig-zag showing partial ring of the circumferential scaffold of the endoluminal prosthesis of FIGS. 1, 2A, and 2B.

Stents tend to have low radial strain (compliance) in the expanded configuration specially ones that are plastically deformable, such as non-degradable metals and metal alloys, such as stainless steel alloys, cobalt chrome alloys, and platinum iridium alloys. This may be harmful to the anatomy the stent is implanted in as it can cause irritation to the lumen or vessel, it can cause fatigue of the stent or of the lumen or vessel over time as a result of having a substantially rigid structure in a dynamically (or constantly) moving environment, and can result in adverse events over time. Typical % radial strain (compliance) approximation for coronary artery ranges from 3% to 5%. Stent technologies, when expanded in a lumen (or mock tube), tend to have % radial strain (composite compliance) usually between 0.1% and 0.5%, typically in the range from 0.1% to 0.3%. It is an objective of this invention to configure a stent, in accordance with the the present invention, to having % radial strain (or composite compliance) ranging from 0.5% to 5%, preferably ranging from 1% to 5%, more preferably ranging between 1% and 5%, most preferably from 1.2% to 5%, or from 1.5% to 5%, after expansion of the stent prosthesis from a crimped configuration to an expanded configuration, or after formation of circumferential discontinuities, when the inner stent diameter is expanded within a lumen (or mock tube) to approximately 110% the inner diameter of the lumen (or mock tube) under physiologic condition, and where the lumen (or mock tube) has a compliance ranging from 4% to 5%, or the stent of the present invention after expansion in a body lumen (or mock tube) would have a substantially similar radial strain (or composite compliance) to that of the anatomy the stent is implanted in, or the stent of the present invention is configured to have a composite compliance of at least 25% of that of the radial strain (compliance) of the anatomy the stent is implanted in after expansion of the stent in such anatomy (such as lumen or mock vessel) or after formation of discontinuities, or the stent of the present invention is configured to have a composite compliance of at least $\frac{1}{3}^{rd}$ of that of the radial strain (compliance) of the anatomy the stent is implanted in after expansion of the stent in such anatomy (such as lumen or mock vessel) or after formation of discontinuities, or the expanded stent may have a composite compliance of at least 50% of the radial strain (compliance) of the anatomy the stent is implanted in, or a composite compliance of at least 65% of the radial strain (compliance) of the anatomy the stent is implanted in, under physiologic conditions. In a preferred example, the stent of the present invention is configured to have a composite compliance after expansion in a body lumen (or a mock tube), or after formation of discontinuities, ranging from 0.7% to 4%, or ranging from 0.9% to 4%, or ranging from 1% to 4%, or ranging from 1.1% to 4%, or ranging from 1.2% to 4%, or ranging from 1.5% to 4%, or ranging from 2% to 4%, wherein the lumen (or mock tube) has a compliance of about 5%, under physiological conditions. In another preferred examples, the stent of the present invention is configured to have an initial composite compliance after expansion in a body lumen (or mock tube), ranging from 0.1% to 0.5%, and has a second composite compliance after the initial compliance, or after formation of discontinuities, ranging from 0.7% to 4%, or the stent is configured to have an initial composite compliance after expansion in a body lumen (or mock tube), ranging from 0.1% to 0.7%, and has a second composite compliance after the initial compliance, or after formation of discontinuities, ranging from 1% to 4%, or the stent is configured to have an initial composite compliance after expansion in a body lumen (or mock tube), ranging from 0.1% to 1%, and has a second composite compliance after the initial compliance, or after formation of discontinuities, ranging from 1.2% to 4%, or ranging from 1.5% to 4%, or ranging from 2% to 4%, and wherein the lumen (or mock tube) compliance is about 5%. In another preferred example, the stent of the present invention is configured to have an initial composite compliance magnitude after expansion in a body lumen (or mock tube) where the lumen diameter ranges from 2.5 mm to 3.5 mm and the lumen (or mock tube) has a compliance of about 5%, and wherein the initial stent composite compliance magnitude after expansion ranges from 0.01 mm to 0.05 mm, or ranges from 0.01 mm to 0.06 mm, or ranges from 0.01 mm to 0.07 mm, and where the stent has a second composite compliance magnitude after the initial compliance, or after formation of discontinuities, ranging from 0.07 mm to 0.15 mm, or ranging from 0.08 to 0.15 mm, or ranging from 0.1 mm to 0.15 mm, under physiologic conditions. Scaffolds in accordance with this invention are configured to circumferentially uncage allowing the stent and the lumen to have % radial compliance as described above. Scaffolds may also be formed to have differing regions of radial compliance (radial strain) along their lengths. For example, as shown in FIG. 16G-10, a scaffold 1070 includes a plurality of rings formed from struts 1074 and crowns 1076, as with previously described examples. Adjacent rings are joined by axially links 178, and separation regions 1072 are formed in each of the rings. In a first end region (or segment) 1080 of the scaffold 1070, each of the rings have three separation regions 1072, making that region highly compliant after expansion, and formation of discontinuities. In a second or middle region (or segment) 1082, each ring includes only a single separation region, making that region less compliant than the first region 1083, and a third region (or segment) 1084 where each ring has a pair of separation regions 1072, making the compliance of the third region somewhere in between that of the first region 1080 and that of the second region 1082 (assuming that all other characteristics of the circumferential rings are similar). The % radial strain (compliance) can be measured utilizing for example the test apparatus in FIG. 35 which is adjustable for selecting the physiologic condition % radial strain (compliance) or displacement approximation and measuring radial strain (composite compliance) of implants, stents, or stent segments under physiologic conditions. It is desirable to have substantially all segments of the stent uncage by uncaging substantially all rings. The stent may have a substantially similar radial strain (compliance) along the entire stent ring segments or can have a variable radial strain (compliance) among various ring segments or regions of the stent. Radial strain (compliance) may be increased or decreased by configuring for example one or more of the following: The number of separation regions per ring, the type of stent design or pattern, the location of the separation regions on each ring, the length, width, and/or thickness of the structural element where the separation region is located on the ring, the pattern of the separation regions along the stent length or segment, to name a few. The magnitude of displacement (expansion and/or contraction) in the expanded stent configuration, in physiological environment, of the stent of this invention, in one example, having the desired % radial compliance, ranges from 0.1 mm to 1 mm, preferably ranges from 0.15 mm to 0.5 mm, more preferably ranges from 0.2 mm to 0.5 mm. The displacement (contraction and/or expansion) magnitude and rate are typically coupled (or synchronized with or corresponding to) with the beating of the heart, the pressure or mean pressure adjacent to the stented segment, and/or contractility of the heart muscle, or other physiologic conditions. It is desirable to have a stent having high initial strength sufficient to support a body lumen in the expanded stent configuration, and at the same time said stent is configured to have one or more % radial strain (compliance) values or ranges along the length (or segments or regions) of the stent rings. Shape memory stents tend to have weaker strength (or crush force) due to the properties and processing of the material. Stent formed from shape memory alloy tend to have closed cell designs to compensate for such weakness in strength. However, it is desirable to have stents formed from shape memory alloys having strength in the expanded configuration and having separation region on at least some rings to uncaging the rings (forming one or more discontinuities in the circumferential ring path sufficient to uncage said rings). The stent formed from shape memory alloy can thus be configured to have high crush resistance in the expanded configuration and the desired displacement or radial strain (compliance) along various segments of the stent rings as described above to accommodate the radial strain (compliance) of the anatomy where the stent is implanted in, or the stent is configured to have the desired radial strain (or compliance). In some cases, it is desirable to have a stent having high crush strength in the expanded configuration, and have radial strain (compliance) or radial displacement magnitude (larger or smaller) by forming separation regions or breaking sections along the circumferential path of the stent rings, uncaging the stent or one or more stent segments and achieving the desired level or range of displacement or radial strain (compliance) for the stent ring or stent segment. In other or same cases, it is desirable to have a stent having high crush strength in the expanded configuration, and have radial strain or radial displacement magnitude (larger or smaller) and/or have contraction magnitude being different from expansion magnitude, by forming separation regions or breaking sections along the circumferential path of the stent rings uncaging the stent or stent segment and achieving the desired level or range of displacement or radial strain for the stent rings or stent segment. In addition to other stent design configurations such as supporting features described in FIGS. 23C and 23D can be utilized to achieve the desired radial strain, expansion magnitude, and/or contraction magnitude. In some cases the stent of this invention can be configured to have high crush resistance in some segments of the stent in the expanded configuration and having substantially low % radial strain in such segments, while achieving certain desired radial strain value or displacement magnitude in other segments of the stent (while having similar crush resistance or lower crush resistance to the other segments of the stent). This can be specially suited for heart valves stents where certain segments require anchoring of the stent and therefore require high crush resistance, while other segments of the stent require higher % radial strain (compliance) or contractility magnitude usually in stent ring segments adjacent to or the segment containing the stent valve. Stents formed with separation regions configured to uncage in the circumferential ring path can have an advantage by accommodating the contractility of the annulus or lumen where it is necessary and have strength and low radial strain (compliance) in areas or segments where it is not necessary, or where it is important to anchor or affix the implant structure.

Figures 11, 16G:
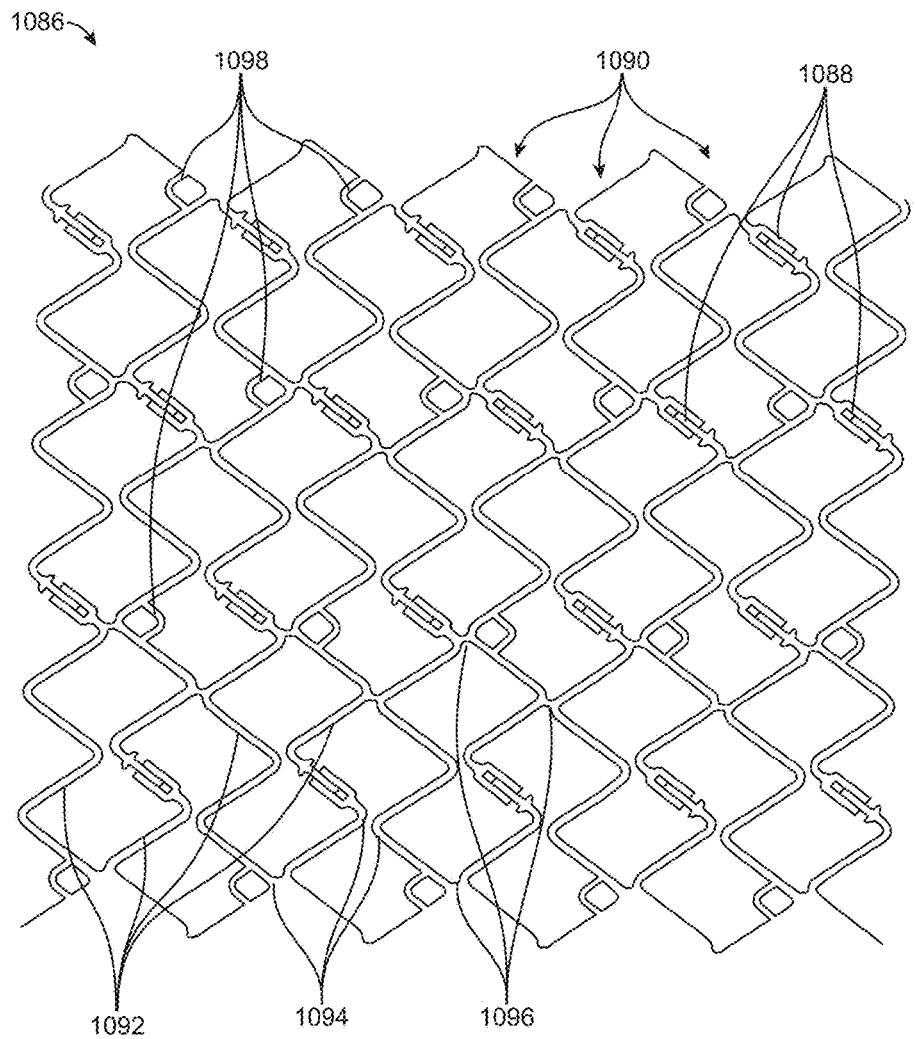

Referring now to FIG. 16G-11. A scaffold 1086 comprising a plurality of circumferential rings 1090 is formed from struts 1092 and crowns 1094, generally is described above. Each of the circumferential rings 1090 includes a pair of separation regions 1088, and adjacent circumferential rings 1090 are joined by axial links 1096. Scaffold 1086 differs from those described previously in at least that it includes a plurality of reinforcement elements or features 1098 attached to adjacent struts 1092 near locations where they are joined into crowns 1094 or crown region or strut region. The struts and crowns of the scaffold 1086 will be formed from any of the non-degradable materials described (or degradable material having high crush resistance) and will typically be of the stent type intended for balloon expansion, but can also be used for shape memory stent type. That is, the primary material of the scaffold 1086 will be formed from a malleable, non-elastic metal or other material in one example. In contrast, the reinforcement features 1098 will be typically formed from a resilient or elastic material, usually a shape-memory metal alloy, a spring stainless steel, or the like. As illustrated, the reinforcement features 1098 will act as a spring to help open the stent from its crimped configuration (not illustrated) to its open configuration (as shown in FIG. 16G-11). When the scaffold 1086 is crimped, the spring-like reinforcement features 1098 will be closed to compress the spring and impart a spring force which helps to open the scaffold during balloon or other expansion. As illustrated, the spring-like reinforcement features 1098 can be located adjacent the separation regions 1088. In this way, the opening force provided by the reinforcement features will offset at least some of the tension imparted to the separation features by balloon expansion. Additionally, the spring-like retention features will enhance the resilience of the open scaffold increasing its compliance within the blood vessel or other body lumen. The reinforcement elements can also help further expand the stent to a second larger configuration after inward recoil from first expanded configuration. The stent in this example have separation regions forming discontinuities after expansion of the stent to the deployed configuration uncaging the stent along the stented segment.

Referring now to FIG. 16H-1 through 16H-5, an additional type of separation region 160 is illustrated. The separation region 160 is formed between a first hollow strut segment 162 and a second hollow strut segment 164. A core 166 has one end received in a central passage 168 of the first hollow strut segment 162 and a second end received in a central passage 170 of the second hollow strut segment 164. The strut segments 162 and 164 will usually be non-degradable, typically being a metal as described elsewhere herein, while the core 166 may be either degradable or non-degradable. In cases where the core 166 is non-degradable, the separation region 160 will typically be initially stabilized with an adhesive and/or a sleeve or other encapsulation during deployment and expansion. After implantation, the biodegradable adhesive and/or encapsulation will degrade, eventually allowing either or both of the hollow strut segments 162 and 164 to axially slide relative to the core 166, thus forming an expansion joint, and/or allowing the stent to further expand.

Alternatively, where the core 166 may be itself biodegradable, in which case the core may be either attached to one or both of the hollow strut segments 62 and 64 or may be free to axially translate relative to either or both of the hollow strut segments 62 and 64. When the core 166 is biodegradable, the biodegradation of the core after implantation will be relied on primarily in one example to achieve separation of the segments 162 and 164.

As a further alternative, a biodegradable core 166 may be joined within either or both of the hollow strut segments 162 and 164 using a biodegradable adhesive. Such designs may provide a further failsafe mechanism for biodegradation and release of the strut segments. Alternatively, the use of multiple biodegradation patterns in the core and surrounding adhesives may allow a sequential biodegradation of the different elements to achieve different levels of expansion and separation between the strut segments.

As shown in FIG. 16H-2, for deployment and expansion, the hollow strut segments 162 and 164 will initially be joined in an abutting fashion with the core 166 serving as a link or stabilizing bar or element. The core 166 may be joined to the hollow struts 162 and 164 by a biodegradable or a non-biodegradable adhesive, depending in part on whether or not the core 166 itself is biodegradable. Alternatively, or additionally, the struts 162 and 164 may be joined by a biodegradable external sleeve 172, as shown in FIG. 16H-3.

As further shown in FIG. 16H-4, a core 174 may include a necked region 176. By properly selecting the size or cross-sectional area of the necked region 176, the biodegradation time for a core formed from a particular biodegradable material may be programmed into the core 174.

Still further alternatively, a core 178 may itself be separated into core segments 180 and 182 joined by a pin 184 received in a hole or passage 186, as shown in FIG. 16H-5. The pin 184 may be formed as part of the core segment 180 itself or may be a separate element or component which freely slides in both the hole 186 and a second hole (not shown) in the first core segment 180.

A separation region with the core design of FIGS. 16H-1 to 16H-3 will usually not totally separate, and some portion of the core 166 will remain in the passage 170 even after a vessel has completed post-implantation remodeling and expansion. This is advantageous as the design does not leave voids in the scaffold structure which supports the tissue.

Such designs will however limit separation of the adjacent strut segments in the radial direction which can limit the expansion of the stent as a whole and reduce expansion in response to vessel remodeling. Provision of a degradable region 176 (FIG. 16H-4) or a pin 184 and a hole 186 (FIG. 16H-5) in the core can allow complete separation under some circumstance which can enhance the complete mobility of the stent to enhance the response to vessel remodeling.

Figures 1, 16I:
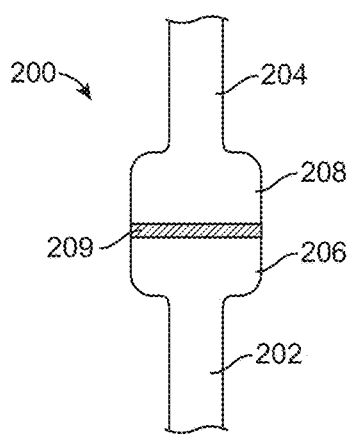
Figures 2, 16I:
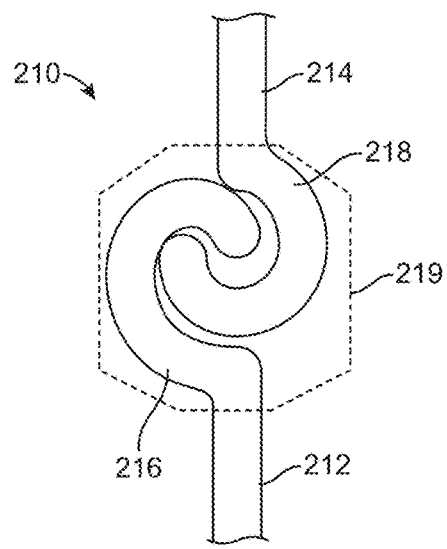
Figures 3, 16I:
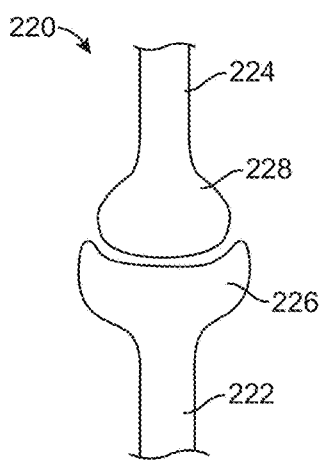
Figures 4, 16I:
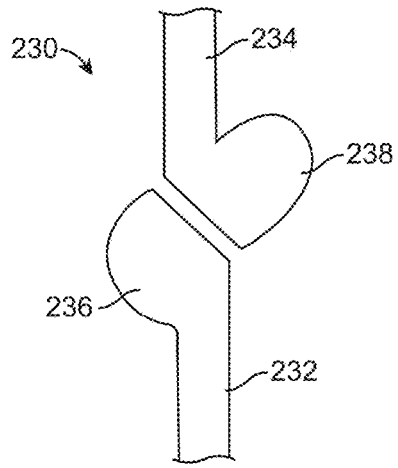
Figures 5, 16I:
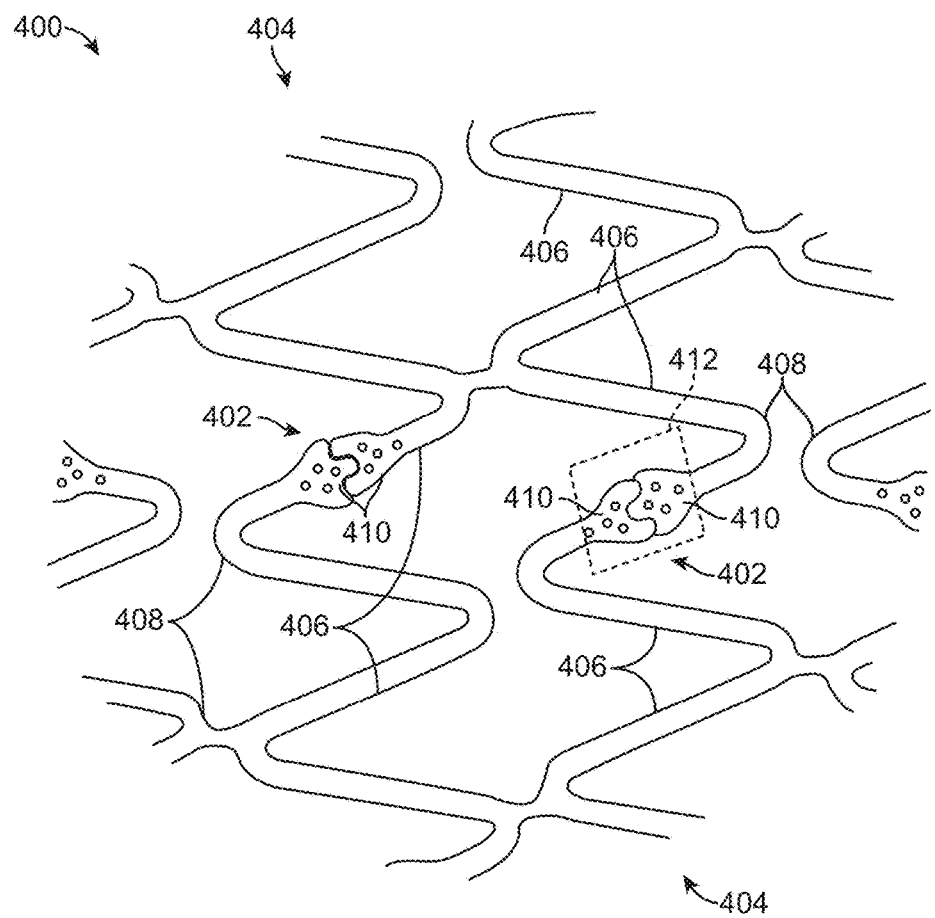
Figures 6, 16I:
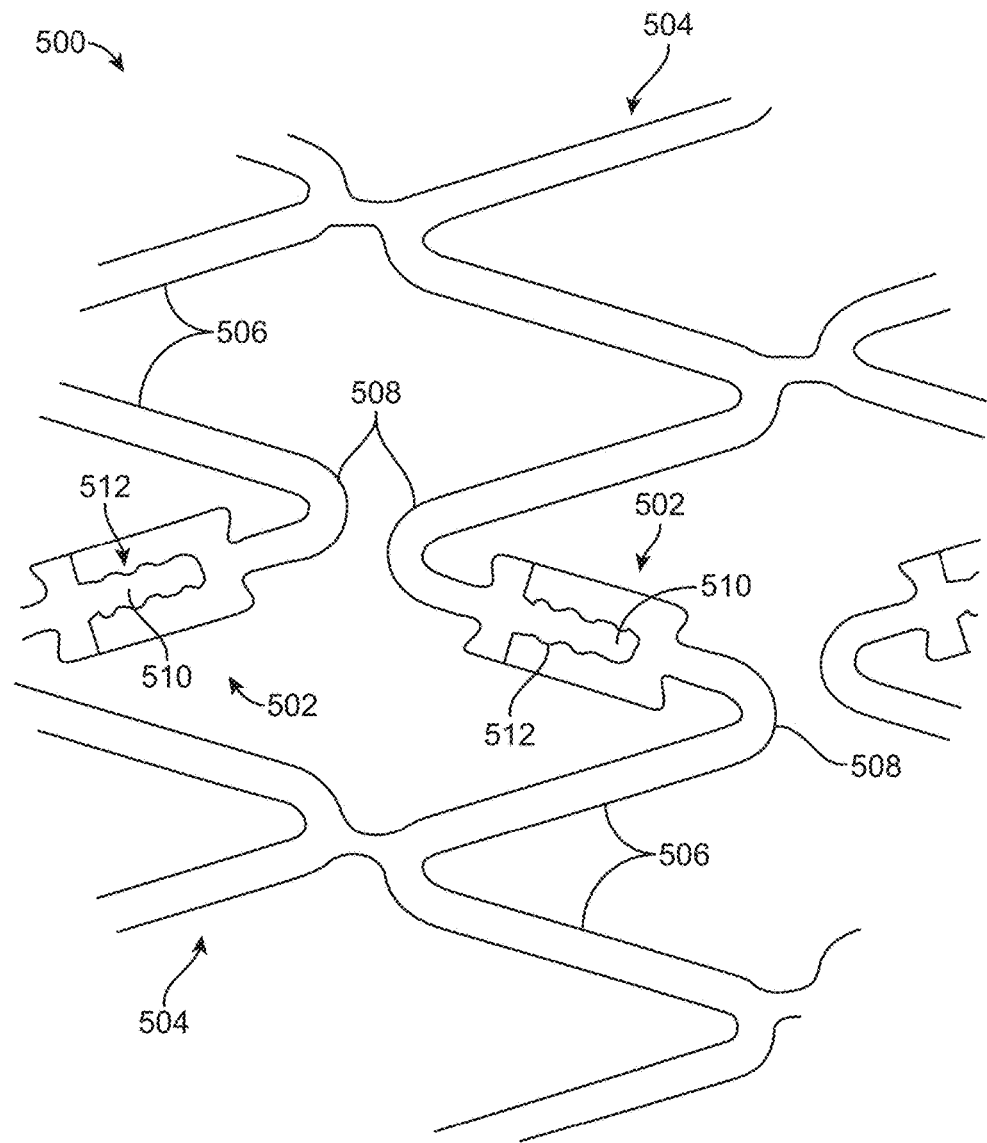

Still further separation regions are illustrated in FIGS. 16I-1 through 16I-4. A butt joint 200 connecting strut segments 202 and 204 has enlarged interface elements 206 and 208 at the terminal end of each strut segment as illustrated in FIG. 16I-1. Opposed surfaces on the respective interface elements are joined with an adhesive, cement, polymer, or any of the other degradable immobilizing materials 9 described herein. Alternatively, the terminal ends may be joined by any of the sleeve-like immobilizing element's described elsewhere herein. A hook joint 210 connecting strut segments 212 and 214 has hook-like interface elements 216 and 218 at the terminal end of each strut segment as illustrated in FIG. 16I-2. Opposed hook surfaces on the respective interface elements may be clasped together to enhance tensile strength of the resulting joint (and hoop strength of the scaffold ring), and may be further immobilized with an adhesive, cement, polymer, or any of the other degradable immobilizing materials described herein. As illustrated, the terminal ends are joined by a sleeve-like immobilizing element 219 which may be formed as described elsewhere herein. FIG. 16I-3 illustrates a joint 220 which is a variation of the butt joint of FIG. 16I-1 Joint 220 has connecting strut segments 222 and 224 with enlarged interface elements 226 and 228 having nesting, curved surfaces at the terminal end of each strut segment. The curved surfaces have a geometry similar to a nerve synapse and allow some bending flexibility in the separation region before and after the immobilizing element (not shown) degrades. The flexibility improves contact if the strut segments become misaligned which can enhance crush resistance of the stent or other prosthesis. Joint 230 has connecting strut segments 232 and 234 with enlarged interface elements 236 and 238 having flat surfaces at the terminal end of each strut segment which are angled or inclined relative to the common axis of the strut segment. The inclined surface can slide relative to each other as the circumferential ring expands or contracts which can improve compliance of the stent or other prosthesis. The interface elements 236 and 238 can be temporarily immobilized by any of the adhesives, cements, polymers, sleeves, or other immobilizing components described elsewhere herein.

Adhesion and immobilization of the terminal ends of adjacent strut segments (can also apply to crown regions) can also be enhanced by creating surface features on those ends. As illustrated for example in FIGS. 16I-5, a portion of a scaffold 400 has short lock-and-key separation regions 402 formed in circumferential rings 404 having struts 406 joined by crowns 408. The terminal ends of at least some of the adjacent strut segments joined by the separation regions 402 have holes, pores, perforations, bumps, or other surface features that provide attachment points for degradable sleeves 412 or other immobilizing elements that circumscribe the separation regions while the scaffold 400 is being deployed. While illustrated on short lock-and-key separation regions 402, the use of such anchoring surface features will find use with long lock-and-key separation regions as well as all types of separation regions which are immobilized by sleeves or other circumscribing immobilizing elements.

As a further embodiment or example, immobilization of the terminal ends of adjacent strut segments on lock-and-key separations regions can be enhanced by creating features on the interfacing surfaces of the "tongue" and "slot" of the lock and key. For example, as illustrated in FIG. 16I-6, a portion of a scaffold 500 has long lock-and-key separation regions 502 formed in circumferential rings 504 having struts 506 joined by crowns 508. Opposed surfaces of the tongue 510 and the slot 512 have undulating or "wavy" topographies which increase the surface are available for bonding with adhesives, cements, polymers, glues, or the like. In addition to increasing the available surface area for bonding, these surface features can physically interlock to further prevent axial separation of the strut segments. In addition to undulations, as illustrated, suitable interface features include serrations, saw-tooth patterns, chevron patterns, ramps, and the like. Such interlock features can be used with all lock-and-key and other separation region designs that have suitably oriented opposed surfaces and that allow radial separation or movement after the initial immobilization has degraded.

Figures 7, 16I:
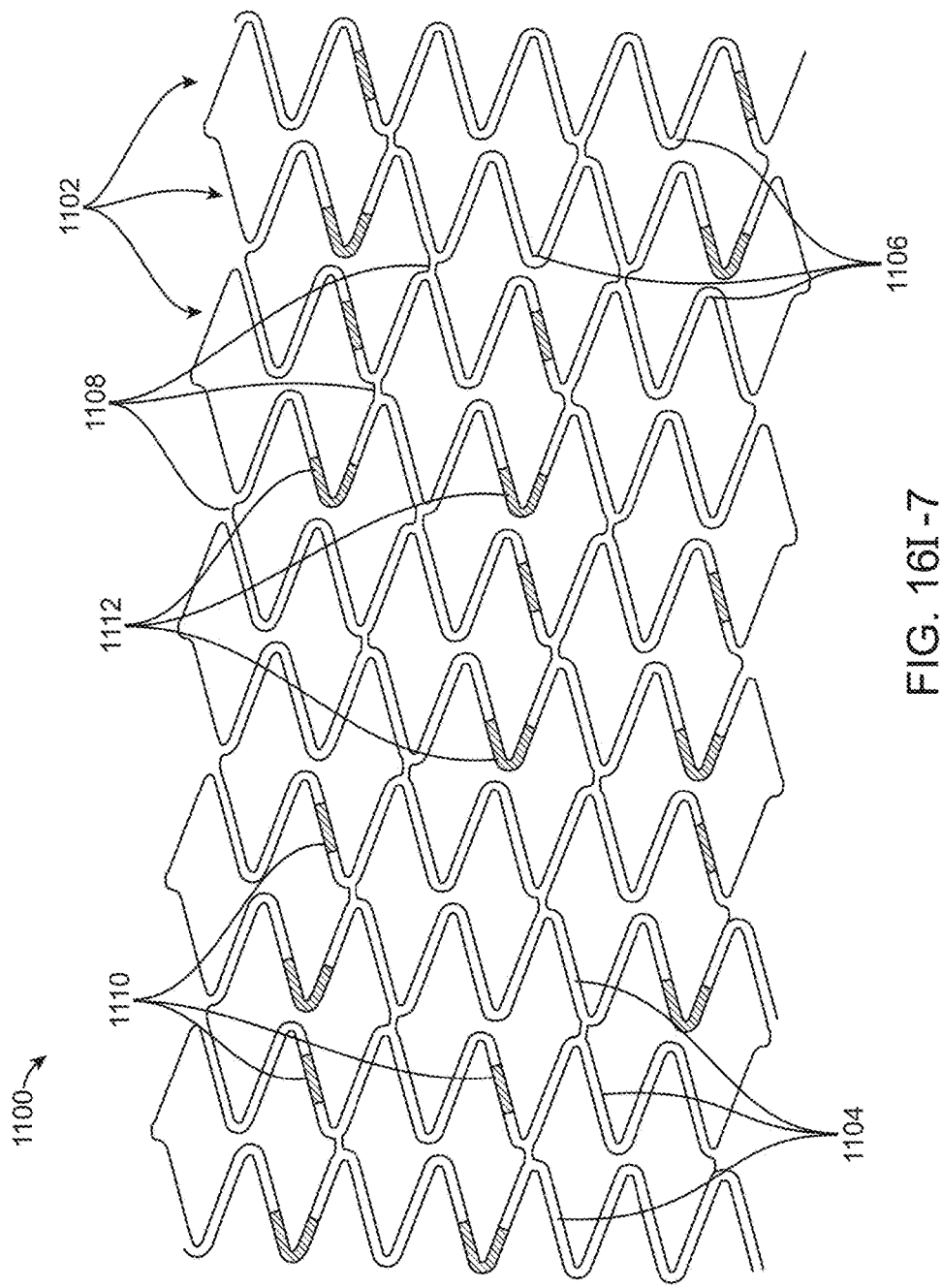
Figures 8A, 16I:
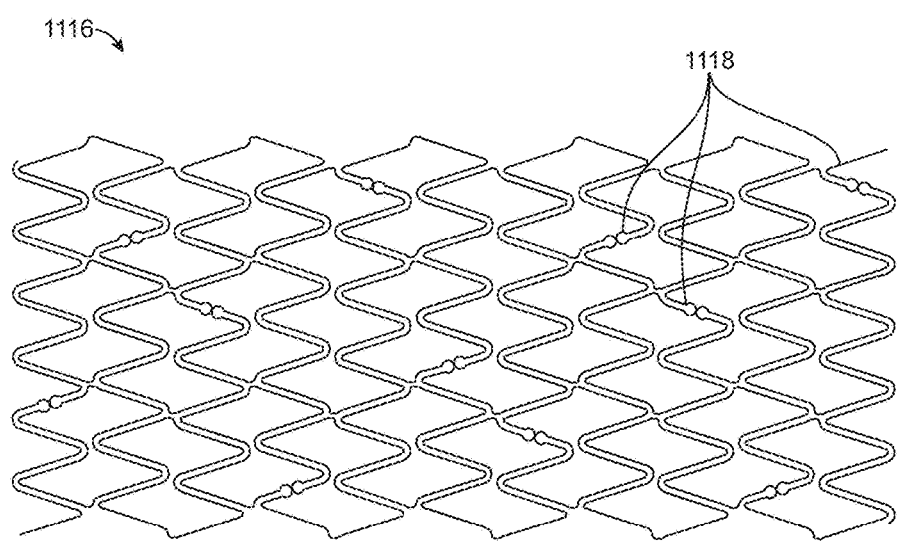
Figures 8B, 16I:
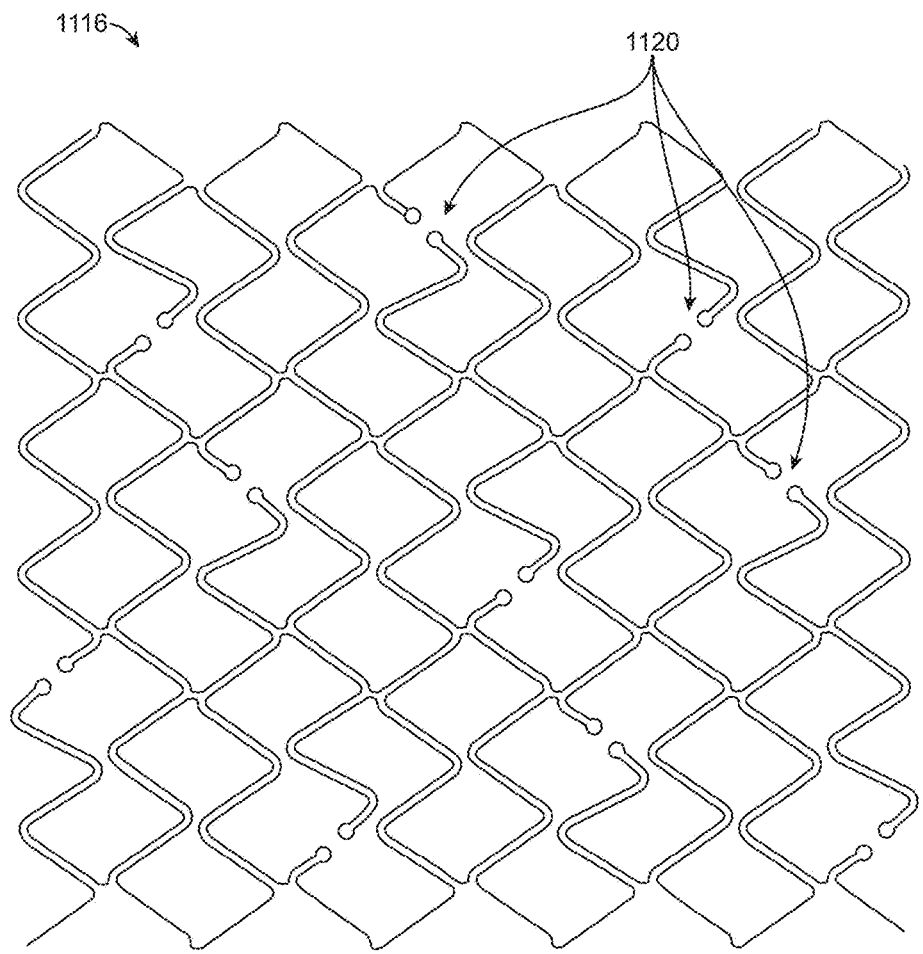

In still further examples of the uncaging stents of the present invention, scaffolds 1100 may be fabricated or modified to have openings, gaps, or breaks within the structures of individual circumferential rings and forming or placing bridging elements to bridge the openings, breaks, or gaps, as illustrated in FIG. 16I-7. Scaffold 1100 comprises of plurality of adjacent circumferential rings 1102 each of which comprises struts 1104 and crowns 1106, arranged generally as described previously herein. Adjacent circumferential rings 1102 are joined by axially links 1108, and openings or breaks may be formed in either the struts as shown at 1110 and/or in the crowns as shown at 1112 and where a bridging elements are formed to bridge said openings or breaks. Exemplary openings and breaks are typically in the form of gaps, as will be described in more detail below. The bridging elements can be formed from degradable material such as degradable polymeric material or degradable metallic material, wherein the degradable material encapsulates the strut or crown region, or is inserted inside (or within) the non-degradable material strut or crown regions ends, or joined as a butt joint with the non-degradable stent material at the ends (or junction) or opening junctions, or other methods of attachment such as FIGS. 16I-A-C. The degradable material degrades from one month to 3 years, preferably degrades from 2 months to 2 years, more preferably degrades from 2 months to 18 months. The stent in this example will have at least one bridging element per ring (two bridging elements per ring are shown in the figure) to sufficiently uncage the said ring. The length and number of bridging elements per ring can determine the magnitude of further expansion and/or displacement magnitude the stent is cable of performing after uncaging. The advantages of such stent configuration is having a stent that uncages after expansion from a crimped configuration to an expanded larger configuration, having high crush resistance in the expanded configuration, yet being able to uncage after expansion, and/or after degradation of at least one bridging element per ring. FIGS. 16I-16A, 16I-16B, and 16I-16C illustrate other examples of bridging elements. Bridging elements for example can bridge all or part of the crown or crown region, and/or all or part of a strut or strut region. Bridging elements in one example can have sizes, shapes, and dimension similar or different to structural elements being bridged. In other examples, bridging elements sizes, shapes, and dimensions are similar to reinforcement elements description described in more detail in other sections of this application. Another example, bridging elements have the shape of a strut or strut region, crown or crown region, or other shapes.

Referring now to FIGS. 16I-8A and 8B, separation regions 1118 in the form of gaps may be configured to contact, touch, or meet when the scaffold is in its crimped configuration, as shown in FIG. 16I-8A. These initially closed gaps 1118 will then open to leave a space, or gap therebetween when the scaffold 1116 is radially expanded or after the scaffold is expanded, as shown in FIG. 16I-8B. Typically, prior to expansion of the scaffold 1116, the gaps 1118 will be free from adhesives, sleeves, or other temporary restraining features which have been employed in other examples of the present invention. The arrangement of the "closed" gaps 1118 is selected so that the "open" gaps 1120 form as the scaffold 1118 is expanded or after scaffold expansion by a balloon or otherwise, so that the expanded scaffold 1116 will have sufficient hoop strength (or crush resistant force) to maintain patency of the blood vessel or other body lumen while allowing an enhanced level of compliance (radial strain) to reduce or eliminate caging of the body lumen, typically a blood vessel, or heart valve, after implantation. The stent having said gaps allow for vaso-dilatation in the stented segment, and/or further expansion after deployment. In another example, the free ends (where the gap is) is coated with an adhesive or a polymer, or other means to hold the gaps in the "closed" position upon expansion of the scaffold from a crimped configuration to a deployed configuration. This allows the structural elements where the gaps are located to have improved vessel (or lumen) support in the gap region, improved uniformity of expansion in the gap region, and improved drug delivery to the tissue adjacent to the gap to suppress neointimal proliferation for example. The gaps can open up when the scaffold is in the expanded configuration immediately, or over time after expansion, uncaging the vessel or lumen. Various adhesives, polymers, and other temporary holding means are described throughout the application. As shown in FIGS. 16I-8A & B, the gaps pattern is such that the gap on adjacent rings are rotationally offset. This allows for improved stent strength or crush resistance in the expanded scaffold configuration by reducing the impact of having a discontinuity in each ring, reduce fish-scaling along any axial path (or line) of the scaffold length, reduce having uncovered vessel or lumen area (or large uncovered area), lower recoil of the scaffold after expansion. The gap can be formed on structural element such as a strut, where the strut is adjacent to axial links (as shown in FIGS. 16I-8A & B), or can also be formed on a strut adjacent to two different axial links, each axial link connecting the ring where the gap is to an adjacent ring (not shown). Gaps can also be formed on struts or other structural elements not adjacent to axial links. As discussed in other examples, the number of gaps from one ring to another can vary. In one example, it might be desired for a bifurcation stent for instance to have several gaps in one or more rings in a mid-segment of the stent, and a lesser number of gaps in rings in other segments of the stent. In one preferred example, having one or more gaps on at least some rings where gaps on adjacent rings are rotationally offset, and having one or more axial links connecting at the at least some rings where at least some of the links connecting adjacent rings are rotationally offset. In one preferred example, having one or more gaps on at least some rings where gaps on adjacent rings are rotationally offset, and having one or more axial links connecting the at least some rings where the links connecting adjacent rings are rotationally offset. In one example, having one or more gaps on at least some rings where no more than two gaps on adjacent rings are axially aligned, and having one or more axial links connecting the at least some rings where the links connecting adjacent rings are rotationally offset. In one example, having one or more gaps on at least some rings where no more than three gaps on adjacent rings are axially aligned, and having one or more axial links connecting the at least some rings where the one or more links connecting some adjacent rings are rotationally offset. In one example, having one or more gaps on at least some rings where no more than three gaps on adjacent rings are axially aligned, and having at least two links connecting adjacent rings. In one example, having one or more gaps on at least some rings where no more than three gaps on adjacent rings are axially aligned, and having at least three links connecting adjacent rings. Gaps are also applicable to other stent design types such as closed cell designs, self-expanding, etc. and other types as discussed throughout this application. The free ends of the gaps can have a variety of shapes and dimensions, for example to be atraumatic ends, to have more strength, to improve coverage, to have more surface area, to name a few. In one example, there is no more than one gap for at least some rings, in other examples, there are two or more gaps for at least some rings, where the gaps on adjacent rings are rotationally offset. The free ends in FIGS. 16I-8A show the two free ends in contact at the free end, but they can also be in contact at regions adjacent to the free end.

Figures 9, 16I:
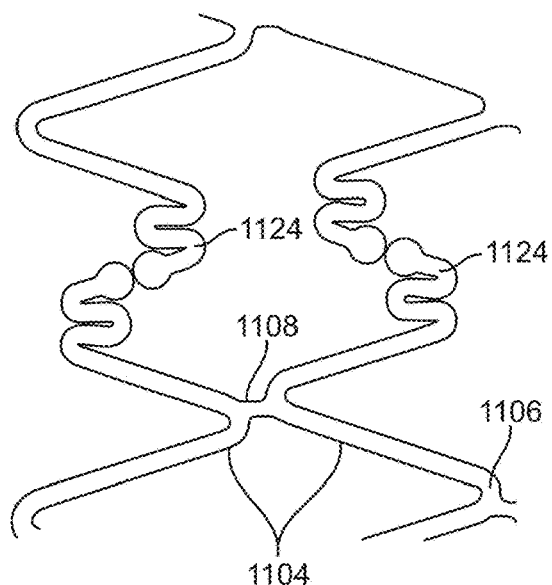
Figures 10, 16I:
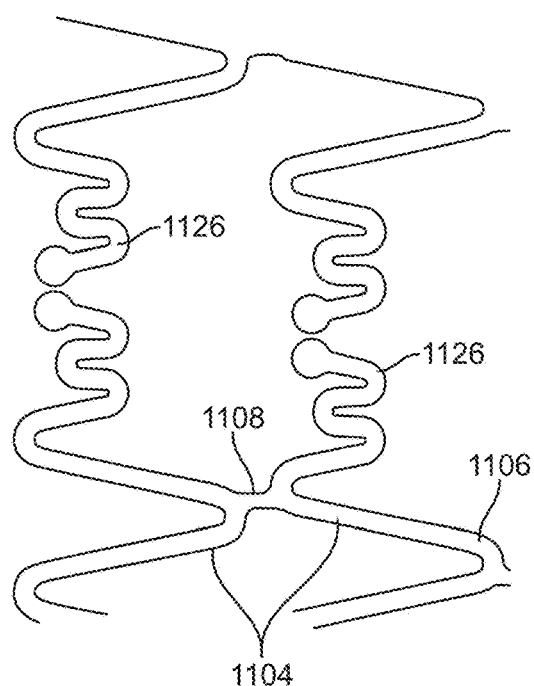
Figures 11A, 16I:
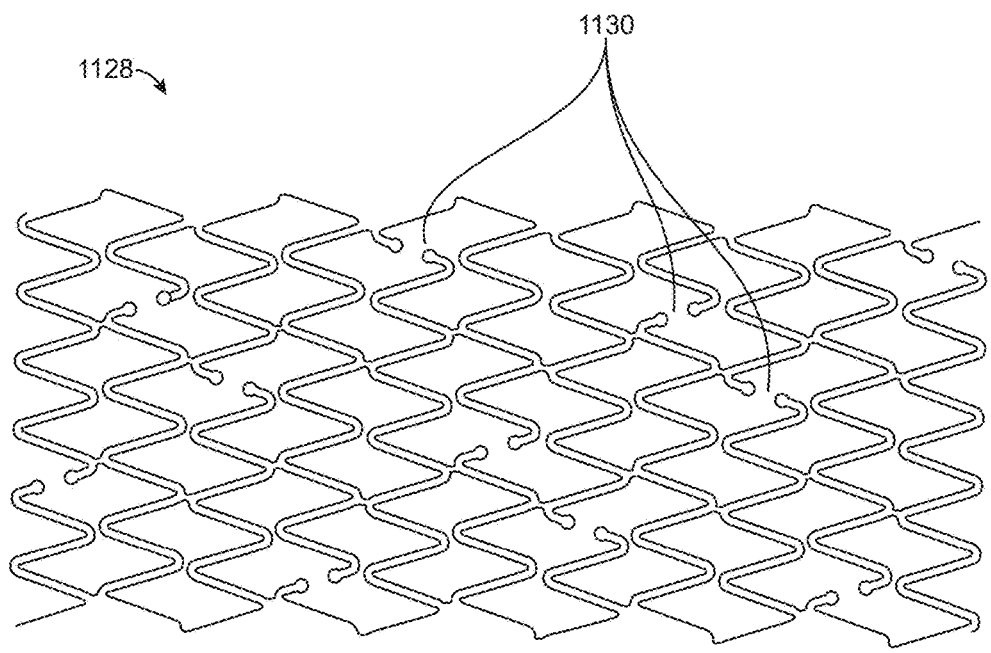
Figures 11B, 16I:
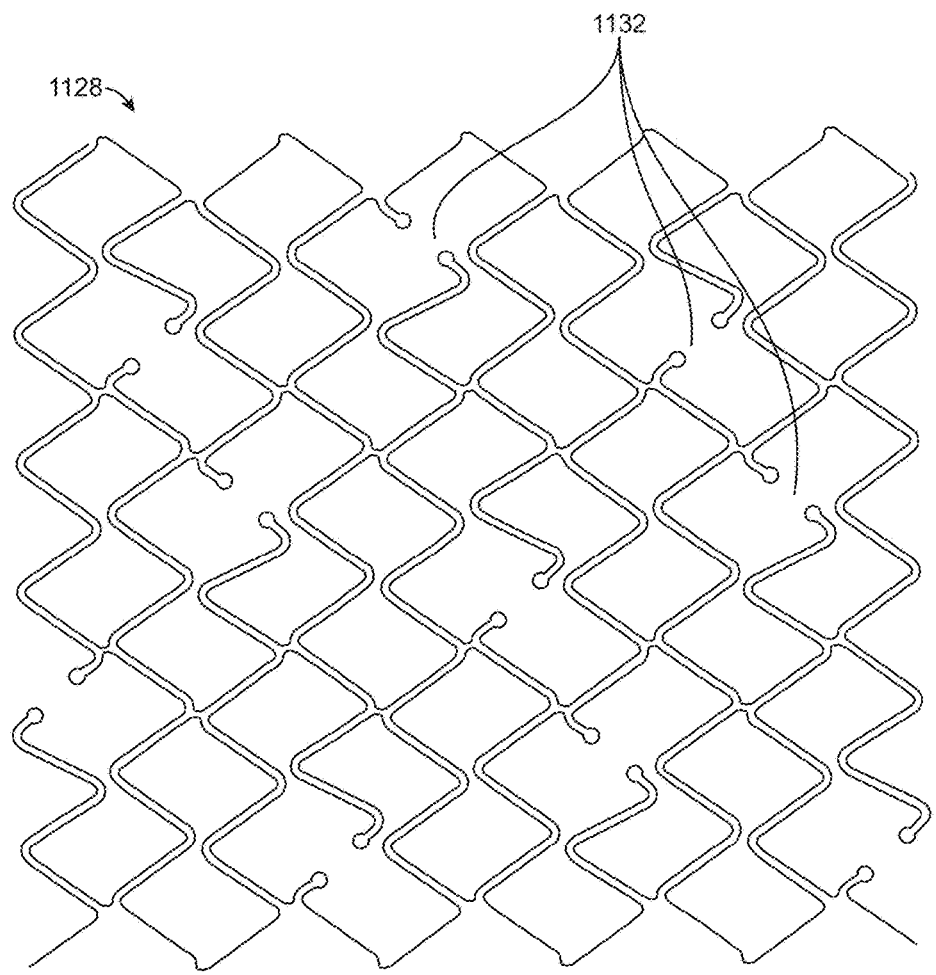
Figures 12A, 16I:
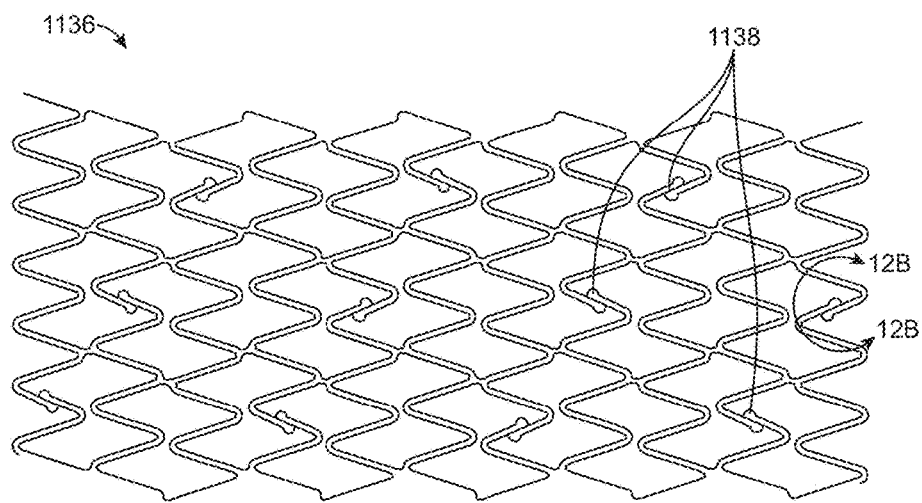
Figures 12B, 16I:
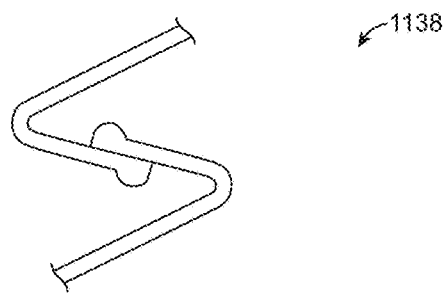

Other examples of gaps structures which are initially closed and open upon expansion or after expansion of the scaffold are illustrated in FIGS. 16I-9 and 10. In FIG. 16I-9, each gap 1124 comprises a pair of short, serpentine segments having tips which engage each other along an axial line when the scaffold is closed. As shown in FIG. 16I-10, each gap structure 1126 comprises a short serpentine segment where the ends of the segment lie generally parallel to each other (but can have other configurations) when the scaffold is in its crimped configuration. The gap structure 1124 shows the ends touching, while the gap structure 1126 shows the end space slightly apart.

Referring now to FIGS. 16I-11A and 11B, a scaffold 1128 comprises circumferential rings as described previously. Gap regions 1130 are formed in the circumferential rings of the scaffold, with the gaps being initially open when the stent in its crimped or unexpanded configuration, as shown in FIG. 16I-11A. The gap regions open further as shown at 1132 in FIG. 16I-11B when the stent it in its radially expanded configuration. The stent with such allow for vaso-dilatation in the stented segment, and/or further expansion after deployment. In another example, the free ends (where the gap is) are connected with a suture or other temporary means to hold the struts together upon expansion of the scaffold from a crimped configuration to a deployed configuration. This allows the structural elements where the gaps are located to have improved vessel (or lumen) support in the gap region, improved uniformity of expansion in the gap region, and improved drug delivery to the tissue adjacent to the gap to suppress neointimal proliferation for example. The gaps can open up further when the scaffold is in the expanded configuration immediately, or over time after expansion, uncaging the vessel or lumen. As shown in FIGS. 16I-11A & B, the gaps pattern is such that the gap on adjacent rings are rotationally offset. This allows for improved stent strength or crush resistance in the expanded scaffold configuration by reducing the impact of having a discontinuity in each ring, reduce fish-scaling along any axial path (or line) of the scaffold length, reduce having uncovered vessel or lumen area (or large uncovered area), lower recoil of the scaffold after expansion. The gap can be formed on structural element such as a strut, where the strut is adjacent to axial links (as shown in FIGS. 16I-8A & B), or can also be formed on a strut adjacent to two different axial links, each axial link connecting the ring where the gap is to an adjacent ring (not shown). Gaps can also be formed on struts or other structural elements not adjacent to axial links. As discussed in other examples, the number of gaps from one ring to another can vary. In one example, it might be desired for a bifurcation stent for instance to have several gaps in one or more rings in a mid-segment of the stent, and a lesser number of gaps in rings in other segments of the stent. In one preferred example, having one or more gaps on at least some rings where gaps on adjacent rings are rotationally offset, and having one or more axial links connecting at the at least some rings where at least some of the links connecting adjacent rings are rotationally offset. In one preferred example, having one or more gaps on at least some rings where gaps on adjacent rings are rotationally offset, and having one or more axial links connecting at the at least some rings where the links connecting adjacent rings are rotationally offset. In one example, having one or more gaps on at least some rings where no more than two gaps on adjacent rings are axially aligned, and having one or more axial links connecting the at least some rings where the links connecting adjacent rings are rotationally offset. In one example, having one or more gaps on at least some rings where no more than three gaps on adjacent rings are axially aligned, and having one or more axial links connecting the at least some rings where the one or more links connecting some adjacent rings are rotationally offset. In one example, having one or more gaps on at least some rings where no more than three gaps on adjacent rings are axially aligned, and having at least two links connecting adjacent rings. In one example, having one or more gaps on at least some rings where no more than three gaps on adjacent rings are axially aligned, and having at least three links connecting adjacent rings. Gaps are also applicable to other stent design types such as closed cell designs, self-expanding, etc. and other types as discussed throughout this application. The free ends of the gaps can have a variety of shapes and dimensions, for example to be atraumatic ends, to have more strength, to improve coverage, to have more surface area, to name a few. In one example, there is no more than one gap for at least some rings, in other examples, there are two or more gaps for at least some rings, where the gaps on adjacent rings are rotationally offset.

Gaps may also be formed with overlapping structures, as shown in FIGS. 16I-12A and 12B. Scaffold 1126 comprises separation regions 1138 where the free or open ends of the struts which have been formed as such or formed and detached from each other are shown to overlap so that they may slide adjacent to each other as the scaffold 1136 is circumferentially opened or after.

Figures 13C, 16I:
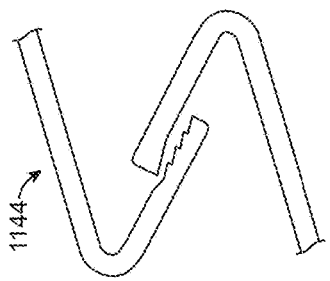
Figures 13F, 16I:
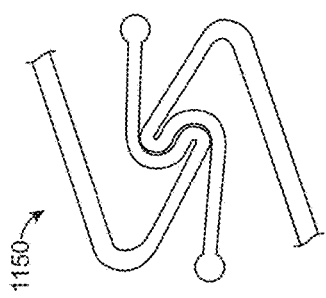
Figures 13B, 16I:
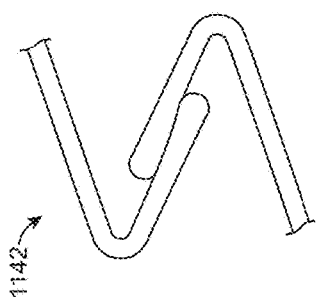
Figures 13E, 16I:
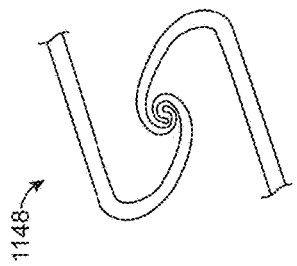
Figures 13A, 16I:
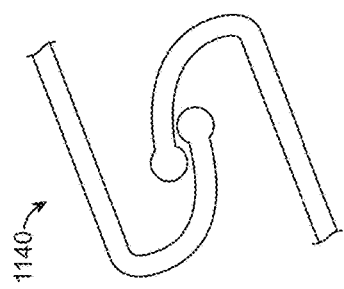
Figures 13D, 16I:
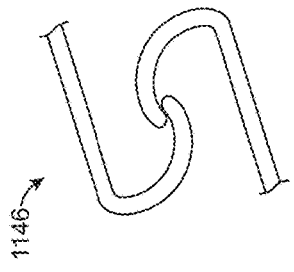
Figures 14A, 16I:
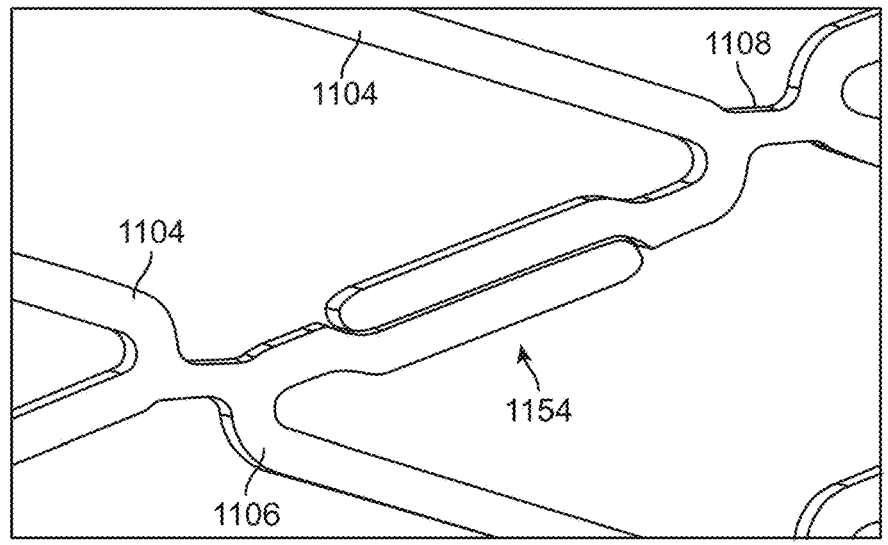
Figures 14B, 16I:
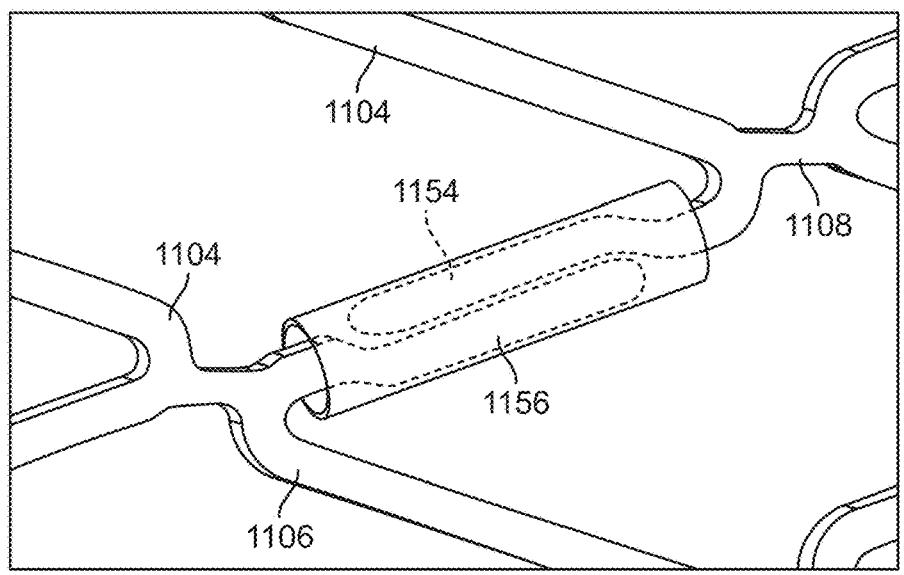
Figures 15A, 16I:
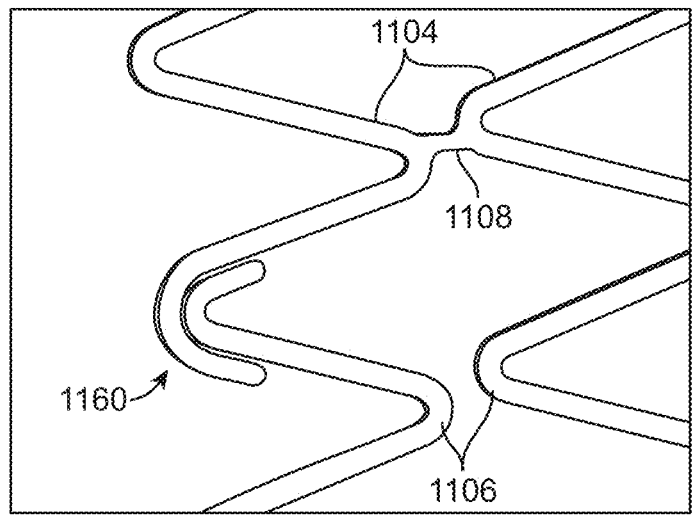
Figures 15B, 16I:
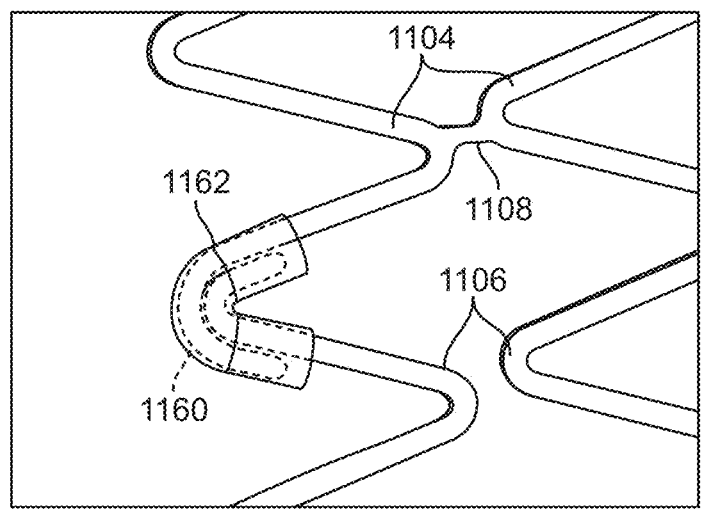
Figures 16A, 16I:
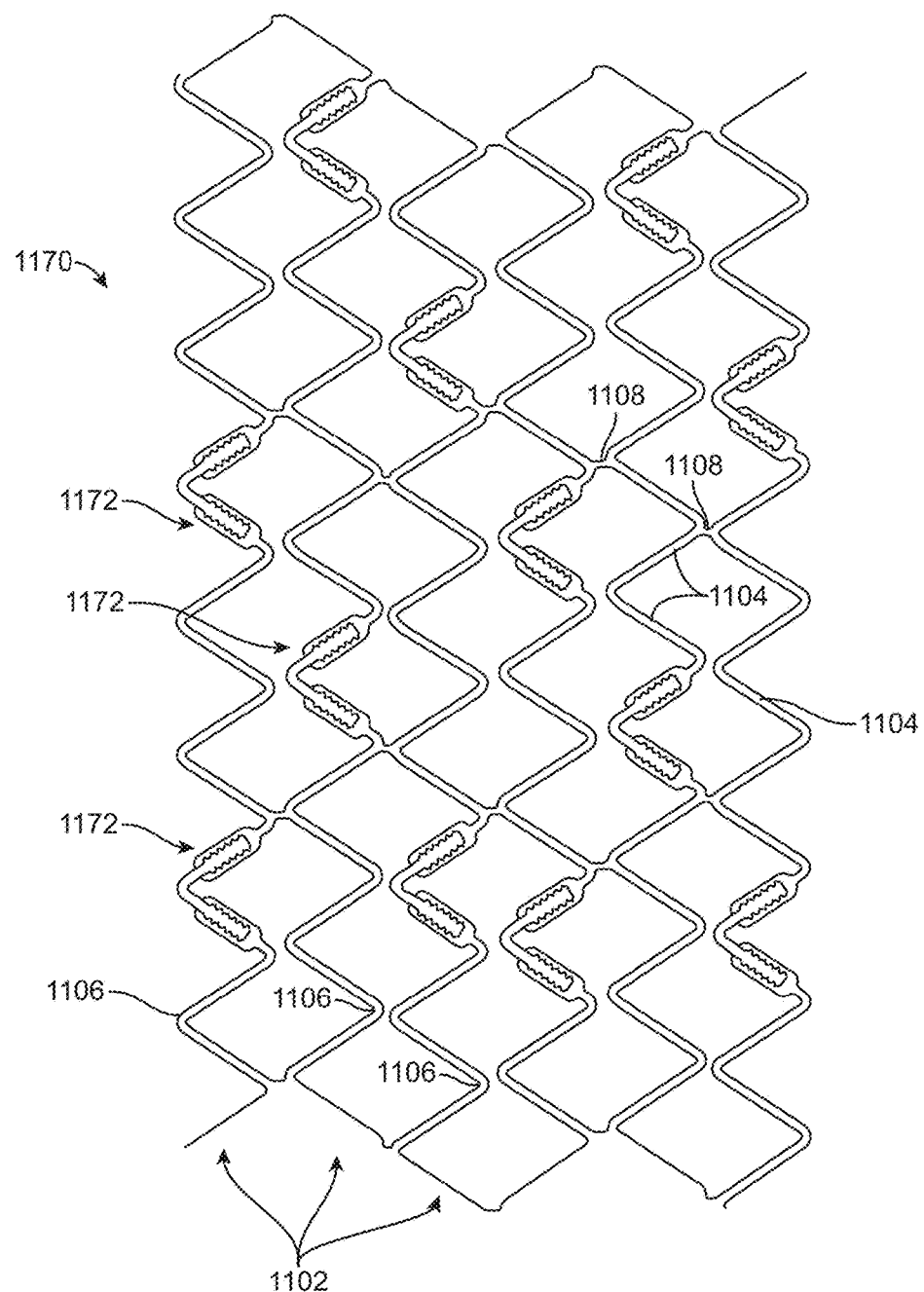
Figures 16B, 16I:
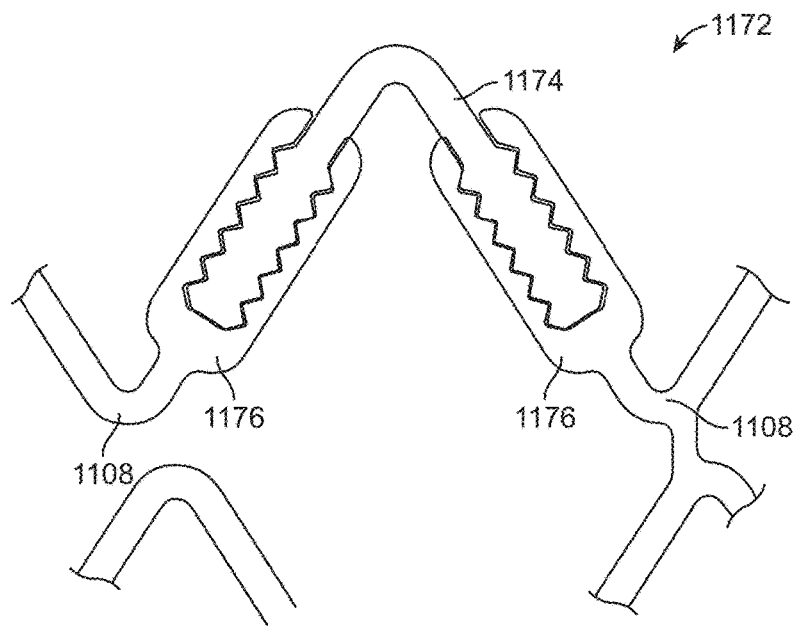
Figures 16C, 16I:
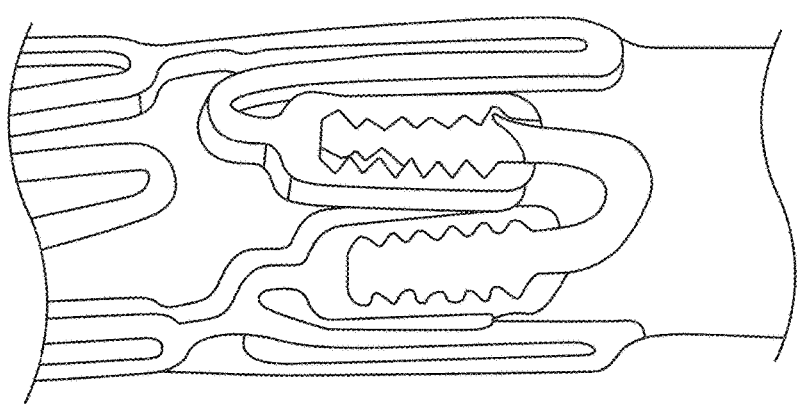

A variety of different overlapping gap structures are illustrated in FIGS. 16I-13A through 13F. A separation region 1140 comprising curved struts with overlapping ball termini is illustrated in FIG. 16I-13A. A separation region 1142 comprising parallel struts having tapered ends is shown in FIG. 16I-13B. A separation region 1144 comprising struts having opposed ratcheting surfaces is shown in FIG. 16I-13C. A separation region 1146 comprising simple curved struts which loosely interlock is shown in FIG. 16I-13D. A separation region 1148 comprising hooked or curved ends on strut segments which interlock is shown in FIG. 16I-3E. The interlocking ends of separation region 1148 will generally permit separation preferably in a radial direction and not in an axially direction as described previously with respect to other embodiments of the separation regions, but can in some cases separate in both. A separation region 1150 with filler struts increasing the coverage and the resulting gap is shown in FIG. 16I-13F.

Referring now to FIGS. 16I-14A and 14B, a separation region 1154 comprising overlapping, offset strut segments can be left free to allow the segments to slide relative to each other as the scaffold is expanded, as shown in FIG. 16I-14A. Alternatively, a sleeve 1156 may be formed over the parallel strut segments, as shown in FIG. 16K-14B. Alternatively, an adhesive material can hold the segments together during expansion (or deployment) from a crimped configuration to an expanded larger configuration. The material is usually temporary degrading over a period ranging from expansion of the stent to after expansion of the stent, typically in a time period ranging from 30 days to 6 months.

While the gap structures of the present invention have been illustrated primarily in the strut regions of the scaffold, they may also be formed in the crown regions. For example, as shown in FIG. 16I-15A, a separation region 1160 may comprise a pair of nested, J-shaped strut ends which together form a crown having a gap therein. Such a nested structure will help keep the struts together as the scaffold is being radially expanded but will allow the struts (crowns) to at least partially separate (or completely separate) in order to enhance compliance of the scaffold after expansion. Optionally, as shown in FIG. 16I-15B, a sleeve 1162 may be placed over the nested crown 1160 in order to enhance the strength of the crown regions as the scaffold is expanded or to enhance strength after expansion. The sleeve will typically be biodegradable so that the separation region allows the strut ends to move relative to each other after the sleeve degrades.

Referring now to FIGS. 16I-16A through 16C, scaffolds 1170 may be formed with separation regions in the form of biodegradable bridge elements 1172 within the crowns of a circumferential ring. In particular, as shown in FIG. 16I-16B, a biodegradable bridge region 1174 may be secured to attachment structures 1176 on adjacent structures of a crown (or although not illustrated, a strut). The bridge element 1174 thus forms a biodegradable crown 1172 in the circumferential ring 1102 of the scaffold 1170. The "crown" bridge 1172 will thus be present as the scaffold is radially expanded and will provide hoop strength and crush resistance in the period following implantation. The degradable bridge 1172 will, however, lessen in strength over time and eventually fully degrade, enhancing the compliance of the scaffold 1170 in order to "uncage" the scaffold after implantation. FIG. 16I-16C is an image of the scaffold 1170 which has been fabricated by the methods of the present invention. The bridging elements as describes previously can contain the ends of the patterned stent structure or be contained within or attached as a butt joint. FIG. 16I-16A is another example of attaching bridging elements to the usually non-degradable frame, providing discontinuities when the degradable bridging element degrade, uncaging the ring and the stent.

Figure 17:
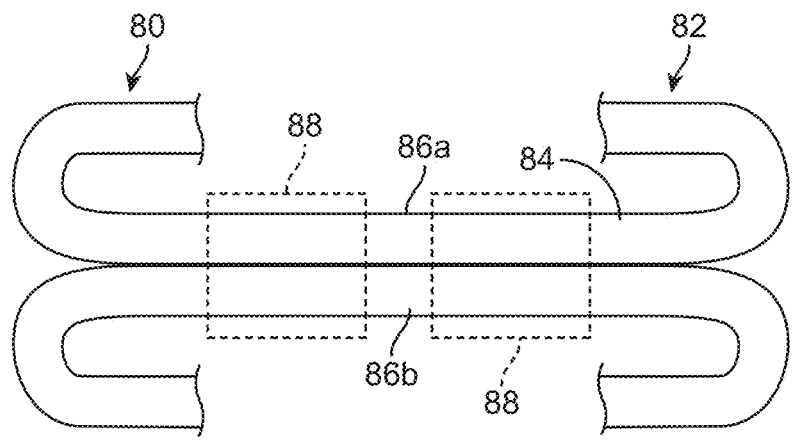
FIG. 17 illustrates a further example of a separation region which may be located between a pair of adjacent circumferential rings in the circumferential scaffolds of the present invention.

Referring now to FIG. 17, serpentine rings 80 and 82 may be formed with a bifurcated joint 84 having an upper element 86 joined to one end of the rings and a lower element 86b attached to the other end of the rings. The joint is held together by degradable constricting elements 88, which may be sleeves, coils, rivets, or any of the other elements described herein which erode or fatigue over time in response to the endoluminal environment and/or the application of external energy.

Figure 18:
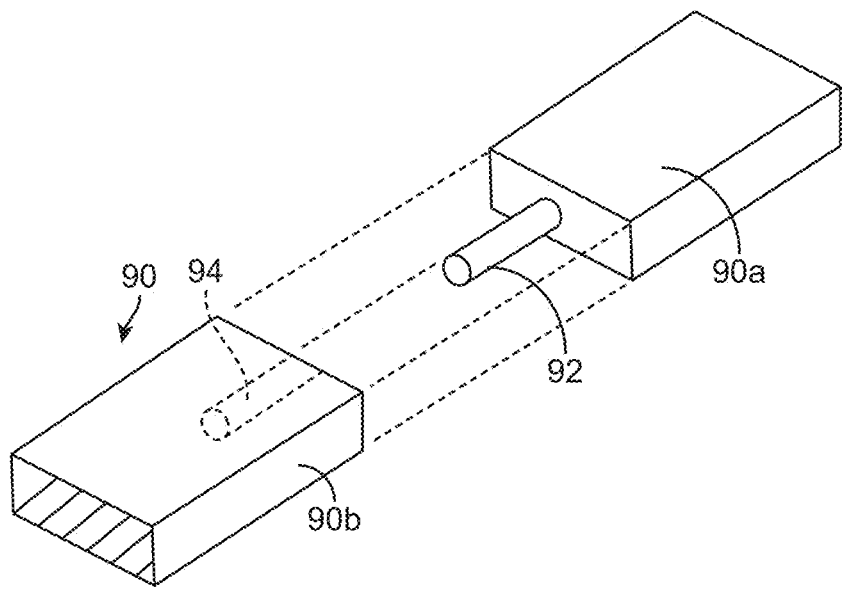
FIG. 18 illustrates the optional use of an alignment pin in a separation region in accordance with the principles of the present invention.

As shown in FIG. 18, the butt joints described above may include a pin received on one segment 90a of a strut 90 which is received in a receptacle 94 received in the other segment 90b of the strut. The pins help maintain structural integrity of the joint prior to breaking of the adhesive or other element holding the ends together.

Figure 19:
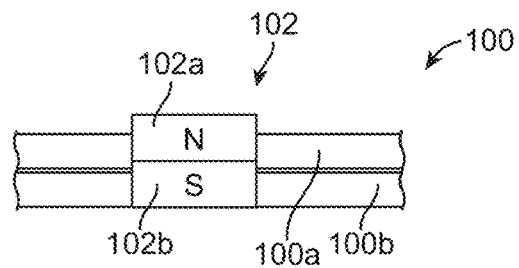
FIG. 19 illustrates a magnetically joined separation region for use in the circumferential rings of the present invention.

Referring now to FIG. 19, as alternatives to adhesives and other biodegradable elements which can hold pre-formed separated segments of the circumferential scaffold together, the present invention may use Magnets. For example, in a bifurcated joint 102 similar to that illustrated in FIG. 17, a magnet 102 having a north pole 102a on an upper element 100 and a south pole of the magnet 102b on the lower segment of the joint. The magnets may comprise high flex magnets of the type which can resist substantial forces, including the forces of expanding the circumferential scaffold. The magnets, however, can be released by application of a greater external magnetic field, for example, from an MRI unit, to release the segments and open the rings of the circumferential scaffold.

Figure 20:
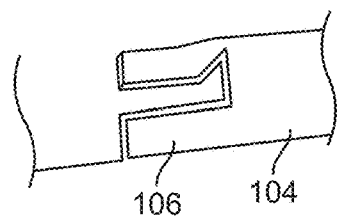
FIG. 20 illustrates an alternative example of connection for a separation region in a strut in accordance with the principles of the present invention.
Figure 21:
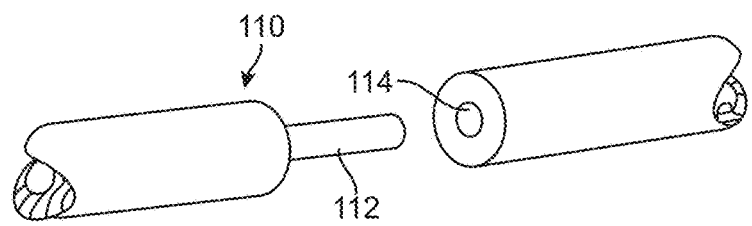
FIG. 21 illustrates an example of an alignment pin in a tubular strut structure in accordance with the principles of the present invention.

FIG. 20 illustrates a different key and lock junction 106 in the strut 104 which has less stress area and therefore allows the stent scaffold to expand while maintaining its structural integrity to provide strength.

The circumferential scaffolds of the present invention may be formed from tubular elements, such as strut 110, and the tubular elements may include pins 112 which can be received in the lumens or receptacles 114 of an adjacent strut segment. This facilitates having a structural integrity for the stent to have sufficient strength upon expansion.

One skilled in the art can appreciate that the location, number, and distribution of said breakage sections is configured to allow the stent prosthesis to be deployed to a larger configuration, to have a structural integrity in the expanded configuration, and to sufficient strength to support a body lumen. This includes breakage sections (or separation regions) on at least some rings, and/or hinges, and/or struts.

III. Non-Degradable Prosthesis (or Degradable with High Crush Resistance) Having Rings with Constrained Hinges Referring now to FIG. 22, adjacent struts 40 of a serpentine ring 14 may be constrained by a sleeve 118 or similar biodegradable constraint. The biodegradable constraint will hold the adjacent strut segments together during expansion of the circumferential scaffold. After implantation, the sleeve 118 or other constraint will erode or degrade over time, and the struts 42 will be freed to expand, thus uncaging or un-jailing the prosthesis. In another example, an adhesive joining the two adjacent elements holding them together after deployment of the stent, then the adhesive degrades freeing the two adjacent element to further expand, uncaging the vessel.

Figure 22:
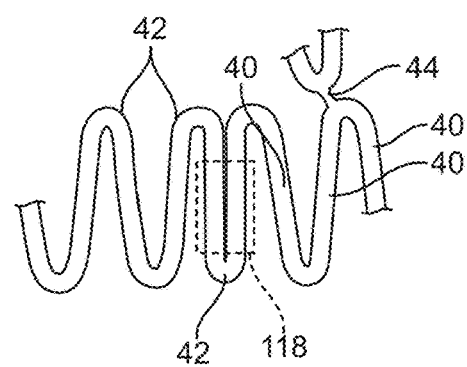
FIG. 22 illustrates the use of a sacrificial constraint such as a sleeve for constraining a hinge region in the circumferential ring in accordance with the principles of the present invention.
Figure 22A:
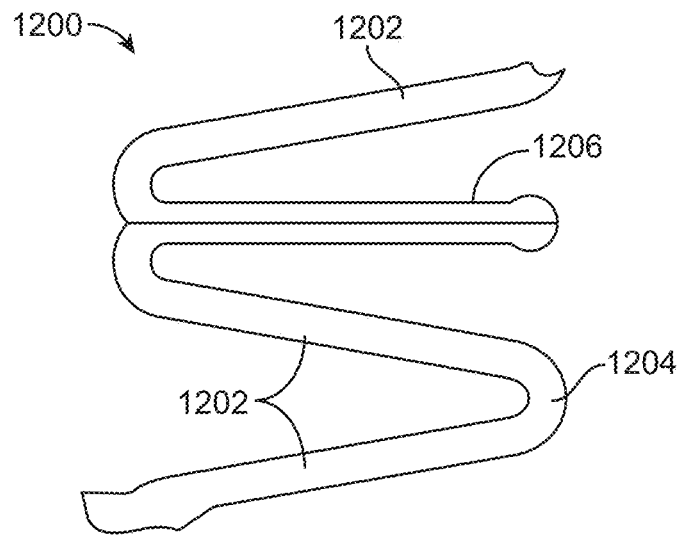
FIG. 22A and FIG. 22B illustrate a further type of separation region where a pair of adjacent struts in a circumferential ring are separated and collapsed in parallel and optionally held together with a degradable sleeve.
Figure 22B:
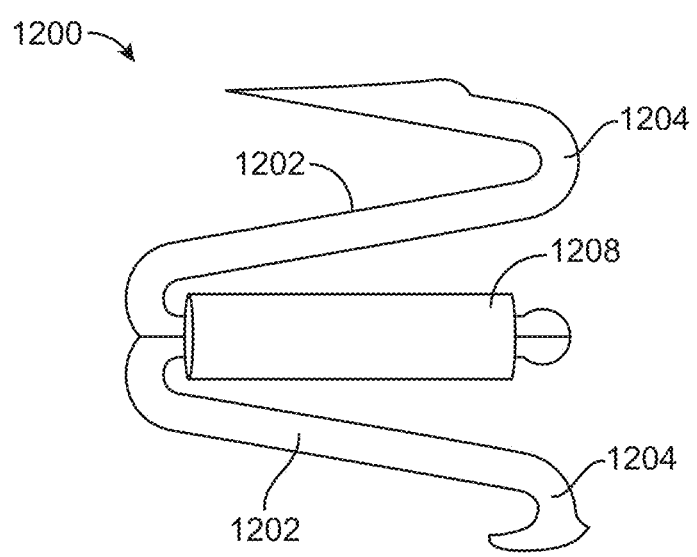

In a variation of the constrained hinge of FIG. 22, a separation region 1200 may be formed between adjacent struts 1202 of the serpentine ring of a scaffold, as shown in FIG. 22A. The adjacent struts 1202 are generally joined by a conventional crown 1204, as illustrated. At certain locations in the ring, however, the adjacent struts may be collapsed and split apart as shown at 1206. The split allows the serpentine ring to open to form a gap, as described with prior embodiments, as the scaffold is expanded. Optionally, the split structure 1206 may be covered with a biodegradable sleeve 1208, as shown in FIG. 22B. With the sleeve in place, the split strut 1206 will not separate until after the sleeve has degraded. Alternatively, an adhesive material is used to join the adjacent 1206 struts to hold the segments together upon expansion of the stent or in the expanded stent configuration. The adhesive degrades over time freeing the segments and uncaging the ring as a result of creating or forming one or more discontinuities along the path of the circumferential ring.

Figure 23A:
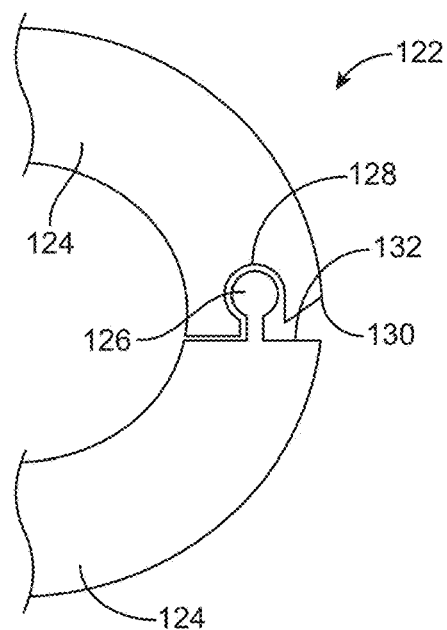
FIGS. 23A and 23B illustrate an example of a joint or separation region placed in a hinge of a circumferential ring in accordance with the principles of the present invention.
Figure 23B:
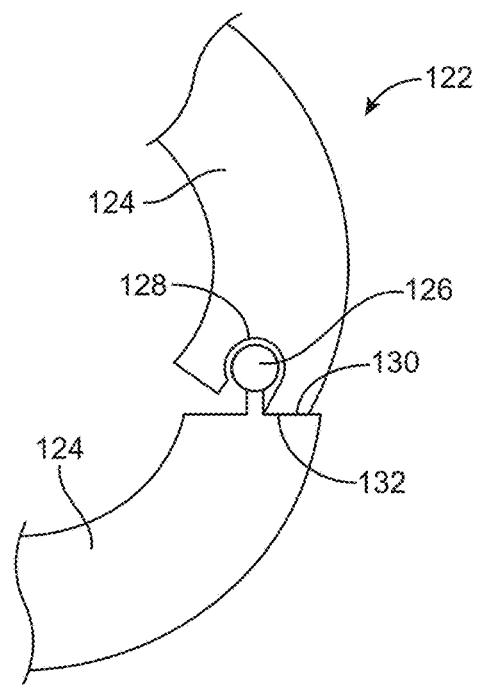

IV. Non-Degradable Prosthesis (or Degradable Having High Crush Resistance) Having Rings with Active Joints Referring now to FIGS. 23A and 23B, an active hinge 122 may be formed which joins struts 124 on a pivot pin 126. The pivot 126 is patterned in one end of a lower port strut segment and received in a slot 128 in the upper strut segment. The slot is asymmetric and has a face 130 which is angled relative to a lower face 132 formed adjacent the pivot pin 126. After the circumferential scaffold including such active joints is expanded, the joint will be compressed by the body lumen so that it can assumes the configuration of FIG. 23A. Over time, however, as luminal remodeling expands the luminal diameter, the joint will be able to open, as illustrated in FIG. 23B, thus lessening any jailing or caging as a result of the prosthesis. In one example, the active hinge is coated with a polymeric material, or with an adhesive material to hold the active hinge in place upon deployment. The active hinge material can also or instead be placed in the straight section of the ring on a strut.

Figure 23C:
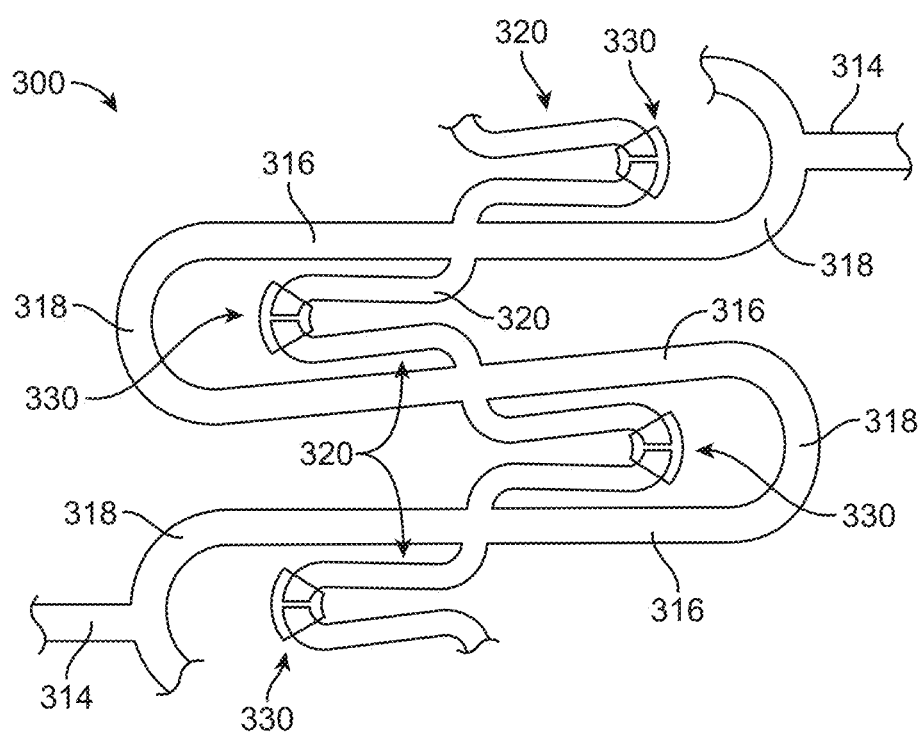
FIGS. 23C and 23D illustrate example of a joint or separation region placed in a hinge with supporting features of a circumferential ring in accordance with the principles of the present invention.
Figure 23D:
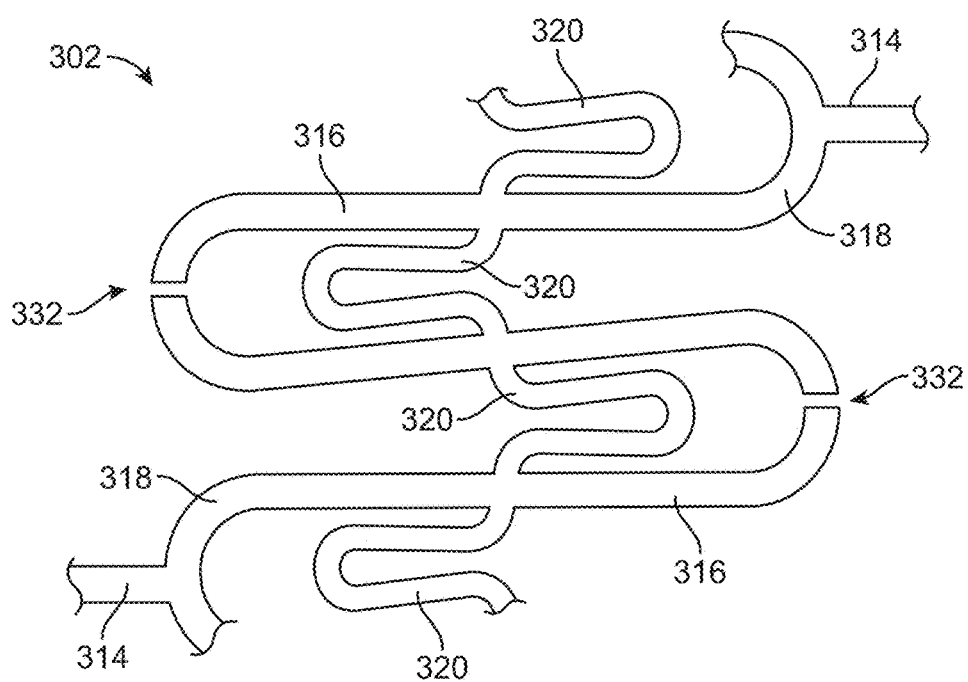

Referring now to FIGS. 23C and 23D, active hinges with supporting features having separation regions are described. Active hinges with supporting features are described in US2008/0177373 (U.S. application Ser. No. 12/016,077) commonly assigned with the present application, the full disclosure of which is incorporated herein by reference.

A portion of a first serpentine ring 300 (FIG. 23C) and a second serpentine ring 302 (FIG. 23D) is joined by axial links 314 to adjacent serpentine rings (not shown). Each serpentine ring 300 comprises pairs of axial struts 316 joined by a hinge-like crown 318 at each end. A supporting feature 320 is disposed between at least some of the adjacent axial struts 316 and connected so that the feature will expand circumferentially as the struts separate as the serpentine ring 300 is expanded during deployment. The supporting features 20 are in a generally closed U-shaped configuration prior to expansion, as shown in FIGS. 23C and 23D, and open into a shallow V-shape along with the opening of the axial struts 316 about the crowns 318 during radial expansion of the serpentine rings 300. Supporting features can take a variety of shapes, contact points, locations, etc., as described in the application above. Supporting features 320 enhance the crush resistance of the stent after radial expansion, help resist recoil, and provide additional area for supporting the vascular or other luminal wall and optionally for delivering drugs into the luminal wall.

While the supporting features enhance the crush resistance, they also enhance the hoop strength which contributes to the undesirable caging effect discussed in detail elsewhere in this application. In order to control the hoop strength, without significantly diminishing the crush resistance, separation regions can be formed in crowns of the supporting features 320 (FIG. 23C) and/or the serpentine ring (FIG. 23D) or in the struts. As shown in FIG. 23C, the crowns of some or all of the supporting features may have separation regions 330. As illustrated, the separation regions 330 comprise a break or discontinuity in the crown which is immobilized by a degradable sleeve as an example formed over the opposed surfaces of the adjacent crown segments, but these separation regions could have any of the structures described elsewhere herein for separation within the vascular or other physiologic environment. As shown in FIG. 23D, separation regions 332 are in some or all of the crowns 316 of serpentine ring 300 (they can also be in struts). As illustrated, the separation regions 332 comprise a break or discontinuity in the crown which is immobilized by an adhesive, cement, or polymer between the opposed surfaces of the adjacent crown segments or on the surfaces, but these separation regions could have any of the structures described elsewhere herein for separation within the vascular or other physiologic environment. In other examples, the separation regions can also or instead be formed on the struts of the supporting features 320.

Figures 1, 23E:
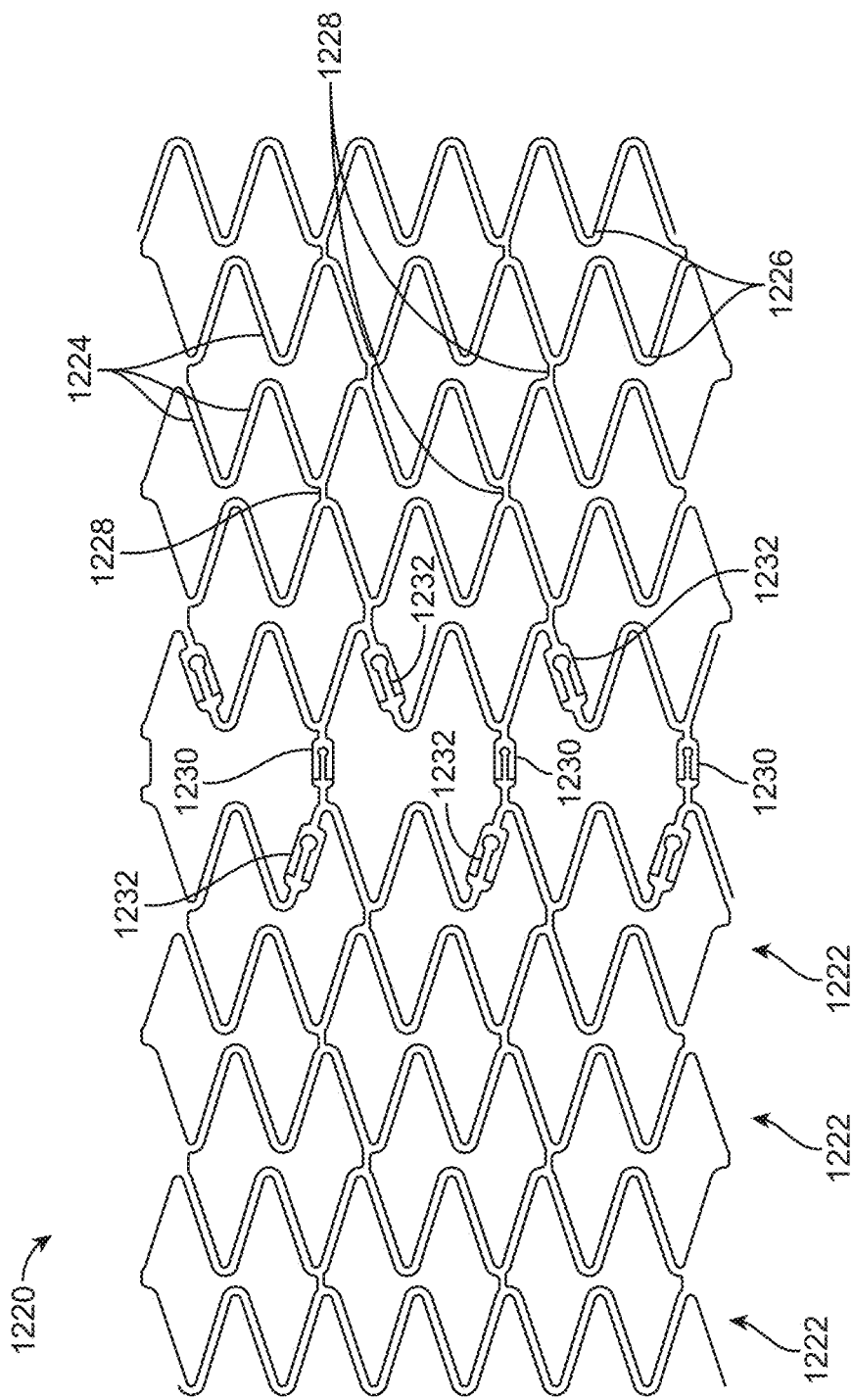
Figures 2, 23E:
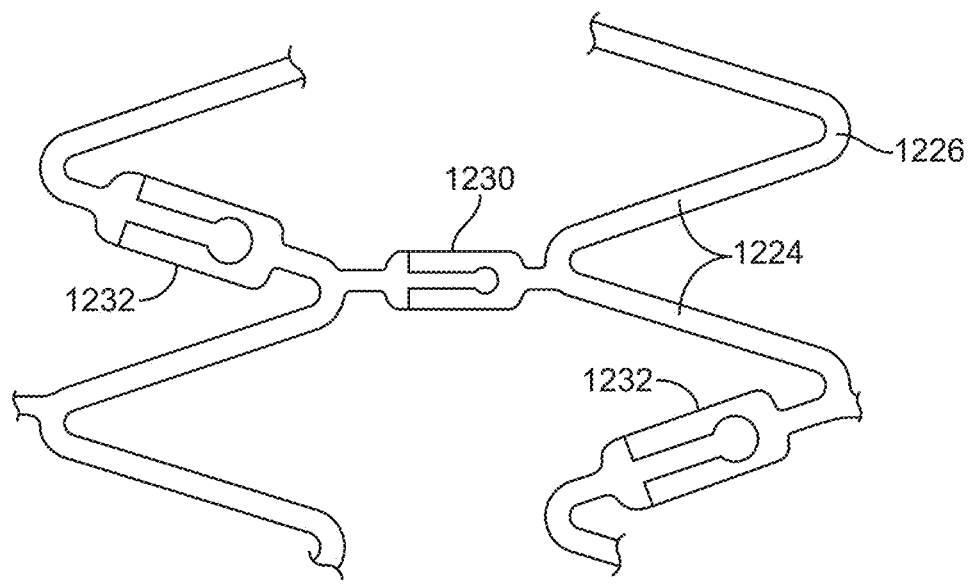
Figures 3, 23E:
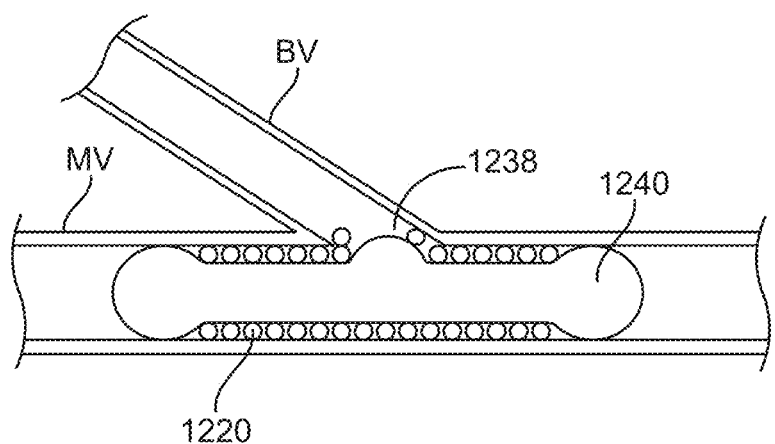

As described, the separation regions of present invention have been employed to enhance compliance (radial strain) of a stent or other luminal prostheses after implantation in a blood vessel or other body lumen such as the annulus of a valve. As shown in FIGS. 23E-1 through 23E-3, however, the separation regions can provide other utilities. For example, a scaffold in 1220 comprising circumferential rings 1222 including struts 1224 and crowns 1226 may be modified with separation regions to enhance opening for access to bifurcations in blood vessels. While the majority of circumferential rings 1222 in scaffold 1220 are joined by non-separating axial links 1128, in at least one location within the stent, adjacent circumferential rings 1222 may be joined by axial links 1230 comprising separation regions. Usually, the circumferential rings on each side of the separating axial links 1230 will also have separation regions 1232 present in at least some locations. In this way, as shown in FIG. 23E-3, after the scaffold 1120 is placed in a main vessel (MV) adjacent to a branch vessel (BV), expansion of a balloon 1240 within the scaffold 1120 will cause preferential opening 1238 over a middle section of the stent which is aligned with the branch vessel. Such preferential opening will occur because the balloon is able to separate the axial links 1230 which are type which preferentially separates in the radial direction (as previously described herein). Additionally, the circumferential rings immediately adjacent to the opening 1238 will also be able to partially expand into the opening by virtue of the separation regions 1232 in those adjacent circumferential rings.

In some examples the shapes of the reinforcing elements can be substantially round (solid round wire or hollow round wire), rectangular, square, egg shaped, or other shapes and geometries. The size of the reinforcing elements in one example are substantially the same size/geometry as the hinges and/or struts they are couple to, and/or smaller size/geometry, and/or or larger size/geometry. In one example, the ends of the reinforcing elements are atraumatic, and/or smooth, and/or have bulbous shape or rounded shape or larger cross sectional area compared to attached or adjacent structural element. In one example the reinforcing elements surface finish is similar to polished vascular metallic stents. In another example, the surface finish is textured surface. In a preferred example, the stent prosthesis is a coronary stent prosthesis. In another example, the stent prosthesis is a vascular stent prosthesis. In another example the stent prosthesis is a non-vascular stent prosthesis.

V. Materials of Construction

Typically, In one example, the non-degradable materials will comprise, or formed from, metals and metal alloy, such as stainless steel, such as 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hatelloy C276, Monel 400, Nickelvac 400, and the like); nickel-cobalt-chromium-molybdenum alloy such as MP35-N; nickel-molybdenum alloy; platinum enriched stainless steel; combination thereof; or the like, and other malleable metals, or plastically deformable when expanded from a crimped configuration to an expanded configuration, of a type commonly employed in stent and prosthesis manufacture. In other examples, however, the non-degradable material may comprise a non-degradable polymer, such as polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; or other materials. In still other examples, the non-degradable material may comprise an elastic metal, such as a shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based alloy such as Fe—Mn—Si; copper-based alloy such as Cu—Zn—Al and Cu—Al—Ni; poly(ε-caprolactone)dimethacrylate; PVDF/PMMA; PVDF/PVA; PLA/PVAc; or other, or the like.

In an example of metal and metal alloy comprise, or composed from: as stainless steel, such as 304V, 304L, and 316LV stainless steel; steel alloy such as mild steel; cobalt based alloy such as cobalt chrome; L605, Elgiloy, Phynox; platinum based alloy such as platinum chromium platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy; shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hatelloy C276, Monel 400, Nickelvac 400, and the like); nickel-cobalt-chromium-molybdenum alloy such as MP35-N; nickel-molybdenum alloy; tungsten or their alloy; platinum enriched stainless steel; magnesium; magnesium alloy with less than 20% zinc or aluminum by weight, without or with one or more impurities of less than 3% iron, silicone, manganese, cobalt, nickel, yttrium, scandium or other rare earth metal; zinc or its alloy; bismuth or its alloy; indium or its alloy, tin or its alloy such as tin-lead; silver or its alloy such as silver-tin alloy; cobalt-iron alloy; iron; iron containing alloys such as 80-55-06 grade cast ductile iron, other cast ductile irons, AISI 1010 steel, AISI 1015 steel, AISI 1430 steel, AISI 8620 steel, AISI 5140 steel, or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In an example of polymeric material comprises, or composed from: polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone;

polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; terpolymer, blends, mixes, or combination thereof of lactides, caprolactones, trimethylene carbonate, and or glycolides such as polylactide, poly(L-lactide), poly-DL-Lactide, polylactide-co-glycolide (e.g., poly(L-lactide-co-glycolide) with 85% L-lactide to 15% glycolide), copolymer of poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); combination thereof.

In some examples or embodiments, the scaffolds and other components of the stents and endoluminal prostheses may be coated for various purposes, including coating to prevent sharp metal edges, as described throughout this application, and/or where coating material comprises, or composed from: polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; terpolymer, blends, mixes, or combination thereof of lactides, caprolactones, trimethylene carbonate, and or glycolides such as polylactide, poly(L-lactide), poly-DL-Lactide, polylactide-co-glycolide (e.g., poly(L-lactide-co-glycolide) with 85% L-lactide to 15% glycolide), copolymer of poly(L-lactide-co-epsilon-caprolactone (e.g., weight ratio of from around 50 to around 95% L-lactide to about 50 to about 5% caprolactone; poly (L-lactide-co-trimethylene carbonate), polytrimethylene carbonate, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); combination thereof, or the like.

In one example, corrodible or degradable metallic or metallic alloy material comprising metal or metal alloy of Nickel; Cobalt; Tungsten and Tungsten alloys; Tungsten alloys of rhenium, cobalt, iron, zirconium, zinc, titanium; Magnesium, Magnesium alloy AZ31, magnesium alloy with less than 20% zinc or aluminum by weight, without or with one or more impurities of less than 3% iron, silicone, manganese, cobalt, nickel, yttrium, scandium or other rare earth metal; zinc or its alloy; bismuth or its alloy; indium or its alloy, tin or its alloy such as tin-lead; silver or its alloy such as silver-tin alloy; cobalt-iron alloy; iron; iron containing alloys such as 80-55-06 grade cast ductile iron, other cast ductile irons, AISI 1010 steel, AISI 1015 steel, AISI 1430 steel, AISI 8620 steel, AISI 5140 steel, or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In another example, suitable materials including suitable stent material including polymeric and metallic (degradable or non-degradable), adhesives, coatings, solder, sleeves, sealants, sealants, potting compounds, fixation materials, cement, energy fixation, elastomers and other type material, include but are not limited to: adhesives such as cyanoacrylate such as polyalkyl-2-cyanoacrylate, methyl-2-cyanoacrylate, ethyl-2-acrylate; n-butyl cyanoacrylate, 2-octyl cyanoacrylate, or others; gorilla glue; lysine based adhesive such as TissueGlu, Sylys Surgical Sealant, or others; fibrin glue; beeswax. Non-degradable adhesives, sealants, and potting compounds such as epoxy; epoxamine; UV-curable from Loctite, Dymax, Master Bond, or other; acrylic; silicone; hot melt; polyurethane; Degradable sleeve materials, stent material, and coatings such as polyester; polylactide and their copolymers and blends; copolymers of lactide, caprolactone, trimethylene carbonate, glycolide; poly(L-lactide), poly-DL-Lactide, polylactide-co-glycolide (e.g., poly (L-lactide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. Corrodible solder or fusible alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.51n4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as Bi57Sn42Ag1, Bi58Sn52, or others. Non-corrodible solder or fusible alloy such as gold or its alloy such as Au80Sn20, Au98Si2, Au87.5Ge12.5, Au82In18. Degradable and non-degradable polymers include: polyester; polylactide and their copolymers and blends; copolymers of lactide, caprolactone, trimethylene carbonate, glycolide; poly(L-lactide), poly-DL-Lactide, polylactide-co-glycolide (e.g., poly(L-lactide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. polyvinyl alcohol; polyvinyl acetate; ethylene-vinyl acetate (a hot-melt glue); phenol formaldehyde resin; polyamide such as nylon 12, nylon 6, nylon 6-6, or others; polyester resins; polyethylene (a hot-melt glue), UHMW, HDPE, LDPE, or others; polychloroprene; polyaryletherketone; polyetheretherketone; polypropylene; polystyrene; polyester; polyethylene terephthalate; polycarbonate; polysulfone; polyphenylsulfone; polyethersulpone, Ultem; polyetherimide; polyurethane; polyvinylchloride; PTFE; FEP; ETFE; PFA; PVDF; polyvinylchloride; acrylobutadiene styrene; polyacetal such as Delrin; polymethylmethacrylate; polystyrene; polyacrylamide, polyphenylsufide; PEBAX; and/or co-polymers, and/or combination thereof. Elastic non-absorbable polymeric or elastomers such as silicone rubber; C-flex; poly(n-butylmethacrylate); poly(n-butylmethacrylate) blended with poly(methamethacrylate), Poly(hexyl methacrylate), and polyvinylpyrrolidone; Kraton; poly(styrene-ethylene/butylene-styrene) (SEBS); poly (styrene-ethylene/propylene-styrene) (SEPS), poly(acrylic acid-b-styrene-b-isobutylene-b-styrene-b-acrylic acid; poly (styrene-b-isobutylene-b-styrene); polybutadiene; PVDF-HFP poly(vinylidene fluoride-hexafluorpropylene); polyvinylpyrrolidone; poly(ethylene-co-vinyl acetate); phosphorylcholine; PEBAX; polyurethane elastomers; Tecoflex; Biomer; Pellethane; corethane; silicone rubber; rubbers; elastomers; blends; copolymers; combination thereof; or the like. Non-corrodible elastic metal or metal alloys such as shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based alloy such as Fe—Mn—Si; copper-based alloy such as Cu—Zn—Al and Cu—Al—Ni; or the like. Metals or metal alloys that have high initial strength and weaken over time include Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230. Non-corrodible (non-degradable) metals or metal alloys such as conventional titanium alloys such as Ti6Al4V, Ti5Al2.5Sn, or Ti-10V-Fe-3Al; stainless steel such as SAF2507; platinum metal and its alloys; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy; shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hatelloy C276, Monel 400, Nickelvac 400, and the like); nickel-cobalt-chromium-molybdenum alloy such as MP35-N; Nickel Alloys such as Ni21Cr17Mo or Haynes 230; or other; nickel-molybdenum alloy; platinum enriched stainless steel; combination thereof; or the like. Corrodible metals or metal alloys (degradable) include nickel, cobalt, tungsten; tungsten alloys of rhenium, cobalt, iron, zirconium, zinc, titanium; magnesium, magnesium alloys, magnesium alloy AZ31, magnesium alloy with less than 20% zinc or aluminum by weight, without or with one or more impurities of less than 3% iron, silicone, manganese, cobalt, nickel, yttrium, scandium or other rare earth metal, AZ31B or MG11li5Al1Zn0.034Sc (LAZ1151); zinc or its alloy such as zinc alloys such as Zn5al, Zn10Al, Zn18Al, Zn30Al; bismuth or its alloy; indium or its alloy, tin or its alloy such as tin-lead, Sn3.9Ag0.6Cu, Sn-3.8Ag-0.7Cu, SnPb, or SnPbAt; silver or its alloy such as silver-tin alloy; cobalt-iron alloy; iron or its alloys such as 80-55-06 grade cast ductile iron, other cast ductile irons, AISI 1010 steel, AISI 1015 steel, AISI 1430 steel, AISI 8620 steel, AISI 5140 steel, Fe29.7Mn8.7Al1C, 30HGSA alloy steel, 4140, C45 steel, Fe36Ni, low carbon steel or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like. Other non-degradable polymeric material includes Parylene, and C-flex.

In further examples or embodiments, the body of the device, or the stent, or the material comprising the body of the device, or the material comprising one or more layers of the body of the device, comprises one or more biologically active agents. In some embodiments, the biologically active agent(s) are selected from the group consisting of anti-proliferative agents, anti-mitotic agents, cytostatic agents, anti-migratory agents, immunomodulators, immunosuppressants, anti-inflammatory agents, anticoagulants, anti-thrombotic agents, thrombolytic agents, anti-thrombin agents, anti-fibrin agents, anti-platelet agents, anti-ischemia agents, anti-hypertensive agents, anti-hyperlipidemia agents, anti-diabetic agents, anti-cancer agents, anti-tumor agents, anti-angiogenic agents, angiogenic agents, anti-bacterial agents, anti-fungal agents, anti-chemokine agents, and healing-promoting agents. In certain embodiments, the body of the device comprises an anti-proliferative agent, anti-mitotic agent, cytostatic agent or anti-migratory agent. In further embodiments, the body of the device comprises an anticoagulant, anti-thrombotic agent, thrombolytic agent, anti-thrombin agent, anti-fibrin agent or anti-platelet agent in addition to an anti-proliferative agent, anti-mitotic agent, cytostatic agent or anti-x migratory agent. It is appreciated that specific examples of biologically active agents disclosed herein may exert more than one biological effect.

Examples of anti-proliferative agents, anti-mitotic agents, cytostatic agents and anti-migratory agents include without limitation inhibitors of mammalian target of rapamycin (mTOR), rapamycin (also called sirolimus), deuterated rapamycin, TAFA93, 40-O-alkyl-rapamycin derivatives, 40-O-hydroxyalkyl-rapamycin derivatives, everolimus {40-O-(2-hydroxyethyl)-rapamycin}, 40-O-(3-hydroxy)propyl-rapamycin, 40-O-[2-(2-hydroxy)ethoxy]ethyl-rapamycin, 40-O-alkoxyalkyl-rapamycin derivatives, biolimus {-40-O-(2-ethoxyethyl)-rapamycin}, 40-O-acyl-rapamycin derivatives, temsirolimus {-40-(3-hydroxy-2-hydroxymethyl-2-methylpropanoate)-rapamycin, or CCI-779}, 40-O-phospho-containing rapamycin derivatives, ridaforolimus (40-dimethylphosphinate-rapamycin, or AP23573), 40(R or S)-heterocyclyl- or heteroaryl-containing rapamycin derivatives, zotarolimus {-40-epi-(N1-tetrazolyl)-rapamycin, or ABT-578}, 40-epi-(N2-tetrazolyl)-rapamycin, 32(R or S)-hydroxy-rapamycin, myolimus (32-deoxo-rapamycin), novolimus (16-O-desmethyl-rapamycin), AP20840, AP23464, AP23675, AP23841, taxanes, paclitaxel, docetaxel, cytochalasins, cytochalasins A through J, latrunculins, and salts, isomers, analogs, derivatives, metabolites, prodrugs and fragments thereof. The IUPAC numbering system for rapamycin is used herein. In certain embodiments, the body of the device comprises myolimus or novolimus. Other drugs include vasoactive agents including vas-dilators and vaso-constrictors, comprising for example, Methergin, acetylcholine, and Nitroglycerine, their analogues, derivatives, and metabolite, to name a few.

Other specific drugs suitable for use on the scaffolds and in the methods of the present invention are described in commonly assigned U.S. Pat. No. 9,119,905, the full disclosure of which is incorporated herein by reference.

VI. Stents Having Helical Backbones

Figure 36:
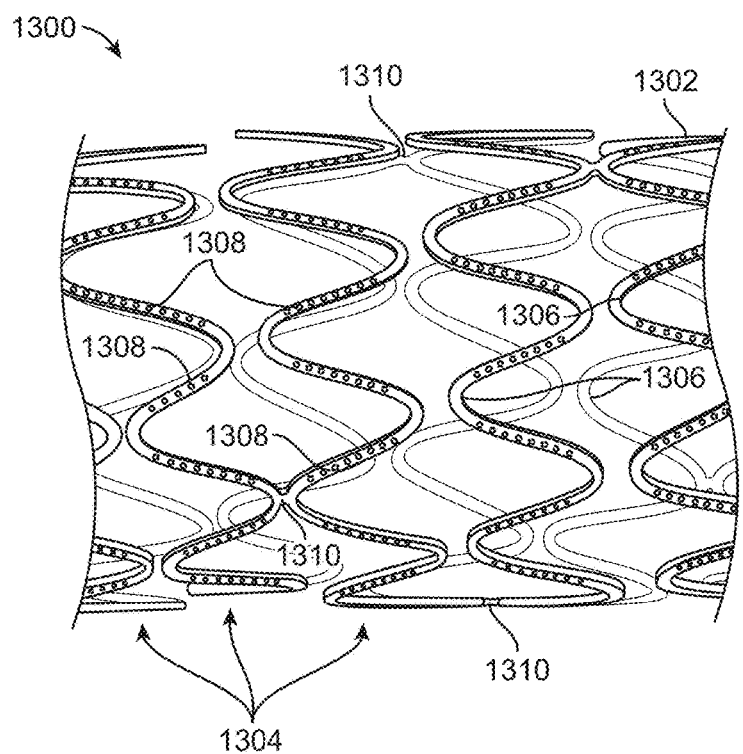
FIG. 36 illustrates a helical stent structure found in the prior art and having a helically wound serpentine backbone (rings).

Referring now to FIG. 36, a prior art helical stent 1300 comprises a scaffold having a helical backbone 1302. The helical backbone 1302 comprises a plurality of adjacent turns (rings) 1304 where individual turns comprise crowns 1306 joined by struts 1308. In prior art stents, at least some of the adjacent turns in such helical stents may joined by permanent axial connectors 1310. The helical backbone is typically formed by bending wire around a mandrel, and the axial connectors 1310 are typically formed by welding or otherwise fusing the adjacent turns together at points where opposed crowns 1306 lie immediately adjacent to one another.

Figure 37:
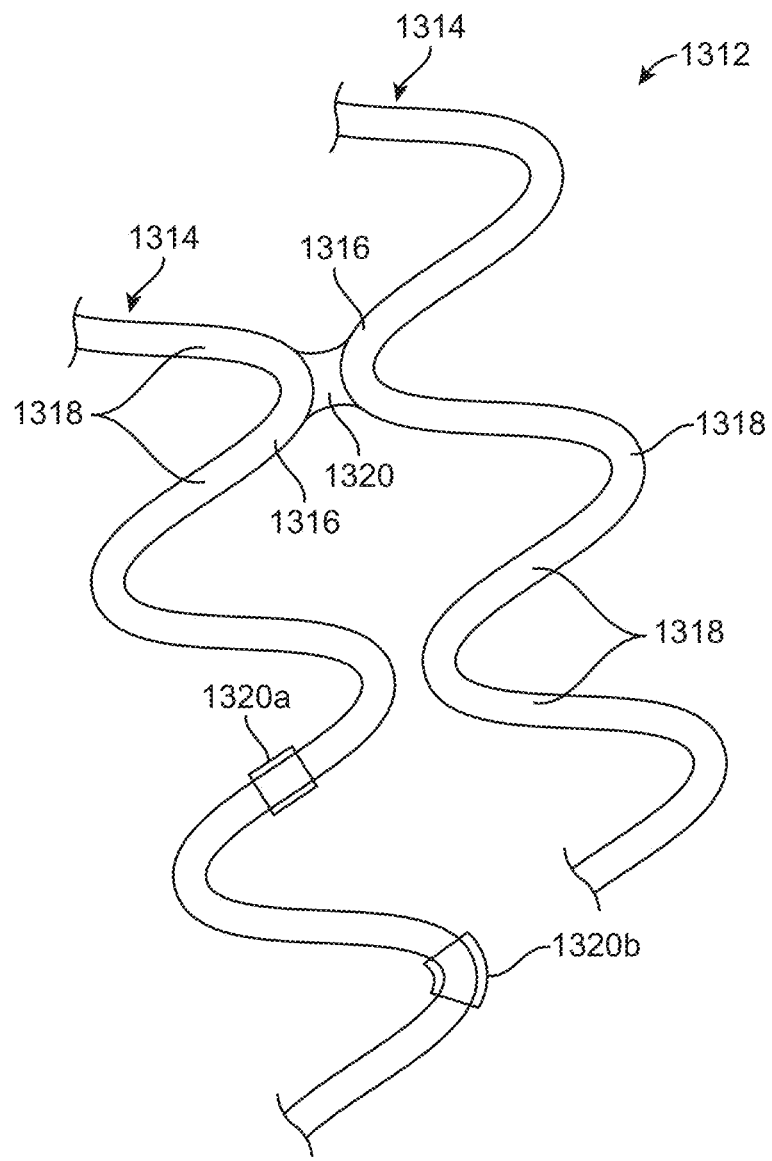
FIG. 37 illustrates a first example or embodiment of a stent with a helical backbone (rings) including separation region between individual turns of the stent rings constructed in accordance with the principles of the present invention, additionally including a separation regions in the crown and strut of a ring.

Referring now to FIG. 37, a helical stent scaffold 1312 constructed in accordance with the principles of the present invention comprises a plurality of turns (rings) 1314 having crowns 1316 and struts 1318. Adjacent crowns may be connected by a separation region 1320 which may be formed as any of the separation regions described elsewhere in this application. Conveniently, when convex regions of axially opposed crowns 1316 lie closely adjacent to each other, as shown in FIG. 37, the crowns may be joined by a biodegradable adhesive, a link, or other material 1316 or structure which bridges the gap therebetween. The biodegradable adhesive, a link, or other material 1316 will be configured to separate after implantation of the stent scaffold 1312 by any of the separation mechanisms described elsewhere herein. Alternatively or in addition to separation regions 1320 between successive turns 1314, the stent scaffold 1312 may have separation regions 1320a and 1320b in at least some of the struts 1318 and crowns 1316, respectively. Depending on the particular pattern of separation regions 1320, 1320a, and 1320b which is selected, the stent scaffold 1312 may be able to expand and contract by forming discontinuities in the separation regions located on at least some circumferential turns (in struts or crown regions), and/or deformation of the rings, e.g. opening of the crowns, and/or by unwinding of the helical backbone of the stent.

Figure 38:
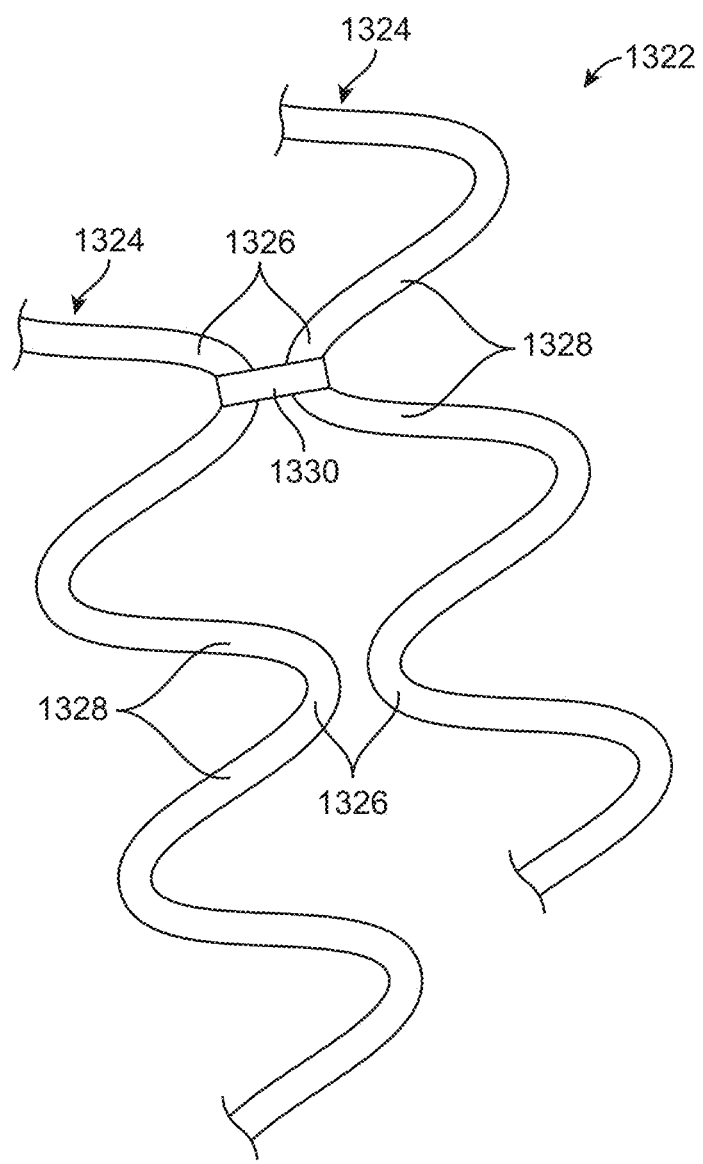
FIG. 38 illustrates a second example or embodiment of a stent with a helical backbone including separation regions (not illustrated) within individual turns of the stent rings constructed in accordance with the principles of the present invention, and a separation region between turns.

Referring now to FIG. 38, another helical stent scaffold 1322 may comprise a plurality of turns (rings) 1324 including crowns 1326 and struts 1328 where adjacent crowns 1326 may be joined a bridging segment 1330 which wraps around the crowns. Such bridging segment may be formed from a bio-degradable or other frangible material as described elsewhere herein in accordance of the principles of the present invention. As with stent scaffold 1312, stent scaffold 1322 may have additional separation regions in at least some of the struts and crowns (not illustrated), respectively. Depending on the particular pattern of separation regions which is selected, the stent scaffold 1322 may be able to expand and contract by forming discontinuities in the separation regions located on at least some circumferential turns (in struts or crown regions), and/or deformation of the rings, e.g. opening of the crowns, and/or by unwinding of the helical backbone of the stent.

Figure 39:
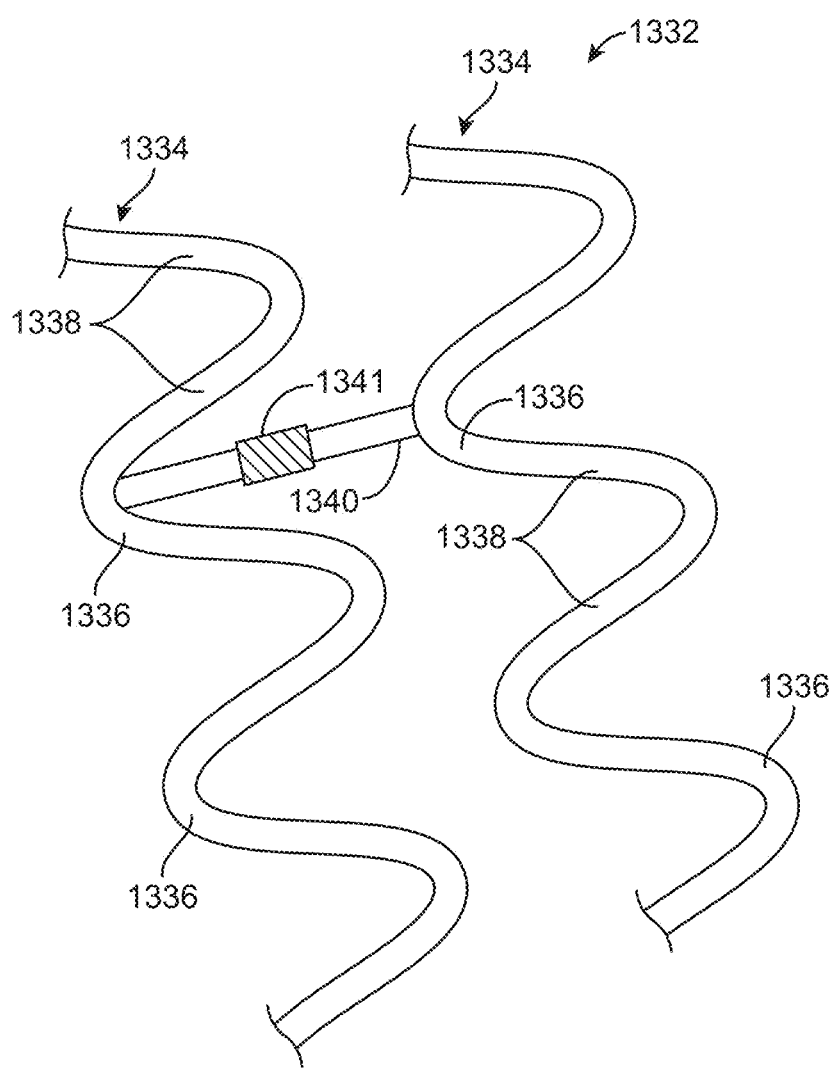
FIG. 39 illustrates a third example or embodiment of a stent with a helical backbone including separation region between individual turns of the stent constructed in accordance with the principles of the present invention.

As shown in FIGS. 36-38, the crowns of each successive turn (rings) of the scaffold are "out-of-phase" so that the convex surfaces of at least most of the crowns are axially opposed and in contact or separated by a very short gap. Referring now to FIG. 39, a helical stent scaffold 1332 may comprise adjacent turns 1334 where the crowns 1336 and struts 1338 are "in phase" so that an axial connector 1340 may span between a convex side of one crown and extend into a concave side of the adjacent crown. The connector 1340 comprises a separation region 1341 which may be formed as any of the separation regions described elsewhere in the present application. However, the separation region 1341 typically will not be sufficient to uncage the circumferential turns (or rings), but rather having one or more separation regions in the strut and/or crown regions (not shown) of each of the turns are needed to circumferentially uncage the turns (rings).

Figure 40:
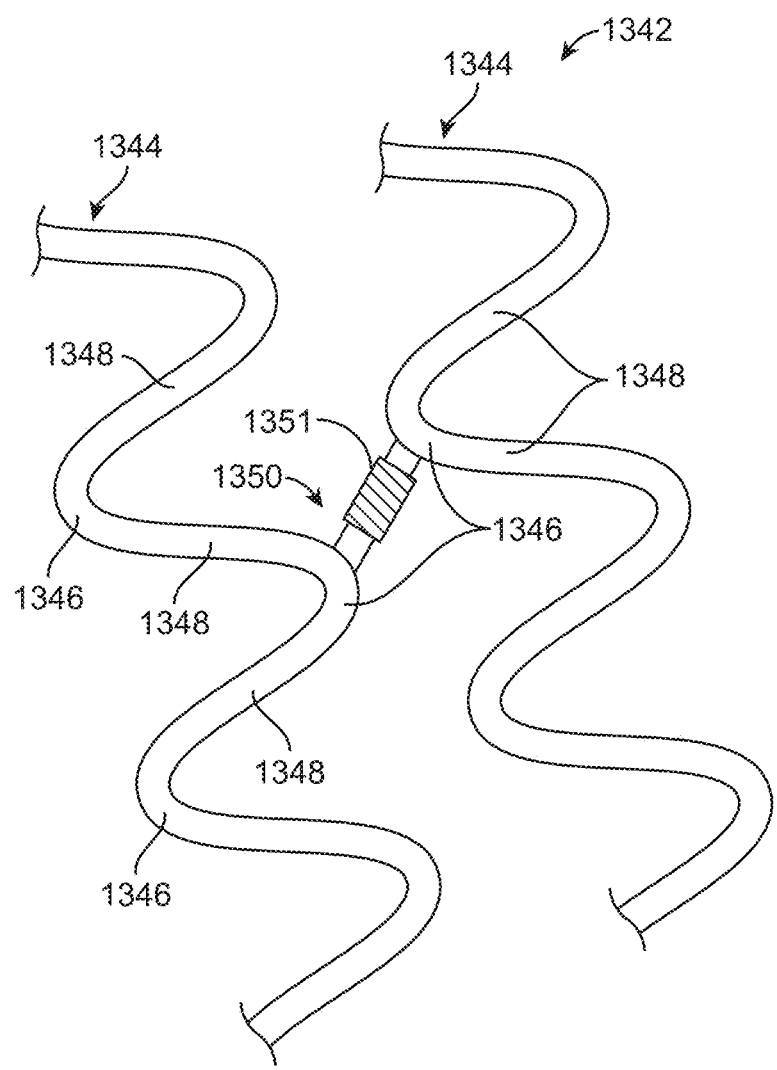
FIG. 40 illustrates a fourth example or embodiment of a stent with a helical backbone including separation regions between individual turns of the stent rings constructed in accordance with the principles of the present invention.

Referring now to FIG. 40, a helical stent scaffold 1342 comprises a plurality of turns 1324, at least some of which will be "in phase" as described previously with reference to FIG. 39. Instead of extending from a convex side of one crown to a concave side of another crown, connectors 1350 may extend between the convex sides of two "out-of-phase" crowns 1346 as illustrated. Again, the connector 1350 includes a separation region 1351 which may comprise any of the separation regions described elsewhere herein. However, the separation region 1351 typically will not be sufficient to uncage the circumferential turns (or rings), but rather having one or more separation regions in the strut and/or crown regions (not shown) of each of the turns are needed to circumferentially uncage the turns (rings).

Figure 41:
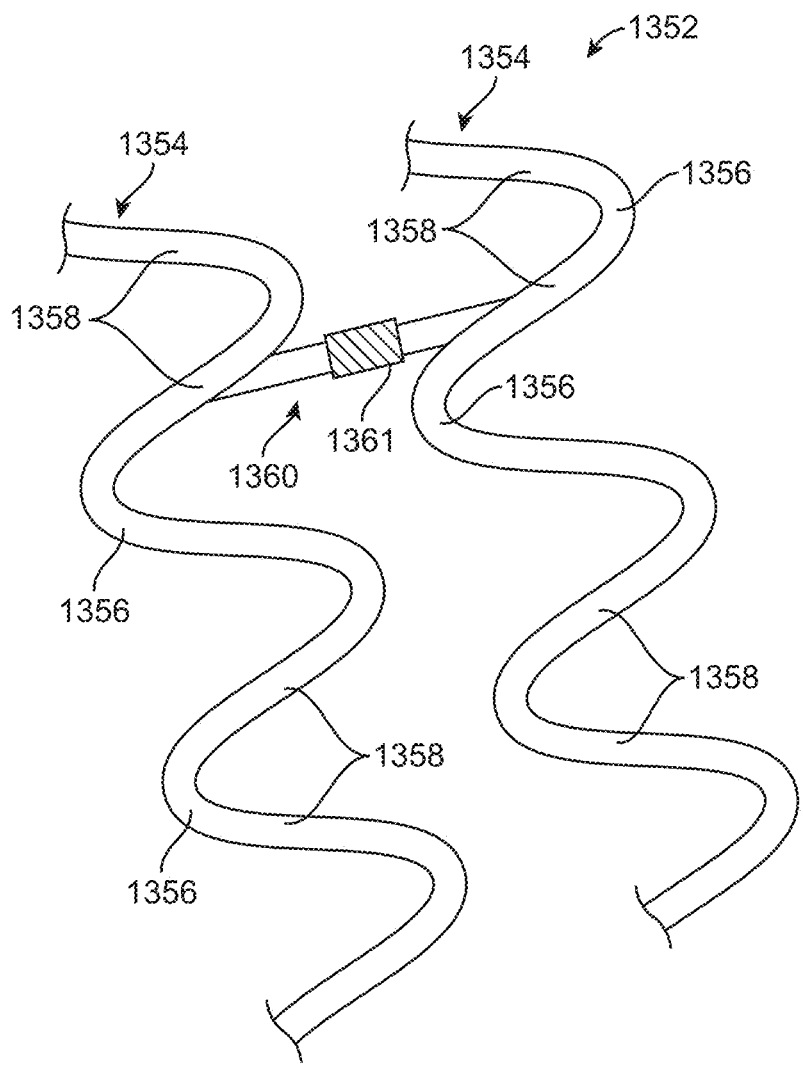
FIG. 41 illustrates a fifth example or embodiment of a stent with a helical backbone including separation regions between individual turns of the stent rings constructed in accordance with the principles of the present invention.

As shown in FIG. 41, a helical stent scaffold 1352 comprising turns 1354 having crowns 1356 and struts 1358 may comprise a connector 1360 which extends between axially spaced-apart struts 1358. Again, the connector 1360 includes a separation region 1361 which may comprise any of the separation regions described elsewhere herein. However, the separation region 1361 typically will not be sufficient to uncage the circumferential turns (or rings), but rather having one or more separation regions in the strut and/or crown regions (not shown) of each of the turns are needed to circumferentially uncage the turns (rings).

Figure 42:
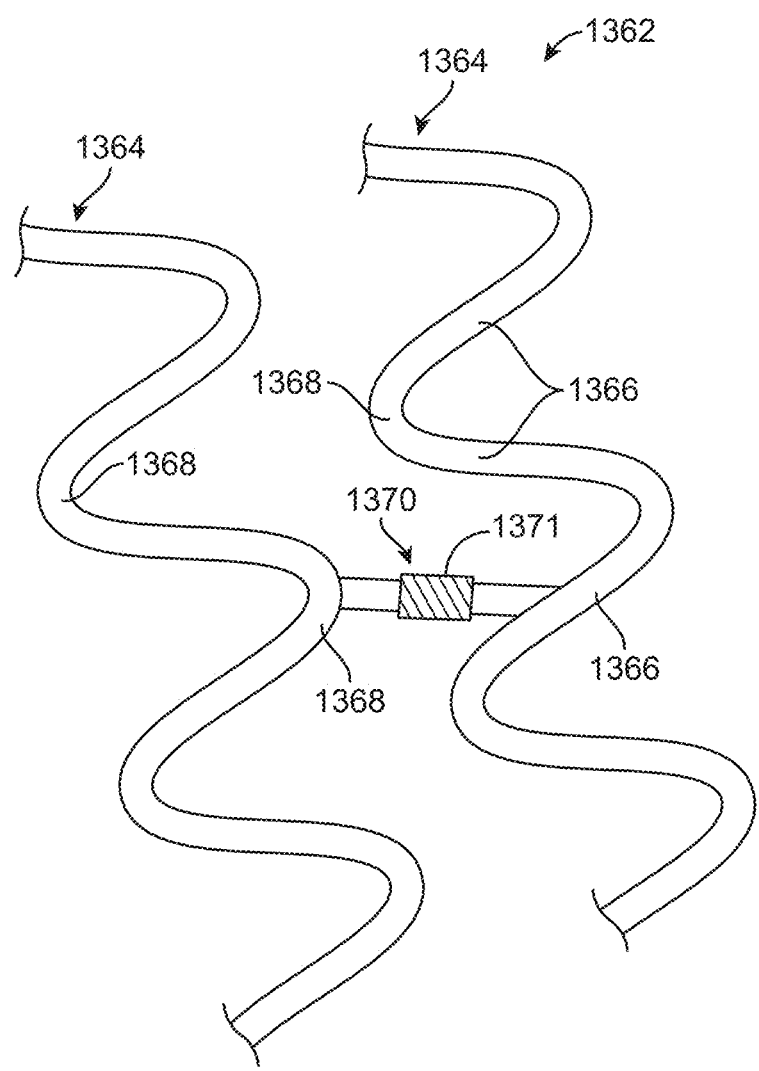
FIG. 42 illustrates a sixth example or embodiment of a stent with a helical backbone including separation regions between individual turns of the stent rings constructed in accordance with the principles of the present invention.

Finally, as illustrated in FIG. 42, a helical stent scaffold 1362 may comprise turns 1364 having struts 1336 and crowns 1368 where a connector 1370 extends between a convex side of one crown 1368 to an adjacent strut 1366. Again, the connector 1370 includes a separation region 1371 which may comprise any of the separation regions described elsewhere herein. However, the separation region 1371 typically will not be sufficient to uncage the circumferential turns (or rings), but rather having one or more separation regions in the strut and/or crown regions (not shown) of each of the turns are needed to circumferentially uncage the turns (rings).

As with stent scaffold 1312, stent scaffolds 1332, 1342, 1352, and 1352 may have additional separation regions in at least some of the struts and crowns (not illustrated), respectively. Depending on the particular pattern of separation regions which is selected, each of the stent scaffolds may be able to expand and contract by having one or more separation regions in at least some turns (in crown or strut regions), and/or deformation of the rings, e.g. opening of the crowns, and/or by unwinding of the helical backbone of the stent.

VII. Circumferentially Linked Closed Cell Stents

Figure 43:
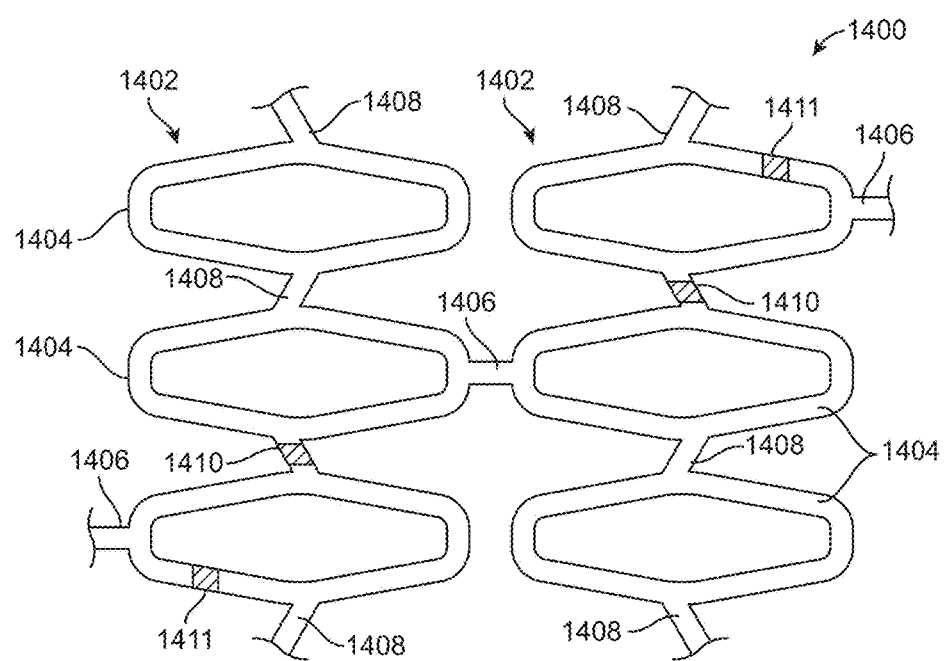
FIG. 43 illustrates a first example or embodiment of a closed-cell stent scaffold joined by circumferential separation regions where the separation regions are located in circumferential connectors of the rings, and sturts, in accordance with the principles of the present invention.

The separation region technology of the present invention may also be applied to closed cell scaffolds on stents and other luminal prostheses. For example, as shown in FIG. 43, a closed cell stent scaffold 1400 comprises a plurality of circumferential rings 1402. Each ring comprises a number of quadrangular closed cells 1404 joined by axial links 1406. The quadrangular closed cells 1404 within each circumferential ring 1402 are joined by circumferential connectors 1408.

In accordance with the present invention, separation regions 1410 and 1411 are formed in at least some of the circumferential rings 1402 in order to enhance compliance of the scaffold after the scaffold is implanted in a blood vessel or other body lumen. For example, separation regions 1410 may be located in one or more of the circumferential connectors 1408 allowing adjacent quadrangular closed cells 1404 to circumferentially separate in response to physiologic forces after implantation. Alternatively, separation regions 1411 may be located within the struts or other elements of the quadrangular closed cells themselves. Typically, the circumferential rings 1402 of the scaffold 1400 are joined by axially aligned links 1406 or other elements which typically remain intact after the separation regions form discontinuities.

Figure 44:
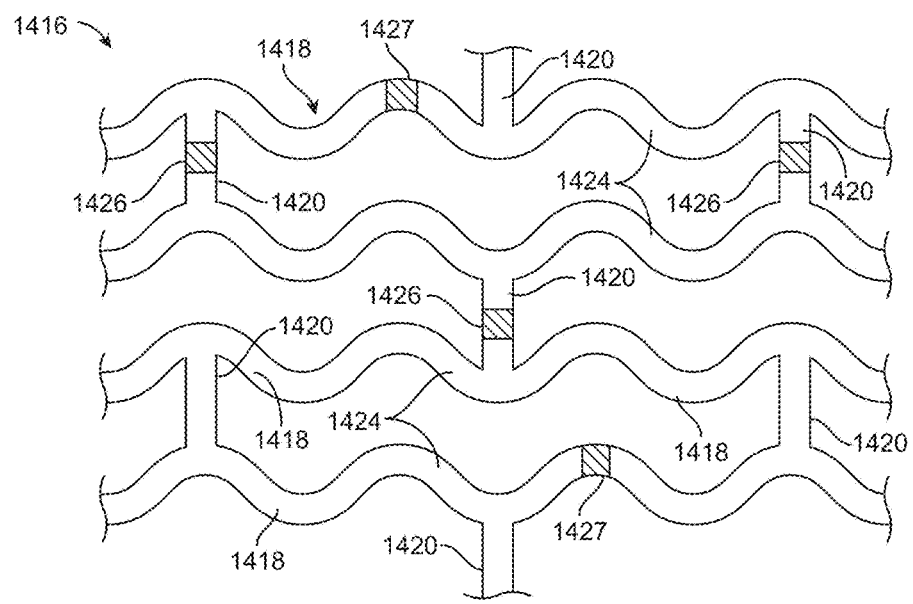
FIG. 44 illustrates a second example or embodiment of a closed-cell stent scaffold joined by circumferential separation regions where the separation regions are located in circumferential connectors of rings and crowns, in accordance with the principles of the present invention.

Another closed cell scaffold 1416 is illustrated in FIG. 44 and includes "closely packed" quadrangular cells 1418, where each cell has serpentine or "wavy" axial elements 1424 and transversely oriented end elements 1420. The end segments 1420 will typically comprise a separation region 1426 in order to enhance circumferential compliance of the stent after implantation. However, separation regions 1427 formed in the axial elements 1424 alone typically will not uncage the scaffold circumferentially. The separation regions 1426 and/or 1427 may be any of the types of separation regions described elsewhere in the present application.

Figure 45:
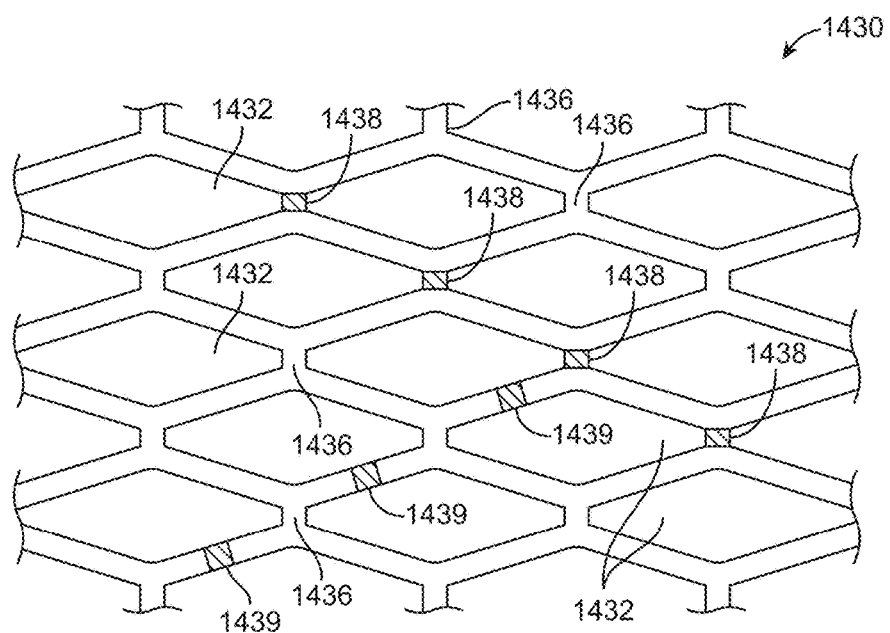
FIG. 45 illustrates a third example or embodiment of a closed-cell stent scaffold joined by circumferential separation regions where the separation regions are located in circumferential connectors of the rings and struts, in accordance with the principles of the present invention.

A closed-cell stent scaffold 1430 illustrated in FIG. 45 comprises a plurality of closely packed diamond-shaped cells 1432. Separation regions 1438 may be provided in the circumferential connectors of the diamond-shaped cells 1432. Alternatively, separation regions 1439 may be provided in the strut elements of the diamond-shaped closed cells 1432.

Figure 46:
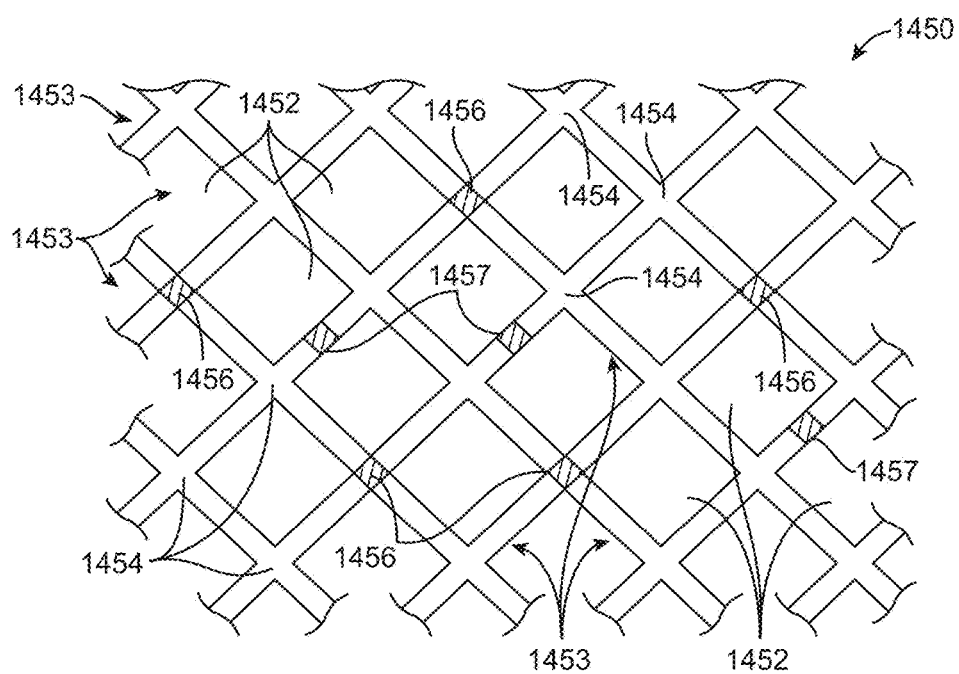
FIG. 46 illustrates a fourth example or embodiment of a closed-cell stent scaffold joined by separation regions in accordance with the principles of the present invention.

In yet another example as shown in FIG. 46, a closed cell stent scaffold 1450 comprises diamond-shaped cells 1452 which are defined by struts 1453 which cross each other at junctions 1454. Separation regions 1456 may be provided at the junctions 1454 and/or separation regions 1457 may be provided in the struts 1453 between junctions. Such closed cell stent scaffold 1450 with diamond-shaped cells are typically patterned by laser cutting or etching from a tubular base structure in a conventional manner. The separation regions may then comprise any of the separation regions described elsewhere herein.

Figure 46A:
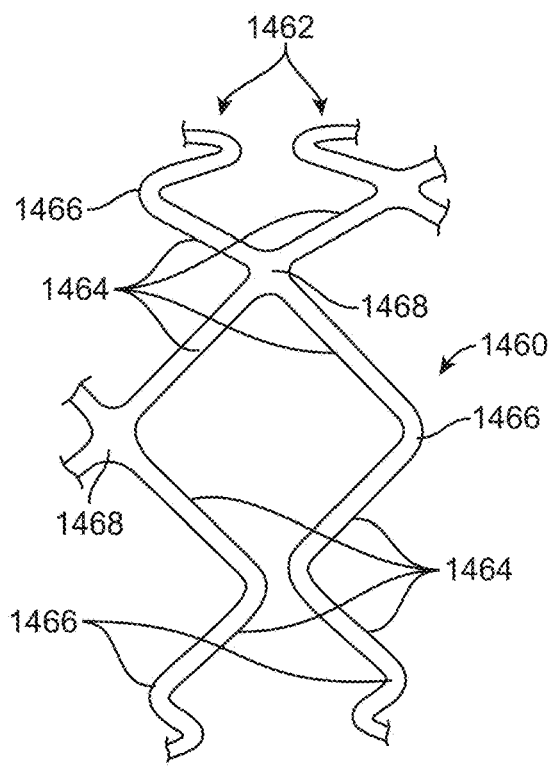
FIGS. 46A and 46B illustrate an example or embodiment of a stent scaffold having zig-zag circumferential rings which are joined by directly attaching crowns, preferably without an intermediate link element.
Figure 46B:
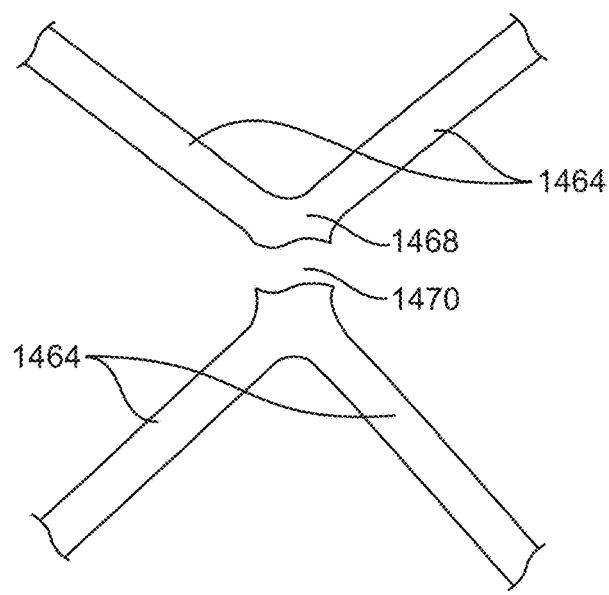

In a still further example as shown in FIGS. 46A and 46B, a stent scaffold 1460 comprises zig-zag circumferential rings 1462 (or may also be other patterns such as serpentine rings) which are formed by struts 1464 which are joined at crowns 1466. Some, but not all axially adjacent crowns in axially adjacent rings 1462 are joined into four-way junctions that join the adjacent rings. The junctions 1468 will act as separation regions, or maybe configured to be a separation region, and can be formed to form discontinuities, break or bisect at locations 1470 to allow circumferential separation of the rings, as shown in FIG. 46B. In this way, adjacent rings 1462 will remain axially joined while they are circumferentially released (or to increase circumferential compliance as described elsewhere herein. The junctions 1468 may be formed in any of the ways described previously, e.g. having preformed breaks joined by degradable sleeves or adhesives, being weakened regions which break in response to fatigue caused by luminal pulsation, or other, or the like.

Figure 47:
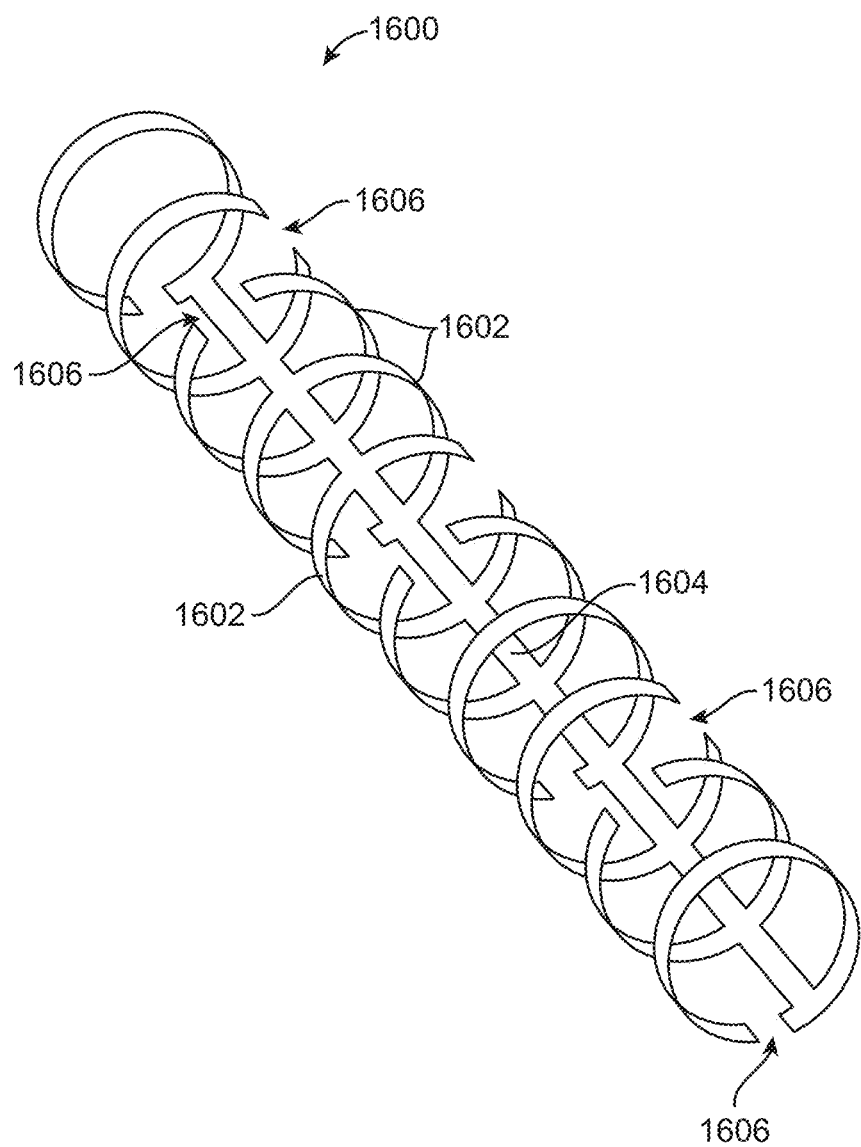
FIG. 47 illustrates a scaffold having a straight backbone with a plurality of circumferential rings having staggered gaps distributed over its length.

In FIG. 47, a scaffold 1600 comprises a plurality of circumferential rings 1602 attached to an axially oriented backbone 1604. Each ring has a gap 1606, where the gaps in at least some of the successive rings are rotationally staggered relative to each other. The purpose of the rotational staggering is to more uniformly distribute the circumferential support while maintaining the elasticity provided by the gap. That is, in designs where the gaps are axially aligned, the circumferential support will be diminished along the side where the gaps are aligned. Such diminished support is reduced or eliminated by staggering the gaps. As illustrated, the gaps 1606 in successive rings are rotationally staggered by 90°, but the degree and pattern of staggering can be varied so long as the circumferential support is maintained. As a further alternative, not illustrated, the scaffold 1600 could have two, three, or more axial backbones, either in parallel, located in successive axial regions of the scaffold.

Figure 48:
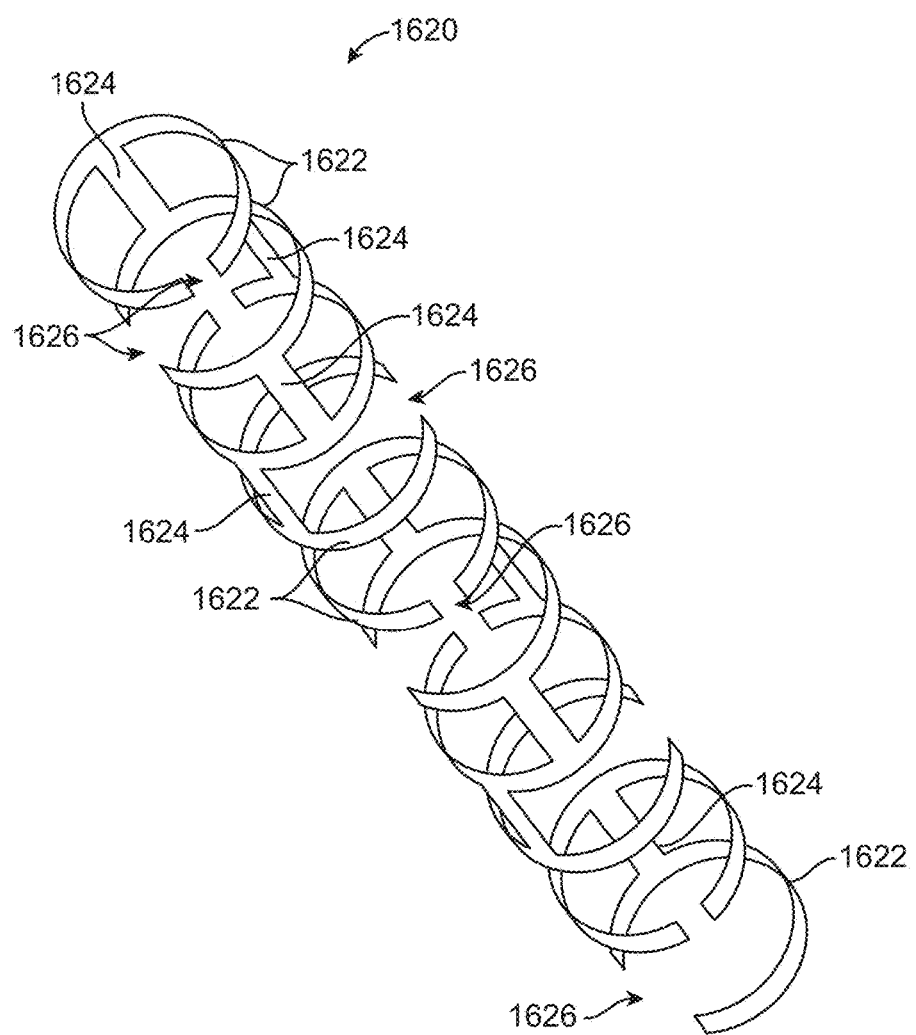
FIG. 48 illustrates a scaf 1239, and fold having a non-aligned backbone segments joining a plurality of circumferential rings having staggered gaps.

In FIG. 48, a scaffold 1620 comprises a plurality of circumferential rings 1602 axially joined by a plurality rotationally staggered links or backbone segments 1624. The plurality segments or links 1624 replace the backbone 1604 of FIG. 47 and maintain the axial integrity of the scaffold 1620. Although a single link or segment 1624 is shown between each successive pair of rings 1622, it will be appreciated that two, three or more segments or links could be located between at least some of the adjacent rings 1622, As with scaffold 1600, each ring 1622 in scaffold 1620 has a gap 1626, where the gaps in at least some of the successive rings 1622 are rotationally staggered relative to each other. The purpose of the rotational staggering is the same as with scaffold 1620, i.e. to more uniformly distribute circumferential support while maintaining the elasticity provided by the gap. As illustrated, the gaps 1626 are located 180° in opposition to the attachment location of at least one segment or link 1624, but other orientations would also find use.

The stent scaffolds 1600 and 1620 may be formed from any of the materials and by any of the fabrication protocols described elsewhere herein. In particular, the scaffolds may be formed by patterning a metal or other tube. Alternatively, the scaffolds could be formed by bending one or more wires into the illustrated patterns, e.g. by bending a single wire into the pattern, turning the wire at one end, and then bending the wire back in a pattern parallel to the previously bent wire.

In one example to measure Vasomotion (constriction or dilation), stent contraction and/or expansion, vessel enlargement, or other tests, in humans or porcine model can be as follows: In a porcine model, an infusion catheter is passed through the guiding catheter and positioned proximal to the site of device implantation. Using a syringe pump, incremental dose levels of acetylcholine ($10^{-7}$, $10^{-6}$, and $10^{-5}$ M) are slowly administered (1.0 ml/min over 3 min), as needed, with a minimum 5-min washout period between each dose. The blood pressure and heart rate are monitored during each infusion to prevent acetylcholine-induced ischemia. The incremental dosing regimen is discontinued when the constriction is visually distinct and the subsequent dose would most likely induce an ischemic event. Angiographic images are acquired prior to and after each dose to capture the effects of acetylcholine for off-line QCA measurements. Following the effective dose of acetylcholine infusion, a bolus of nitroglycerin (300 mg) is administered to assess the vasodilatory response, and an angiogram is captured for off-line QCA analysis. In the case of acetylcholine infusion, a vasoconstriction in the distal non-device implanted segment would result in reduced contrast flow in the distal segment as well as the device implanted segment due to reduced blood flow resulting in an artefactual reduction in the vessel diameter in the device implanted segment. To avoid this artifact, the lumen diameter at the midsection of the device implanted segment was chosen for all analysis for better accuracy. As for humans, measure mean lumen diameters by QCA after baseline saline infusion and sub-selective intracoronary administration of acetylcholine infused through a microcatheter at increasing dose from $10^{-8}$ M to $10^{-6}$ M. For methergin test, QCA is measured 5 min after intravenous bolus injection of methergin (0.4 mg). Both tests are terminated by intracoronary administration of 200 µg of nitroglycerin. The change in the lumen diameter following the treatment with the vasoactive substance is measured using off-line end-diastolic QCA angiographic acquisitions during pre-dose, post-acetylcholine or methergin, and post nitroglycerin infusions. A sub-segment analysis of the artery is performed to determine the mean lumen diameter (MLD) changes of the device implanted segments and the 5-mm proximal and distal edges. Absolute MLD differences (deltas) (post-infusion–pre-infusion) is assessed as well as relative percentage MLD changes (post-infusion–preinfusion/re-infusion×100%). The data provides measurements and magnitude of the implanted device and/or vessel to undergo vasomotion (vasodilation and/or vasoconstriction), expansion of the stent, and/or contraction of the stent, and/or enlargement of the stented vessel segment, and/or contraction of the stented vessel segment. An example for evaluation of vasomotion by IVUS:Vasomotion could also be assessed in porcine model and humans through measurement of lumen areas by IVUS preferably in a mid-section of the device implanted segment and/or the implanted segment of the artery arteries at the same position in the end-diastolic and end-systolic state. The absolute difference in the lumen cross-sectional area observed from systole to diastole within the mid-section of the device implanted segment ($\Delta$LA) will provide the necessary information to evaluate the ability and magnitude of the implanted device and/or vessel to undergo vasomotion (vasodilation and/or vasoconstriction), expansion of the stent, and/or contraction of the stent, and/or enlargement of the stented vessel segment, and/or contraction of the stented vessel segment.

VIII. Stent Prostheses Having Displacement Regions Such as Circumferential Displacement Regions.

Figure 49:
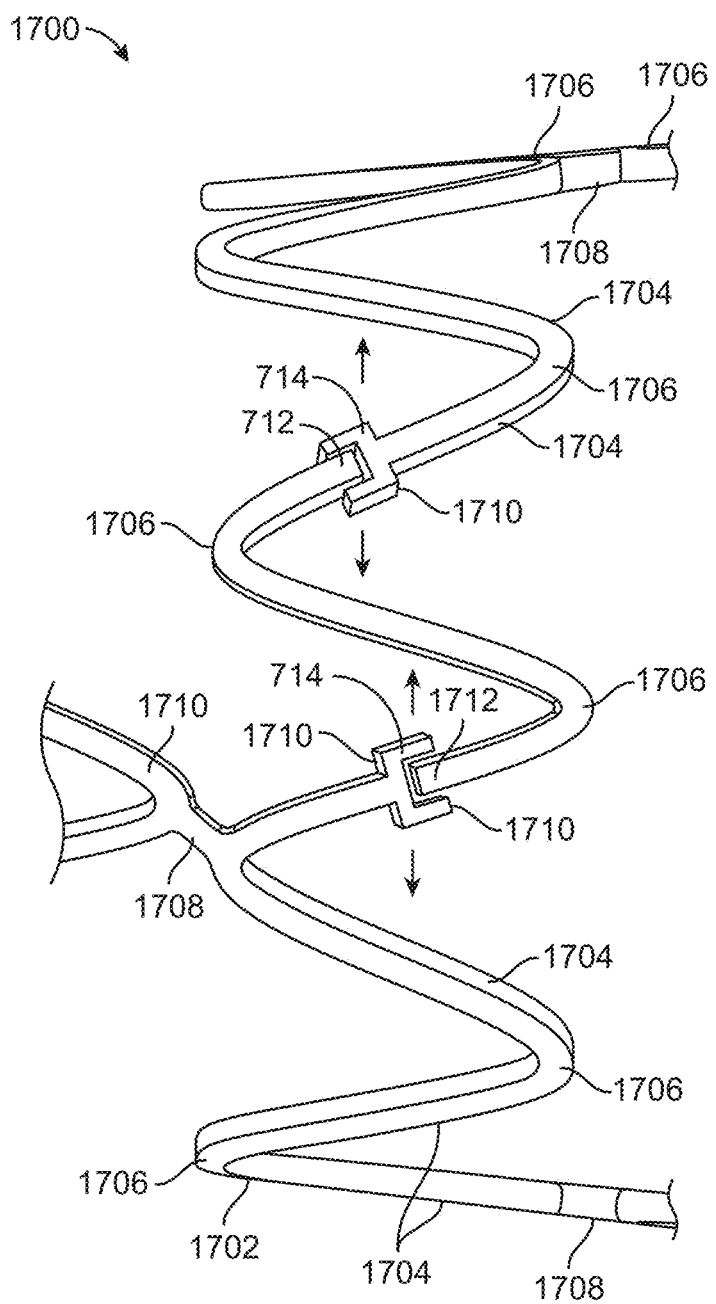
FIG. 49 illustrates an exemplary circumferential ring of a stent prosthesis modified to include a pair of circumferential displacement regions in individual struts thereof.

FIG. 49 illustrates a single partial circumferential ring 1702 of a stent prosthesis 1700 formed from struts 1704 and crowns 1706, where two of the struts have displacement regions such as circumferential displacement regions 1710 constructed in accordance with the principles of the present invention. The circumferential partial ring 1702 is connected to axially adjacent circumferential rings (not fully shown) by axial links 1708. In contrast to the separation regions described previously, these displacement regions 1710 may be configured to provide an elastic region for expanding and/or contracting the circumferential dimension of a circumferential ring, not just separation as previously described.

Figure 50:
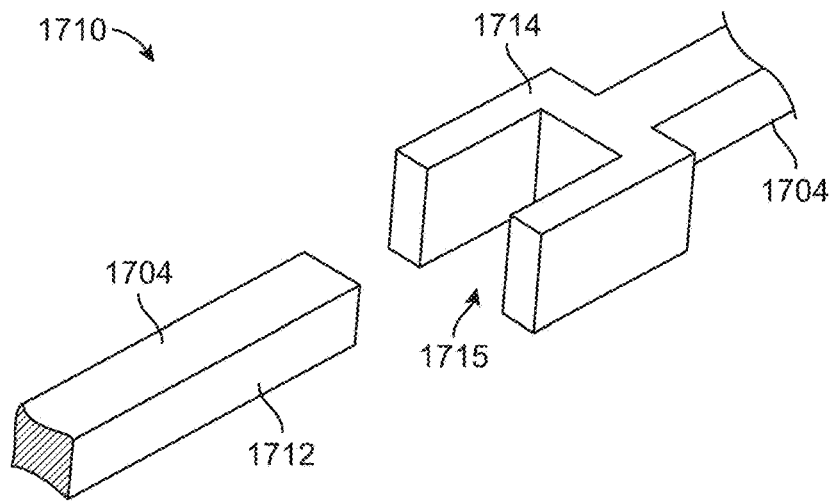
FIGS. 50-52 illustrate the circumferential displacement regions of FIG. 49 in greater detail.
Figure 51:
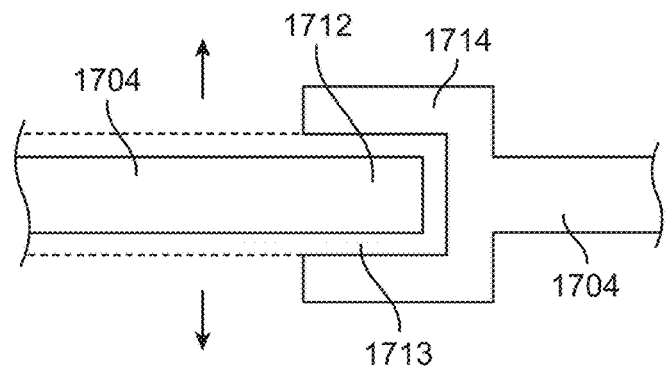
Figure 52:
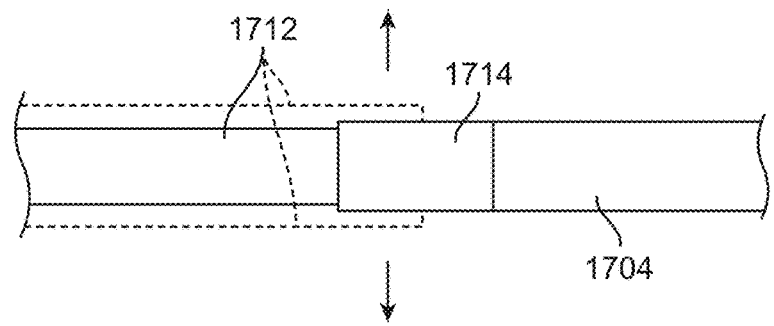

FIG. 50 is a perspective view of the circumferential displacement region 1710 shown with a male terminal or attachment region 1712 on a strut segment 1704 separated from a female terminal or attachment region 1714 formed as a fork or clevis at the terminal end of a adjacent strut segment 1704. An opening or cavity 1715 in the female attachment region 1714 is oversized compared to the width of the male region 1712 of strut 1704, as best seen in FIG. 51, to create a buffer zone 1713 between the male and female attachment regions. The broken lines in FIG. 51 indicate the range of lateral motion available to the male attachment region 1712 of strut 1704, which allows the strut to move in the directions of the arrows shown in FIG. 51. FIG. 52 shows that the male attachment region 1712 is also able to move up and down relative to a horizontal plane of the strut 1704, also as shown in broken line and indicated by the arrows of FIG. 52. While similar "lock-and-key" separation regions have been shown previously in this application, when used as a circumferential displacement region, the free space or buffer region between the outer surfaces of the male elements 1712 and the inner surfaces of the female region 1714 will generally be greater to allow more freedom of movement.

Figure 53:
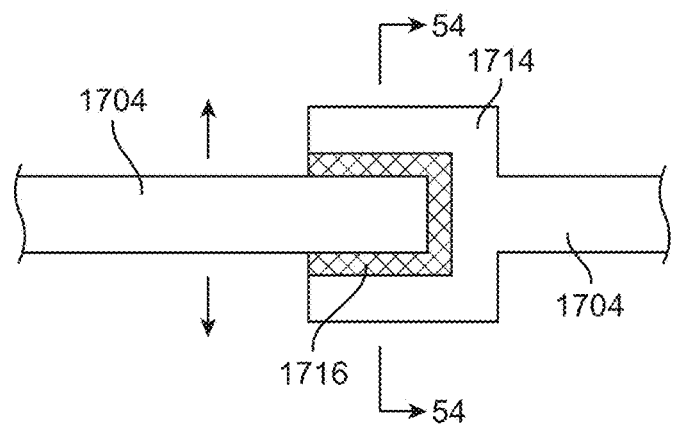
FIGS. 53 and 54 illustrate a first alternative construction of a circumferential displacement region of a type which could be employed in the circumferential ring of FIG. 49.
Figure 54:
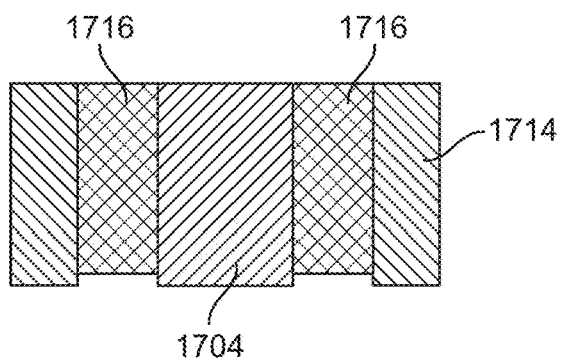

Referring now to FIGS. 53 and 54, the buffer zone 1713 between the outer surfaces of the male element 1712 and the inner surfaces of the female element 1714 may optionally be filled with an elastic cushion material 1716. Suitable cushion materials include but are not limited to silicones, silicone rubber; C-flex; poly(n-butylmethacrylate); poly(n-butylmethacrylate) blended with poly(methamethacrylate), Poly (hexyl methacrylate), and polyvinylpyrrolidone; Kraton; poly(styrene-ethylene/butylene-styrene) (SEBS); poly(styrene-ethylene/propylene-styrene) (SEPS), poly(acrylic acid-b-styrene-b-isobutylene-b-styrene-b-acrylic acid; poly(styrene-b-isobutylene-b-styrene); polybutadiene; polyisoprene; Polystyrene butadiene rubber (SBR), Polyethylene-propylene-diene (EPDM); PVDF-HFP poly(vinylidene fluoride-hexafluorpropylene); polyvinylpyrrolidone; poly(ethylene-co-vinyl acetate); phosphorylcholine; PEBAX; polyurethane elastomers; Tecoflex; Biomer; Pellethane; corethane; silicone rubber; rubbers; natural rubbers; elastomers; blends; copolymers; combination thereof; or the like. The cushioning materials will typically adhere to both the male attachment region 1712 and the female attachment region 1714 so that the cushion materials will usually provide a permanent or long term interconnection. The elastic nature of the material, however, allows the cushion to act as an elastic connector to provide a controlled, elastic interaction between the two adjacent strut segments 1704.

Figure 55:
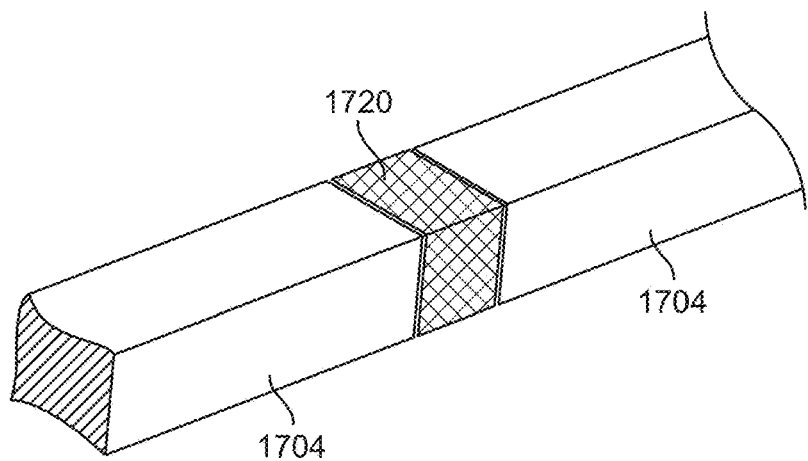
FIG. 55 illustrates a second alternative construction of a displacement region such as a circumferential displacement region of a type which could be employed in the circumferential ring of FIG. 49.

As shown in FIG. 55, in some cases, two butt ends of adjacent strut segments 1704 may be directly connected with a region 1720 of elastic material which acts to elastically link the two struts together, serving as an elastic displacement region.

Referring now to FIGS. 56, 57, and 58A and 58B, a further embodiment of a displacement regions such as circumferential displacement region 1710 comprises a strut segment 1704 having a female attachment region 1720 with a channel 1718 formed over a top surface. A male attachment region 1722 is formed at the end of an adjacent strut segment 1704 and configured to be received in the channel 1718, as best seen in FIGS. 57 and 58A, so that the strut may move laterally as well as upwardly relative to the strut end 1720. Downward movement of the strut end 1718, however, will be limited by the closed bottom of the channel 1718. The gap or empty space between the strut end 1722 and the inner wall of the channel 1718 may be empty (FIG. 58A) or may filled with an elastic material 1728 (FIG. 58B), as generally described with prior examples or embodiments.

Figure 59:
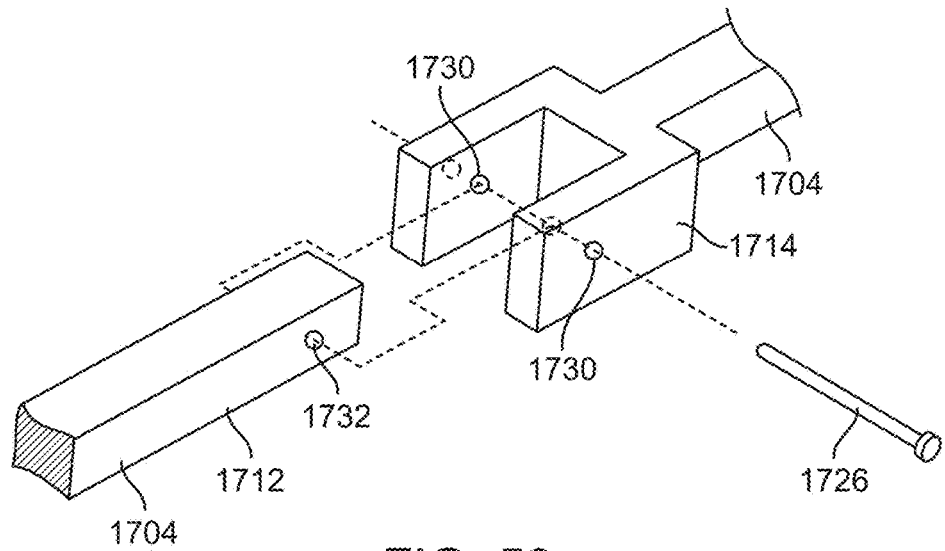
FIGS. 59 and 60 illustrate a fifth alternative construction of a displacement region such as a circumferential displacement region of a type which could be employed in the circumferential ring of FIG. 49.
Figure 60:
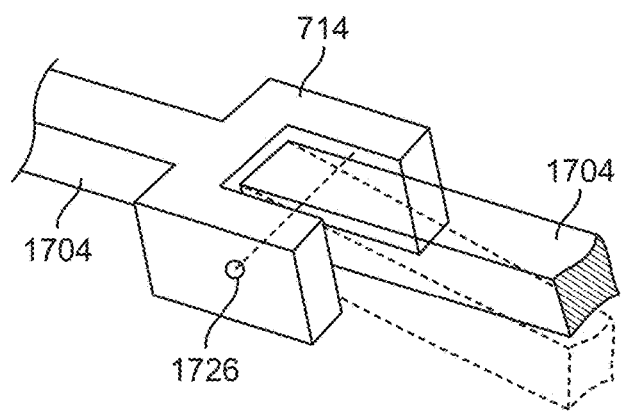

Referring now to FIGS. 59 and 60, a further example of a displacement region constructed in accordance with the principles of the present invention will be described. A first strut segment 1704 has a clevis-type end region 714 with a pair of aligned holes or apertures 1730 in the opposed walls of the clevis 1714. A male attachment end 1712 of the other strut segment 1704 also has a hole 1732 formed therethrough. Once the male end 1712 of the strut 1714 is in the female clevis 1714, as shown in FIG. 60, the pin 1726 may be passed through the aligned holes to provide for a pivoting arrangement. The gap between the male end 1712 and the interior of the female clevis 1714 may be open, as illustrated in FIG. 60, or may be filled with an elastomeric material as described previously with other embodiments.

Figure 61:
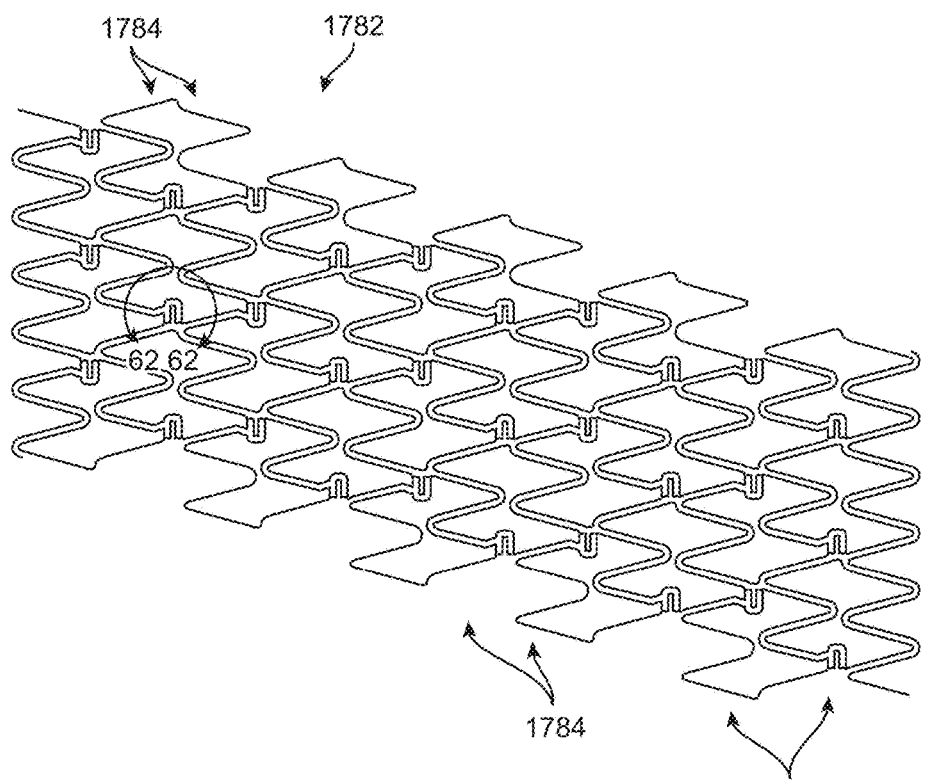
FIGS. 61, 62A and 62B illustrate an alternative stent prosthesis structure having displacement region such as circumferential displacement regions present on axial links adjoining adjacent circumferential stent rings.
Figure 62A:
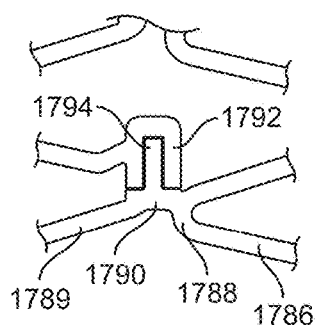
Figure 62B:
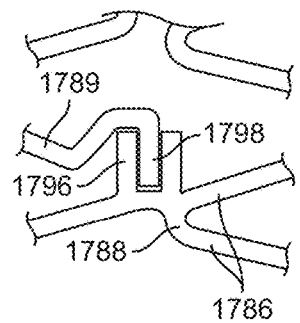

Referring now to FIGS. 61, 62A and 62B, an alternative stent structure 1782 comprises a plurality of circumferentially ring 1784, where axially adjacent circumferential rings are joined by axial links 1790, as best seen in FIG. 62A. The axial links 1790 will extend from a crown 1788 on one circumferential ring, while being attached to single strut 1789 on the adjacent circumferential ring. The adjacent circumferential ring is further attached to the axial link 1790 by a cap 1792 which is received over a short pin 1794, as seen in FIG. 62A. This lock-and-key junction allows displacement and flexibility between the adjacent circumferential rings. While the presence of a short straight segment on the axial link 1790 is shown in FIG. 62A, it will be appreciated that the link 1790 could carry a female coupling element 1796 while the single strut 1789 may terminate in the short pin element 1798, as shown in FIG. 62B. The axial link 1790 typically remains intact after formation of discontinuity.

Figure 63:
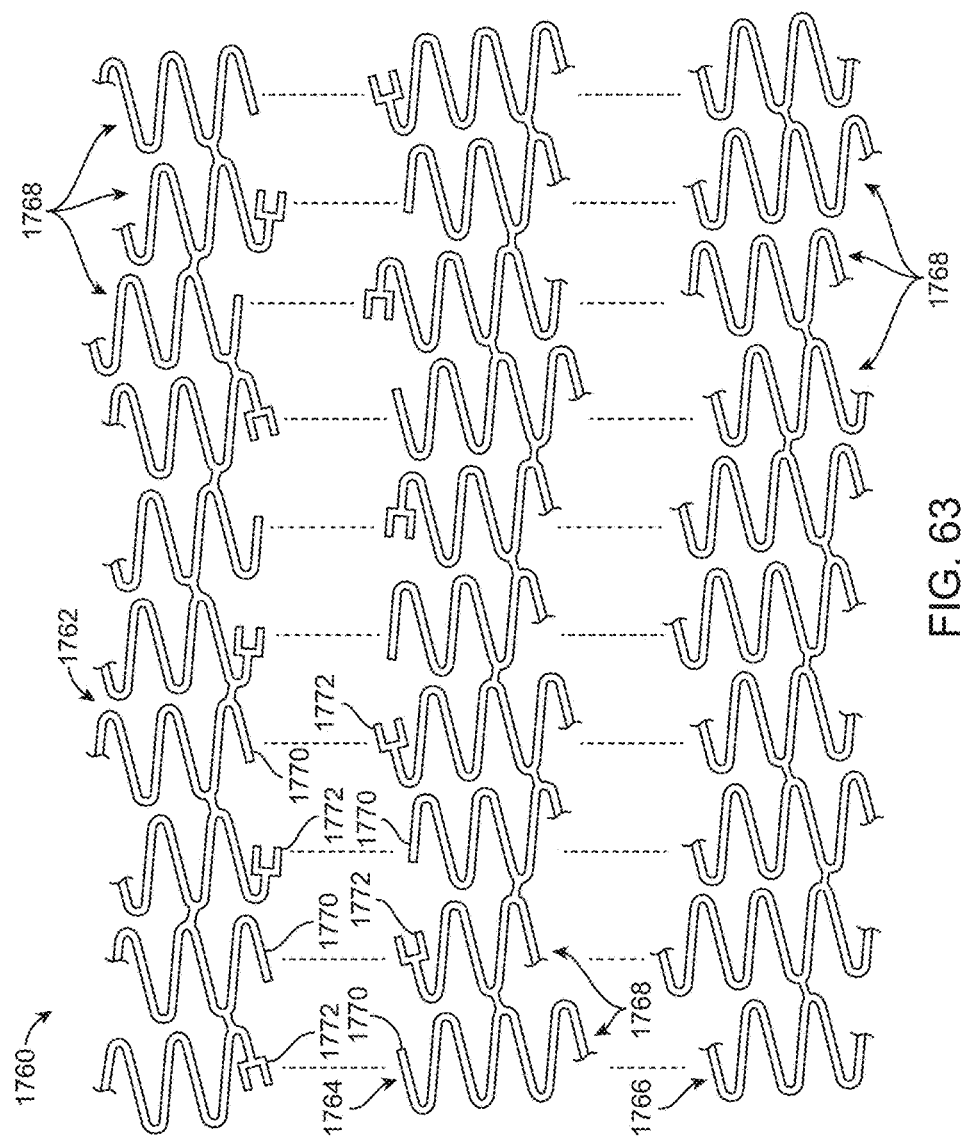
FIG. 63 illustrates a stent structure fabricated as three separate panels intended for subsequent assembly into a complete stent.

Referring now to FIG. 63, a stent prosthesis according to the present invention may be fabricated by forming two or more separate panels and thereafter joining those panels into a cylindrical stent structure. As illustrated, a stent prosthesis 1760 may be fabricated by first forming separate panels 1762, 1764 and 1766. The separate panels will typically be formed or patterned from a sheet of metal or polder material by well know laser cutting or chemical etching techniques. Each panel may, for example, comprise a plurality of circumferential ring segments 1768, where each ring segment may further comprise struts and crowns as described for many previous embodiments. In each panel, however, the ends of the circumferential rings will terminate in an attachment element. In particular, as illustrated, some of the attachment elements may be male attachment elements 1770 and others may be female attachment elements 1772. In particular, these may comprise the key-and-lock attachment elements described previously herein.

The attachment elements on each panel will be specifically arranged so that the panels may be attached together for formation into the stent prosthesis. For example, the terminal ends of the circumferential ring segments 1768 may have male and female attachment elements, while the adjacent terminal end on the adjacent panel would have a mating female or male element so that the elements may be joined.

Figure 64A:
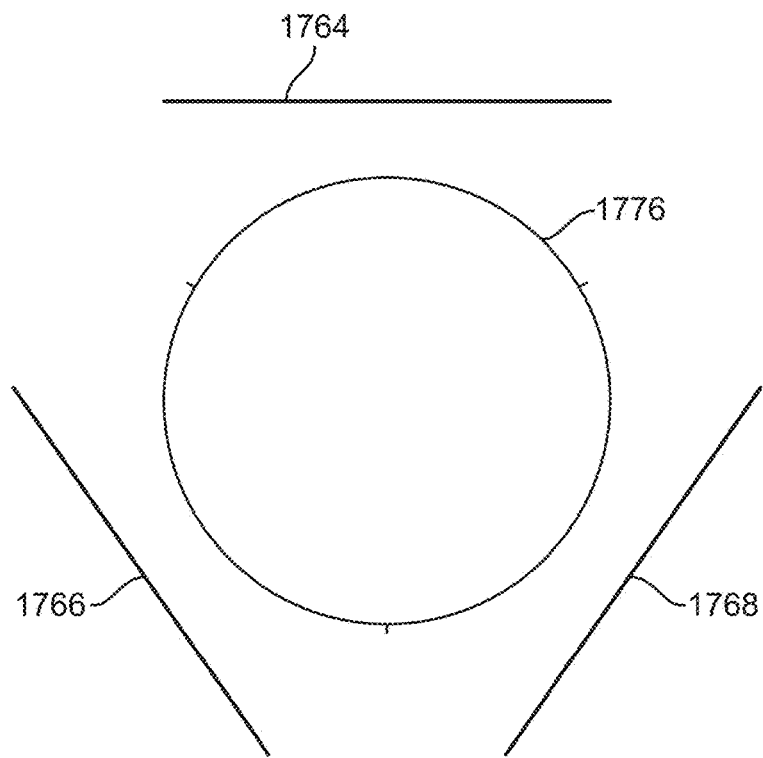
FIGS. 64A-64D illustrate exemplary steps for fabricating the panels of FIG. 63 into a complete stent structure.
Figure 64B:
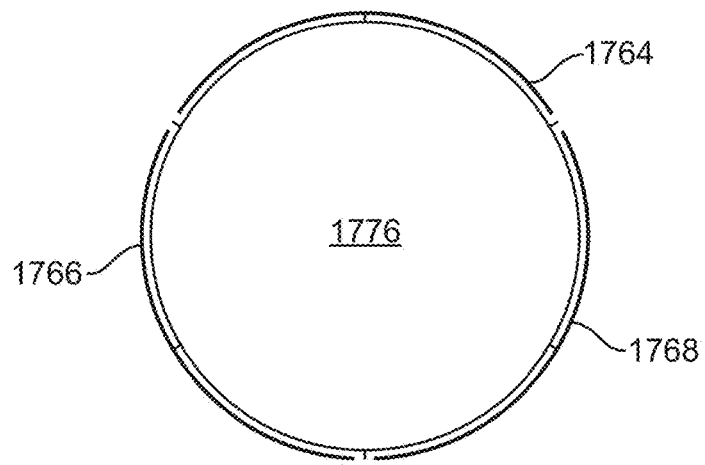
Figure 64C:
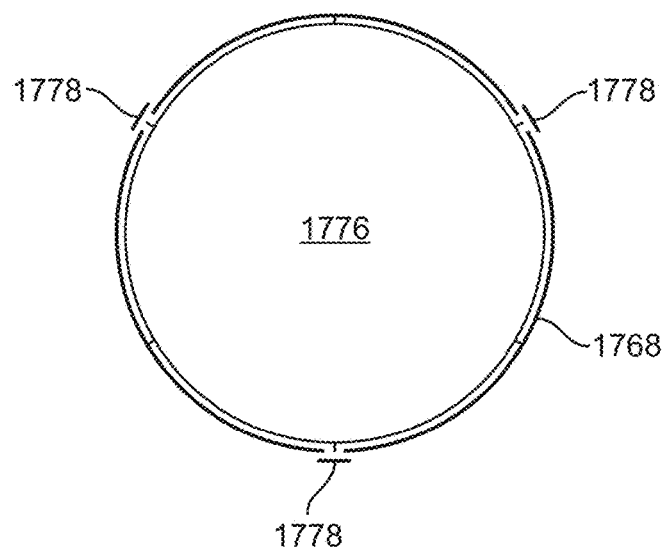
Figure 64D:
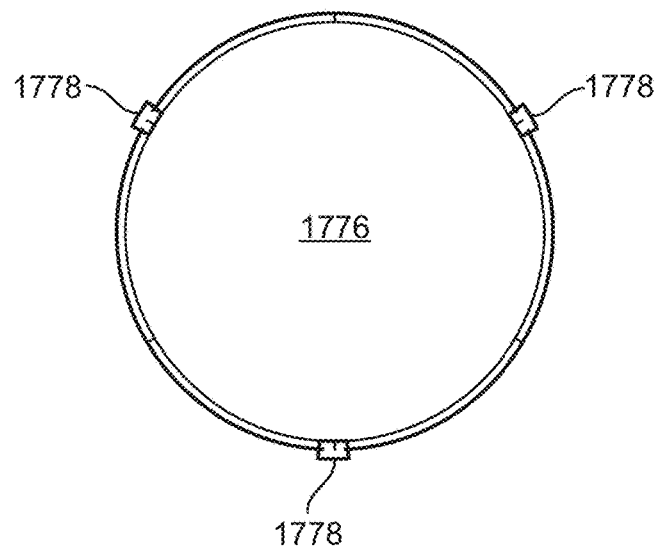

As shown schematically in FIGS. 64A and 64B. The panels in 1764, 1766, and 1768 may be formed over a cylindrical mandrel 1776, and the terminal ends of the individual circumferential ring segments then joined by coupling elements 1778, as shown in FIGS. 64C and 64D. The coupling elements may be sleeves, adhesives, elastic cushion materials or the like. Alternatively, the terminal ends of the circumferential ring segments may be joined by mechanically interlocking the ends without any further glue, adhesives, or filling materials.

Figure 65:
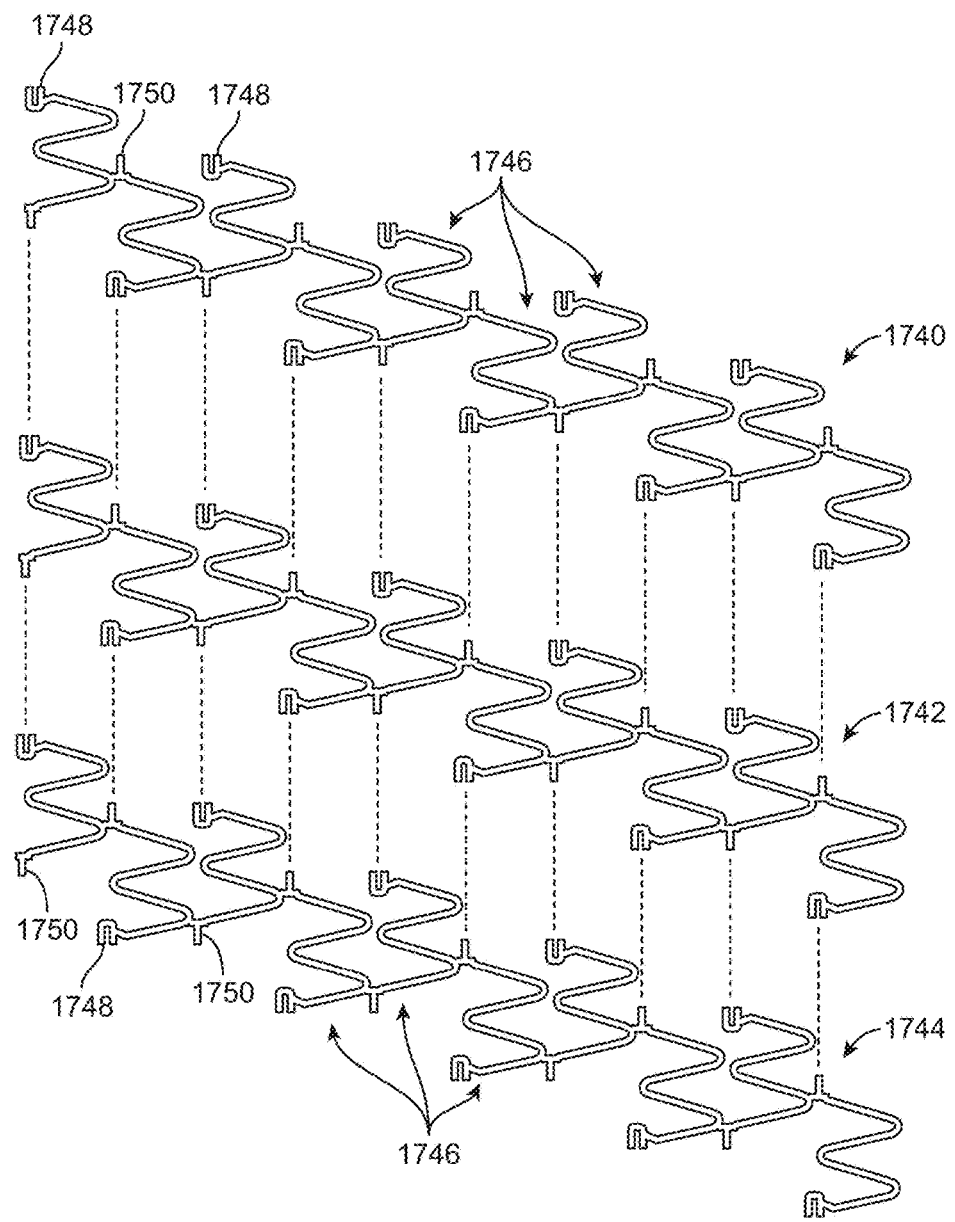
FIG. 65 illustrates three stent fabrication panels having an alternative construction corresponding to the stent prosthesis of FIGS. 61, 62A and 62B.

Referring now to FIG. 65, the stent pattern of FIG. 61 may be modified to comprise three separate panels 1740, 1742, and 1744 which may be fabricated into the stent in a manner similar to that described for 64A-64D. In particular, each individual ring segment 1746 will terminate in a plurality of female attachment elements 1748 and male attachment elements 1750 which are arranged to mate as the panels 1740, 1742, and 1744 are brought together. Thus, the female attachment elements 1748 and male attachment elements 1750 can act both as attachments points for assembling the complete stent prosthesis an as circumferential displacement regions on the assembled stent prosthesis.

Figure 66:
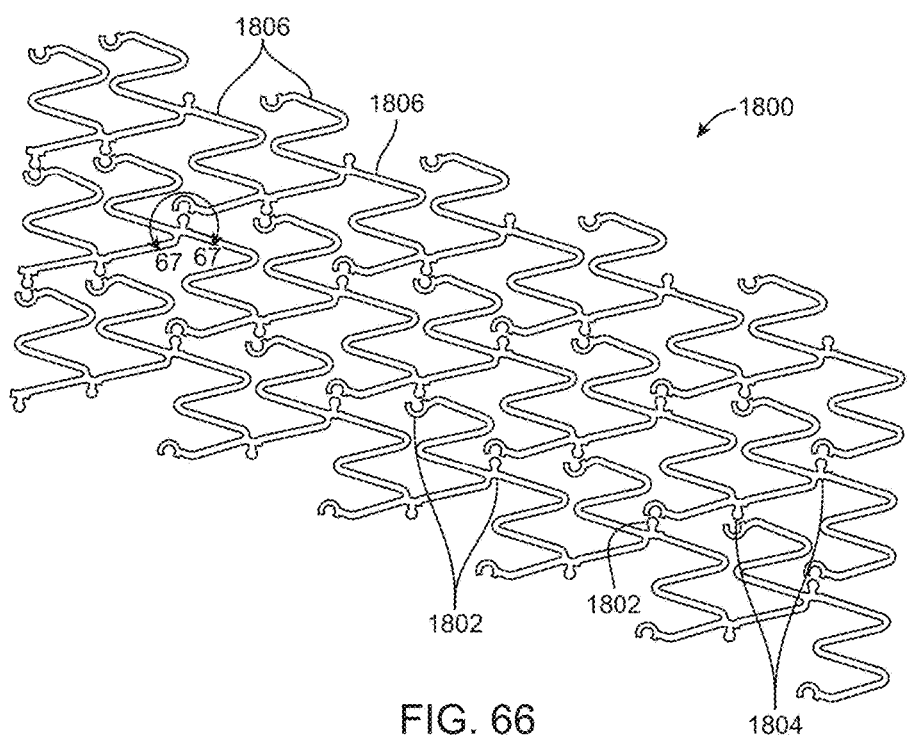
FIGS. 66 and 67 illustrate a second alternative stent prosthesis structure having displacement regions such as circumferential displacement regions present adjacent to axial links adjoining adjacent circumferential stent rings.
Figure 67:
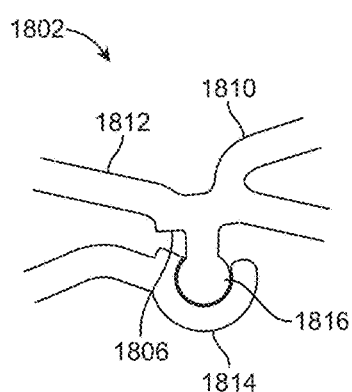

Referring now to FIGS. 66 and 67, a second alternative stent structure 1800 has displacement regions 1802 formed on or adjacent to axial links 1804 between adjacent circumferential rings 1806. The axial links 1804 will extend from a crown 1810 on one circumferential ring, while being attached to single strut 1812 on the adjacent circumferential ring. The adjacent circumferential ring is further attached to the axial link 1804 by a cap 1814 which is received over a disc 1816, as seen in FIG. 67. Such a "lock-and-key" junction allows displacement or discontinuity in the circumferential ring.

Figure 84:
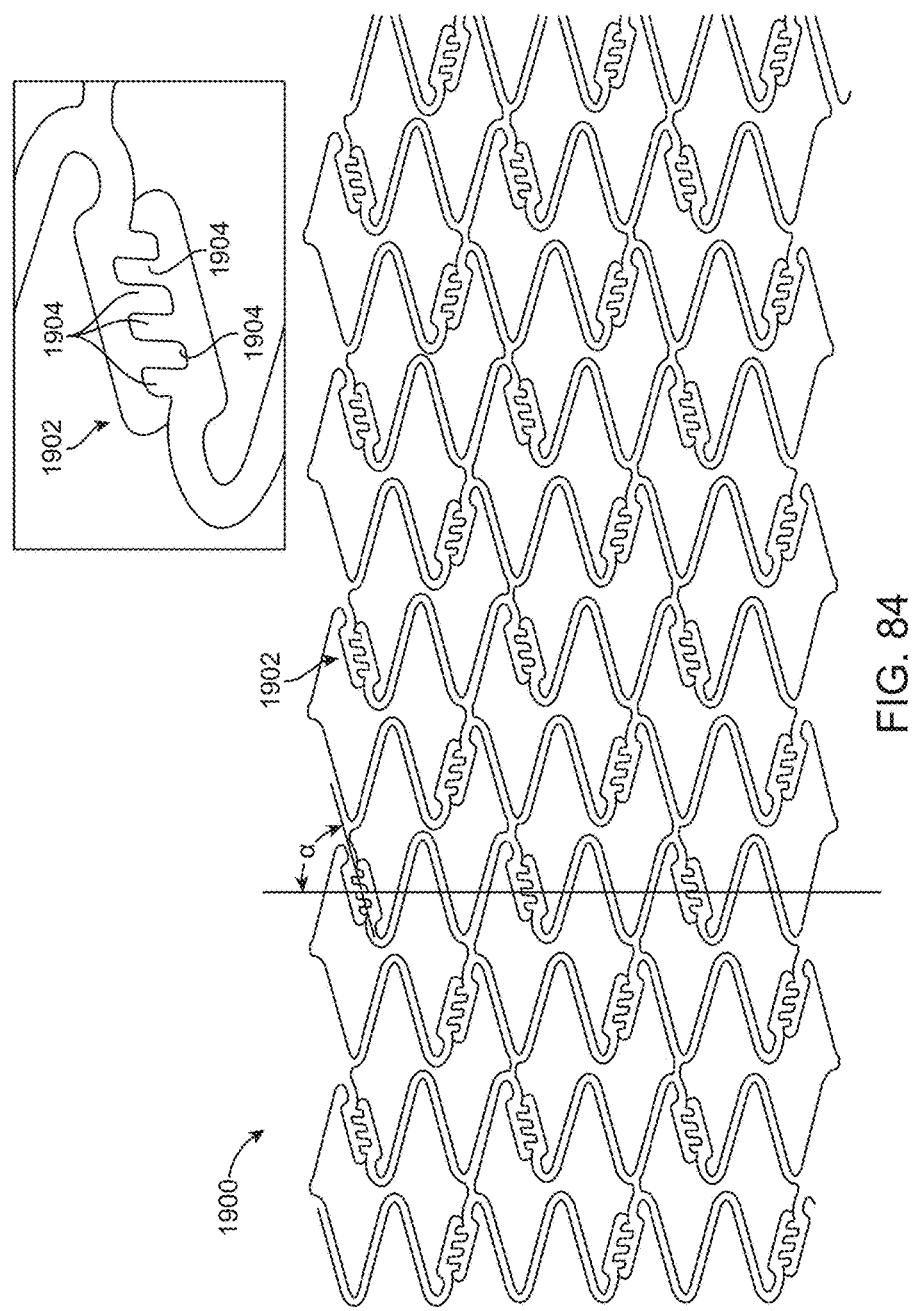
FIG. 84 illustrates an alternative example of a stent prosthesis structure having displacement regions (separation regions or discontinuities) such as circumferential displacement regions present at approximately 45 degree angles in the crimped configuration.

Referring now to FIG. 84, an alternative stent structure 1900 has separation regions 1902 comprising interlocking combs with one or more interlocking teeth 1904. The interlocking combs allow control over the direction of separation. While the separation regions are oriented at an angle α of about 60° relative to the circumference of the stent in the crimped stent position (or 30° relative to the longitudinal axis of the stent), allowing them to resist separating when the stent is expanded from a crimped configuration to an expanded configuration. However, after expansion, the separation regions 1902 move toward a circumferential alignment, allowing the teeth 1904 of the comb to slide in and out of their position. The angle of the interlocking comb in the crimped configuration can be from 0° to 75°, preferably be from 20° to 65°, and more preferable be from 30° to 60°. The angle of the interlocking comb separation regions in the expanded stent configuration compared to the stent longitudinal length is approximately 90°, but can also range from 65° to 120°, preferably ranges from 75° to 110°, more preferably ranges from 80° to 100°. The separation region of this type preferably are substantially aligned with the circumference of the stent in the expanded stent configuration.

Figure 85:
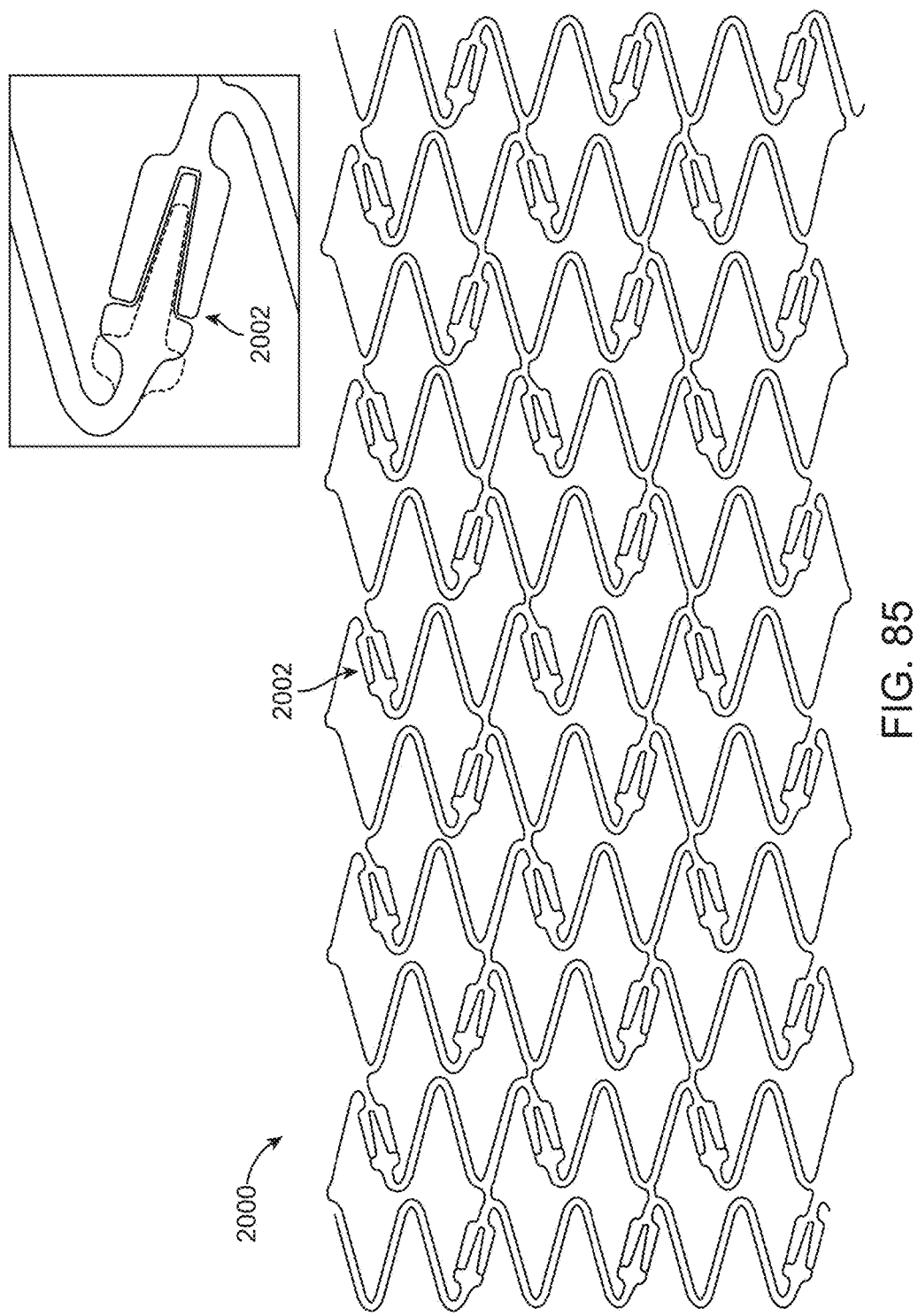
FIG. 85 illustrates an alternative example of a stent prosthesis structure having displacement regions (separation regions or discontinuities) such as circumferential displacement regions present in a configuration that allows a wider range of alignment.

Referring now to FIG. 85, stent structure 2000 comprises separation regions 2002 having a "lock-and key" structure with tapered geometry. As shown in broken line, the tapered geometry allows a greater lateral separation between the male and female elements as the elements are drawn apart than would be the case for non-tapered elements. This increased lateral separation allows the struts and other structural elements of the stent ring freer movement relative to each other in a wide range of alignment, such as a keystone or trapezoidal shape. This allows for more forgiving movements of structural elements, preferably in the circumferential direction, even when the structural elements are not perfectly aligned in a circumferential direction. For example, if the taper on the keystone element is about 10°, the elements will continue to move in the circumferential direction easier (or more freely) if they are aligned within 10° of the circumferential direction. Other shapes such as trapezoid shapes can also be beneficial.

Figure 86C:
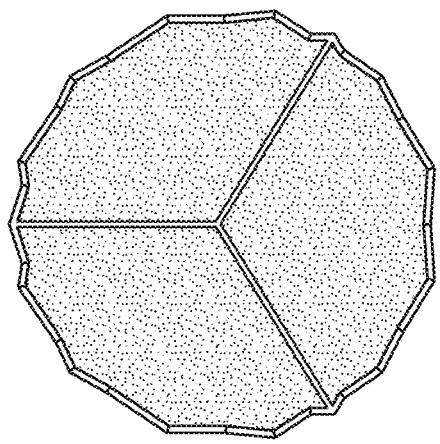
FIGS. 86A-86C illustrate an example of a prior art stent prosthesis coupled to a tricuspid valve for placement in an aortic valve annulus to replace the native aortic valve.
Figure 86B:
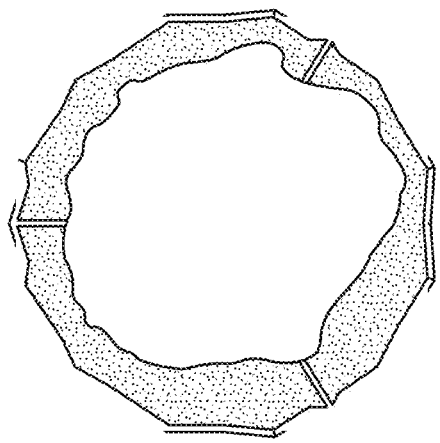
Figure 86A:
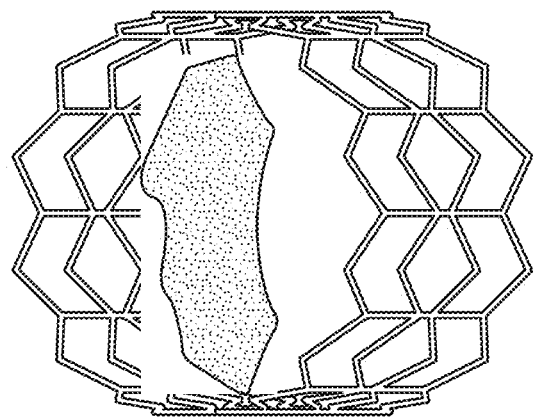

Referring now to FIG. 86, an example of a prior art stent for valve replacement showing the stent and stent pattern in FIG. 86A with the valve in an open position, a top view of the stent with the valve in an open position 86B, and a top view of the stent with the valve (tricuspid) in the closed position 86C. The valve is coupled to the stent, and a skirt covers at least one circumferential segment of the stent. The stent typically have one or more circumferential rings, have sinusoidal pattern, closed cell pattern, or combination pattern, or other. The stents are typically balloon expandable, or self-expanding stents prosthesis, can be retrievable or adjustable before implantation, and although can be deployed surgically, are typically inserted into the body percutaneously, or introduced into the valve region via an atrium region, a ventricle region such as apical approach, or a trans-septum approach, for example. The valve can be bicuspid valve, a tricuspid valve, or other types of valve. The valve to be replaced or repaired can be the aortic valve, the mitral valve, the tricuspid valve, or other valves in the body.

Referring now to FIGS. 87A-D, a stent 2100 for valve replacement (valve not shown) has the stent pattern comprising one or more sinusoidal, circumferential rings. At least some of the one or more rings have one or more separation regions, discontinuities, and/or joints, with four lock-and-key separation regions 2102 being illustrated. The illustrated separation regions 2102 are located symmetrically fashion about a single ring 2104 of the stent 2100. In other examples, however, the separation regions may be located asymmetrically, may be placed on more than one ring, and may be positioned (or placed) in a variety of patterns along the circumferential path of one or more rings of the stent. In still other examples, the separation regions may be placed on two or more adjacent rings that are, two or more non-adjacent rings, on every other ring, on every third ring, or in other patterns. The separation region can be any of the types described in this application including discontinuities, etc. In another example, as shown in FIG. 87D, one or more hinges 2106 or other joints can be placed on at least one ring as described above. Also, other types of joints can be utilized such as ratchet, hinge, saddle, condyloid, ball and socket, plane, or other, etc. The stent prosthesis separation region or joints can be configured in a variety of patterns where at least some of circumferential rings separation regions are aligned longitudinally (longitudinal stent length) on adjacent rings, aligned in other type patterns, in order to achieve one or more of uncaging, changing in shape configuration, displacement direction and/or magnitude, of one or more rings, when the stent is in the expanded configuration. In one example, at least one region of the valve material is coupled to one separation region or joint on the stent prosthesis. In another example, at least two valve material regions are coupled to two separation regions or joints on the stent prosthesis, in a third example, at least three valve regions are coupled to three separation regions or joints on the stent prosthesis. In another example, at least one valve region is coupled (or connected) to a stent circumferential structural element adjacent to a separation region or joint on the stent. In another example, at least one valve material region is connected to a circumferential structural element above and/or below a separation region or a joint on the stent ring(s). In another example, the valve material is substantially connected to one circumferential ring having one or more separation regions or joints on the stent. In another example, the valve material is substantially connected to at least two circumferential rings having one or more separation regions or joints on the stent. In another example, the valve material is substantially connected to one circumferential ring adjacent to a ring having one or more separation regions or joints on the stent. The stent has sufficient strength in the expanded configuration to support a valve annulus or a body lumen. The stent can optionally have supporting features such as those described in FIGS. 23C, 23D, or other type of features to further enhance strength of the stent prosthesis in the expanded configuration. The one or more separation regions and/or joints on at least one ring (or circumferential element) of the stent prosthesis are configured to allow one or more of the following after stent expansion to said at least one ring (or circumferential element) and/or to the stent: increase radial strain, increase radial strain while decreasing the strength from the initial deployed strength, change of the radial strain magnitude after expansion of the stent, change of the strength magnitude after expansion of the stent, decrease in strength after expansion, change of the stent shape configuration, change of the displacement and/or magnitude in at least one direction, increase in the displacement in at least one direction, decrease in the displacement in at least one direction, preventing or minimizing valvular leaks after implantation, preventing or minimizing valve regurgitation after implantation, change of the at least one ring shape and/or the stent shape after expansion to one or more of: a tear drop shape configuration, an oblong shape configuration, an oval shape configuration, a football shape configuration, a saddle type shape configuration, a shape configuration contouring (or more fitting, or more suited) to a valve annulus after stent expansion or after said valve annulus have changed shape configuration, other type shape configuration. In one example, the at least one ring and/or the stent in the expanded configuration has an initial shape, wherein the shape changes after expansion, or after the valve annulus shape configuration changes after stent expansion, or the at least one ring and/or stent in the expanded configuration has an initial shape, wherein the shape is substantially tubular, and wherein the shape configuration changes to substantially non tubular after expansion. The one or more separation regions and/or joints are configured as described throughout this application, wherein said regions and/or joints are held together upon expansion of the stent from a crimped configuration to an expanded configuration and wherein the separation regions and/or joints have discontinuities and/or allowed to move in at least one direction after expansion, preferably in a time period ranging from 1 day to one year after expansion, more preferably in a time period ranging from 1 month to 9 months after expansion. The means of holding the separation regions and/or joints together to prevent movement or separation are described throughout this application. In another example, the separation regions and/or joints are configured to not be held together upon expansion from a crimped configuration to an expanded larger configuration. In another example, more typically where the stent prosthesis is patterned from a shape memory alloy, the stent continues to apply force against the annulus region potentially damaging it, or the stent does not conform well to the shape of the annulus well causing some blood leakage, in such example, the one or more separation region on at least one ring (and/or the stent) can help reduce such force and better conform to the annulus shape. The at least one ring and/or the stent strength decreases, thereby reducing the force on the annulus (or lumen). The radial strain, displacement, and other parameters, have been previously described in the application. In one example, the stent prosthesis is secured to a fixation implant in the annulus or adjacent to the annulus to provide additional support or strength to the stent prosthesis after at least some of the separation regions and/or joints have discontinuities and/or are allowed to move.

Referring now to FIGS. 88A-88D, a stent 2120 for use in forming a prosthetic valve is constructed similarly to stent 2100 of FIGS. 87A-87D. Instead of symmetrically spacing the separation regions 2122, however, stent 2120 has three separation regions 2122 clustered closely on a single serpentine ring 2126, and the separation regions may optionally have hinges 2124 or other joints a shown in FIG. 88D. Having separation regions clustered around one or more stent segments (or regions) can be appreciated to perform one or more of the objectives of this invention.

Referring now to FIGS. 89A-89D, a closed cell stent 2130 for use in forming a prosthetic valve has four lock-and-key separation regions 2132 located symmetrically about a single ring 2134 of the stent 2130. The separation regions may optionally have hinges 2136 or other joints a shown in FIG. 89D.

Referring now to FIGS. 90A-90D, a stent 2140 for use in forming a prosthetic valve is constructed similarly to stent 2130 of FIGS. 88A-88D. Instead of symmetrically spacing the separation regions 2142, however, stent 2122 has three separation regions 2142 clustered closely on a single serpentine ring 2144, and the separation regions may optionally have hinges 2146 or other joints a shown in FIG. 90D.

Figure 91A:
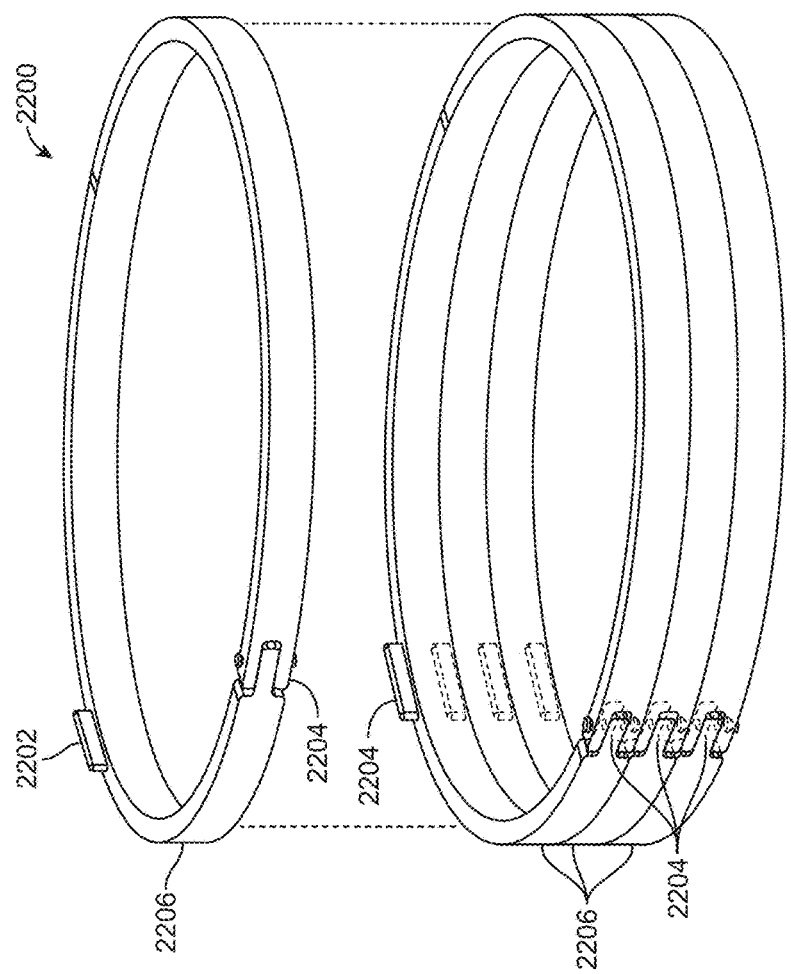
FIGS. 91A-91E illustrate an example of a fixation implant having at least one joint allowing a displacement in at least one direction, and change in shape configuration, after expansion.
Figure 91B:
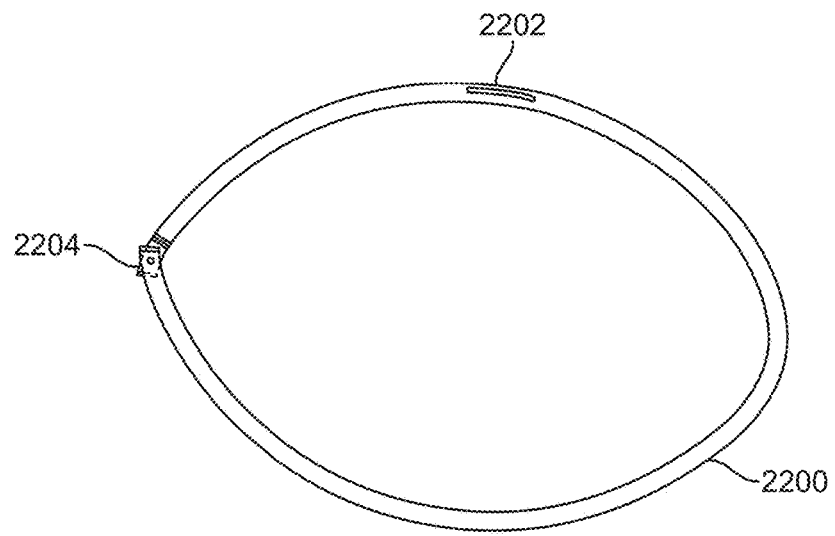
Figure 91C:
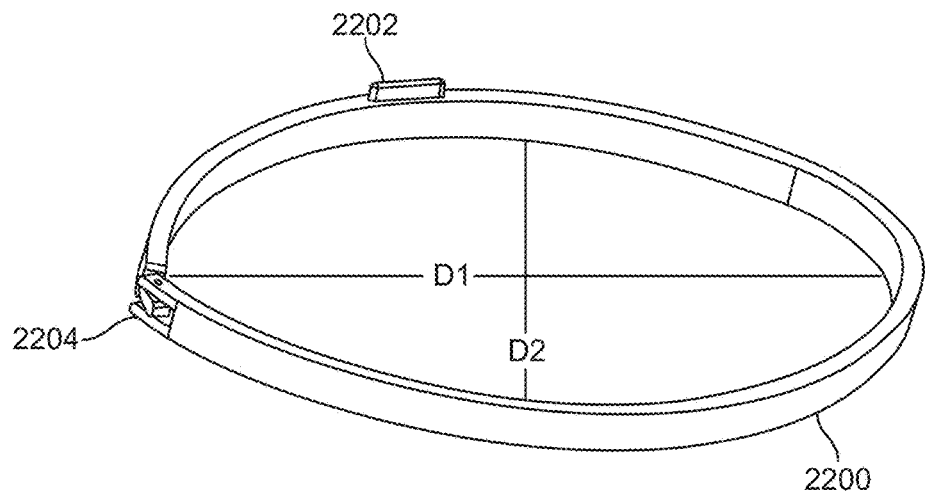
Figure 91D:
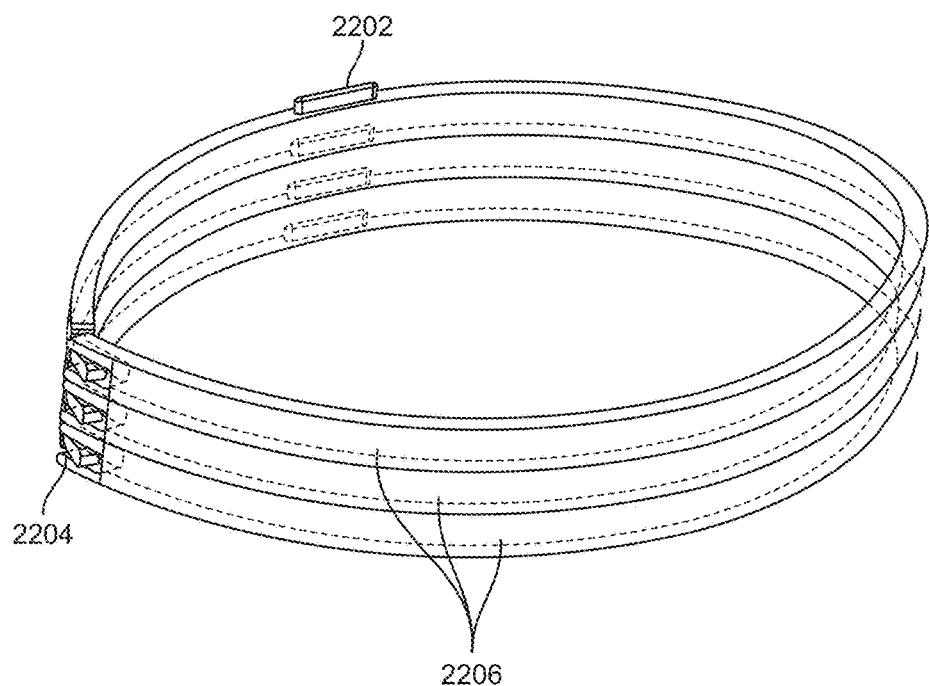
Figure 91E:
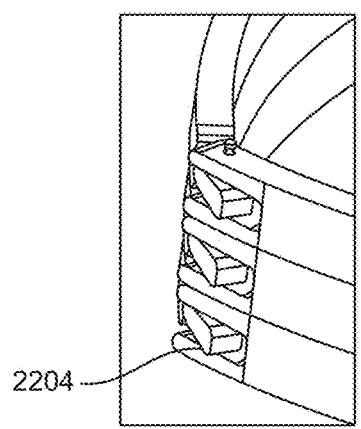

Referring now to FIG. 91A, a fixation implant 2200 comprises one or more rings 2206 each having one or more joints 2204. The implant 2200 may be coupled to a valve annulus, adjacent to a valve annulus, above a valve annulus (superior), below a valve annulus (inferior), or some combination thereof, for performing annuloplasty, implanting a valve, or for any other purpose. Each ring in a stack of rings can have a similar shape and geometry, or two or more rings can have different shapes or geometries, so long as the ring or rings are suitable for implantation within the annulus, the superior region to the annulus, or the inferior region to the annulus. The ring and/or stack of rings are configured to attach to the annulus, annulus tissue, or tissue adjacent to the annulus in a variety of ways such as sutures, clips, hooks, etc. Fixation element 2202 may be provided on some or all of the rings, a plurality of such elements may be provided along the length of the fixation implant. The fixation implant 2200 can be configured to receive (or to be coupled to) a valve or a stent containing a valve to replace the natural defective valve of the body (not shown in the drawings). The stent in one example can have at least one ring having one or more separation regions and/or joint. Alternatively, the fixation implant can be attach to (or be coupled with) the native valve, to one or more regions of the native valve, attached to one or more regions adjacent to the valve or valve region (such as chordae tendinese) to improve the function of the native valve, to reduce regurgitation of the vale, and/or to reduce blood leakage of the valve. The fixation implant ring and/or stack of rings are configured to have separation region and/or joints in accordance with the principles of this application to allow one or more of the following: shape configuration changes after implantation of said ring and/or stack of rings, to allow displacement in at least one direction, or to allow displacement changes in at least one direction, to allow changes in displacement in D1 and D2 after implantation of fixation implant, to allow increase radial strain, and other as described in this application, as shown for a single ring in in FIGS. 91B and 91C and for a three ring implant in FIGS. 91D and 91E.

The various figures illustrate some examples but are not limited to such examples, where the change in shape or displacement in x-axis, y-axis, orthogonal to the plane axis, or combination thereof, etc. Various configurations of separation regions and/or joint are possible to achieve various shape type configurations, displacement direction and displacement magnitude, allowing the fixation implant to better conform to the annulus of the valve and/or the valve leaflets, and or a valve region, such that the functionality of the valve is improved, regurgitation of the valve is minimized or prevented, and/or blood leakage is minimized or prevented. The adaptive compliance, displacement, and/or shape configuration to the annulus, annulus valve, or tissue adjacent to the annulus, improves the functionality of the native valve, after implantation of the fixation implant, and/or after change to the annulus shape, or configuration. In one example of the stackable configuration, the number of separation regions and/or joints can be different or the same, the location of separation regions and/or joints can be different or same, to allow for one or more of change in shape configuration, displacement in one or more direction, and/or radial strain of the fixation implant. Typically, the fixation implant is affixed to the tissue in a plurality of places to secure the fixation implant to the said tissue, and wherein the shape configuration changes, displacement changes, or radial compliance changes occur about, or adjacent to, said separation regions and/or joint. In one example, the stackable rings can have varying shape changes configuration, displacement, and/or radial compliance, from one ring to an adjacent ring. The ring and/or stackable rings can also be configured to receive a stent prosthesis for valve replacement. In one example, the ring and/or stackable rings can affect the shape, displacement, or radial compliance of the stent as a result of ring and/or stackable ring changes in shape, displacement, and/or compliance. Alternatively, the ring and/or stackable rings can be adapted to receive a stent prosthesis having one or more separation regions and/or joints. In this case, the ring and/or stackable ring can amplify the shape changes, displacement magnitude, and/or compliance of the stent prosthesis (and/or valve contained within the stent prosthesis), or can further secure and provide strength to the stent prosthesis. In one example the rings and/or stackable rings are implanted percutaneously by having multiple folding joints along the path of the circumferential length of the ring, wherein the joints when opened or expanded provide the ring in the open position. Some of the joints are configured to be held in place once open while other are held in place while open and after implantation are configured to move or to have a displacement in one or more directions. Means to hold the separation regions and/or joints are described elsewhere in this application.

Referring now to FIGS. 92A-92F, a fixation implant 2210 comprises one ring 2212 (FIG. 92A) or three rings 2212 (FIG. 92B), each ring having two diametrically opposed joints 2214. The implant 2210 may be coupled to a valve annulus, adjacent to a valve annulus, above a valve annulus (superior), below a valve annulus (inferior), or some combination thereof, for performing annuloplasty, implanting a valve, or for any other purpose. Each ring 2214 is capable of bending radially inwardly and outwardly at each joint 2214, as shown in by arrows D1 and D2 in FIGS. 92C and 92D for a single ring and in FIGS. 92E and 92F for a three ring stack. Fixation elements 2216 are usually provided on at last the terminal ring in each stack.

Figure 92A:
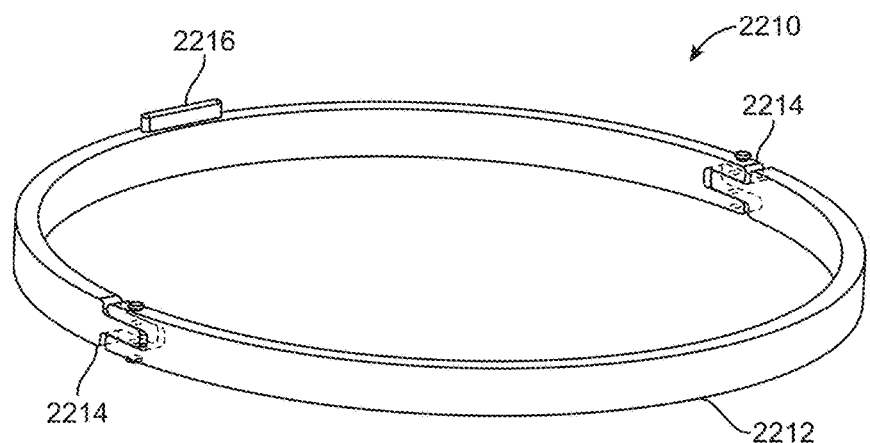
FIGS. 92A-92F illustrate an example of a fixation implant having two joints allowing displacement in at least one direction (or dimension), and change in shape configuration, after expansion.
Figure 92B:
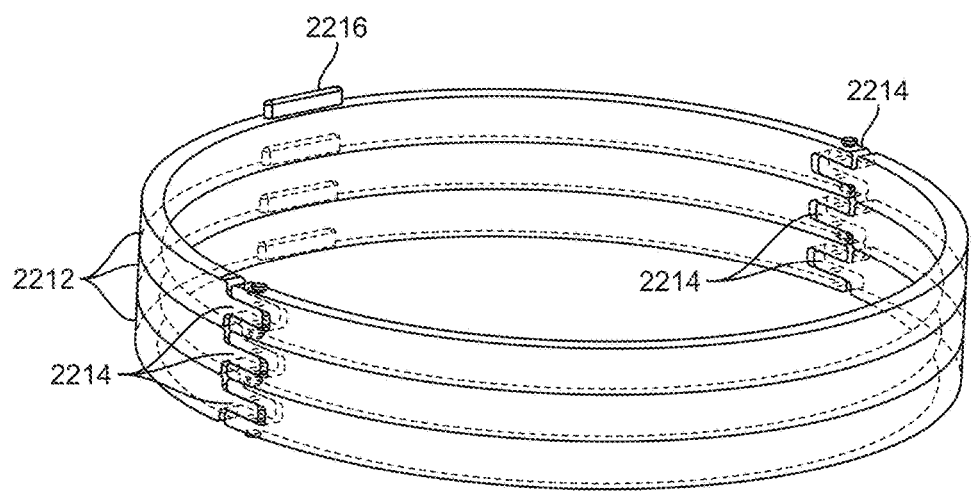
Figure 92C:
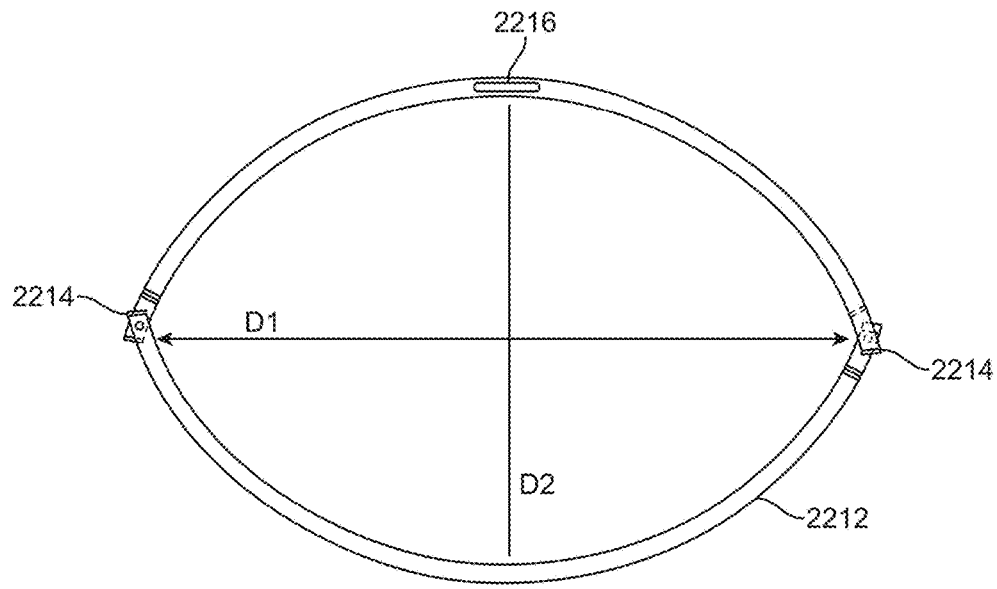
Figure 92D:
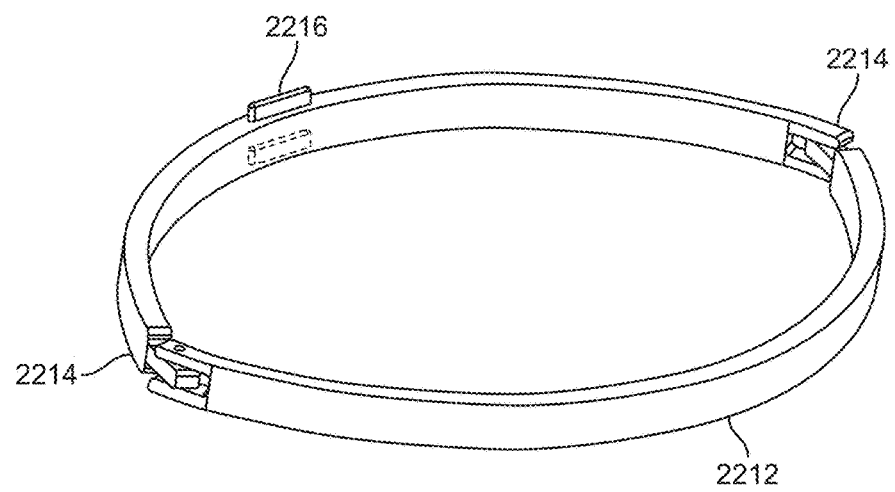
Figure 92E:
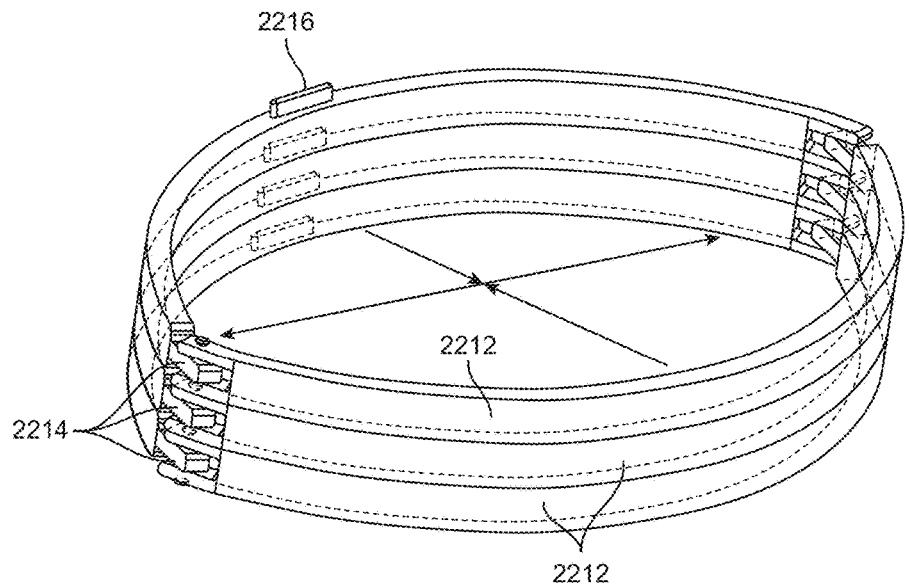
Figure 92F:
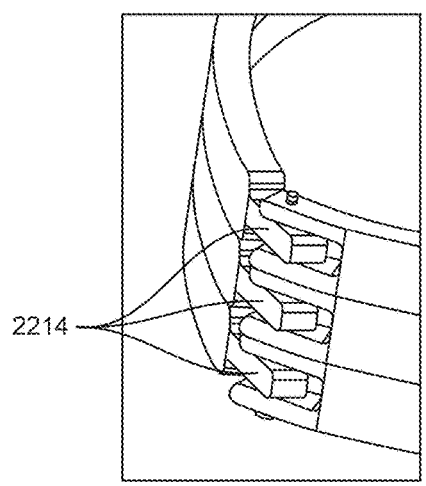

Referring now to FIGS. 93A-93E, a fixation implant 2220 comprises one ring 2222 (FIG. 93A) or three rings 2222 (FIG. 93B), each ring having two diametrically opposed joints 2224. The implant 2220 may be coupled to a valve annulus, adjacent to a valve annulus, above a valve annulus (superior), below a valve annulus (inferior), or some combination thereof, for performing annuloplasty, implanting a valve, or for any other purpose. Each ring 2224 is capable of bending in a lateral plane at each joint 2214, as shown in FIGS. 92C and 92D for a single ring and in FIGS. 92E and 92F for a three ring stack. Fixation elements 2216 are usually provided on at last the terminal ring in each stack.

Figure 93A:
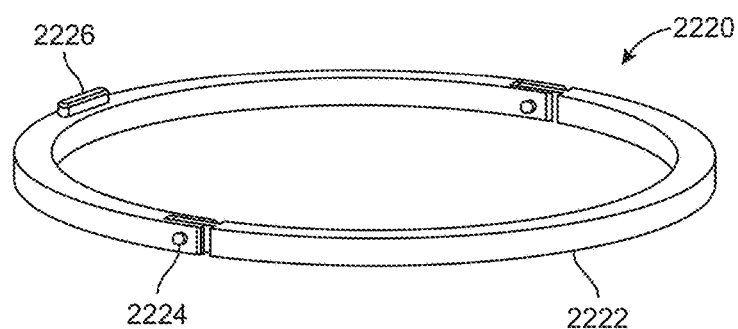
FIGS. 93A-93E illustrate an example of a fixation implant having two joints allowing for displacement (or movement) in an axis orthogonal to plane of the hoop.
Figure 93B:
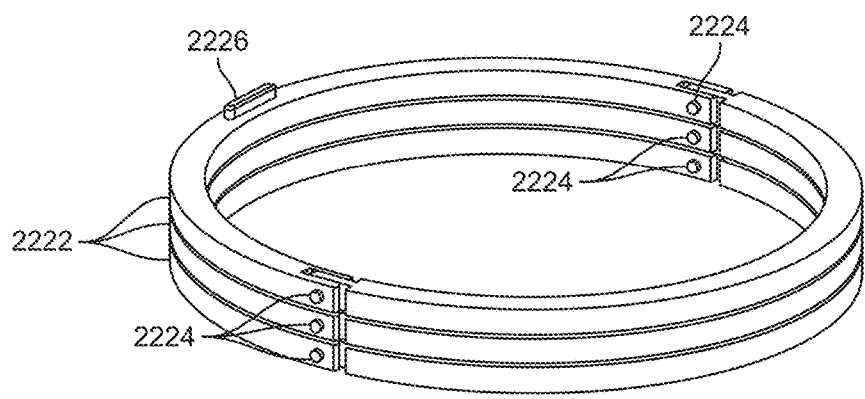
Figure 93C:
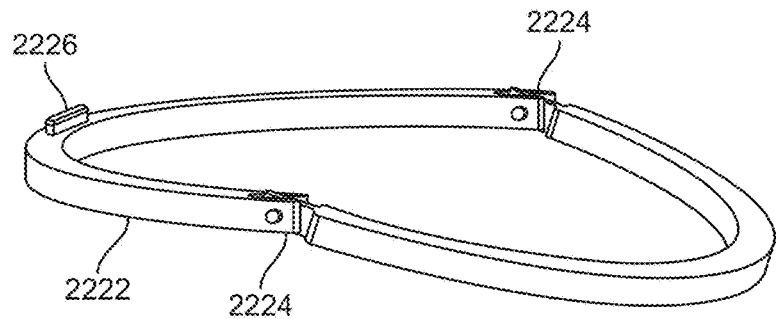
Figure 93D:
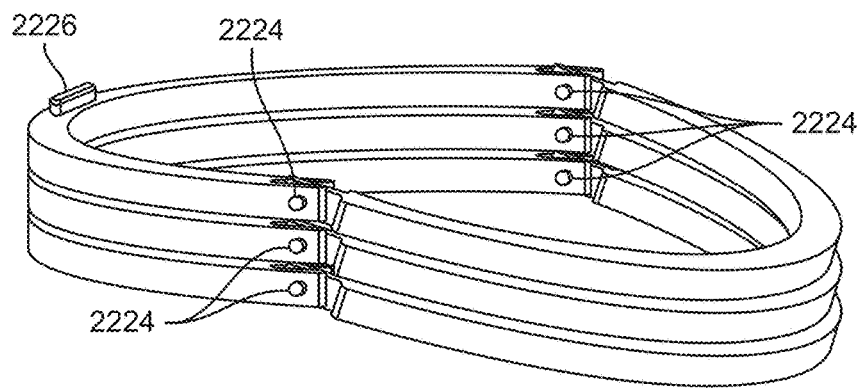
Figure 93E:
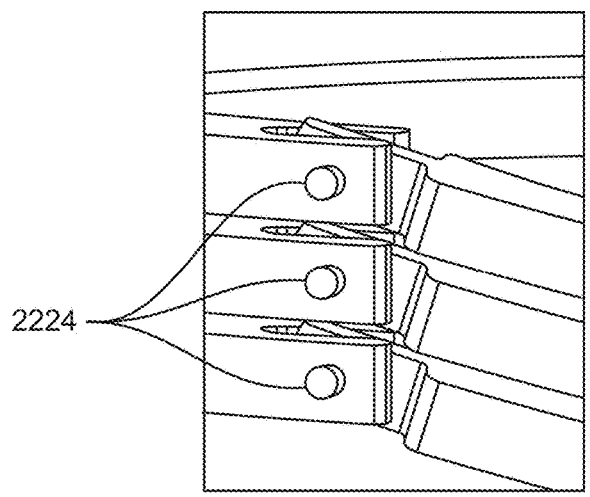
Figure 94A:
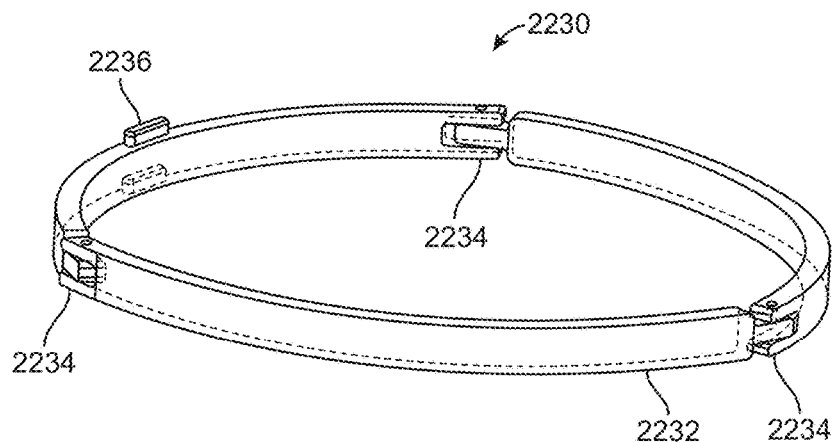
FIGS. 94A-94B illustrate a fixation implant having three joints allowing for movement in at least one direction, and change in shape configuration.
Figure 94B:
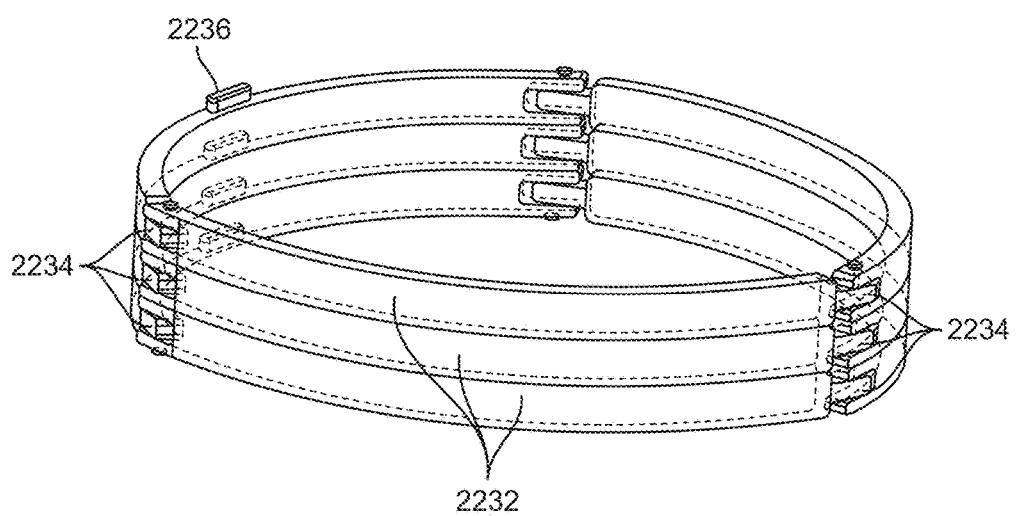

Referring now to FIGS. 94A and 93B, a fixation implant 2230 comprises one ring 2232 (FIG. 94A) or three rings 2232 (FIG. 94B), each ring having three joints 2234 symmetrically spaced about its circumference. The implant 2230 may be coupled to a valve annulus, adjacent to a valve annulus, above a valve annulus (superior), below a valve annulus (inferior), or some combination thereof, for performing annuloplasty, implanting a valve, or for any other purpose. Each ring 22234 is capable of bending radially inwardly and outwardly. Fixation elements 2236 are usually provided on at last the terminal ring in each stack.

Figure 95A:
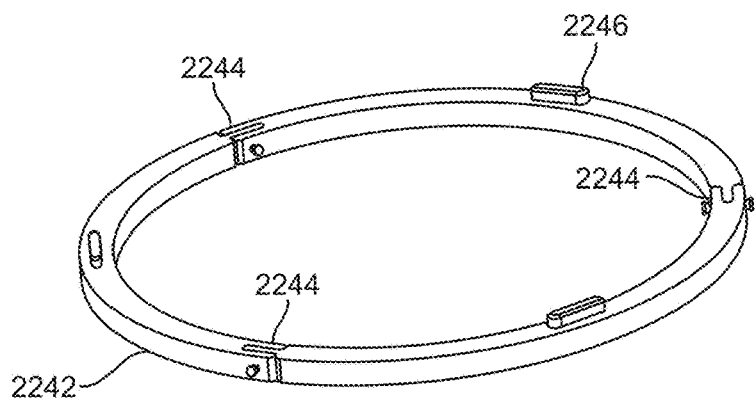
FIGS. 95A-95C illustrate a fixation implant having three joints allowing for movement (or displacement) in at least one direction (or dimension) being in an axis orthogonal to the plane of hoop.
Figure 95B:
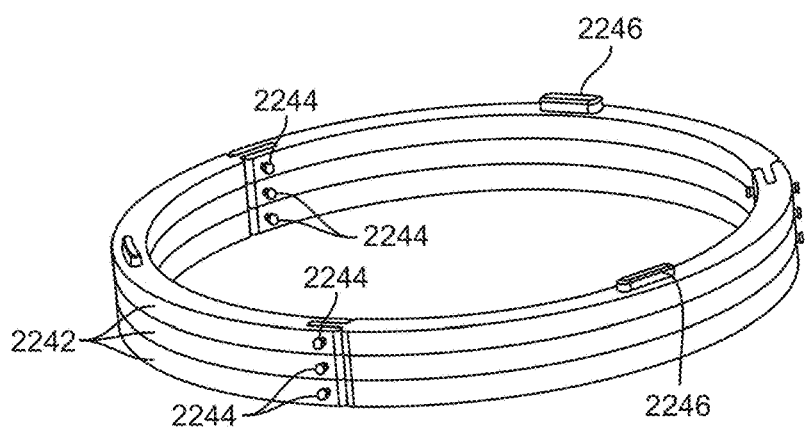
Figure 95C:
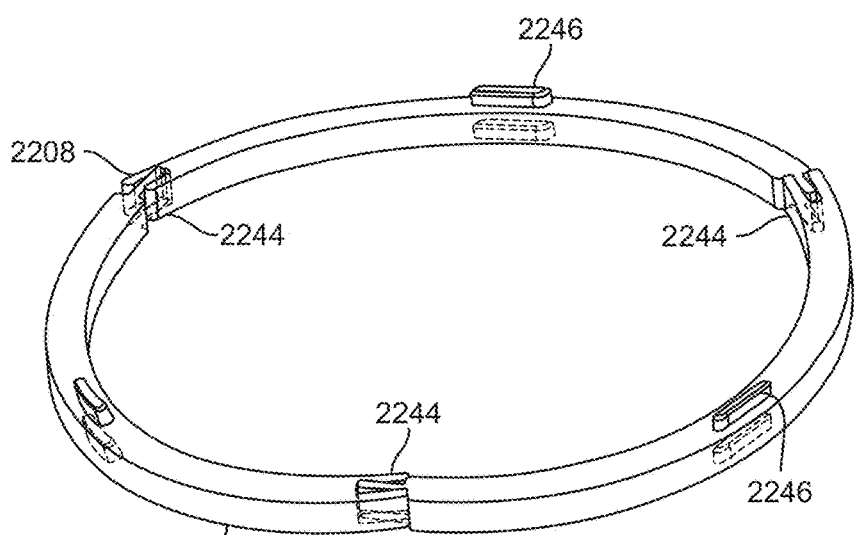

Referring now to FIGS. 95A-95C, a fixation implant 2240 comprises one ring 2242 (FIG. 95A) or three rings 2242 (FIG. 95B), each ring having three joints 2234 symmetrically spaced about its circumference. The implant 2240 may be coupled to a valve annulus, adjacent to a valve annulus, above a valve annulus (superior), below a valve annulus (inferior), or some combination thereof, for performing annuloplasty, implanting a valve, or for any other purpose. Each ring 2234 is capable of bending in lateral plane, as shown in FIG. 95C. Fixation elements 2246 are usually provided on at last the terminal ring in each stack.

Figure 96A:
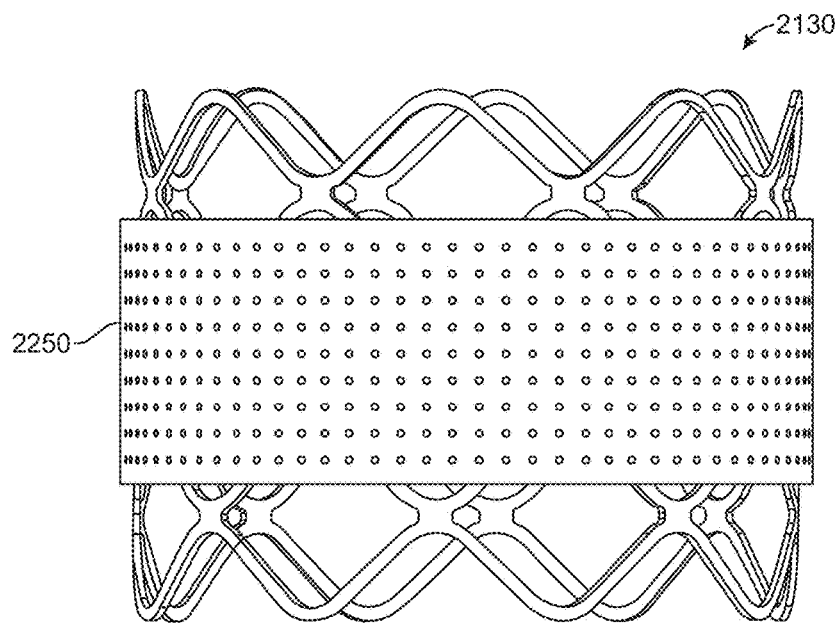
FIGS. 96A-96B illustrate a stent for valve replacement having separation regions (or joints) and having a skirt on the outside of the stent having perforations. The stent is coupled to a valve (not shown).
Figure 96B:
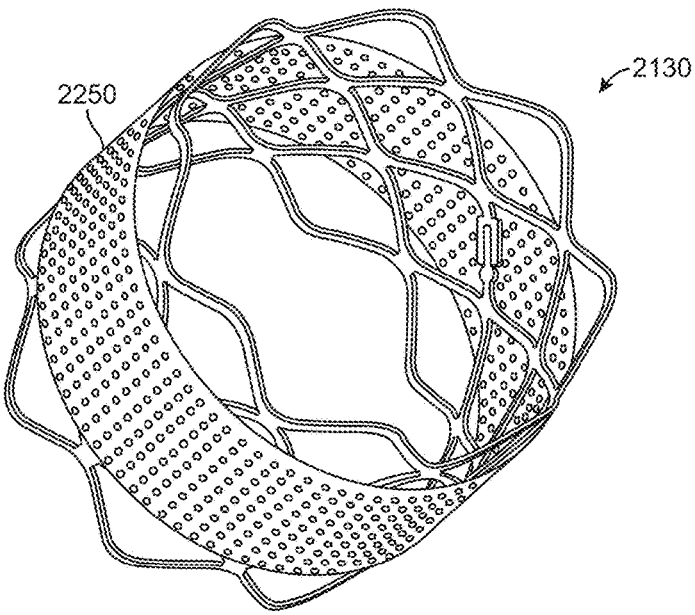

Referring now FIGS. 96A and 96 B, a skirt 2250 formed for example from a polymeric material having perforations is configured to cover at least one circumferential region (or segment) of a stent prosthesis on the outside as shown or on the inside (not shown). For convenience, the skirt 250 is shown to cover the closed cell stent 2130 illustrated in FIGS. 89A-89D and described above. In another example (not illustrated), a second skirt may cover over at least one segment or region of the first skirt either on the same surface region of the first skirt (outer surface region, outer surface region) or on the other surface region (inner surface region, outer surface region). In one example, the separation regions and/or joints after formation of discontinuities or being allowed to move, allow blood to flow between one skirt and the annulus tissue (the shown figure), and/or between the two skirts, to trap blood in between, and prevent leakage of the blood after implantation.

The bending or opening resistance of the crowns of a serpentine or other scaffold ring can be adjusted in various ways. For example, the force required to open or separate the struts connected to a common crown can be controlled by forming an opening or void in the crown and optionally filling that opening or void with a reinforcement material. As shown in FIGS. 97A-97G, the crown region 2300 joining a first strut 2302 and a second strut 2304 can have any one of a variety of voids formed therein. The voids can be formed by any conventional stent fabrication technique, such as laser cutting, chemical etching, or the like. Suitable geometries include the rectangular void 2306, as shown in FIG. 97A; a triangular void 2308, as shown in FIG. 97B; a crescent shaped void 2310, as shown in FIG. 97C; and a quarter annulus void 2312, as shown in FIG. 97D. In other instances, a plurality of voids may be provided, such as a plurality of circular voids 2314 as illustrated in FIG. 97E. In still other instances, voids having different geometries can be provided in a single crown, such as a circular void 2316 and a crescent-shaped void 2318 as illustrated in FIG. 97F. Additionally, the voids need not always oriented in a luminal-abluminal direction. In some instances, they can be oriented in a circumferential direction as with void 2320 in FIG. 97G.

Figure 98A:
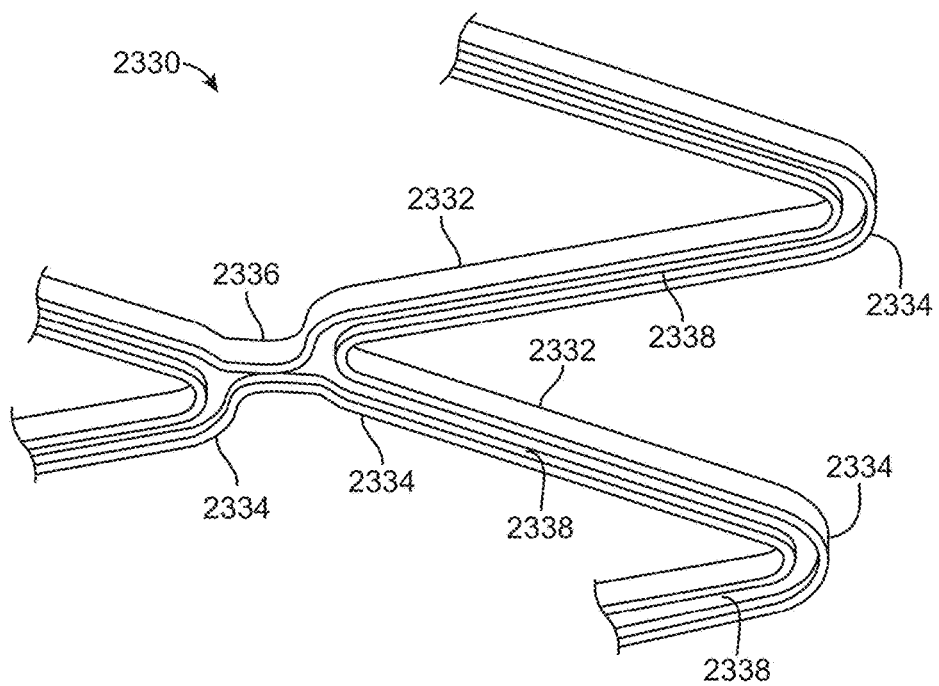
FIGS. 98A and 98B illustrate stent crowns, struts, and links having voids formed as channels (FIG. 98A) and slots (FIG. 98B).

The voids in the scaffolds of the present invention need not extend fully through a thickness or width of the stents scaffold. In other instances, they may be formed as channels in all or a portion of the stents. In particular, a stent scaffold 2330 illustrated in FIG. 98A may include struts 2332, crowns 2334, and axial links 2336, some or all of which have a channel 2338 formed along a length or curvature thereof. These channels may optionally be filled with reinforcement materials as described elsewhere herein.

Figure 98B:
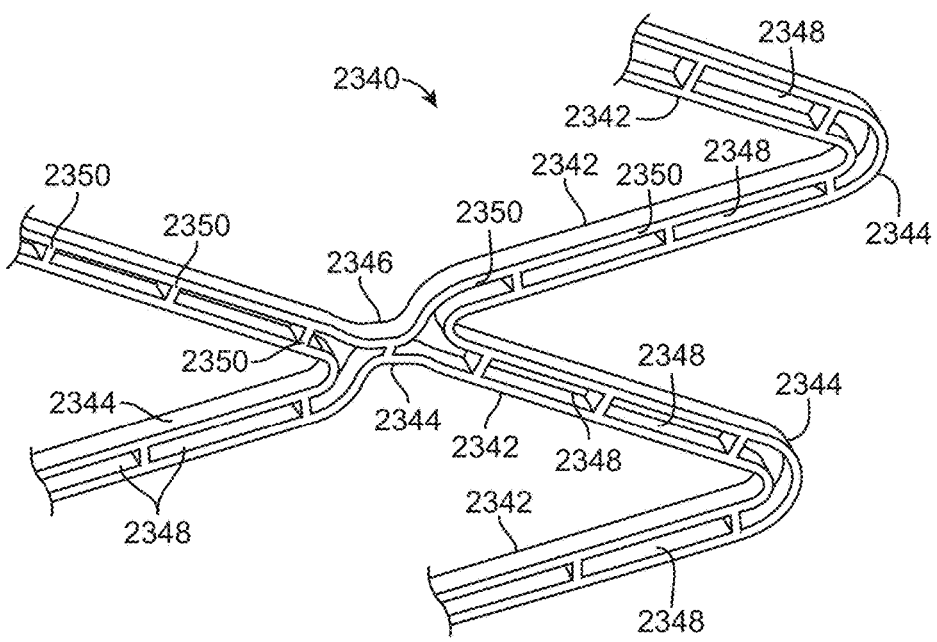
Figure 100A:
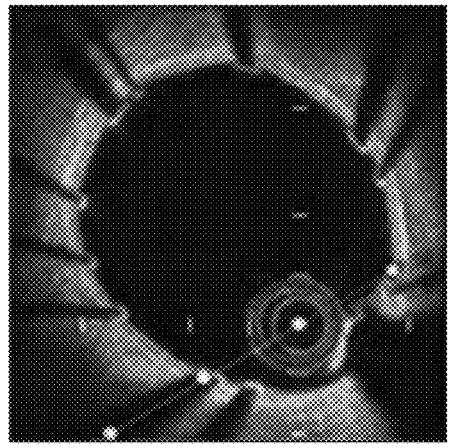
FIGS. 100A-100D are OCT images of stents of the present invention showing the separation regions forming discontinuities in the scaffolds of the present invention after implantation in a porcine artery.
Figure 100B:
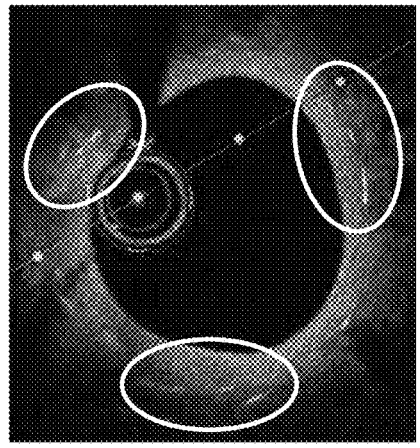
Figure 100C:
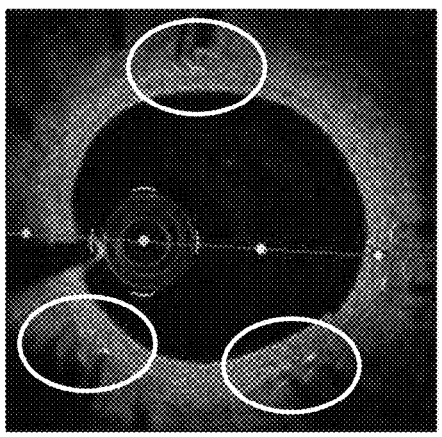
Figure 100D:
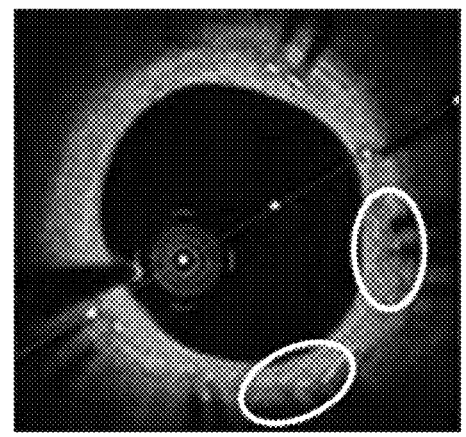

Still further alternatively, a scaffold structure 2340 as illustrated in FIG. 98B, may include struts 2342, crowns 2344, and axial links 2346 connecting adjacent rings, each of which may include one or a plurality of slots 2348 formed there through. Slots 2348 are shown to penetrate fully through a thickness of the strut, crown, and in some cases optionally axial link. It would be appreciated, however, that the slots could be changed into channels which do not fully penetrate the thickness of the stent component but which are separated by a plurality of separation walls 2350. Referring now to FIGS. 99A-99C. Crown regions 2350 joining a first strut 2352 and a second strut 2354, are end-out in various ways. For example, in FIG. 99A each strut 2352 and 2354 may first be tapered by forming a ramp 2356 to reduce the thickness of the strut before joining in to the crown 2350. The crown 2350 may further be end or reduced in its width as indicated by arrows W. Alternatively, as shown in FIG. 99B, the crown 2350 may be end only in the width W. Alternatively, as shown in FIG. 99C, the crown 2350 is reduced in thickness by the transition of ramps 2358, but there is no further reduction in width. In all these embodiments, the crown will have a reduced strength so that it is open with a lesser opening force and if the crown region had not been thinned, it would be appreciated that at least a portion of the strength may be returned by coating, layering, laminating, or otherwise adding a reinforcing material over all or portion of the thinned-out region of the crown as described elsewhere herein. The reinforcement material will typically be selected so that it will degrade over time in a vascular or other luminal or physiologic environment so that the compliance of the crown may be increased after implantation of the associated stent scaffold.

EXAMPLES

The following Examples are offered by way of illustration, not by way of limitation:

Example 1

Figure 24A:
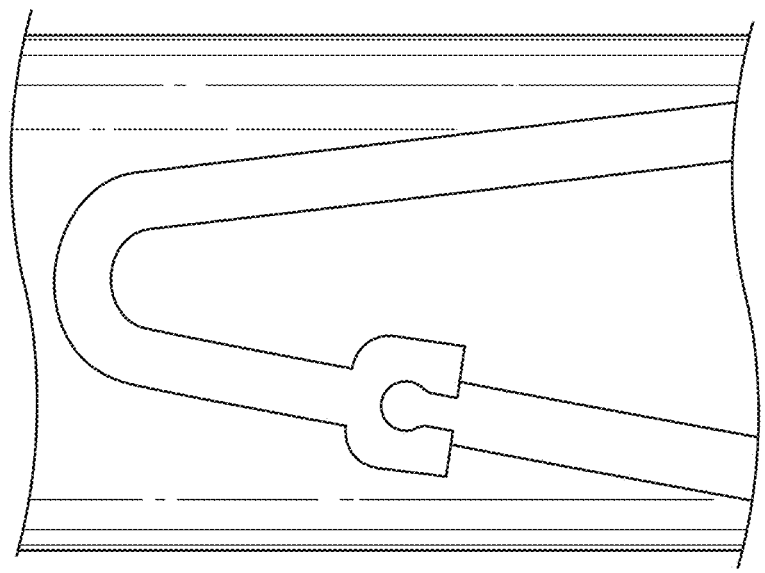
FIGS. 24A, 24B, 25A-25C, 26A-26C, 27A, 27B, 28-31, 32, 32A, 32B, 33, 33A, 33B, 34 and 35 illustrate stents fabricated and tested in accordance with the principles of the present invention.
Figure 24B:
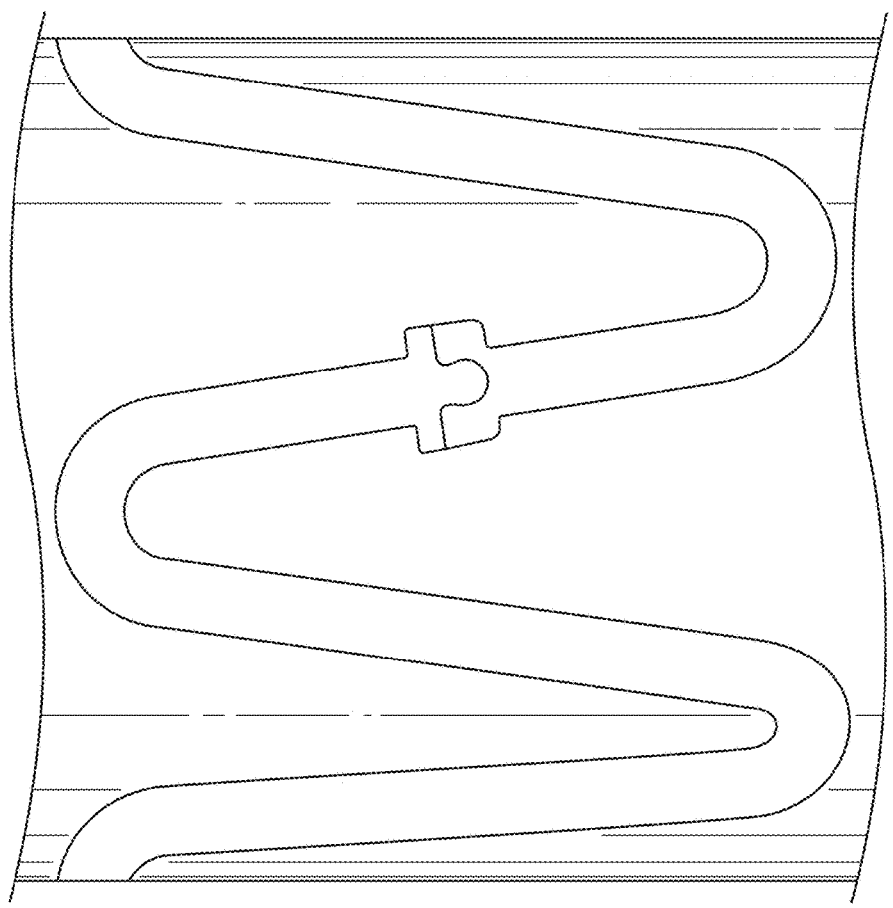
Figure 25A:
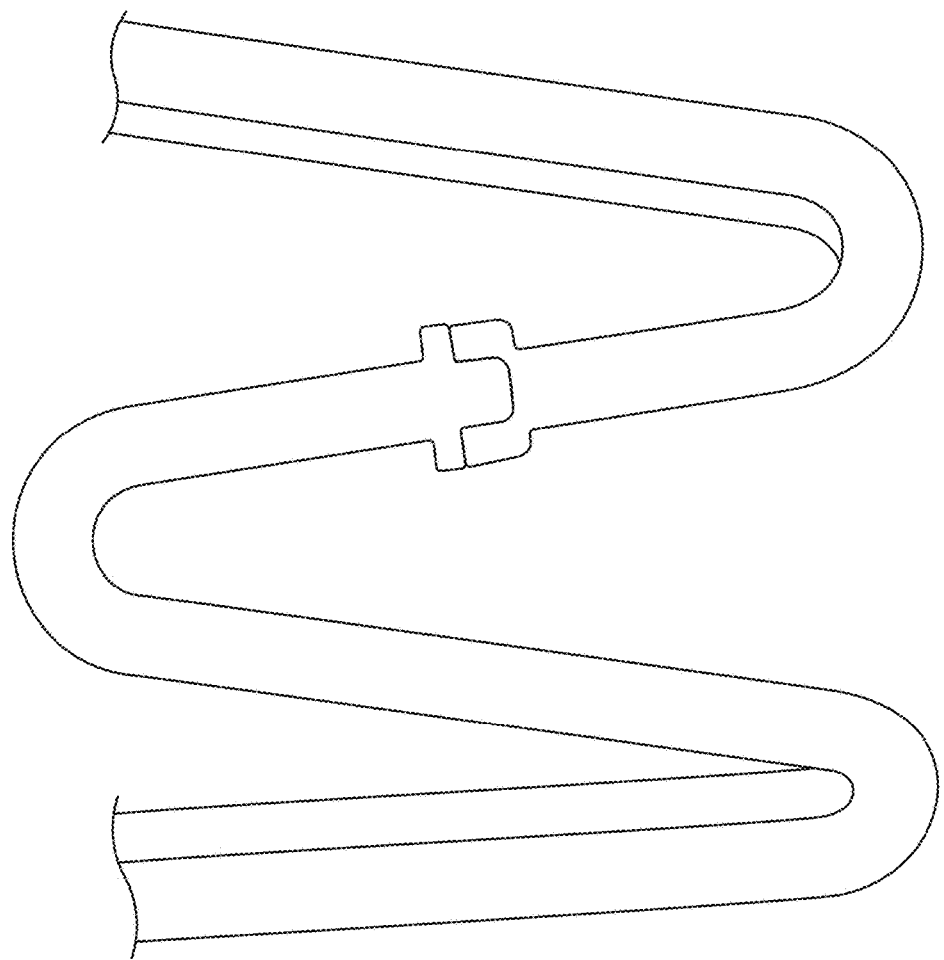
Figure 25B:
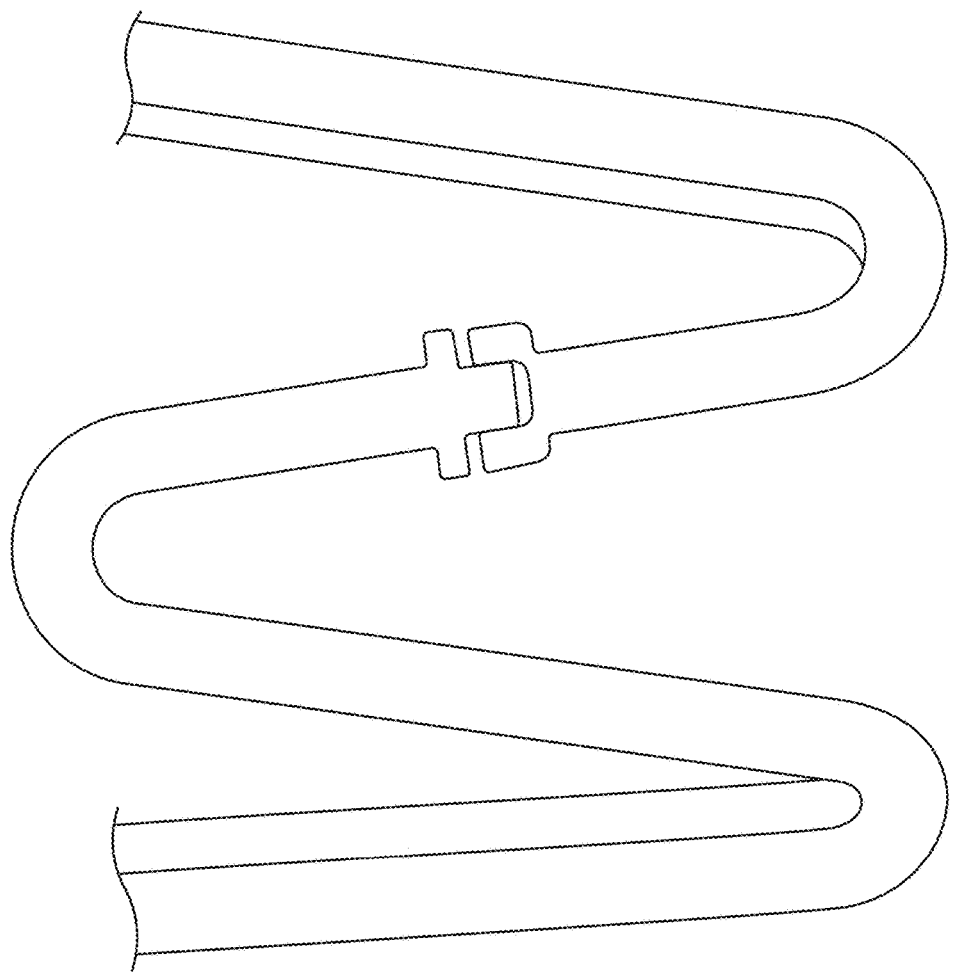
Figure 25C:
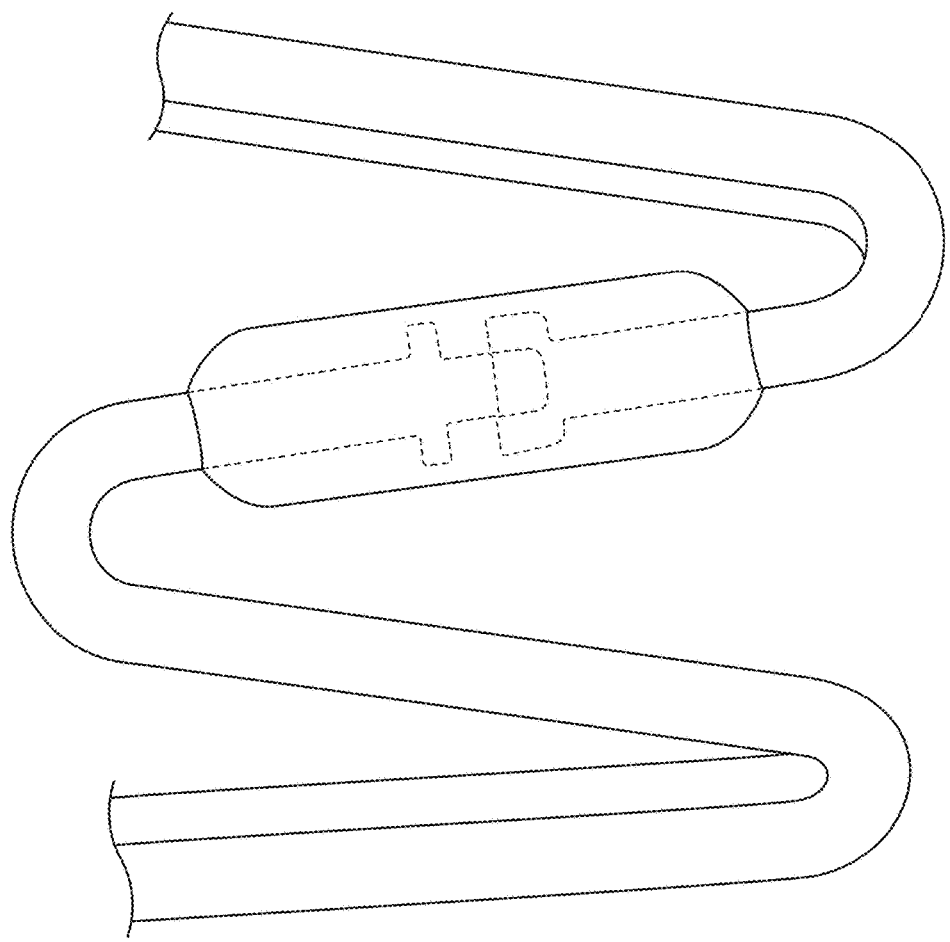
Figure 26A:
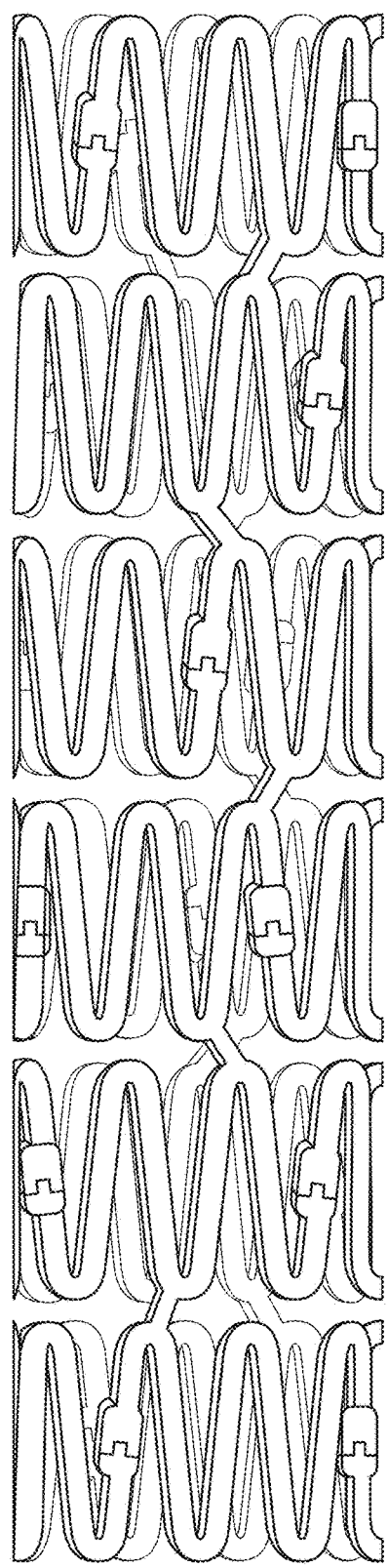
Figure 26B:
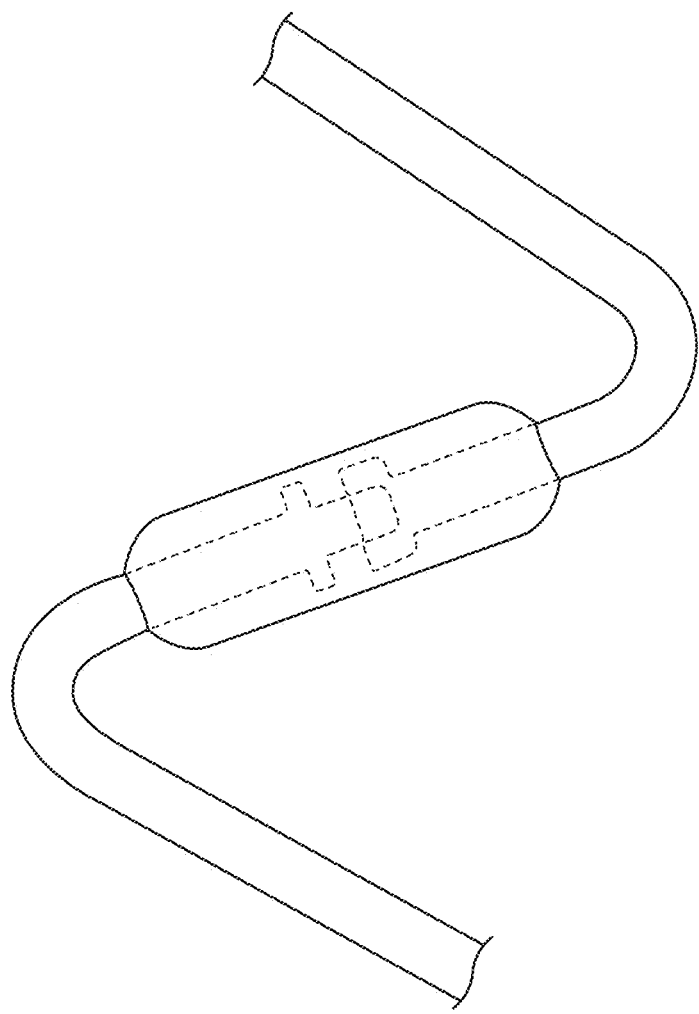
Figure 26C:
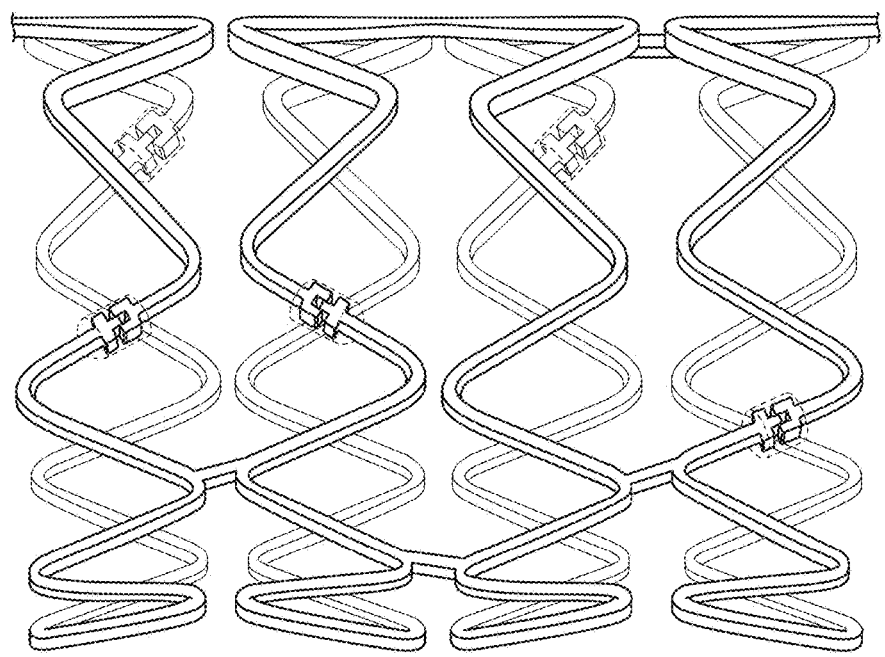

A 9 mm long, 0.063 inch OD annealed L605 cobalt chrome tube having a wall thickness of about 0.004 inches was marked with stent pattern "similar to FIG. 16 G-4 with shorter tongues" having a key and lock design. The key and lock design had either (1) a closed ended configuration to restrict separation to a radially in or out displacement direction (FIG. 24A) or (2) an open ended configuration to allow separation by both by a radially in or out displacement direction and/or by an axial displacement direction (FIG. 24B) after detachment or forming a discontinuity. After laser cutting the open ended configuration with a femtosecond laser (FIG. 25A), the stent was cleaned in a hydrochloric acid solution for 2 minutes to remove islands that have not fallen between the struts, scale and debris, and rinsed in water to remove residual acid. A mandrel was placed inside the stent, and any islands remaining were removed. The stent was then electro-polished in 10% sulfuric acid in ethylene glycol at 20 amps for about 40 seconds. After electro-polishing (FIG. 25B), short sleeves to join the then free ends of the adjacent segments of the stent struts were made from 0.3 mm lengths of tubing made from a biodegradable 50:50 poly(DL-lactide-co-glycolide) with a 0.007 inch ID and a thickness of 0.0018 inch. These sleeves were slipped over each key and lock element, and the stent was then heated at 120° C. in an oven for 10 minutes to melt the polymer tubing and allowed the melted polymer to flow into and over the elements adjacent to the key and lock element (FIG. 25C). As illustrated, the key and lock components had stubs, wings, anchors, or the like to improve attachment after bonding with the polymer. This polymer adjacent to the key and lock and adjacent to the surface of these components effectively locked the key to the lock together until the polymer degrades over a preselected time period, typically in 1 to 3 months, to the point where the sleeve no longer can hold the key and lock together or polymer adhesion can be overcome by the pulling forces under physiological conditions, resulting in separation of the struts and uncaging of the stent (or at least regions/segments of the stent), further expansion of the stent or at least segments/regions of the stent, and/or vessel enlargement (or at least segments or regions of the vessel) and/or to allow vasomotion. The stent has sufficient radial strength after being balloon expanded to a deployed configuration, and have sufficient hoop strength to support the artery after expansion. The key and lock are substantially held together until the polymer degrades or softens to the point that it no longer can hold the key and lock together or the polymer adhesion is overcome by the pulling forces under physiological conditions, resulting in their detachment or separation, or form discontinuities. The stent was coated with a drug polymer matrix containing Novolimus, an m-tor inhibitor to reduce tissue stenosis and/or restenosis. The 3×9 mm stent as cut has a 0.063" OD (FIG. 26A). The cut/patterned stent was crimped onto a 3.0 mm balloon catheter, packaged, and sterilized using E-beam. The stent was expanded with a 3 mm balloon catheter and tested, under conditions simulating physiological conditions, for flat plate compression force without detachment of the key and lock elements FIGS. 26B and 26 C). After compression, the stent was post-dilated back to 3 mm diameter, and soak in dichloromethane to degrade/dissolve the biodegradable 50:50 poly(DL-lactide-co-glycolide) (see Table 1). This effectively detached (separated, formed discontinuities of) all the keys from locks on the stent. The stent was re-tested for flat plate compression (see Table 1). The stent in this example after detachment (after formation of discontinuities in the separation regions) has a decreased strength, yet continues to have sufficient strength to support a body lumen. However, the radial strain (compliance) of the stent (composite compliance) after forming discontinuities improved (or increased) compared to upon expansion (or immediately after expansion), allowing the stented segment to, uncage, allowing the stented segment to have radial compliance closer to the lumen prior to stent implantation, and/or allowing the stent to further expand and/or contract, and/or allow for lumen enlargement. The high radial strength upon deployment is desired to push open the plaque and maintain the open lumen.

TABLE 1

Flat plate compression of stent with attached and detached key and lock separation region elements.

| Type | Flat plate 10% Radial Compression strength (N) |
|---|---|
| 9 mm Stent with attached (held together) separation region elements using biodegradable 50:50 Poly (DL-lactide-co-glycolide) | 0.67 |
| 9 mm Stent above with separation region elements detached forming discontinuities | 0.22 |

Example 2

Figure 27A:
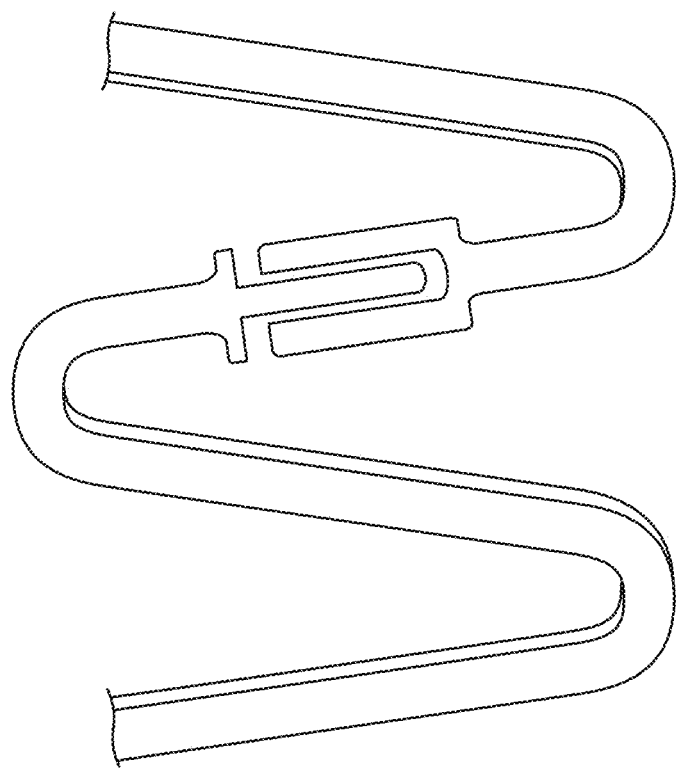
Figure 27B:
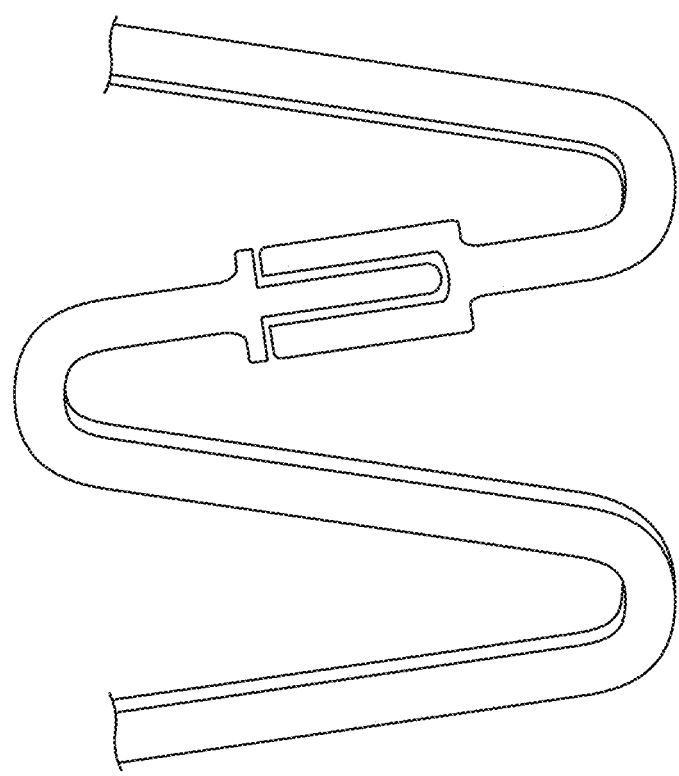
Figure 28:
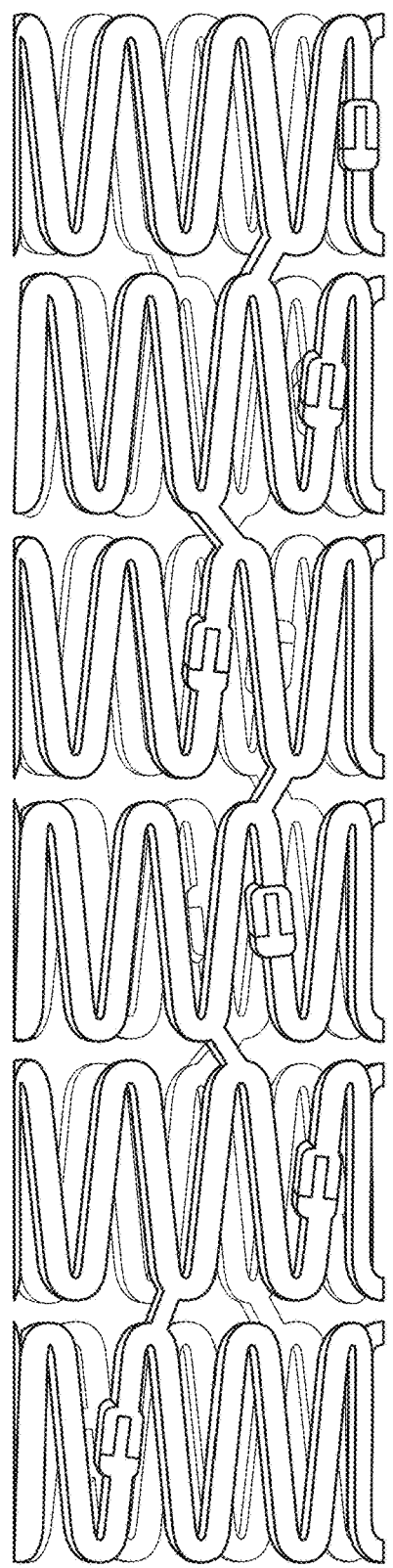
Figure 29:
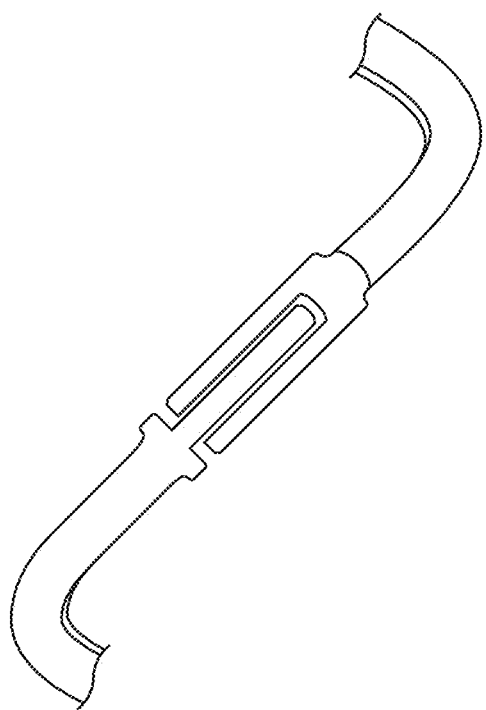
Figure 30:
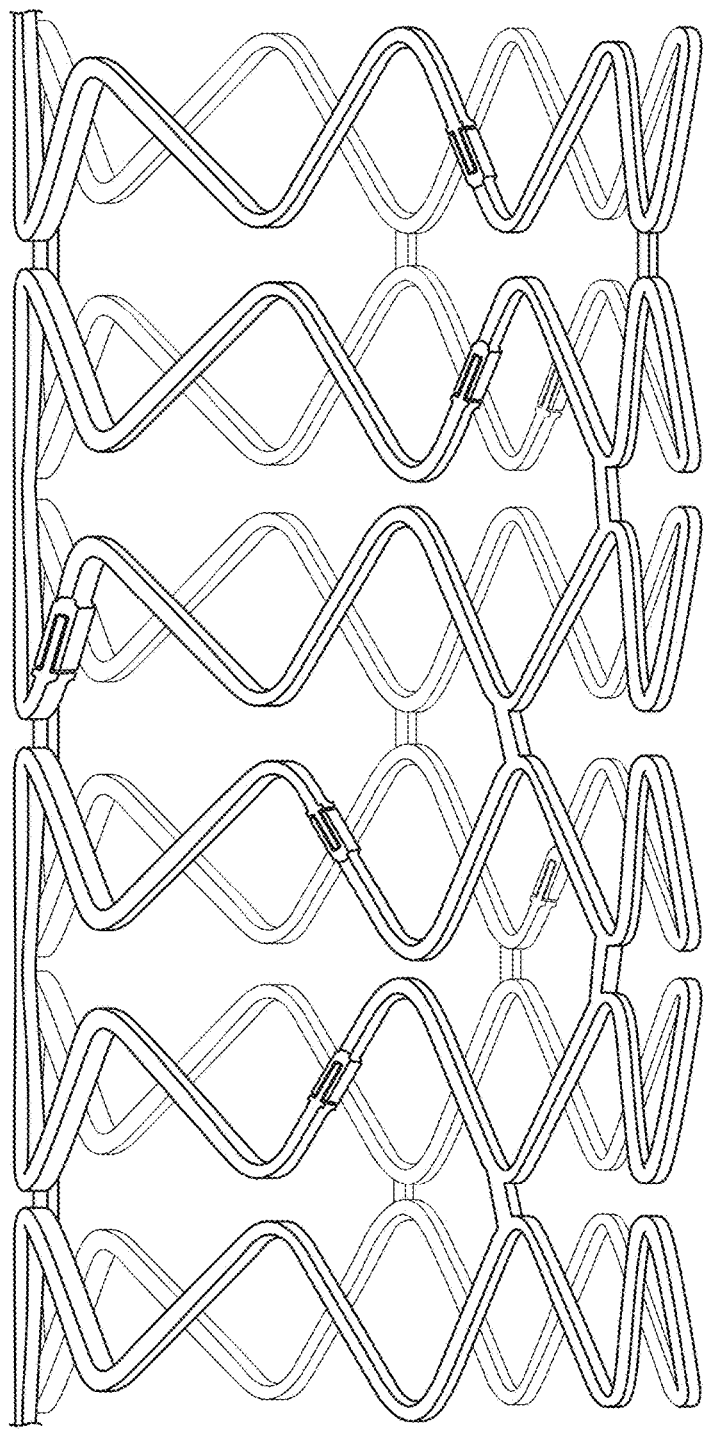

A 14 mm long, 0.063 inch OD annealed L605 cobalt chrome tube having a wall thickness of about 0.004 inch was marked with stent pattern having a "long" key and lock design similar to that shown in FIGS. 16g-1 to 16G-3 above. This design allowed the key and lock design to move both up and down (radial relative to a tubular axis) as well as in and out (parallel to a tubular axis) directions (FIG. 27A) while at the same time, the long key and lock protects the adjacent tissue as the key is sliding out of the lock. After cutting/patterning, the stent was cleaned in a 20% 1N hydrochloric acid solution for 2 minutes to remove islands that have not fallen between the struts, scale and debris, and rinsed in water to remove residual acid. A mandrel was placed inside the stent, and any island remaining were removed. The stent was then electro-polished in 10% sulfuric acid in ethylene glycol at 20 amp for about 40 seconds. After electro-polishing, a 150 mg/mL solution of biodegradable 50:50 poly(DL-lactide-co-glycolide) in dichloromethane solvent was applied adjacent to each long key and lock element. After a few seconds to allow for partial evaporation of the solvent, the tip of a soldering iron is placed adjacent to the element to reflow the polymer between the key and lock and on top of the lock. The stent was then heated at 120° C. oven for 10 minutes to melt the polymer tubing and allowed it to flow into and over the elements adjacent to the key and lock element (FIG. 27B). In addition to the key and lock, the key and lock components have stubs or wings or the like to protect adjacent tissue from being stab by the lock as well as to improve attachment after bonding with the polymer. This polymer in between the key and lock and adjacent to the surface of these components effectively locks the key to the lock together forming the separation region until the polymer degrades in 1 to 3 months to the point that it no longer can hold the key and lock together or the degrading polymer adhesion is overcome by the pulling forces under physiological conditions, resulting in their detachment and uncaging of the stent and/or the vessel and/or allowing vasomotion after detachment and/or allowing the stent to further expand. The stent has sufficient strength and can support the artery immediately after expansion. The stent is coated with a drug polymer matrix containing Novolimus, an immunosuppressant to reduce tissue stenosis and/or restenosis. The 3×14 mm stent as cut has a 0.063" OD (FIG. 28). The cut stent was crimped onto a 3.0 mm balloon, packaged, and sterilized using E-beam. The stent was expanded with a 3 mm balloon catheter and tested for flat plate compression strength (FIGS. 29 and 30). After compression, the stent was post-dilated back to 3 mm diameter, and soaked in dichloromethane to dissolve the biodegradable 50:50 poly(DL-lactide-co-glycolide) (see Table 1) to form discontinuities simulating physiologic conditions. This effectively detached all the keys from locks on the stent. The stent was re-tested for flat plate compression strength (see Table 2). The stent is tested either separately, or expanded within a thin tube into the inner wall of the thin tube (sufficiently expanded to embed into the inner wall of the thin tube). The use of thin tube is especially important when the stent is configured to separate into two or more longitudinal segments, the tube thus providing a containment means to perform the strength or compliance tests by testing composite strength or composite (the stent and the tube together) compliance of the stented tube, mimicking the composite compliance of the stented segment).

TABLE 2

Flat plate radial compression strength of stent with attached and detached key and lock elements.

| Type | Radial strength flat plate (10% Compression) (N) |
|---|---|
| 14 mm Stent with attached (held together) separation regions using biodegradable 50:50 Poly (DL-lactide-co-glycolide) | 1.07 |
| 14 mm Stent above with separation regions detached (discontinuities formed) | 0.31 |

Example 3

Figure 31:
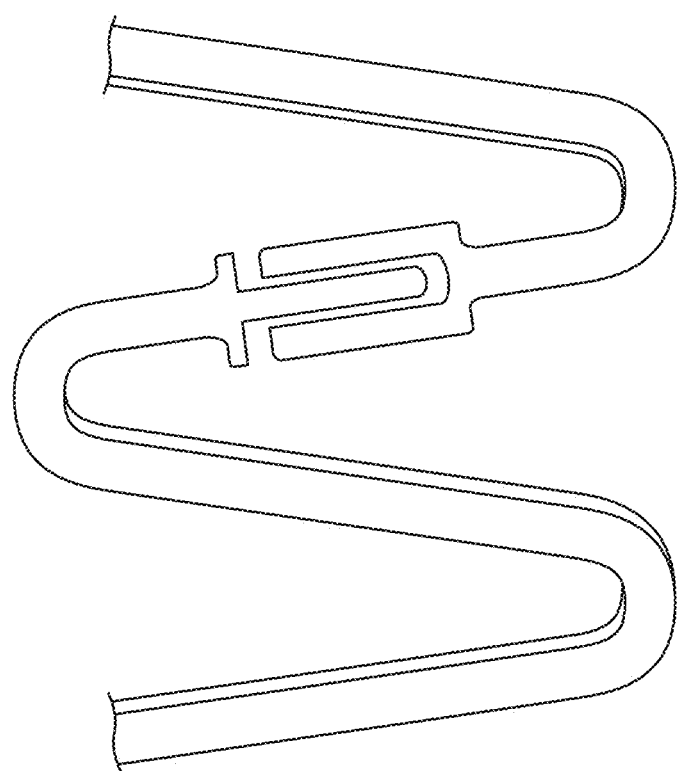
Figure 32:
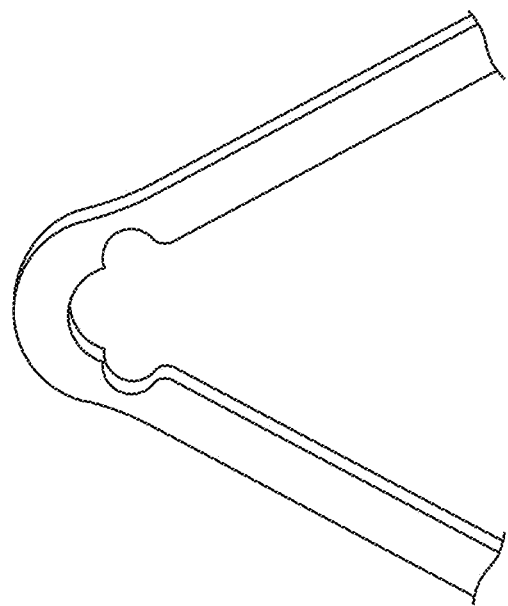
Figure 32A:
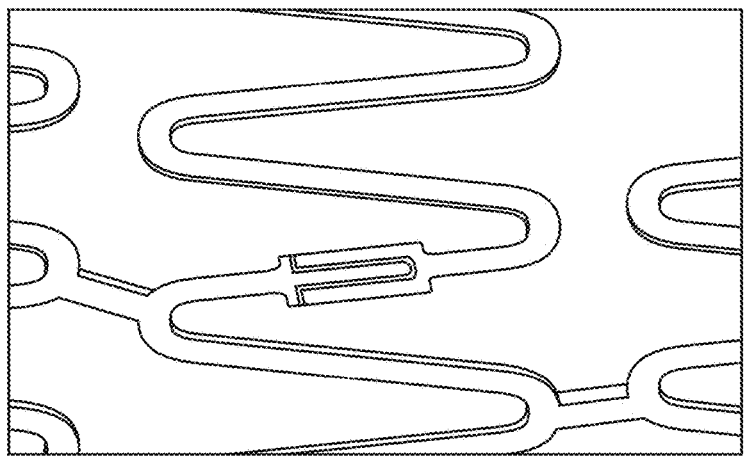
Figure 32B:
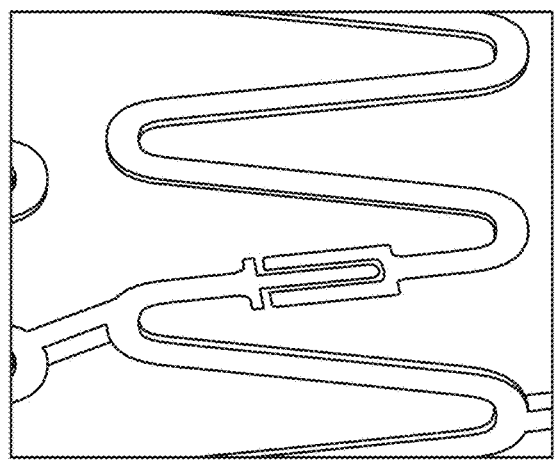
Figure 33:
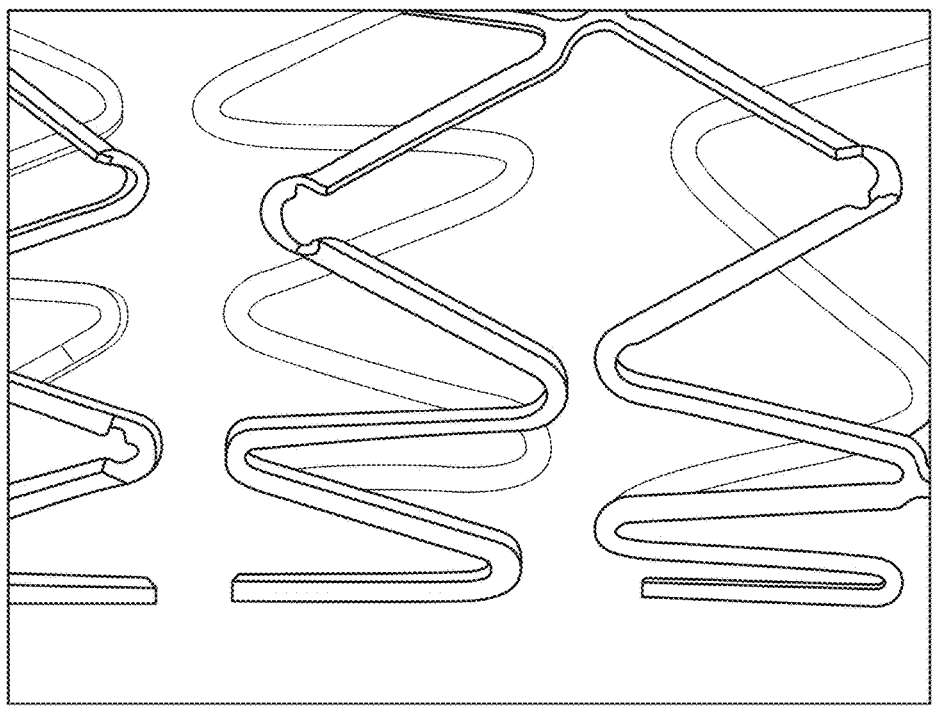
Figure 33A:
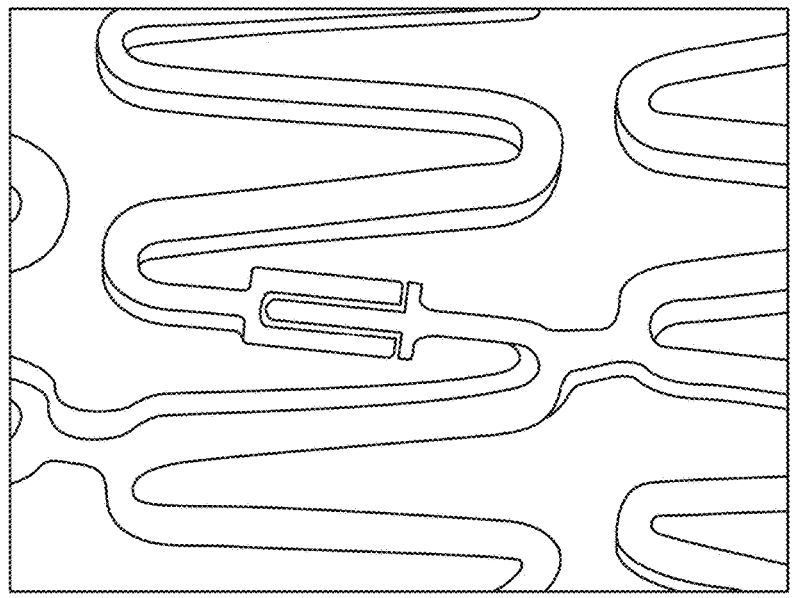
Figure 33B:
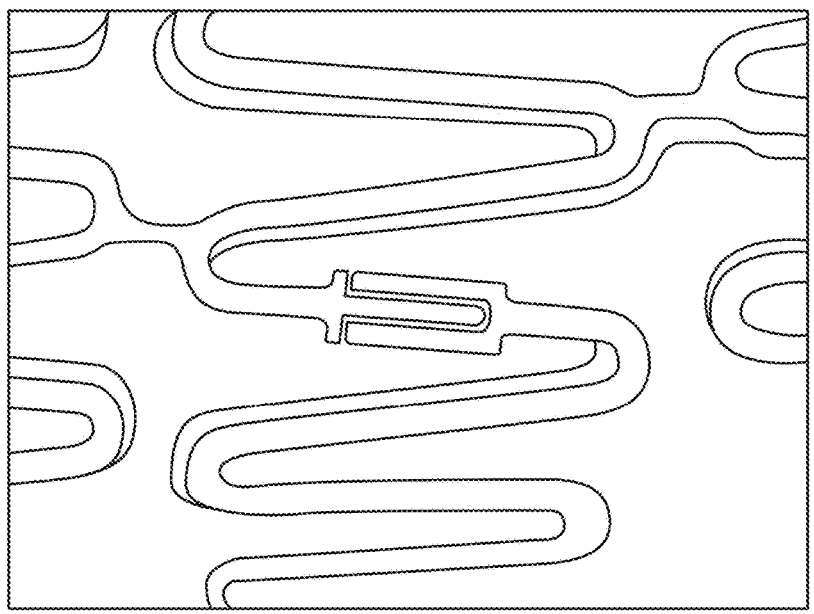

A 9 mm long, 0.063 inch OD annealed L605 cobalt chrome tube having a wall thickness of 0.004 inch was marked with stent pattern having a "long" key and lock design similar to that shown in FIGS. 16g-1 to 16G-3 above. This design allowed the key and lock design to move both up and down as well as in and out directions (FIG. 31) while at the same time, the long key and lock protects the adjacent tissue as the key is sliding out of the lock. After laser cutting, the stent was cleaned in a 20% 1N hydrochloric acid solution for 2 minutes to remove islands that have not fallen between the struts, scale and debris, and rinsed in water to remove residual acid. A mandrel was placed inside the stent, and any island remaining were removed. The stent was then electro-polished in 10% sulfuric acid in ethylene glycol at 20 amps for about 40 seconds. After electro-polishing (FIGS. 32A/B), the entire stent is coated with a polymer poly(lactide-co-caprolactone) at different thickness (FIGS. 33A/B) in order to control discontinuities formation (or detachment) times (duration after implantation). The polymer around the key and lock and adjacent to the surface of these components effectively locks the key to the lock together (hold them together) providing separation regions until the polymer starts to degrade, and/or degrades, and or softens in about 1 months to 6 months to the point that it no longer can hold the key and lock together or the polymer adhesion because it has become brittle and is overcome by the pulling forces under physiological conditions, resulting in their detachment and uncaging of the stent and/or the vessel and/or allowing vasomotion after detachment (formation of discontinuities). However, the stent has strength sufficient to support the artery after expansion. All stents were placed over 3.5×14 mm balloon catheters and crimped using iris crimper using the following parameters: 45° C. temperature; 50 psi crimp pressure; Medium speed for 45 seconds then 2-minute hot hold. The stents were crimped to about 0.048" OD. The stents were packaged, and then sterilized using E-beam. They were measured for profile, and then expanded by inflating the balloon to 8 atm. The stents were tested for radial strength using flat plate compression, and radial strength iris test (Table 3).

TABLE 3

Results of flat plate compression and radial strength

| # | Profile | Coating Thickness | Expanded OD | Radial strength (10% Radial Compression (Flat Plate))* | Radial Strength using IRIS |
|---|---------|-------------------|-------------|---------------------------------------------------------|----------------------------|
| 1 | 0.0492" | 47 um | 3.93 mm | 1.1 N | 14.2 psi |
| 3 | 0.0474" | 35 um | 3.89 mm | 1.3 N | 16.8 psi |
| 4 | 0.0480" | 35 um | 3.87 mm | 1.0 N | 18.2 psi |
| 5 | 0.0499" | 23 um | 3.95 mm | 1.2 N | 16.5 psi |
| 6 | 0.0477" | 23 um | 3.93 mm | 1.0 N | 17.1 psi |

*All results scaled to 10 full functional rings = 3.5 × 14 mm stent.

Example 3.5

In this example, stents according to example 3 were built with the addition of another polymer coating (PLLA) over the poly(lactide-co-caprolactone) in various thicknesses to provide longer time duration for separation region to detach after deployment in physiologic conditions. The duration for detachment ranges from 2 months to 1 year.

Example 4

Figure 34:
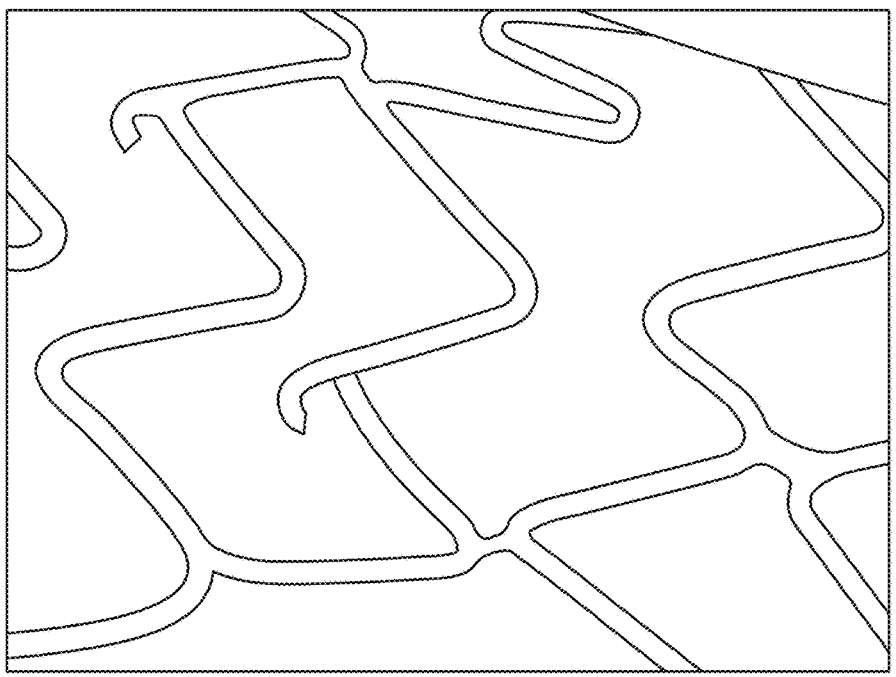

A 0.065" OD 304 Stainless Steel tube with 0.005" thickness was laser cut with a Femtosecond laser into a stent pattern with 14 rings with 8 crowns per ring. Each ring had 3 crowns having two notches. (FIGS. 32 and 33) These notches were present to promote the fracture or separation by fatigue by systolic and diastolic contractions of the artery at some time after expansion. After cutting, the stent was cleaned in a 20% 1N hydrochloric acid solution for 2 minutes to remove islands that have not fallen between the struts, scale and debris, and rinsed in water to remove residual acid. A mandrel was placed inside the stent, and any islands remaining were removed. The stent was then electropolished in 10% sulfuric acid in ethylene glycol at 30 amps for about 40 seconds. Upon expansion in a 3 mm silicone tubing and subjected to accelerated fatigue using fatigue tester shown in FIG. 35, there was at least one crown with notches fracturing or separating after 98 days. This stent immediately after expansion (FIG. 34) had an iris radial strength of 15 psi, and a radial strength using flat plate compression 10% strength of 1.19N.

Example 5

Figure 35:
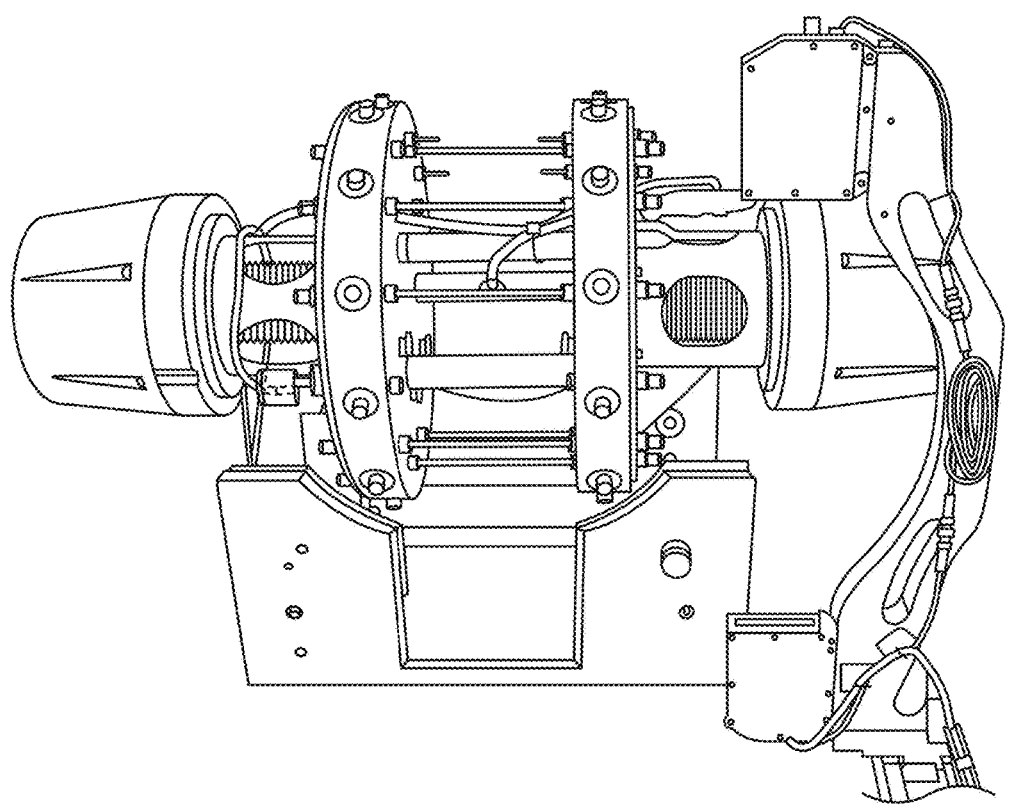

A sample stent built in accordance with Example 1 and tested against a commercially available DESyne control non-degradable metallic stent were each tested in order to compare their radial strains (composite compliances) in an in vitro model. The material and equipment used were: (1) aE0215 Bose Electroforce 9110-12 Stent Graft Tester with Laser Micrometer, (2) a clear elastic silicone mock artery, 3.2 mm ID×0.5 mm wall, 10 A durometer, and (3) a microscope. Each stent was deployed into the mock artery at 10 atm pressure, sufficient to seat the stent against the artery. There was an approximately 2 cm gap between the stents. The test stent was dipped into dichloromethane for approximately 1 minute to substantially degrade/dissolve the coating holding the separation regions together and therefore forming discontinuities and uncage the stent (simulating physiological conditions to form discontinuities in the separation regions). The tube with stents was then loaded into the Bose Electroforce Stent Graft Tester as shown in FIG. 35. The Bose Electroforce Stent Graft Tester was set to run the vessel at approximately 5% inner diameter distension (compliance) to approximately simulate physiological conditions. Published literature indicates that for coronary arteries the healthy vessel distension (compliance) is in the range of 3.0%-5.0%. The stents were cycled for approximately 1,000,000 cycles at about 2 Hz-5 Hz. During the testing, the ID distension of the un-stented section of tube and both stents was measured with the laser micrometer. The tube radial strain (simulating vessel compliance) was measured to be 5% in the un-stented section. The DESyne stent reduced radial strain (compliance) from approximately 5% to approximately 1% immediately and maintained the composite compliance at 1%. This result is consistent with a prior study of non-degradable metal and/or metal alloy commercially available stents conducted for stents radial strain which showed these stents to range in radial strain (composite compliance) from 0.2 to 0.3% (In the prior study, Un-stented tube section radial strain (compliance) was 4.4%, DESyne stent was 0.3%, Synergy stent was 0.2%, and Orisiro stent was 0.3%, radial strain (composite compliance)). The test sample stent initially reduced radial strain (composite compliance) to 1% (the discontinuities in the separation regions were not fully formed or detached) but increased to and stabilized at a radial strain of about 2-3% as the discontinuities formed. The test sample configured in accordance with the present invention showed that the initial composite compliance of the stent (the stented segment including the tube compliance) had an initial compliance and the compliance increased after the separation regions formed discontinuities. The test also showed that current control initial composite compliance (the stented segment compliance) did not change over time. The test sample also showed that composite compliance as the discontinuities formed discontinuities was about 200%-300% larger than the composite compliance of the control sample (having no separation regions within the rings).

Example 6

A PLLA based polymeric tube with 0.156 inch ID unit and 150 micron wall thickness is laser patterned into a stent frame comprising structural elements. The structural elements consist of a plurality of sinusoidal rings, and each ring consisting of struts joined by crowns. Each ring is connected to an adjacent ring via two links 180° apart. The structural elements have four surface regions, abluminal surface region, luminal surface region, and two side surface regions. The stent structural elements thickness ranged from about 50 microns (to accommodate the pieces of metal reinforcement element) to 150 microns (thickness of polymeric material adjacent to the fitted metal pieces) and the width of the structural elements is about 150 microns. The stent strut length is approximately 1 mm in length. The stent pattern comprises further creating slots on the crown region of every crown, on every ring. The slots are created from the abluminal surface region and extend into the two struts adjacent to each crown. A mandrel is inserted into the stent for support, and placed under a microscope and press fitting instrument. A piece of L605 Co/Cr solid wire reinforcement element having a diameter of 80 microns and about 1.5 mm length is press fitted into each of the slots created by the laser pattern contouring to the crown region and extending at least partially into the two adjacent strut regions of each crown. At least one of the links connecting adjacent rings is also fitted with a piece of the metal wires reinforcement elements (either with a separate metal piece or with the same metal piece of the adjacent crown metal piece). The abluminal side of the wire is partially protruding (about 10 microns) from the abluminal surface region after press fitting the wire into each slot. The stent is rotated and the pieces of metal are inserted into every slot until all the slots are occupied with wires. The wire pieces' ends are deburred or electropolished so they are rounded and atraumatic to adjacent tissue after the polymer is degraded. The stent is then coated with a polymer drug matrix comprising PLLA-PGA polymer coating and rapamycin drug in the concentration of 3:2 polymer to drug matrix. The amount of drug is about 5 micrograms per mm length of the stent. The stent is patterned to form a 3.0 mm stent diameter by 14 mm length. The stent is then crimped onto a 3.0 mm diameter by 15 mm working length balloon delivery system using heat (about 45° C.) and pressure. The unit is packaged and sent for e-beam sterilization. The unit is expanded in water at about 37° C. from the crimped configuration to 3.0 mm diameter (labeled diameter of the stent). It is tested for inward recoil after deployment (expansion), and also tested for the radial strength force to obtain 10% compression between two flat plates (flat plate 10% compression test), and compared against a sample that has no metallic pieces in the non-slotted crown regions such that the structural elements dimensions are 120 microns thick by 150 micron width (no slots formed). The flat plate 10% compression test of the PLLA based polymeric material stent strength is about 0.17N (or 0.012 N/mm stent length) while the wire reinforced PLLA stent flat plate is about 0.25N (or 0.018 N/mm stent length). The inward recoil of the polymeric material stent is about 5% and increased over time to about 7% after expansion. The recoil of the wire reinforced stent is about 4% and remains about 4% after expansion. The polymeric material frame is configured to degrade between 3 months and 2 years leaving behind the atraumatic pieces of metallic wire (reinforcement elements) in the vessel wall, maintaining substantially the pattern of the reinforcement elements after deployment. The reinforcement elements after the polymeric material frame degrades will have discontinuities in the strut regions on every ring in this example, uncaging the stent and/or vessel wall (or body lumen). In this example, the stent with reinforcement elements has increased strength by about 1.47 times the stent without reinforcement elements. Typically, the range of the strength increases from 20% to 300%, more typically the stent with reinforcement elements strength will range from 0.25 N/mm stent length to 0.07 N/mm stent length, using a 10% flat plate compression test, and the dimension for the more typically example range from 80 microns thick to 120 microns thick, while the width dimension ranges from 80 microns wide to 150 microns wide. The inward recoil in this example is improved either with lower recoil or by having a low recoil that is substantially maintained after deployment (expansion).

Example 7

An example similar to example 6 where at least one of the crowns in at least some rings does not contain reinforcement elements. In these crowns there are no slots formed.

Example 8

An example similar to example 6 where the reinforcement elements are embedded completely (in the crown and strut regions). A polymeric coating comprising the same polymeric material of the frame is coated on top of the reinforcement elements having a thickness of about 10 microns to fully cover the reinforcement elements, before the drug coating matrix is applied.

Example 9

A magnesium based alloy with 0.063 inch ID and 120 micron wall thickness metallic tube is laser patterned into a stent frame comprising structural elements. The structural elements consist of a plurality of sinusoidal rings, and each ring consisting of struts joined by crowns. Each ring is connected to an adjacent ring in via two 180° apart links. The structural elements have four surface regions, abluminal surface region, luminal surface region, and two side surface regions. The stent structural elements thickness ranged from about 50 microns (to accommodate the pieces of metal) to 120 microns (thickness of polymeric material adjacent to the fitted metal pieces) and the width of the structural elements is about 150 microns. The stent struts length is approximately 1 mm. The stent pattern comprises further creating slots on the crown region of every crown, on every ring. The slots are created from the abluminal surface region and extend into the two struts adjacent to each crown. A mandrel is inserted into the stent for support, and placed under a microscope and press fitting instrument. A piece of L605 Co/Cr solid wire reinforcement element having a diameter of 70 microns and about 1.5 mm length is press fitted into each of the slots created by the laser pattern contouring to the crown region and extending at least partially into the two adjacent strut regions of each crown. At least one of the links connecting two rings in this example is also fitted with a piece of the metal wires (or the piece from the adjacent crown). The abluminal surface region of the reinforcement element is substantially contained within the abluminal surface region after press fitting the reinforcement element (or flush with the abluminal surface region of the stent frame). The stent is rotated and the pieces of metal reinforcement elements are inserted into every slot until all the slots are occupied with reinforcement elements. The wire pieces' ends are deburred or electropolished so they are rounded and atraumatic to adjacent tissue before press fitting them into the stent slots. The stent is then coated with a 5 micron thick PLLA based polymeric material coating to further secure the reinforcement elements in the stent frame slots. The stent is then coated with a polymer drug matrix comprising PLLA-PGA polymer coating and rapamycin drug in the concentration of 3:2 polymer to drug matrix. The amount of drug is 5 micrograms per mm length of the stent. The stent is patterned to form a 3.0 mm stent diameter by 14 mm length. The stent is then crimped onto a balloon delivery system using heat and pressure and crimped onto the balloon delivery system. The unit is packaged and sent for e-beam sterilization. The unit is expanded in air. The sample is tested for inward recoil, and the force to obtain 10% compression between two flat plates (flat plate 10% compression test), and compared against a sample that has no metallic pieces (reinforcement elements) and no slotted regions such that the structural elements dimensions are 120 microns thick by 150 micron width. The flat plate 10% compression test of the magnesium based material stent strength is about 0.2N (or 0.014 N/mm length) while the reinforced magnesium stent flat plate is about 0.25N (or 0.018 N/mm stent length). The inward recoil of the magnesium material stent is about 5% and increased over time to about 7% after expansion. The recoil of the reinforced stent is about 4% and remains maintained at about 4% after expansion. The stent magnesium alloy material frame is configured to degrade in a period ranging from 1 month to 2 years leaving behind the atraumatic pieces of metallic wire (reinforcement elements) in the vessel wall. The PLLA polymeric material and drug coating matrix are configured to degrade in a period ranging from 3 months to 3 years. In this example, the stent with reinforcement elements has increased strength of about 1.25 times the stent without reinforcement elements. Typically, the range of the strength increases from 20% to 300%, more typically the stent with reinforcement elements strength will range from 0.025 N/mm stent length to 0.07 N/mm stent length, using a 10% flat plate compression test, and the dimension for the more typically example range from 80 microns thick to 120 microns thick, while the width dimension ranges from 80 microns wide to 150 microns wide. The inward recoil in this example is improved either with lower recoil or by having a low recoil that is substantially maintained after deployment (expansion).

Example 10

An example similar to examples 6 or 9, where the reinforcing elements are flattened wire having a substantially rectangle cross section measuring 76 microns thickness by about 64 microns width.

Example 11

An example similar to example 9, where the reinforcement elements are attached to the outer surface (abluminal surface region) of the magnesium crown and/or strut regions using UV light cure adhesive such as Dymax 1161-M, Loctite 3525, or the like, low viscosity epoxy such as Masterbond EP41SMed, cyanoacrylate such as J&J Dermabond Advance Topical Skin Adhesive, Ferndale Laboratories Mastisol Liquid Adhesive, Loctite Super Glue Gel, combination thereof, or the like. These adhesive material are used for attach temporary crowns to tissue, topical application to hold closed easily approximated skin edges of wounds from surgical incisions, temporary sutures, and other applications. The adhesive is applied on between and or on top of the reinforcement elements and the magnesium structural element. The stent frame does not contain slots in this example.

Example 12

An example similar example 9, where the reinforcement elements are attached to the outer surface (abluminal) of the magnesium crown and/or strut regions by laser welding using a pulsed YAG laser, diode-pumped fiber laser, fiber laser, or other lasers. The stent frame in this example does not contain slots.

Example 13

An example where the stent is formed from a tube comprises a cobalt chrome alloy layer that is either sandwich between, on top (abluminal), or on the bottom (luminal) of a magnesium alloy layer. The tubing is patterned into a stent. At least some regions on at least some rings (or at least some crown regions, and/or strut regions, on at least some rings) have the cobalt chrome alloy layer substantially removed by laser, chemical means, or mechanical means, to provide the stent to uncage in (or over) said rings after expansion under physiological conditions, where the cobalt chrome alloy provides for the reinforcement elements, and where the stent uncages after the magnesium alloy layer degrades. Optionally, the stent prosthesis is coated with a layer of polymer to control degradation of the stent prosthesis or to further control degradation of the stent prosthesis. The stent is optionally coated with a drug polymer matrix. Alternatively, the layering of magnesium alloy layer and the cobalt chrome alloy layer can take place after patterning.

Example 14

An example where the stent is formed from a tube comprises a cobalt chrome alloy layer that is on top (abluminal) or inside (luminal) of a PLLA based polymeric material layer. The tube is patterned into a stent. At least some regions on at least some rings (or at least some crown regions, and/or strut regions, on at least some rings) have the cobalt chrome alloy layer substantially removed by laser, chemical means, or mechanical means, to provide the stent to uncage after expansion in a body lumen or in water at 37° C., in (or over) said rings after expansion under physiological conditions, where the cobalt chrome alloy provides for the reinforcement elements, and where the stent uncages after the PLLA based polymeric material layer degrades. Optionally, the stent is optionally coated with a drug polymer matrix. Alternatively, the layering of the PLLA based polymer layer and the Cobalt Chrome alloy layer can take place after patterning.

Example 15

An example where the stent is formed from a cobalt chrome alloy layer formed as a sheet layer (having the degradable material layer on top, or on the bottom of the cobalt chrome layer), and where the sheet is patterned, and then treated to remove the cobalt chrome material layer from the at least some crowns and/or strut regions. The sheet is rolled and attached (or fused) forming a patterned stent. The removal of the CoCr layer can take place before rolling and attaching the stent, or after.

Example 16

An example similar to example 1 or 4, where at least one (preferably at least two) crowns on at least some rings (preferably on each ring) contains stainless spring steel, superelastic nitinol, or shape memory nitinol material, reinforcement elements. The spring steel, or superelastic nitinol, is first bent to the contour of the stent crown (or expansion region) prior to attachment to the stent, and configured to having a bias to open at various conditions such as in air, ambient temperature, body temperature, or other. These reinforcement elements have the propensity to spring outward (or open) to further expand the stent after deployment (expansion). For shape memory nitinol, they are biased to open when they reach (or substantially reach) a program temperature (such as about body temperature) and thus further expand the stent after deployment or as the degradable material degrades. After expansion of the stent, the spring, superelastic, or shape memory material, will bias the crown (the crown where the reinforcement elements are attached to or embedded in) to further expand, said expansion occurring from a range from after deployment to substantial degradation of the frame material (containing said reinforcement elements or attached to) time period, where the further expansion ranges from 0.05 mm to 0.5 mm in diameter. Alternatively, the reinforcement elements can be shaped in an expansion region (crown) shape where the ends of the reinforcement element crown are connected (attached or embedded) to two adjacent struts (preferably where the inner surface of the reinforcement elopement crown is facing the inner surface of the crown joining the two struts), and where the reinforcement element crown is attached along any region of the struts, preferably attached to about a mid-region of the struts.

Example 17

A non-degradable stent formed from a wire or plurality of wires comprising Cobalt Chrome alloy where the wire has a diameter of 80 microns. The wire is shaped into a stent pattern comprising a plurality of sinusoidal rings (or turns), the rings comprising crowns and struts. Each ring is connected to an adjacent ring in two locations that are 180° apart, each location is at or adjacent to the intersection region of adjacent crowns. At least one, preferably at least some crown regions and/or at least some strut regions, on at least some rings are cut (or severed) using laser separating the cut region (or forming a discontinuity), each end of the cut structural element is deburred and rounded. The two ends of the cut region are held together (or contained) by applying or placing a PLLA based degradable polymeric sleeve over the two ends of each of the cut structural element and heated to a temperature close to or above melting point of the polymeric degradable material so that the material softens (or melts) holding in place said structural element ends together. The two ends of the cut structural element are abutting (in other example the two ends are apart forming a gap ranging from 1 micron to 200 microns). Optionally, a degradable adhesive such as cyanoacrylate is applied at the cut region joining the two cut region ends of the struts and/or crowns on said at least some rings. The stent after expansion (deployment) in a body lumen (or in water at 37° C.) has sufficient strength to support a body lumen. The stent uncages over the at least some rings (preferably over the entire stented segment), and/or further expands, and/or responds to a therapeutic vasodilator, and/or enlarges the body lumen in the stented segment.

Example 18

A non-degradable stent formed from a wire or plurality of wires comprising Cobalt Chrome alloy where the wire has a diameter of 100 microns. The wire is shaped into a stent pattern comprising a plurality of sinusoidal rings, the rings comprising crowns and struts. Each ring is connected to an adjacent ring in two locations that are 180° apart, each location is at or adjacent to the intersection region of adjacent crowns. Two strut regions 180° apart (with the subsequent ring cut struts being 90° offset), on every ring are cut (or severed) using laser separating the cut region (or forming a discontinuity), each end of the cut structural element is deburred and rounded the edges. The two ends of the cut region are mechanically treated to create or form a hollow core in the cut wire regions ranging in length from 1 micron to 50 microns. The hollow wire core diameter is about 45 microns. A degradable PLLA based polymer filament bridging element having a diameter of approximately 40 microns and a length of about 25 microns is fitted into the hollow wire core region at the cut region bridging the two cut ends of the structural element. The region is heated to melt of soften the polymer further securing the junction (or holding together the junction). Optionally, the junction is held together (or contained) by applying or placing a PLLA based degradable polymeric sleeve (extending approximately 100 microns in length and 15 microns in thickness) over the two ends of the cut structural element and bridging element (the PLLA based degradable filament) and heated to a temperature above Tg and below Tm, or Tm+/−20 C, of the polymeric degradable material so that the material softens (or melts) holding in place said structural element ends together. The bridging element is extending into the hollow wire core about 20 microns in each direction (length) and the bridging element gap (between the two cut structural elements ends) is about 5 microns. The formed stent is 3.5 mm by 18 mm length.

Alternatively, the two ends of the cut structural element can be abutting (while the bridging element is substantially inside the hollow wire core joining the two cut ends).

Alternatively, the sleeve containing the hollow wire core cut region can also be the bridging element between the two cut ends of the structural element.

Optionally, a degradable adhesive such as cyanoacrylate is applied at the cut region joining the two cut region ends of the struts and/or crowns on said at least some rings.

Alternatively, at least some one crown on at least some rings are cut in the crown region. Alternatively, at least one crown and/or strut, on at least some rings are cut in the crown and/or strut regions.

Alternatively, the stent prosthesis can be formed from a tubular body comprising Cobalt Chrome alloy and patterned into a stent, where the structural elements to be cut are either patterned and then treated to be removed (or cut), or where the stent is patterned with the structural elements cut (or removed).

Alternatively, the stent is formed from a sheet comprising Cobalt Chrome, patterned and rolled into a stent, or rolled into a tube and patterned into a stent. The structural elements to be removed (or cut can take place at any of the steps before rolling into a tube, and/or patterning, and/or after patterning.

The stent is then coated with a polymer drug matrix comprising PLLA-PGA polymer coating and rapamycin drug in the concentration of 3:2 polymer to drug matrix. The amount of drug is about 5 micrograms per mm length of the stent. Alternatively, the drug can be coated on the stent prosthesis without a polymer. Alternatively, the drug can be filled into the hollow wire core and is configured to be released through holes placed preferably on strut regions or substantially non deformable regions of the stent. The bridging elements can also contain a drug and releases the drug over time.

The 3.5 mm by 18 mm length stent is crimped onto a 3.5 mm by 20 mm length delivery system, packages, and sterilized using e-beam sterilization. The stent is deployed in air (or water at 37 C.°) and tested for strength and recoil. The flat plate radial strength 10% compression test of the stent prosthesis is about 1N (or 0.057 N/mm stent length). The inward recoil of the stent is about 5% and remained substantially the same after deployment. The stent bridging elements are configured to degrade in a period ranging from 1 month to 2 years leaving behind the patterned stent with two separate (discontinued) struts for each ring. The stent after expansion (deployment) in a body lumen (or in water at 37 C) has sufficient strength to support a body lumen. The stent uncages, and/or further expands, and/or responds to a therapeutic vasodilator, and/or enlarges the body lumen, in the stented segment (over the entire stented segment).

Example 19

A non-degradable stent formed from a wire or plurality of wires comprising Cobalt Chrome alloy where the wire has a diameter of 100 microns. The wire is shaped into a stent pattern comprising a plurality of sinusoidal rings, the rings comprising crowns and struts. Each ring is connected to an adjacent ring in two locations that are 180° apart, each location is at or adjacent to the intersection region of adjacent crowns. Two strut regions 180° apart (with the subsequent ring cut struts being 90° offset), on every ring are cut (or severed) using laser separating the cut region, forming a discontinuity (gap), each end of the cut structural element is deburred and rounded the edges. The formed stent is 3.5 mm by 18 mm length.

Alternatively, at least some one crown on at least some rings are cut in the crown region forming a gap. Alternatively, at least one crown and/or strut, on at least some rings are cut in the crown and/or strut regions forming a gap. Alternatively, the stent prosthesis can be formed from a tubular body comprising Cobalt Chrome alloy and patterned into a stent, where the structural elements to be cut are either patterned and then treated to be removed (or cut), or where the stent is patterned with the structural elements cut (or removed) forming discontinuities (or gaps).

Alternatively, the stent is formed from a sheet comprising Cobalt Chrome, patterned and rolled into a tubular stent, or rolled into a tube and patterned into a stent. The structural elements to be removed (or cut can take place at any of the steps before rolling into a tube, and/or patterning, and/or after patterning, forming the gaps. The stent is then coated with a polymer drug matrix comprising PLLA-PGA polymer coating and rapamycin drug in the concentration of 3:2 polymer to drug matrix. The amount of drug is about 5 micrograms per mm length of the stent. Alternatively, the drug can be coated on the stent prosthesis without a polymer. Alternatively, the drug can be filled into the hollow wire core and is configured to be released through holes placed preferably on strut regions or substantially non deformable regions of the stent.

The 3.5 mm by 18 mm length stent is crimped onto a 3.5 mm by 20 mm length delivery system, packages, and sterilized using e-beam sterilization. The stent is deployed in air (or water at 37 C.°) and tested for strength and recoil.

In a preferred alternative, the stent is formed as a tubular stent where the cut struts are aligned in a nested parallel configuration to each other in the crimped configuration. The struts are configured to have an indentation (or groove) and a hook on the other strut. The stent upon expansion to the deployed configuration is expanded in a substantially uniform pattern and the struts support one another to open in a substantially uniform configuration because of the groove and hook, where the coverage of the structural elements in the gap region in the expanded stent configuration using a maximum circular diameter ranges from 0.7 mm to 1.5 mm.

In another preferred alternative, the stent is formed as a tubular stent where the cut struts to are aligned in a nested parallel configuration to each other in the crimped configuration. The stent upon expansion to the deployed configuration is expanded in a substantially uniform pattern and the struts support one another to open in a substantially uniform configuration, where the coverage of the structural elements in the gap region in the expanded stent configuration using a maximum circular diameter ranges from 0.7 mm to 1.5 mm.

The flat plate 10% compression test of the stent prosthesis in the expanded configuration is about 0.6N (or 0.033 N/mm stent length). The inward recoil of the stent is about 6% and remained substantially the same after deployment. The stent degradable polymer coating configured to degrade in a period ranging from 3 months to 2 years.

The stent is formed having discontinuities (gaps). The stent is expandable from a crimped configuration to an expanded larger configuration and have sufficient strength to support a body lumen. The stent is configured to uncage the body lumen after deployment (or upon deployment), exhibit vaso-dilatation ability (or lumen vasodilation), and/or further expand to a larger stent expanded configuration. The stent structure remains in the body lumen (or lumen wall) substantially in the patterned stent configuration with two separate (discontinued) struts for each ring.

The stent after expansion (deployment) in a body lumen (or in water at 37° C.) has sufficient strength to support a body lumen. The stent uncages, and/or further expands, and/or responds to a therapeutic vasodilator, and/or enlarges the body lumen, in the stented segment (over the entire stented segment).

It is appreciated that various combinations of the examples and/or aspects and/or embodiments of the disclosure throughout this application can be combined in whole or in part and remain within the scope of this disclosure and application.

Example 20

Figure 35A:
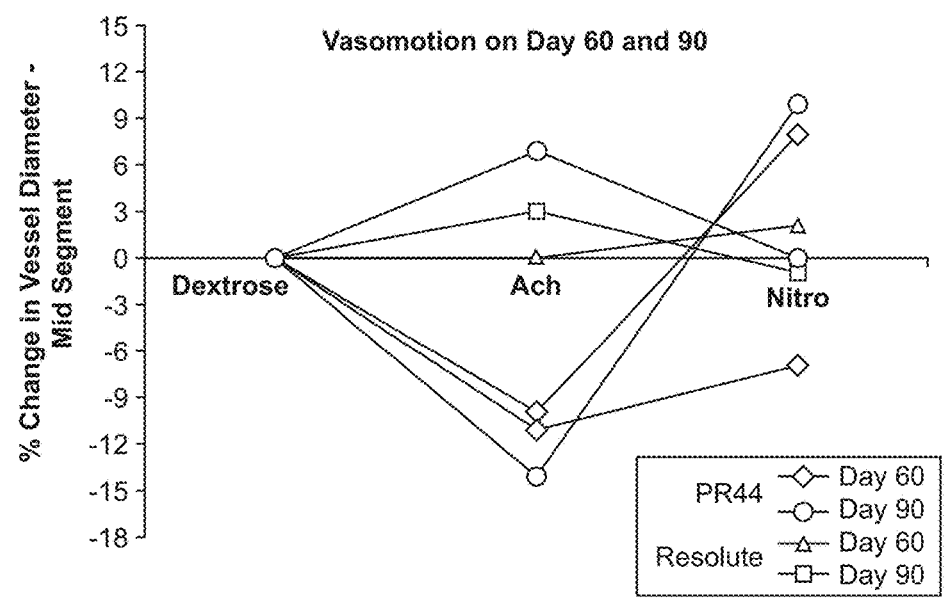
FIG. 35A is a graph showing the % change in vessel diameter of the mid segment of the stent implanted in the coronary artery of a porcine model as described in Example 20.

The Test stent configured in accordance with this invention having three separation regions every ring were evaluated in the preclinical animal study, the Elixir Medical Novolimus drug eluting coronary stent "PR44" which was available in size of 3.25×14 mm, 3.5×14 mm. The stent was "Resolute"—a FDA approved Zotarolimus drug eluting stent from Medtronic, USA which was available in size of 3.0×15 mm. The test and control stents were implanted in the coronary arteries of domestic farm pigs at a balloon to artery ratio of 1:1.1 (10% overstretch). Vasomotion testing with Acetylcholine in the device implanted vessels were performed as described below at the 60 and 90 day time points following device implantation: Acetylcholine was infused at 1.25 ml/min for 3 minutes into the coronary artery via a catheter in the following sequence: a) control (5% dextrose in saline); b) two incremental acetylcholine infusions: concentrations of $10^{-6}$ and $10^{-5}$ M; and c) 0.5 mg/ml of nitroglycerine as a bolus intracoronary injection. Following the baseline angiographic imaging, angiography was repeated immediately after each infusion (designated post-dextrose, post-ACH1 and post-ACH2 angiographies), except for the injection of nitroglycerin (designated post-nitro angiography). For the post-nitro angiography, a period of at least 3 minutes was allowed to elapse before imaging was performed. At least 3 minute time period was allowed to elapse between each angiogram and the following infusion. Once the tests are completed for the first vessel, the test was repeated in the next vessel. A time period of at least 5 minutes was allowed to elapse between each artery. Angiographic measurements were performed for each artery at the various steps of the vasomotion tests. Measurements were made at the stent segment (in at least 3 locations: proximal segment, mid-segment, and distal segment, as well as on at least one un-stented segment (distal to stent (scaffold)). The mid segment can give a more accurate measurement as it has less noise or interference from unstented segments affecting the proximal or distal segments of the stent. For each selected angiogram, mean lumen diameter was measured and the percent change in lumen diameter was calculated to determine the presence or absence of vasomotion following the infusion of the vasoactive substance. Vasomotion testing was performed at the 60 and 90 day time points in the test and control device implanted vessels and the percent change in the lumen diameter following the infusion of acetylcholine and nitroglycerin is shown in FIG. 35A. Results showed significant change in the lumen diameter in the mid-segment of the test PR44 device following acetylcholine ($10^{-5}$ M) and bolus nitroglycerin injection in contrast to the no or minimal change (as also observed in published studies) observed with the control Resolute stent. PR44 stent exhibited uncaging of the stent within 60 days and within 90 days time period from implantation, allowed vessel remodeling within two months period and within three months period, and allowed vessel response to vaso-constriction and vaso-dilation (after introduction of vaso-active agents or substances), following acetylcholine and/or nitroglycerin infusion. In contrast to the caged Resolute stent, which exhibited minimal or no change, change from baseline after Acetylcholine treatment for PR44 was +0.21 mm to −0.3 mm while the resolute control was +0.06 mm to −0.01 mm. Change from baseline after Nitroglycerin treatment for PR44 was +0.17 mm to −0.2 mm while the resolute control was +0.05 mm to −0.02 mm.

At about 6 months following stent implantation, following the vasomotion testing, the angiographic mean diameter change at about the mid-length of the stented segment of the PR44 implanted vessels (n=3), was 0.17 mm. In the case of control Resolute stent implanted vessel segments (n=3), the angiographic mean diameter change at about the mid length of the stented segment was 0.03 mm. These data demonstrate the stent configured to have separation regions, within the circumferential rings, in accordance with the present invention exhibited vasomotion of about 5.67 times the vasomotion of the control stent without separation regions. The stent of the present invention also demonstrated uncaging of the stent or the stented vessel segment, and allowed substantially greater vasomotion when compared to a control stent without separation regions. The control stent exhibited little vasomotion.

Example 21

Stents are commonly used to hold open body lumens in mammalian anatomic structures. Such stents typically are non-degradable stents, have sufficient strength to support, or hold open, a body lumen after deployment (expansion of the stent) and substantially maintain such strength after expansion, and/or substantially maintain such high strength after expansion for a long time such as at least 10 years, or more usually for the life of the stent. However, such stents have circumferential structural elements (such as rings for example), extending around the stent circumference, therefore caging the lumen with the circumferential structural elements, and causing large compliance (or radial strain) mismatch between the stent and the stented lumen, causing a composite compliance that is small in the stented segment (smaller than the lumen and stent), or large stiffness mismatch, between the stent and the lumen, thereby aggravating the lumen which can cause inflammation and re-occlusion of the body lumen over time. In addition, such large mismatch significantly diminishes the ability of the lumen over the stented segment from exhibiting vaso-motion, and/or diminishes the lumen ability from further expansion, and/or diminishes the lumen ability from further expansion and/or contraction, under physiological conditions.

The stents of the present invention are configured to address one or more of the issues described above. Although it is important for the stent to have sufficient (or high) strength initially after expansion to support a body lumen, such (high) strength can be detrimental to the lumen in the long run in one example due to the continuous irritation to the body lumen and/or due to large compliance or stiffness mismatch. It is desired in such example to have a stent configured to have an high initial strength, and a decreased strength after expansion (after initial strength) as described in some of the examples in this application. The stent is configured to have decreased strength after expansion of the stent, and/or after the body lumen is open, and/or after the lumen starts to heal, and/or after the lumen heals, and/or after at least some cellular or tissue covers at least some of the stent struts. Even though the stent strength decreases after expansion, the stent still has sufficient strength to hold the lumen open, or has sufficient strength to substantially maintain the lumen open, or has sufficient strength to support a body lumen. One or more reasons for having a reduced stent being sufficient are that the stent is capable of substantially maintaining the expanded configuration without the need for the initial strength magnitude, and/or that the lumen has started to heal, or has healed, exerting less crush force on the stent, and/or that the lumen after expansion has remodeled to the expanded configuration and requires less support or less stent strength to maintain it in the open configuration. Furthermore, the stent in some examples of the present invention are configured to have higher radial strain (compliance) after expansion compared to prior art, and/or have higher radial strain (compliance) after expansion that is closer the lumen compliance before stenting, and/or have less radial strain mismatch between the stent and body lumen, and/or is less stiff after expansion compared to initial stiffness in the expanded configuration, and/or being able to further expand after an initial inward recoil, and/or exhibit further expansion and/or contraction, and/or exhibit vaso-motion in the stented segment, under physiologic conditions.

The stents in the present invention are configured to uncage, or to uncage circumferentially, by configuring the stent to have one or more discontinuities, or one or more discontinuities, along the circumferential path of the structural elements (such as the rings), thereby uncaging the circumferential elements (or the stent) and providing for a compliance (or radial strain), or stiffness that is closer to the body lumen. The stent in a preferred example continues to provide (or maintains) lumen support through the patterned stent structure after expansion and/or after formation of discontinuities. The stent structure in another preferred example maintains one or more connections of substantially all adjacent rings after expansion, or maintains one or more connections of at least some adjacent rings in another example. In another preferred example, the initial stent strength after expansion is reduced after an initial higher strength upon expansion (or immediately after expansion), and/or is reduced as (or while) the compliance (or radial strain) increases.

A discontinuity in the present example is illustrated as a separation region in circumferential structural elements. The discontinuity in another example can also be a discontinuity in (for example) material properties, or other mechanical properties that allow increased motion in at least some stent segments after stent expansion.

The configuration of having one or more discontinuities affects the stress on the stent material. A continuous tubular stent holds open a lumen by forming a substantially rigid "hoop" of material—a discontinuity in the ring changes the stress state of the stent from hoop stress to bending stress (with some tangential stress induced by hoop stresses in the artery) in one example, as the area of the discontinuity is free to flex or bend, and the remaining semi-circular portion of the stent reacts to this flexing.

Figure 68:
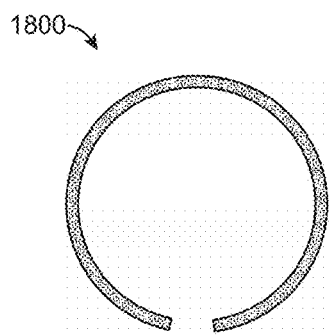
FIG. 68 illustrates a single discontinuity in circumference, forming a "C shaped" open stent.

As an example, a stent 1820 can have a single discontinuity 1822, as illustrated in FIG. 68, to create the longest moment arm in the stent, and therefore has the possibility of creating a large flexural or bending stress. Multiple discontinuities in a ring offer multiple regions of the lumen to return to substantially their original state of compliance or closer to it, while shortening the moment arms, reducing the flexural and/or bending stresses in the stent segments. Three discontinuities 1824 are illustrated in FIG. 69 and five discontinuities 1826 are illustrated in FIG. 70.

Figure 69:
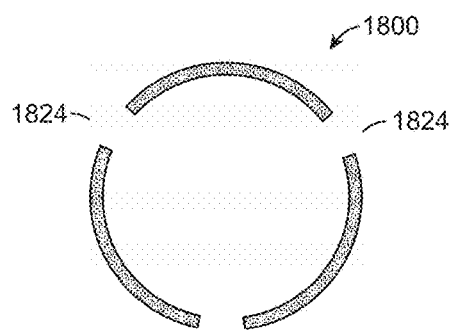
FIG. 69 illustrates three discontinuities in circumference, forming three stent strips (stent sections, or stent segments) along the stent length, while maintaining connection (axial links) between adjacent rings.
Figure 70:
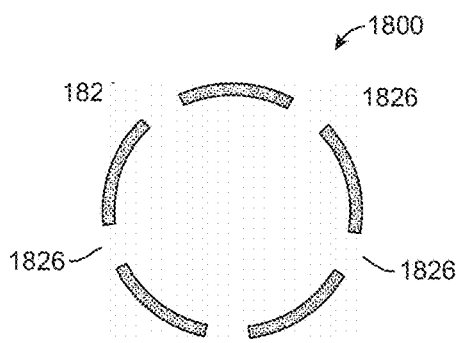
FIG. 70 illustrates five discontinuities in circumference, forming five stent strips (stent sections, or stent segments) along the stent length, while maintaining connections (axial links) between adjacent rings

FIGS. 68-70 are sectional views of the stent 1820 and the circumferential position(s) of the discontinuity(ies) can vary throughout the length of the stent, in patterns including (for example) a straight line of discontinuities along the stent length, a zig-zag pattern of discontinuities along the stent length, a spiral pattern of discontinuities along the stent length, or a random arrangement of discontinuities along the stent length. In a preferred example, the strips maintain their connections between adjacent rings.

Figure 71:
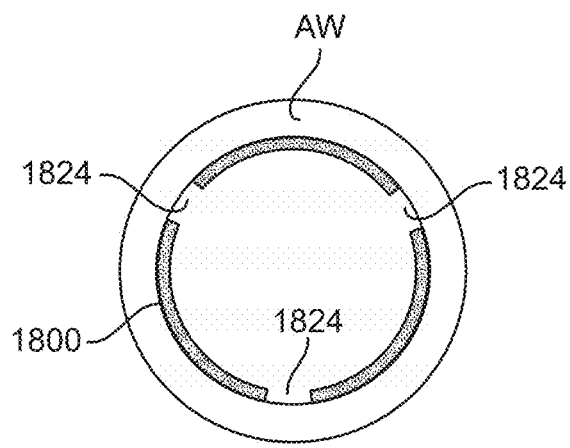
FIG. 71 shows a stent in a lumen in a relaxed position.
Figure 72:
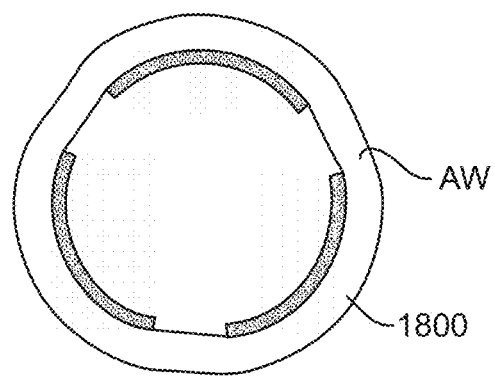
FIG. 72 shows a stent in a lumen in an outwardly flexed position.

Stents with longitudinal discontinuity(ies) such as stent 1800 with three discontinuities 1824, allow the stent segments to radially expand and contract, as shown in FIGS. 71-72, which in turn allow an arterial wall AW to expand/contract circumferentially, resulting in a more natural movement in the anatomical lumen. This increased motion could, for example allow for increased blood flow by allowing increased luminal motion and/or increased cross sectional area of the lumen.

To evaluate the differences (for example, in radial strain or compliance, stiffness, maximum displacement, and change in cross sectional area) in configurations of the stents with discontinuities (compared to prior art stent which does not have discontinuities), in how they react under physiologic conditions such as under pulsatile blood pressure, a Finite Element Model of an artery and stent was constructed and analyzed. FEA is a powerful tool to compare various configurations and generate results similar and/or comparatively similar to bench or in-vivo testing. The FEA model was subject to a pressure of 80 mmHg to simulate a full cycle of blood pressure variance (diastolic to systolic) but can also be modeled at a different pressure change such as 176 mmHg (3.4 psi). The artery was modeled with a thickness of 0.25 mm, as an elastic member with a Poisson's ratio of 0.45 and an elastic modulus of 362 psi in order to approximate an arterial compliance of 4% under 80 mmHg pressure. Other physiologic conditions including other arterial compliances and/or simulated pressure levels may be utilized in other examples. The stent material used for all test samples and analyses was the same non-degradable stainless steel alloy material patterned into a stent and configured as in Table 3 for the relevant parameters:

TABLE 3

| Design | Stent Outer Diameter | Stent Thickness | Stent Length* | Number of Crowns per Ring | Number of Links per Ring |
|---|---|---|---|---|---|
| "Prior art stent", no circumferential Discontinuities (Control example) | 4 mm | 80 µm | 9.6 mm | 6 | 3 |
| Stent having no circumferential Discontinuities and no axial links connecting adjacent rings | 4 mm | 80 µm | 9.6 mm | 6 | 0 |

TABLE 3-continued

| Design | Stent Outer Diameter | Stent Thickness | Stent Length* | Number of Crowns per Ring | Number of Links per Ring |
|---|---|---|---|---|---|
| Stent having 3 Discontinuities per ring | 4 mm | 100 µm | 9.6 mm | 6 | 3 |
| Stent having 4 Discontinuities per ring | 4 mm | 100 µm | 11.3 mm | 8 | 4 |
| Stent having Spiral Ring, each ring having 3 Discontinuities | 4 mm | 80 µm | 12.6 mm | **7 | ***2.5 |
| Stent having Spiral Ring, each ring having 3 Discontinuities | 4 mm | 100 µm | 12.6 mm | **7 | ***2.5 |

*Since the analysis is at a slice in the approximate center of the artery, Stent Length would not affect the analysis and is presented for information only.
**The "Spiral Rings" model is constructed in a continuous spiral. It has 7 crowns for every 360° of spiral.
***Due to the nature of the spiral rings design, the average number of links between two rings per turn of the spiral ring design is reported.

The stents in Table 3 above are substantially the same except for the thickness (as noted) and for the number of crowns (as noted), and whether they have discontinuities or not (as noted), and the whether they have axial links or not (and how many links, as noted), and the lengths (as noted). The stent circumferential rings were substantially perpendicular to the stent longitudinal axis in all test samples except the spiral pattern which has circumferential rings that are at an angle (or offset) to the longitudinal length of the stent.

Figure 74:
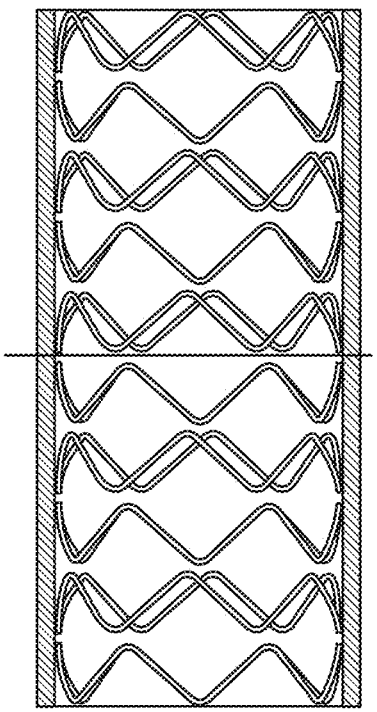
FIG. 73 and FIG. 74 illustrate a center section of a stent in between adjacent rings.
Figure 73:
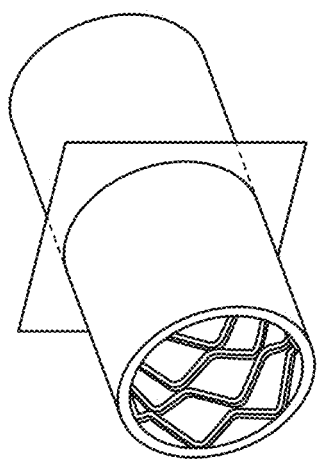

To characterize the deformation or displacement of each design, a slice through the approximate center was taken, and the nodal displacements of the internal diameter of the artery wall were examined, as shown in FIGS. 73 and 74. These slices correspond approximately to the location of links (when present) in the design (it is also the location between adjacent rings, or between adjacent crowns on adjacent rings), and were located close to the middle of the stent to eliminate any local effects of the end of the stents, and make the results applicable to stents of arbitrary length.

The FEA model was run and the following were the results:

Maximum Diameter, and Radial Strain, and vaso-motion for the different designs are presented below. The displacement data from the finite element analysis (from a section between the rings of the stent) was analyzed to determine the maximum diameter of the I.D. of the artery (as defined by the two points on the I.D. farthest apart), and the area of the deformed shape determined by numerical integration using radial coordinates around the circumference of the arterial shape. The area is used to calculate an equivalent circular radius, and from that, equivalent radial strain. The radial strain is then compared to the radial strain in the unstented artery, to determine percent of vasomotion retained, as tabulated in Table 4 below.

TABLE 4

| Design | Between Ring Maximum Diameter at 80 mmHg pressure | Between Ring Radial Strain, % (based on cross sectional luminal area) | Between Ring Percent of vasomotion retained (compared to un-stented artery, based on cross sectional area.) |
| --- | --- | --- | --- |
| Artery Only, 80 mmHg Pressure | 4.16 mm | 4.0% | 100.0% |
| "Prior art stent", with no circumferential Discontinuities (Control example) | 4.034 mm | 0.44% | 11.1% |
| Stent having no circumferential Discontinuities and no axial links connecting adjacent rings | 4.035 mm | 0.45% | 11.4% |
| Stent having 3 Discontinuities per ring | 4.07 mm | 1.4% | 34.1% |
| Stent having 4 Discontinuities per ring | 4.09 mm | 1.5% | 38.3% |
| Stent having Spiral Ring, each ring having 3 Discontinuities | 4.10 mm | 1.9% | 47.6% |
| Stent having Spiral Ring, each ring having 3 Discontinuities | 4.09 mm | 1.8% | 46.1% |

Figure 75:
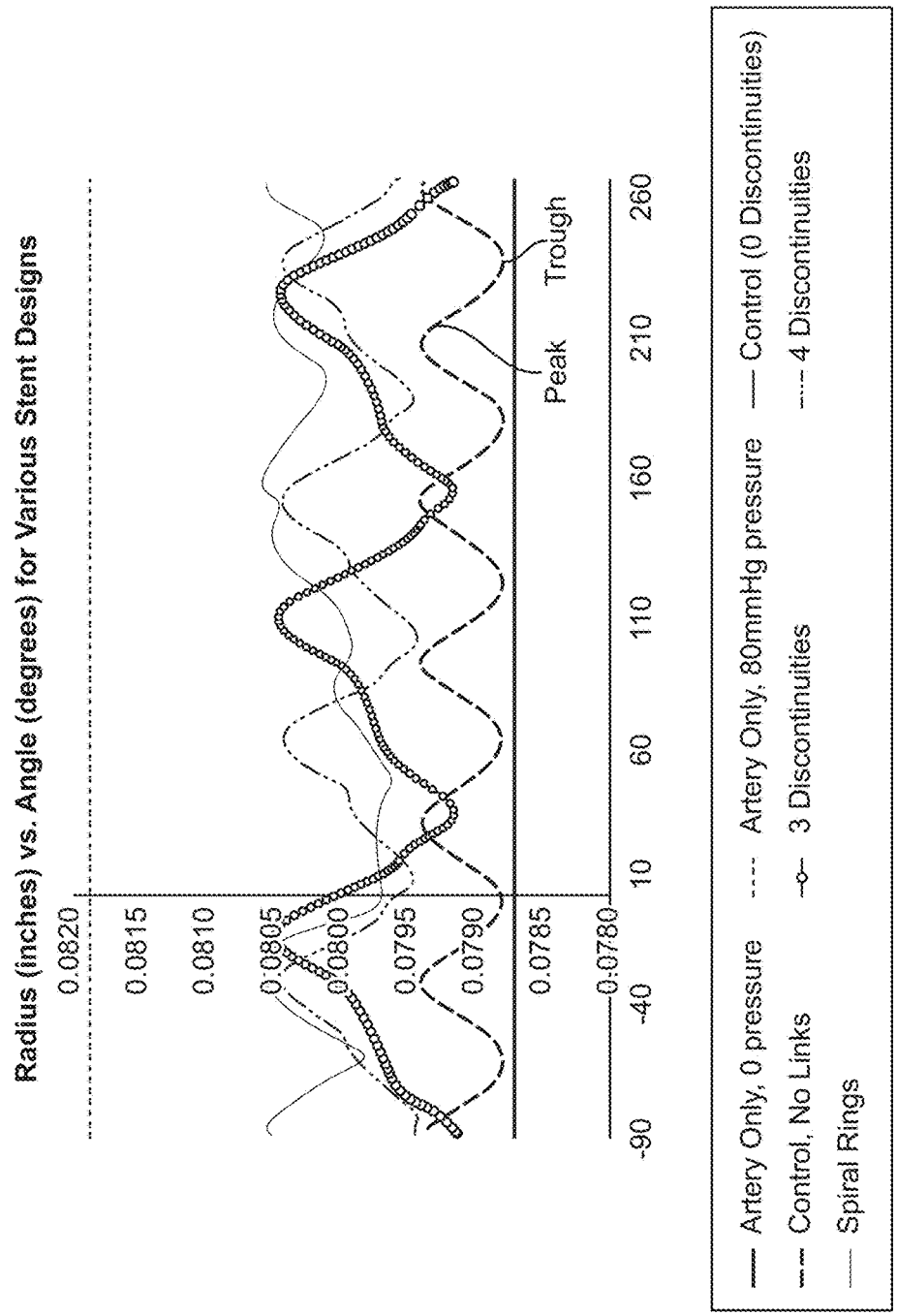
FIG. 75 illustrates the cyclic nature of the arterial displacement with a stent in place.

FIG. 75 illustrates the cyclic nature of the arterial displacement with a stent in place. For example, for the prior art stent having "0 discontinuities", and for the stent having "0 discontinuities" and no axial links stents, their curves are almost superimposed, the low point of the displacement curves corresponds to the point in close proximity to the crown of a ring near the section (which is between two adjacent rings) under examination, which is held relatively stiffly as a result of having no circumferential discontinuities. It is worth noting that even though the second sample has no axial links connecting adjacent rings, the stiffness and radial compliance of the stent/artery system are similar to the prior art stent/artery system stiffness and radial compliance. The peaks are at the points farthest from the crowns of the stent (mid ring segment).

Figure 77:
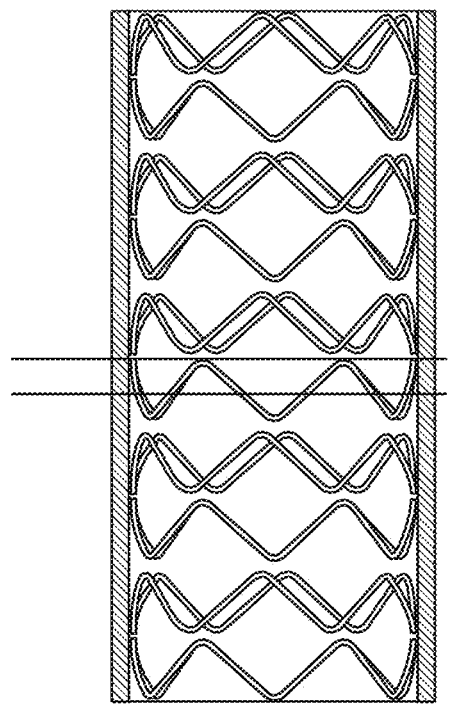
FIGS. 76 and 77 illustrate an alternative FEA model run at another section of the artery. This section is located near the middle of a ring.
Figure 76:
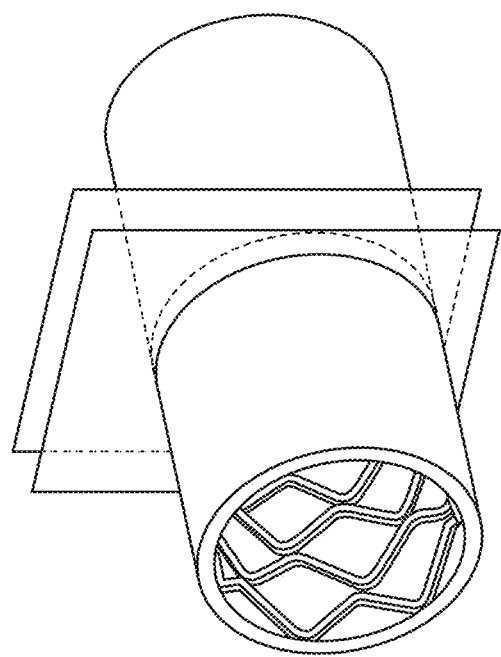

The FEA model was also run at another section of the artery, as shown in FIGS. 76 and 77. The section used above was between adjacent rings, but a second section of interest would be in the middle of a ring ("Mid-Ring" section). Note that a straight section through the spiral stent strikes each of the seven crowns at a different position, from between adjacent rings to mid-rings, and back to between adjacent rings (for the next turn of the spiral).

Figure 78:
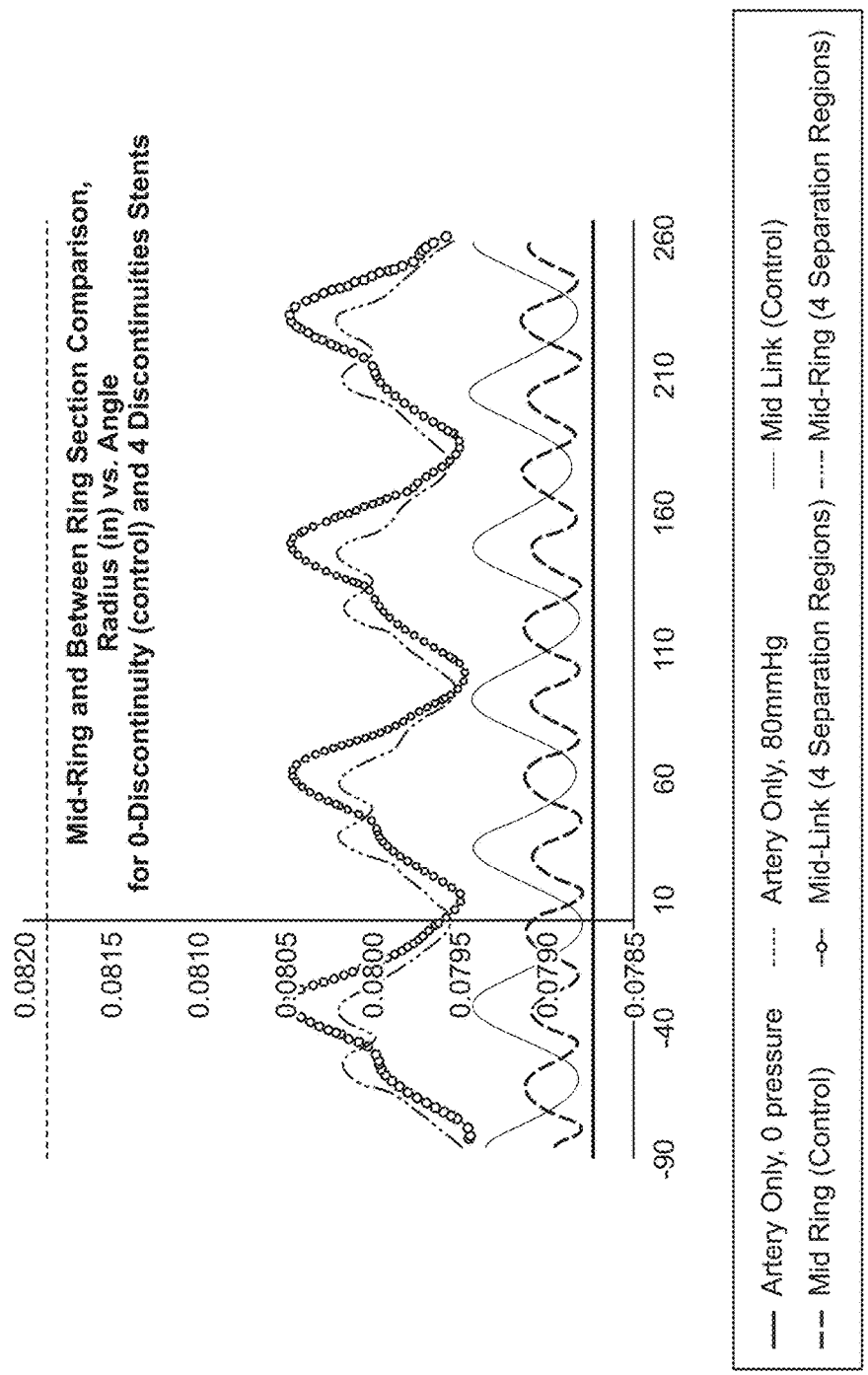
FIG. 78 illustrates the cyclic nature of arterial (luminal) displacement at mid-ring and between ring sections.

Mid-Ring Vs. Between Adjacent Ring Results:

The FEA model results showed that the "prior art" (control) stent having no discontinuities and sample two having no discontinuities and no axial links were substantially the same for all parameters evaluated in this example. For the purpose of illustrating the analysis of the Mid-Ring results, the "prior art" (control) stent versus a stent having four discontinuities were chosen. Looking at the difference in displacement graphically between the control (0 discontinuities) and 4-discontinuities graph shows the difference between sections taken between adjacent rings (between adjacent crowns), and mid-ring sections both qualitatively and quantitatively in FIG. 78.

Note that the periodicity of each graph doubles from between ring sections to mid-ring sections, because the artery in those sections touches the stent a greater number of times (for example, from approaching 6 crowns to crossing 12 struts). In the stent with discontinuities, this periodicity is masked by the (larger) periodic radial expansion of the discontinuities. For this reason, the section location has a greater effect on the displacement (both peak and average) compared to the prior art 0 discontinuity stent (control). Table 5 below compares mid-ring data to the data from the between ring section table for radial strain and for cross sectional area (vasomotion).

TABLE 5

| Design | Between Ring Radial Strain (%) | Mid Ring Radial Strain (%) | Percent of vasomotion (cross sectional area) retained (compared to un-stented artery) Between Ring Section | Percent of vasomotion (cross sectional area) retained (compared to un-stented artery) Mid-Ring Section |
| --- | --- | --- | --- | --- |
| Artery Only, 80 mmHg | 4.0% | | 100.0% | |
| 0 Discontinuities (control) | 0.44% | 0.3% | 11.1% | 7.1% |
| 0 Discontinuities, No Links | 0.45% | 0.3% | 11.4% | 7.1% |
| 3 Discontinuities | 1.4% | 1.3% | 34.1% | 31.9% |
| 4 Discontinuities | 1.5% | 1.5% | 38.3% | 36.8% |
| Spiral Ring, 3 Sep. Regions (80) | 1.9% | | 47.6% | |
| Spiral Ring, 3 Sep. Regions (100) | 1.8% | | 46.1% | |

Figure 79:
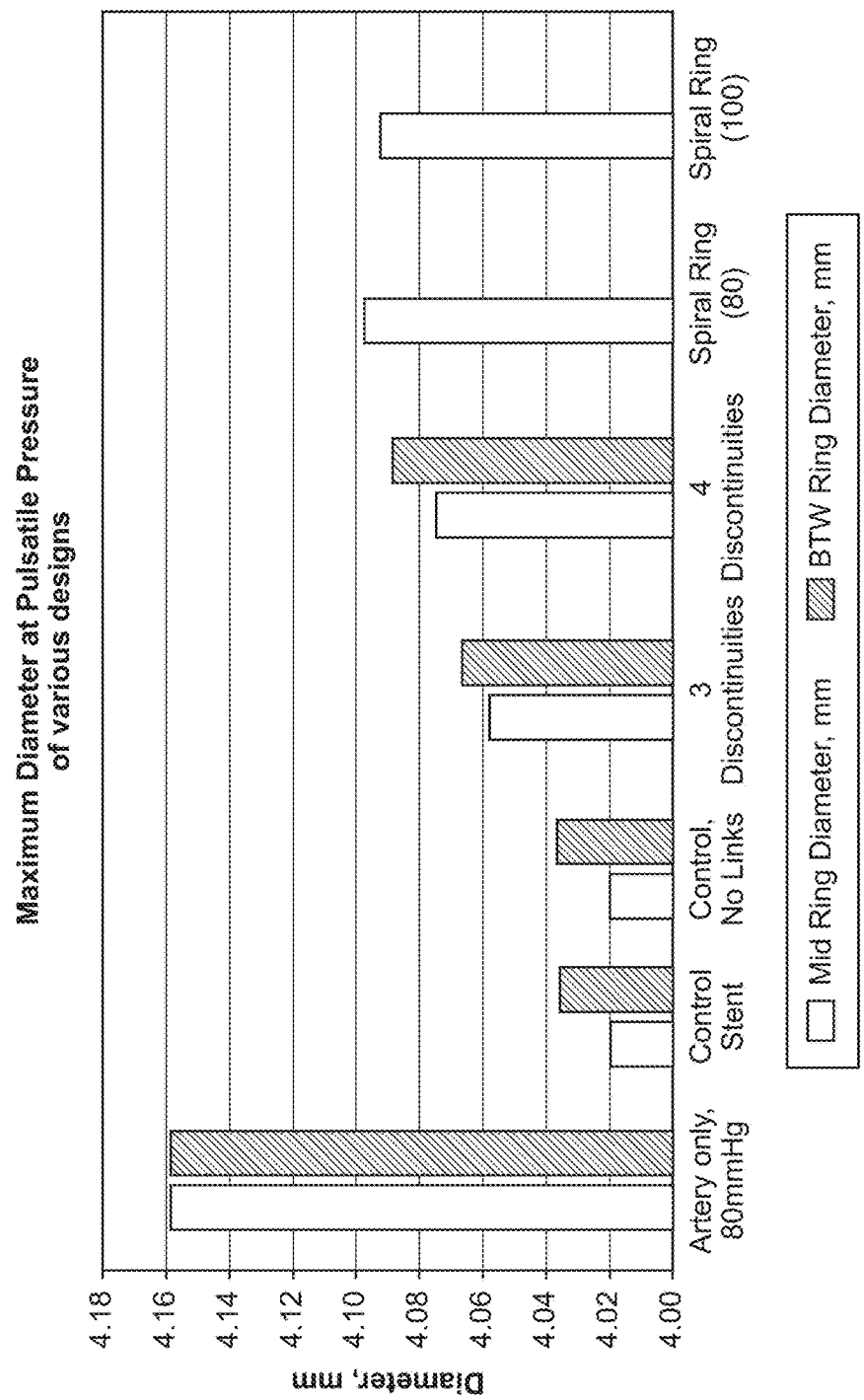
FIGS. 79 and 80 illustrate a comparison in luminal maximum diameter and luminal area for different stent designs.
Figure 80:
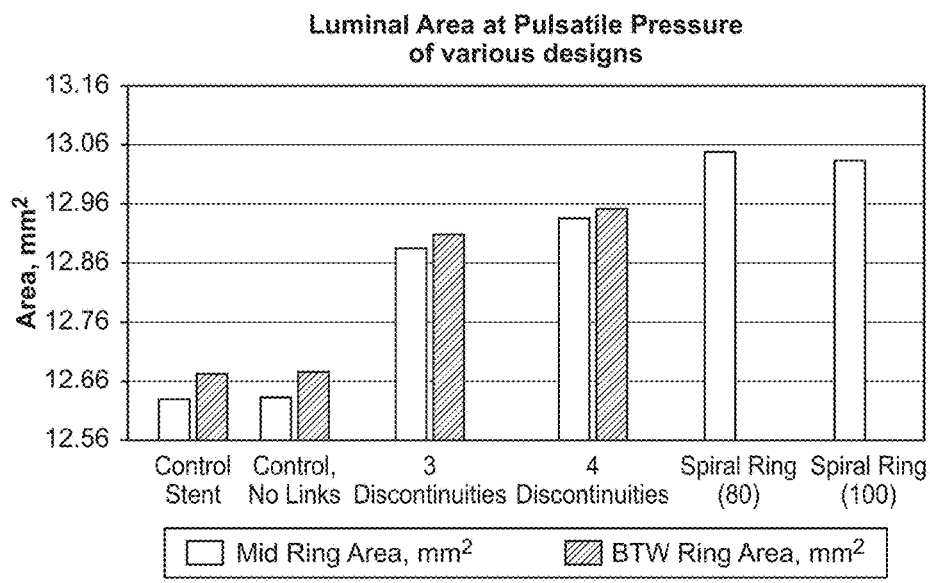

FIGS. 79 and 80 illustrate the comparison in Luminal Maximum Diameter and Luminal Area for each of the above designs.

Figure 81:
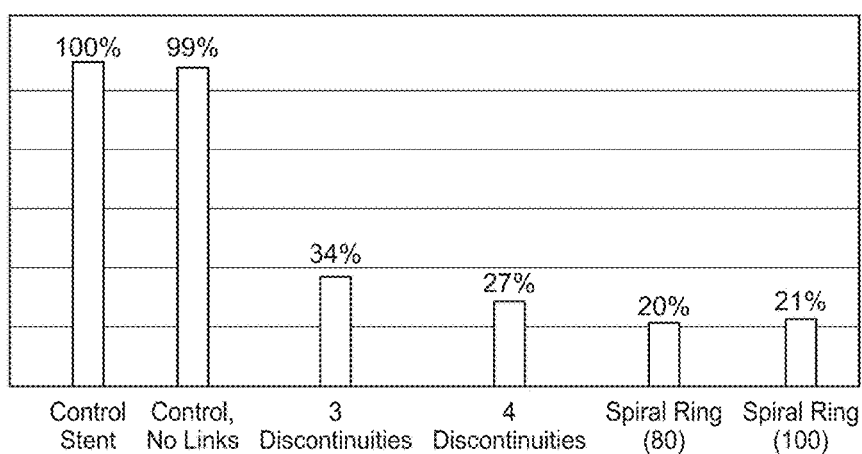
FIG. 81 compares radial strengths of modified stents with strength of a control stent.

Finally, the mid-ring can also produce radial strength data comparisons. That is, the pressure required to compress the artery/stent system by a given amount is inversely proportional to the diametric change at the stent (which is approximated by the mid-ring displacements). See FIG. 81.

Figure 82:
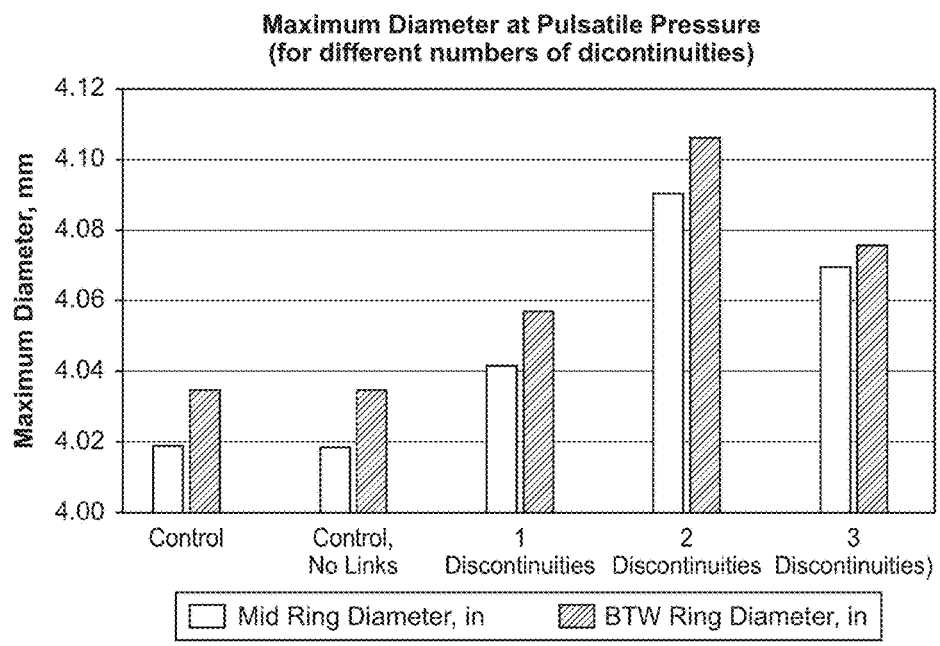
FIGS. 82-83 illustrate a comparison in luminal maximum diameter and luminal area for stents with different number of discontinuities per ring, and control stent.
Figure 83:
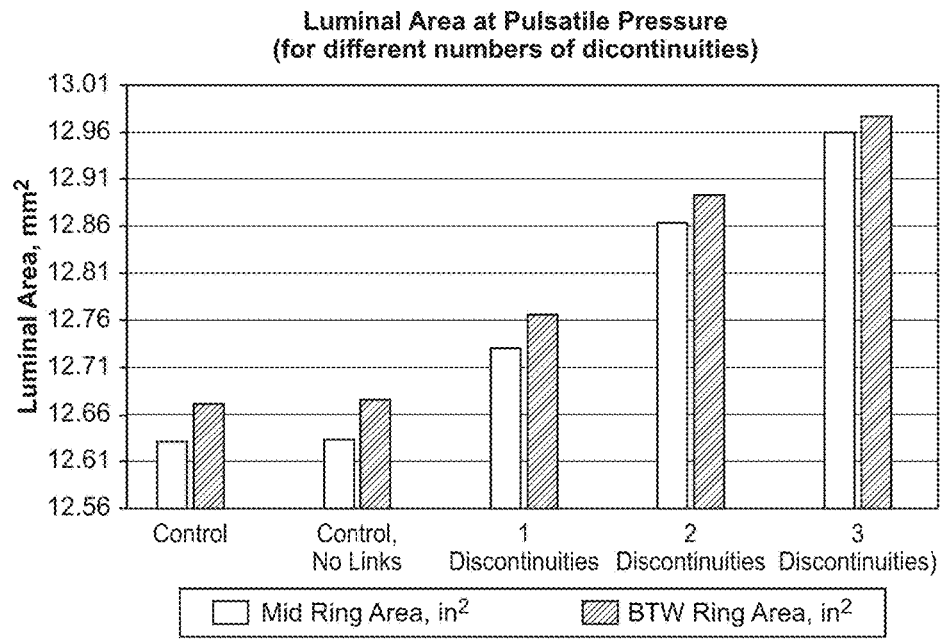

The FEA model was also used to analyze a control stent configured to have differing numbers of discontinuities of equal segments or strips. For example, a single discontinuity can form a "C" shaped discontinuity along the stent length that can open (or uncage the stent) where the two discontinuities can separate to form two strips along the length of the stent, and so on. The maximum diameter and cross-sectional area of each configuration is shown in FIGS. 82 and 83.

It is noteworthy that the motion induced by two discontinuities is along a diametric line (as illustrated below), which resulted in greater increase in diameter compared to the design with three discontinuities. Change in luminal area however grows consistently greater with number of discontinuities and showed luminal area was greater with three discontinuities compared to two.

Note that the compliance of the stent or stent-artery system referred to in the example is the composite compliance.

Example 21 demonstrated that stents with and without axial links had comparable composite compliances and comparable radial strengths, and had little or no differences in the radial strength or composite compliance of the expanded rings or scaffold. Therefore, stents (or scaffold) with no axial links had little or no change in composite compliance and radial strength compared to stents with axial links. In contrast, scaffolds having separation regions within the circumferential ring structures according to the present invention had increased composite compliance and decreased radial strength of the expanded rings or scaffold after formation of discontinuities.

Example 22

A porcine animal having a control scaffold (DESyne, Elixir Medical Inc,) and a test scaffolds of (PR100RG) having a 6-crown 3-link pattern having three evenly spaced separation regions per ring, with the axial links connecting adjacent rings was tested and followed up for about 5 months. The test device was coated with a fast degrading lactide copolymer covering the separation regions including the gaps within the separation regions, and covering the stent surfaces (luminal, abluminal, and two side surface). The coating had an abluminal thickness of about 10 microns. The stent was also coated with a top coated of novolimus and a lactide copolymer drug matrix. The test scaffold and a control scaffold (DESyne, Elixir Medical Inc,) were implanted in the coronary arteries of domestic pig following which they were serially imaged by angiography and Optimal Coherence Tomography (OCT) at time points from baseline (after expansion (implantation), 2, 3, and about 5 months. The devices were evaluated in vivo at multiple time points by OCT imaging to assess device formation of discontinuities within the rings, uncaging, uncaging of the stented segment, as well as changes in device area, and lumen areas (study reference: ELX 080). OCT imaging was performed following device implantations (baseline) and at the follow-up time points above. Still images from the OCT pullback of the test device implanted vessel segment at baseline and at the follow-up time points are shown in FIGS. 100A-100D. Discontinuities were observed in the device as early as the 2 month follow up time point and subsequent follow up time points as shown in (FIG. 100 B-D). Examples of the discontinuities in the OCT images are shown within the circled areas of the OCT images. The discontinuities show formation of gaps, or struts out of plane with one another (or struts having different radii from the center of the image or with respect to each other). The control stent (not shown in the figure) having no separation regions within the rings, had no formation of discontinuities.

Figure 101A:
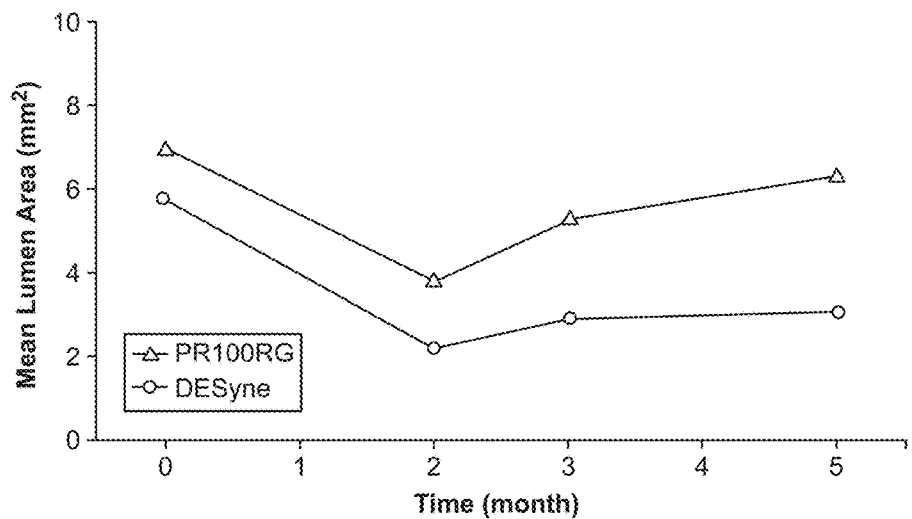
FIGS. 101A and 101B are plots of the stents and luminal mean areas for the test scaffolds of the present invention, and the control scaffolds (not having separation regions), after implantation in a porcine artery.
Figure 101B:
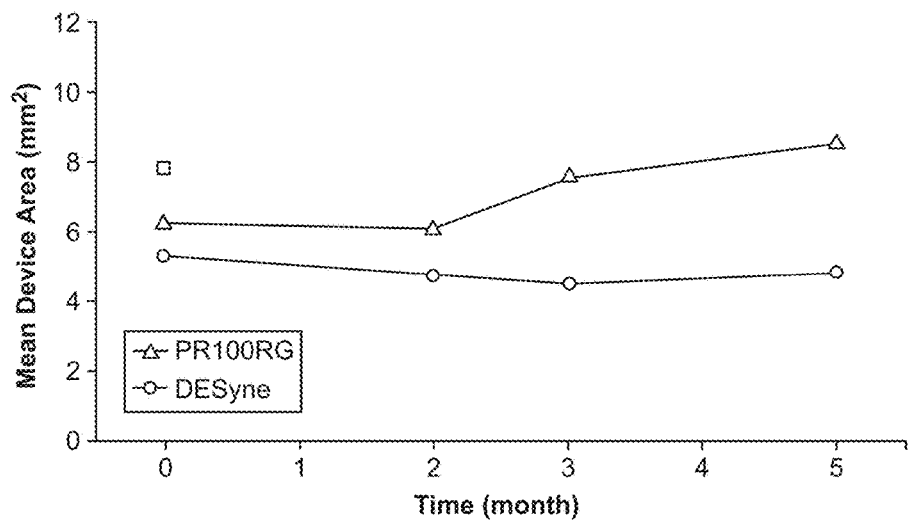

Graphical representations of the test results for the test scaffold (PR100RG) of the present invention, and of the control stent (DESyne) using OCT measurements that were taken at three random points along the length of each scaffold (at about a proximal, at about a mid, and at about a distal point of the scaffold length), averaged as a mean for each follow up time point, are shown for baseline, 2, 3, and 5 months follow up time points, showing stents and luminal mean areas for the test scaffolds of the present invention, and for the control scaffolds (not having separation regions), after implantation in porcine arteries, are shown in FIGS. 101A and 101B. The test scaffold showed some reduction in mean scaffold area at the 2 months time point, the time period where the vessel is healing from injury. However, the test scaffold mean area increased at the 3 months time point and further increased at the 5 months time point. In this example, the scaffold mean area at 3 months and 5 months time period were larger than the baseline mean scaffold area. The mean scaffold area at about the 5 months time point increased from the mean lumen area at baseline. The control scaffold mean area showed a similar reduction at the 2 months time point but remained substantially the same at the 5 months time point. The mean scaffold area for the test scaffold increased from baseline to the 5 months follow up timepoint indicating formation of discontinuities, uncaging of the stent or uncaging of the rings having separation regions. In contrast, the control scaffold mean area remained substantially the same or slightly smaller from baseline to the 5 months time point follow up.

The FIG. 101A shows the mean lumen area increasing for the test scaffold from the 3 months time point to the 5 months time point, after an initial reduction of mean lumen area at the two months follow up due to neointimal cell proliferation and the healing process. In contrast, the control stent has substantially the same mean lumen area from the 3 months time point to the 5 months time point, after a similar initial reduction at the 2 months time points due to neointimal cell proliferation and the healing process. The test scaffold mean lumen area demonstrated further expansion (or continued expansion), after the initial reduction due to the healing phase, over the 5 months follow up time point, indicating uncaging of the scaffold segment (stented vessel segment). In contrast, the control stent had some mean lumen area recovery (increase) at the 3 months time point, after the initial reduction due to the neointimal cell proliferation and the healing process. However, the mean lumen area after the recovery from the healing phase at 3 months remained substantially the same at the 5 months follow up time period, indicating continued caging of the vessel (or stented segment of the vessel).

Example 23

The composite compliances of conventional 3.5 mm diameter control stent without separation regions and 3.5 mm diameter test stents with separation regions according to the present were tested according to the specific protocol set forth above for measuring composite and compared. The conventional stent under examination were 8 crown, no-discontinuity cobalt chromium stents with a strut thickness of approximately 0.08 mm. The stent having separation regions were 6 crown stents with 3 discontinuities per ring, arranged in a spiral pattern along the length of the stent. The cobalt chromium strut thickness was approximately 0.075 mm, with a coating thickness of approximately 0.01 mm. The reference artery measurement was averaged across both tests, and the compliance of the stented segments compared to the compliance of the reference artery. The results are in Table 6 below.

TABLE 6

| | Diameter Measurements | | |
| --- | --- | --- | --- |
| Test Condition | Stent-Mock Vessel segment mid-stent (average of 4 samples) (no discontinuities) | Present Invention Stent-Mock Vessel segment mid-stent average of 4 samples (after formation of discontinuities) | Reference artery (average of 4 samples) |
| 0 pressure | 3.49 mm | 3.71 mm | 3.48 mm |
| 176 mmHg | 3.50 mm | 3.76 mm | 3.73 mm |
| Change from 0 pressure to 176 mmHg | 0.01 mm | 0.05 mm | 0.25 mm |
| Percent change in diameter from 0 pressure to 176 mmHg (composite compliance) at 176 mmHg | 0.4% | 1.2% | 7.2% |

The stent with discontinuities, configured in accordance of the present invention, displayed approximately 3 times the diameter change of the control stent without discontinuities, indicating an increase in compliance that makes the stented segment with discontinuities behave closer to the reference artery than the control stented segment without discontinuities. The composite compliance of the test stent at 176 mmHg was about 3 times the compliance of the control stent at 176 mmHg.

Although certain embodiments or examples of the disclosure have been described in detail, variations and modifications will be apparent to those skilled in the art, including embodiments or examples that may not provide all the features and benefits described herein. It will be understood by those skilled in the art that the present disclosure extends beyond the specifically disclosed embodiments or examples to other alternative or additional examples or embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments and examples may be made and still fall within the scope of the present disclosure. Accordingly, it should be understood that various features and aspects of the disclosed embodiments can be combined with or substituted for one another in order to form varying modes or examples of the present disclosure. Thus, it is intended that the scope of the present disclosure herein disclosed should not be limited by the particular disclosed embodiments or examples described above. For all of the embodiments and examples described above, the steps of any methods for example need not be performed sequentially.

What is claimed is:

1. An endoluminal prosthesis comprising: a helical scaffold having a multiplicity of adjacent helical turns comprising a plurality of struts joined by crowns, wherein at least some helical turns are axially connected to adjacent helical turns, said scaffold being expandable from a crimped configuration to a deployed configuration; wherein at least some helical turns include at least one separation region configured to be held together during expansion and to separate after expansion of the scaffold to the deployed configuration in a physiologic environment.

2. An endoluminal prosthesis as in claim 1, wherein at least one separation region is formed in each turn of the helical scaffold.

3. An endoluminal prosthesis as in claim 1, wherein at least some of the separation regions are formed in crowns.

4. An endoluminal prosthesis as in claim 1, wherein at least some of the separation regions are formed in struts.

5. An endoluminal prosthesis as in claim 1, wherein all helical turns are axially connected to adjacent helical turns, and wherein said turns remain axially connected after expansion of the scaffold in a physiologic environment.

6. An endoluminal prosthesis as in claim 1, wherein all of the adjacent helical turns are axially connected and wherein at least some of said turns remain axially connected after expansion of the scaffold in a physiologic environment.

7. An endoluminal prosthesis as in claim 1, wherein at least some helical turns are axially connected to adjacent helical turns, and wherein said turns remain axially connected after expansion of the scaffold in a physiologic environment.

8. An endoluminal prosthesis as in claim 7, wherein the scaffold separates along separation lines which extend from a first end of the scaffold to a second end of the scaffold into two or more axially connected segments after expansion of the scaffold in a physiologic environment and separation of said separation regions.

9. An endoluminal prosthesis as in claim 1, wherein at least some of the adjacent helical turns are axially connected, wherein at least one axial connection comprises a separation region, said separation region being configured to separate after expansion of the scaffold in a physiologic environment.

10. An endoluminal prosthesis as in claim 9, wherein the separation regions are disposed between crowns on adjacent turns in the helical scaffold, between struts on adjacent turns in the helical scaffold, or between a crown on one turn and a strut on an adjacent turn in the helical scaffold.

11. An endoluminal prosthesis as in claim 9, wherein at least some of the separation regions between adjacent helical turns of the helical scaffold comprise a lock and key.

12. An endoluminal prosthesis as in claim 9, wherein at least some axial connections between adjacent helical turns remain intact after all separation regions have separated after expansion of the scaffold in a physiologic environment.

13. An endoluminal prosthesis as in claim 1, wherein the adjacent crowns on adjacent helical turns in the helical scaffold are out-of-phase so that the convex surfaces of at least some of the adjacent crowns are axially opposed and in contact or separated by a gap.

14. An endoluminal prosthesis as in claim 1, wherein the adjacent crowns on adjacent helical turns in the helical scaffold are in-phase so that a convex surface of one crown is connected to a concave side of an adjacent crown by an axial strut.

15. An endoluminal prosthesis as in claim 1, wherein the adjacent turns in the helical scaffold are axially connected, wherein said axial connections are formed by a link, by fusing together portions of said adjacent turns, by soldering together portions of said adjacent turns, or by adhesively connecting portions of said adjacent turns.

16. An endoluminal prosthesis as in claim 1, wherein the plurality of struts joined by crowns are formed in a serpentine or zig-zag pattern.

17. An endoluminal prosthesis as in claim 1, wherein at least some of the adjacent turns are axially connected in two or more locations, wherein at least one axial connection remains connected after expansion of the scaffold in a physiologic environment.

18. An endoluminal prosthesis as in claim 1, wherein the helical scaffold is formed from a tube, a bent wire, or a rolled sheet.

19. An endoluminal prosthesis as in claim 1, wherein at least some of the adjacent turns are axially connected, wherein each said axial connection comprises a separation region, said separation regions being configured to separate after expansion of the scaffold in a physiologic environment.

20. An endoluminal prosthesis as in claim 1, wherein at least some of the separation regions in the helical scaffold comprise a lock and key.

21. An endoluminal prosthesis as in claim 20, wherein the lock and key comprises a ball and socket, disc and cap, tongue in slot, interlocking combs, interlocking teeth, interlocking hooks, grooves or V's or U's with suitable opposing shapes, or wavy or undulating interlocking surfaces or shapes.

22. An endoluminal prosthesis as in claim 1, wherein at least some of the separation regions in the helical scaffold comprise a male and female connection.

23. An endoluminal prosthesis as in claim 1, wherein said helical turns are configured to form a continuous circumferential path around said scaffold and wherein the said separation regions form one or more discontinuities in said helical turns after expansion of the scaffold in a physiologic environment, providing a discontinuous circumferential path in said at least some helical turns.

24. An endoluminal prosthesis as in claim 1, wherein the separation region comprises a coating, a sleeve, a solder, and/or adhesive which degrades after expansion of the scaffold in the physiologic environment.

25. An endoluminal prosthesis as in claim 1, wherein at least some of said separation regions comprise an elastic material disposed in, over, and/or adjacent to said separation region and wherein the elastic material remains intact after expansion in a physiologic environment.

26. An endoluminal prosthesis as in claim 1, wherein the helical scaffold further comprises at least one drug.

27. An endoluminal prosthesis as in claim 1, wherein the helical scaffold further comprises a polymer coating, wherein the polymer coating comprises polylactide, poly-L-lactic acid, poly-DL-lactide, polylactide-co-glycolide, poly(lactic-co-glycolide), poly(n-butylmethacrylate), ethylene vinyl acetate, poly(ethylene-co-vinyl acetate), polyvinyl pyrrolidone, parylene, PVDF-HFP poly(vinylidene fluoride hexafluoropropylene), polystyrene, poly(L-lactide-co-epsilon-caprolactone), or poly(styrene-b-isobutylene-b-styrene).

28. An endoluminal prosthesis as in claim 1, wherein said scaffold is configured to expand from a crimped configuration to an initial expanded configuration and following an inward recoil from said initial configuration, further expand to a second expanded configuration.

29. An endoluminal prosthesis as in claim 1, wherein all crowns of at least some helical turns are free from separation regions.

30. An endoluminal prosthesis as in claim 1, wherein each helical turn has from one to five struts having a separation region.

* * * * *